United States Patent
Yu et al.

(10) Patent No.: US 10,836,772 B2
(45) Date of Patent: *Nov. 17, 2020

(54) DNA POLYMERASE IIIC INHIBITORS AND USE THEREOF

(71) Applicant: Acurx Pharmaceuticals, LLC, White Plains, NY (US)

(72) Inventors: Xiang Y. Yu, Acton, MA (US); Li H. Xing, Lexington, MA (US); Minghua Wang, Acton, MA (US); Casey McComas, Phoenixville, PA (US); Michael Silverman, Marblehead, MA (US); Richard Soll, Middleton, MA (US)

(73) Assignee: Acurx Pharmaceuticals, LLC, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/901,752

(22) Filed: Jun. 15, 2020

(65) Prior Publication Data

US 2020/0308180 A1 Oct. 1, 2020

Related U.S. Application Data

(62) Division of application No. 16/720,724, filed on Dec. 19, 2019.

(60) Provisional application No. 62/783,754, filed on Dec. 21, 2018.

(51) Int. Cl.
*A61K 31/519* (2006.01)
*A61P 31/04* (2006.01)
*C07D 487/04* (2006.01)

(52) U.S. Cl.
CPC .......... *C07D 487/04* (2013.01); *A61K 31/519* (2013.01); *A61P 31/04* (2018.01)

(58) Field of Classification Search
CPC .................................................. C07D 487/04
See application file for complete search history.

(56) References Cited

U.S. PATENT DOCUMENTS

| | | | |
|---|---|---|---|
| 6,926,763 B2 | 8/2005 | Wright et al. | |
| 7,456,288 B2 | 11/2008 | Rao et al. | |
| 8,293,919 B2 | 10/2012 | Guiles et al. | |
| 8,716,320 B2 | 5/2014 | Guiles et al. | |
| 8,796,292 B2 | 8/2014 | Wright et al. | |
| 2008/0242661 A1 | 10/2008 | Dykes et al. | |
| 2012/0232077 A1 | 9/2012 | Wright et al. | |

OTHER PUBLICATIONS

International Search Report (PCT/ISA/220 & PCT/ISA/210) issued in PCT Application No. PCT/US2019/067351 dated Feb. 19, 2020 (three (3) pages).

Written Opinion (PCT/ISA/237) issued in PCT Application No. PCT/US2019/067351 dated Feb. 19, 2020 (eight (8) pages).
Pubchem, "5-(Benzylamino)-6-ethyl-1,3-dimethylpyrazolo[4,3-d]pyrimidin-7-one," May 29, 2009, Retrieved from the internet <URL: http://pubchem.ncbi.nlm.nih.gov/compound/39894331; p. 2 (nine (9) pages).
Pubchem, "5-(6,7-Dimethoxy-1-methyl-3,4-dihydro-1H-isoquinolin-2-yl)-1-methyl-6-propylpyrazolo[4,3-d]pyrimidin-7-one" Dec. 1, 2012, Retrieved from the Internet <URL: https://pubchem.ncbi.nlm.nih.gov/compound/69325229; page 2 (six (6) pages.
Wright et al., "Inhibition of Bacillus subtilis DNA Polymerase III by Arylhydrazinopyrimidine," Biochimica et Biophysica Acta, 1976, pp. 37-48, vol. 432 (12 pages).
Tarantino et al., "Inhibitors of DNA polymerase III as novel antimicrobial agents against Gram-positive eubacteria," Antimicrobial Agents and Chemotherapy, 1999, pp. 1982-1987, vol. 43, No. 8 (six (6) pages).
Tarantino et al., "6-Anilinouracil-Based Inhibitors of Bacillus subtilis DNA Polymerase III: Antipolymerase and Antimicrobial Structure-Activity Relationships Based on Substitution at Uracil N3," J. Med. Chem., 1999, pp. 2035-2040, vol. 42, No. 11 (six (6) pages).
Daly et al., "In vitro antimicrobial activity of novel anilinouracils which selectively inhibit DNA polymerase III of Gram-positive bacteria," Antimicrobial Agents and Chemotherapy, 2000, pp. 2217-2221, vol. 44, No. 8 (five (5) pages).
Ali et al., "Design and Synthesis of Novel Antibacterial Agents with Inhibitory Activity against DNA Polymerase III," Bioorganic & Medicinal Chemistry Letters, 2001, pp. 2185-2188, vol. 11 (four (4) pages).
Muto et al., "SHEA Guideline for Preventing Nosocomial Transmission of Multidrug-Resistant Strains of *Staphylococcus aureus* and *Enterococcus*," Infection Control and Hospital Epidemiology, 2003, 362-386 (26 pages).
Ali et al., "Novel Pyrazolo [3,4-d]pyrimidine-Based Inhibitors of *Staphylococcus aureus* DNA Polymerase III: Design, Synthesis, and Biological Evaluation," J. Med. Chem., 2003, pp. 1824-1830, vol. 46, No. 10 (seven (7) pages).
Zhi et al., "Synthesis of Substituted 6-Anilinouracils and Their Inhibition of DNA Polymerase IIIC and Gram-Positive Bacterial Growth", J. Med. Chem., 2003, pp. 2731-2739, vol. 46, No. 13 (nine (9) pages).

(Continued)

*Primary Examiner* — Susanna Moore

(74) *Attorney, Agent, or Firm* — Crowell & Moring LLP

(57) ABSTRACT

The present invention relates to compounds and methods useful for inhibiting the DNA polymerase IIIC enzyme. The invention also provides pharmaceutically acceptable compositions comprising compounds of the present invention and methods of using said compositions in the treatment of Gram-positive bacterial infections.

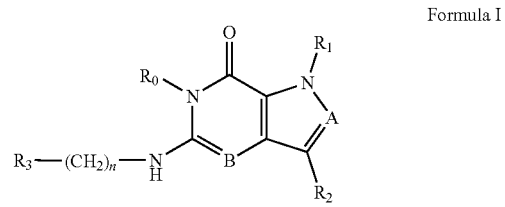

Formula I

6 Claims, No Drawings

(56) References Cited

OTHER PUBLICATIONS

Wright et al., "Active site directed inhibitors of replication-specific bacterial DNA polymerases," Bioorganic & Medicinal Chemistry Letters, 2005, pp. 729-732, vol. 15 (four (4) pages).
Kuhl et al., "Biological Characterization of Novel Inhibitors of the Gram-Positive DNA Polymerase IIIC Enzyme," Antimicrobial Agents and Chemotherapy, 2005, pp. 987-995, vol. 49, No. 3 (nine (9) pages).
Zhi et al., "Hybrid Antibacterials. DNA polymerase topoisomerase inhibitors," J. Med. Chem., 2006, pp. 1455-1465, vol. 49 (27 pages).
Evans et al., "Structure of PolC reveals unique DNA binding and fidelity determinants," Proc Natl Acad Sci US A, 2008, pp. 20695-20700, vol. 105, No. 52 (six (6) pages).
Cer et al., "IC50-to-Ki: a web-based tool for converting IC50 to Ki values for inhibitors of enzyme activity and ligand binding," Nucleic Acids Research, 2009, pp. W441-W445, vol. 37 (five (5) pages).
Hookman et al., "Clostridium difficile associated infection, diarrhea and colitis," World J. Gastroenterol, 2009, pp. 1554-1580, vol. 15 (27 pages).
Torti et al., "Clostridium difficile DNA polymerase IIIC: Basis for activity of Anti-Bacterial Compounds," Current Enzyme Inhibition, 2011, pp. 147-153, vol. 7, No. 3 (seven (7) pages).
Xu et al., "7-Alkyl-N2-substituted-3-deazaquanines. Synthesis, DNA polymerase III inhibition and antibacterial activity," Bioorganic & Medicinal Chemistry Letters, 2011, pp. 4197-4202, vol. 21 (seven (7) pages).
Dvoskin et al., "A novel agent effective against Clostridium difficile Infection," Antimicrobial Agents and Chemotherapy, 2012, pp. 1624-1626, vol. 56 (four (4) pages).
Magill et al., "Changes in Prevalence of Health Care-Associated Infections in U.S. Hospitals," The New England Journal of Medicine, 2018, pp. 1732-1744, vol. 379 (13 pages).
Xu et al., "Discovery and development of DNA polymerase IIIC inhibitors to treat Gram-positive infections," Bioorganic & Medicinal Chemistry, 2019, pp. 3209-3217, vol. 27, No. 15 (nine (9) pages).
Zhi et al., "Synthesis and Antibacterial Activity of 3-Substituted-6-(3-ethyl-4-methylanilino) uracils" J. Med. Chem. 2005, 48, 7063-7074 and Supporting Information (29 pages).
Kornberg et al., "DNA Replication: Second Edition," Chapter 5 : Prokaryotic DNA Polymerases Other Than E. coli Pol I, Section 5-7, 1992, pp. 182-185 (six (6) pages).
Stella (J. Pharmaceutical Sciences, 2010, 99(12), pp. 4755-4765).
United States Office Action issued in U.S. Appl. No. 16/901,598 dated Jul. 2, 2020 (23 pages).

DNA POLYMERASE IIIC INHIBITORS AND USE THEREOF

CROSS REFERENCE TO RELATED APPLICATIONS

This application is a divisional of U.S. application Ser. No. 16/720,724, filed Dec. 19, 2019, the disclosures of which are expressly incorporated by reference herein.

CROSS REFERENCE TO RELATED APPLICATIONS

This application claims priority to and the benefit of U.S. Provisional Application No. 62/783,754, filed Dec. 21, 2018, the contents of which are incorporated herein by reference.

TECHNICAL FIELD OF THE INVENTION

The present invention relates to compounds and methods useful for inhibiting DNA polymerase IIIC (pol IIIC) enzyme. The invention also provides pharmaceutically acceptable compositions comprising compounds of the present invention and methods of using said compositions in the treatment of Gram-positive bacterial infections.

BACKGROUND OF THE INVENTION

Bacterial pathogens pose a serious threat to public health. Aerobic and anaerobic gram-positive bacteria with multi-drug resistance to a diverse range of antibiotics have emerged as a major treatment challenge.

Two Gram-positive pathogens, *Staphylococcus aureus* and *Enterococcus faecalis/faecium*, account for the majority of nosocomial diseases (Muto, et al.). A third organism, *Streptococcus pneumoniae*, is generally a community-acquired pathogen. These organisms are aerobic bacteria, i.e. ones that grow in oxygen-containing atmospheres.

*Staphylococcus aureus* is the most frequent cause of nosocomial bacteremia and skin/wound infection and the second most frequent cause of nosocomial lower respiratory infection. The appearance of community-acquired methicillin-resistant *Staphylococcus aureus* (MRSA) has become a serious public health concern. MRSA strains are becoming increasingly multi-drug resistant over time. In many areas of the world, MRSA infections represent the majority of sporadic staphylococcal infections with community-onset. These strains also have been associated with numerous outbreaks of localized (skin and skin structure) and invasive (bacteremic) infections.

*Enterococcus faecalis* and *Enterococcus faecium* cause nosocomial septicemia, endocarditis, and infections of wounds and the urinary tract. Vancomycin-resistant phenotypes were first reported in enterococci (vancomycin-resistant enterococci, or VRE) in 1987, many years after the introduction of the drug into widespread clinical use. Today >30% of the ICU *Enterococcus faecalis* infections are VRE. There are few or no treatment options for certain illnesses caused by VRE including bloodstream infections, surgical site and urinary tract infections. The incidence of VRE is approximately 20,000 patients per year in the United States alone.

*Streptococcus pneumoniae* is the most common bacterial cause of meningitis, community-acquired pneumonia, acute otitis media, and sinusitis. In the United States it is estimated that *Streptococcus pneumoniae* accounts annually for 3000-6000 cases of pneumo-coccal meningitis, a half million cases of pneumonia, more than 12,000 cases of bacteremia, and 6 million cases of otitis media. Annual mortality from *Streptococcus pneumoniae*-induced disease is estimated to be 40,000 in the United States and 3-5 million globally. There has been increased identification of penicillin-resistant *Streptococcus pneumoniae* (PRSP). The emergence and spread of drug-resistant strains of pneumococcus have complicated treatment of these common infections.

Anaerobic bacteria, i.e. those which grow in oxygen-depleted atmospheres, are also a public health problem. *Clostridium difficile* has been increasingly associated with disease in human patients, often as a result of treatment with certain antibiotic drugs. The most common disease is referred to as *Clostridium difficile*-associated diarrhea (CDAD).

One approach toward solving the problem of bacteria with multi-drug resistance involves the development of effective antibacterial agents capable of selectively attacking new bacterial targets. DNA pol IIIC enzyme has been shown to be crucial in the replicative DNA synthesis of Gram-positive bacteria (Komberg, et al.). Because DNA pol IIIC enzyme shows little homology to mammalian or Gram-negative bacterial DNA polymerases, it is an attractive target for inhibition in the discovery of new Gram-positive selective antibacterial agents.

DNA pol IIIC enzyme is specifically required by low G:C Gram-positive organisms (both aerobes and anaerobes) for chromosome replication. DNA pol IIIC enzyme, encoded by the structural gene polC, is one of the two essential replication-specific DNA polymerases in Gram-positive bacteria. The polC is absent from the eubacteria with high G:C content and the Gram-negative eubacteria as well as eukaryotic cells, but is strongly conserved in a broad group of Gram-positive pathogens.

Thus, DNA pol III is essential for the replication of the host chromosome of the low G:C content gram-positive bacterial. When its action is blocked, chromosomal DNA fails to replicate and the bacterial host dies. The essential structure of this pol IIIC is strongly conserved in abroad group of low G:C content gram-positive pathogens, including *Staphylococcus*, *Streptococcus*, *Enterococcus*, and *Mycoplasma* (Tarantino, et al. Antimicrobial Agents and Chemotherapy, August 1999, 1982-87).

Although DNA pol IIIC inhibitors have shown Gram-positive antibacterial activity and in vivo protective activity, the lack of "druggable" features of the compounds, such as suitability of a parenteral formulation or favorable pharmacokinetics, has hampered their development. Therefore, there remains a need to identify compounds that may be effectively used to inhibit DNA pol III C, and thus to treat and inhibit bacterial infections.

SUMMARY OF THE INVENTION

The present invention relates to DNA pol HIC inhibitors which are useful against Gram-positive microorganisms, including antibiotic-resistant strains such as vancomycin-resistant Enterococci, methicillin-resistant *Staphylococcus aureus*, penicillin-resistant *Streptococcus pneumoniae* and Gram-positive anaerobe *Clostridium difficile*.

In one aspect, the invention features compounds having the formula shown below:

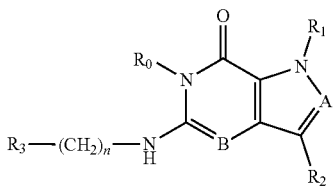

Formula I or a pharmaceutically acceptable salt thereof
wherein A and B are, independently, N, CH or $R_1$;
wherein n is 0-3;
wherein $R_1$ is $(CH_2)_m$—$\{(V)_o$—$(CH_2)_p\}_q$—W;
  in which V is $CH_2$, CH=CH, C≡C, CO, O, S, SO, $SO_2$, $NR_4$, $CHR_5$, OC(O), (O)CO, $CONR_6$, $NR_7CO$, $SO_2NH$, $NHSO_2$; $C_{3-8}$ cycloalkyl,
  wherein each of $R_4$, $R_6$, and $R_7$ is, independently, H or $C_{1-6}$ alkyl;
  wherein $R_5$ is OH or $C_{1-6}$ alkyl, $CH(R_8R_9)$, and
  wherein each of $R_8$ and $R_9$ is, independently, H, halo, or $C_{1-6}$ alkyl;
  wherein W is H, halo, substituted or unsubstituted $C_{1-6}$ alkyl, substituted or unsubstituted $C_{3-8}$ cycloalkyl, substituted or unsubstituted $C_{2-8}$ heterocyclyl, substituted or unsubstituted $C_{6-14}$ aryl, substitute d or unsubstituted $C_{1-10}$ heteroaryl, $NH_2$, CN, $OR_{10}$, $SR_{11}$, $COR_{12}$, $OCOR_{13}$, $NR_{14}COR_{15}$, $NR_{16}R_{17}$, $NR_{18}(CO)NHR_{19}$, $CH(CO_2R_{20})_2$, $CO_2R_{21}$, $NHSO_2R_{22}$, $CONR_{23}R_{24}$, $CH_2CO_2R_{25}$, $S(O)R_{26}$ or $S(O_2)R_{27}$
  wherein each of $R_{10}$-$R_{27}$ is, independently, H, substituted or unsubstituted $C_{1-6}$ alkyl, substituted or unsubstituted $C_{3-8}$ cycloalkyl, substituted or unsubstituted $C_{2-8}$ heterocyclyl, substituted or unsubstituted $C_{6-14}$ aryl, substituted or unsubstituted $C_{1-10}$ heteroaryl,
  wherein m is 1-5, o is 0-4, p is 0-4, and q is 0-4;
wherein $R_2$ is H, halo, CN, substituted or unsubstituted $C_{1-6}$ alkyl, $CO_2R_{21}$, $CONR_{23}R_{24}$, substituted or unsubstituted $C_{2-8}$ heterocyclyl or substituted or unsubstituted $C_{1-10}$ heteroaryl,
wherein $R_3$ is $C_{6-14}$ aryl or $C_{1-10}$ heteroaryl with substituted by one or more substituents selected from the group consisting of F, Cl, Br, I, $C_{1-6}$ alkyl, OH, CN, $C_{1-6}$-alkyl, $CF_3$, $CHF_2$, $CF_3CH_2$, $OCH_3$ and $OCF_3$,
wherein $R_0$ is H, $CH_2OPO(OH)_2$, $CH_2CONHCH_2(CH_2)_t$$OPO(OH)_2$, $CH_2OCOCH_2(CH_2)_t OPO(OH)_2$, COO$(CH_2)_t OPO(OH)_2$, $CH_2OPO(OH)OPO(OH)_2$,
or $(CR_{30}R_{31}O)_s$—X—Y—$(CR_{30}R_{31})$—$OPO(OR_{28})(OR_{29})$;
wherein X is a direct bond or (C=O), Y is a direct bond or oxygen
s is 0 or 1
t is 1, 2, or 3
$R_{28}$ and $R_{29}$ each are independently hydrogen or a hydrolysable ester group, wherein when
$R_{28}$ is hydrogen, $R_{29}$ may be —$P(O)OR_{32}OR_{33}$;
$R_{30}$ and $R_{31}$ each are independently hydrogen or $C_{1-4}$ alkyl; and
$R_{32}$ and $R_{33}$ each are independently hydrogen or a hydrolysable ester group
or an optical isomer thereof, an isotopic isomer thereof a prodrug or a pharmaceutically acceptable salt thereof.
Specific compounds of the above formulae are described herein. The invention encompasses all enantiomeric, racemic, tautomeric and diastereomeric forms, and mixtures thereof, of the compounds described herein.

The invention further features pharmaceutical compositions including a compound of formula I and a pharmaceutically acceptable carrier.

In another aspect, the invention features a formulation of a compound of formula I suitable for coating a surface, e.g., of a medical device as described herein. In such a formulation, the compound of the invention may be mixed with a suitable biocompatible coating agent or may be covalently or otherwise bound (e.g., electrostatically or as a ligand) to the coating agent.

In another aspect, the invention features a method for inhibiting bacterial growth including the step of contacting an area (e.g., media or surfaces such as those of a medical device) prone to bacterial growth with a compound of formula I.

The invention also features a method for treating an animal for a Gram-positive bacterial infection including the step of administering to the animal using a therapeutically effective amount of a compound of formula I.

In various embodiments of the invention, the compounds of the invention are useful for treating or preventing infections or inhibiting or preventing growth of Gram-positive bacteria, including but not limited to, *Staphylococcus aureus*; methicillin-resistant *Staphylococcus aureus*; *Enterococcus faecalis*; *Enterococcus faecium*; vancomycin-resistant *enterococcus*; *Streptococcus pneumoniae*; others microbes in the *Bacillus, Staphylococcus, Streptococcus*, and *Enterococcus* genera; and any other Gram-positive microbes that produce DNA pol IIIC enzyme.

DETAILED DESCRIPTION OF THE INVENTION

The features and other details of the invention will now be more particularly described. It will be understood that particular embodiments described herein are shown by way of illustration and not as limitation of the invention. The principle feature of this invention can be employed in various embodiments without departing from the scope of the invention.

Definitions

The term "alkyl" is defined as a branched or unbranched saturated acyclic hydrocarbon group, preferably having from 1 to 6 carbon atoms. Examples include methyl; ethyl; n-propyl; iso-propyl; n-butyl; iso-butyl; sec-butyl; tert-butyl; pentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methyl-pentyl; 1,1-dimethylbutyl; 1,2-dimethylbutyl; 1,3-dimethyl-butyl; 2,2-dimethylbutyl; 2,3-dimethylbutyl; 3,3-dimethyl-butyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and hexyl. An alkyl group may be unsubstituted or substituted, as described herein.

The term "cycloalkyl" is defined as a monocyclic or bicyclic structure having only carbon atoms in the ring(s), in which each ring desirably has three to eight members. Exemplary cycloalkyl groups include cyclopropyl; cyclobutyl; cyclopentyl; and cyclohexyl. A cycloalkyl group may be unsubstituted or substituted, as described herein.

The term "heterocyclyl" is defined as a monocyclic, bicyclic, or multicyclic heterocyclic ring system not including an aromatic ring. Each ring preferably includes 2 to 8, carbon atoms and 1 to 4 oxygen, nitrogen, and/or sulfur atoms. Examples include aziridinyl, azetidinyl, morpholinyl, oxazolidinyl, oxazolinyl, oxecanyl, oxepanyl, oxiranyl, piperazinyl, piperidinyl, pyranyl, pyrrolidinyl, tetrahydrofuranyl, tetrahydropyranyl, tetrahydrothienyl, and tetrahydrothiopyranyl. A heterocyclyl group may be unsubstituted or substituted, as described herein.

The term "aryl" is defined as a monocyclic, bicyclic, or multicyclic carbocyclic ring system having one or more aromatic rings. Each ring preferably includes from 6-14 carbon atoms. Examples include phenyl, naphthyl, 1,2-dihydronaphthyl, 1,2,3,4-tetrahydronaphthyl, fluorenyl, indanyl, and indenyl. An aryl group may be unsubstituted or substituted, as described herein.

The term "heteroaryl" is defined as a monocyclic, bicyclic, or multicyclic heterocyclic ring system having one or more aromatic rings. Each ring preferably includes 1 to 10 carbon atoms and 1 to 4 oxygen, nitrogen, and/or sulfur atoms. Examples include benzimidazolyl, benzofuranyl, benzotriazolyl, firyl, imidazolyl, indolyl, isobezofuranyl, isoquinolinyl, isoxazolyl, oxazolyl, purinyl, pyrazinyl, pyridazinyl, pyridinyl, pyrimidinyl, pyrrolyl, quinolinyl, tetrazolyl, thienyl, triazinyl, and triazolyl. A heteroaryl group may be unsubstituted or substituted, as described herein.

The term "halo" is defined as fluoro, bromo, chloro, or iodo.

The term "alkoxy" is defined as —OR, wherein R is an alkyl group.

The term "aryloxy" is defined as —OR, wherein R is an aryl group.

The term "alkylamino" is defined as —NHR, wherein R is an alkyl group.

The term "arylamino" is defined as —NHR, wherein R is an aryl group.

The term "alkylsufonyl" is defined as —SOR$_2$, wherein R is an alkyl group.

The term "arylsufonyl" is defined as —SOR$_2$, wherein R is an aryl group.

The term "alkylthio" is defined as —SR, wherein R is an alkyl group.

The term "arylamino" is defined as —NHR, wherein R is an aryl group.

The term "alkylthio" is defined as —SR, wherein R is an alkyl group.

The term "arylthio" is defined as —SR, wherein R is an aryl group.

The term "quaternary amino" is defined as —NRR'R''$^+$, wherein R, R', and R'' are independently alkyl, aryl, heteroaryl, and heterocyclyl.

The term "substituted" is defined as that one or more hydrogen atoms of a group or portion of a group are replaced by substituents, including, but not limited to, $C_{1-6}$ alkoxy, $C_{6-14}$ aryloxy, sulfhydryl (—SH), $C_{1-6}$ alkylthio, $C_{6-14}$ arylthio, amino (—NH$_2$), $C_{1-6}$ alkylamino, $C_{6-14}$arylamino, disubstituted amino, quaternary amino, hydroxyl (—OH), carboxyl (—COOR), halo, cyano (—CN), azido (—N$_3$), oxo, —C(O)—$C_{1-6}$ alkyl, —C(O)—$C_{3-8}$ cycloalkyl, —C(O)—$C_{6-14}$ aryl, —C(O)—$C_{1-10}$ heteroaryl, C(O)—$C_{2-8}$ heterocyclyl, $C_{1-6}$ alkylsulfonyl, (SO$_2$)O—$C_{1-6}$ alkyl, —(SO$_2$)O—$C_{3-8}$ cycloalkyl, —(SO$_2$)O—$C_{3-8}$ cycloalkyl, —(SO$_2$)—$C_{6-14}$aryl, —(SO$_2$)O—$C_{6-14}$aryl, —(SO$_2$)—$C_{1-10}$heteroaryl, —(SO$_2$)O—$C_{1-10}$heteroaryl, —(SO$_2$)—$C_{2-8}$ heterocyclyl, and —(SO$_2$)O—$C_{2-8}$ heterocyclyl.

In addition, alkyl, aryl, cycloalkyl, heteroaryl, and heterocyclyl groups may be substitute d with $C_{6-14}$ aryl, $C_{3-8}$ cycloalkyl, $C_{1-10}$ heteroaryl or $C_{2-8}$ heterocyclyl groups. Cycloalkyl, heteroaryl, and heterocyclyl groups may also be substituted with an alkyl group. Substituents can be substituted as described for the parent groups, e.g., with, halogen, trifluoromethyl, hydroxyl, or carboxyl.

The terms "administration" or "administering" as used herein mean a method of giving one or more unit doses of an antimicrobial pharmaceutical composition to an animal (e.g., topical, oral, intravenous, intraperitoneal, or intramuscular administration). The method of administration may vary depending on various factors, e.g., the components of the pharmaceutical composition, site of the potential or actual infection, microbe involved, and severity of the actual microbial infection.

By "animal" is meant any animal susceptible to a Gram-positive bacterial infection. Such as animal may include humans, dogs, cats, pigs, cows, horses, goats, chickens, turkeys, sheep, rats, mice, and rabbits, as well as other animals kept for commercial purposes or as pets. The term an "animal susceptible to a microbial infection" is defined as an animal that is at increased risk, relative to the general population, of contracting a microbial infection. Examples of such animals include those that have recently undergone a surgical procedure, or immunocompromised humans, e.g., those with AIDS (acquired immunodeficiency syndrome) or those having transplants for which immunosuppressive drugs are required. Such animals can be identified using methods known to one of ordinary skill in the art.

The term "coating agent" is defined as a biocompatible compound or mixture of compounds suitable for coating a surface. Suitable coating agents are known in the art. Exemplary coating agents include, but are not limited to, polymers, e.g., polyethylene glycol, hypromellose, hydroxypropyl cellulose, polytetrafluoroethylene, methylcellulose, polyvinyl alcohol or other polymers that are biocompatible.

The term an "effective amount" of a compound is defined as an amount which, when administered to a site of infection or potential infection, such as a medium such as a eukaryotic cell culture or a patient, will achieve a specified level of microbial inhibition or prevention of establishment of a microbial infection, respectively.

The term "inhibiting" is defined as reducing the cellular growth rate of the microbe by at least 80%. In certain embodiments, the growth can be inhibited by 90%, 95%, or even 99% or more. The degree of inhibition can be ascertained, for example, by an in vitro growth assay, e.g., by a standard liquid culture technique. Compounds showing inhibition of colony formation at minimal inhibitory concentrations (MICs) of <100 µg/ml, more preferably <10 µg/ml, are particularly useful.

The term "medium" is defined as any substance, liquid or solid, on which or in which a microbe may be present or in which prevention of the presence of a microbe is desired. Exemplary media include culture media (e.g., agar or broth), food, medical supplies (e.g., sterile fluids), medical devices (e.g., catheters), countertops, and other surfaces.

The term "microbial infection" is defined as the invasion of a host animal by pathogenic microbe. For example, the infection may include the excessive growth of a microbe that is normally present in or on the body of an animal or growth of a microbe that is not normally present in or on the animal. More generally, a microbial infection can be any situation in which the presence of a microbial population(s) is damaging to a host animal. Thus, an animal is "suffering" from a microbial infection when an excessive amount of a microbial population is present in or on the animal's body, or when the presence of a microbial population(s) is damaging the cells or other tissue of the animal. In one embodiment, the number of a particular genus or species of microbe is at least 2, 4, 6, or 8 times the number normally found in the animal.

Examples of microbes include, but are not limited to, Gram-positive or any other class of bacteria.

By "pharmaceutically acceptable salts" are meant those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal (e.g., sodium or potassium), alkaline earth metal (e.g. magnesium), ammonium and $NR_4+$ (where R is $C_{1-4}$alkyl) salts. Preferred salts include hydrochlorides, hydrobromides, sulfates, mesylates, maleates, tartrates, and fumarates. References hereinafter to a compound according to the invention include compounds of the general formulae shown, as well as their pharmaceutically acceptable salts.

By "prevention" of microbial growth or infection is defined as the application of a compound of the invention such that microbial growth or infection does not occur. The amount of a compound of the invention necessary for prevention of microbial growth can be ascertained, for example, by an in vitro growth assay, e.g., by a standard liquid culture technique. The amount of a compound of the invention necessary for the prevention of microbial infection may be ascertained, for example, by an in vivo assay, e.g., by determining the amount of compound that must be administered in order to prevent infection in a study animal, e.g., a guinea pig after inoculation with a microbe. In general, compounds showing prevention at suitable concentrations, e.g., <100 μg/ml, more preferably <10 μg/ml, are useful for further examination as therapeutic agents.

The term "treating" is defined as the medical management of a patient with the intent that a cure, amelioration, or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

The term "therapeutically effective amount" is defined as an amount which, when administered to an animal in need, will alleviate at least some of the symptoms of a bacterial infection.

In the context of prophylaxis, a "therapeutically effective amount" is an amount which, when administered to an animal susceptible to bacterial infection, will help inhibit or otherwise reduce the likelihood of such an infection.

The details of one or more embodiments of the invention are set forth in the accompanying description below. Other features, objects, and advantages of the invention will be apparent from the description and from the claims.

The present invention relates, in one embodiment, to compounds according to Formula I.

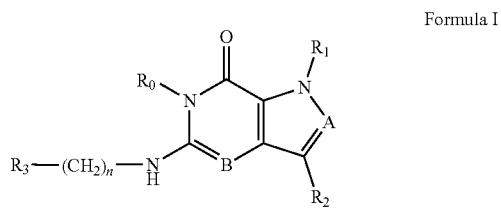

Formula I

In some embodiments, $R_1$ may be H, methyl, other substituted or unsubstituted alkyl, cyclic and heterocyclyl groups as illustrated below.

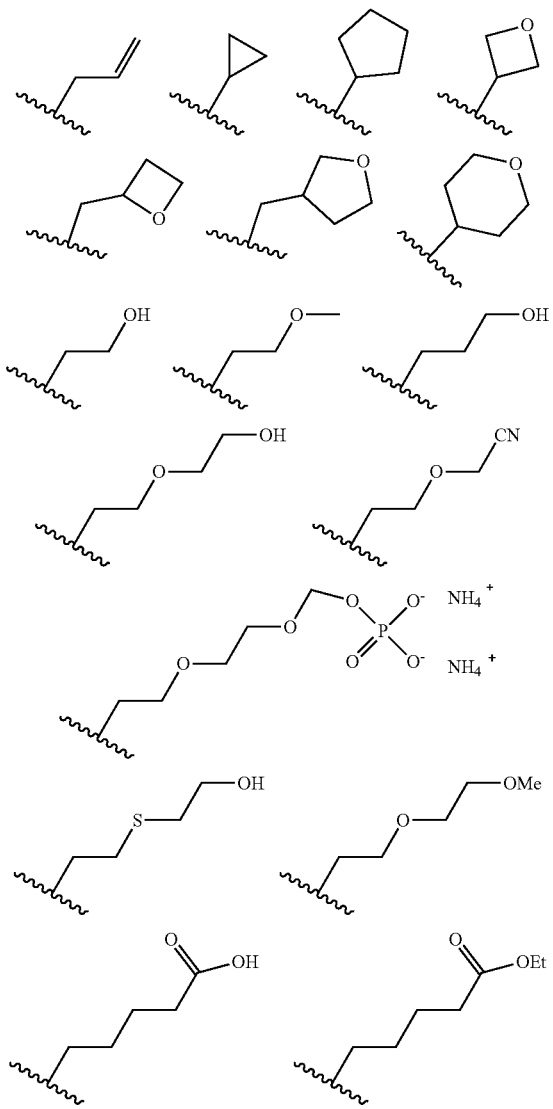

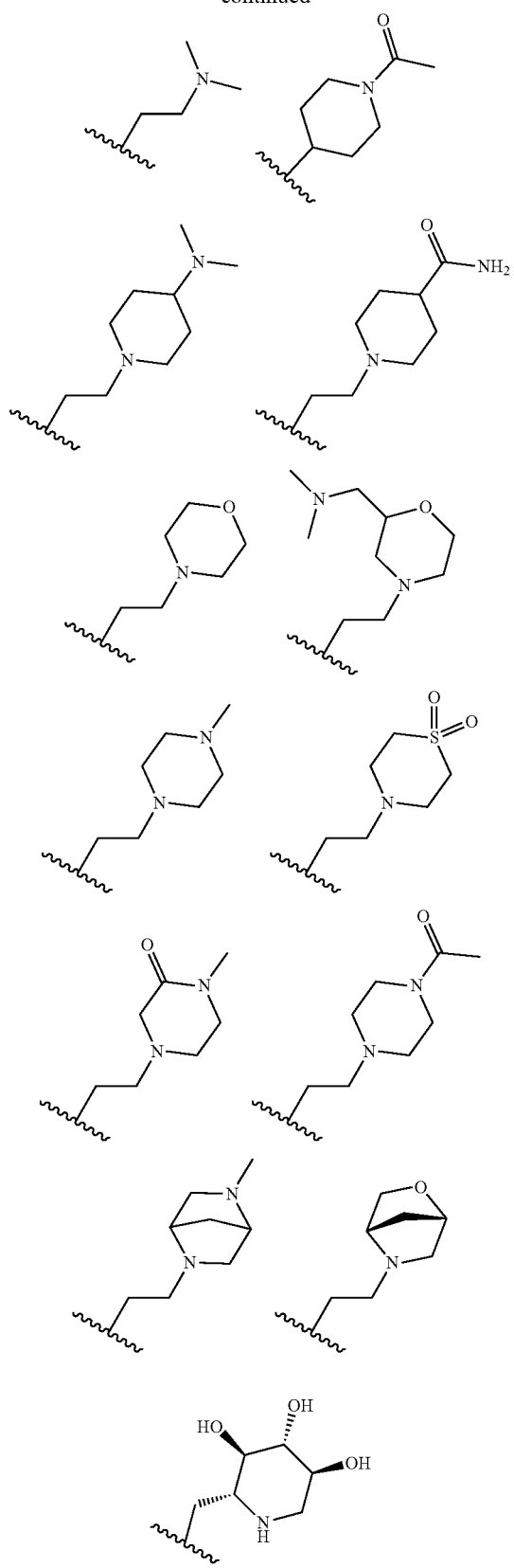
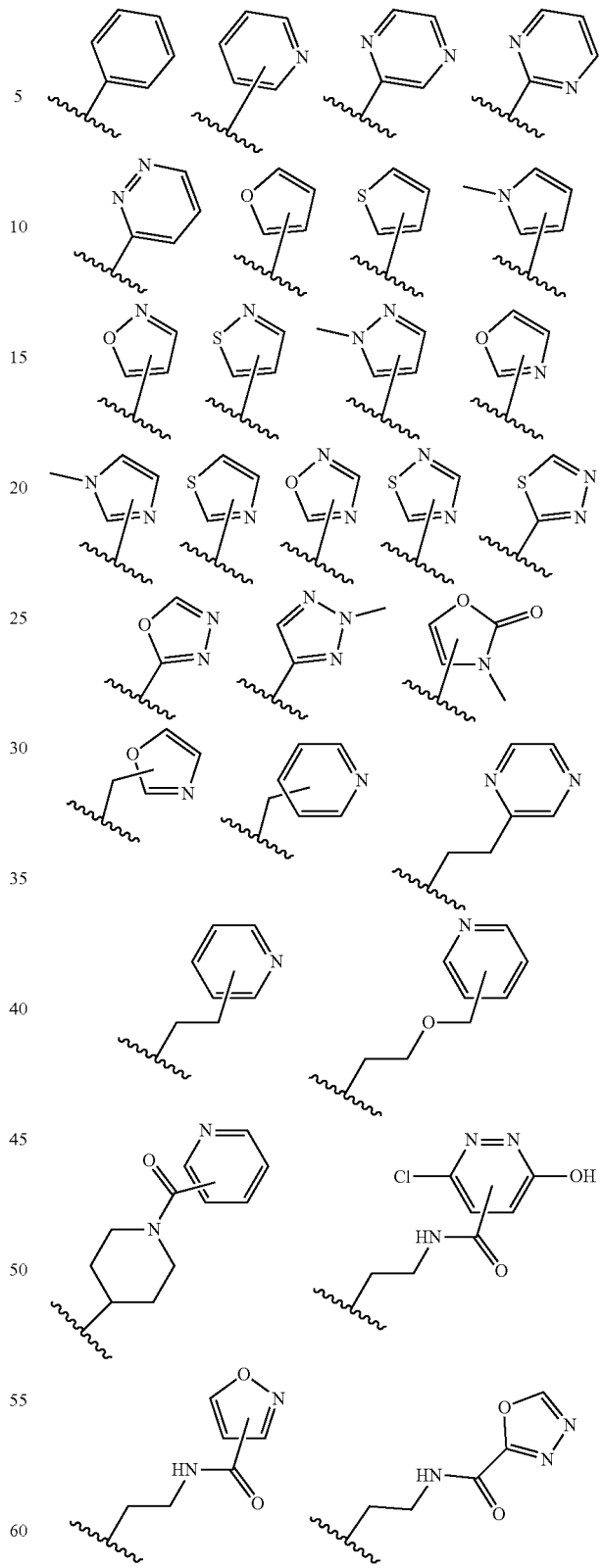
In some embodiments, $R_1$ may also be substituted or unsubstituted aryl and heteroaryl groups as illustrated below.
In some embodiments, $R_2$ is H, halo, CN, substituted or unsubstituted $C_{1-6}$ alkyl, $CO_2R_{21}$, $CONR_{23}R_{24}$, substituted or unsubstituted $C_{2-8}$ heterocyclyl or substituted or unsubstituted $C_{1-10}$ heteroaryl.

In some embodiments, R₃ may be substituted or unsubstituted aryl and heteroaryl groups as illustrated below.

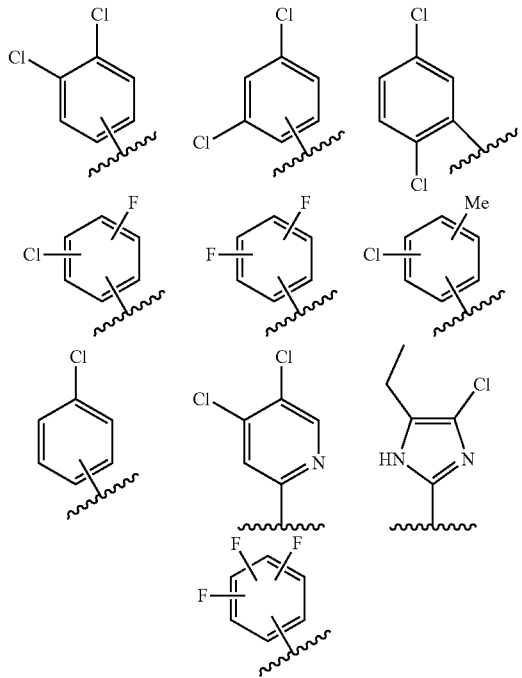

Antibacterial Compounds
Preferred compounds include:
5-((3,4-Dichlorobenzyl)amino)-1-methyl-1H-pyrazolo[4,3-d]pyrimidin-7(6H)-one,
5-((3,4-Dichlorobenzyl)amino)-3-fluoro-1-methyl-1H-pyrazolo[4,3-d]pyrimidin-7(6H)-one,
1-Allyl-5-((3,4-dichlorobenzyl)amino)-1H-pyrazolo[4,3-d]pyrimidin-7(6H)-one,
4-(5-((3,4-Dichlorobenzyl)amino)-7-oxo-6,7-dihydro-1H-pyrazolo[4,3-d]pyrimidin-1-yl)butyl acetate,
1-(Cyclobutylmethyl)-5-((3,4-dichlorobenzyl)amino)-1H-pyrazolo[4,3-d]pyrimidin-7(6H)-one,
5-[(3,4-Cichlorophenyl)methylamino]-1-phenyl-6H-pyrazolo[4,3-d]pyrimidin-7-one,
1-Cyclopropyl-5-((3,4-dichlorobenzyl)amino)-1H-pyrazolo[4,3-d]pyrimidin-7(6H)-one,
Cyclopentyl-5-((3,4-dichlorobenzyl)amino)-1H-pyrazolo[4,3-d]pyrimidin-7(6H)-one,
Cethyl 5-(5-chloro-7-methoxy-pyrazolo[4,3-d]pyrimidin-1-yl) pentanoate,
5-[(3,4-Cichlorophenyl)methylamino]-1-(4-pyridyl)-6H-pyrazolo[4,3-d]pyrimidin-7-one,
3-Chloro-5-((3,4-dichlorobenzyl)amino)-1-(2-methoxyethyl)-1H-pyrazolo[4,3-d]pyrimidin-7(6H)-one,
5-((3,4-Cichlorobenzyl)amino)-3-fluoro-1-(2-methoxyethyl)-1H-pyrazolo[4,3-d]pyrimidin-7(6H)-one,
3-Chloro-5-((3,4-dichlorobenzyl)amino)-1-(oxazol-4-ylmethyl)-1H-pyrazolo[4,3-d]pyrimidin-7(6H)-one,
1-(2-(4-Acetylpiperazin-1-yl)ethyl)-5-((3,4-dichlorobenzyl)amino)-1H-pyrazolo[4,3-d]pyrimidin-7(6H)-one hydrochloride,
5-((3,4-Dichlorobenzyl)amino)-1-(2-(2-hydroxyethoxy)ethyl)-1H-pyrazolo[4,3-d]pyrimidin-7(6H)-one,
5-((3,4-Dichlorobenzyl)amino)-1-(2-methoxyethyl)-1H-pyrazolo[4,3-d]pyrimidin-7(6H)-one,
5-((3,4-Dichlorobenzyl)amino)-1-((4-methylmorpholin-2-yl)methyl)-1H-pyrazolo[4,3-d]pyrimidin-7(6H)-one hydrochloride,
5-((3,4-Dichlorobenzyl)amino)-1-(1-(3-methylpicolinoyl)piperidin-4-yl)-1H-pyrazolo[4,3-d]pyrimidin-7(6H)-one hydrochloride,
5-((3,4-Difluorobenzyl)amino)-3-fluoro-1-(2-(2-hydroxyethoxy)ethyl)-1H-pyrazolo[4,3-d]pyrimidin-7(6H)-one,
5-((4-Chloro-3-methylbenzyl)amino)-1-methyl-1H-pyrazolo[4,3-d]pyrimidin-7(6H)-one,
5-((3,4-Dichlorobenzyl)amino)-1,3-dimethyl-1H-pyrazolo[4,3-d]pyrimidin-7(6H)-one,
5-((3,4-Dichlorobenzyl)amino)-1-(2-morpholinoethyl)-1H-pyrazolo[4,3-d]pyrimidin-7(6H)-one hydrochloride,
5-((3,4-Dichlorobenzyl)amino)-1-(4-hydroxybutyl)-1H-pyrazolo[4,3-d]pyrimidin-7(6H)-one),
5-((3,4-Dichlorobenzyl)amino)-1-(thiazol-2-ylmethyl)-1H-pyrazolo[4,3-d]pyrimidin-7(6H)-one,
5-((3,4-Dichlorobenzyl)amino)-1-(oxetan-3-ylmethyl)-1H-pyrazolo[4,3-d]pyrimidin-7(6H)-one,
5-((3,4-Dichlorobenzyl)amino)-1-((tetrahydrofuran-3-yl)methyl)-1H-pyrazolo[4,3-d]pyrimidin-7(6H)-one,
5-((3,4-Dichlorobenzyl)amino)-1-(tetrahydro-2H-pyran-4-yl)-1H-pyrazolo[4,3-d]pyrimidin-7(6H)-one,
5-((3,4-Dichlorobenzyl)amino)-1-(oxetan-2-ylmethyl)-1H-pyrazolo[4,3-d]pyrimidin-7(6H)-one,
5-((3,4-Dichlorobenzyl)amino)-1-(3-hydroxypropyl)-1H-pyrazolo[4,3-d]pyrimidin-7(6H)-one,
5-((3,4-Dichlorobenzyl)amino)-1-(2-(pyrazin-2-yl)ethyl)-1H-pyrazolo[4,3-d]pyrimidin-7(6H)-one hydrochloride,
5-((3,4-Dichlorobenzyl)amino)-1-isopropyl-1H-pyrazolo[4,3-d]pyrimidin-7(6H)-one,
5-((3,4-Dichlorobenzyl)amino)-1-(5-methoxypentyl)-1H-pyrazolo[4,3-d]pyrimidin-7(6H)-one,
5-((3,4-Dichlorobenzyl)amino)-1-((2-methoxyethoxy)methyl)-1H-pyrazolo[4,3-d]pyrimidin-7(6H)-one,
5-((3,4-Dichlorobenzyl)amino)-1-(oxetan-3-yl)-1H-pyrazolo[4,3-d]pyrimidin-7(6H)-one,
5-((3,4-Dichlorobenzyl)amino)-1-(1-(pyridin-3-ylsulfonyl)piperidin-4-yl)-1H-pyrazolo[4,3-d]pyrimidin-7(6H)-one hydrochloride,
(E)-5-((3,4-dichlorobenzyl)amino)-1-(4-methoxybut-2-en-1-yl)-1H-pyrazolo[4,3-d]pyrimidin-7(6H)-one,
Ethyl 5-(5-((3,4-dichlorobenzyl)amino)-7-oxo-6,7-dihydro-1H-pyrazolo[4,3-d]pyrimidin-1-yl)pentanoate,
Isopropyl 5-(5-((3,4-dichlorobenzyl)amino)-7-oxo-6,7-dihydro-1H-pyrazolo[4,3-d]pyrimidin-1-yl)pentanoate,
Ethyl 4-(5-((3,4-dichlorobenzyl)amino)-7-oxo-6,7-dihydro-1H-pyrazolo[4,3-d]pyrimidin-1-yl)butanoate,
Methyl 3-(5-((3,4-dichlorobenzyl)amino)-7-oxo-6,7-dihydro-1H-pyrazolo[4,3-d]pyrimidin-1-yl)propanoate,
5-((3,4-Dichlorobenzyl)amino)-1-(1-(pyridin-2-ylmethyl)piperidin-4-yl)-1H-pyrazolo[4,3-d]pyrimidin-7(6H)-one dihydrochloride,
5-((3,4-Dichlorobenzyl)amino)-1-(1-(pyridin-3-ylmethyl)piperidin-4-yl)-1H-pyrazolo[4,3-d]pyrimidin-7(6H)-one dihydrochloride,
5-((3,4-Dichlorobenzyl)amino)-1-(1-(pyridin-4-ylmethyl)piperidin-4-yl)-1H-pyrazolo[4,3-d]pyrimidin-7(6H)-one dihydrochloride,
5-[(3,4-Dichlorophenyl)methylamino]-1-[1-(oxazole-4-carbonyl)-4-piperidyl]-6H-pyrazolo[4,3-d]pyrimidin-7-one,
5-[(3,4-Dichlorophenyl)methylamino]-1-[1-(thiazole-2-carbonyl)-4-piperidyl]-6H-pyrazolo[4,3-d]pyrimidin-7-one,
5-((3,4-Dichlorobenzyl)amino)-1-(1-(4-methoxypicolinoyl)piperidin-4-yl)-1H-pyrazolo[4,3-d]pyrimidin-7(6H)-one hydrochloride, 5-((3,4-Dichlorobenzyl)amino)-1-(1-(4-methylpicolinoyl)piperidin-4-yl)-1H-pyrazolo[4,3-d]pyrimidin-7(6H)-one hydrochloride, 5-[(3,4-Dichlorophenyl)methylamino]-3-fluoro-1-[2-(2-hydroxyethoxy)ethyl]-6H-pyrazolo[4,3-d]pyrimidin-7-one, 3-Chloro-5-[(3,4-dichlorophenyl)methylamino]-1-[2-(2-hydroxyethoxy)ethyl]-6H-pyrazolo[4,3-d]pyrimidin-7-one, 5-((3,4-Difluorobenzyl)amino)-3-fluoro-1-(oxazol-4-ylmethyl)-1H-pyrazolo[4,3-d]pyrimidin-7(6H)-one, 3-Chloro-5-((3,4-dichlorobenzyl)amino)-1-(1-nicotinoylpiperidin-4-yl)-1H-pyrazolo[4,3-d]pyrimidin-7(6H)-one hydrochloride, Ammonium (2-(2-(5-((3,4-dichlorobenzyl)amino)-7-oxo-6,7-dihydro-1H-pyrazolo[4,3-d]pyrimidin-1-yl)ethoxy)ethoxy)methyl phosphate, (5-((3,4-Dichlorobenzyl)amino)-1-(2-(2-hydroxyethoxy)ethyl)-7-oxo-1H-pyrazolo[4,3-d]pyrimidin-6(7H)-yl)methyl dihydrogen phosphate, or an optical isomer thereof an isotopic isomer thereof a prodrug or a pharmaceutically acceptable salt thereof Methods of Synthesis The following examples are given for the purpose of illustrating the invention, but not for limiting the scope or spirit of the invention.

Compounds of the invention, including those specifically disclosed herein above and herein below, may be prepared as described in the following schemes. For example, the compounds of Formula I may be prepared as described in Schemes below, which are known to those of skill in the art for making fragments and combinations thereof.

In some of the schemes provided herein, a compound may be shown in parentheses. A person of skill in the relevant art will recognize that a compound shown in parentheses indicates a mixture of isomers that is used or produced in a reaction.

Methods of Synthesis

Scheme A

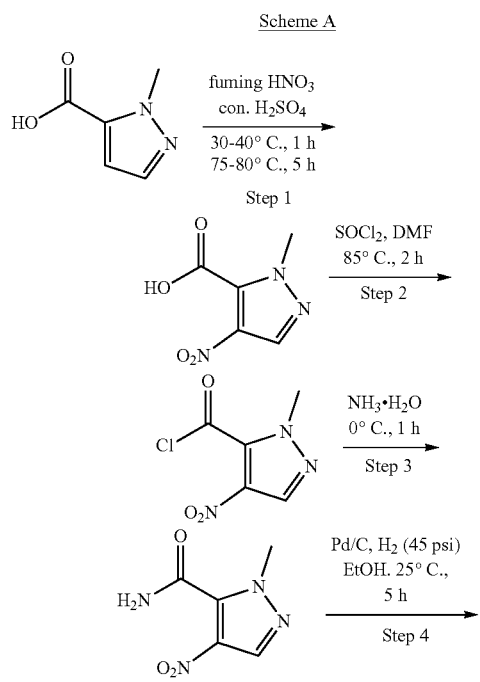

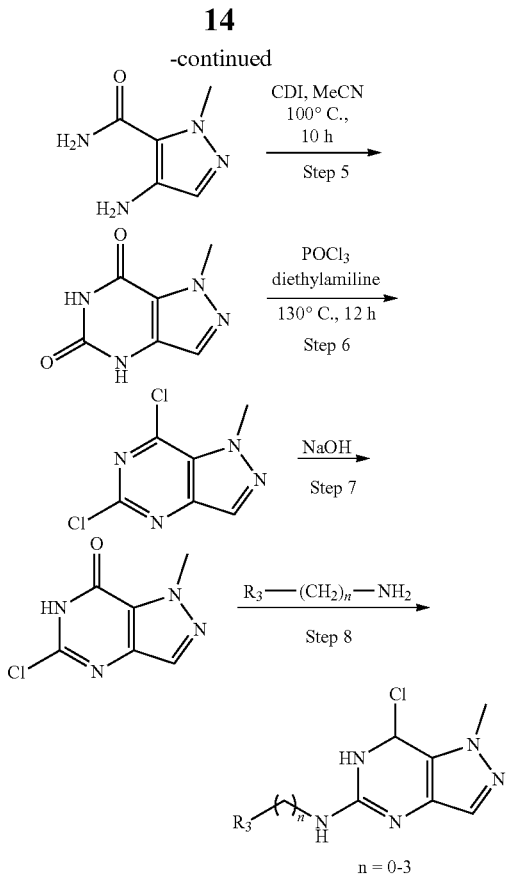

General Procedures for Preparing Compounds in Scheme A

Preparation of 1-methyl-4-nitro-1H-pyrazole-5-carboxylic Acid (Step 1 in Scheme A)

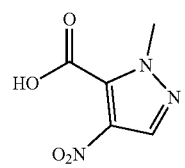

To a solution of fuming $HNO_3$ (24.73 g 392.50 mmol, 16.38 mL, 1.5 eq) in $H_2SO_4$ (119.84 g, 1.22 mol, 65.13 mL, 4.67 eq) was added 2-methylpyrazole-3-carboxylic acid (33 g, 261.67 mmol, 1 eq) in portions at 20° C.–25° C. The mixture was stirred at 30° C.–40° C. for an hour and then at 75° C.–80° C. for 5 hours. TLC indicated the starting material was consumed and one major new spot with larger polarity was detected. The reaction mixture was poured into ice-water (150 mL) slowly. There was some solid precipitated. The solid was collected after filtered and the solid was washed with water (50 mL) and petroleum ether (50 mL). The solid was concentrated under reduced pressure and then used in the next step without further purification. 2-Methyl-4-nitro-pyrazole-3-carboxylic acid (37 g, 216.23 mmol, 82.64% yield) was obtained as white solid. $^1$H NMR (DMSO-$d_6$, 400 MHz) δ 8.30 (s, 1H), 3.96 (s, 3H).

Preparation of 1-methyl-4-nitro-1H-pyrazole-5-carbonyl Chloride (Step 2 in Scheme A)

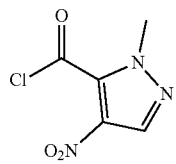

A solution of 2-methyl-4-nitro-pyrazole-3-carboxylic acid (35 g, 204.55 mmol, 1 eq) and DMF (149.51 mg, 2.05 mmol, 157.38 μL, 0.01 eq) in SOCl$_2$ (150 mL) was stirred at 85° C. for an hour. TLC showed the reaction was complete. The reaction mixture was cooled and the solvent was removed under reduced pressure. The crude was used to the next step without further purification. 2-Methyl-4-nitro-pyrazole-3-carbonyl chloride (38 g 200.47 mmol, 98.01% yield) was obtained as colorless oil.

Preparation of 1-methyl-4-nitro-1H-pyrazole-5-carboxamide (Step 3 in Scheme A)

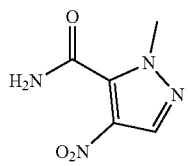

To NH$_3$—H$_2$O (150 mL) was added 2-methyl-4-nitro-pyrazole-3-carbonyl chloride (38 g 200.47 mmol, 1 eq) dropwise at 0° C. The mixture was stirred at 25° C. for an hour. TLC and LC-MS showed the reaction was complete. There was some solid formed. After filtered, the solid was collected. The aqueous was extracted with EtOAc (80 μA×5). The combined organic layer was washed with brine (50 mL×1), dried over Na$_2$SO$_4$, filtered and concentrated under reduced pressure. The combined crude was used to the next step without further purification. 2-Methyl-4-nitro-pyrazole-3-carboxamide (32 g, 188.10 mmol, 93.83% yield) was obtained as pale yellow solid. $^1$H NMR (DMSO-d$_6$, 400 MHz) δ 8.48 (s, 1H), 8.32 (s, 1H), 8.27 (s, 1H), 3.86 (s, 3H).

Preparation of 4-amino-1-methyl-1H-pyrazole-5-carboxamide (Step 4 in Scheme A)

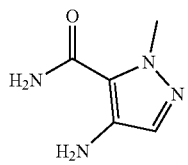

A mixture of 2-methyl-4-nitro-pyrazole-3-carboxamide (32 g, 188.10 mmol, 1 eq) and 10% Pd/C (3 g) in EtOH (600 mL) was stirred at 25° C. for 5 hours under H$_2$ (45 psi.). TLC indicated no starting material remained and one major new spot with larger polarity was detected. After filtered, the filtrate was concentrated under reduced pressure. The crude was used to the next step without further purification. 4-Amino-2-methyl-pyrazole-3-carboxamide (23 g, 164.12 mmol, 87.25% yield) was obtained as purple solid. $^1$H NMR (DMSO-d$_6$, 400 MHz) δ 7.37 (s, 2H), 7.01 (s, 1H), 4.39 (s, 2H), 3.89 (s, 3H).

Preparation of 1-methyl-1H-pyrazolo[4,3-d]pyrimidine-5,7(4H,6H)-dione (Step 5 in Scheme A)

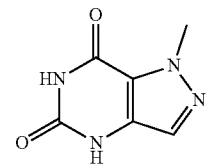

To a mixture of 4-amino-2-methyl-pyrazole-3-carboxamide (23 g, 164.12 mmol, 1 eq) in CH$_3$CN (500 mL) was added CDI (34.60 g 213.35 mmol, 1.3 eq) in portions over an hour at 100° C. Then the mixture was heated at 100° C. for 12 hours under N$_2$. There was grey solid formed. LC-MS showed no starting material remained. Several new peaks were shown on LC-MS and ~80% of the desired compound was detected. After filtered at 90° C., the solid was collected. The crude was used to the next step without further purification. 1-Methyl-4H-pyrazolo[4,3-d]pyrimidine-5,7-dione (25 g, 150.48 mmol, 91.69% yield) was obtained as grey solid. $^1$H NMR (DMSO-d$_6$, 400 MHz) δ 11.10 (s, 1H), 10.95 (s, 1H), 7.35 (s, 1H), 4.05 (s, 3H).

Preparation of 5,7-dichloro-1-methyl-$^1$H-pyrazolo[4,3-d]pyrimidine (Step 6 in Scheme A)

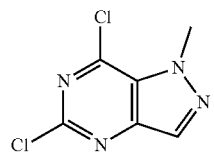

To a solution of 1-methyl-4H-pyrazolo[4,3-d]pyrimidine-5,7-dione (26 g, 156.50 mmol, 1 eq) in POCl$_3$ (239.96 g, 1.56 mol, 145.43 mL, 10 eq) was added DBU (142.95 g, 938.98 mmol, 141.53 mL, 6 eq) dropwise at 50° C. under N$_2$. The mixture was stirred at 85° C. for 12 hours. LC-MS showed no starting material remained. The mixture was poured into ice water (1 L) and then extracted with EtOAc (200 mL×6). The combined organic layer was washed with sat. NaHCO$_3$ to pH=7 and brine (100 mL×1), dried over Na$_2$SO$_4$, filtered and concentrated under reduced pressure. The residue was purified by flash silica gel chromatography (Biotage®; 80 g SepaFlash® Silica Flash Column, Eluent of 020% Ethyl acetate/Petroleum ether gradient at 150 mL/min). The eluent was removed under reduced pressure to give 5,7-dichloro-1-methyl-pyrazolo[4,3-d]pyrimidine (14 g, 68.96 mmol, 44.06% yield) as pale yellow oil. $^1$H NMR (CDC$_3$, 400 MHz) δ 8.17 (s, 1H), 4.40 (s, 3H).

Preparation of 5-chloro-1-methyl-1H-pyrazolo[4,3-d]pyrimidin-7(6H)-one (Step 7 in Scheme A)

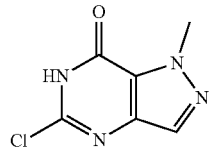

To a solution of 5,7-dichloro-1-methyl-pyrazolo[4,3-d]pyrimidine (14 g, 68.96 mmol, 1 eq) in dioxane (140 mL) and H$_2$O (100 mL) was added a solution of NaOH (2.76 g, 68.96 mmol, 1 eq) in H$_2$O (20 mL) dropwise at 0° C. Then the mixture was stirred at 100° C. for 6 hours. TLC and LC-MS showed that ~10% of 5,7-dichloro-1-methyl-pyrazolo[4,3-d]pyrimidine was remained. The organic solvent was removed under reduced pressure. The aqueous was extracted with MTBE (120 mL×2) to recover the starting material. Then the aqueous was made pH=5 with 2N HC. There was white solid formed. The solid was collected after filtered and concentrated under reduced pressure. The residue was used to the next step without further purification. 5-Chloro-1-methyl-6H-pyrazolo[4,3-d]pyrimidin-7-one (12.7 g, 68.80 mmol, 99.78% yield) was obtained as white solid. H NMR (CDCl$_3$, 400 MHz) δ 7.85 (s, 1H), 4.30 (s, 3H).

Preparation of Compounds in Scheme A (Step 8 in Scheme A)

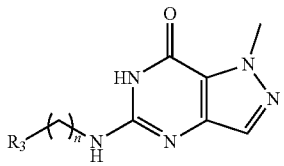

A solution of 5-chloro-1-methyl-6H-pyrazolo[4,3-d]pyrimidin-7-one (541.76 μmol, 1 eq), R$_3$(CH$_2$)NH$_2$ (1.63 mmol, 3 eq) and base (no base or TEA or DIEA) or TFA in solvent (t-BuOH or i-PrOH or NMP) (6 mL/mmol) was heated at (100° C. 160° C.) for a period of time (4 hours 20 hours). LC-MS and HPLC showed the reaction was complete. The reaction mixture was quenched with H$_2$O and extracted with EtOAc. The combined organic layers were washed with brine, dried over Na$_2$SO$_4$, filtered and concentrated under reduced pressure. The residue was purified by prep-HPLC. Columns: a) Luna C18 100 mm×30 mm 5 μm; b) Phenomenex Luna C18 150 mm×30 mm 5 μm; c) Waters Xbridge 150 mm×25 mm 5 μm; d) Nano-micro Kromasil C18 100 mm×30 mm 5 μm; e) Boston Prime C18 150 mm×30 mm 5 μm; f) Phenomenex Luna C18 150 mm×30 mm 5 μm; g) Waters Xbridge 150 mm×25 mm 5 μm; h) Xtimate C18 150 mm×25 mm 5 μm; i) Xbridge 150 mm×30 mm 10 μm. Mobile phase: a) [water (0.1% TFA)-MeCN], B %: 1%-55%, 10 mins; b) [water (0.05% HCl)-MeCN], B %: 5%-35%, 8 mins c) [water (10 mM NH$_4$HCO$_3$)-MeCN], B %: 5%-50%, 20 mins); d) [water (0.04% NH$_3$—H$_2$O+10 mM NH$_4$HCO$_3$)-MeCN], B %: 15%-60%, 10.5 mins; e) [water (10 mM NH$_4$HCO$_3$)-MeCN]; B %: 1%-25%, 10 mins. The aqueous solution was lyophilized to give desired product.

Compound 1

Preparation of 5-((4-chloro-3-fluorobenzyl)amino)-1-methyl-1H-pyrazolo[4,3-d]pyrimidin-7(6H)-one (Step 8 in Scheme A)

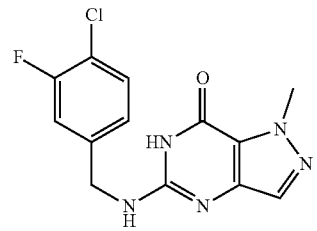

A solution of 5-chloro-1-methyl-6H-pyrazolo[4,3-d]pyrimidin-7-one (0.1 g, 541.76 μmol, 1 eq) and (4-chloro-3-fluoro-phenyl)methanamine (259.38 mg, 1.63 mmol, 198.39 μL, 3 eq) in t-BuOH (3 mL) was heated at 100° C. for 16 hours. LC-MS and HPLC showed 5-chloro-1-methyl-6H-pyrazolo[4,3-d]pyrimidin-7-one was consumed completely and one main peak with desired mass was detected. The reaction mixture was quenched with H$_2$O (5 mL) at 25° C. and then extracted with EtOAc (10 mL×3). The combined organic layers were washed with brine (10 mL), dried over Na$_2$SO$_4$, filtered and concentrated under reduced pressure. The residue was purified by prep-HPLC (column: Waters Xbridge 150 mm×25 mm 5 μm; mobile phase: [water (10 mM NH$_4$HCO$_3$)-MeCN]; B %: 25%-45%, 20 mins). The aqueous solution was lyophilized to give 5-[(4-chloro-3-fluoro-phenyl)methylamino]-1-methyl-6H-pyrazolo[4,3-d]pyrimidin-7-one (71.8 mg, 233.34 μmol, 43.07% yield) as pale yellow solid. $^1$H NMR (DMSO-d$_6$, 400 MHz) δ 7.60~7.50 (m, 2H), 7.38 (d, J=10.4 Hz, 1H), 7.21 (d, J=8.0 Hz, 1H), 4.53 (d, J=4.4 Hz, 2H), 4.07 (s, 3H). HPLC: 99.03% (220 nm), 99.12% (215 nm), 96.82% (254 nm). MS (ESI): mass calcd. For C$_{13}$H$_{11}$ClFN$_5$O 307.06, m/z found 308.0 [M+H]$^+$.

Compound 2

5-((3,4-Dichlorobenzyl)amino)-1-methyl-1H-pyrazolo[4,3-d]pyrimidin-7(6H)-one) was prepared according to the procedure described herein for step 8 in Scheme A.

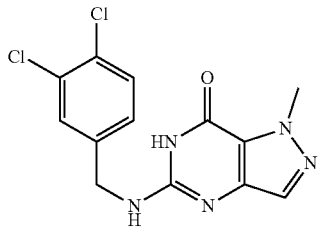 [SMILES: Cn1ncc2nc(NCc3ccc(Cl)c(Cl)c3)[nH]c(=O)c21]

The procedure yielded the desired compound (0.8 g, 2.45 mmol, 64.54% yield) as an off white solid. $^1$H NMR (DMSO-d$_6$, 400 MHz) δ 11.09 (s, 1H), 7.57~7.55 (m, 2H), 7.50 (s, 1H), 7.31 (t, J=2.0 Hz, 1H), 6.67 (s, 1H), 4.44 (d, J=6.0 Hz, 2H), 4.04 (s, 3H). HPLC: 99.17% (220 nm), 98.91% (215 nm), 100.00% (254 nm). MS (ESI): mass calcd. For C$_{13}$H$_{11}$C$_{12}$N$_5$O 323.03, m/z found 324.0 [M+H]$^+$.

Compound 3

5-(Benzylamino)-1-methyl-1H-pyrazolo[4,3-d]pyrimidin-7(6H)-one) was prepared according to the procedure described herein for step 8 in Scheme A.

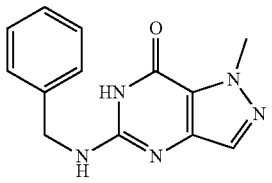 [SMILES: Cn1ncc2nc(NCc3ccccc3)[nH]c(=O)c21]

The procedure yielded the desired compound (70.8 mg, 271.41 μmol, 41.75% yield) as an off white solid. $^1$H NMR (DMSO-d$_6$, 400 MHz) δ 7.57 (s, 1H), 7.35~7.25 (m, 5H), 6.93 (s, 1H), 4.50 (d, J=5.2 Hz, 2H), 4.07 (s, 3H). HPLC: 100.00% (220 nm), 100.00% (215 nm), 100.00% (254 nm). MS (ESI): mass calcd. For C$_{13}$H$_{13}$N$_5$O 255.11, m/z found 256.1 [M+H]$^+$.

Compound 4

1-Methyl-5-((pyridin-2-ylmethyl)amino)-1H-pyrazolo[4,3-d]pyrimidin-7(6H)-one) was prepared according to the procedure described herein for Step 8 in Scheme A

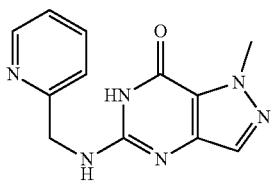 [SMILES: Cn1ncc2nc(NCc3ccccn3)[nH]c(=O)c21]

The procedure yielded the desired compound (90.4 mg, 352.76 μmol, 54.26%) as a yellow solid. $^1$H NMR (DMSO-d$_6$, 400 MHz) δ 8.67 (d, J=5.2 Hz, 1H), 8.12 (t, J=7.6 Hz, 1H), 7.66 (d, J=8.0 Hz, 1H), 7.58 (t, J=6.4 Hz, 1H), 7.52 (s, 1H), 7.07 (s, 1H), 4.71 (d, J=3.6 Hz, 2H), 4.07 (s, 3H). HPLC: 100.00% (220 nm), 100.00% (215 nm), 100.00% (254 nm). MS (ESI): mass calcd. For C$_{12}$H$_{12}$N$_6$O 256.11, m/z found 257.2 [M+H]$^+$.

Compound 5

1-Methyl-5-(3-pyridylmethylamino)-6H-pyrazolo[4,3-d]pyrimidin-7-one) was prepared according to the procedure described herein for step 8 in Scheme A.

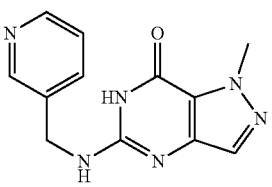 [SMILES: Cn1ncc2nc(NCc3cccnc3)[nH]c(=O)c21]

The procedure yielded the desired compound (149.1 mg, 581.82 μmol, 89.50% yield) as a yellow solid. $^1$H NMR (DMSO-d$_6$, 400 MHz) δ 8.81 (s, 1H), 8.72 (d, J=4.4 Hz, 1H), 8.34 (d, J=8.0 Hz, 1H), 7.87 (dd, J=7.6 Hz, 5.2 Hz, 1H), 7.52 (s, 1H), 6.98~6.97 (m, 1H), 4.63 (d, J=5.6 Hz, 2H), 4.06 (s, 3H). HPLC: 97.28% (220 nm), 96.72% (215 nm), 100.00% (254 nm). MS(ESI): mass calcd. For C$_{12}$H$_{12}$N$_6$O 256.11, m/z found 257.1 [M+H]$^+$.

Compound 6

1-Methyl-5-((pyridin-4-ylmethyl)amino)-1H-pyrazolo[4,3-d]pyrimidin-7(6H)-one) was prepared according to the procedure described herein for step 8 in Scheme A.

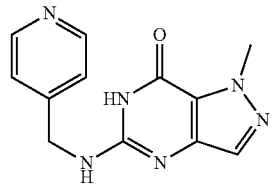 [SMILES: Cn1ncc2nc(NCc3ccncc3)[nH]c(=O)c21]

The procedure yielded the desired compound (89.9 mg, 350.81 μmol, 53.96%) as a yellow solid. $^1$H NMR (DMSO-d$_6$, 400 MHz) δ 8.80 (d, J=4.8 Hz, 2H), 7.91 (d, J=5.6 Hz, 2H), 7.46 (s, 1H), 7.11 (s, 1H), 4.75 (d, J=3.6 Hz, 2H), 4.06 (s, 3H). HPLC: 96.79% (220 nm), 96.31% (215 nm), 98.37% (254 nm). MS (ESI): mass calcd. For C$_{12}$H$_{12}$N$_6$O 256.11, m/z found 257.1 [M+H]$^+$.

Compound 7

5-((3,4-Difluorobenzyl)amino)-1-methyl-1H-pyrazolo[4,3-d]pyrimidin-7(6H)-one) was prepared according to the procedure described herein for step 8 in Scheme A.

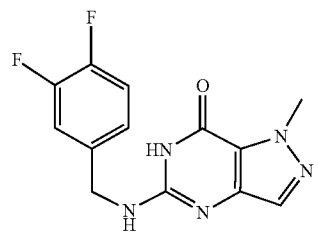 [SMILES: Cn1ncc2nc(NCc3ccc(F)c(F)c3)[nH]c(=O)c21]

The procedure yielded the desired compound (0.1288 g 442.22 μmol, 81.63%) as a pale yellow solid. $^1$H NMR (DMSO-d$_6$, 400 MHz) δ 7.54 (s, 1H), 7.42~7.35 (m, 2H), 7.18 (d, J=3.6 Hz, 1H), 6.67 (s, 1H), 4.60 (d, J=5.6 Hz, 2H), 4.06 (s, 3H). HPLC: 100.00% (220 nm), 100.00% (215 nm), 100.00% (254 nm). MS (ESI): mass calcd. For C$_{13}$H$_{11}$F$_2$N$_5$O 291.09, m/z found 292.1 [M+H]$^+$.

Compound 8

5-((3,4-Dichlorophenethyl)amino)-1-methyl-$^1$H-pyrazolo[4,3-d]pyrimidin-7(6H)-one) was prepared according to the procedure described herein for step 8 in Scheme A.

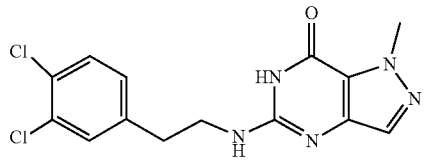 [SMILES: Cn1ncc2nc(NCCc3ccc(Cl)c(Cl)c3)[nH]c(=O)c21]

The procedure yielded the desired compound (0.119 g, 351.87 μmol, 98.20%) as a yellow solid. $^1$H NMR (DMSO-d$_6$, 400 MHz) δ 7.58~7.53 (m, 3H), 7.26 (dd, J=8.4 Hz, 2.0 Hz, 1H), 6.40 (s, 1H), 4.06 (s, 3H), 3.50 (s, 2H), 2.85 (t, J=6.8 Hz, 2H). HPLC: 98.20% (220 nm), 97.79% (215 nm), 98.10% (254 nm). MS (ESI): mass calcd. For C$_{14}$H$_{13}$C$_2$N$_5$O 337.05, m/z found 338.1 [M+H]$^+$.

Compound 9

5-((3,4-Dichlorophenyl)amino)-1-methyl-1H-pyrazolo[4,3-d]pyrimidin-7(6H)-one) was prepared according to the procedure described herein for step 8 in Scheme A.

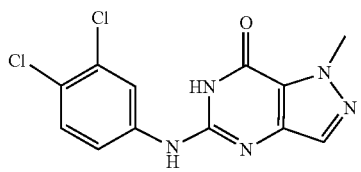 [SMILES: Cn1ncc2nc(Nc3ccc(Cl)c(Cl)c3)[nH]c(=O)c21]

The procedure yielded the desired compound (46.3 mg, 149.29 μmol, 27.56% yield) as a pale yellow solid. H NMR (DMSO-$d_6$, 400 MHz) δ 11.06 (s, 1H), 8.86 (s, 1H), 8.10 (d, J=2.4 Hz, 1H), 7.76 (s, 1H), 7.58~7.53 (m, 1H), 7.51~7.47 (m, 1H), 4.12 (s, 3H). HPLC: 100.00% (220 nm), 100.00% (215 nm), 100.00% (254 nm). MS (ESI): mass calcd. For $C_{12}H_9Cl_2N_5O$ 309.02, m/z found 310.0 [M+H]$^+$.

Compound 10

1-Methyl-5-(phenylamino)-1H-pyrazolo[4,3-d]pyrimidin-7(6H)-one was prepared according to the procedure described herein for step 8 in Scheme A.

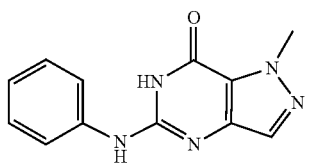 [SMILES: Cn1ncc2nc(Nc3ccccc3)[nH]c(=O)c21]

The procedure yielded the desired compound (100 mg, 391.73 μmol, 60.26% yield) as a pale yellow solid. $^1$H NMR (DMSO-$d_6$, 400 MHz) δ 8.52 (s, 1H), 7.70 (s, 1H), 7.62 (d, J=7.6 Hz, 2H), 7.33 (t, J=8.0 Hz, 2H), 7.01 (t, J=7.6 Hz, 1H), 4.11 (s, 3H). HPLC: 100.00% (220 nm), 100.00% (215 nm), 99.20% (254 nm). MS (ESI): mass calcd. For $C_{12}H_{11}N_5O$ 241.10, m/z found 242.1 [M+H]$^+$.

Compound 11

1-Methyl-5-((pyrimidin-2-ylmethyl)amino)-1H-pyrazolo[4,3-d]pyrimidin-7(6H)-one was prepared according to the procedure described herein for step 8 in Scheme A.

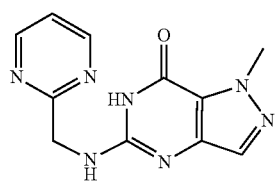 [SMILES: Cn1ncc2nc(NCc3ncccn3)[nH]c(=O)c21]

The procedure yielded the desired compound (31 mg, 120.50 μmol, 22.24% yield) as a light brown solid. $^1$H NMR (DMSO-$d_6$, 400 MHz) δ 8.81 (d, J=4.8 Hz, 2H), 7.55 (s, 1H), 7.43 (t, J=4.8 Hz, 1H), 6.88 (s, 1H), 4.69 (d, J=4.4 Hz, 2H), 4.07 (s, 3H). HPLC: 100.00% (220 nm), 100.00% (215 nm), 100.00% (254 nm). MS (ESI): mass calcd. For $C_{11}H_{11}N_7O$ 257.10, m/z found 258.1 [M+H]$^+$.

Compound 12

1-Methyl-5-((pyrazin-2-ylmethyl)amino)-1H-pyrazolo[4,3-d]pyrimidin-7(6H)-one was prepared according to the procedure described herein for step 8 in Scheme A.

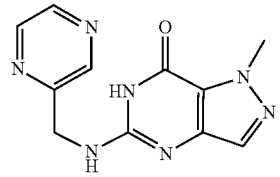 [SMILES: Cn1ncc2nc(NCc3cnccn3)[nH]c(=O)c21]

The procedure yielded the desired compound (30.6 mg, 118.95 μmol, 21.96% yield) as a white solid. $^1$H NMR (DMSO-$d_6$, 400 MHz) δ 8.66 (s, 1H), 8.60~8.59 (m, 1H), 8.53 (s, 1H), 7.52 (d, J=1.2 Hz, 1H), 6.81 (t, J=5.2 Hz, 1H), 4.64 (d, J=5.2 Hz, 2H), 4.06 (s, 3H). HPLC: 100.00% (220 nm), 100.00% (215 nm), 100.00% (254 nm). MS (ESI): mass calcd. For $C_{11}H_{11}N_7O$ 257.10, m/z found 258.1 [M+H]$^+$.

Compound 13

5-(((1H-indazol-5-yl)methyl)amino)-1-methyl-1H-pyrazolo[4,3-d]pyrimidin-7(6H)-one was prepared according to the procedure described herein for step 8 in Scheme A.

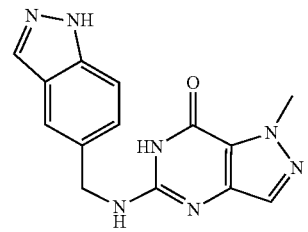 [SMILES: Cn1ncc2nc(NCc3ccc4[nH]ncc4c3)[nH]c(=O)c21]

The procedure yielded the desired compound (56.6 mg, 191.13 μmol, 35.28% yield) as a white solid. $^1$H NMR (DMSO-$d_6$, 400 MHz) δ 13.01 (s, 1H), 10.78 (s, 1H), 8.03 (s, 1H), 7.69 (s, 1H), 7.55 (s, 1H), 7.50 (d, J 8.4 Hz, 1H), 7.35 (dd, J=1.2 Hz, 8.4 Hz, 1H), 6.42 (s, 1H), 4.55 (d, J=5.2 Hz, 2H), 4.07 (s, 3H). HPLC: 99.72% (220 nm), 99.71% (215 nm), 100.00% (254 nm). MS (ESI): mass calcd. For $C_{14}H_{13}N_7O$ 295.12, m/z found 296.1 [M+H]$^+$.

Compound 14

5-(((1H-indol-5-yl)methyl)amino)-1-methyl-1H-pyrazolo[4,3-d]pyrimidin-7(6H)-one was prepared according to the procedure described herein for step 8 in Scheme A.

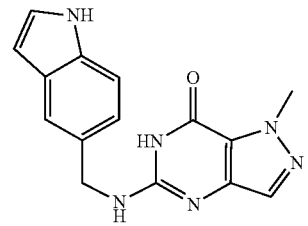 [SMILES: Cn1ncc2nc(NCc3ccc4[nH]ccc4c3)[nH]c(=O)c21]

The procedure yielded the desired compound (38.4 mg, 130.47 μmol, 24.08% yield) as an orange solid. $^1$H NMR (DMSO-$d_6$, 400 MHz) δ 11.08 (s, 1H) 7.61 (s, 1H), 7.52 (s, 1H), 7.37 (d, J=8.4 Hz, 1H), 7.33 (t, J=2.8 Hz, 1H), 7.09 (dd, J=1.6 Hz, 8.4 Hz, 1H), 7.04~6.81 (m, 1H), 6.40 (d, J=2.0 Hz, 1H), 4.54 (d, J=4.8 Hz, 2H), 4.08 (s, 3H). HPLC: 96.92% (220 nm), 96.82% (215 nm), 99.08% (254 nm). MS (ESI): mass calcd. For C$_{15}$H$_{14}$N$_6$O 294.12, m/z found 295.1 [M+H]$^+$.

Compound 15

1-Methyl-5-((thiazol-4-ylmethyl)amino)-1H-pyrazolo[4,3-d]pyrimidin-7(6H)-one was prepared according to the procedure described herein for step 8 in Scheme A.

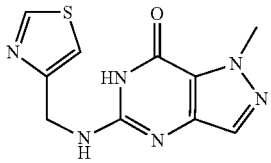 [SMILES: Cn1ncc2nc(NCc3cscn3)[nH]c(=O)c21]

The procedure yielded the desired compound (66.9 mg, 255.06 μmol, 58.85% yield) as a white solid. $^1$H NMR (DMSO-d$_6$, 400 MHz) δ 9.09 (d, J=2.0 Hz, 1H), 7.55 (s, 1H), 7.51 (d, J=0.8 Hz, 1H), 6.49 (s, 1H), 4.59 (d, J=5.2 Hz, 1H), 4.06 (s, 3H). HPLC: 100.00% (220 nm), 100.00% (215 nm), 100.00% (254 nm). MS (ESI): mass calcd. For C$_{10}$H$_{10}$N$_6$OS 262.06, m/z found 263.0 [M+H]$^+$.

Compound 16

5-(((1H-pyrazol-3-yl)methyl)amino)-1-methyl-1H-pyrazolo[4,3-d]pyrimidin-7(6H)-one was prepared according to the procedure described herein for step 8 in Scheme A.

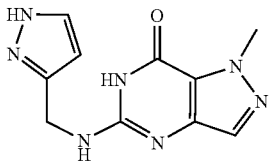 [SMILES: Cn1ncc2nc(NCc3cc[nH]n3)[nH]c(=O)c21]

The procedure yielded the desired compound (118.8 mg, 484.42 μmol, 89.42% yield) as a white solid. $^1$H NMR (DMSO-d$_6$, 400 MHz) δ 7.67 (d, J=1.6 Hz, 1H), 7.62 (s, 1H), 7.13 (s, 1H), 6.24 (d, J=1.6 Hz, 1H), 4.49 (s, 2H), 4.08 (s, 3H). HPLC: 98.38% (220 m), 97.78% (215 nm), 100.00% (254 nm). MS (ESI): mass calcd. For C$_{14}$H$_{18}$N$_{10}$O 245.10, m/z found 246.1 [M+H]$^+$.

Compound 17

5-(((2H-1,2,3-triazol-4-yl)methyl)amino)-1-methyl-H-pyrazolo[4,3-d]pyrimidin-7(6H)-one was prepared according to the procedure described herein for step 8 in Scheme A.

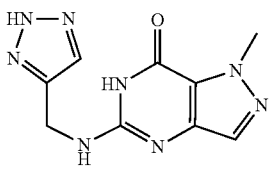 [SMILES: Cn1ncc2nc(NCc3cn[nH]n3)[nH]c(=O)c21]

The procedure yielded the desired compound (55.9 mg, 227.03 μmol, 41.91% yield) as a white solid. $^1$H NMR (DMSO-d$_6$, 400 MHz) δ 7.78 (s, 1H), 7.60 (s, 1H), 6.75 (s, 1H), 4.55 (d, J=4.4 Hz, 2H), 4.07 (s, 3H). HPLC: 100.00% (220 nm), 100.00% (215 nm), 100.00% (254 nm). MS (ESI): mass calcd. For C$_9$H$_{10}$N$_8$O 246.10, m/z found 247.1 [M+H]$^+$.

Compound 18

5-((Benzo[d]thiazol-2-ylmethyl)amino)-1-methyl-1H-pyrazolo[4,3-d]pyrimidin-7(6H)-one was prepared according to the procedure described herein for Step 8 in Scheme A.

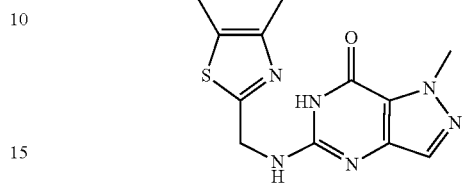

The procedure yielded the desired compound (73.3 mg, 234.67 μmol, 43.32% yield) as a white solid. $^1$H NMR (DMSO-d$_6$, 400 MHz) δ 8.02 (d, J=7.6 Hz, 1H), 7.94 (d, J=8.0 Hz, 1H), 7.55 (s, 1H), 7.49 (t, J=8.4 Hz, 1H), 7.40 (t, J=8.0 Hz, 1H), 7.03 (s, 1H), 4.90 (d, J=5.6 Hz, 2H), 4.08 (s, 3H). HPLC: 96.43% (220 nm), 96.13% (215 nm), 97.34% (254 nm). MS (ESI): mass calcd. For C$_{14}$H$_{12}$N$_6$OS 312.08, m/z found 313.1 [M+H]$^+$.

Compound 19

5-(((1H-benzo[d]imidazol-5-yl)methyl)amino)-1-methyl-1H-pyrazolo[4,3-d]pyrimidin-7(6H)-one was prepared according to the procedure described herein for Step 8 in Scheme A.

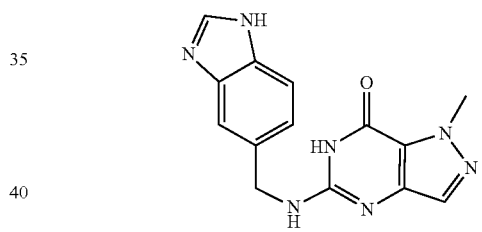

The procedure yielded the desired compound (44.5 mg, 149.58 μmol, 22.01% yield) as a white solid. $^1$H NMR (DMSO-d$_6$, 400 MHz) δ 9.41 (s, 1H), 7.80 (d, J=8.8 Hz, 1H), 7.75 (s, 1H), 7.55 (d, J=8.4 Hz, 1H), 7.52 (d, J=3.2 Hz, 1H), 6.70 (m, 1H), 4.65 (t, J=6.0 Hz, 2H), 4.06 (s, 3H). HPLC: 99.26% (220 nm), 98.34% (215 nm), 98.34% (254 nm). MS (ESI): mass calcd. For C$_{14}$H$_{13}$N$_7$O 295.12, m/z found 296.2 [M+H]$^+$.

Compound 20

1-Methyl-5-((thiazol-5-ylmethyl)amino)-1H-pyrazolo[4,3-d]pyrimidin-7(6H)-one was prepared according to the procedure described herein for Step 8 in Scheme A.

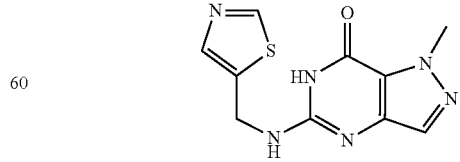

The procedure yielded the desired compound (19.7 mg, 75.11 μmol, 13.86% yield) as a light yellow solid. $^1$H NMR (DMSO-d$_6$, 400 MHz) δ 10.17 (s, 1H), 8.93 (s, 1H), 7.82 (s, 1H), 7.59 (s, 1H), 6.65 (t, J=4.8 Hz, 1H), 4.67 (d, J=5.6 Hz, 2H), 4.07 (s, 3H). HPLC: 96.83% (220 nm), 96.38% (215 nm), 96.83% (254 nm). MS (ESI): mass calcd. For $C_{10}H_{10}N_6OS$ 262.06, m/z found 263.0 [M+H]$^+$.

Compound 21

1-Methyl-5-((oxazol-5-ylmethyl)amino)-1H-pyrazolo[4,3-d]pyrimidin-7(6H)-one was prepared according to the procedure described herein for Step 8 in Scheme A.

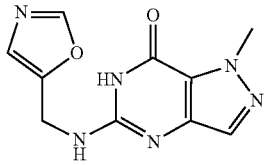

The procedure yielded the desired compound (39.5 mg, 160.42 μmol, 29.61% yield) as a white solid. $^1$H NMR (DMSO-d$_6$, 400 MHz) δ 8.30 (s, 1H), 7.59 (s, 1H), 7.06 (s, 1H), 6.70 (s, 1H), 4.55 (d, J=5.2 Hz, 2H), 4.07 (s, 3H). HPLC: 96.01% (220 nm), 95.85% (215 nm), 100.00% (254 nm). MS (ESI): mass calcd. For $C_{10}H_{10}N_6O_2$ 246.09, m/z found 247.1 [M+H]$^+$.

Compound 22

5-(((1H-imidazol-2-yl)methyl)amino)-1-methyl-1H-pyrazolo[4,3-d]pyrimidin-7(6H)-one was prepared according to the procedure described herein for Step 8 in Scheme A.

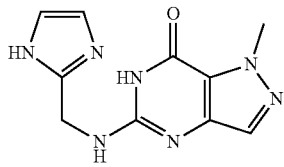

The procedure yielded the desired compound (26.4 mg, 107.27 μmol, 19.80% yield) as a white solid. $^1$H NMR (DMSO-d$_6$, 400 MHz) δ 7.57 (s, 1H), 6.94 (s, 2H), 6.51 (s, 1H), 4.44 (d, J=5.2 Hz, 2H), 4.06 (s, 3H). HPLC: 99.65% (220 nm), 98.40% (215 nm), 100.00% (254 nm). MS (ESI): mass calcd. For $C_{10}H_{11}N_7O$ 245.10, m/z found 246.1 [M+H]$^+$.

Compound 23

1-Methyl-5-((pyridazin-3-ylmethyl)amino)-1H-pyrazolo[4,3-d]pyrimidin-7(6H)-one was prepared according to the procedure described herein for Step 8 in Scheme A.

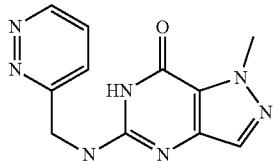

The procedure yielded the desired compound (4.9 mg, 19.05 μmol, 3.52% yield) as a pale brown solid. $^1$H NMR (DMSO-d$_6$, 400 MHz) δ 9.15 (dd, J=2.8 Hz, 4.0 Hz, 1H), 7.69~7.64 (m, 2H), 7.54 (s, 1H), 7.05~6.96 (m, 1H), 4.78 (d, J=5.2 Hz, 2H), 4.07 (s, 3H). HPLC: 99.18% (220 nm), 98.00% (215 nm), 98.57% (254 nm). MS (ESI): mass calcd. For $C_{11}H_{11}N_7O$ 257.10, m/z found 258.1 [M+H]$^+$.

Compound 24

5-((3-Chloro-4-fluorobenzyl)amino)-1-methyl-1H-pyrazolo[4,3-d]pyrimidin-7(6H)-one was prepared according to the procedure described herein for Step 8 in Scheme A.

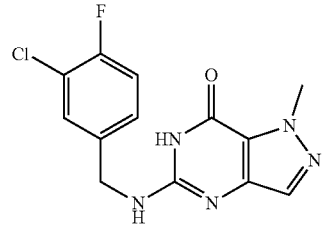 [SMILES: Cn1ncc2nc(NCc3ccc(F)c(Cl)c3)[nH]c(=O)c21]

The procedure yielded the desired compound (139 mg, 451.72 μmol, 83.38% yield) as a white solid. $^1$H NMR (DMSO-d$_6$, 400 MHz) δ 7.55~7.54 (m, 2H), 7.37~7.35 (m, 2H), 6.87 (s, 1H), 4.47 (d, J=5.2 Hz, 2H), 4.07 (s, 3H). HPLC: 98.59% (220 nm), 97.69% (215 nm), 99.20% (254 nm). MS (ESI): mass calcd. For $C_{13}H_{11}ClFN_5O$ 307.06, m/z found 308.0 [M+H]$^+$.

Compound 25

5-((4-chlorobenzyl)amino)-1-methyl-1H-pyrazolo[4,3-d]pyrimidin-7(6H)-one was prepared according to the procedure described herein for Step 8 in Scheme A.

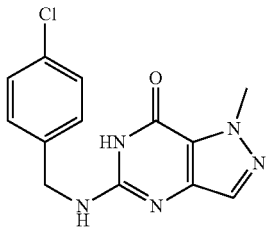 [SMILES: Cn1ncc2nc(NCc3ccc(Cl)cc3)[nH]c(=O)c21]

The procedure yielded the desired compound (23.1 mg, 79.73 μmol, 14.72% yield) as an off white solid. $^1$H NMR (DMSO-d$_6$, 400 MHz) δ 7.84 (s, 1H), 7.62 (s, 1H), 7.46~7.35 (m, 4H), 4.57 (d, J=3.6 Hz, 2H), 4.09 (s, 3H). HPLC: 99.48% (220 nm), 99.72% (215 nm), 98.92% (254 nm). MS (ESI): mass calcd. For $C_{13}H_{12}ClN_5O$ 289.07, m/z found 290.1 [M+H]$^+$.

Compound 26

5-((3-Chlorobenzyl)amino)-1-methyl-1H-pyrazolo[4,3-d]pyrimidin-7(6H)-one was prepared according to the procedure described herein for Step 8 in Scheme A.

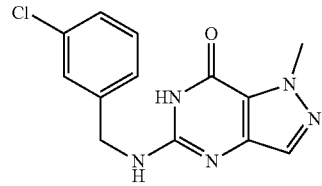 [SMILES: Cn1ncc2nc(NCc3cccc(Cl)c3)[nH]c(=O)c21]

The procedure yielded the desired compound (157.9 mg, 391.09 μmol, 72.19% yield, TFA) as a white solid. $^1$H NMR (DMSO-d$_6$, 400 MHz) δ 7.57 (s, 1H), 7.40 (s, 1H), 7.36 (d, J=7.5 Hz, 1H), 7.33~7.28 (m, 2H), 7.04 (s, 1H), 4.51 (d, J=5.4 Hz, 2H), 4.07 (s, 3H). HPLC: 97.49% (220 nm), 97.20% (215 nm), 98.84% (254 nm). MS (ESI): mass calcd. For $C_{13}H_{12}CN_5O$ 289.07, m/z found 290.1 [M+H]$^+$.

Compound 27

5-((2-Chlorobenzyl)amino)-1-methyl-1H-pyrazolo[4,3-d]pyrimidin-7(6H)-one was prepared according to the procedure described herein for Step 8 in Scheme A.

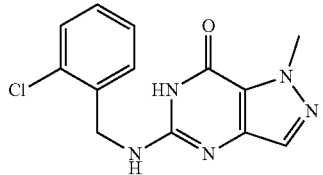 [SMILES: Cn1ncc2nc(NCc3ccccc3Cl)[nH]c(=O)c21]

The procedure yielded the desired compound (93.2 mg, 313.84 μmol, 57.93% yield) as a white solid. $^1$H NMR (DMSO-d$_6$, 400 MHz) δ 7.55 (s, 1H), 7.47~7.45 (m, 1H), 7.41~7.38 (m, 1H), 7.34~7.29 (m, 2H), 6.68~6.67 (m, 1H), 5.55 (d, J=5.6 Hz, 2H), 4.07 (s, 3H). HPLC: 97.56% (220 nm), 97.45% (215 nm), 98.61% (254 nm). MS (ESI): mass calcd. For C$_{13}$H$_{12}$CN$_5$O 289.07, m/z found 290.1 [M+H]$^+$.

Compound 28

5-((2,4-Dichlorobenzyl)amino)-1-methyl-1H-pyrazolo[4,3-d]pyrimidin-7(6H)-one was prepared according to the procedure described herein for Step 8 in Scheme A.

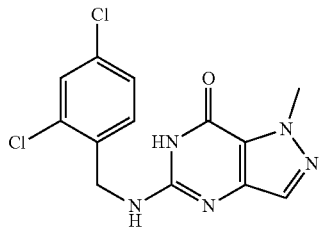 [SMILES: Cn1ncc2nc(NCc3ccc(Cl)cc3Cl)[nH]c(=O)c21]

The procedure yielded the desired compound (92.6 mg, 276.14 μmol, 50.97% yield) as an off white solid. $^1$H NMR (DMSO-d$_6$, 400 MHz) δ 7.62 (d, J=1.8 Hz, 1H), 7.53 (s, 1H), 7.42~7.35 (m, 2H), 6.63 (s, 1H), 4.51 (d, J=6.0 Hz, 2H), 4.06 (s, 3H). HPLC: 96.67% (220 nm), 96.29% (215 nm), 100.00% (254 nm). MS (ESI): mass calcd. For C$_{13}$H$_{11}$C2N$_5$O 323.03, m/z found 324.0 [M+H]$^+$.

Compound 29

5-((2,3-Dichlorobenzyl)amino)-1-methyl-1H-pyrazolo[4,3-d]pyrimidin-7(6H)-one was prepared according to the procedure described herein for Step 8 in Scheme A.

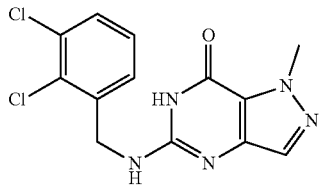 [SMILES: Cn1ncc2nc(NCc3cccc(Cl)c3Cl)[nH]c(=O)c21]

The procedure yielded the desired compound (55 mg, 169.67 μmol, 31.32% yield) as a white solid. $^1$H NMR (DMSO-d$_6$, 400 MHz) δ 11.14 (s, 1H), 7.56~7.53 (m, 2H), 7.33 (d, J=5.2 Hz, 2H), 6.64 (s, 1H), 5.56 (d, J=6.0 Hz, 2H), 4.06 (s, 3H). HPLC: 100.00% (220 nm), 100.00% (215 nm), 100.00% (254 nm). MS (ESI): mass calcd. For C$_{13}$H$_{11}$C$_{12}$N$_5$O 323.03, m/z found 324.0 [M+H]$^+$.

Compound 30

5-((2,6-Dichlorobenzyl)amino)-1-methyl-1H-pyrazolo[4,3-d]pyrimidin-7(6H)-one was prepared according to the procedure described herein for Step 8 in Scheme A.

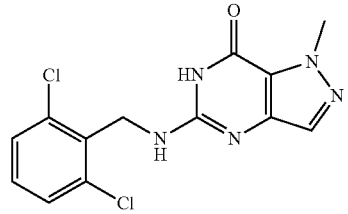 [SMILES: Cn1ncc2nc(NCc3c(Cl)cccc3Cl)[nH]c(=O)c21]

The procedure yielded the desired compound (26.5 mg, 81.75 μmol, 15.09% yield) as a white solid. $^1$H NMR (DMSO-d$_6$, 400 MHz) δ 10.55 (s, 1H), 7.61 (s, 1H), 7.54~7.52 (m, 2H), 7.40~7.38 (m, 1H), 6.24 (s, 1H), 4.68 (d, J=4.0 Hz, 2H), 4.06 (s, 3H). HPLC: 100.00% (220 nm), 100.00% (215 nm), 100.00% (254 nm). MS (ESI): mass calcd. For C$_{13}$H$_{11}$C$_{12}$N$_5$O 323.03, m/z found 324.0 [M+H]$^+$.

Compound 31

5-((3-Chloro-4-methylbenzyl)amino)-1-methyl-1H-pyrazolo[4,3-d]pyrimidin-7(6H)-one was prepared according to the procedure described herein for Step 8 in Scheme A.

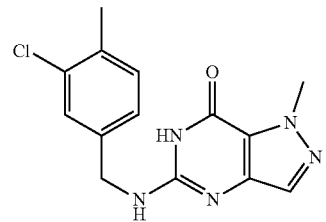 [SMILES: Cc1ccc(CNc2nc3cnn(C)c3c(=O)[nH]2)cc1Cl]

The procedure yielded the desired compound (106.2 mg, 349.63 μmol, 64.54% yield) as a white solid. $^1$H NMR (DMSO-d$_6$, 400 MHz) δ 7.56 (s, 1H), 7.38 (s, 1H), 7.31 (d, J=7.6 Hz, 1H), 7.20 (d, J=8.0 Hz, 1H), 6.82 (s, 1H), 4.46 (d, J=5.2 Hz, 2H), 4.08 (s, 3H), 2.30 (s, 3H). HPLC: 97.09% (220 nm), 96.49% (215 nm), 98.94% (254 nm). MS (ESI): mass caled. For C$_{14}$H$_{14}$ClN$_5$O 303.09, m/z found 304.0 [M+H]$^+$.

Compound 32

5-((3,4-Dimethoxybenzyl)amino)-1-methyl-1H-pyrazolo[4,3-d]pyrimidin-7(6H)-one was prepared according to the procedure described herein for Step 8 in Scheme A.

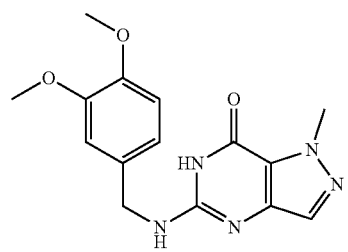 [SMILES: COc1ccc(CNc2nc3cnn(C)c3c(=O)[nH]2)cc1OC]

The procedure yielded the desired compound (91.3 mg, 289.54 μmol, 59.38% yield) as a white solid. H NMR (DMSO-d$_6$, 400 MHz) δ 7.57 (s, 1H), 6.98 (s, 1H), 6.93~6.83 (m, 2H), 6.74 (s, 1H), 4.39 (d, J=5.2 Hz, 2H), 4.07 (s, 3H), 3.73 (d, J=5.2 Hz, 6H). HPLC: 99.37% (220 nm), 99.36% (215 nm), 100.00% (254 nm). MS (ESI): mass calcd. For $C_{15}H_{17}N_5O_3$ 315.13, m/z found 316.1 [M+H]$^+$.

Compound 33

5-((3,4-Dimethylbenzyl)amino)-1-methyl-1H-pyrazolo[4,3-d]pyrimidin-7(6H)-one was prepared according to the procedure described herein for Step 8 in Scheme A.

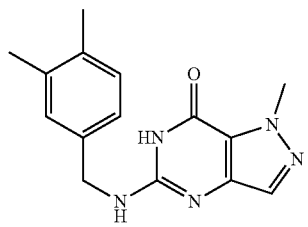 [SMILES: Cc1ccc(CNc2nc3cnn(C)c3c(=O)[nH]2)cc1C]

The procedure yielded the desired compound (117 mg, 412.95 µmol, 84.69% yield as a white solid. $^1$H NMR (DMSO-d$_6$, 400 MHz) δ 7.56 (s, 1H), 7.09 (d, J=5.6 Hz, 2H), 7.05 (d, J=5.6 Hz, 1H), 6.59 (s, 1H), 4.39 (d, J=4.8 Hz, 2H), 4.07 (s, 3H), 2.19 (d, J=4.8 Hz, 6H). HPLC: 100.00% (220 nm), 100.00% (215 nm), 100.00% (254 nm). MS (ESI): mass calcd. For $C_{15}H_{17}N_5O$ 283.14, m/z found 284.1 [M+H]$^+$.

Compound 34

5-((4-Chloro-3-methoxybenzyl)amino)-1-methyl-H-pyrazolo[4,3-d]pyrimidin-7(6H)-one was prepared according to the procedure described herein for Step 8 in Scheme A.

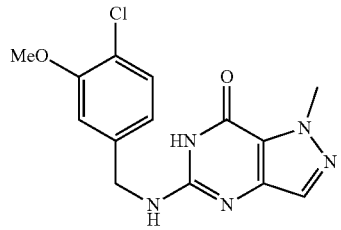 [SMILES: COc1cc(CNc2nc3cnn(C)c3c(=O)[nH]2)ccc1Cl]

The procedure yielded the desired compound (92.1 mg, 288.04 µmol, 59.08% yield) as a white solid. $^1$H NMR (DMSO-d$_6$, 400 MHz) δ 7.55 (s, 1H), 7.36 (d, J=8.0 Hz, 1H), 7.15 (d, J=1.6 Hz, 1H), 6.91 (dd, J=8.0 Hz, J=1.6 Hz, 1H), 6.56 (s, 1H), 4.46 (d, J=8.0 Hz, 2H), 4.07 (s, 3H), 3.83 (s, 3H). HPLC: 100.00% (220 nm), 98.52% (215 nm), 100.00% (254 nm). MS (ESI): mass calcd. For $C_{14}H_{14}ClN_5O_2$ 319.08, m/z found 320.1 [M+H]$^+$.

Compound 35

5-((4-Chloro-3-methylbenzyl)amino)-1-methyl-1H-pyrazolo[4,3-d]pyrimidin-7(6H)-one was prepared according to the procedure described herein for Step 8 in Scheme A.

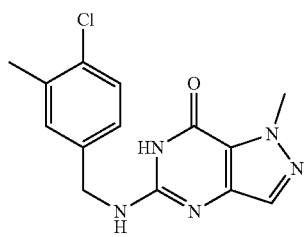 [SMILES: Cc1cc(CNc2nc3cnn(C)c3c(=O)[nH]2)ccc1Cl]

The procedure yielded the desired compound (102.3 mg, 336.79 µmol, 69.07% yield) as a pale white solid. $^1$H NMR (DMSO-d$_6$, 400 MHz) δ 7.56 (s, 1H), 7.37 (d, J=8.0 Hz, 1H), 7.31 (s, 1H), 7.18 (d, J=8.0 Hz, 1H), 6.97 (s, 1H), 4.46 (d, J=4.0 Hz, 2H), 4.07 (s, 3H), 2.31 (s, 3H). HPLC: 99.90% (220 nm), 99.86% (215 nm), 98.42% (254 nm). MS (ESI): mass calcd. For $C_{14}H_{14}ClN_5O$ 303.09, m/z found 304.1 [M+H]$^+$.

Compound 36

5-(((4,5-Dichloropyridin-2-yl)methyl)amino)-1-methyl-1H-pyrazolo[4,3-d]pyrimidin-7(6H)-one-2,2,2-trifluoroacetate was prepared according to the procedure described herein for Step 8 in Scheme A.

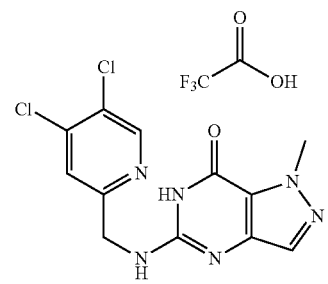

The procedure yielded the desired compound (35.8 mg, 110.10 µmol, 33.87% yield) as a white solid. $^1$H NMR (DMSO-d$_6$, 400 MHz) δ 11.20 (s, 1H), 8.73 (s, 1H), 7.69 (s, 1H), 7.53 (s, 1H), 6.73 (s, 1H), 4.58 (d, J=5.6 Hz, 2H), 4.07 (s, 3H). HPLC: 100.00% (220 nm), 100.00% (215 nm), 96.16% (254 nm). MS (ESI): mass calcd. For $C_{12}H_{10}Cl_2N_6O$ 324.03, m/z found 325.0 [M+H]$^+$.

Compound 37

5-(((4,5-Dichloro-1H-imidazol-2-yl)methyl)amino)-1-methyl-1H-pyrazolo[4,3-d]pyrimidin-7(6H)-one was prepared according to the procedure described herein for Step 8 in Scheme A.

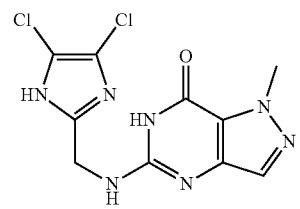 [SMILES: Cn1ncc2nc(NCc3nc(Cl)c(Cl)[nH]3)[nH]c(=O)c21]

The procedure yielded the desired compound (23.2 mg, 73.85 µmol, 16.41% yield) as a white solid. $^1$H NMR (DMSO-d$_6$, 400 MHz) δ 7.57 (s, 1H), 6.55 (s, 1H), 4.42 (d, J=5.6 Hz, 2H), 4.07 (s, 3H). HPLC: 100.00% (220 nm), 100.00% (215 nm), 100.00% (254 nm). MS (ESI): mass calcd. For $C_{10}H_9Cl_2N_7O$ 313.02, m/z found 314.0 [M+H]$^+$.

Compound 38

5-(((4-Chloro-5-ethyl-1H-imidazol-2-yl)methyl)amino)-1-methyl-1H-pyrazolo[4,3-d]pyrimidin-7(6H)-one hydrochloride was prepared according to the procedure described herein for Step 8 in Scheme A.

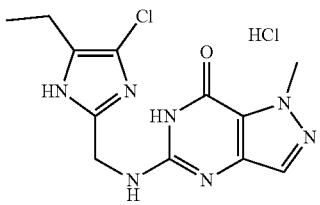 [SMILES: CCc1[nH]c(CNc2nc3cnn(C)c3c(=O)[nH]2)nc1Cl ; Cl]

The procedure yielded the desired compound (8.4 mg, 27.01 μmol, 9.97% yield) as a white solid. $^1$H NMR (DMSO-d$_6$, 400 MHz) δ 7.59 (s, 1H), 7.19 (s, 1H), 4.61 (d, J=2.4 Hz, 2H), 4.09 (s, 3H), 2.56 (q, J=7.6 Hz, 2H), 1.15 (t, J=7.6 Hz, 3H). HPLC: 98.96% (220 nm), 98.49% (215 nm), 99.11% (254 nm). MS (ESI): mass calcd. For C$_{12}$H$_{15}$C$_{12}$N$_7$O 307.09, m/z found 308.1 [M+H]$^+$.

Compound 39

5-((1,3-Dihydroisobenzofuran-5-yl)amino)-1-methyl-1H-pyrazolo[4,3-d]pyrimidin-7(6H)-one was prepared according to the procedure described herein for Step 8 in Scheme A.

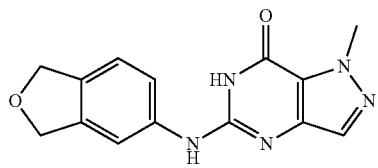 [SMILES: Cn1ncc2nc(Nc3ccc4c(c3)COC4)[nH]c(=O)c21]

The procedure yielded the desired compound (26.8 mg, 92.37 μmol, 42.63% yield) as a yellow solid. $^1$H NMR (DMSO-d$_6$, 400 MHz) δ 8.54 (s, 1H), 7.70 (s, 1H), 7.68 (s, 1H), 7.43 (d, J=8.0 Hz, 1H), 7.24 (d, J=8.4 Hz, 1H), 5.00 (s, 2H), 4.96 (s, 2H), 4.11 (s, 3H). HPLC: 97.64% (220 nm), 96.24% (215 nm), 98.52% (254 nm). MS (ESI): mass calcd. For C$_{14}$H$_{13}$N$_5$O$_2$ 283.11, m/z found 284.1 [M+H]$^+$.

Scheme B-1

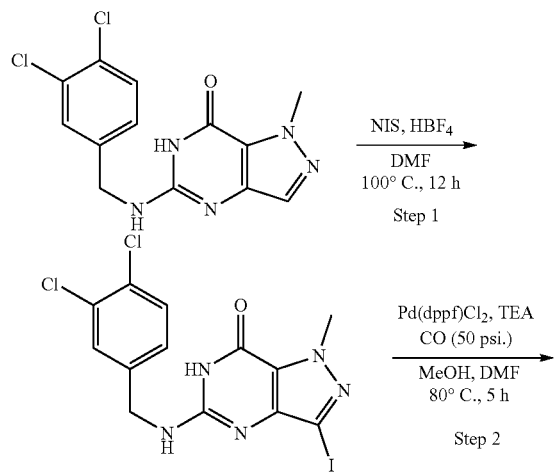

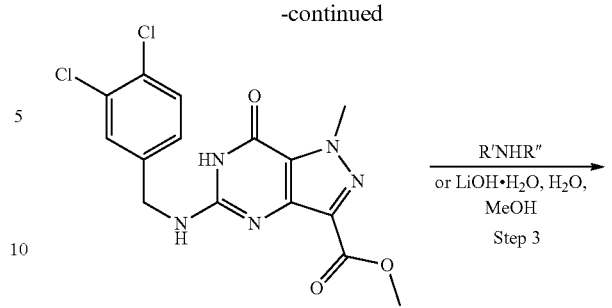

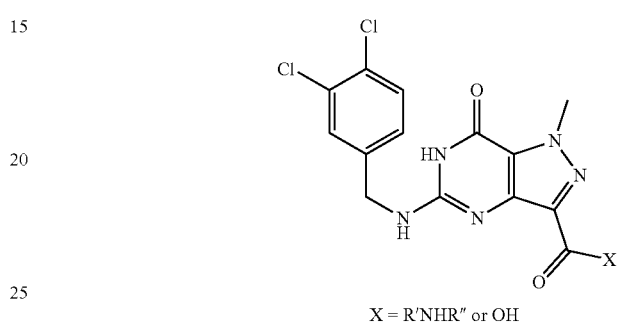

Compound 40

Methyl 5-((3,4-dichlorobenzyl)amino)-1-methyl-7-oxo-6,7-dihydro-1H-pyrazolo[4,3-d]pyrimidine-3-carboxylate was prepared according to the procedure described herein for Steps 1-2 in Scheme B-1.

Preparation of 5-((3,4-dichlorobenzyl)amino)-3-iodo-1-methyl-$^1$H-pyrazolo[4,3-d]pyrimidin-7(6H)-one (Step 1 in Scheme B-1)

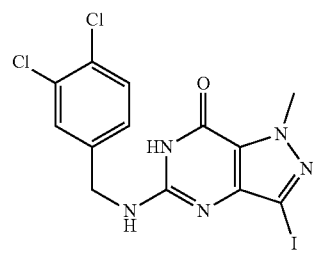

HBF$_4$ (677.22 mg, 7.71 mmol, 480.30 μL, 2.5 eq) was added to a mixture of 5-[(3,4-dichlorophenyl)methylamino]-1-methyl-6H-pyrazolo[4,3-d]pyrimidin-7-one (1 g, 3.08 mmol, 1 eq) and NIS (694.03 mg, 3.08 mmol, 1 eq) in MeCN (8 mL). The mixture was stirred at 100° C. for 4 hours. LC-MS showed the reaction was complete. There was some yellow solid formed. After filtered, the solid was collected after washed with H$_2$O (8 mL) and EtOAc (8 mL). Compound 5-[(3,4-dichlorophenyl)methylamino]-3-iodo-1-methyl-6H-pyrazolo[4,3-d]pyrimidin-7-one (730 mg, 1.62 mmol, 52.58% yield) was obtained as yellow solid. $^1$H NMR (DMSO-d$_6$, 400 MHz) δ 11.21 (s, 1H), 7.70 (d, J=1.6 Hz, 1H), 7.58 (d, J=8.0 Hz, 1H), 7.39 (dd, J=8.4 Hz, 2.0 Hz, 1H), 6.70 (t, J=6.0 Hz, 1H), 4.46 (d, J=9.6 Hz, 2H), 4.07 (s, 3H).

Preparation of methyl 5-((3,4-dichlorobenzyl)amino)-1-methyl-7-oxo-6,7-dihydro-1H-pyrazolo[4,3-d]pyrimidine-3-carboxylate (Step 2 in Scheme B-1)

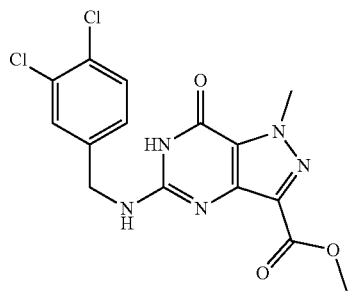 [SMILES: COC(=O)c1nn(C)c2c(=O)[nH]c(NCc3ccc(Cl)c(Cl)c3)nc12]

To a solution of 5-[(3,4-dichlorophenyl)methylamino]-3-iodo-1-methyl-6H-pyrazolo[4,3-d]pyrimidin-7-one (300 mg, 666.58 mol, 1 eq) and TEA (269.80 mg, 2.67 mmol, 371.12 μL, 4 eq) in MeOH (10 mL) and DMF (3 mL) was added Pd(dppf)$C_{12}$ (97.55 mg, 133.32 μmol, 0.2 eq) under $N_2$ atmosphere. The suspension was degassed and purged with CO for 3 times. The mixture was stirred at 80° C. for 5 hours under CO (50 psi.). LC-MS showed the reaction was complete. After filtered, the filtrate was concentrated under reduced pressure. The residue was purified by flash silica gel chromatography (Biotage®; 4 g SepaFlash® Silica Flash Column, Eluent of 0~100% Ethylacetate/Petroleum ether gradient at 65 mL/min). The eluent was removed under reduced pressure. 50 mg of the obtained crude product was further purified by prep-HPLC (column: Nano-micro Kromasil C18 100 mm×30 mm 8 μm; mobile phase: [water (0.1% TFA)-MeCN]; B %: 45%-70%, 10 mins). The solvent was removed under freeze drying. Compound methyl 5-[(3,4-dichlorophenyl)methylamino]-1-methyl-7-oxo-6H-pyrazolo[4,3-d]pyrimidine-3-carboxylate (9.8 mg, 25.54 μmol, 3.83% yield, 99.62% purity) was obtained as white solid for delivery. $^1$H NMR (DMSO-$d_6$, 400 MHz) δ 11.32 (s, 1H), 7.72 (s, 1H), 7.58 (d, J=8.4 Hz, 1H), 7.42 (d, J=8.4 Hz, 1H), 6.88 (s, 1H), 4.47 (d, J=5.6 Hz, 2H), 4.13 (s, 3H), 3.83 (s, 3H). HPLC: 99.62% (220 nm), 99.52% (215 nm), 99.35% (254 nm). MS (ESI): mass calcd. For $C_{15}H_{13}C2N_5O_3$ 381.04, m/z found 382.1 [M+H]$^+$.

Preparation of Compounds in Scheme B-1 (Step 3 in Scheme B-1)

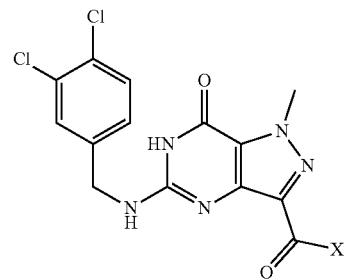

A mixture of methyl 5-[(3,4-dichlorophenyl)methylamino]-1-methyl-7-oxo-6H-pyrazolo[4,3-d]pyrimidine-3-carboxylate (784.93 μmol, 1 eq), LiOH—$H_2O$ (2.35 mmol, 3 eq) in MeOH (2 mL) and $H_2O$ (2 mL) (or in MeNH$_2$ (2 M in EtOH, 15.7 mmol, 7.85 mL, 20 eq)) was stirred at 25° C. for a period of time (1 hour-12 hours). LC-MS showed the reaction was complete. The reaction mixture was concentrated under reduced pressure. The residue was purified by prep-HPLC. Column: Nano-micro Kromasil C18 100 mm×30 mm 8 μm. Mobile phase: [water (0.1% TFA)-MeCN]; B %: 35%-65%, 10 mins). The solvent was removed under freeze drying to give desired product.

Compound 41

Preparation of 5-((3,4-dichlorobenzyl)amino)-1-methyl-7-oxo-6,7-dihydro-1H-pyrazolo[4,3-d]pyrimidine-3-carboxylic Acid (Step 3 in Scheme B-1)

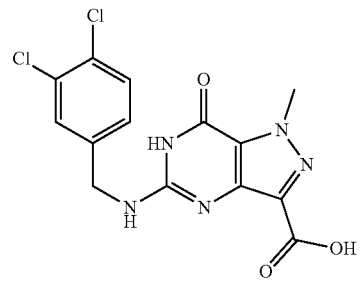 [SMILES: Cn1nc(C(=O)O)c2nc(NCc3ccc(Cl)c(Cl)c3)[nH]c(=O)c21]

The procedure yielded the desired compound (14.1 mg, 37.32 μmol, 4.75% yield, 97.44% purity) as a light brown solid. $^1$H NMR (DMSO-$d_6$, 400 MHz) δ 11.25 (s, 1H), 10.64 (s, 1H), 7.73 (s, 1H), 7.59~7.55 (m, 1H), 7.47~7.32 (m, 1H), 6.77 (s, 1H), 4.55~4.47 (m, 2H), 4.12 (s, 3H). HPLC: 97.44% (220 nm), 97.47% (215 nm), 98.21% (254 nm). MS (ESI): mass calcd. For $C_{14}H_{11}C_{12}N_5O_3$ 367.02, m/z found 368.0 [M+H]$^+$.

Compound 42

Preparation of 5-((3,4-dichlorobenzyl)amino)-N,1-dimethyl-7-oxo-6,7-dihydro-1H-pyrazolo[4,3-d]pyrimidine-3-carboxamide (Step 3 in Scheme B-1)

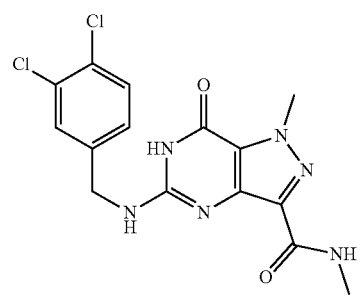 [SMILES: CNC(=O)c1nn(C)c2c(=O)[nH]c(NCc3ccc(Cl)c(Cl)c3)nc12]

A mixture of methyl 5-[(3,4-dichlorophenyl)methylamino]-1-methyl-7-oxo-6H-pyrazolo[4,3-d]pyrimidine-3-carboxylate (50 mg, 130.82 μmol, 1 eq) in MeNH$_2$ (2 M in EtOH, 1.31 mL, 20 eq) was stirred at 25° C. for 12 hours. LC-MS showed the reaction was complete. The reaction mixture was concentrated under reduced pressure. The residue was purified by prep-HPLC (column: Nano-micro Kromasil C18 100 mm×30 mm 8 μm; mobile phase: [water (0.1% TFA)-MeCN]; B %: 35%-55%, 10 mins). The solvent was removed under freeze drying. Compound 5-[(3,4-dichlorophenyl)methylamino]-N,1-dimethyl-7-oxo-6H-pyrazolo[4,3-d]pyrimidine-3-carboxamide (5.8 mg, 15.02 µmol, 11.48% yield, 98.71% purity) was obtained as brown solid. ¹H NMR (DMSO-d₆, 400 MHz) δ 11.42 (s, 1H), 7.94 (d, J=4.8 Hz, 1H), 7.66 (s, 1H), 7.60 (d, J=8.4 Hz, 1H), 7.37 (d, J=7.2 Hz, 1H), 7.03 (t, J=5.6 Hz, 1H), 4.50 (d, J=5.6 Hz, 2H), 4.09 (s, 3H), 2.82 (d, J=4.8 Hz, 3H). HPLC: 98.71% (220 nm), 98.32% (215 nm), 96.98% (254 nm). MS (ESI): mass calcd. For $C_{15}H_{14}C2N_6O_2$ 380.06, m/z found 381.1 [M+H]⁺.

Compound 43

5-((3,4-Dichlorobenzyl)amino)-N,N,1-trimethyl-7-oxo-6,7-dihydro-1H-pyrazolo[4,3-d]pyrimidine-3-carboxamide was prepared according to the procedure described herein for Step 3 in Scheme B-1.

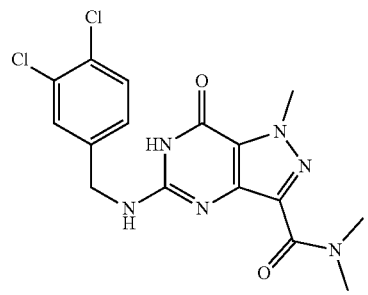 [SMILES: CN(C)C(=O)c1nn(C)c2c(=O)[nH]c(NCc3ccc(Cl)c(Cl)c3)nc12]

The procedure yielded the desired compound (3.3 mg, 7.80 µmol, 5.96% yield) as a brown solid. ¹H NMR (DMSO-d₆, 400 MHz) δ 11.24 (s, 1H), 7.59~7.57 (m, 2H), 7.33 (d, J=8.0 Hz, 1H), 6.73 (s, 1H), 4.44~4.45 (m, 2H), 4.09 (s, 3H), 2.96 (s, 3H), 2.82 (s, 3H). HPLC: 93.37% (220 nm), 90.08% (215 nm), 92.84% (254 nm). MS (ESI): mass calcd. For $C_{16}H_{16}C2N_6O_2$ 394.07, m/z found 395.1 [M+H]⁺.

Compound 44

Preparation of 5-((3,4-dichlorobenzyl)amino)-1,3-dimethyl-1H-pyrazolo[4,3-d]pyrimidin-7(6H)-one (Step 1 in Scheme B-2)

A mixture of 5-[(3,4-dichlorophenyl)methylamino]-3-iodo-1-methyl-6H-pyrazolo[4,3-d]pyrimidin-7-one (0.2 g 444.38 µmol, 1 eq), 2,4,6-trimethyl-1,3,5,2,4,6-trioxatriborinane (334.71 mg, 1.33 mmol, 372.73 µL, 50% in THF, 3 eq), Pd(dppf)Cl₂ (48.77 mg, 66.66 µmol, 0.15 eq) and K₂CO₃ (184.26 mg, 1.33 mmol, 3 eq) in dioxane (10 mL) was stirred at 120° C. for 10 hours under N₂. LC-MS showed the reaction was complete. After filtered, the filtrate was concentrated under reduced pressure. The residue was purified by prep-HPLC (column: Luna C18 100 mm×30 mm 5 µm; mobile phase: [water (0.1% TFA)-MeCN]; B %: 35%-50%, 10 mins) to give 5-[(3,4-dichlorophenyl)methylamino]-1,3-dimethyl-6H-pyrazolo[4,3-d]pyrimidin-7-one (22.4 mg, 66.23 µmol, 14.90% yield) as off-white solid. ¹H NMR (DMSO-d₆, 400 MHz) δ 10.98 (s, 1H), 7.64 (s, 1H), 7.58 (d, J=8.4 Hz, 1H), 7.36 (d, J=7.6 Hz, 1H), 6.56 (s, 1H), 4.46 (d, J=4.8 Hz, 2H), 3.98 (s, 3H), 2.20 (s, 3H). HPLC: 97.11% (220 nm), 95.73% (215 nm), 100.00% (254 nm). MS (ESI): mass calcd. For $C_{14}H_{13}C_{12}N_5O$ 337.05, m/z found 338.2 [M+H]⁺.

Scheme B-2

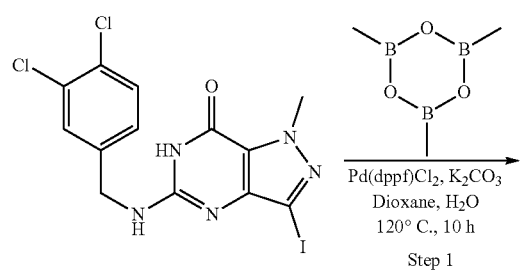

Scheme B-3

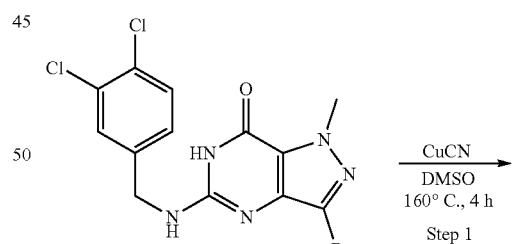

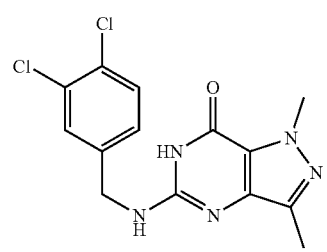

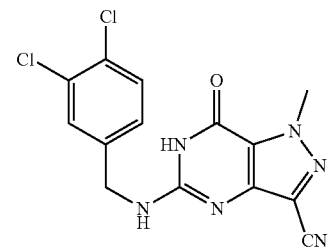

Compound 45

Preparation of 5-((3,4-dichlorobenzyl)amino)-1-methyl-7-oxo-6,7-dihydro-1H-pyrazolo[4,3-d]pyrimidine-3-carbonitrile (Step 1 in Scheme B-3)

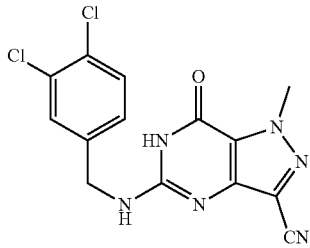 [SMILES: Cn1nc(C#N)c2nc(NCc3ccc(Cl)c(Cl)c3)[nH]c(=O)c21]

A mixture of 3-bromo-5-[(3,4-dichlorophenyl)methylamino]-1-methyl-6H-pyrazolo[4,3-d]pyrimidin-7-one (50 mg, 124.05 µmol, 1 eq) and CuCN (12.22 mg, 136.46 µmol, 29.81 µL, 1.1 eq) in DMSO (1 mL) was stirred at 160° C. for 4 hours. LC-MS showed the reaction was complete. The reaction mixture was filtered to remove the insoluble. The filtrate was purified by prep-HPLC (column: Welch Xtimate C18 100 mm×25 mm 3 µm; mobile phase: [water (0.1% TFA)-MeCN]; B %: 30%-60%, 12 mins) for the first time and then was purified by prep-HPLC (column: Welch Xtimate C18 150 mm×25 mm 5 µm; mobile phase: [water (10 mM $NH_4HCO_3$)-MeCN]; B %: 40%-65%, 10.5 mins) for the second time. The solvent was removed under freeze drying. Compound 5-[(3,4-dichlorophenyl)methylamino]-1-methyl-7-oxo-6H-pyrazolo[4,3-d]pyrimidine-3-carbonitrile (5.3 mg, 14.75 µmol, 11.89% yield, 97.20% purity) was obtained as white solid. $^1$H NMR (DMSO-$d_6$, 400 MHz) δ 7.63~7.59 (m, 2H), 7.35 (d, J=8.0 Hz, 1H), 7.00 (s, 1H), 4.51 (d, J=5.6 Hz, 2H), 4.14 (s, 3H). HPLC: 97.20% (220 nm), 96.95% (215 nm), 95.24% (254 nm). MS (ESI): mass calcd. For $C_{14}H_{10}C_2N_6O$ 348.03, m/z found 349.0 [M+H]$^+$.

Scheme B-4

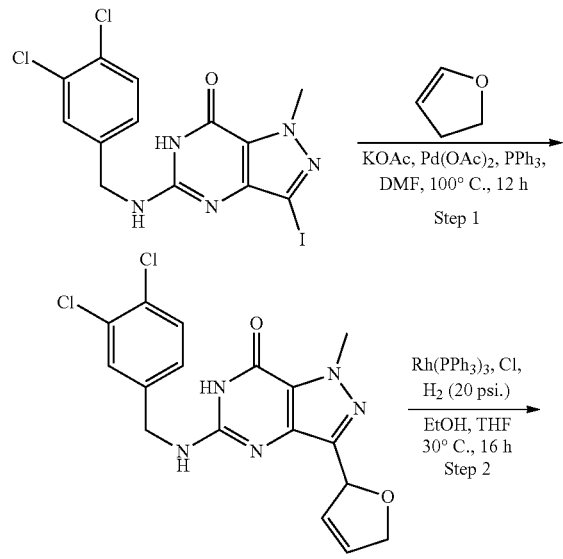

Compound 46

Preparation of 5-((3,4-dichlorobenzyl)amino)-3-(2,5-dihydrofuran-2-yl)-1-methyl-1H-pyrazolo[4,3-d]pyrimidin-7(6H)-one (Step 1 in Scheme B-4)

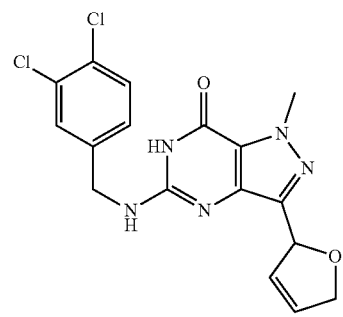 [SMILES: Cn1nc(C2C=CCO2)c2nc(NCc3ccc(Cl)c(Cl)c3)[nH]c(=O)c21]

A mixture of 5-[(3,4-dichlorophenyl)methylamino]-3-iodo-1-methyl-6H-pyrazolo[4,3-d]pyrimidin-7-one (0.3 g, 666.58 µmol, 1 eq), 2,3-dihydrofuran (233.60 mg, 3.33 mmol, 252.00 µL, 5 eq), AcOK (163.54 mg, 1.67 mmol, 2.5 eq), Pd(OAc)$_2$ (29.93 mg, 133.32 µmol, 0.2 eq) and PPh$_3$ (17.48 mg, 66.66 µmol, 0.1 eq) in DMF (1 mL) was degassed and purged with N$_2$ for 3 times and then the mixture was stirred at 100° C. for 12 hours under N$_2$ atmosphere. LCMS and HPLC showed the reaction was complete. The reaction mixture was cooled to room temperature and quenched with H$_2$O (5 mL) at 0° C. The mixture was extracted with EtOAc (8 mL×3). The combined organic layers were washed with brine (5 mL×1), dried over Na$_2$SO$_4$, filtered and concentrated under reduced pressure. 0.45 g (crude) of 5-[(3,4-dichlorophenyl)methylamino]-3-(2,5-dihydrofuran-2-yl)-1-methyl-6H-pyrazolo[4,3-d]pyrimidin-7-one (0.6 g, crude) was obtained as light yellow solid. 0.15 g of the crude was further purified by prep-HPLC (column: Xtimate C18 100 mm×30 mm 3 µm; mobile phase: [water (0.04% HCl)-MeCN]; B %: 40%-55%, 10 mins). MeCN was removed under reduced pressure at 30° C. The aqueous was dried over lyophilization to give 5-[(3,4-dichlorophenyl)methylamino]-3-(2,5-dihydrofuran-2-yl)-1-methyl-6H-pyrazolo[4,3-d]pyrimidin-7-one (24.9 mg, 62.01 µmol, 9.30% yield, 97.685% purity) as light yellow solid for delivery. $^1$H NMR (DMSO-$d_6$, 400 MHz) δ 7.63~7.58 (m, 2H), 7.35 (d, J=7.6 Hz, 1H), 6.97 (s, 1H), 6.08 (d, J=4.4 Hz, 1H), 5.88 (dd, J=18.0 Hz, 20 Hz z, 2H), 4.70~4.67 (m, 1H), 4.57 (s, 1H), 4.46 (s, 2H), 4.02 (s, 3H). HPLC: 97.69% (220 nm), 97.64% (215 nm), 98.97% (254 nm). MS (ESI): mass calcd. For $C_{17}H_{15}Cl_2N_5O_2$ 391.06, m/z found 392.1 [M+H]$^+$.

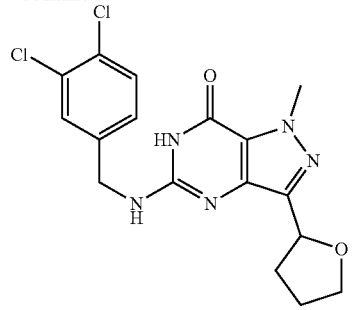

Compound 47

Preparation of 5-((3,4-dichlorobenzyl)amino)-1-methyl-3-(tetrahydrofuran-2-yl)-1H-pyrazolo[4,3-d]pyrimidin-7(6H)-one (Step 2 in Scheme B-4)

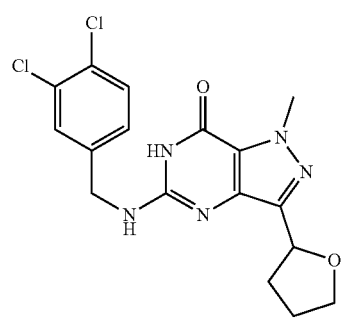 [SMILES: Cn1nc(C2CCCO2)c2nc(NCc3ccc(Cl)c(Cl)c3)[nH]c(=O)c21]

To a solution of 5-[(3,4-dichlorophenyl)methylamino]-3-(2,5-dihydrofuran-2-yl)-1-methyl-6H-pyrazolo[4,3-d]pyrimidin-7-one (0.3 g 229.45 μmol, 1 eq) in EtOH (50 mL) and THF (50 mL) was added Rh(PPh$_3$)$_3$Cl (21.23 mg, 22.95 μmol, 0.1 eq). The suspension was degassed and purged with H$_2$ for 3 times. The mixture was stirred at 30° C. for 16 hours under H$_2$ (20 psi.). LCMS and HPLC showed the reaction was complete. After filtered, the filtrate was concentrated under reduced pressure. The residue was purified by prep-HPLC (column: Phenomenex Luna C18 100 mm×30 mm 5 μm; mobile phase: [water (0.05% HCl)-MeCN]; B %: 35%-55%, 12 mins). MeCN was removed under reduced pressure at 30° C. The residue was dried over lyophilization. Compound 5-[(3,4-dichlorophenyl)methylamino]-1-methyl-3-tetrahydrofuran-2-yl-6H-pyrazolo[4,3-d]pyrimidin-7-one (20.7 mg, 49.82 μmol, 21.71% yield, 94.90% purity) was obtained as yellow solid. $^1$H NMR (DMSO-d$_6$, 400 MHz) δ 7.61~7.57 (m, 2H), 7.33 (d, J=8.0 Hz, 1H), 6.92~6.81 (m, 1H), 4.93 (t, J=6.8 Hz, 1H), 4.46 (s, 2H), 4.01 (s, 3H), 3.82~3.79 (m, 1H), 3.72~3.69 (m, 1H), 2.23~2.20 (m, 1H), 2.07~2.05 (m, 2H), 2.03~1.87 (m, 1H). HPLC: 94.90% (220 nm), 94.45% (215 nm), 98.07% (254 nm). MS (ESI): mass calcd. For C$_{17}$H$_7$C$_{12}$N$_5$O$_2$ 393.08, m/z found 394.0 [M+H]$^+$.

Scheme B-5

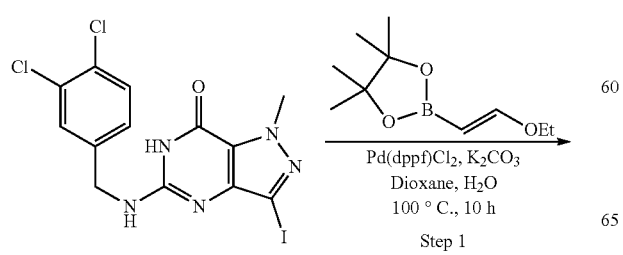

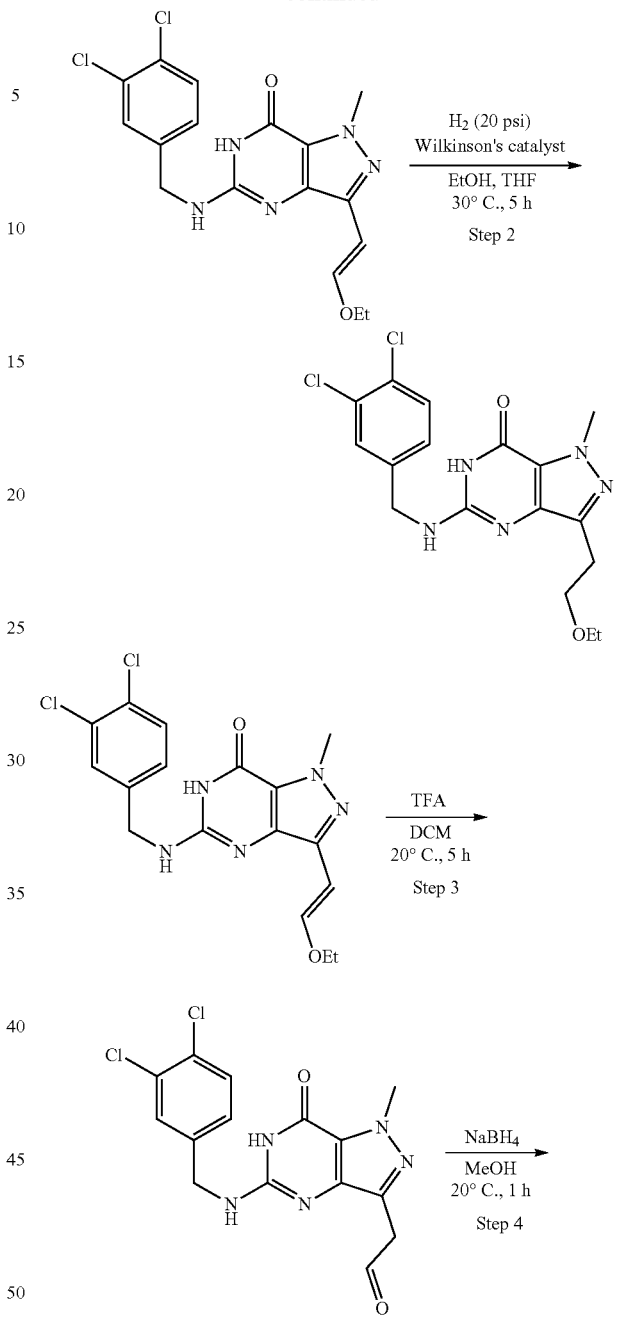

Compound 48

Preparation of 5-((3,4-dichlorobenzyl)amino)-3-(2-hydroxyethyl)-1-methyl-1H-pyrazolo[4,3-d]pyrimidin-7(6H)-one Preparation of (E)-5-((3,4-dichlorobenzyl)amino)-3-(2-ethoxyvinyl)-1-methyl-1H-pyrazolo[4,3-d]pyrimidin-7(6H)-one (Step 1 in Scheme B-5)

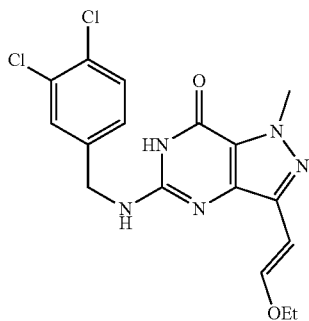 [SMILES: CCO/C=C/c1nn(C)c2c(=O)[nH]c(NCc3ccc(Cl)c(Cl)c3)nc12]

A mixture of 5-[(3,4-dichlorophenyl)methylamino]-3-iodo-1-methyl-6H-pyrazolo[4,3-d]pyrimidin-7-one (0.5 g 1.11 mmol, 1 eq), 2-[(E)-2-ethoxyvinyl]-4,4,5,5-tetramethyl-1,3,2-dioxaborolane (880.18 mg, 4.44 mmol, 4 eq), $K_2CO_3$ (460.62 mg, 3.33 mmol, 3 eq) and Pd(dppf)$C_{12}$ (121.94 mg, 166.64 μmol, 0.15 eq) in dioxane (12 mL) and $H_2O$ (3 mL) was stirred at 100° C. for 10 hours under $N_2$. LCMS and HPLC showed the reaction was complete. The solvent was removed under reduced pressure. The residue was purified by flash silica gel chromatography (Biotage®; 12 g SepaFlash® Silica Flash Column, Eluent of 0100% Ethyl acetate/Petroleum ether gradient at 50 mL/min). The eluent was removed under reduced pressure. Compound 5-[(3,4-dichlorophenyl)methylamino]-3-[(E)-2-ethoxyvinyl]-1-methyl-6H-pyrazolo-[4,3-d]pyrimidin-7-one (0.34 g, 862.39 μmol, 77.63% yield) was obtained as off white solid. $^1$H NMR (DMSO-$d_6$, 400 MHz) δ 11.09 (s, 1H), 7.62~7.56 (m, 3H), 7.34 (dd, J=2.0 Hz, 5.2 Hz, 1H), 6.62 (t, J=5.6 Hz, 1H), 5.77 (d, J=12.8 Hz, 1H), 5.25 (d, J=11.2 Hz, 1H), 4.46 (d, J=5.6 Hz, 2H), 3.91 (s, 3H), 3.82 (t, J=6.8 Hz, 2H), 1.21 (t, J=6.8 Hz, 3H).

Compound 49

Preparation of 5-((3,4-dichlorobenzyl)amino)-3-(2-ethoxyethyl)-1-methyl-1H-pyrazolo[4,3-d]pyrimidin-7(6H)-one (Step 2 in Scheme B-5)

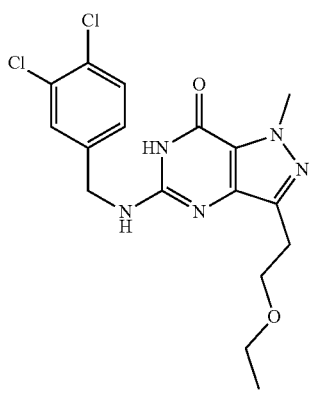 [SMILES: CCOCCc1nn(C)c2c(=O)[nH]c(NCc3ccc(Cl)c(Cl)c3)nc12]

A mixture of 5-[(3,4-dichlorophenyl)methylamino]-3-[(E)-2-ethoxyvinyl]-1-methyl-6H-pyrazolo[4,3-d]pyrimidin-7-one (0.15 g, 380.46 μmol, 1 eq) and Rh(PPh$_3$)$_3$Cl (35.20 mg, 38.05 μmol, 0.1 eq) in EtOH (50 mL) and THF (20 mL) was stirred at 30° C. for 5 hours under $H_2$ (20 psi.). HPLC and LCMS indicated the reaction was complete. After filtered, the filtrate was concentrated under reduced pressure. The residue was purified by prep-HPLC (column: Nano-micro Kromasil C18 100 mm×30 mm 5 μm; mobile phase: [water (0.1% TFA)-MeCN]; B %: 35%-55%, 10 mins). The eluent was removed under lyophilization. Compound 5-[(3, 4-dichlorophenyl)methylamino]-3-(2-ethoxyethyl)-1-methyl-6H-pyrazolo[4,3-d]pyrimidin-7-one (71.7 mg, 180.94 μmol, 47.56% yield) was obtained as white solid. $^1$H NMR (DMSO-$d_6$, 400 MHz) δ 11.08 (s, 1H), 7.62 (d, J=2.4 Hz, 1H), 7.57 (d, J=8.0 Hz, 1H), 7.34 (dd, J=2.0 Hz, 8.0 Hz, 1H), 6.62 (s, 1H), 4.44 (d, J=5.2 Hz, 2H), 3.99 (s, 3H), 3.82 (t, J=2.8 Hz, 2H), 3.35 (q, J=6.8 Hz, 2H), 2.84 (t, J=7.6 Hz, 2H), 1.03 (t, J=6.8 Hz, 3H). HPLC: 99.64% (220 nm), 99.62% (215 nm), 100.00% (254 nm). MS (ESI): mass calcd. For $C_{17}H_{19}Cl_2N_5O_2$ 395.09, m/z found 396.1 [M+H]$^+$.

Preparation of 2-(5-((3,4-dichlorobenzyl)amino)-1-methyl-7-oxo-6,7-dihydro-1H-pyrazolo[4,3-d]pyrimidin-3-yl)acetaldehyde (Step 3 in Scheme B-5)

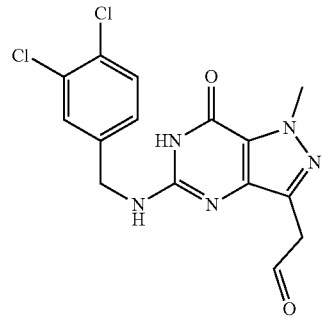 [SMILES: Cn1nc(CC=O)c2nc(NCc3ccc(Cl)c(Cl)c3)[nH]c(=O)c21]

To a mixture of 5-[(3,4-dichlorophenyl)methylamino]-3-[(E)-2-ethoxyvinyl]-1-methyl-6H-pyrazolo[4,3-d]pyrimidin-7-one (0.15 g 380.46 μmol, 1 eq) in DCM (10 mL) was added TFA (1 mL) dropwise at 0° C. Then the mixture was stirred at 20° C. for 5 hours. LCMS showed the reaction complete. The mixture was poured into water (10 mL) and the organic layer was separated. The aqueous was extracted with DCM (20 mL×5). The combined organic layer was washed with sat. NaHCO$_3$ to pH=7, dried over Na$_2$SO$_4$, filtered and concentrated under reduced pressure. The residue was used to the next step without further purification. Compound 2-[5-[(3,4-dichlorophenyl)methylamino]-1-methyl-7-oxo-6H-pyrazolo[4,3-d]pyrimidin-3-yl]acetaldehyde (0.1 g, 273.07 μmol, 71.77% yield) was obtained as yellow solid. $^1$H NMR (DMSO-$d_6$, 400 MHz) δ 11.08 (s, 1H), 9.67 (s, 1H), 7.62~7.55 (m, 2H), 7.34 (dd, J=2.0 Hz, 8.0 Hz, 1H), 6.59 (s, 1H), 4.42 (d, J=5.6 Hz, 2H), 4.05 (s, 3H), 3.75 (d, J=2.0 Hz, 2H).

Preparation of 5-((3,4-dichlorobenzyl)amino)-3-(2-hydroxyethyl)-1-methyl-1H-pyrazolo[4,3-d]pyrimidin-7(6H)-one (Step 4 in Scheme B-5)

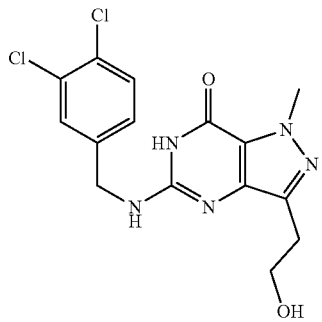 [SMILES: Cn1nc(CCO)c2nc(NCc3ccc(Cl)c(Cl)c3)[nH]c(=O)c21]

To a solution of 2-[5-[(3,4-dichlorophenyl)methylamino]-1-methyl-7-oxo-6H-pyrazolo[4,3-d]pyrimidin-3-yl]acetaldehyde (0.1 g, 273.07 μmol, 1 eq) in MeOH (5 mL) was added NaBH$_4$ (30.99 mg, 819.22 μmol, 3 eq) in portions at 0° C. Then the mixture was stirred at 20° C. for an hour. LCMS showed the reaction was complete. The mixture was quenched with ice water (5 mL) slowly and extracted with EtOAc (10 mL×4). The combined organic layer was washed with brine (5 mL×2), dried over Na$_2$SO$_4$, filtered and concentrated under reduced pressure. The residue was purified by prep-HPLC (column: Nano-micro Kromasil C18 100 mm×30 mm 5 μm mobile phase: [water (0.1% TFA)-MeCN]; B %: 20%-40%, 10 mins). The eluent was removed under lyophilization. Compound 5-[(3,4-dichlorophenyl)methylamino]-3-(2-hydroxyethyl)-1-methyl-6H-pyrazolo[4,3-d]pyrimidin-7-one (83.8 mg, 227.58 μmol, 83.34% yield) was obtained as white solid. $^1$H NMR (DMSO-d$_6$, 400 MHz) δ 7.64 (d, J=2.0 Hz, 1H), 7.59 (d, J=8.4 Hz, 1H), 7.37 (dd, J=2.0 Hz, 8.4 Hz, 1H), 6.63 (s, 1H), 4.46 (d, J=5.6 Hz, 2H), 4.00 (s, 3H), 3.67 (t, J=7.2 Hz, 2H), 2.80 (t, J=7.2 Hz, 2H). HPLC: 100.00% (220 nm), 99.85% (215 nm), 100.00% (254 nm). MS (ESI): mass calcd. For C$_{15}$H$_{15}$C$_{12}$N$_5$O$_2$ 367.06, m/z found 368.1 [M+H]$^+$.

Scheme B-6

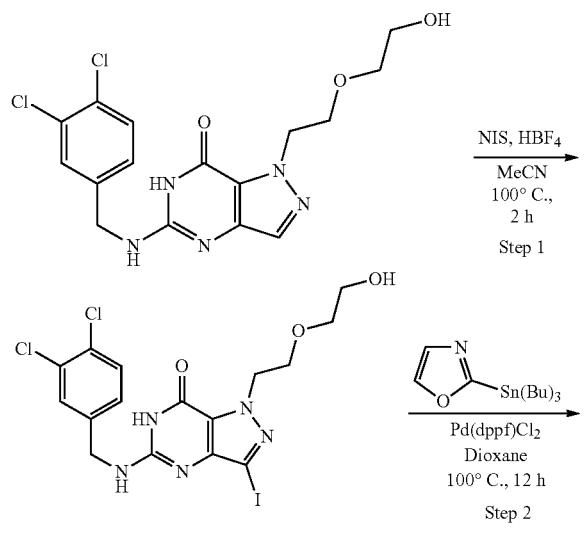

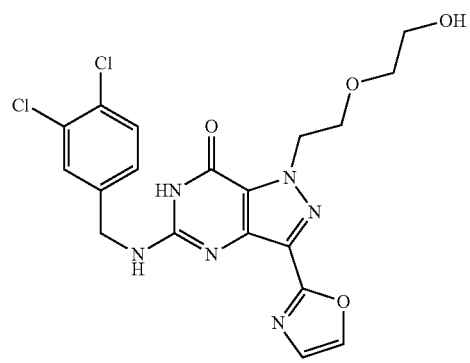

Compound 50

Preparation of 5-((3,4-dichlorobenzyl)amino)-1-(2-(2-hydroxyethoxy)ethyl)-3-(oxazol-2-yl)-1H-pyrazolo[4,3-d]pyrimidin-7(6H)-one Preparation of 5-((3,4-dichlorobenzyl)amino)-1-(2-(2-hydroxyethoxy)ethyl)-3-iodo-1H-pyrazolo[4,3-d]pyrimidin-7(6H)-one (Step 1 in Scheme B-6)

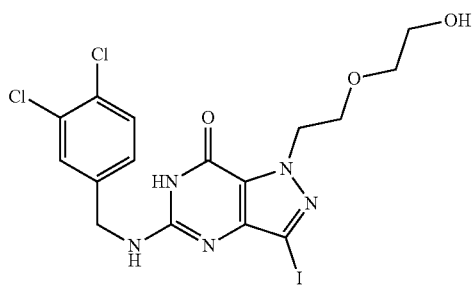 [SMILES: O=c1[nH]c(NCc2ccc(Cl)c(Cl)c2)nc2c(I)nn(CCOCCO)c12]

To a solution of 5-[(3,4-dichlorophenyl)methylamino]-1-[2-(2-hydroxyethoxy)ethyl]-6H-pyrazolo[4,3-d]pyrimidin-7-one (0.1 g, 251.10 μmol, 1 eq) and NIS (73.44 mg, 326.43 μmol, 1.3 eq) in MeCN (2 mL) was added HBF$_4$ (55.12 mg, 627.76 μmol, 39.10 μL, 2.5 eq) dropwise. The mixture was stirred at 100° C. for 10 hours. TLC showed the reaction was complete. H$_2$O (5 mL) was added to the reaction mixture. The reaction mixture was extracted with EtOAc (10 mL×3). The combined organic layers were washed with brine (5 mL×2), dried over Na$_2$SO$_4$, filtered and concentrated under reduced pressure. Compound 5-((3,4-dichlorobenzyl)amino)-1-(2-(2-hydroxyethoxy)ethyl)-3-iodo-1H-pyrazolo[4,3-d]pyrimidin-7(6H)-one (0.12 g, 228.95 μmol, 91.18% yield) was obtained as brown solid. $^1$H NMR (DMSO-d$_6$, 400 MHz) δ 7.70 (s, 1H), 7.60~7.57 (m, 2H), 7.40 (dd, J 8.0 Hz, J 2.0 Hz, 1H), 6.72 (t, J 5.6 Hz, 1H), 4.56 (d, J 5.2 Hz, 2H), 4.46 (d, J 5.2 Hz, 2H), 3.78 (t, J 6.0 Hz, 2H), 3.40~3.38 (m, 4H).

Preparation of 5-((3,4-dichlorobenzyl)amino)-1-(2-(2-hydroxyethoxy)ethyl)-3-(oxazol-2-yl)-1H-pyrazolo[4,3-d]pyrimidin-7(6H)-one (Step 2 in Scheme B-6)

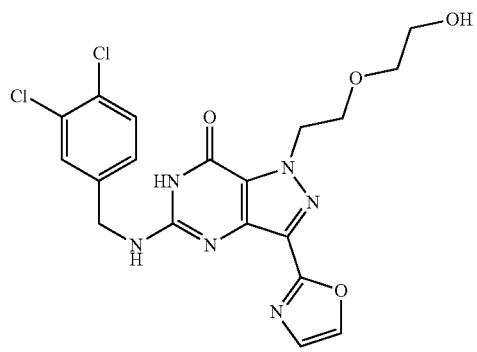 [SMILES: O=c1[nH]c(NCc2ccc(Cl)c(Cl)c2)nc2c(-c3ncco3)nn(CCOCCO)c12]

A mixture of 5-[(3,4-dichlorophenyl)methylamino]-1-[2-(2-hydroxyethoxy)ethyl]-3-iodo-6H-pyrazolo[4,3-d]pyrimidin-7-one (55 mg, 104.93 µmol, 1 eq), tributyl(oxazol-2-yl)stannane (375.77 mg, 1.05 mmol, 10 eq) and Pd(dppf)C$l_2$ (15.36 mg, 20.99 µmol, 0.2 eq) in dioxane (2 mL) was degassed and purged with N$_2$ for 3 times and then the mixture was stirred at 100° C. for 12 hours under N$_2$ atmosphere. LCMS and HPLC showed the reaction was complete. The reaction mixture was concentrated under reduced pressure. The residue was purified by prep-HPLC (column: Phenomenex Luna C18 100 mm×30 mm 5 µm; mobile phase: [water (0.04% HCl)-MeCN]; B %: 20%-50%, 10 mins). MeCN was removed under reduced pressure at 30° C. The residue was dried over lyophilization. Compound 5-((3,4-dichlorobenzyl)amino)-1-(2-(2-hydroxyethoxy)ethyl)-3-(oxazol-2-yl)-1H-pyrazolo[4,3-d]pyrimidin-7(6H)-one (14.0 mg, 28.83 µmol, 27.48% yield, 95.832% purity) was obtained as light yellow solid. $^1$H NMR (DMSO-d$_6$, 400 MHz) δ 8.22 (s, 1H), 7.81 (s, 1H), 7.58~7.57 (m, 1H), 7.47~7.41 (m, 2H), 7.07 (s, 1H), 4.66 (s, 2H), 4.50 (s, 2H), 3.85 (s, 2H), 3.59 (s, 2H), 3.45 (s, 2H). HPLC: 95.83% (220 nm), 95.77% (215 nm), 98.53% (254 nm). MS (ESI): mass calcd. For C$_{19}$H$_{18}$C$l_2$N$_6$O$_4$ 464.08, m/z found 465.0 [M+H]$^+$.

Scheme B-7

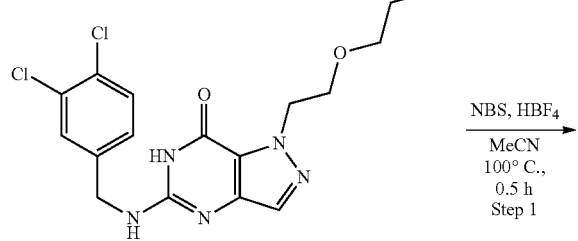

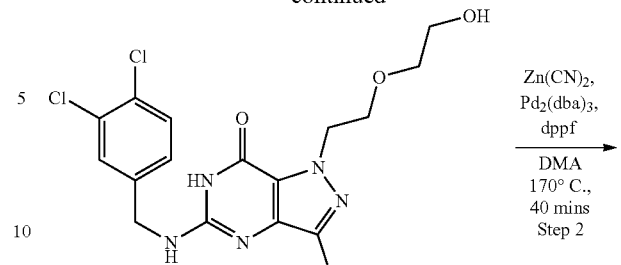

Compound 51

Preparation of 5-((3,4-dichlorobenzyl)amino)-1-(2-(2-hydroxyethoxy)ethyl)-7-oxo-6,7-dihydro-1H-pyrazolo[4,3-d]pyrimidine-3-carbonitrile Compound 52

Preparation of 3-bromo-5-((3,4-dichlorobenzyl)amino)-1-(2-(2-hydroxyethoxy)ethyl)-1H-pyrazolo[4,3-d]pyrimidin-7(6H)-one (Step 1 in Scheme B-7)

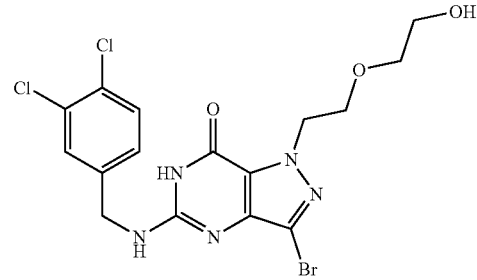 [SMILES: O=c1[nH]c(NCc2ccc(Cl)c(Cl)c2)nc2c(Br)nn(CCOCCO)c12]

To a mixture of 5-[(3,4-dichlorophenyl)methylamino]-1-[2-(2-hydroxyethoxy)ethyl]-6H-pyrazolo[4,3-d]pyrimidin-7-one (230 mg, 577.54 µmol, 1 eq) and NBS (113.07 mg, 635.29 µmol, 1.1 eq) in MeCN (3 mL) was added HBF$_4$ (126.79 mg, 1.44 mmol, 89.92 µL, 2.5 eq). The mixture was stirred at 100° C. for half an hour. TLC showed the reaction was complete. The reaction mixture was quenched with H$_2$O (5 mL) and extracted with EtOAc (8 mL×3). The combined organic layers were washed with sat. NaHCO$_3$ (10 mL), dried over Na$_2$SO$_4$, filtered and concentrated under reduced pressure. The residue was purified by flash silica gel chromatography (Biotage®; 4 g SepaFlash® Silica Flash Column, Eluent of 0~100% Ethyl acetate/Methanol at 30 mL/min). The eluent was removed under reduced pressure. Compound 3-bromo-5-[(3,4-dichlorophenyl)methylamino]-1-[2-(2-hydroxyethoxy)ethyl]-6H-pyrazolo[4,3-d]pyrimidin-7-one (190 mg, crude) was obtained as white solid. $^1$H NMR (DMSO-d$_6$, 400 MHz) δ 11.27 (s, 1H), 7.66 (d, J=1.6 Hz, 1H), 7.59 (d, J=8.4 Hz, 1H), 7.37 (dd, J=8.4 Hz, 1.6 Hz, 1H), 6.76 (t, J=5.6 Hz, 1H), 4.57~4.52 (m, 3H), 4.47 (d, J=5.6 Hz, 2H), 3.78 (t, J=5.6 Hz, 2H), 3.41~3.37 (m, 4H). HPLC: 99.39% (220 nm), 99.22% (215 nm), 99.59% (254 nm). MS (ESI): mass calcd. For C$_{16}$H$_{16}$BrCl$_2$N$_5$O$_3$ 474.98, m/z found 476.0 [M+H]$^+$.

Preparation of 5-((3,4-dichlorobenzyl)amino)-1-(2-(2-hydroxyethoxy)ethyl)-7-oxo-6,7-dihydro-1H-pyrazolo[4,3-d]pyrimidine-3-carbonitrile (Step 2 in Scheme B-7)

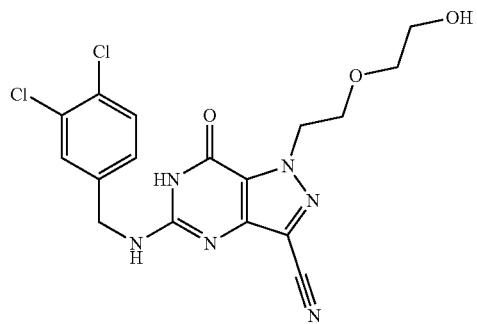 [SMILES: N#Cc1nn(CCOCCO)c2c(=O)[nH]c(NCc3ccc(Cl)c(Cl)c3)nc12]

A mixture of 3-bromo-5-[(3,4-dichlorophenyl)methylamino]-1-[2-(2-hydroxyethoxy)ethyl]-6H-pyrazolo[4,3-d]pyrimidin-7-one (40 mg, 83.83 µmol, 1 eq), Zn(CN)$_2$ (29.53 mg, 251.50 µmol, 3 eq), dppf (7.44 mg, 13.41 µmol, 0.16 eq) and Pd$_2$(dba)$_3$ (6.14 mg, 6.71 µmol, 0.08 eq) in DMA (0.5 mL) was degassed and purged with N$_2$ for 3 times and then the mixture was stirred at 170° C. for 40 mins under N$_2$ atmosphere. LC-MS showed the reaction was complete. After filtered, the filtrate was purified by prep-HPLC (column: Phenomenex Gemini-NX 150 30 mm×5 µm; mobile phase: [water (10 mM NH$_4$HCO$_3$)-MeCN]; B %: 20%-50%, 8 mins). The solvent was removed under freeze drying. Compound 5-[(3,4-dichlorophenyl)methylamino]-1-[2-(2-hydroxyethoxy)ethyl]-7-oxo-6H-pyrazolo[4,3-d]pyrimidine-3-carbonitrile (27.7 mg, 64.67 µmol, 19.28% yield, 98.81% purity) was obtained as white solid. $^1$H NMR (DMSO-d$_6$, 400 MHz) δ 7.63 (d, J=1.6 Hz, 1H), 7.59 (d, J=8.4 Hz, 1H), 7.35 (dd, J=8.4 Hz, 1.6 Hz, 1H), 7.05 (t, J=5.6 Hz, 1H), 4.66 (t, J=5.2 Hz, 2H), 4.51 (d, J=6.0 Hz, 3H), 3.84 (t, J=5.2 Hz, 2H), 3.39 (s, 4H). HPLC: 98.81% (220 nm), 98.60% (215 nm), 98.43% (254 nm). MS (ESI): mass calcd. For C$_{17}$H$_{16}$C2N$_6$O$_3$ 422.07, m/z found 423.0 [M+H]$^+$.

Scheme B-8

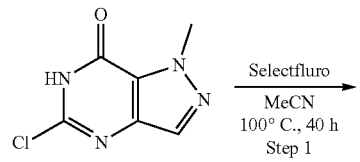

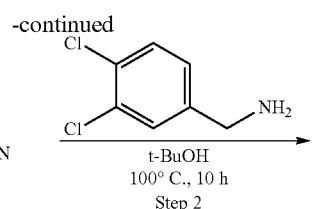

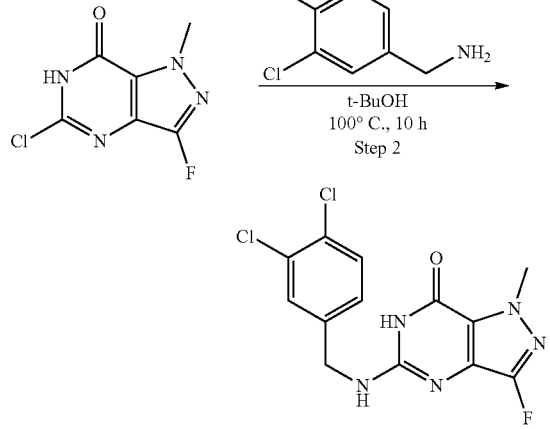

Compound 53

Preparation of 5-((3,4-dichlorobenzyl)amino)-3-fluoro-1-methyl-1H-pyrazolo[4,3-d]pyrimidin-7(6H)-one Preparation of 5-chloro-3-fluoro-1-methyl-$^1$H-pyrazolo[4,3-d]pyrimidin-7(6H)-one (Step 1 in Scheme B-8)

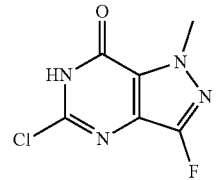

A mixture of 5-chloro-1-methyl-6H-pyrazolo[4,3-d]pyrimidin-7-one (0.5 g, 2.71 mmol, 1 eq) and Select F (2.88 g 8.13 mmol, 3 eq) in MeCN (15 mL) was stirred at 100° C. for 40 hours. LCMS and HPLC showed ~20% 5-chloro-1-methyl-1H-pyrazolo[4,3-d]pyrimidin-7(6H)-one was remained and ~40% was desired peak. The solvent was removed under reduced pressure. The residue was dissolved in water (20 mL) and stirred at 20° C. for 15 mins. After filtered, the solid was collected. The residue was used to the next step without further purification. Compound 5-chloro-3-fluoro-1-methyl-6H-pyrazolo[4,3-d]pyrimidin-7-one (0.4 g, 1.97 mmol, 72.90% yield) was obtained as yellow solid. H NMR (DMSO-d$_6$, 400 MHz) δ 4.13 (s, 3H).

Preparation of 5-((3,4-dichlorobenzyl)amino)-3-fluoro-1-methyl-$^1$H-pyrazolo[4,3-d]pyrimidin-7(6H)-one (Step 2 in Scheme B-8)

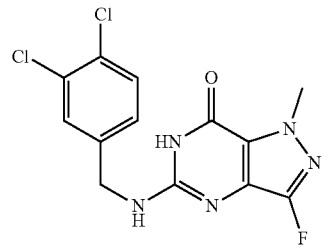 [SMILES: Cn1nc(F)c2nc(NCc3ccc(Cl)c(Cl)c3)[nH]c(=O)c21]

A mixture of 5-chloro-3-fluoro-1-methyl-6H-pyrazolo[4,3-d]pyrimidin-7-one (0.1 g, 493.65 µmol, 1 eq) and (3,4- dichlorophenyl)methanamine (173.81 mg, 987.30 µmol, 131.67 µL, 2 eq) in t-BuOH (3 mL) was stirred at 100° C. for 10 hours under N₂. LCMS and HPLC showed the reaction was complete. The solvent was removed under reduced pressure. The residue was purified by prep-HPLC (column: Luna C8 100 mm×30 mm 5 µm; mobile phase: [water (0.1% TFA)-MeCN]; B %: 35%-60%, 10 mins). The eluent was removed under lyophilization. Compound 5-[(3,4-dichlorophenyl)methylamino]-3-fluoro-1-methyl-6H-pyrazolo[4,3-d]pyrimidin-7-one (15.6 mg, 45.59 µmol, 9.24% yield) was obtained as white solid. $^1$H NMR (DMSO-$d_6$, 400 MHz) δ 11.28 (s, 1H), 7.60~7.58 (m, 2H), 7.32 (dd, J=2.0 Hz, 8.4 Hz, 1H), 6.68 (t, J=5.6 Hz, 1H), 4.46 (d, J=5.6 Hz, 2H), 3.95 (s, 3H). HPLC: 95.42% (220 nm), 94.90% (215 nm), 100.00% (254 nm). MS (ESI): mass calcd. For $C_{13}H_{10}C_2FN_5O$ 341.02, m/z found 342.0 [M+H]$^+$.

Scheme B-9

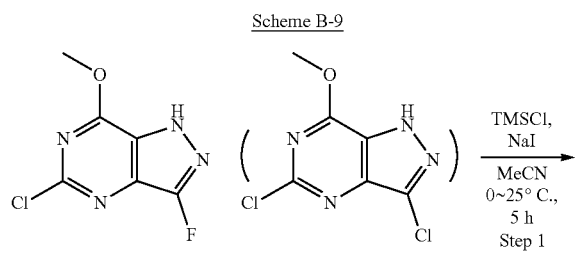

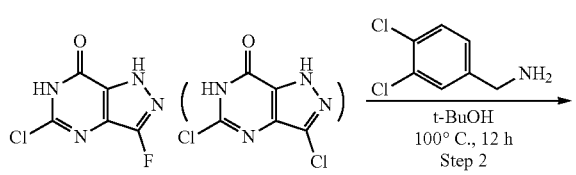

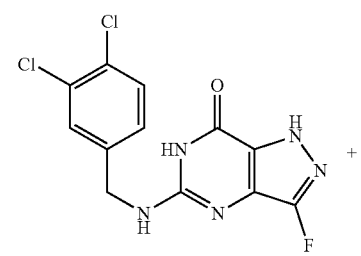

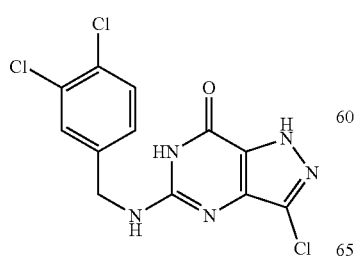

Compound 54 and Compound 55

Preparation of 5-((3,4-dichlorobenzyl)amino)-3-fluoro-1H-pyrazolo[4,3-d]pyrimidin-7(6H)-one and 3-chloro-5-((3,4-dichlorobenzyl)amino)-1H-pyrazolo[4,3-d]pyrimidin-7(6H)-one Preparation of 5-chloro-3-fluoro-1H-pyrazolo[4,3-d]pyrimidin-7(6H)-one and 3,5-dichloro-1H-pyrazolo[4,3-d]pyrimidin-7(6H)-one (Step 1 in Scheme B-9)

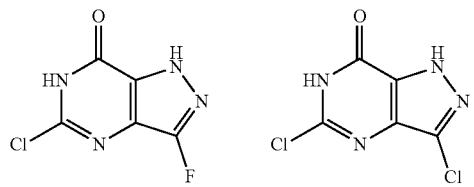 [SMILES: O=c1[nH]c(Cl)nc2c(F)n[nH]c12 ; O=c1[nH]c(Cl)nc2c(Cl)n[nH]c12]

To a mixture of 5-chloro-3-fluoro-7-methoxy-1H-pyrazolo[4,3-d]pyrimidine (100 mg, 493.65 µmol, 1 eq) and 3,5-dichloro-7-methoxy-1H-pyrazolo[4,3-d]pyrimidine (493.65 µmol, 1 eq) in MeCN (1 mL) was added NaI (295.97 mg, 1.97 mmol, 4 eq) and TMSCl (214.52 mg, 1.97 mmol, 250.61 µL, 4 eq) at 0° C. Then the mixture was stirred at 25° C. for 5 hours. TLC indicated the reaction was complete. The reaction mixture was quenched with H₂O (1 mL) and concentrated under reduced pressure. The aqueous was extracted with EtOAc (1 mL×3). The combined organic layers were washed with brine (1 mL), dried over Na₂SO₄, filtered and concentrated under reduced pressure. A mixture of compound 5-chloro-3-fluoro-1,6-dihydro pyrazolo[4,3-d]pyrimidin-7-one (100 mg, crude) and 3,5-dichloro-1,6-dihydro pyrazolo[4,3-d]pyrimidin-7-one was obtained as brown solid. MS (ESI): mass calcd. For $C_5H_2ClFN_4O$ 187.99 m/z found 189.0 [M+H]+; $C_5H_2Cl_2N_4O$ 203.96 m/z found 205.0 [M+H]$^+$.

Preparation of 5-((3,4-dichlorobenzyl)amino)-3-fluoro-1H-pyrazolo[4,3-d]pyrimidin-7(6H)-one and 3-chloro-5-((3,4-dichlorobenzyl)amino)-1H-pyrazolo[4,3-d]pyrimidin-7(6H)-one (Step 2 in Scheme B-9)

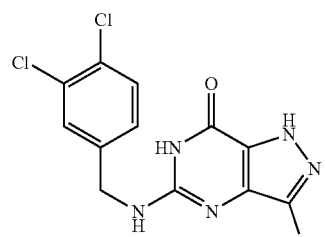

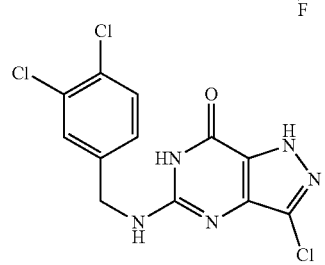

To a mixture of 5-chloro-3-fluoro-1,3a,6,7a-tetrahydropyrazolo[4,3-d]pyrimidin-7-one (130 mg, 682.19 μmol, 1 eq) and 3,5-dichloro-1,3a,6,7a-tetrahydropyrazolo[4,3-d]pyrimidin-7-one (682.19 μmol, 1 eq) in t-BuOH (4 mL) was added (3,4-dichlorophenyl)methanamine (240.19 mg 1.36 mmol, 181.96 μL, 2 eq). The mixture was stirred at 100° C. for 12 hours. HPLC showed the reaction was complete. The reaction mixture was concentrated under reduced pressure. The residue was purified by prep-HPLC (column: Welch Xtimate C18 100 mm×25 mm 3 μm; mobile phase: [water (0.1% TFA)-MeCN]; B %: 30%-50%, 12 mins). The solvent was removed under freeze drying. 5-[(3,4-Dichlorophenyl)methylamino]-3-fluoro-1,6-dihydropyrazolo[4,3-d]pyrimidin-7-one (Compound 54) (6.6 mg, 18.94 μmol, 2.78% yield, 94.16% purity) was obtained as white solid. $^1$H NMR (DMSO-$d_6$, 400 MHz) δ 13.19 (s, 1H), 11.19 (s, 1H), 7.60~7.58 (m, 2H), 7.34 (dd, J=8.4 Hz, 2.0 Hz, 1H), 6.68 (t, J=5.6 Hz, 1H), 4.47 (d, J=6.0 Hz, 2H). HPLC: 94.16% (220 nm), 90.65% (215 nm), 90.27% (254 nm). MS (ESI): mass calcd. For $C_{12}H_8Cl_2FN_5O$ 327.01, m/z found 328.0 [M+H]$^+$. 3-Chloro-5-[(3,4-dichlorophenyl)methylamino]-1,6-dihydropyrazolo[4,3-d]pyrimidin-7-one (Compound 55) (8.2 mg, 23.34 μmol, 4.45% yield, 98.1% purity) was obtained as off white solid. $^1$H NMR (DMSO-$d_6$, 400 MHz) δ 13.85 (s, 1H), 11.17 (s, 1H), 7.64 (d, J=1.6 Hz, 1H), 7.60 (d, J=8.0 Hz, 1H), 7.36 (dd, J=8.4 Hz, 2.0 Hz, 1H), 6.73 (t, J=5.6 Hz, 1H), 4.49 (d, J=6.4 Hz, 2H). HPLC: 98.10% (220 nm), 98.04% (215 nm), 99.41% (254 nm). MS (ESI): mass calcd. For $C_{12}H_8Cl_3N_5O$ 342.98, m/z found 344.0 [M+H]$^+$.

Scheme C-1

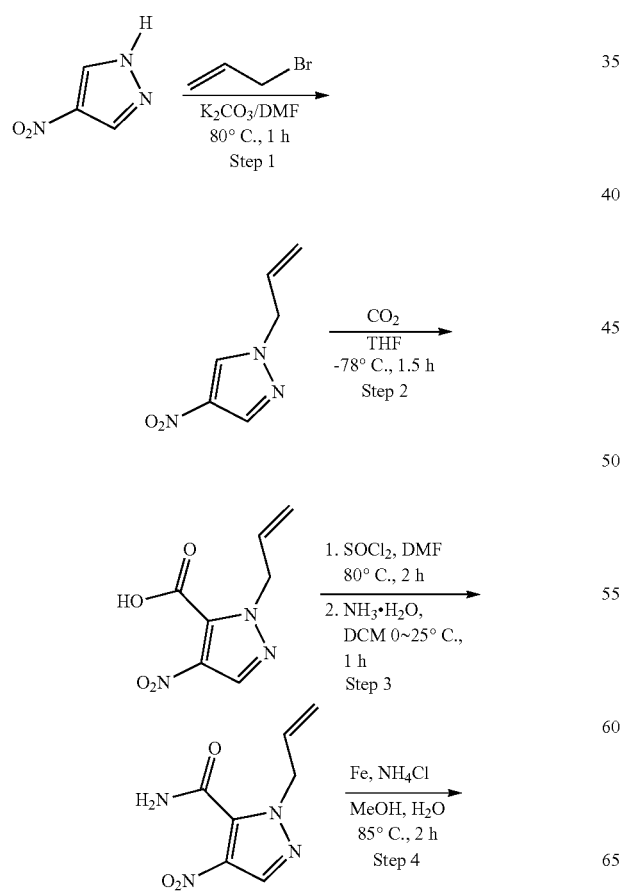

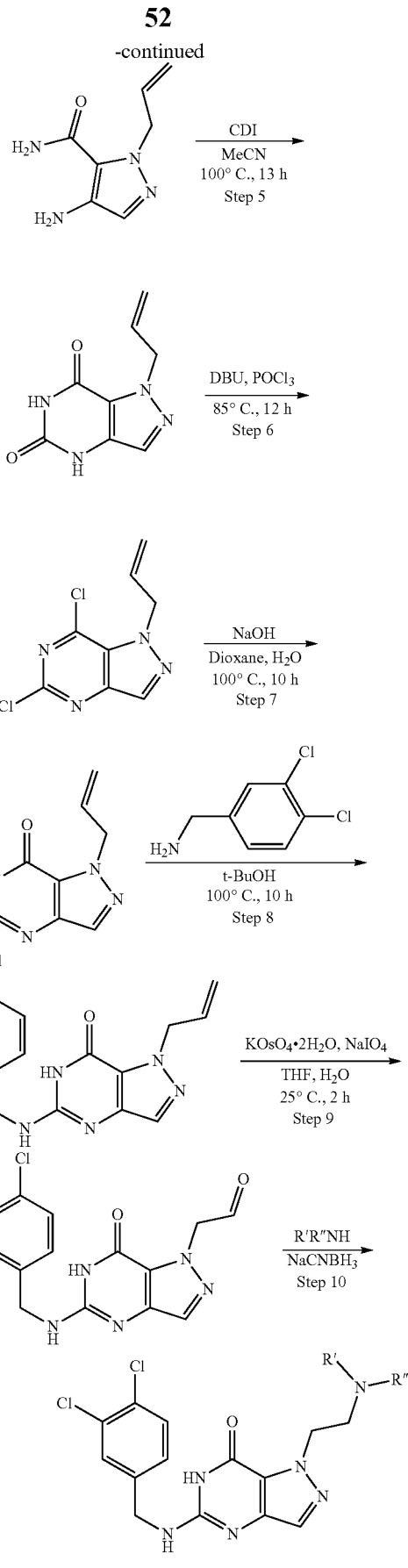

General Procedures for Preparing Compounds in Scheme C-1

Preparation of 1-allyl-4-nitro-pyrazole (Step 1 in Scheme C-1)

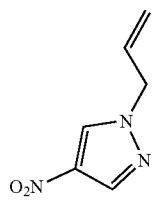

To a solution of 4-nitro-1H-pyrazole (200 g, 1.77 mol, 1 eq) in DMF (1 L) was added 3-bromoprop-1-ene (235.29 g, 1.94 mol, 1.1 eq) and $K_2CO_3$ (488.74 g, 3.54 mol, 2 eq) at 25° C. under $N_2$. Then the mixture was stirred at 80° C. for an hour. TLC showed the reaction was complete. The reaction mixture was quenched with ice water (500 mL) at 0° C. and then extracted with MTBE (500 mL×3). The combined organic layers were washed with brine (300 mL×6), dried over $Na_2SO_4$, filtered and concentrated under reduced pressure to give 1-allyl-4-nitro-pyrazole (270 g, 1.76 mol, 99.71% yield) as brown oil. H NMR ($CDCl_3$, 400 MHz) δ 8.16 (s, 1H), 8.09 (s, 1H), 6.07~6.00 (m, 1H), 5.44~5.34 (m, 2H), 4.78 (d, J=6.0 Hz, 2H).

Preparation of 2-allyl-4-nitro-pyrazole-3-carboxylic Acid (Step 2 in Scheme C-1)

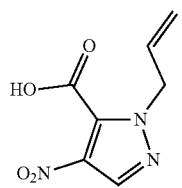

To a solution of 1-allyl-4-nitro-pyrazole (50 g 326.50 mmol, 1 eq) in THF (500 mL) was added LiHMDS (1 M, 489.75 mL, 1.5 eq) dropwise at −78° C. under $N_2$. After that, the mixture was stirred at −78° C. for an hour. Then dry $CO_2$ was bubbled to the above mixture for half an hour. TLC showed ~30% of the starting material was remained and a new spot was formed with lager polarity. The reaction mixture (5 batches) was quenched with water (2.5 L) at 0° C. and then adjusted to pH=8~9 with sat.$Na_2CO_3$. The mixture was extracted with MTBE (1 L×3) to recover 1-allyl-4-nitro-pyrazole. The aqueous layer was then adjusted to pH=1 with 2N HCl and then extracted with EtOAc (2 L×3). The combined organic layers were washed with brine (1 L), dried over $Na_2SO_4$, filtered and concentrated under reduced pressure to give 2-allyl-4-nitro-pyrazole-3-carboxylic acid (200 g, 1.01 mol, 62.14% yield) as brown oil. $^1$H NMR (DMSO-$d_6$, 400 MHz) δ 8.34 (s, 1H), 6.02~5.94 (m, 1H), 5.25 (dd, J=10.4 Hz, 1.2 Hz, 1H), 5.10 (dd, J=17.2 Hz, 1.2 Hz, 1H), 4.90 (d, J=5.6 Hz, 2H).

Preparation of 2-allyl-4-nitro-pyrazole-3-carboxamide (Step 3 in Scheme C-1)

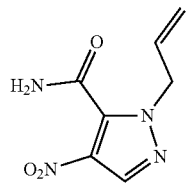

A solution of 2-allyl-4-nitro-pyrazole-3-carboxylic acid (65 g, 329.70 mmol, 1 eq) in $SOCl_2$ (200 mL) and DMF (5 mL) was stirred at 80° C. for 2 hours. TLC showed the reaction was complete. The reaction mixture was concentrated under reduce pressure to give 1-allyl-5-(chlorosylmethyl)-4-nitro-pyrazole (80 g, crude) as brown oil. A solution of 2-allyl-4-nitro-pyrazole-3-carbonyl chloride (80 g, 371.07 mmol, 1 eq) in DCM (50 mL) was added to $NH_3$—$H_2O$ (200 mL) dropwise at 0° C. and then the mixture was stirred at 25° C. for an hour. TLC showed the reaction was complete. There was some solid formed. After filtered, the solid was collected and the filtrate was extracted with EtOAc (200 mL×3). The combined organic layers were washed with brine (100 mL), dried over $Na_2SO_4$, filtered and concentrated under reduced pressure. The combined residue was purified by flash silica gel chromatography (Biotage®; 330 g SepaFlash® Silica Flash Column, Eluent of 050% Ethyl acetate/Petroleum ether gradient at 200 mL/min) to give 2-allyl-4-nitro-pyrazole-3-carboxamide (22 g 112.15 mmol, 30.22% yield) as light yellow solid. $^1$H NMR (DMSO-$d_6$, 400 MHz) δ 8.48 (s, 1H), 8.31 (s, 1H), 8.29 (s, 1H), 6.0~5.92 (m, 1H), 5.24 (dd, J=10.4 Hz, 0.8 Hz, 1H), 5.13 (dd, J=17.2 Hz, 1.0 Hz, 1H), 4.81 (br d, J=5.6 Hz, 2H).

Preparation of 2-allyl-4-amino-pyrazole-3-carboxamide (Step 4 in Scheme C-1)

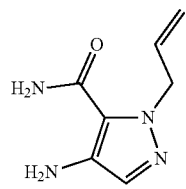

To a solution of 2-allyl-4-nitro-pyrazole-3-carboxamide (22 g, 112.15 mmol, 1 eq) in MeOH (150 mL) and $H_2O$ (50 mL) was added $NH_4Cl$ (12.00 g, 224.30 mmol, 2 eq) and Fe (18.79 g, 336.45 mmol, 3 eq) at 25° C. The mixture was stirred at 85° C. for 2 hours. TLC indicated 2-allyl-4-nitro-pyrazole-3-carboxamide was consumed completely and one major new spot with larger polarity was detected. The reaction mixture was filtered and the filter cake was washed with MeOH (100 mL). The combined filtrate was concentrated under reduced pressure. The residue was diluted with water (50 mL) and extracted with DCM and i-PrOH (v:v=3:1, 100 mL×3). The combined organic layers were washed with brine (50 mL), dried over $Na_2SO_4$, filtered and concentrated under reduced pressure to give 2-allyl-4-aminopyrazole-3-carboxamide (17.5 g, 105.31 mmol, 93.90% yield) as brown oil. $^1$H NMR (DMSO-$d_6$, 400 MHz) δ 7.37 (s, 2H), 7.08 (s, 1H), 5.93~5.84 (m, 1H), 5.04 (dd, J=10.4 Hz, 1.6 Hz, 1H), 4.96 (d, J=5.2 Hz, 2H), 4.88 (dd, J=17.2, 1.6 Hz, 1H), 4.35 (s, 2H).

Preparation of 1-allyl-4H-pyrazolo[4,3-d]pyrimidine-5,7-dione (Step 5 in Scheme C-1)

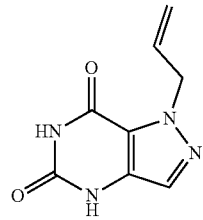

To a solution of 2-allyl-4-amino-pyrazole-3-carboxamide (17.5 g, 105.31 mmol, 1 eq) in MeCN (250 mL) was added CDI (22.20 g, 136.90 mmol, 1.3 eq) in portions over an hour at 100° C. under N$_2$. Then the mixture was heated at 100° C. for 12 hours. LC-MS showed the reaction was complete. The reaction mixture was filtered at 100° C. and washed the cake with MeCN (100 mL×3) to give 1-allyl-4H-pyrazolo[4,3-d]pyrimidine-5,7-dione (15.2 g, 79.09 mmol, 75.11% yield) as off-white solid. $^1$H NMR (DMSO-$d_6$, 400 MHz) δ 11.14 (s, 1H), 11.00 (s, 1H), 7.40 (s, 1H), 6.03~5.94 (m, 1H), 5.14 (d, J=7.2 Hz, 1H), 5.03~4.97 (m, 3H).

Preparation of 1-allyl-5,7-dichloro-pyrazolo[4,3-d]pyrimidine (Step 6 in Scheme C-1)

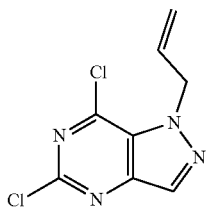

To a solution of 1-allyl-4H-pyrazolo[4,3-d]pyrimidine-5,7-dione (15 g, 78.05 mmol, 1 eq) in POCl$_3$ (119.68 g, 780.54 mmol, 72.53 mL, 10 eq) was added DBU (71.30 g, 468.32 mmol, 70.59 mL, 6 eq) dropwise at 50° C. under N$_2$. Then the mixture was stirred at 85° C. for 12 hours. TLC showed 1-allyl-4H-pyrazolo[4,3-d]pyrimidine-5,7-dione was consumed completely and one new spot with lower polarity was detected. The reaction mixture was cooled to room temperature and poured into ice water (200 mL) slowly at 0° C. and then extracted with EtOAc (200 mL×3). The combined organic layers were washed with sat. Na$_2$CO$_3$ to pH=7~8 and then washed with brine (100 mL), dried over Na$_2$SO$_4$, filtered and concentrated under reduced pressure to give 1-allyl-5,7-dichloro-pyrazolo[4,3-d]pyrimidine (17 g, 74.21 mmol, 95.08% yield) as brown oil. $^1$H NMR (DMSO-$d_6$, 400 MHz) δ 8.56 (s, 1H), 6.12~6.05 (m, 1H), 5.35~5.30 (dd, J=4.8, 1.6 Hz, 2H), 5.21 (dd, J=10.8 Hz, 0.8 Hz, 1H), 4.94 (dd, J=17.2 Hz, 1.2 Hz, 1H).

Preparation of 1-allyl-5-chloro-1H-pyrazolo[4,3-d]pyrimidin-7(6H)-one (Step 7 in Scheme C-1)

To a solution of 1-allyl-5,7-dichloro-pyrazolo[4,3-d]pyrimidine (6.8 g, 29.69 mmol, 1 eq) in dioxane (60 mL) was added NaOH (1 M, 29.69 mL, 1 eq) at 25° C. The mixture was stirred at 100° C. for 10 hours. TLC and LC-MS showed the reaction was complete. The organic solvent was removed under reduced pressure. The aqueous was made pH=5 with 2N HCl. There was some solid formed. The solid was collected after filtered and then concentrated under reduced pressure. The residue was used to the next step without further purification. Compound 1-allyl-5-chloro-6H-pyrazolo[4,3-d]pyrimidin-7-one (5.5 g, 26.11 mmol, 87.97% yield) was obtained as pale yellow solid. $^1$H NMR (DMSO-$d_6$, 400 MHz) δ 13.32 (s, 1H), 8.00 (s, 1H), 6.07~5.99 (m, 1H), 5.18~5.13 (m, 3H), 4.99 (d, J=17.2 Hz, 1H).

Compound 56

Preparation of 1-allyl-5-((3,4-dichlorobenzyl)amino)-1H-pyrazolo[4,3-d]pyrimidin-7(6H)-one (Step 8 in Scheme C-1)

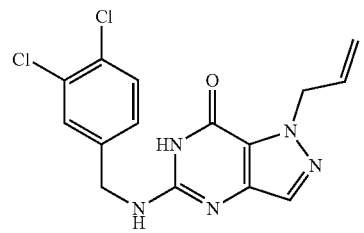 [SMILES: C=CCn1ncc2nc(NCc3ccc(Cl)c(Cl)c3)[nH]c(=O)c21]

A solution of 1-allyl-5-chloro-6H-pyrazolo[4,3-d]pyrimidin-7-one (4 g, 18.99 mmol, 1 eq) and (3,4-dichlorophenyl)methanamine (10.03 g, 56.97 mmol, 7.60 mL, 3 eq) in t-BuOH (60 mL) was heated at 100° C. for 10 hours. LC-MS showed the reaction was complete. The solvent was removed under reduced pressure. The residue was dissolved in EtOAc (200 mL) and washed with 0.005N HCl (50 mL×10). The organic layer was dried over Na$_2$SO$_4$, filtered and concentrated under reduced pressure. The residue was triturated with EtOAc (30 mL). After filtered, the solid was collected. Compound 1-allyl-5-[(3,4-dichlorophenyl)methylamino]-6H-pyrazolo[4,3-d]pyrimidin-7-one (3 g, 8.49 mmol, 44.70% yield, 99.09% purity) was obtained as white solid and 59.6 mg was delivered. $^1$H NMR (DMSO-$d_6$, 400 MHz) δ 11.08 (s, 1H), 9.58~7.56 (m, 3H), 7.31 (dd, J=8.4 Hz, 2.0 Hz, 1H), 6.56 (t, J=5.6 Hz, 1H), 6.01~5.97 (m, 1H), 5.11 (d, J=10.4 Hz, 1H), 5.03 (d, J=5.6 Hz, 2H), 4.96 (d, J=15.6 Hz, 1H), 4.46 (d, J=6.0 Hz, 2H). HPLC: 99.08% (220 nm), 99.08% (215 nm), 100.00% (254 nm). MS (ESI): mass calcd. For C$_{15}$H$_{13}$C$_{12}$N$_5$O 349.05, m/z found 350.0 [M+H]$^+$.

Preparation of 2-(5-((3,4-dichlorobenzyl)amino)-7-oxo-6,7-dihydro-1H-pyrazolo[4,3-d]pyrimidin-1-yl)acetaldehyde (Step 9 in Scheme C-1)

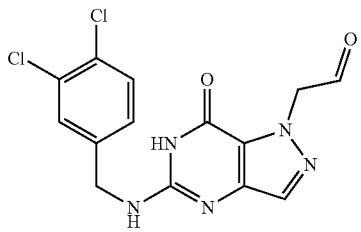 [SMILES: O=CCn1ncc2nc(NCc3ccc(Cl)c(Cl)c3)[nH]c(=O)c21]

A mixture of 1-allyl-5-[(3,4-dichlorophenyl)methylamino]-6H-pyrazolo[4,3-d]pyrimidin-7-one (1 g, 2.86 mmol, 1 eq) and $K_2O_sO_{4-2}H_2O$ (105.21 mg, 285.55 µmol, 0.1 eq) in THF (20 mL) and $H_2O$ (20 mL) was stirred at 25° C. for half an hour. Then $NaIO_4$ (1.83 g, 8.57 mmol, 3 eq) was added and the mixture was stirred at 25° C. for 1.5 hours. TLC showed the reaction was complete. After filtered, the filtrate was extracted with EtOAc (30 mL×3). The combined organic layer was washed with sat. $Na_2SO_3$ (10 mL), brine (10 mL×1), dried over $Na_2SO_4$, filtered and concentrated under reduced pressure. The residue was used to the next step without further purification. Compound 2-[5-[(3,4-dichlorophenyl)methylamino]-7-oxo-6H-pyrazolo[4,3-d]pyrimidin-1-yl]acetaldehyde (0.8 g, 2.27 mmol, 79.55% yield) was obtained as off white solid. $^1$H NMR (DMSO-$d_6$, 400 MHz) δ 11.15 (s, 1H), 9.65 (s, 1H), 7.65 (s, 1H), 7.59~7.57 (m, 2H), 7.32 (d, J=8.0 Hz, 1H), 6.60 (t, J=6.0 Hz, 1H), 5.36 (s, 2H), 4.48 (d, J=6.0 Hz, 2H).

Preparation of Compounds in Scheme C-1 (Step 10 in Scheme C-1)

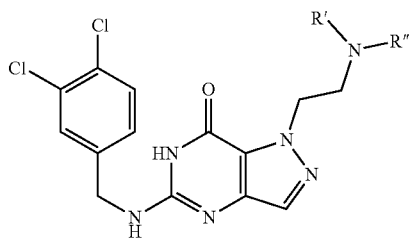

To a solution of 2-[5-[(3,4-dichlorophenyl)methylamino]-7-oxo-6H-pyrazolo[4,3-d]pyrimidin-1-yl]acetaldehyde (4.26 mmol, 1 eq) and R'NHR" (5.11~85.2 mmol, 1.2 20 eq) in MeOH or DCM (4 mL/mmol) was added $NaBH_3CN$ (5.11~12.78 mmol, 1.2 3 eq) in portions at 0° C. Then the mixture was stirred at 0° C. 80° C. for a period of time (2 hours 10 hours). LCMS and HPLC showed the reaction was complete. The reaction mixture was quenched with $H_2O$ at 0° C. and then extracted with EtOAc. The combined organic layers were washed with brine, dried over $Na_2SO_4$, filtered and concentrated under reduced pressure. The residue was purified by prep-HPLC. Column: a) Luna C18 100 mm×30 mm 5 µm; b) Phenomenex Luna C18 150 mm×30 mm 5 µm; c) Nano-micro Kromasil C18 100 mm×30 mm 5 µm; d) Boston Prime C18 150 mm×30 mm 5 µm; e) Phenomenex Luna C18 150 mm×30 mm 5 µm; f) Xbridge 150 mm×30 mm 10 µm. Mobile phase: a) [water (0.1% TFA)-MeCN]; B %: 15%-55%, 10 mins; b) [water (0.05% HCl)-MeCN]; B %: 1%-55%, 8 mins or 10 mins or 12 mins; c) [water (0.04% $NH_3$—$H_2O$+10 mM $NH_4HCO_3$)-MeCN]; B %: 40%-60%, 10.5 mins. MeCN was removed under reduced pressure. The aqueous was dried over lyophilization.

Compound 57

Preparation of 5-((3,4-dichlorobenzyl)amino)-1-(2-morpholinoethyl)-1H-pyrazolo[4,3-d]pyrimidin-7(6H)-one hydrochloride (Step 10 in Scheme C-1)

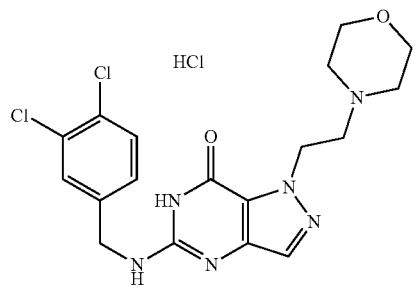 [SMILES: O=c1[nH]c(NCc2ccc(Cl)c(Cl)c2)nc2cnn(CCN3CCOCC3)c12 ; Cl]

To a mixture of 2-[5-[(3,4-dichlorophenyl)methylamino]-7-oxo-6H-pyrazolo[4,3-d]pyrimidin-1-yl]acetaldehyde (1.5 g, 4.26 mmol, 1 eq) and morpholine (1.11 g, 12.78 mmol, 1.12 mL, 3 eq) in MeOH (15 mL) was added $NaBH_3CN$ (401.49 mg, 6.39 mmol, 1.5 eq) in portions at 0° C. and then the mixture was stirred at 25° C. for 2 hours. LC-MS showed the reaction was complete. The mixture was quenched with ice water (10 mL) at 0° C. and the organic solvent was removed under reduced pressure. The aqueous was extracted with EtOAc (20 mL×5). The combined organic layer was washed with brine (20 mL), dried over $Na_2SO_4$, filtered and concentrated under reduced pressure. The filtrate was purified by prep-HPLC (HCl condition column: Phenomenex luna C18 250 mm×50 mm 10 µm; mobile phase: [water (0.05% HCl)-MeCN]; B %: 5%-35%, 20 mins). The solvent was removed under freeze drying. Compound 5-[(3,4-dichlorophenyl)methylamino]-1-(2-morpholinoethyl)-6H-pyrazolo[4,3-d]pyrimidin-7-one (460 mg, 1.08 mmol, 25.36% yield, 99.38% purity) was obtained as white solid. $^1$H NMR (DMSO-$d_6$, 400 MHz) δ 10.75 (s, 1H), 7.70 (s, 1H), 7.62~7.59 (m, 2H), 7.52 (s, 1H), 7.35 (dd, J=8.0 Hz, 1.6 Hz, 1H), 4.86 (t, J=6.0 Hz, 2H), 4.54 (d, J=5.2 Hz, 2H), 3.97~3.93 (m, 2H), 3.74~3.68 (m, 2H), 3.65~3.60 (m, 2H), 3.48~3.45 (m, 2H), 3.13~3.10 (m, 2H). HPLC: 99.38% (220 nm), 99.42% (215 nm), 98.29% (254 nm). MS (ESI): mass calcd. For $C_{18}H_{21}Cl_3N_6O_2$ 422.10, m/z found 423.1 [M+H]$^+$.

Compound 58

5-((3,4-Dichlorobenzyl)amino)-1-(2-(4-methylpiperazin-1-yl)ethyl)-1H-pyrazolo[4,3-d]pyrimidin-7(6H)-one was prepared according to the procedure described herein for Step 10 in Scheme C-1.

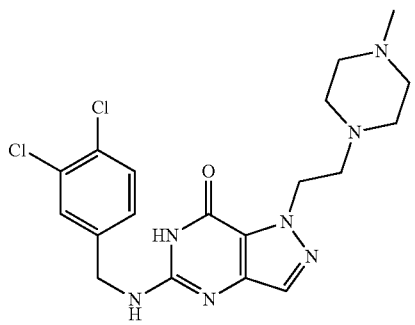 [SMILES: CN1CCN(CCn2ncc3nc(NCc4ccc(Cl)c(Cl)c4)[nH]c(=O)c32)CC1]

The procedure yielded the desired compound (58.7 mg, 134.53 μmol, 31.59% yield) as an off-white solid. $^1$H NMR (DMSO-d$_6$, 400 MHz) δ 11.36~10.84 (m, 1H), 9.38~9.32 (m, 1H), 7.60~7.58 (m, 3H), 7.3 (dd, J=8.4 Hz, 2.0 Hz, 1H), 6.71~6.68 (m, 1H), 4.56 (t, J=6.0 Hz, 2H), 4.47 (d, J=5.6 Hz, 2H), 3.36~3.30 (m, 2H), 3.07~3.04 (m, 2H), 2.95~2.84 (m, 4H), 2.74 (s, 3H), 2.38~2.27 (m, 2H). HPLC: 99.58% (220 nm), 99.44% (215 m), 100.00% (254 nm). MS (ESI): mass calcd. For $C_{19}H_{23}C_2N_7O$ 435.13, m/z found 436.2 [M+H]$^+$.

Compound 59

5-((3,4-Dichlorobenzyl)amino)-1-(2-(1,1-dioxidothiomorpholino)ethyl)-1H-pyrazolo[4,3-d]pyrimidin-7(6H)-one was prepared according to the procedure described herein for Step 10 in Scheme C-1

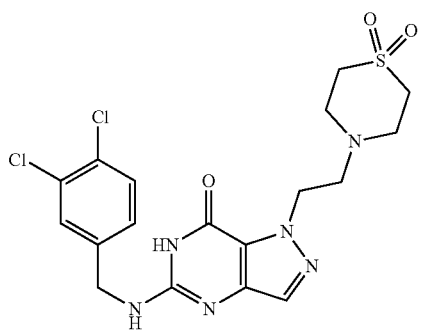 [SMILES: O=c1[nH]c(NCc2ccc(Cl)c(Cl)c2)nc2cnn(CCN3CCS(=O)(=O)CC3)c12]

The procedure yielded the desired compound (22.3 mg, 47.31 μmol, 11.11% yield) as a white solid. $^1$H NMR (DMSO-d$_6$, 400 MHz) δ 7.62 (s, 1H), 7.5~7.54 (m, 2H), 7.31 (dd, J=8.4 Hz, 2.0 Hz, 1H), 4.64 (t, J=6.0 Hz, 2H), 4.46 (s, 2H), 3.29~3.27 (m, 6H), 3.21~3.18 (m, 4H). HPLC: 99.85% (220 nm), 94.04% (215 nm), 100.00% (254 nm). MS (ESI): mass caled. For $C_{18}H_{20}C_2N_6O_3S$ 470.07, m/z found 471.1 [M+H]$^+$.

Compound 60

5-((3,4-Dichlorobenzyl)amino)-1-(2-(4-methyl-3-oxopiperazin-1-yl)ethyl)-1H-pyrazolo[4,3-d]pyrimidin-7(6H)-one was prepared according to the procedure described herein for Step 10 in Scheme C-1.

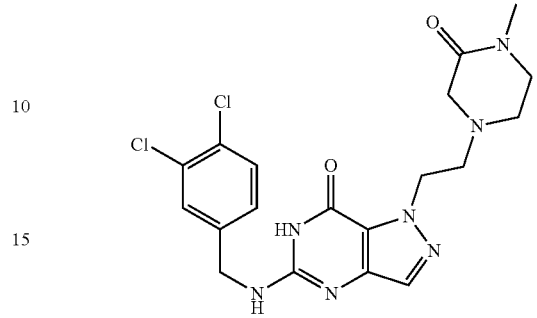

The procedure yielded the desired compound (69.1 mg, 153.45 μmol, 36.03% yield) as an off-white solid. $^1$H NMR (DMSO-d$_6$, 400 MHz) δ 11.25 (s, 1H), 7.65 (s, 1H), 7.61~7.55 (m, 2H), 7.33 (dd, J=8.4 Hz, 1.6 Hz, 1H), 6.81 (s, 1H), 4.72 (s, 2H), 4.48 (d, J=6.0 Hz, 2H), 3.58 (s, 2H), 3.37 (s, 4H), 3.25 (s, 2H), 2.82 (s, 3H). HPLC: 100.00% (220 nm), 100.00% (215 nm), 100.00% (254 nm). MS (ESI): mass calcd. For $C_{19}H_{21}C_2N_7O_2$ 449.11, m/z found 450.2 [M+H]$^+$.

Compound 61

5-((3,4-Dichlorobenzyl)amino)-1-(2-(methylamino)ethyl)-1H-pyrazolo[4,3-d]pyrimidin-7(6H)-one was prepared according to the procedure described herein for Step 10 in Scheme C-1.

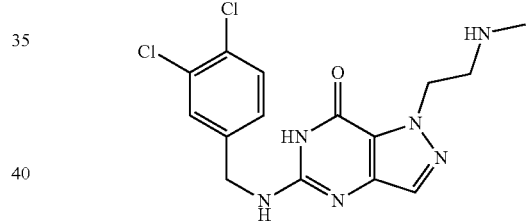

The procedure yielded the desired compound (30.5 mg, 83.05 μmol, 19.50% yield) as an off white solid. $^1$H NMR (DMSO-d$_6$, 400 MHz) δ 11.25 (s, 1H), 8.45 (s, 2H), 7.64 (s, 1H), 7.57~7.54 (m, 2H), 7.28 (dd, J=6.0 Hz, 2.0 Hz, 1H), 6.79~6.76 (m, 1H), 4.68 (t, J=5.6 Hz, 2H), 4.45 (d, J=6.0 Hz, 2H), 3.39~3.36 (m, 2H), 2.56 (s, 3H). HPLC: 98.94% (220 nm), 98.62% (215 nm), 97.58% (254 nm). MS (ESI): mass caled. For $C_{15}H_{16}C_{12}N_6O$ 366.08, m/z found 367.1 [M+H]$^+$.

Compound 62

1-[2-(tert-Butylamino)ethyl]-5-[(3,4-dichlorophenyl)methylamino]-6H-pyrazolo[4,3-d]pyrimidin-7-one was prepared according to the procedure described herein for Step 10 in Scheme C-1.

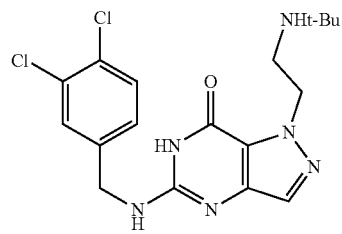

The procedure yielded the desired compound (20.3 mg, 48.83 μmol, 24.46% yield) as a white solid. $^1$H NMR (DMSO-d$_6$, 400 MHz) δ 7.59~7.57 (m, 2H), 7.54 (s, 1H), 7.32 (dd, J=1.2 Hz, 8.4 Hz, 1H), 6.58 (s, 1H), 4.47 (d, J=6.0 Hz, 2H), 4.42 (t, J=6.8 Hz, 2H), 2.86 (t, J=6.8 Hz, 2H), 0.96 (s, 9H). HPLC: 98.11% (220 nm), 98.18% (215 nm), 100.00% (254 nm). MS (ESI): mass calcd. For C$_8$H$_{22}$C$_{12}$N$_6$O 408.12, m/z found 409.1 [M+H]$^+$.

Compound 63

1-(2-Aminoethyl)-5-[(3,4-dichlorophenyl)methylamino]-6H-pyrazolo[4,3-d]pyrimidin-7-one was prepared according to the procedure described herein for Step 10 in Scheme C-1.

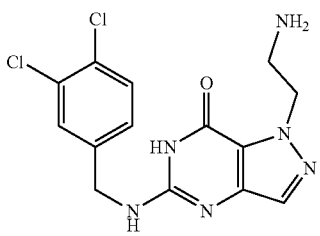 [SMILES: NCCn1ncc2nc(NCc3ccc(Cl)c(Cl)c3)[nH]c(=O)c21]

The procedure yielded the desired compound (34.9 mg, 98.81 μmol, 34.80% yield) as a white solid. $^1$H NMR (DMSO-d$_6$, 400 MHz) δ 11.30 (s, 1H), 7.89 (s, 3H), 7.66 (s, 1H), 7.58 (m, 2H), 7.32 (q, J=2.0 Hz, 1H), 6.84 (t, J=5.2 Hz, 1H), 4.65 (t, J=6.0 Hz, 2H), 4.46 (s, 2H), 3.27 (t, J=6.0 Hz, 2H). HPLC: 99.19% (220 nm), 98.71% (215 nm), 100.00% (254 nm). MS (ESI): mass calcd. For C$_{14}$H$_{14}$C$_{12}$N$_6$O 352.06, m/z found 353.1 [M+H]$^+$.

Compound 64

1-(2-(4-Acetylpiperazin-1-yl)ethyl)-5-((3,4-dichlorobenzyl)amino)-1H-pyrazolo[4,3-d]pyrimidin-7(6H)-one hydrochloride was prepared according to the procedure described herein for Step 10 in Scheme C-1.

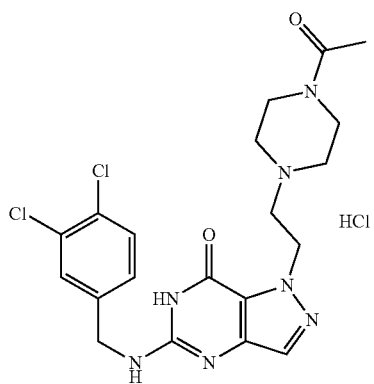 [SMILES: CC(=O)N1CCN(CCn2ncc3nc(NCc4ccc(Cl)c(Cl)c4)[nH]c(=O)c32)CC1 ; Cl]

The procedure yielded the desired compound (0.293 g, 585.05 μmol, 20.60% yield) as a white solid. $^1$H NMR (DMSO-d$_6$, 400 MHz) δ 11.01 (s, 1H), 7.87 (s, 1H), 7.73 (s, 1H), 7.64~7.61 (m, 2H), 7.37 (m, 1H), 4.90~4.87 (m, 2H), 4.59 (d, J=4.4 Hz, 2H), 4.40~4.37 (m, 1H), 4.01~3.98 (m, 1H), 3.62 (s, 2H), 3.50~3.43 (m, 3H), 3.07~2.98 (m, 3H), 2.02 (s, 3H). HPLC: 99.87% (220 nm), 99.77% (215 nm), 100.00% (254 nm). MS (ESI): mass calcd. For C$_{20}$H$_{24}$C$_{13}$N$_7$O$_2$ 463.13, m/z found 464.1 [M+H]$^+$.

Compound 65

5-((3,4-Dichlorobenzyl)amino)-1-(2-(4-hydroxypiperidin-1-yl)ethyl)-1H-pyrazolo[4,3-d]pyrimidin-7(6H)-one hydrochloride was prepared according to the procedure described herein for Step 10 in Scheme C-1.

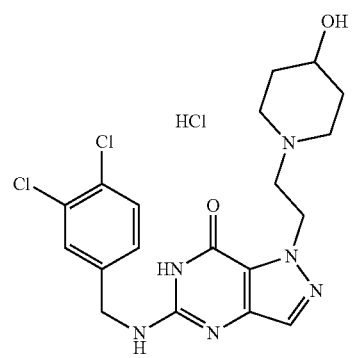 [SMILES: O=c1[nH]c(NCc2ccc(Cl)c(Cl)c2)nc2cnn(CCN3CCC(O)CC3)c12 ; Cl]

The procedure yielded the desired compound (25.4 mg, 51.62 μmol, 18.18% yield, HCl) as a white solid. $^1$H NMR (DMSO-d$_6$, 400 MHz) δ 10.03 (s, 1H), 7.68~7.60 (m, 3H), 7.34~7.33 (m, 2H), 4.84 (s, 2H), 4.50 (d, J=10.4 Hz, 2H), 4.01 (s, 1H), 3.94~3.90 (m, 1H), 3.33 (s, 1H), 3.17 (s, 1H), 2.98 (s, 1H), 1.98~1.87 (m, 3H), 1.73~1.60 (m, 2H), 1.17 (s, 1H). HPLC: 95.87% (220 nm), 95.31% (215 nm), 99.13% (254 nm). MS (ESI): mass calcd. For C$_{19}$H$_{23}$C3N$_6$O$_2$ 436.12, m/z found 437.1 [M+H]$^+$.

Compound 66

1-(2-(5-((3,4-Dichlorobenzyl)amino)-7-oxo-6,7-dihydro-1H-pyrazolo[4,3-d]pyrimidin-1-yl)ethyl)piperidine-4-carboxamide hydrochloride hydrochloride was prepared according to the procedure described herein for Step 10 in Scheme C-1.

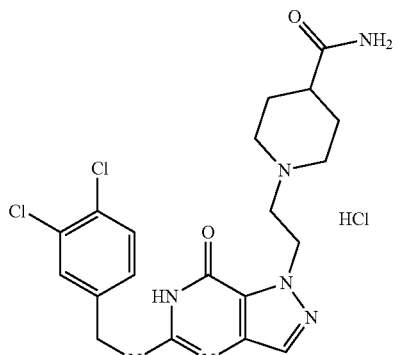

The procedure yielded the desired compound (24.9 mg, 51.41 μmol, 18.10% yield) as a white solid. $^1$H NMR (DMSO-d$_6$, 400 MHz) δ 9.48 (s, 1H), 7.71~7.67 (m, 1H), 7.63~7.57 (m, 2H), 7.41 (s, 1H), 7.34 (d, J=8.4 Hz, 1H), 7.01 (s, 1H), 6.93 (s, 1H), 4.84 (t, J=6.0 Hz, 2H), 4.50 (d, J=5.6 Hz, 2H), 3.58 (s, 4H), 3.03~2.88 (m, 2H), 2.39 (s, 2H), 1.92 (d, J=13.4 Hz, 2H), 1.82~1.66 (m, 2H). HPLC: 95.87% (220 nm), 95.70% (215 nm), 94.38% (254 nm). MS (ESI): mass calcd. For C$_2$H$_{24}$C3N$_7$O$_2$ 463.13, m/z found 464.2 [M+H]$^+$.

Compound 67

5-((3,4-Dichlorobenzyl)amino)-1-(2-(4-(dimethylamino)piperidin-1-yl)ethyl)-1H-pyrazolo[4,3-d]pyrimidin-7(6H)-one dihydrochloride was prepared according to the procedure described herein for Step 10 in Scheme C-1.

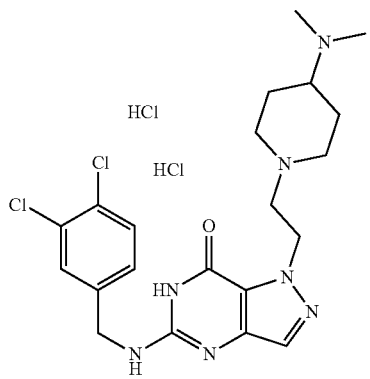 [SMILES: CN(C)C1CCN(CCn2ncc3nc(NCc4ccc(Cl)c(Cl)c4)[nH]c(=O)c32)CC1 ; Cl ; Cl]

The procedure yielded the desired compound (42.0 mg, 76.61 μmol, 26.98% yield) as a white solid. H NMR (DMSO-d$_6$, 400 MHz) δ 11.05 (s, 1H), 10.42~10.30 (m, 1H), 7.69 (s, 1H), 7.63~7.50 (m, 2H), 7.34 (d, J=8.0 Hz, 1H), 4.90~4.82 (m, 2H), 4.51 (d, J=5.2 Hz, 2H), 3.80~3.70 (m, 4H), 3.32 (s, 1H), 2.99 (s, 2H), 2.71 (d, J=4.8 Hz, 6H), 2.27 (d, J=14.0 Hz, 2H), 1.99 (d, J=12.4 Hz, 2H). HPLC: 98.01% (220 nm), 97.80% (215 nm), 97.50% (254 nm). MS (ESI): mass calcd. For $C_{21}H_{29}Cl_4N_7O$ 463.17, m/z found 464.2 [M+H]$^+$.

Compound 68

1-(2-((1S,4S)-2-oxa-5-azabicyclo[2.2.1]heptan-5-yl)ethyl)-5-((3,4-dichlorobenzyl)amino)-1H-pyrazolo[4,3-d]pyrimidin-7(6H)-one hydrochloride was prepared according to the procedure described herein for Step 10 in Scheme C-1.

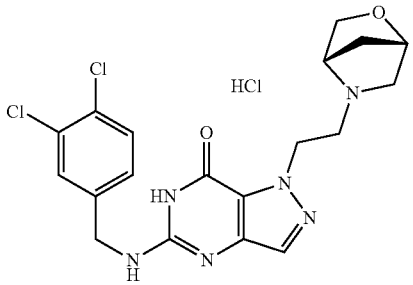 [SMILES: O=c1[nH]c(NCc2ccc(Cl)c(Cl)c2)nc2cnn(CCN3C[C@@H]4C[C@H]3CO4)c12 ; Cl]

The procedure yielded the desired compound (26.3 mg, 55.26 μmol, 19.46% yield) as a white solid. $^1$H NMR (DMSO-d$_6$, 400 MHz) δ 11.21~10.52 (m, 1H), 7.70 (s, 1H), 7.61 (d, J=8.4 Hz, 2H), 7.36 (d, J=8.4 Hz, 1H), 4.86~4.74 (m, 2H), 4.66~4.52 (m, 4H), 4.13 (d, J=10.4 Hz, 1H), 3.78~3.66 (m, 2H), 3.54~3.47 (m, 2H), 3.13~2.96 (m, 1H), 2.28~1.95 (m, 2H). HPLC: 99.12% (220 nm), 98.61% (215 nm), 99.33% (254 nm). MS (ESI): mass calcd. For $C_{19}H_{21}Cl_3N_6O_2$ 434.10, m/z found 435.0 [M+H]$^+$.

Compound 69

5-((3,4-Dichlorobenzyl)amino)-1-(2-(5-methyl-2,5-diazabicyclo[2.2.1]heptan-2-yl)ethyl)-1H-pyrazolo[4,3-d]pyrimidin-7(6H)-one dihydrochloride was prepared according to the procedure described herein for Step 10 in Scheme C-1.

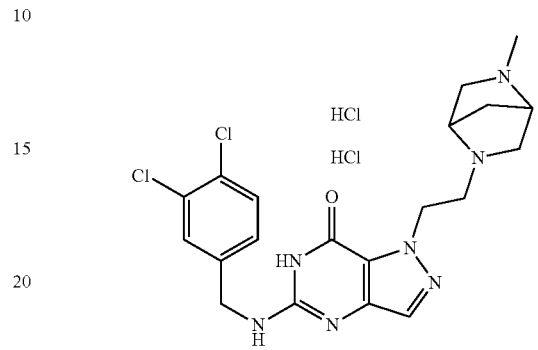

The procedure yielded the desired compound (26.9 mg, 57.25 μmol, 28.80% yield) as a white solid. $^1$H NMR (DMSO-d$_6$, 400 MHz) δ 7.66 (s, 1H), 7.58 (s, 2H), 7.32 (d, J=8.4 Hz, 1H), 6.99 (s, 1H), 4.77 (s, 2H), 4.49 (d, J=5.6 Hz, 2H), 4.33 (s, 1H), 3.93 (s, 2H), 3.34~3.32 (m, 4H), 3.17 (s, 1H), 2.82 (s, 3H), 2.46 (s, 2H). HPLC: 95.42% (220 nm), 94.46% (215 nm), 93.04% (254 nm). MS (ESI): mass calcd. For $C_{20}H_{25}Cl_4N_7O$ 447.13, m/z found 448.1 [M+H]$^+$.

Compound 70

5-((3,4-Dichlorobenzyl)amino)-1-(2-(3-hydroxyazetidin-1-yl)ethyl)-1H-pyrazolo[4,3-d]pyrimidin-7(6H)-one hydrochloride was prepared according to the procedure described herein for Step 10 in Scheme C-1.

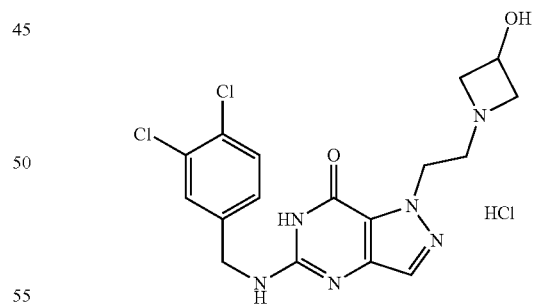

The procedure yielded the desired compound (33.8 mg, 71.91 μmol, 25.32% yield) as a white solid. $^1$H NMR (DMSO-d$_6$, 400 MHz) δ 10.33~10.04 (m, 1H), 7.70 (d, J=2.8 Hz, 1H), 7.61 (d, J=8.4 Hz, 2H), 7.36 (dd, J=8.4 Hz, 1.6 Hz, 1H), 4.68~4.65 (m, 2H), 4.56~4.50 (m, 2H), 4.41~4.34 (m, 1H), 4.26~4.22 (m, 1H), 4.13~4.07 (m, 1H), 3.78~3.76 (m, 2H), 3.68~3.64 (m, 2H). HPLC: 94.83% (220 nm), 94.29% (215 nm), 95.83% (254 nm). MS (ESI): mass calcd. For $C_{17}H_{19}Cl_3N_6O_4$ 408.09, m/z found 409.1 [M+H]$^+$.

Compound 71

5-((3,4-Dichlorobenzyl)amino)-1-(2-(4-(2-hydroxyethyl)piperazin-1-yl)ethyl)-1H-pyrazolo[4,3-d]pyrimidin-7(6H)-one dihydrochloride was prepared according to the procedure described herein for Step 10 in Scheme C-1.

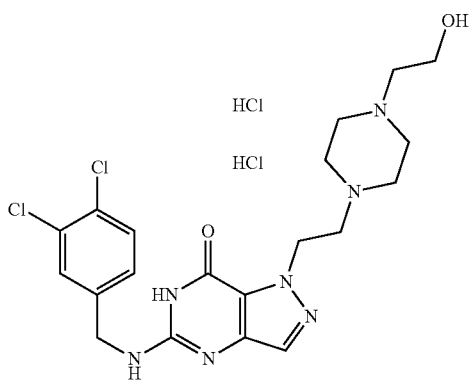 [SMILES: O=c1[nH]c(NCc2ccc(Cl)c(Cl)c2)nc2cnn(CCN3CCN(CCO)CC3)c12 ; Cl ; Cl]

The procedure yielded the desired compound (28.3 mg, 52.38 μmol, 18.45% yield) as a white solid. $^1$H NMR (DMSO-d$_6$, 400 MHz) δ 7.67 (s, 1H), 7.61 (d, J=2.4 Hz, 1H), 7.59 (d, J=8.4 Hz, 1H), 7.34 (dd, J=2.4 Hz, 8.6 Hz, 1H), 4.79 (t, J=6.0 Hz, 2H), 4.54 (d, J=5.2 Hz, 2H), 3.75~3.73 (m, 10H), 3.21 (s, 2H), 2.50 (d, J=1.6 Hz, 2H). HPLC: 99.82% (220 nm), 99.75% (215 nm), 99.72% (254 nm). MS (ESI): mass calcd. For $C_{20}H_{27}C4N_7O_2$ 465.14, m/z found 466.1 [M+H]$^+$.

Compound 72

4-(2-(5-((3,4-Dichlorobenzyl)amino)-7-oxo-6,7-dihydro-1H-pyrazolo[4,3-d]pyrimidin-1-yl)ethyl)-N,N-dimethylmorpholine-2-carboxamide hydrochloride was prepared according to the procedure described herein for Step 10 in Scheme C-1.

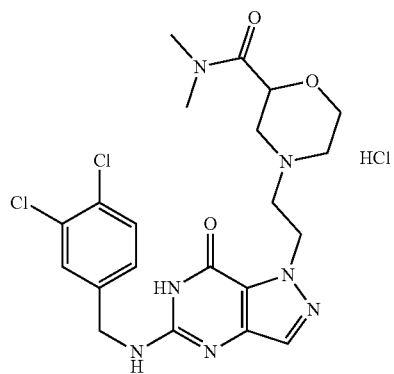 [SMILES: CN(C)C(=O)C1CN(CCn2ncc3nc(NCc4ccc(Cl)c(Cl)c4)[nH]c(=O)c32)CCO1 ; Cl]

The procedure yielded the desired compound (26 mg, 48.14 μmol, 16.95% yield, 98.662% purity, HCl) as light yellow solid. H NMR (DMSO-d$_6$, 400 MHz) δ 11.03 (s, 1H), 7.68 (s, 1H), 7.59 (s, 2H), 7.33 (d, J=8.0 Hz, 1H), 7.24 (s, 1H), 4.88 (s, 2H), 4.69~4.56 (m, 1H), 4.51 (s, 2H), 4.13~4.02 (m, 1H), 3.96~3.85 (m, 1H), 3.68 (s, 4H), 3.23~3.09 (m, 2H), 3.00 (s, 3H), 2.90~2.82 (m, 3H). HPLC: 98.66% (220 nm), 98.61% (215 nm), 99.05% (254 nm). MS (ESI): mass calcd. For $C_2H_{26}C3N_7O_3$ 493.14, m/z found 494.1 [M+H]$^+$.

Compound 73

5-((3,4-Dichlorobenzyl)amino)-1-(2-(2-(((dimethylamino)methyl) morpholino)ethyl)-1H-pyrazolo[4,3-d]pyrimidin-7(6H)-one dihydrochloride was prepared according to the procedure described herein for Step 10 in Scheme C-1.

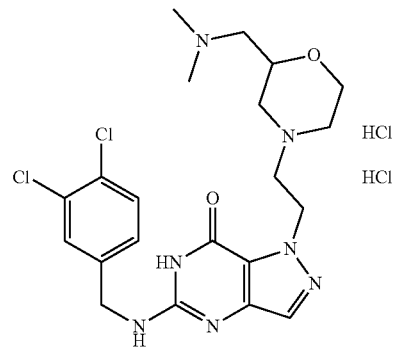 [SMILES: CN(C)CC1CN(CCn2ncc3nc(NCc4ccc(Cl)c(Cl)c4)[nH]c(=O)c32)CCO1 ; Cl ; Cl]

The procedure yielded the desired compound (33.7 mg, 66.33 μmol, 23.36% yield) as a white solid. $^1$H NMR (DMSO-d$_6$, 400 MHz) δ 10.37 (s, 2H), 7.68 (s, 1H), 7.60 (s, 2H), 7.34 (d, J=8.8 Hz, 2H), 4.87 (s, 2H), 4.52 (s, 2H), 4.30 (s, 2H), 4.07~4.05 (m, 2H), 3.90~3.88 (m, 1H), 3.40~3.24 (m, 2H), 3.20~3.16 (m, 4H), 3.79 (s, 6H). HPLC: 94.95% (220 nm), 93.86% (215 nm), 99.71% (254 nm). MS (ESI): mass calcd. For $C_{21}H_{29}C4N_7O_2$ 479.16, m/z found 480.2 [M+H]$^+$.

Compound 74

Preparation of 5-((3,4-dichlorobenzyl)amino)-1-(2-(piperazin-1-yl)ethyl)-1H-pyrazolo[4,3-d]pyrimidin-7(6H)-one Preparation of tert-butyl 4-(2-(5-((3,4-dichlorobenzyl)amino)-7-oxo-6,7-dihydro-1H-pyrazolo[4,3-d]pyrimidin-1-yl)ethyl)piperazine-carboxylate (Step 10 in Scheme C-1)

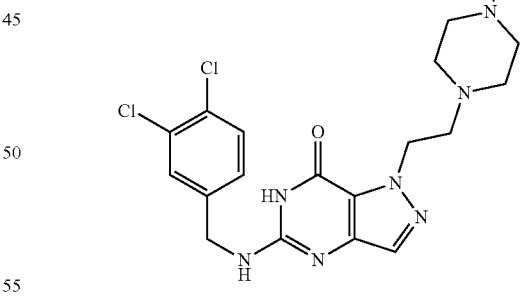

A mixture of 2-[5-[(3,4-dichlorophenyl)methylamino]-7-oxo-6H-pyrazolo[4,3-d]pyrimidin-1-yl]acetaldehyde (0.18 g, 511.11 μmol, 1 eq), tert-butyl piperazine-1-carboxylate (114.23 mg, 613.33 μmol, 1.2 eq) and AcOH (3.07 mg, 51.11 μmol, 2.92 μL, 0.1 eq) in MeOH (4 mL) was stirred at 25° C. for 2 hours. Then NaBH$_3$CN (38.54 mg, 613.33 μmol, 1.2 eq) was added at 0° C. in portions and the mixture was stirred at 25° C. for 2 hours. LC-MS showed the reaction was complete. The mixture was quenched with ice water (5 mL) and the organic solvent was removed under reduced pressure. The aqueous was extracted with EtOAc (10 mL×3). The combined organic layer was washed with brine (10 mL×1), dried over Na$_2$SO$_4$, filtered and concentrated under reduced pressure. The residue was used to the next step without further purification. Compound tert-butyl 4-[2-[5-[(3,4-dichlorophenyl)methylamino]-7-oxo-6H-pyrazolo[4,3-d]pyrimidin-1-yl]ethyl]piperazine-1-carboxylate (0.2 g, 382.83 µmol, 74.90% yield) was obtained as pale brown solid. MS (ESI): mass calcd. For C$_{23}$H$_{29}$C2N$_7$O$_3$ 521.17, m/z found 522.2 [M+H]$^+$.

Preparation of 5-((3,4-dichlorobenzyl)amino)-1-(2-(piperazin-1-yl)ethyl)-1H-pyrazolo[4,3-d]pyrimidin-7(6H)-one

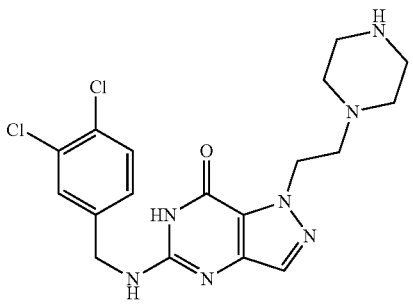 [SMILES: O=c1[nH]c(NCc2ccc(Cl)c(Cl)c2)nc2cnn(CCN3CCNCC3)c12]

To a mixture of tert-butyl 4-[2-[5-[(3,4-dichlorophenyl)methylamino]-7-oxo-6H-pyrazolo[4,3-d]pyrimidin-1-yl]ethyl]piperazine-1-carboxylate (0.2 g, 382.83 µmol, 1 eq) in EtOAc (5 mL) was added HCl/EtOAc (4M, 2.87 mL, 30 eq) and the mixture was stirred at 25° C. for 2 hours. LC-MS and HPLC showed the reaction was complete. There was some solid formed. After filtered, the solid was collected. The solid was purified by prep-HPLC (column: Luna C18 100 mm×30 mm 5 u; mobile phase: [water (0.1% TFA)-MeCN]; B %: 20%-35%, 10 mins). Compound 5-[(3,4-dichlorophenyl)methylamino]-1-(2-piperazin-1-ylethyl)-6H-pyrazolo[4,3-d]pyrimidin-7-one (60.2 mg, 142.55 µmol, 37.24% yield) was obtained as off white solid. $^1$H NMR (DMSO-d$_6$, 400 MHz) δ 11.2211.05 (m, 1H), 8.57~8.54 (m, 2H), 7.60~7.58 (m, 3H), 7.32 (dd, J=8.4 Hz, 2.0 Hz, 1H), 6.72 (t, J=6.0 Hz, 1H), 4.56 (t, J=6.0 Hz, 2H), 4.47 (d, J=6.0 Hz, 2H), 3.08~3.02 (m, 4H), 2.71~2.69 (m, 2H), 2.68~2.63 (m, 4H). HPLC: 100.00% (220 nm), 99.04% (215 nm), 100.00% (254 nm). MS (ESI): mass calcd. For C$_{18}$H$_{21}$C$_{12}$N$_7$O 421.12, m/z found 422.1 [M+H]$^+$.

Compound 75

Preparation of 5-(3,4-dichlorobenzyl)amino)-1-(2,3-dihydroxypropyl)-1H-pyrazolo[4,3-d]pyrimidin-7(6H)-one

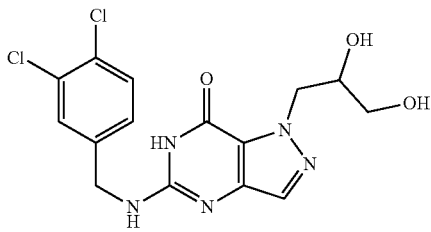 [SMILES: O=c1[nH]c(NCc2ccc(Cl)c(Cl)c2)nc2cnn(CC(O)CO)c12]

To a solution of 1-allyl-5-[(3,4-dichlorophenyl)methylamino]-6H-pyrazolo[4,3-d]pyrimidin-7-one (0.1 g, 285.55 µmol, 1 eq.) (step 8 in Scheme C-1) in THF (0.5 mL) and H$_2$O (0.5 mL) was added K$_2$O$_3$O$_4$.2H$_2$O (10.52 mg, 28.55 µmol, 0.1 eq). After half an hour, NMO (100.35 mg, 856.65 µmol, 90.41 µL, 3 eq) was added. The mixture was stirred at 25° C. for 3 hours. LC-MS and HPLC showed the reaction was complete. The organic solvent was removed under reduced pressure. The aqueous was extracted with EtOAc (8 mL×3). The combined organic layers were washed with brine (10 mL×2), dried over Na$_2$SO$_4$, filtered and concentrated under reduced pressure. The residue was purified by prep-HPLC (column: Luna C18 100 mm×30 mm 5 µm; mobile phase: [water (0.1% TFA)-MeCN]; B %: 25%-40%, mins) to give 5-((3,4-dichlorobenzyl)amino)-1-(2,3-dihydroxypropyl)-1H-pyrazolo[4,3-d]pyrimidin-7(6H)-one (48.5 mg, 126.23 µmol, 44.21% yield, 100% purity) as yellow solid. $^1$H NMR (DMSO-d$_6$, 400 MHz) δ 11.05~11.03 (m, 1H), 7.62~7.54 (m, 3H), 7.32 (dd, J=1.6 Hz, 8.0 Hz, 1H), 6.67~6.62 (m, 1H), 4.48 (d, J=5.6 Hz, 2H), 4.42 (t, J=6.0 Hz, 2H), 3.93~3.90 (m, 1H), 3.34~3.31 (m, 2H). HPLC: 100.00% (220 nm), 100.00% (215 nm), 96.43% (254 nm). MS (ESI): mass calcd. For C$_{15}$H$_{15}$C$_{12}$N$_5$O$_3$ 383.06, m/z found 384.1 [M+H]$^+$.

Compound 76

Preparation of 5-((3,4-dichlorobenzyl)amino)-1-(2-hydroxyethyl)-1H-pyrazolo[4,3-d]pyrimidin-7(6H)-one

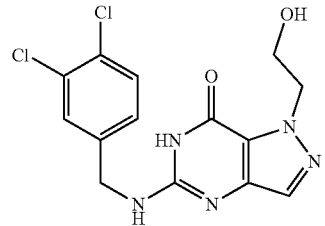 [SMILES: O=c1[nH]c(NCc2ccc(Cl)c(Cl)c2)nc2cnn(CCO)c12]

To a mixture of 2-[5-[(3,4-dichlorophenyl)methylamino]-7-oxo-6H-pyrazolo[4,3-d]pyrimidin-1-yl]acetaldehyde (0.15 g, 425.92 µmol, 1 eq) (Step 9 in Scheme C-1) in MeOH (3 mL) was added NaBH$_4$ (24.17 mg, 638.89 µmol, 1.5 eq) in portions at 0° C. Then the mixture was stirred at 25° C. for an hour. LC-MS showed the reaction was complete. The mixture was quenched with sat. NH$_4$Cl (1 mL) at 0° C. and then the organic solvent was removed under reduced pressure. The residue was dissolved in EtOAc (30 mL) and washed with brine (5 mL×1). The organic layer was dried over Na$_2$SO$_4$, filtered and concentrated under reduced pressure. The residue was purified by prep-HPLC (column: Luna C18 100 mm×30 mm 5 µm; mobile phase: [water (0.1% TFA)-MeCN]; B %: 25%-40%, 10 mins). The eluent was removed by lyophylization. Compound 5-((3,4-dichlorobenzyl)amino)-1-(2-hydroxyethyl)-1H-pyrazolo[4,3-d]pyrimidin-7(6H)-one (54.4 mg, 152.85 µmol, 35.89% yield, 99.52% purity) was obtained as white solid. $^1$H NMR (DMSO-d$_6$, 400 MHz) δ 7.60~7.57 (m, 3H), 7.33 (dd, J=8.4 Hz, 2.0 Hz, 1H), 6.83 (s, 1H), 4.50~4.45 (m, 4H), 3.74 (t, J=6.0 Hz, 2H). HPLC: 99.52% (220 nm), 98.91% (215 nm), 100.00% (254 nm). MS (ESI): mass calcd. For C$_{14}$H$_{13}$C$_{12}$N$_5$O$_2$ 353.04, m/z found 354.1 [M+H]$^+$.

Compound 77

Preparation of 5-((3,4-dichlorobenzyl)amino)-1H-pyrazolo[4,3-d]pyrimidin-7(6H)-one (Step 10 in Scheme C-1)

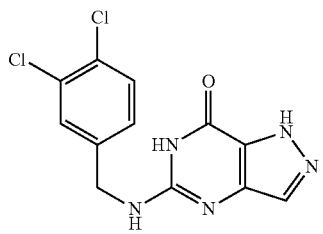 [SMILES: O=c1[nH]c(NCc2ccc(Cl)c(Cl)c2)nc2cn[nH]c12]

A mixture of 2-[5-[(3,4-dichlorophenyl)methylamino]-7-oxo-6H-pyrazolo[4,3-d]pyrimidin-1-yl]acetaldehyde (0.15 g, 425.92 µmol, 1 eq), tert-butyl piperazine-1-carboxylate (95.19 mg, 511.11 µmol, 1.2 eq) and AcOH (2.56 mg, 42.59 µmol, 2.44 µL, 0.1 eq) in DCM (5 mL) was stirred at 25° C. for an hour. Then NaBH(OAc)$_3$ (108.32 mg, 511.11 µmol, 1.2 eq) was added and the mixture was stirred at 25° C. for 3 hours. LC-MS and HPLC showed no of 2-[5-[(3,4-dichlorophenyl)methylamino]-7-oxo-6H-pyrazolo[4,3-d]pyrimidin-1-yl]acetaldehyde was remained. Mainly one new peak was shown on LC-MS and which was 5-((3,4-dichlorobenzyl)amino)-1H-pyrazolo[4,3-d]pyrimidin-7(6H)-one. The mixture was quenched with ice water (5 mL) and then extracted with EtOAc (10 mL×3). The combined organic layer was washed with brine (10 mL×1), dried over Na$_2$SO$_4$, filtered and concentrated under reduced pressure. The residue was purified by prep-HPLC (column: Luna C18 100 mm×30 mm 5 µm; mobile phase: [water (0.1% TFA)-MeCN]; B %: 20%-45%, 10 mins). After lyophylization, the obtained was washed with MeOH (2 mL) and EtOAc (1 mL). Compound 5-[(3,4-dichlorophenyl)methylamino]-1,6-dihydropyrazolo[4,3-d]pyrimidin-7-one (24.3 mg, 78.35 µmol, 18.40% yield) was obtained as white solid. $^1$H NMR (DMSO-d$_6$, 400 MHz) δ 11.04~10.88 (m, 1H), 7.69 (s, 1H), 7.60~7.58 (m, 2H), 7.34 (dd, J=8.4 Hz, 2.0 Hz, 1H), 6.78~6.71 (m, 1H), 4.49 (d, J=6.0 Hz, 2H). HPLC: 98.28% (220 nm), 97.37% (215 nm), 100.00% (254 nm). MS (ESI): mass calcd. For C$_{12}$H$_9$Cl$_2$N$_5$O 309.02, m/z found 310.0 [M+H]$^+$.

Compound 78

Preparation of 1,1'-(azanediylbis(ethane-2,1-diyl))bis(5-((3,4-dichlorobenzyl)amino)-1H-pyrazolo[4,3-d]pyrimidin-7(6H)-one (Step 10 in Scheme C-1)

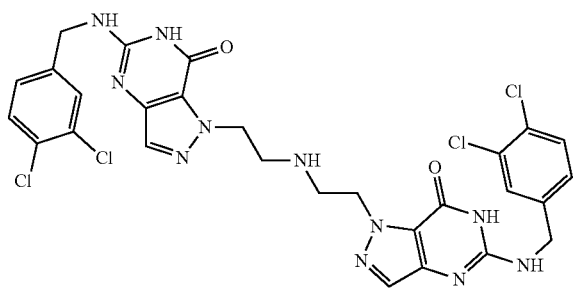 [SMILES: O=c1[nH]c(NCc2ccc(Cl)c(Cl)c2)nc2cnn(CCNCCn3ncc4nc(NCc5ccc(Cl)c(Cl)c5)[nH]c(=O)c43)c12]

A mixture of 2-[5-[(3,4-dichlorophenyl)methylamino]-7-oxo-6H-pyrazolo[4,3-d]pyrimidin-1-yl]acetaldehyde (0.1 g, 283.95 µmol, 1 eq) and AcONH$_4$ (218.73 mg, 2.84 mmol, 10 eq) in MeOH (3 mL) was stirred at 25° C. for 2 hours. Then NaBH$_3$CN (26.77 mg, 425.92 µmol, 1.5 eq) was added at 0° C. in portions and the mixture was stirred at 25° C. for 10 hours. LC-MS and HPLC showed the reaction was complete. Mainly 5-[(3,4-dichlorophenyl)methylamino]-1-[2-[2-[5-[(3,4-dichlorophenyl)methylamino]-7-oxo-6H-pyrazolo[4,3-d]pyrimidin-1-yl]ethylamino]ethyl]-6H-pyrazolo[4,3-d]pyrimidin-7-one was formed. The mixture was quenched with ice water (5 mL) and the organic solvent was removed under reduced pressure. The aqueous was extracted with EtOAc (10 mL×3). The combined organic layer was washed with brine (10 mL×1), dried over Na$_2$SO$_4$, filtered and concentrated under reduced pressure. The residue was purified by prep-HPLC (column: Luna C18 100 mm×30 mm 5 u; mobile phase: [water (0.1% TFA)-MeCN]; B %: 30%-55%, 10 mins). Compound 5-[(3,4-dichlorophenyl)-methylamino]-1-[2-[2-[5-[(3,4-dichlorophenyl)methylamino]-7-oxo-6H-pyrazolo[4,3-d]pyrimidin-1-yl]ethylamino]ethyl]-6H-pyrazolo[4,3-d]pyrimidin-7-one (38.1 mg, 55.27 µmol, 19.46% yield) was obtained as white solid. H NMR (DMSO-d$_6$, 400 MHz) δ 11.31 (s, 2H), 8.74 (s, 2H), 7.64 (s, 2H), 7.60~7.57 (m, 4H), 7.31 (dd, J=8.4 Hz, 2.0 Hz, 2H), 6.80~6.78 (m, 2H), 4.70 (t, J=6.0 Hz, 4H), 4.48 (d, J=6.0 Hz, 4H), 3.47 (t, J=5.6 Hz, 4H). HPLC: 100.00% (220 nm), 99.46% (215 nm), 100.00% (254 nm). MS (ESI): mass calcd. For C$_{28}$H$_{25}$Cl$_4$N$_{11}$O$_2$ 687.09, m/z found 688.2 [M+H]$^+$.

Scheme C-2

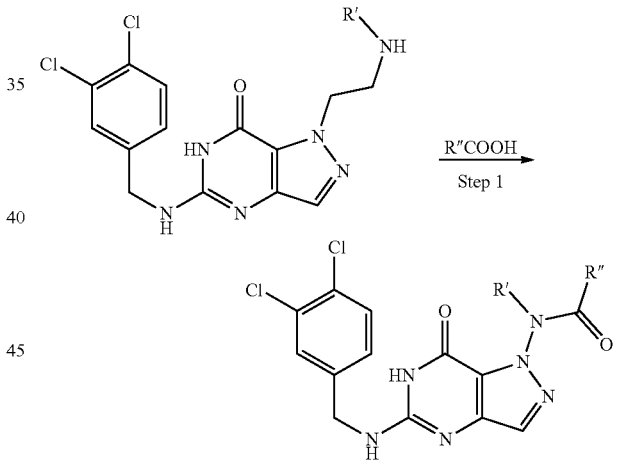

General Procedures for Preparing Compounds in Scheme C-2

Preparation of Compounds (Step 1 in Scheme C-2)

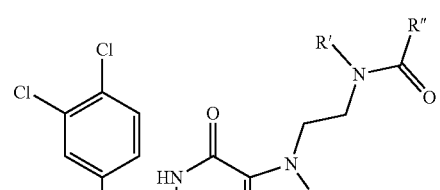

A mixture of 1-(R'-aminoethyl)-5-[(3,4-dichlorophenyl)methylamino]-6H-pyrazolo[4,3-d]pyrimidin-7-one (283.12 µmol, 1 eq), R"COOH (283.12 µmol~368.06 µmol, 1 eq~1.3 eq), EDCl (339.74 µmol, 1.2 eq), HOBt (56.62 µmol, 0.2 eq) and DIEA (849.36 mol, 147.94 µL, 3 eq) in DMF (3 mL/mmol) was stirred at 20° C. 25° C. for 10 hours 12 hours. The reaction mixture was stirred at 0° C.~25° C. for a time period (1 hour 3 hours). LC-MS showed the reaction was complete. The reaction mixture was quenched with H₂O and then extracted with EtOAc. The combined organic layers were washed with brine, dried over Na₂SO₄, filtered and concentrated under reduced pressure. The residue was purified by prep-HPLC. Column: Luna C18 100 mm×30 mm 5 µm or Nano-micro Kromasil C18 100 mm×30 mm 5 µm; Mobile phase: [water (0.1% TFA)-MeCN]; B %: 20%-45%, 10 mins or 20 mins). The aqueous solution was lyophilized to give desired compound.

Compound 79

Preparation of N-(2-(5-((3,4-dichlorobenzyl)amino)-7-oxo-6,7-dihydro-1H-pyrazolo[4,3-d]pyrimidin-1-yl)ethyl)-3,5-dimethylisoxazole-4-carboxamide (Step 1 in Scheme C-2)

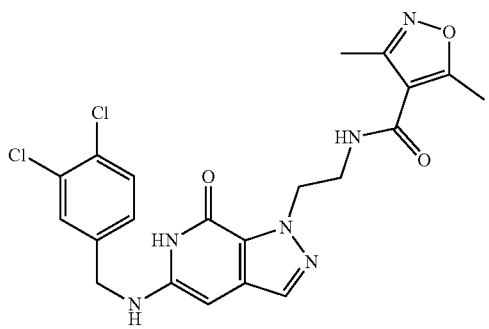 [SMILES: Cc1noc(C)c1C(=O)NCCn1ncc2cc(NCc3ccc(Cl)c(Cl)c3)[nH]c(=O)c21]

A mixture of 1-(2-aminoethyl)-5-[(3,4-dichlorophenyl)methylamino]-6H-pyrazolo[4,3-d]pyrimidin-7-one (0.1 g 283.12 µmol, 1 eq), 3,5-dimethylisoxazole-4-carboxylic acid (39.96 mg 283.12 µmol, 48.14 µL, 1 eq), EDCl (65.13 mg, 339.74 µmol, 1.2 eq), HOBt (7.65 mg, 56.62 µmol, 0.2 eq) and DIEA (109.77 mg, 849.36 µmol, 147.94 µL, 3 eq) in DMF (1 mL) was stirred at 25° C. for 12 hours. LC-MS showed the reaction was complete. After filtered, the filtrate was purified by prep-HPLC (column: Luna C18 100 mm×30 mm 5 µm; mobile phase: [water (0.1% TFA)-MeCN]; B %: 30%-45%, 10 mins). Compound N-[2-[5-[(3,4-dichlorophenyl)-methylamino]-7-oxo-6H-pyrazolo[4,3-d]pyrimidin-1-yl]ethyl]-3,5-dimethyl-isoxazole-4-carboxamide (29.2 mg, 58.90 µmol, 20.80% yield, 96.077% purity) was obtained as white solid. ¹H NMR (DMSO-d₆, 400 MHz) δ 7.96 (t, J=5.2 Hz, 1H), 7.60 (s, 1H), 7.57 (d, J=6.0 Hz, 2H), 7.32 (d, J=8.4 Hz, 1H), 6.73~6.72 (m, 1H), 4.55 (t, J=5.2 Hz, 2H), 4.47 (d, J=5.6 Hz, 2H), 3.62 (t, J=4.8 Hz, 2H), 2.41 (s, 3H), 2.18 (s, 3H). HPLC: 96.08% (220 nm), 96.58% (215 nm), 100.00% (254 nm). MS (ESI): mass calcd. For C20H₁₉C2N₇O₃ 475.09, m/z found 476.1 [M+H]⁺.

Compound 80

N-(2-(5-((3,4-dichlorobenzyl)amino)-7-oxo-6,7-dihydro-1H-pyrazolo[4,3-d]pyrimidin-1-yl)ethyl)-N,3,5-trimethyl-isoxazole-4-carboxamide was prepared according to the procedure described herein for Step 1 in Scheme C-2.

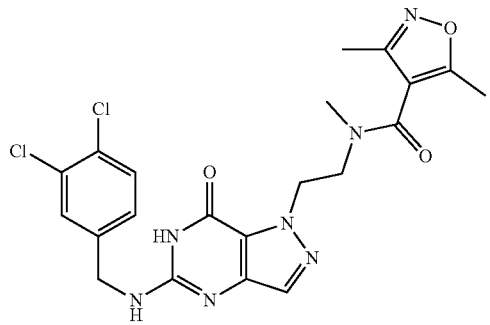 [SMILES: Cc1noc(C)c1C(=O)N(C)CCn1ncc2nc(NCc3ccc(Cl)c(Cl)c3)[nH]c(=O)c21]

The procedure yielded the desired compound (29.5 mg, 60.16 µmol, 44.19% yield) as an off white solid. ¹H NMR (DMSO-d₆, 400 MHz) δ 10.86~10.33 (m, 1H), 7.63~7.49 (m, 3H), 7.34 (d, J=7.6 Hz, 1H), 6.56~6.39 (m, 1H), 4.61 (s, 2H), 4.50 (d, J=5.6 Hz, 2H), 3.87 (t, J=5.2 Hz, 2H), 2.85 (s, 3H), 2.23 (s, 3H), 1.98 (s, 3H). HPLC: 98.05% (220 nm), 88.25% (215 nm), 100.00% (254 nm). MS (ESI): mass calcd. For C₂₁H₂₁C₁₂N₇O₃ 489.11, m/z found 490.2 [M+H]⁺.

Compound 81

6-Chloro-N-(2-(5-((3,4-dichlorobenzyl)amino)-7-oxo-6,7-dihydro-1H-pyrazolo[4,3-d]pyrimidin-1-yl)ethyl)-3-hydroxy-N-methylpyridazine-4-carboxamide was prepared according to the procedure described herein for Step 1 in Scheme C-2.

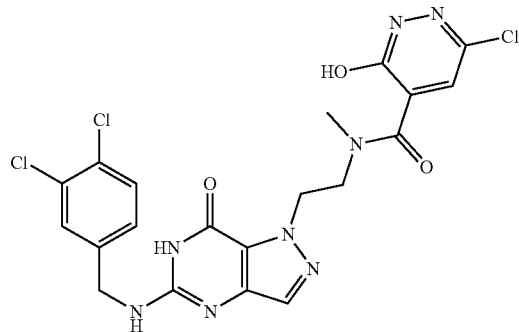 [SMILES: CN(CCn1ncc2nc(NCc3ccc(Cl)c(Cl)c3)[nH]c(=O)c21)C(=O)c1cc(Cl)nnc1O]

The procedure yielded the desired compound (34.2 mg, 65.30 µmol, 23.98% yield) as a light yellow solid. ¹H NMR (DMSO-d₆, 400 MHz) δ 13.40 (s, 1H), 7.61~7.51 (m, 3H), 7.35 (d, J=8.0 Hz, 1H), 7.25 (s, 0.5H), 6.67 (s, 0.5H), 6.57~6.42 (m, 1H), 4.73~4.60 (m, 1H), 4.58~4.52 (m, 1H), 4.51 (d, J=4.0 Hz, 2H), 3.88~3.78 (m, 1H), 3.69~3.60 (m, 2H), 2.95 (s, 2H), 2.74 (s, 1H). HPLC: 97.50% (220 nm), 96.618% (215 nm), 100.00% (254 nm). MS (ESI): mass calcd. For C₂₀H₁₇C₁₃N₈O₃S 522.05, m/z found 523.1 [M+H]⁺.

Compound 82

Preparation of N-(2-(5-((3,4-dichlorobenzyl)amino)-7-oxo-6,7-dihydro-1H-pyrazolo[4,3-d]pyrimidin-1-yl)ethyl)-N-methylisoxazole-4-carboxamide was prepared according to the procedure described herein for Step 1 in Scheme C-2.

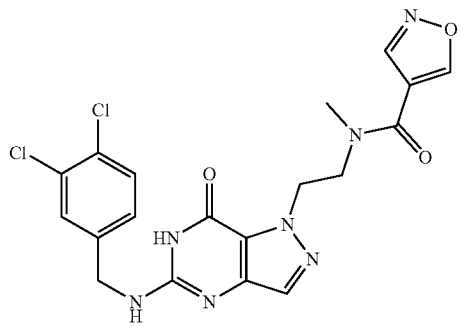 [SMILES: CN(CCn1ncc2nc(NCc3ccc(Cl)c(Cl)c3)[nH]c(=O)c21)C(=O)c1cnoc1]

The procedure yielded the desired compound (25.1 mg, 54.30 μmol, 24.92% yield) as an off white solid. $^1$H NMR (DMSO-$d_6$, 400 MHz) δ 9.10 (s, 1H), 8.56 (s, 1H), 7.58 (d, J=7.2 Hz, 1H), 7.57~7.51 (m, 2H), 7.37~7.31 (m, 1H), 6.57~6.47 (m, 1H), 4.62 (t, J=5.6 Hz, 2H), 4.50 (d, J=5.2 Hz, 2H), 3.86 (t, J=5.6 Hz, 2H), 2.94 (s, 3H). HPLC: 99.73% (220 m), 99.65% (215 nm), 100.00% (254 nm). MS (ESI): mass calcd. For $C_{19}H_{17}C_{12}N_7O_3$ 461.08, m/z found 462.1 [M+H]$^+$.

Compound 83

Preparation of 6-chloro-N-(2-(5-((3,4-dichlorobenzyl)amino)-7-oxo-6,7-dihydro-1H-pyrazolo[4,3-d]pyrimidin-1-yl)ethyl)-3-hydroxypyridazine-4-carboxamide was prepared according to the procedure described herein for Step 1 in Scheme C-2.

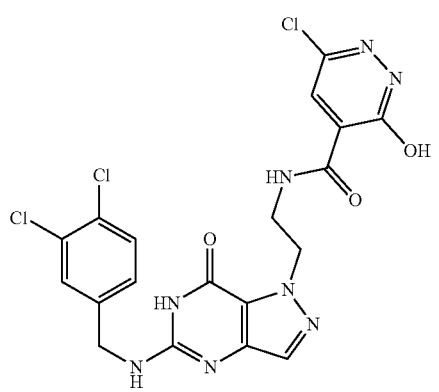 [SMILES: O=C(NCCn1ncc2nc(NCc3ccc(Cl)c(Cl)c3)[nH]c(=O)c21)c1cc(Cl)nnc1O]

The procedure yielded the desired compound (19 mg, 37.27 μmol, 18.81% yield) as a light yellow solid. $^1$H NMR (DMSO-$d_6$, 400 MHz) δ 13.92 (s, 1H), 11.10 (s, 1H), 9.38 (t, J=6.4 Hz, 1H), 7.93 (s, 1H), 7.60~7.56 (m, 3H), 7.33~7.30 (m, 1H), 6.55 (s, 1H), 4.58 (t, J=5.6 Hz, 2H), 4.46 (d, J=5.6 Hz, 2H), 3.76 (t, J=5.6 Hz, 2H). HPLC: 100.00% (220 nm), 100.00% (215 nm), 96.43% (254 nm). MS (ESI): mass calcd. For $C_{19}H_{15}C_{13}N_8O_3$ 508.03, m/z found 509.1 [M+H]$^+$.

Compound 84

Preparation of 3-chloro-N-(2-(5-((3,4-dichlorobenzyl)amino)-7-oxo-6,7-dihydro-1H-pyrazolo[4,3-d]pyrimidin-1-yl)ethyl)-6-hydroxypyridazine-4-carboxamide was prepared according to the procedure described herein for Step 1 in Scheme C-2.

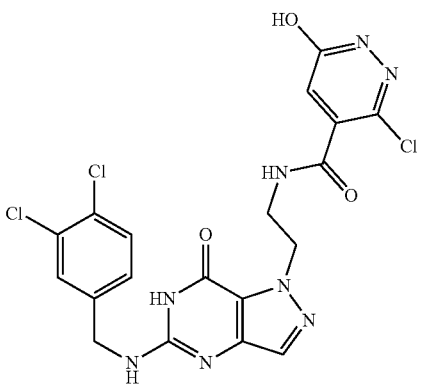 [SMILES: O=C(NCCn1ncc2nc(NCc3ccc(Cl)c(Cl)c3)[nH]c(=O)c21)c1cc(O)nnc1Cl]

The procedure yielded the desired compound (3.7 mg, 6.08 μmol, 2.15% yield) as a white solid. $^1$H NMR (DMSO-$d_6$, 400 MHz) δ 13.36 (s, 1H), 8.83 (s, 1H), 7.60~7.57 (m, 3H), 7.32 (d, J=8.4 Hz, 1H), 6.64 (s, 1H), 6.83~6.62 (m, 1H), 4.55 (t, J=5.6 Hz, 2H), 4.47 (t, J=5.6 Hz, 2H), 3.62 (s, 2H). HPLC: 97.29% (220 nm), 97.48% (215 nm), 98.52% (254 nm). MS (ESI): mass calcd. For $C_{19}H_{15}C_{13}N_8O_3$ 508.03, m/z found 509.1 [M+H]$^+$.

Compound 85

Preparation of 3,6-dichloro-N-(2-(5-((3,4-dichlorobenzyl)amino)-7-oxo-6,7-dihydro-1H-pyrazolo[4,3-d]pyrimidin-1-yl)ethyl)-N-methylpyridazine-4-carboxamide was prepared according to the procedure described herein for Step 1 in Scheme C-2.

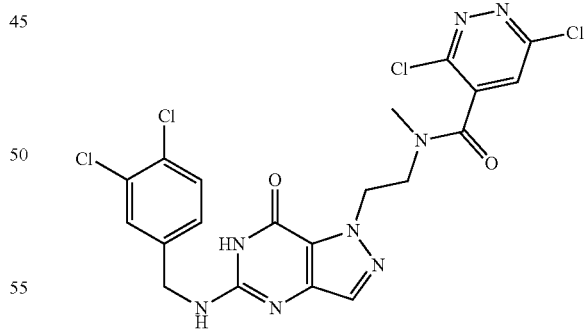

The procedure yielded the desired compound (35 mg, 64.55 μmol, 11.85% yield) as a light yellow solid. $^1$H NMR (DMSO-$d_6$, 400 MHz) δ 7.92 and 7.43 (s, 1H), 7.67~7.55 (m, 3H), 7.38~7.30 (m, 1H), 6.83~6.59 (m, 1H), 4.73~4.66 (m, 1H), 4.51~4.47 (m, 3H), 3.97~3.88 (m, 1H), 3.77~3.66 (m, 1H), 3.65~3.52 (m, 1H), 3.01 and 2.71 (s, 3H). HPLC: 100.00% (220 nm), 100.00% (215 nm), 100.00% (254 nm). MS (ESI): mass calcd. For $C_{20}H_{16}C4N_8O_2$ 540.02, m/z found 541.1 [M+H]$^+$.

Compound 86

Preparation of N-(2-(5-((3,4-dichlorobenzyl)amino)-7-oxo-6,7-dihydro-1H-pyrazolo[4,3-d]pyrimidin-1-yl)ethyl)isoxazole-4-carboxamide was prepared according to the procedure described herein for Step 1 in Scheme C-2.

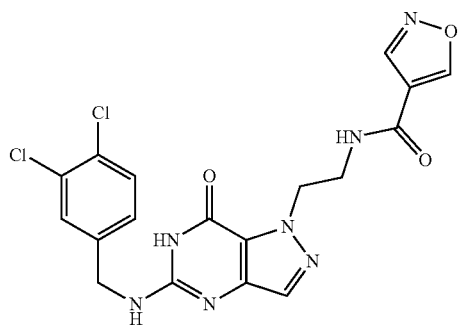 [SMILES: O=C(NCCn1ncc2nc(NCc3ccc(Cl)c(Cl)c3)[nH]c(=O)c21)c1cnoc1]

The procedure yielded the desired compound (20.4 mg, 45.24 μmol, 10.65% yield) as a white solid. $^1$H NMR (DMSO-d$_6$, 400 MHz) δ 8.26 (s, 1H), 8.09 (s, 1H), 7.79 (t, J=5.6 Hz, 1H), 7.60~7.54 (m, 3H), 7.33 (dd, J=8.4 Hz, 2.0 Hz, 1H), 6.65 (s, 1H), 4.48 (d, J=3.6 Hz, 4H), 3.51 (d, J=5.6 Hz, 2H). HPLC: 99.41% (220 nm), 100.00% (215 nm), 100.00% (254 nm). MS (ESI): mass calcd. For C$_{18}$H$_{15}$C$_{12}$N$_7$O$_3$ 447.06, m/z found 448.1 [M+H]$^+$.

Compound 87

Preparation of 3-chloro-N-(2-(5-((3,4-dichlorobenzyl)amino)-7-oxo-6,7-dihydro-1H-pyrazolo[4,3-d]pyrimidin-1-yl)ethyl)-6-hydroxy-N-methylpyridazine-4-carboxamide was prepared according to the procedure described herein for Step 1 in Scheme C-2.

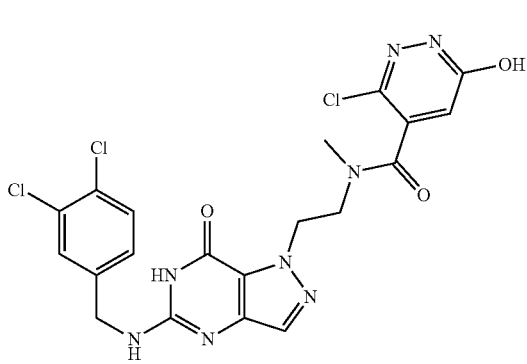 [SMILES: CN(CCn1ncc2nc(NCc3ccc(Cl)c(Cl)c3)[nH]c(=O)c21)C(=O)c1cc(O)nnc1Cl]

The procedure yielded the desired compound (21.4 mg, 40.86 μmol, 17.04% yield) as a white solid. $^1$H NMR (DMSO-d$_6$, 400 MHz) δ 13.14 (s, 1H), 7.60~7.54 (m, 2H), 7.35 (t, J=6.4 Hz, 1H), 6.76 and 6.44 (s, 1H), 6.52 (s, 1H), 4.68 (t, J=5.6 Hz, 1H), 4.59 (t, J=6.0 Hz, 1H), 4.50 (s, 2H), 3.89 (d, J=4.0 Hz, 1H), 3.71 (t, J=5.6 Hz, 1H), 2.92 (s, 1H), 2.76 (s, 2H). HPLC: 99.82% (220 nm), 99.84% (215 nm), 100.00% (254 nm). MS (ESI): mass calcd. For C$_{20}$H$_{17}$C3N$_8$O$_3$ 522.05, m/z found 523.1 [M+H]$^+$.

Scheme C-3

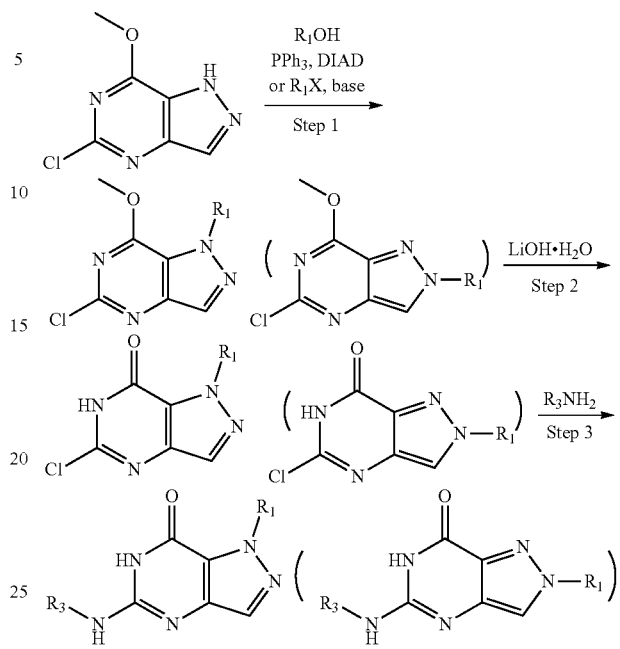

General Procedures for Preparing Compounds in Scheme C-3

Preparation of Compounds (Step 1 in Scheme C-3)

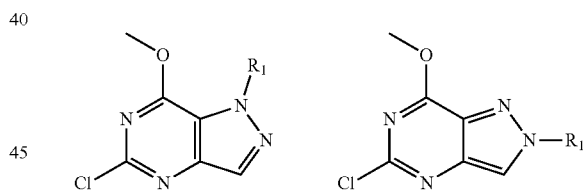

To a solution of 5-chloro-7-methoxy-H-pyrazolo[4,3-d]pyrimidine (5.42 mmol, 1 eq), R$_1$OH (5.42 mmol 16.26 mmol, 1 eq 3 eq) and PPh$_3$ (5.96 mmol 10.84 mmol, 1.1 eq 2 eq) in THF (3 mL/mmol 10 mL/mmol) was added DIAD (5.96 mmol 10.84 mmol, 1.1 eq 2 eq) dropwise at 0° C. Then the mixture was stirred at 0° C. 25° C. for 2 hours 16 hours. TLC showed the reaction was complete. The mixture was quenched with ice water and the organic layer was separated. The aqueous was extracted with EtOAc. The combined organic layer was washed with brine, dried over Na$_2$SO$_4$, filtered and concentrated under reduced pressure. The residue was purified by flash silica gel chromatography (Biotage®; 20 g or 40 g SepaFlash® Silica Flash Column, Eluent of 0~100% Ethylacetate/Petroleum or 0~20% MeOH/Ethylacetate ether gradient at 35 mL/min or 80 mL/min). The eluent was removed under reduced pressure to give the desired product.

Preparation of Compounds (Step 2 in Scheme C-3)

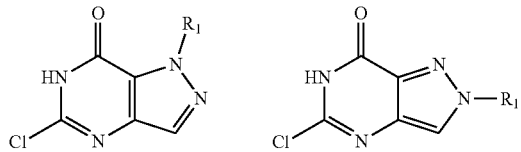

To a solution of 5-chloro-7-methoxy-1-R$_1$-1H-pyrazolo[4,3-d]pyrimidine (4.36 mmol, 1 eq) in MeOH (3 mL/mmol 5 mL/mmol) or THF (3 mL/mmol 5 mL/mmol) and H$_2$O (3 mL/mmol 5 mL/mmol) was added LiOH—H$_2$O (13.08 mmol 21.80 mmol, 3 eq 5 eq). The mixture was stirred at 20° C. 25° C. for 2 hours 16 hours. TLC showed the reaction was complete. The reaction mixture was concentrated under reduced pressure. The aqueous was made pH=6 with 3N HCl and then extracted with EtOAc. The combined organic layers were washed with brine, dried over Na$_2$SO$_4$, filtered and concentrated under reduced pressure to give desired product.

Preparation of Compounds (Step 3 in Scheme C-3)

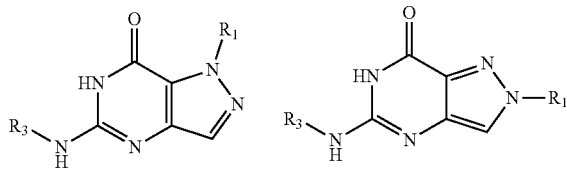

A mixture of 5-chloro-1-R$_1$-1H-pyrazolo[4,3-d]pyrimidin-7(6H)-one (3.87 mmol, 1 eq), R$_3$NH$_2$ (162.66 mmol 216.88 mmol, 1.5 eq 2 eq) and DIEA (11.61 mmol, 3 eq, DIEA was added only when R$_3$NH$_2$ was HCl salt) in t-BuOH or t-AmOH or NMP (3 mL/mmol 10 mL/mmol) was stirred at 100° C. 160° C. for 3 hours 40 hours. LC-MS showed the reaction was complete. The reaction mixture was concentrated under reduced pressure. The residue was purified by prep-HPLC. Column: a) Phenomenex Luna C18 250 mm×50 mm 10 μm; b) Phenomenex Luna C18 100 mm×30 mm 5 μm; c) Phenomenex Luna C18 150 mm×30 mm 5 μm; d) Luna C18 100 mm×30 mm 5 μm; e) Boston Prime C18 150 mm×30 mm 5 μm; f) Nano-micro Kromasil C18 100 mm×30 mm 5 μm; g) Welch Xtimate C18 100 mm×25 mm 3 μm; h) Xtimate C18 100 mm×30 mm 3 μm; i) Kromasil C18 (250 50 mm 10 μm); j) Phenomenex Gemini-NX 150 30 mm×5 μm; k) Welch Xtimate C18 150 mm×25 mm 5 μm; l) Xtimate C18 150 mm×25 mm 5 μm; m) Xtimate C18 100 mm×30 mm 3 μm. Mobile phase: a) [water (0.1% TFA)-MeCN]; B %: 10%-70%, 10 mins or 20 mins; b) [water (0.05% HCl)-MeCN]; B %: 10%-70%, 10 mins or 20 mins; c) [water (10 mM NH$_4$HCO$_3$)-MeCN]; B %: 10%-85%, 8 mins or 20 mins. The solvent was removed under freeze drying to give desired product.

Compound 88

Preparation of 5-((3,4-dichlorobenzyl)amino)-1-(2-(2-hydroxyethoxy)ethyl)-1H-pyrazolo[4,3-d]pyrimidin-7(6H)-one Preparation of 2-(2-(5-chloro-7-methoxy-1H-pyrazolo[4,3-d]pyrimidin-1-yl)ethoxy)ethanol (Step 1 in Scheme C-3)

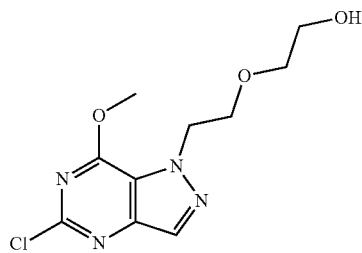 [SMILES: COc1nc(Cl)nc2cnn(CCOCCO)c12]

To a solution of 5-chloro-7-methoxy-1H-pyrazolo[4,3-d]pyrimidine (1 g 5.42 mmol, 1 eq), 2-(2-hydroxyethoxy)ethanol (1.15 g 10.84 mmol, 1.03 mL, 2 eq) and PPh$_3$ (2.13 g, 8.13 mmol, 1.5 eq) in THF (10 mL) was added DIAD (1.64 g, 8.13 mmol, 1.58 mL, 1.5 eq) dropwise at 0° C. The mixture was stirred at 25° C. for 2 hours. TLC indicated the reaction was complete. The reaction mixture was quenched with H$_2$O (15 mL) and then concentrated under reduced pressure to remove the organic solvent. The aqueous was extracted with EtOAc (20 mL×3). The combined organic layers were washed with brine (10 mL), dried over Na$_2$SO$_4$, filtered and concentrated under reduced pressure. The residue was purified by flash silica gel chromatography (Biotage®; 20 g SepaFlash® Silica Flash Column, Eluent of 060% Ethylacetate/Petroleum ether gradient at 60 mL/min). The eluent was removed under reduced pressure. Compound 2-[2-(5-chloro-7-methoxy-pyrazolo[4,3-d]pyrimidin-1-yl)ethoxy]ethanol (1.19 g, 4.36 mmol, 80.55% yield) was obtained as yellow oil. $^1$H NMR (DMSO-d$_6$, 400 MHz) δ 8.26 (s, 1H), 4.66 (t, J=5.6 Hz, 2H), 4.52~4.45 (m, 1H), 4.16 (s, 3H), 3.84 (t, J=5.6 Hz, 2H), 3.37~3.35 (m, 4H). Compound 2-[2-(5-chloro-7-methoxy-pyrazolo[4,3-d]pyrimidin-2-yl)ethoxy]ethanol (440 mg, 1.61 mmol, 29.78% yield) was obtained as yellow solid. $^1$H NMR (DMSO-d$_6$, 400 MHz) δ 8.64 (s, 1H), 4.64~4.61 (m, 2H), 4.12 (s, 3H), 3.91 (t, J=5.2 Hz, 2H), 3.44~3.41 (m, 4H).

Preparation of 5-chloro-1-(2-(2-hydroxyethoxy)ethyl)-1H-pyrazolo[4,3-d]pyrimidin-7(6H)-one (Step 2 in Scheme C-3)

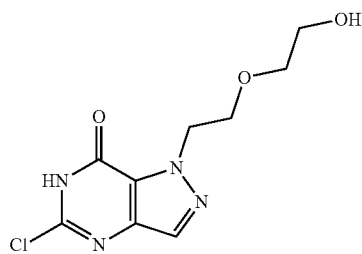 [SMILES: O=c1[nH]c(Cl)nc2cnn(CCOCCO)c12]

A mixture of 2-[2-(5-chloro-7-methoxy-pyrazolo[4,3-d]pyrimidin-1-yl)ethoxy]ethanol (1.19 g, 4.36 mmol, 1 eq) and LiOH—H₂O (732.45 mg, 17.46 mmol, 4 eq) in THF (10 mL) and H₂O (10 mL) was stirred at 20° C. for 5 hours. TLC indicated the reaction was complete. The reaction mixture was concentrated under reduced pressure to remove THF and then the aqueous was adjusted to pH=4 with 3N HCl. The aqueous was extracted with EtOAc (25 mL×4). The combined organic layers were washed with brine (20 mL), dried over Na₂SO₄, filtered and concentrated under reduced pressure to give 5-chloro-1-[2-(2-hydroxyethoxy)ethyl]-6H-pyrazolo[4,3-d]pyrimidin-7-one (1.3 g, crude) as yellow oil. ¹H NMR (DMSO-d₆, 400 MHz) δ 8.06 (s, 1H), 7.78 (s, 1H), 4.62 (t, J=5.2 Hz, 2H), 4.38 (t, J=4.8 Hz, 2H), 3.83~3.75 (m, 5H).

Preparation of 5-((3,4-dichlorobenzyl)amino)-1-(2-(2-hydroxyethoxy)ethyl)-1H-pyrazolo[4,3-d]pyrimidin-7(6H)-one (Step 3 in Scheme C-3)

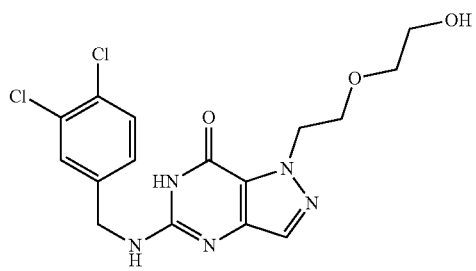 [SMILES: O=c1[nH]c(NCc2ccc(Cl)c(Cl)c2)nc2cnn(CCOCCO)c12]

A mixture of (3,4-dichlorophenyl)methanamine (1.36 g, 7.73 mmol, 1.03 mL, 2 eq) and 5-chloro-1-[2-(2-hydroxyethoxy)ethyl]-6H-pyrazolo[4,3-d]pyrimidin-7-one (1 g, 3.87 mmol, 1 eq) in t-BuOH (6 mL) was stirred at 100° C. for 16 hours. LC-MS showed the reaction was complete. The reaction mixture was concentrated under reduced pressure. The residue was purified by prep-HPLC (column: Phenomenex luna C18 250 mm×50 mm 10 µm; mobile phase: [water (0.1% TFA)-MeCN]; B %: 10%-40%, 20 mins). The aqueous solution was lyophilized to give 5-[(3,4-dichlorophenyl)methylamino]-1-[2-(2-hydroxyethoxy)ethyl]-6H-pyrazolo[4,3-d]pyrimidin-7-one (0.99 g, 2.45 mmol, 63.34% yield, 98.50% purity) as white solid. 30.1 mg has been delivered. ¹H NMR (DMSO-d₆, 400 MHz) δ 7.61~7.57 (m, 3H), 7.33 (dd, J=2.0, 8.4 Hz, 1H), 6.82 (s, 1H), 4.57 (t, J=5.6 Hz, 2H), 4.49 (d, J=5.2 Hz, 2H), 3.79 (t, J=5.6 Hz, 2H), 3.42~3.37 (m, 4H). HPLC: 97.84% (220 nm), 98.14% (215 nm), 98.77% (254 nm). MS (ESI): mass calcd. For C₁₆H₇Cl₂N₅O₃ 397.07, m/z found 398.0 [M+H]⁺.

Compound 89

5-((3,4-Dichlorobenzyl)amino)-1-(4-hydroxybutyl)-1H-pyrazolo[4,3-d]pyrimidin-7(6H)-one was prepared according to the procedures described herein for Steps 1-3 in Scheme C-3.

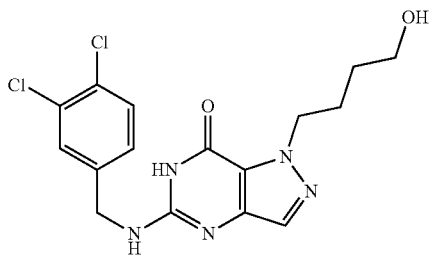 [SMILES: O=c1[nH]c(NCc2ccc(Cl)c(Cl)c2)nc2cnn(CCCCO)c12]

The procedure yielded the desired compound (378.3 mg, 986.58 µmol, 46.04% yield) as a white solid. ¹H NMR (DMSO-d₆, 400 MHz) δ 11.07 (s, 1H), 7.62~7.58 (m, 2H), 7.56 (s, 1H), 7.34 (dd, J=2.0 Hz, 8.4 Hz, 1H), 6.62 (s, 1H), 4.48 (d, J=5.6 Hz, 2H), 4.43 (t, J=6.8 Hz, 2H), 3.37 (t, J=6.8 Hz, 2H), 1.82~1.75 (m, 2H), 1.38~1.26 (m, 2H). HPLC: 99.69% (220 nm), 99.76% (215 nm), 100.00% (254 nm). MS (ESI): mass calcd. For C₆H₇C₂N₅O₂ 381.08, m/z found 382.2 [M+H]⁺.

Compound 90

4-(5-((3,4-Dichlorobenzyl)amino)-7-oxo-6,7-dihydro-1H-pyrazolo[4,3-d]pyrimidin-1-yl)butyl acetate was prepared according to the procedures described herein for Steps 1-3 in Scheme C-3.

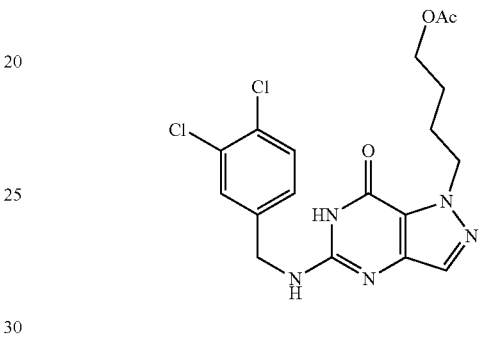

The procedure yielded the desired compound (0.03 g, 70.71 µmol, 77.48% yield) as a white solid. ¹H NMR (CDC₃, 400 MHz) δ 11.28 (s, 1H), 7.57 (s, 1H), 7.43 (d, J=1.6 Hz, 1H), 7.34 (d, J=8.0 Hz, 1H), 7.16 (d, J=1.6 Hz, 1H), 5.45 (s, 1H), 4.54 (d, J=5.2 Hz, 2H), 4.46 (t, J=6.8 Hz, 2H), 4.02 (t, J=6.4 Hz, 2H), 1.94 (s, 3H), 1.83~1.91 (m, 2H), 1.49~1.53 (m, 2H). HPLC: 98.46% (220 nm), 98.15% (215 nm), 98.76% (254 nm). MS (ESI): mass calcd. For C₁₈H₁₉C₁₂N₅O₃ 423.1, m/z found 424.0 [M+H]⁺.

Compound 91

5-((3,4-Dichlorobenzyl)amino)-1-(thiazol-2-ylmethyl)-1H-pyrazolo[4,3-d]pyrimidin-7(6H)-one was prepared according to the procedures described herein for Steps 1~3 in Scheme C-3.

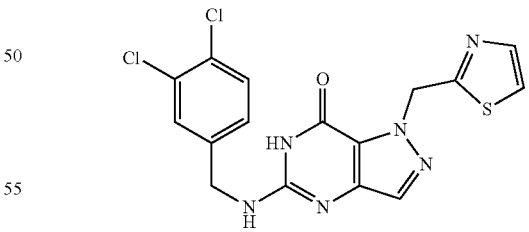

The procedure yielded the desired compound (71.4 mg, 175.31 µmol, 42.66% yield) as a light yellow solid. ¹H NMR (DMSO-d₆, 400 MHz) δ 7.75 (d, J=3.2 Hz, 1H), 7.70 (s, 1H), 7.68 (d, J=3.2 Hz, 1H), 7.62 7.57 (m, 2H), 7.34 (dd, J=2.0 Hz, 8.4 Hz, 1H), 6.85 (d, J=2.0 Hz, 1H), 5.96 (s, 2H), 4.50 (d, J=5.6 Hz, 2H). HPLC: 100.00% (220 nm), 100.00% (215 nm), 100.00% (254 nm). MS (ESI): mass calcd. For C₁₆H₁₂C₂N₆OS 406.02, m/z found 406.9 [M+H]⁺.

Compound 92

5-((3,4-Dichlorobenzyl)amino)-1-(oxazol-4-ylmethyl)-1H-pyrazolo[4,3-d]pyrimidin-7(6H)-one) was prepared according to the procedures described herein for Steps 1~3 in Scheme C-3.

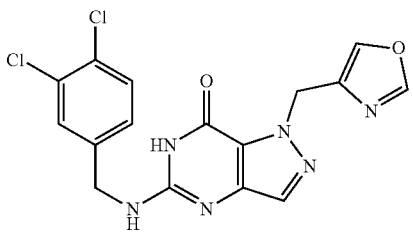 [SMILES: O=c1[nH]c(NCc2ccc(Cl)c(Cl)c2)nc2cnn(Cc3cocn3)c12]

The procedure yielded the desired compound (290.5 mg, 741.49 μmol, 15.42% yield) as an off white solid. $^1$H NMR (DMSO-d$_6$, 400 MHz) δ 11.13 (s, 1H), 8.29 (s, 1H), 7.96 (s, 1H), 7.63~7.54 (m, 3H), 7.32 (dd, J=2.0 Hz, 8.4 Hz, 1H), 6.59 (s, 1H), 5.55 (s, 2H), 4.47 (d, J=5.6 Hz, 2H). HPLC: 99.86% (220 nm), 99.88% (215 nm), 100.00% (254 nm). MS (ESI): mass calcd. For C$_{16}$H$_{12}$Cl$_2$N$_6$O$_2$ 390.04, m/z found 391.0 [M+H]$^+$.

Compound 93

5-((3,4-Dichlorobenzyl)amino)-1-((5-oxopyrrolidin-2-yl)methyl)-1H-pyrazolo[4,3-d]pyrimidin-7(6H)-one was prepared according to the procedures described herein for Steps 1-3 in Scheme C-3.

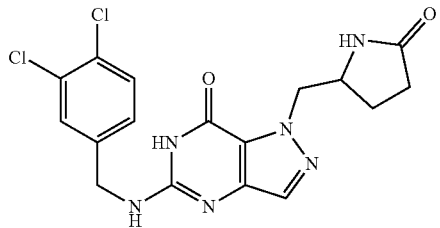 [SMILES: O=C1CCC(Cn2ncc3nc(NCc4ccc(Cl)c(Cl)c4)[nH]c(=O)c32)N1]

The procedure yielded the desired compound (63.7 mg, 156.41 μmol, 46.52% yield) as a white solid. $^1$H NMR (DMSO-d$_6$, 400 MHz) δ7.64 (s, 1H), 7.61~7.58 (m, 3H), 7.33 (dd, J=8.4 Hz, 2.0 Hz, 1H), 6.68 (s, 1H), 4.50~4.46 (m, 3H), 4.42~4.36 (m, 1H), 3.95 (d, J=5.6 Hz, 2H), 2.01 (t, J=5.6 Hz, 3H), 1.80~1.77 (m, 1H). HPLC: 100.00% (220 nm), 100.00% (215 nm), 100.00%(254 nm). MS (ESI): mass calcd. For C$_{17}$H$_6$Cl$_2$N$_6$O$_2$ 406.07, m/z found 407.1 [M+H]$^+$.

Compound 94

5-((3,4-Dichlorobenzyl)amino)-1-(2-(2-oxopyrrolidin-1-yl)ethyl)-1H-pyrazolo[4,3-d]pyrimidin-7(6H)-one) was prepared according to the procedures described herein for Steps 1-3 in Scheme C-3.

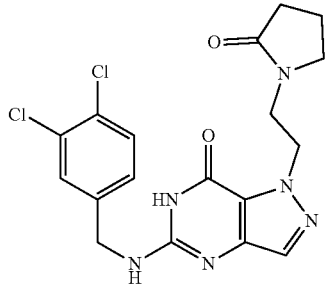 [SMILES: O=C1CCCN1CCn1ncc2nc(NCc3ccc(Cl)c(Cl)c3)[nH]c(=O)c21]

The procedure yielded the desired compound (90.4 mg, 210.81 μmol, 59.38% yield) as an off white solid. $^1$H NMR (DMSO-d$_6$, 400 MHz) δ 7.59~7.57 (m, 2H), 7.54 (s, 1H), 7.33 (dd, J=1.6 Hz, 8.4 Hz, 1H), 6.78 (m, 1H), 4.51 (t, J=5.2 Hz, 2H), 4.47 (d, J=5.6 Hz, 2H), 3.56 (t, J=5.6 Hz, 2H), 3.17 (t, J=6.8 Hz, 2H), 2.05 (t, J=8.4 Hz, 2H), 1.79~1.77 (m, 2H). HPLC: 98.24% (220 nm), 98.21% (215 nm), 100.00% (254 nm). MS (ESI): mass calcd. For C$_{18}$H$_{18}$C$_{12}$N$_6$O$_2$ 420.09, m/z found 421.1 [M+H]$^+$.

Compound 95

1-(2-(2-(2-Butoxyethoxy)ethoxy)ethyl)-5-((3,4-dichlorobenzyl)amino)-1H-pyrazolo[4,3-d]pyrimidin-7(6H)-one) was prepared according to the procedures described herein for Steps 1-3 in Scheme C-3.

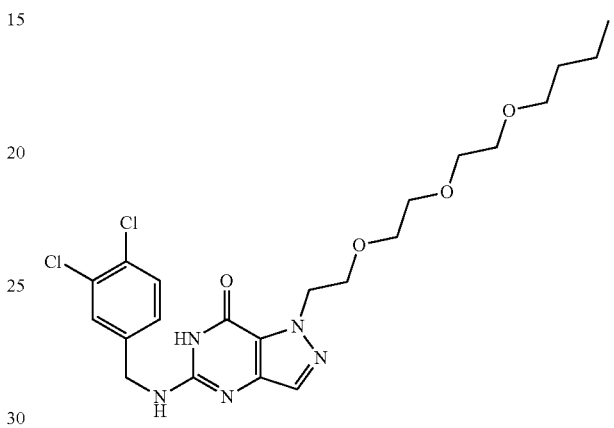

The procedure yielded the desired compound (77.5 mg, 155.50 μmol, 29.37% yield) as a white solid. $^1$H NMR (DMSO-d$_6$, 400 MHz) δ 7.61~7.57 (m, 3H), 7.33 (dd, J=1.6 Hz, 2.0 Hz, 1H), 6.72 (s, 1H), 4.56 (t, J=5.6 Hz, 2H), 4.48 (d, J=5.6 Hz, 2H), 3.79 (t, J=5.6 Hz, 2H), 3.48~3.44 (m, 2H), 3.43~3.37 (m, 6H), 3.32 (t, J=6.8 Hz, 2H), 1.47~1.38 (m, 2H), 1.31~1.22 (m, 2H), 0.85 (t, J=7.2 Hz, 3H). HPLC: 99.05% (220 nm), 97.64% (215 nm), 100.00% (254 nm). MS (ESI): mass calcd. For C$_{22}$H$_{29}$C2N$_5$O$_4$ 497.16, m/z found 498.2 [M+H]$^+$.

Compound 96

5-((3,4-Dichlorobenzyl)amino)-1-(((2R,3R,4R,5S)-3,4,5-trihydroxypiperidin-2-yl)methyl)-1H-pyrazolo[4,3-d]pyrimidin-7(6H)-one) was prepared according to the procedures described herein for Steps 1-3 in Scheme C-3.

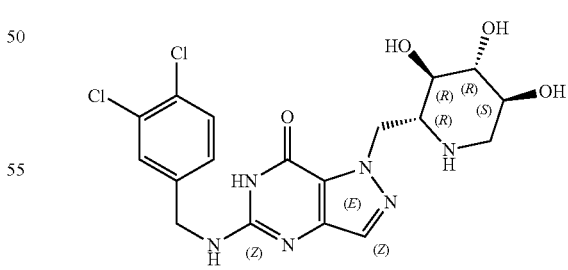

The procedure yielded the desired compound (20 mg, 41.73 μmol, 6.69% yield) as a white solid. H NMR (DMSO-d$_6$, 400 MHz) δ 8.97~8.95 (m, 1H), 8.67 (br s, 1H), 7.70 (s, 1H), 7.60~7.58 (m, 2H), 7.32 (dd, J=2.0 Hz, 8.4 Hz, 1H), 6.88 (br s, 1H), 4.93 (br d, J=13.2 Hz, 1H), 4.67~4.61 (m, 1H), 4.49 (d, J=6.0 Hz, 2H), 3.55~3.43 (m, 2H), 3.30~3.21 (m, 2H), 3.12 (d, J=8.0 Hz, 1H), 2.70~2.64 (m, 1H). HPLC:

94.99% (220 nm), 94.77% (215 nm), 98.18% (254 nm). MS (ESI): mass calcd. For $C_{18}H_{20}C_{12}N_6O_4$ 454.09, m/z found 455.09 [M+H]$^+$.

Compound 97

5-((3,4-Dichlorobenzyl)amino)-1-((1-methyl-1H-imidazol-2-yl)methyl)-1H-pyrazolo[4,3-d]pyrimidin-7(6H)-one was prepared according to the procedures described herein for Steps 1-3 in Scheme C-3.

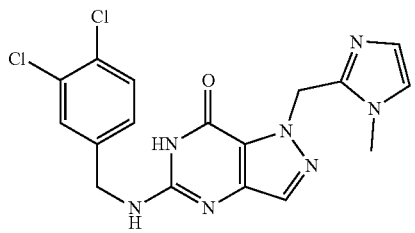 [SMILES: Cn1ccnc1Cn1ncc2nc(NCc3ccc(Cl)c(Cl)c3)[nH]c(=O)c21]

The procedure yielded the desired compound (21 mg, 51.95 μmol, 13.04% yield) as a white solid. $^1$H NMR (DMSO-d$_6$, 400 MHz) δ 7.80 (s, 1H), 7.59~7.53 (m, 3H), 7.34~7.32 (m, 1H), 7.07 (s, 1H), 7.03 (s, 1H), 6.75 (s, 1H), 5.71 (s, 2H), 4.47 (d, J=4.4 Hz, 2H), 3.64 (s, 3H). HPLC: 95.33% (220 nm), 94.77% (215 nm), 93.17% (254 nm). MS (ESI): mass calcd. For $C_{17}H_{15}C_{12}N_7O$ 403.07, m/z found 404.1 [M+H]$^+$.

Compound 98 tert-Butyl 3-(5-((3,4-dichloro benzyl)amino)-7-oxo-6,7-dihydro-1H-pyrazolo[4,3-d]pyrimidin-1-yl)pyrrolidine-1-carboxylate was prepared according to the procedures described herein for Steps 1-3 in Scheme C-3.

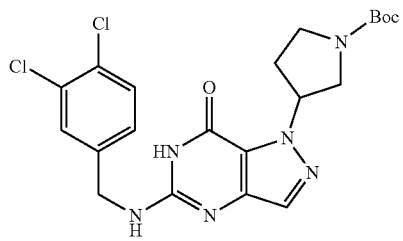 [SMILES: CC(C)(C)OC(=O)N1CCC(n2ncc3nc(NCc4ccc(Cl)c(Cl)c4)[nH]c(=O)c32)C1]

The procedure yielded the desired compound (26.4 mg, 54.15 μmol, 36.80% yield) as a white solid. $^1$H NMR (DMSO-d$_6$, 400 MHz) δ 7.67 (s, 1H), 7.64 (s, 1H), 7.61 (d, J=8.0 Hz, 1H), 7.36 (dd, J=8.4 Hz, 2.0 Hz, 1H), 5.57 (s, 1H), 4.57 (d, J=4.4 Hz, 2H), 3.71~3.68 (m, 1H), 3.57~3.53 (m, 1H), 3.46~3.41 (m, 2H), 2.33~2.30 (m, 2H), 1.39 (d, J=8.0 Hz, 9H). HPLC: 98.32% (220 nm), 98.63% (215 nm), 96.81% (254 nm). MS (ESI): mass calcd. For $C_{21}H_{24}C2N_6O_3$ 478.13, m/z found 479.2 [M+H]$^+$.

Compound 99

Preparation of 1-(2-(2-aminoethoxy)ethyl)-5-((3,4-dichlorobenzyl)amino)-1H-pyrazolo[4,3-d]pyrimidin-7(6H)-one hydrochloride Compound 100 tert-Butyl(2-(2-(5-((3,4-dichlorobenzyl)amino)-7-oxo-6,7-dihydro-1H-pyrazolo[4,3-d]pyrimidin-1-yl)ethoxy)ethyl) carbamate was prepared according to the procedures described herein for Steps 1-3 in Scheme C-3.

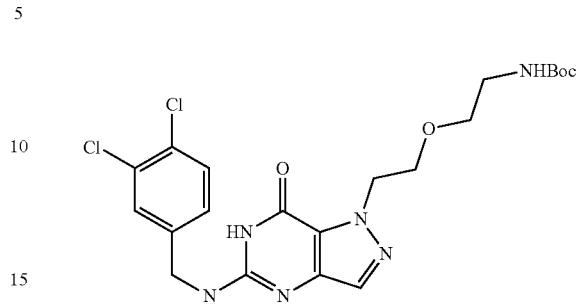

The procedure yielded the desired compound (350 mg, 697.88 μmol, 62.42% yield) as a white solid. $^1$H NMR (DMSO-d$_6$, 400 MHz) δ 11.09 (s, 1H), 7.62~7.52 (m, 3H), 7.33 (dd, J=2.0 Hz, 8.4 Hz, 1H), 6.65 (s, 1H), 4.55 (t, J=5.2 Hz, 2H), 4.47 (d, J=6.0 Hz, 2H), 3.77 (t, J=5.6 Hz, 2H), 3.33 (t, J=6.4 Hz, 2H), 2.98 (q, J=6.0 Hz, 2H), 1.35 (s, 9H). HPLC: 99.17% (220 nm), 99.07% (215 nm), 99.62% (254 nm). MS (ESI): mass calcd. For $C21H_{26}C_{12}N_6O_4$ 496.14, m/z found 497.2 [M+H]$^+$.

Preparation of 1-(2-(2-aminoethoxy)ethyl)-5-((3,4-dichlorobenzyl)amino)-1H-pyrazolo[4,3-d]pyrimidin-7(6H)-one hydrochloride

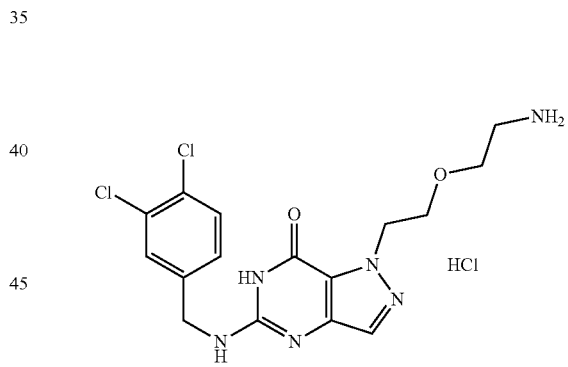

A mixture of tert-butyl N-[2-[2-[5-[(3,4-dichlorophenyl)methylamino]-7-oxo-6H-pyrazolo[4,3-d]pyrimidin-1-yl]ethoxy]ethyl]carbamate (Compound 100) (0.1 g 201.06 μmol, 1 eq) in HC/EtOAc (20 mL) and EtOAc (5 mL) was stirred at 20° C. for 5 hours. LC-MS showed the reaction was complete. The reaction mixture was concentrated under reduced pressure. Compound 1-[2-(2-aminoethoxy)ethyl]-5-[(3,4-dichlorophenyl)methylamino]-6H-pyrazolo[4,3-d]pyrimidin-7-one (70 mg, 159.76 mol, 79.46% yield, 98.989% purity, HCl) was obtained as white solid. $^1$H NMR (DMSO-d$_6$, 400 MHz) δ 7.83 (s, 3H), 7.65~7.57 (m, 3H), 7.35 (d, J=8.4 Hz, 1H), 4.62 (t, J=5.6 Hz, 2H), 4.53 (s, 2H), 3.85 (t, J=5.6 Hz, 2H), 3.57 (t, J=5.2 Hz, 2H), 2.90 (d, J=5.2 Hz, 2H). HPLC: 98.99% (220 nm), 98.52% (215 nm), 100.00% (254 nm). MS (ESI): mass calcd. For $C_{16}H_9C_3N_6O_2$ 396.09, m/z found 397.1 [M+H]$^+$.

Compound 101

1-((1H-1,2,4-triazol-1-yl)methyl)-5-((3,4-dichlorobenzyl)amino)-1H-pyrazolo[4,3-d]pyrimidin-7(6H)-one hydrochloride was prepared according to the procedures described herein for Steps 1-3 in Scheme C-3.

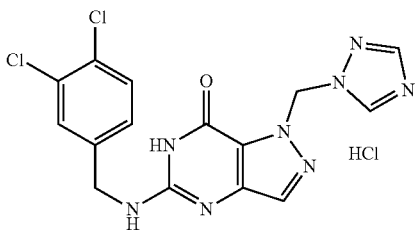 [SMILES: O=c1[nH]c(NCc2ccc(Cl)c(Cl)c2)nc2cnn(Cn3cncn3)c12 ; Cl]

The procedure yielded the desired compound (34.7 mg, 77.16 µmol, 21.34% yield, HCl) as a white solid. $^1$H NMR (DMSO-$d_6$, 400 MHz) δ 8.75 (s, 1H), 7.99 (s, 1H), 7.74 (s, 1H), 7.61~7.57 (m, 2H), 7.35~7.32 (m, 2H), 6.74 (s, 2H), 4.52 (d, J=4.8 Hz, 2H). HPLC: 95.10% (220 nm), 94.99% (215 nm), 100.00% (254 nm). MS (ESI): mass calcd. For $C_{15}H_{13}C3N_8O$ 390.05, m/z found 391.0 [M+H]$^+$.

Compound 102

5-((3,4-Dichlorobenzyl)amino)-1-((tetrahydrofuran-2-yl)methyl)-1H-pyrazolo[4,3-d]pyrimidin-7(6H)-one was prepared according to the procedures described herein for Steps 1-3 in Scheme C-3.

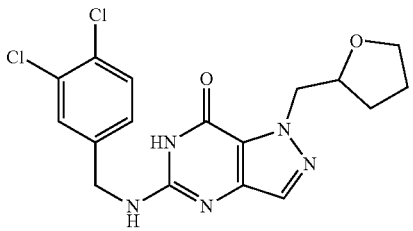 [SMILES: O=c1[nH]c(NCc2ccc(Cl)c(Cl)c2)nc2cnn(CC3CCCO3)c12]

The procedure yielded the desired compound (48.8 mg, 123.40 µmol, 52.38% yield) as a white solid. $^1$H NMR (DMSO-$d_6$, 400 MHz) δ 7.87~7.53 (m, 4H), 7.37 (dd, J=1.6 Hz, 8.4 Hz, 1H), 4.57 (d, J=4.8 Hz, 2H), 4.55~4.50 (m, 1H), 4.36 (dd, J=5.2 Hz, 13.6 Hz, 1H), 4.24~4.18 (m, 1H), 3.73~3.71 (m, 1H), 3.62~3.57 (m, 1H), 1.93~1.72 (m, 3H), 1.69~1.57 (m, 1H). HPLC: 99.70% (220 nm), 99.50% (215 nm), 99.40% (254 nm). MS (ESI): mass calcd. For $C_{17}H_{17}C_{12}N_5O_2$ 393.08, m/z found 394.1 [M+H]$^+$.

Compound 103

2-((1H-1,2,4-triazol-1-yl)methyl)-5-((3,4-dichlorobenzyl)amino)-2H-pyrazolo[4,3-d]pyrimidin-7(6H)-one hydrochloride was prepared according to the procedures described herein for Steps 1-3 in Scheme C-3.

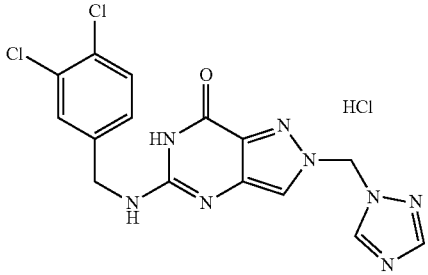 [SMILES: O=c1[nH]c(NCc2ccc(Cl)c(Cl)c2)nc2cn(Cn3cncn3)nc12 ; Cl]

The procedure yielded the desired compound (21.1 mg, 45.65 µmol, 12.62% yield, HCl) as a white solid. $^1$H NMR (DMSO-$d_6$, 400 MHz) δ 8.93~8.87 (m, 2H), 8.35 (s, 1H), 8.07 (s, 1H), 7.73~7.62 (m, 2H), 7.42 (t, J=5.6 Hz, 1H), 6.75 (s, 2H), 4.74 (s, 2H). HPLC: 92.54% (220 nm), 91.99% (215 nm), 93.12% (254 nm). MS (ESI): mass calcd. For $C_{15}H_{13}C_3N_8O$ 390.05, m/z found 391.0 [M+H]$^+$.

Compound 104

5-((3,4-Dichlorobenzyl)amino)-1-(2-((2-hydroxyethyl)thio)ethyl)-1H-pyrazolo[4,3-d]pyrimidin-7(6H)-one was prepared according to the procedures described herein for Steps 1-3 in Scheme C-3.

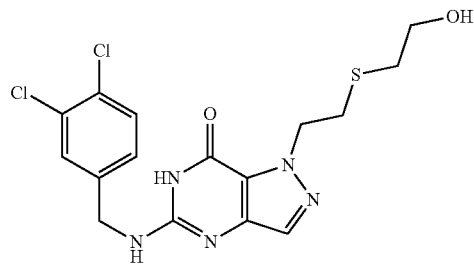 [SMILES: O=c1[nH]c(NCc2ccc(Cl)c(Cl)c2)nc2cnn(CCSCCO)c12]

The procedure yielded the desired compound (184.5 mg, 436.26 µmol, 52.11% yield) as a white solid. $^1$H NMR (DMSO-$d_6$, 400 MHz) δ 10.47 (s, 1H), 7.68~7.47 (m, 3H), 7.33 (dd, J=2.0 Hz, 8.4 Hz, 1H), 6.64 (s, 1H), 4.77 (s, 1H), 4.58 (t, J=6.8 Hz, 2H), 4.47 (d, J=6.0 Hz, 2H), 3.52 (q, J=6.0 Hz, 2H), 2.93 (t, J=7.2 Hz, 2H), 2.56 (t, J=6.8 Hz, 2H). HPLC: 97.97% (220 nm), 97.21% (215 nm), 100.00% (254 nm). MS (ESI): mass calcd. For $C_{16}H_{17}C_{12}N_5O_2S$ 413.05, m/z found 414.0 [M+H]$^+$.

Compound 105

1-((1,4-Dioxan-2-yl)methyl)-5-((3,4-dichlorobenzyl)amino)-1H-pyrazolo[4,3-d]pyrimidin-7(6H)-one was prepared according to the procedures described herein for Steps 1-3 in Scheme C-3.

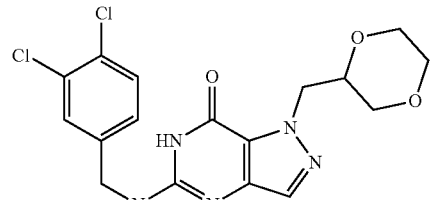

The procedure yielded the desired compound (89.6 mg, 210.89 µmol, 57.08% yield) as a white solid. $^1$H NMR (DMSO-$d_6$, 400 MHz) δ 7.63 (s, 3H), 7.33 (dd, J=2.0 Hz, 8.4 Hz, 1H), 6.77 (s, 1H), 4.57 (dd, J=7.2 Hz, 13.6 Hz, 1H), 4.48 (d, J=5.6 Hz, 2H), 4.37 (dd, J=5.2 Hz, 14.0 Hz, 1H), 3.95~3.90 (m, 1H), 3.71 (s, 2H), 3.60 (s, 1H), 3.48~3.44 (m, 2H), 3.32 (dd, J=9.6 Hz, 11.6 Hz, 1H). HPLC: 96.56% (220 nm), 95.74% (215 nm), 98.80% (254 nm). MS (ESI): mass calcd. For $C_{17}H_{17}C_{12}N_5O_3$ 409.07, m/z found 410.0 [M+H]$^+$.

Compound 106

5-((3,4-Dichlorobenzyl)amino)-1-(1,3-dimethoxypropan-2-yl)-1H-pyrazolo[4,3-d]pyrimidin-7(6H)-one was prepared according to the procedures described herein for Steps 1-3 in Scheme C-3.

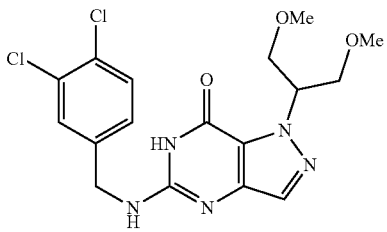 [SMILES: COCC(COC)n1ncc2nc(NCc3ccc(Cl)c(Cl)c3)[nH]c(=O)c21]

The procedure yielded the desired compound (68.5 mg, 158.02 μmol, 62.01% yield) as a white solid. $^1$H NMR (DMSO-d$_6$, 400 MHz) δ 7.65~7.54 (m, 3H), 7.33 (d, J=7.6 Hz, 1H), 6.91 (s, 1H), 5.44 (s, 1H), 4.49 (d, J=3.6 Hz, 2H), 3.75 (t, J=9.6 Hz, 2H), 3.63 (dd, J=4.8 Hz, 10.0 Hz, 2H), 3.17 (s, 6H). HPLC: 95.10% (220 nm), 94.43% (215 nm), 97.70% (254 nm). MS (ESI): mass calcd. For C$_{17}$H$_{19}$C$_{12}$N$_5$O$_3$ 411.09, m/z found 412.1 [M+H]$^+$.

Compound 107

5-((3,4-Dichlorobenzyl)amino)-1-(1,3-dihydroxypropan-2-yl)-1H-pyrazolo[4,3-d]pyrimidin-7(6H)-one was prepared according to the procedures described herein for Steps 1-3 in Scheme C-3.

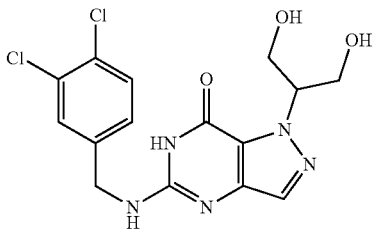 [SMILES: O=c1[nH]c(NCc2ccc(Cl)c(Cl)c2)nc2cnn(C(CO)CO)c12]

The procedure yielded the desired compound (17.5 mg, 43.55 μmol, 10.65% yield) as a white solid. $^1$H NMR (DMSO-d$_6$, 400 MHz) δ 7.59 (d, J=4.4 Hz, 3H), 7.33 (d, J=6.8 Hz, 1H), 6.81 (s, 1H), 5.14~5.00 (m, 1H), 4.49 (d, J=3.6 Hz, 2H), 3.74 (d, J=5.6 Hz, 4H). HPLC: 95.62% (220 nm), 95.60% (215 nm), 95.24% (254 nm). MS (ESI): mass calcd. For C$_{15}$H$_{15}$C$_{12}$N$_5$O$_3$ 383.06, m/z found 384.1 [M+H]$^+$.

Compound 108

5-((3,4-Dichlorobenzyl)amino)-1-(2-((tetrahydro-2H-pyran-4-yl)oxy)ethyl)-1H-pyrazolo[4,3-d]pyrimidin-7(6H)-one) was prepared according to the procedures described herein for Steps 1-3 in Scheme C-3.

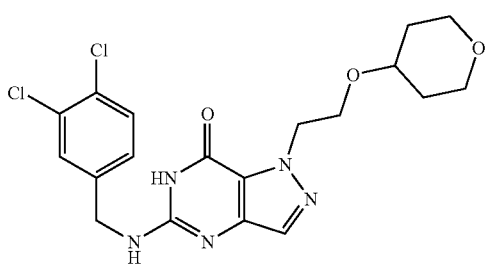 [SMILES: O=c1[nH]c(NCc2ccc(Cl)c(Cl)c2)nc2cnn(CCOC3CCOCC3)c12]

The procedure yielded the desired compound (71.1 mg, 161.56 μmol, 32.17% yield) as a white solid. H NMR (DMSO-d$_6$, 400 MHz) δ 7.99 (s, 1H), 7.69~7.64 (m, 2H), 7.62 (d, J=7.6 Hz, 1H), 7.38 (d, J=8.4 Hz, 1H), 4.62~4.56 (m, 4H), 3.81 (t, J=5.2 Hz, 2H), 3.68 (s, 2H), 3.45~3.43 (m, 1H), 3.29~3.22 (m, 2H), 1.75~1.68 (m, 2H), 1.30~1.21 (m, 2H). HPLC: 99.60% (220 nm), 99.70% (215 nm), 100.00% (254 nm). MS (ESI): mass calcd. For C$_{19}$H$_{21}$C2N$_5$O$_3$ 437.10, m/z found 438.1 [M+H]$^+$.

Compound 109

5-((3,4-Dichlorobenzyl)amino)-1-(pyridin-2-ylmethyl)-1H-pyrazolo[4,3-d]pyrimidin-7(6H)-one hydrochloride was prepared according to the procedures described herein for Steps 1-3 in Scheme C-3.

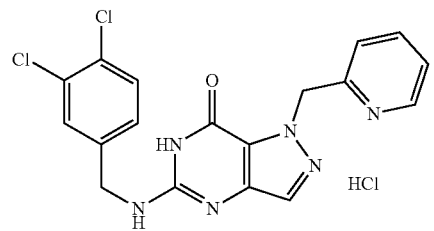 [SMILES: O=c1[nH]c(NCc2ccc(Cl)c(Cl)c2)nc2cnn(Cc3ccccn3)c12 ; Cl]

The procedure yielded the desired compound (55.4 mg, 117.21 μmol, 29.49% yield) as a white solid. $^1$H NMR (DMSO-d$_6$, 400 MHz) δ 8.58 (d, J=4.8 Hz, 1H), 7.94~7.92 (m, 1H), 7.71 (s, 1H), 7.63~7.60 (m, 2H), 7.45~7.43 (m, 1H), 7.37~7.35 (m, 2H), 7.12 (d, J=8.0 Hz, 1H), 5.82 (s, 2H), 4.54 (d, J=5.2 Hz, 2H). HPLC: 92.60% (220 nm), 90.01% (215 nm), 95.32% (254 nm). MS (ESI): mass calcd. For C$_{18}$H$_{15}$C$_{13}$N$_6$O 400.06, m/z found 401.0 [M+H]$^+$.

Compound 110

5-((3,4-Dichlorobenzyl)amino)-1-(2-(pyridin-3-yl)ethyl)-1H-pyrazolo[4,3-d]pyrimidin-7(6H)-one hydrochloride was prepared according to the procedures described herein for Steps 1-3 in Scheme C-3.

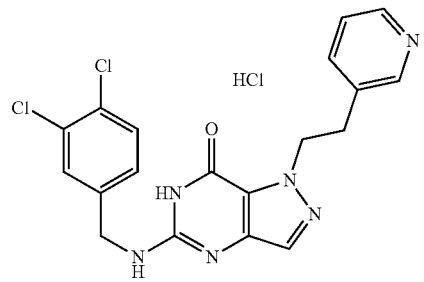 [SMILES: O=c1[nH]c(NCc2ccc(Cl)c(Cl)c2)nc2cnn(CCc3cccnc3)c12 ; Cl]

The procedure yielded the desired compound (131.7 mg, 287.85 μmol, 34.50% yield) as a white solid. $^1$H NMR (DMSO-d$_6$, 400 MHz) δ 8.77 (d, J=5.2 Hz, 1H), 8.72 (s, 1H), 8.28 (d, J=8.4 Hz, 1H), 8.05~7.89 (m, 2H), 7.67~7.56 (m, 3H), 7.37 (d, J=8.4 Hz, 1H), 4.79 (t, J=6.4 Hz, 2H), 4.58 (d, J=3.6 Hz, 2H), 3.36 (t, J=6.4 Hz, 2H). HPLC: 98.74% (220 nm), 98.50% (215 nm), 99.11% (254 nm). MS (ESI): mass calcd. For C$_{19}$H$_{17}$C3N$_6$O 414.08, m/z found 415.0 [M+H]$^+$.

Compound 111

5-((3,4-Dichlorobenzyl)amino)-1-(2-(pyridin-2-yl)ethyl)-1H-pyrazolo[4,3-d]pyrimidin-7(6H)-one hydrochloride was prepared according to the procedures described herein for Steps 1-3 in Scheme C-3.

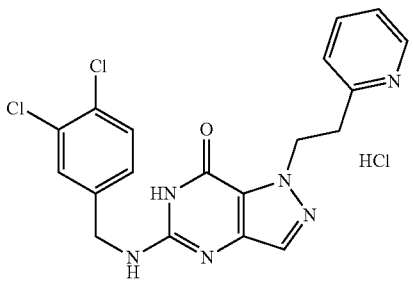 [SMILES: O=c1[nH]c(NCc2ccc(Cl)c(Cl)c2)nc2cnn(CCc3ccccn3)c12 ; Cl]

The procedure yielded the desired compound (66.3 mg, 157.39 μmol, 45.68% yield) as a white solid. $^1$H NMR (DMSO-d$_6$, 400 MHz) δ 8.76 (d, J=5.2 Hz, 1H), 8.43~8.36 (m, 1H), 7.87 (d, J=6.4 Hz, 1H), 7.76 (d, J=8.0 Hz, 1H), 7.64~7.56 (m, 2H), 7.52 (s, 1H), 7.37~7.34 (m, 1H), 4.90 (t, J=6.4 Hz, 2H), 4.57 (d, J=5.2 Hz, 2H), 3.57 (s, 2H). HPLC: 98.58% (220 nm), 98.30% (215 nm), 98.93% (254 nm). MS (ESI): mass calcd. For $C_{19}H_{17}C_{13}N_6O$, 414.08 m/z found 415.1 [M+H]$^+$.

Compound 112

5-((3,4-Dichlorobenzyl)amino)-1-(pyrazin-2-ylmethyl)-1H-pyrazolo[4,3-d]pyrimidin-7(6H)-one hydrochloride was prepared according to the procedures described herein for Steps 1-3 in Scheme C-3.

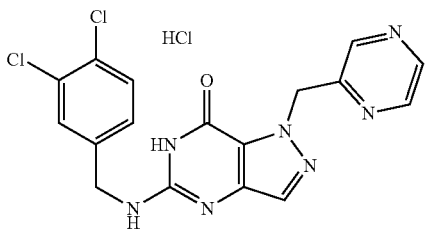 [SMILES: O=c1[nH]c(NCc2ccc(Cl)c(Cl)c2)nc2cnn(Cc3cnccn3)c12 ; Cl]

The procedure yielded the desired compound (43.3 mg, 92.57 μmol, 34.74% yield) as a white solid. $^1$H NMR (DMSO-d$_6$, 400 MHz) δ 8.56 (s, 2H), 8.49 (s, 1H), 7.68 (s, 1H), 7.65~7.58 (m, 2H), 7.46~7.30 (m, 2H), 5.83 (s, 2H), 4.54 (d, J=4.8 Hz, 2H). HPLC: 93.80% (220 nm), 92.74% (215 nm), 99.63% (254 nm). MS (ESI): mass calcd. For $C_{17}H_{14}C3N_7O$ 401.06, m/z found 402.0 [M+H]$^+$.

Compound 113

5-[(3,4-Dichlorophenyl)methylamino]-1-(3-pyridylmethyl)-6H-pyrazolo[4,3-d]pyrimidin-7-one was prepared according to the procedures described herein for Steps 1-3 in Scheme C-3.

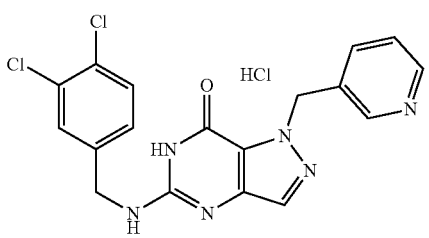 [SMILES: O=c1[nH]c(NCc2ccc(Cl)c(Cl)c2)nc2cnn(Cc3cccnc3)c12 ; Cl]

The procedure yielded the desired compound (87.3 mg, 196.51 μmol, 57.13% yield) as a white solid. $^1$H NMR (DMSO-d$_6$, 400 MHz) δ 8.80~8.75 (m, 2H), 8.19 (d, J=8.4 Hz, 1H), 7.88 (dd, J=5.6 Hz, 8.0 Hz, 1H), 7.71 (s, 1H), 7.63~7.56 (m, 2H), 7.46~7.27 (m, 2H), 5.83 (s, 2H), 4.53 (d, J=5.2 Hz, 2H). HPLC: 98.52% (220 nm), 91.50% (215 nm), 99.46% (254 nm). MS (ESI): mass calcd. For $C_{18}H_{15}C_{13}N_6O$ 400.06, m/z found 401.0 [M+H]$^+$.

Compound 114

5-((3,4-Dichlorobenzyl)amino)-1-(pyrimidin-2-ylmethyl)-1H-pyrazolo[4,3-d]pyrimidin-7(6H)-one was prepared according to the procedures described herein for Steps 1-3 in Scheme C-3.

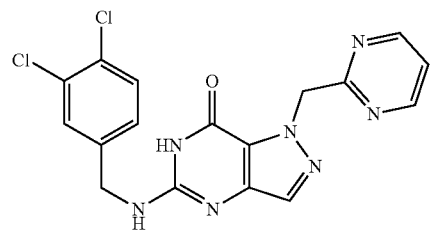 [SMILES: O=c1[nH]c(NCc2ccc(Cl)c(Cl)c2)nc2cnn(Cc3ncccn3)c12]

The procedure yielded the desired compound (54.7 mg, 128.84 μmol, 41.78% yield) as a light yellow solid. H NMR (DMSO-d$_6$, 400 MHz) δ 8.73 (d, J=4.8 Hz, 2H), 7.67 (d, J=10.0 Hz, 2H), 7.62 (d, J=8.4 Hz, 1H), 7.45~7.35 (m, 2H), 5.85 (s, 2H), 4.57 (d, J=4.0 Hz, 2H). HPLC: 94.74% (220 nm), 93.84% (215 nm), 98.88% (254 nm). MS (ESI): mass calcd. For $C_{17}H_{13}C_{12}N_7O$ 401.06, m/z found 402.0 [M+H]$^+$.

Compound 115

5-((3,4-Dichlorobenzyl)amino)-1-(2-(2-(2-hydroxyethoxy)ethoxy)ethyl)-1H-pyrazolo[4,3-d]pyrimidin-7(6H)-one was prepared according to the procedures described herein for Steps 1-3 in Scheme C-3.

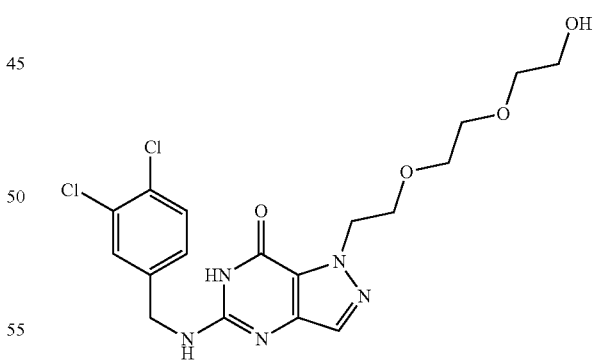

The procedure yielded the desired compound (420 mg, 947.33 μmol, 68.28% yield) as a white solid. $^1$H NMR (DMSO-d$_6$, 400 MHz) δ 7.61~7.52 (m, 3H), 7.31 (dd, J=2.0 Hz, 8.4 Hz, 1H), 6.79 (t, J=4.4 Hz, 1H), 4.55 (t, J=5.6 Hz, 2H), 4.46 (d, J=5.6 Hz, 2H), 3.77 (s, 2H), 3.47~3.43 (m, 4H), 3.41 (d, J=4.4 Hz, 2H), 3.34~3.30 (m, 2H). HPLC: 99.76% (220 nm), 99.59% (215 nm), 99.72% (254 nm). MS (ESI): mass calcd. For $C_{18}H_{21}C2N_5O_4$ 441.10, m/z found 442.1 [M+H]$^+$.

Compound 116

5-((3,4-Dichlorobenzyl)amino)-1-(2-(2-(2-(2-hydroxyethoxy)ethoxy) ethoxy)ethyl)-1H-pyrazolo[4,3-d]pyrimidin-7(6H)-one was prepared according to the procedures described herein for Steps 1-3 in Scheme C-3.

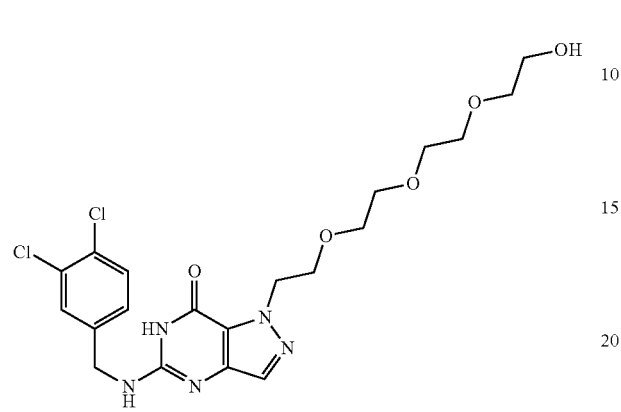

The procedure yielded the desired compound (106.3 mg, 214.99 μmol, 53.25% yield) as a white solid. H NMR (DMSO-d$_6$, 400 MHz) δ 7.63~7.55 (m, 3H), 7.33 (dd, J=1.6 Hz, 8.4 Hz, 1H), 6.75 (s, 1H), 4.57 (t, J=5.6 Hz, 2H), 4.48 (d, J=5.6 Hz, 2H), 3.79 (t, J=6.0 Hz, 2H), 3.48~3.45 (m, 4H), 3.43 (s, 6H), 3.39~3.36 (m, 2H). HPLC: 98.36% (220 nm), 97.32% (215 nm), 98.29% (254 nm). MS (ESI): mass calcd. For $C_{20}H_{25}C_{12}N_5O_5$ 485.12, m/z found 486.1 [M+H]$^+$.

Compound 117

5-((3,4-Dichlorobenzyl)amino)-1-(2-(pyrimidin-2-yl)ethyl)-1H-pyrazolo[4,3-d]pyrimidin-7(6H)-one was prepared according to the procedures described herein for Steps 1-3 in Scheme C-3.

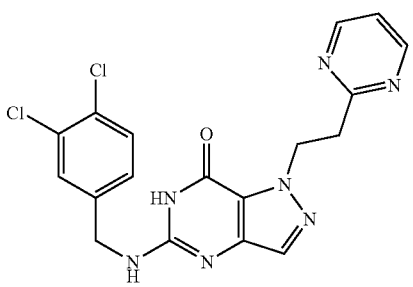 [SMILES: O=c1[nH]c(NCc2ccc(Cl)c(Cl)c2)nc2cnn(CCc3ncccn3)c12]

The procedure yielded the desired compound (9.8 mg, 21.84 μmol, 20.14% yield) as a white solid. $^1$H NMR (DMSO-d$_6$, 400 MHz) δ 8.70 (d, J=4.8 Hz, 2H), 7.60~7.56 (m, 2H), 7.52~7.48 (m, 1H), 7.37~7.31 (m, 2H), 6.83 (s, 1H), 4.88 (t, J=7.2 Hz, 2H), 4.48 (d, J=5.6 Hz, 2H), 3.43~3.41 (m, 2H). HPLC: 92.75% (220 nm), 91.04% (215 nm), 98.20% (254 nm). MS (ESI): mass calcd. For $C_8H_5C_{12}N_7O$ 415.07, m/z found 416.0 [M+H]$^+$.

Compound 118

5-((3,4-Dichlorobenzyl)amino)-1-(oxetan-3-ylmethyl)-1H-pyrazolo[4,3-d]pyrimidin-7(6H)-one was prepared according to the procedures described herein for Steps 1-3 in Scheme C-3.

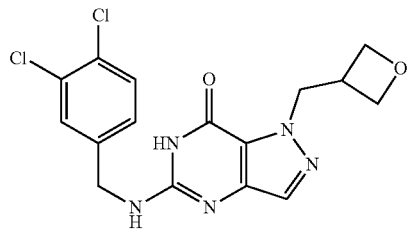 [SMILES: O=c1[nH]c(NCc2ccc(Cl)c(Cl)c2)nc2cnn(CC3COC3)c12]

The procedure yielded the desired compound (84.1 mg, 207.55 μmol, 24.97% yield) as a white solid. $^1$H NMR (DMSO-d$_6$, 400 MHz) δ 10.75 (s, 1H), 7.66~7.53 (m, 3H), 7.32 (dd, J=1.6 Hz, 8.0 Hz, 1H), 6.59 (s, 1H), 4.72 (d, J=7.6 Hz, 2H), 4.60 (dd, J=6.0 Hz, 7.6 Hz, 2H), 4.47 (d, J=6.0 Hz, 2H), 4.40 (t, J=6.4 Hz, 2H), 3.45~3.37 (m, 1H). HPLC: 93.84% (220 nm), 88.55% (215 nm), 98.29% (254 nm). MS (ESI): mass caled. For $C_{16}H_{15}C_{12}N_5O_2$ 379.06, m/z found 380.0 [M+H]$^+$.

Compound 119

5-((3,4-Dichlorobenzyl)amino)-1-(tetrahydrofuran-3-yl)-1H-pyrazolo[4,3-d]pyrimidin-7(6H)-one was prepared according to the procedures described herein for Steps 1-3 in Scheme C-3.

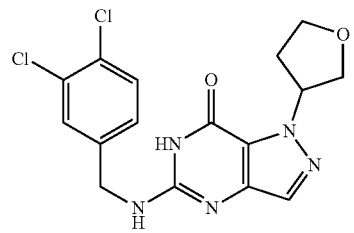 [SMILES: O=c1[nH]c(NCc2ccc(Cl)c(Cl)c2)nc2cnn(C3CCOC3)c12]

The procedure yielded the desired compound (70.4 mg, 174.59 μmol, 20.01% yield) as a white solid. $^1$H NMR (DMSO-d$_6$, 400 MHz) δ 7.60~7.57 (m, 3H), 7.32 (d, J 8.0 Hz, 1H), 6.85 (s, 1H), 5.65 (t, J 4.4 Hz, 1H), 4.48 (d, J 5.6 Hz, 2H), 4.03~3.96 (m, 2H), 3.85~3.81 (m, 2H), 2.37~2.31 (m, 2H). HPLC: 94.30% (220 nm), 91.72% (215 nm), 90.52% (254 nm). MS (ESI): mass calcd. For $C_{16}H_{15}C_{12}N_5O_2$ 379.06, m/z found 380.1 [M+H]$^+$.

Compound 120

5-((3,4-Dichlorobenzyl)amino)-1-((tetrahydrofuran-3-yl)methyl)-1H-pyrazolo[4,3-d]pyrimidin-7(6H)-one was prepared according to the procedures described herein for Steps 1-3 in Scheme C-3.

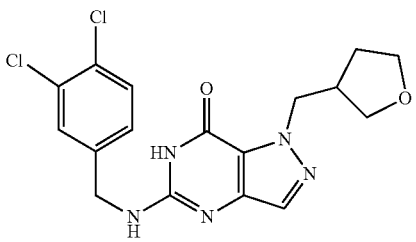 [SMILES: O=c1[nH]c(NCc2ccc(Cl)c(Cl)c2)nc2cnn(CC3CCOC3)c12]

The procedure yielded the desired compound (72.6 mg, 181.68 μmol, 21.03% yield) as a white solid. $^1$H NMR (DMSO-d$_6$, 400 MHz) δ 7.65~7.60 (m, 4H), 7.37 (d, J 8.0 Hz, 1H), 4.57 (s, 2H), 4.46~4.40 (m, 2H), 3.74~3.71 (m, 4H), 2.75~2.72 (m, 1H), 1.88~1.84 (m, 1H), 1.67~1.57 (m, 1H). HPLC: 98.66% (220 nm), 98.29% (215 nm), 98.84% (254 nm). MS (ESI): mass calcd. For C$_{17}$H$_7$Cl$_2$N$_5$O$_2$ 393.08, m/z found 394.0 [M+H]$^+$.

Compound 121

5-((3,4-Dichlorobenzyl)amino)-1-(tetrahydro-2H-pyran-4-yl)-1H-pyrazolo[4,3-d]pyrimidin-7(6H)-one was prepared according to the procedures described herein for Steps 1-3 in Scheme C-3.

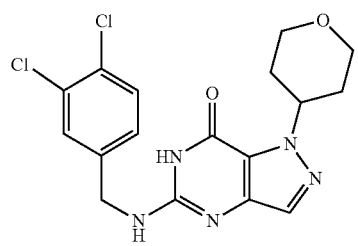 [SMILES: O=c1[nH]c(NCc2ccc(Cl)c(Cl)c2)nc2cnn(C3CCOCC3)c12]

The procedure yielded the desired compound (102.6 mg, 257.22 μmol, 36.39% yield) as a white solid. $^1$H NMR (DMSO-d$_6$, 400 MHz) δ 7.60~7.56 (m, 3H), 7.32 (dd, J=1.6 Hz, 8.4 Hz, 1H), 6.65 (s, 1H), 5.13~4.96 (m, 1H), 4.47 (d, J=5.6 Hz, 2H), 3.97 (dd, J=3.2 Hz, 11.2 Hz, 2H), 3.47~3.44 (m, 2H), 2.10~2.00 (m, 2H), 1.89~1.84 (m, 2H). HPLC: 98.84% (220 nm), 98.20% (215 nm), 100.00% (254 nm). MS (ESI): mass calcd. For C$_7$H$_{17}$C2N$_5$O$_2$ 393.08, m/z found 394.0 [M+H]$^+$.

Compound 122

5-((3,4-Dichlorobenzyl)amino)-1-(oxetan-2-ylmethyl)-1H-pyrazolo[4,3-d]pyrimidin-7(6H)-one was prepared according to the procedures described herein for Steps 1-3 in Scheme C-3.

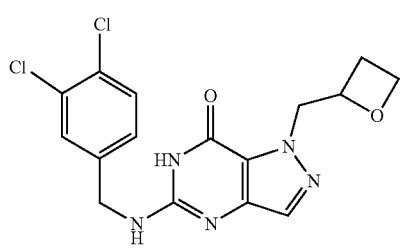 [SMILES: O=c1[nH]c(NCc2ccc(Cl)c(Cl)c2)nc2cnn(CC3CCO3)c12]

The procedure yielded the desired compound (8.0 mg, 19.89 μmol, 11.97% yield) as a white solid. $^1$H NMR (DMSO-d$_6$, 400 MHz) δ7.65~7.53 (m, 3H), 7.32 (d, J=7.6 Hz, 1H), 6.60 (s, 1H), 5.02~4.95 (m, 1H), 4.76~4.69 (m, 1H), 4.65~4.56 (m, 1H), 4.51~4.41 (m, 3H), 4.36~4.29 (m, 1H), 2.65~2.57 (m, 2H). HPLC: 94.54% (220 nm), 93.72% (215 nm), 98.31% (254 nm). MS (ESI): mass calcd. For C$_{16}$H$_{15}$C$_{12}$N$_5$O$_2$ 379.06, m/z found 380.0 [M+H]$^+$.

Compound 123

5-((3,4-Dichlorobenzyl)amino)-1-(3-hydroxypropyl)-1H-pyrazolo[4,3-d]pyrimidin-7(6H)-one was prepared according to the procedures described herein for Steps 1-3 in Scheme C-3.

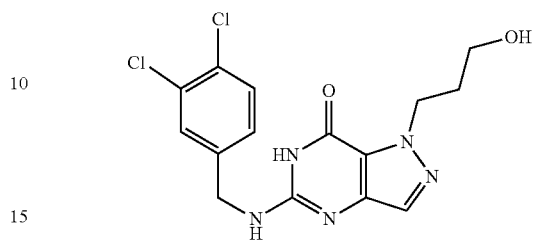

The procedure yielded the desired compound (27.8 mg, 75.50 μmol, 19.18% yield) as an off white solid. $^1$H NMR (DMSO-d$_6$, 400 MHz) δ 11.07 (s, 1H), 7.59~7.57 (m, 2H), 7.53 (s, 1H), 7.32 (dd, J=2.0 Hz, 8.4 Hz, 1H), 6.59~6.50 (m, 1H), 4.54~4.44 (m, 4H), 3.38 (t, J=6.0 Hz, 2H), 1.94~1.87 (m, 2H). HPLC: 100.00% (220 nm), 83.10% (215 nm), 98.33% (254 nm). MS (ESI): mass calcd. For C$_{15}$H$_{15}$C$_{12}$N$_5$O$_2$ 367.06, m/z found 368.0 [M+H]$^+$.

Compound 124

5-((3,4-Dichlorobenzyl)amino)-1-(2-(pyrazin-2-yl)ethyl)-1H-pyrazolo[4,3-d]pyrimidin-7(6H)-one hydrochloride was prepared according to the procedures described herein for Steps 1-3 in Scheme C-3.

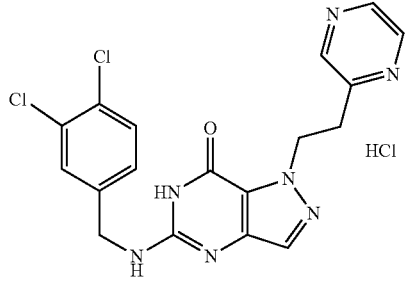 [SMILES: O=c1[nH]c(NCc2ccc(Cl)c(Cl)c2)nc2cnn(CCc3cnccn3)c12 ; Cl]

The procedure yielded the desired compound (24.1 mg, 49.93 μmol, 19.19% yield) as a white solid. $^1$H NMR (DMSO-d$_6$, 400 MHz) δ 8.51 (d, J 2.8 Hz, 1H), 8.45 (d, J 2.0 Hz, 1H), 8.40 (s, 1H), 7.60~7.58 (m, 2H), 7.52 (s, 1H), 7.33 (dd, J 8.4 Hz, J 2.0 Hz, 1H), 7.01 (s, 1H), 4.81 (t, J 6.8 Hz, 2H), 4.49 (d, J 5.6 Hz, 2H), 3.31 (t, J 7.2 Hz, 2H). HPLC: 93.79% (220 nm), 91.00% (215 nm), 100.00% (254 nm). MS (ESI): mass calcd. For C$_{18}$H$_{16}$C$_{13}$N$_7$O 415.07, m/z found 416.0 [M+H]$^+$.

Compound 125

5-((3,4-Difluorobenzyl)amino)-1-(oxetan-2-ylmethyl)-1H-pyrazolo[4,3-d]pyrimidin-7(6H)-one was prepared according to the procedures described herein for Steps 1~3 in Scheme C-3.

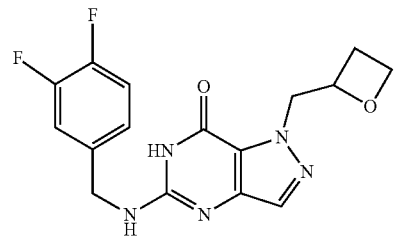 [SMILES: O=c1[nH]c(NCc2ccc(F)c(F)c2)nc2cnn(CC3CCO3)c12]

The procedure yielded the desired compound (18.3 mg, 52.58 μmol, 50.62% yield) as a white solid. $^1$H NMR (DMSO-d$_6$, 400 MHz) δ 11.00 (s, 1H), 7.59 (s, 1H), 7.42~7.33 (m, 2H), 7.18 (s, 1H), 6.53 (s, 1H), 5.03~4.93 (m, 1H), 4.79~4.69 (m, 1H), 4.66~4.57 (m, 1H), 4.48~4.42 (m, 3H), 4.36~4.30 (m, 1H), 2.63~2.58 (m, 1H), 2.42~2.37 (m, 1H). HPLC: 99.80% (220 nm), 99.76% (215 nm), 100.00% (254 nm). MS (ESI): mass calcd. For C$_{16}$H$_{15}$F$_2$N$_5$O$_2$ 347.12, m/z found 348.2 [M+H]$^+$.

Compound 126

Preparation of 5-((3,4-dichlorobenzyl)amino)-1-(2-methoxyethyl)-1H-pyrazolo[4,3-d]pyrimidin-7(6H)-one Preparation of 5-chloro-7-methoxy-1-(2-methoxyethyl)-1H-pyrazolo[4,3-d]pyrimidine (Step 1 in Scheme C-3)

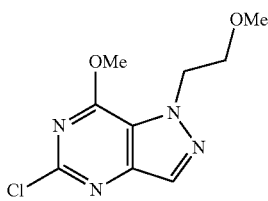 [SMILES: COCCn1ncc2nc(Cl)nc(OC)c21]

To a mixture of 5-chloro-7-methoxy-1H-pyrazolo[4,3-d]pyrimidine (1 g, 5.42 mmol, 1 eq) and 1-bromo-2-methoxyethane (978.90 mg, 7.04 mmol, 661.42 μL, 1.3 eq) in DMF (10 mL) was added Cs$_2$CO$_3$ (3.53 g, 10.84 mmol, 2 eq) at 20° C. Then the mixture was stirred at 20° C. for 3 hours. TLC showed the reaction was complete. The mixture was poured into ice water (20 mL) slowly and then extracted with EtOAc (20 mL×3). The combined organic layer was washed with brine (10 mL×4), dried over Na$_2$SO$_4$, filtered and concentrated under reduced pressure. The residue was purified by flash silica gel chromatography (Biotage®; 12 g SepaFlash® Silica Flash Column, Eluent of 0~35% Ethyl acetate/Petroleum ether gradient at 40 mL/min). The eluent was removed under reduced pressure. Compound 5-chloro-7-methoxy-2-(2-methoxyethyl)pyrazolo[4,3-d]pyrimidine (0.6 g, 2.47 mmol, 45.64% yield) was obtained as white solid. $^1$H NMR (CDC$_3$, 400 MHz) δ 8.05 (s, 1H), 4.71 (t, J=5.6 Hz, 2H), 4.23 (s, 3H), 3.82 (t, J=5.6 Hz, 2H), 3.29 (s, 3H). Compound 5-chloro-7-methoxy-1-(2-methoxyethyl)pyrazolo[4,3-d]pyrimidine (0.5 g, 2.06 mmol, 38.033% yield) was obtained as white solid. $^1$H NMR (CDCl$_3$, 400 MHz) δ 8.09 (s, 1H), 4.58 (t, J=5.2 Hz, 2H), 4.23 (s, 3H), 3.85 (t, J=5.6 Hz, 2H), 3.32 (s, 3H).

Preparation of 5-chloro-1-(2-methoxyethyl)-1H-pyrazolo[4,3-d]pyrimidin-7(6H)-one (Step 2 in Scheme C-3)

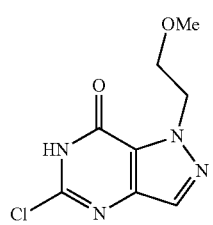 [SMILES: COCCn1ncc2nc(Cl)[nH]c(=O)c21]

A solution of 5-chloro-7-methoxy-1-(2-methoxyethyl) pyrazolo[4,3-d]pyrimidine (0.6 g, 2.47 mmol, 1 eq) and LiOHH$_2$O (311.25 mg, 7.42 mmol, 3 eq) in MeOH (5 mL) and H$_2$O (5 mL) was stirred at 20° C. for 3 hours. TLC showed the reaction was complete. The organic solvent was removed under reduced pressure. The aqueous was made pH=6~7 with 2N HCl slowly and some solid formed. The solid was collected after filtered. The aqueous was then extracted with EtOAc (20 mL×2). The combined organic layer was washed with brine (5 mL), dried over Na$_2$SO$_4$, filtered and concentrated under reduced pressure. Compound 5-chloro-1-(2-methoxyethyl)-6H-pyrazolo[4,3-d]pyrimidin-7-one (0.5 g, 2.19 mmol, 88.45% yield) was obtained as white solid. $^1$H NMR (DMSO-d$_6$, 400 MHz) δ 13.30 (s, 1H), 7.98 (s, 1H), 4.68 (t, J=5.2 Hz, 2H), 3.75 (t, J=5.6 Hz, 2H), 3.19 (s, 3H).

Preparation of 5-((3,4-dichlorobenzyl)amino)-1-(2-methoxyethyl)-1H-pyrazolo[4,3-d]pyrimidin-7(6H)-one (Step 3 in Scheme C-3)

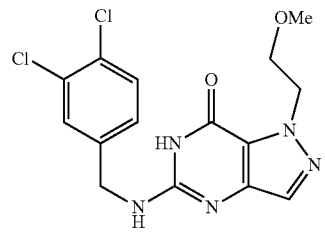 [SMILES: COCCn1ncc2nc(NCc3ccc(Cl)c(Cl)c3)[nH]c(=O)c21]

A solution of 5-chloro-1-(2-methoxyethyl)-6H-pyrazolo[4,3-d]pyrimidin-7-one (500.00 mg, 2.19 mmol, 1 eq) and (3,4-dichlorophenyl)methanamine (769.97 mg, 4.37 mmol, 583.31 μL, 2 eq) in t-BuOH (5 mL) was heated at 100° C. for 30 hours. TLC showed the reaction was complete. The solvent was removed under reduced pressure. The residue was purified by prep-HPLC (column: Phenomenex luna C18 250 mm×50 mm 10 μm; mobile phase: [water (0.05% HCl)-MeCN]; B %: 25%-55%, 10 mins). Compound 5-[(3,4-dichlorophenyl)methylamino]-1-(2-methoxyethyl)-6H-pyrazolo[4,3-d]pyrimidin-7-one (510.7 mg, 1.38 mmol, 63.00% yield, 99.34% purity) was obtained as white solid. H NMR (DMSO-d$_6$, 400 MHz) δ 7.63~7.59 (m, 3H), 7.35 (dd, J=2.0 Hz, 8.4 Hz, 1H), 4.59 (t, J=5.6 Hz, 2H), 4.54 (d, J=8.8 Hz, 2H), 3.72 (t, J=5.2 Hz, 2H), 3.19 (s, 3H). HPLC: 99.34% (220 nm), 99.77% (215 nm), 97.94% (254 nm). MS (ESI): mass calcd. For C$_{15}$H$_{15}$C$_{12}$N$_5$O$_2$ 367.06, m/z found 368.0 [M+H]$^+$.

Compound 127

1-Benzyl-5-((3,4-dichlorobenzyl)amino)-1H-pyrazolo[4,3-d]pyrimidin-7(6H)-one was prepared according to the procedures described herein for Steps 1-3 in Scheme C-3.

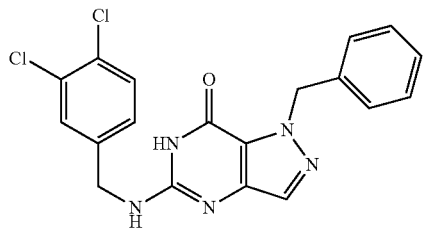 [SMILES: O=c1[nH]c(NCc2ccc(Cl)c(Cl)c2)nc2cnn(Cc3ccccc3)c12]

The procedure yielded the desired compound (119.5 mg, 294.94 µmol, 38.44% yield) as a pale white solid. $^1$H NMR (DMSO-$d_6$, 400 MHz) δ 7.62 (s, 1H), 7.60~7.57 (m, 2H), 7.34~7.24 (m, 4H), 7.21 (d, J=6.8 Hz, 2H), 6.90 (s, 1H), 5.62 (s, 2H), 4.49 (d, J=5.6 Hz, 2H). HPLC: 98.79% (220 nm), 98.73% (215 nm), 99.28% (254 nm). MS (ESI): mass calcd. For $C_{19}H_{15}C_{12}N_5O$ 399.07, m/z found 400.0 [M+H]$^+$.

Compound 128

5-((3,4-Dichlorobenzyl)amino)-2-(2-methoxyethyl)-2H-pyrazolo[4,3-d]pyrimidin-7(6H)-one was prepared according to the procedures described herein for Steps 1-3 in Scheme C-3.

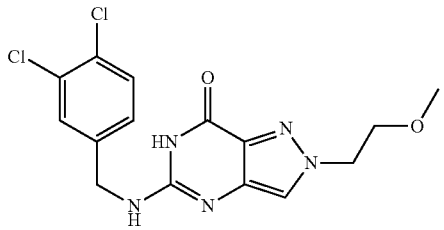 [SMILES: COCCn1cc2nc(NCc3ccc(Cl)c(Cl)c3)[nH]c(=O)c2n1]

The procedure yielded the desired compound (161.8 mg, 439.41 µmol, 66.98% yield) as a white solid. $^1$H NMR (DMSO-$d_6$, 400 MHz) δ 7.85 (s, 1H), 7.61~7.59 (m, 2H), 7.33 (dd, J=2.0 Hz, 8.4 Hz, 1H), 7.10 (s, 1H), 4.49 (t, J=5.6 Hz, 2H), 4.38 (t, J=5.2 Hz, 2H), 3.80 (t, J=6.8 Hz, 2H), 3.22 (s, 3H). HPLC: 98.12% (220 nm), 98.18% (215 nm), 100.00% (254 nm). MS (ESI): mass calcd. For $C_{15}H_{15}C_{12}N_5O_2$ 367.06, m/z found 368.1 [M+H]$^+$.

Compound 129

2-Benzyl-5-((3,4-dichlorobenzyl)amino)-2H-pyrazolo[4,3-d]pyrimidin-7(6H)-one was prepared according to the procedures described herein for Steps 1-3 in Scheme C-3.

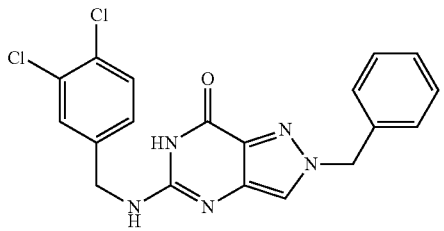 [SMILES: O=c1[nH]c(NCc2ccc(Cl)c(Cl)c2)nc2cn(Cc3ccccc3)nc12]

The procedure yielded the desired compound (49.5 mg, 123.67 µmol, 21.49% yield) as a white solid. H NMR (DMSO-$d_6$, 400 MHz) δ 10.99 (s, 1H), 7.98 (s, 1H), 7.60~7.58 (m, 2H), 7.36~7.33 (m, 2H), 7.32~7.28 (m, 4H), 6.91 (s, 1H), 5.43 (s, 2H), 4.48 (d, J=5.6 Hz, 2H). HPLC: 98.07% (220 nm), 97.98% (215 nm), 99.17% (254 nm). MS (ESI): mass calcd. For $C_{19}H_{15}C_{12}N_5O$ 399.07, m/z found 400.1 [M+H]$^+$.

Compound 130

5-((3,4-Dichlorobenzyl)amino)-1-isopropyl-1H-pyrazolo[4,3-d]pyrimidin-7(6H)-one was prepared according to the procedures described herein for Steps 1-3 in Scheme C-3.

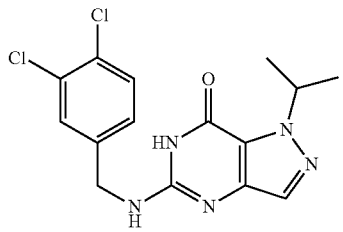 [SMILES: CC(C)n1ncc2nc(NCc3ccc(Cl)c(Cl)c3)[nH]c(=O)c21]

The procedure yielded the desired compound (77.2 mg, 219.18 µmol, 51.27% yield) as a white solid. $^1$H NMR (DMSO-$d_6$, 400 MHz) δ 7.60~7.57 (m, 3H), 7.33 (dd, J=1.2 Hz, 8.4 Hz, 1H), 6.96 (s, 1H), 5.22~5.19 (m, 1H), 4.49 (d, J=5.2 Hz, 2H), 1.41 (s, 6H). HPLC: 100.00% (220 nm), 100.00% (215 nm), 100.00% (254 nm). MS (ESI): mass caled. For $C_{15}H_{15}C_{12}N_5O$ 351.07, m/z found 352.1 [M+H]$^+$.

Compound 131

5-((3,4-Dichlorobenzyl)amino)-1-(5-methoxypentyl)-1H-pyrazolo[4,3-d]pyrimidin-7(6H)-one was prepared according to the procedures described herein for Steps 1-3 in Scheme C-3.

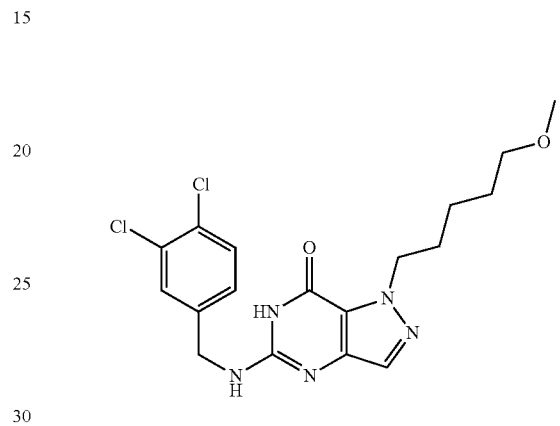

The procedure yielded the desired compound (73.6 mg, 175.20 µmol, 18.97% yield) as a white solid. $^1$H NMR (DMSO-$d_6$, 400 MHz) δ 7.60~7.56 (m, 2H), 7.55 (s, 1H), 7.33 (dd, J=2.0 Hz, 8.0 Hz, 1H), 6.71 (s, 1H), 4.48 (d, J=6.0 Hz, 2H), 4.41 (t, J=6.8 Hz, 2H), 3.25 (t, J=6.4 Hz, 2H), 3.17 (s, 3H), 1.79~1.75 (m, 2H), 1.50~1.44 (m, 2H), 1.24~1.18 (m, 2H). HPLC: 97.67% (220 nm), 97.65% (215 nm), 98.85% (254 nm). MS (ESI): mass calcd. For $C_{18}H_{21}C2N_5O_2$ 409.11, m/z found 410.0 [M+H]$^+$.

Compound 132

5-((3,4-Dichlorobenzyl)amino)-2-isopropyl-2H-pyrazolo[4,3-d]pyrimidin-7(6H)-one was prepared according to the procedures described herein for Steps 1-3 in Scheme C-3.

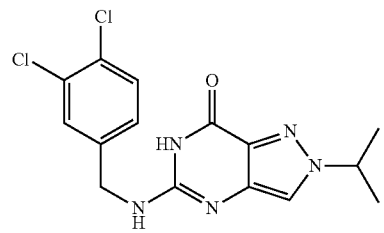 [SMILES: CC(C)n1cc2nc(NCc3ccc(Cl)c(Cl)c3)[nH]c(=O)c2n1]

The procedure yielded the desired compound (48.0 mg, 136.28 µmol, 31.88% yield) as a white solid. $^1$H NMR (DMSO-$d_6$, 400 MHz) δ 7.86 (s, 1H), 7.59~7.57 (m, 2H), 7.31 (dd, J=2.0 Hz, 8.4 Hz, 1H), 6.56~6.48 (m, 1H), 4.59~4.55 (m, 1H), 4.44 (d, J=6.0 Hz, 2H), 1.43 (d, J=6.8 Hz, 6H). HPLC: 100.00% (220 nm), 100.00% (215 nm), 100.00% (254 nm). MS (ESI): mass calcd. For $C_{15}H_{15}C_{12}N_5O$ 351.07, m/z found 352.1 [M+H]$^+$.

Compound 133

5-((3,4-Dichlorobenzyl)amino)-2-(5-methoxypentyl)-2H-pyrazolo[4,3-d]pyrimidin-7(6H)-one was prepared according to the procedures described herein for Steps 1-3 in Scheme C-3.

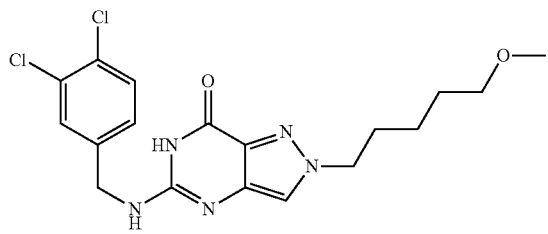 [SMILES: COCCCCCn1cc2nc(NCc3ccc(Cl)c(Cl)c3)[nH]c(=O)c2n1]

The procedure yielded the desired compound (68.3 mg, 166.46 µmol, 18.03% yield) as a white solid. $^1$H NMR (DMSO-d$_6$, 400 MHz) δ 10.75 (s, 1H), 7.83 (s, 1H), 7.62~7.55 (m, 2H), 7.32 (dd, J=2.0 Hz, 8.4 Hz, 1H), 6.62 (s, 1H), 4.46 (d, J=6.0 Hz, 2H), 4.19 (t, J=7.2 Hz, 2H), 3.27 (t, J=6.4 Hz, 2H), 3.18 (s, 3H), 1.85~1.79 (m, 2H), 1.51~1.46 (m, 2H), 1.26~1.20 (m, 2H). HPLC: 100.00% (220 nm), 100.00% (215 nm), 100.00% (254 nm). MS (ESI): mass calcd. For C$_{18}$H$_{21}$C$_{12}$N$_5$O$_2$ 409.11, m/z found 410.0 [M+H]$^+$.

Compound 134

1-(Cyclobutylmethyl)-5-((3,4-dichlorobenzyl)amino)-1H-pyrazolo[4,3-d]pyrimidin-7(6H)-one was prepared according to the procedures described herein for Steps 1-3 in Scheme C-3.

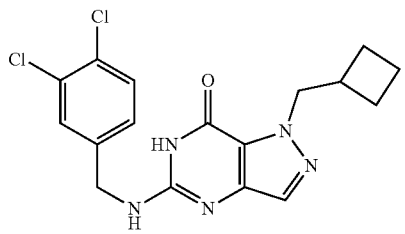 [SMILES: O=c1[nH]c(NCc2ccc(Cl)c(Cl)c2)nc2cnn(CC3CCC3)c12]

The procedure yielded the desired compound (150 mg, 396.56 µmol, 52.58% yield) as a white solid. $^1$H NMR (DMSO-d$_6$, 400 MHz) δ 7.63~7.59 (m, 3H), 7.35 (dd, J=2.0 Hz, 8.0 Hz, 1H), 4.54 (d, J=4.8 Hz, 2H), 4.46 (d, J=7.6 Hz, 2H), 2.75 (td, J=7.6 Hz, 15.2 Hz, 1H), 1.96~1.87 (m, 2H), 1.85~1.72 (m, 4H). HPLC: 96.51% (220 nm), 96.27% (215 nm), 93.88% (254 nm). MS (ESI): mass calcd. For C$_{17}$H$_7$C$_2$N$_5$O 377.08, m/z found 378.1 [M+H]$^+$.

Compound 135

2-(Cyclobutylmethyl)-5-((3,4-dichlorobenzyl)amino)-2H-pyrazolo[4,3-d]pyrimidin-7(6H)-one was prepared according to the procedures described herein for Steps 1-3 in Scheme C-3.

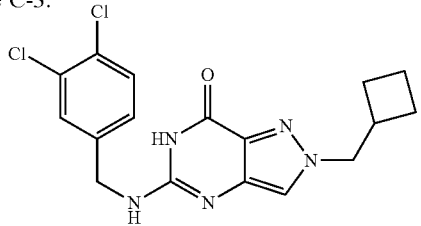

The procedure yielded the desired compound (141.9 mg, 375.14 µmol, 59.69% yield) as a white solid. $^1$H NMR (DMSO-d$_6$, 400 MHz) δ 11.1210.37 (m, 1H), 7.83 (s, 1H), 7.60~7.58 (m, 2H), 7.33 (dd, J=2.0 Hz, 8.4 Hz, 1H), 6.86 (s, 1H), 4.48 (d, J=5.6 Hz, 2H), 4.23 (d, J=7.2 Hz, 2H), 2.8278 (m, 1H), 2.00~1.93 (m, 2H), 1.86~1.73 (m, 4H). HPLC: 100.00% (220 nm), 100.00% (215 nm), 100.00% (254 nm). MS (ESI): mass calcd. For C$_{17}$H$_7$Cl$_2$N$_5$O 377.08, m/z found 378.1 [M+H]$^+$.

Compound 136

5-((3,4-Dichlorobenzyl)amino)-1-(2-(2-methoxyethoxy)ethyl)-1H-pyrazolo[4,3-d]pyrimidin-7(6H)-one was prepared according to the procedures described herein for Steps 1-3 in Scheme C-3.

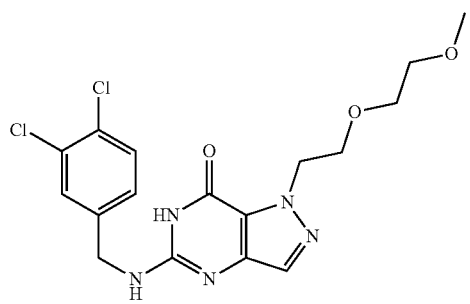 [SMILES: COCCOCCn1ncc2nc(NCc3ccc(Cl)c(Cl)c3)[nH]c(=O)c21]

The procedure yielded the desired compound (61.5 mg, 149.17 µmol, 30.36% yield) as a white solid. $^1$H NMR (DMSO-d$_6$, 400 MHz) δ 9.48 (s, 1H), 7.60~7.54 (m, 3H), 7.32 (dd, J=2.0, 8.2 Hz, 1H), 6.76~6.59 (m, 1H), 4.56 (t, J=5.8 Hz, 2H), 4.47 (d, J=6.0 Hz, 2H), 3.78 (t, J=5.8 Hz, 2H), 3.46 (dd, J=3.2 Hz, 4.4 Hz, 2H), 3.34 (dd, J=3.8 Hz, 5.8 Hz, 2H), 3.16 (s, 3H). HPLC: 98.08% (220 nm), 97.73% (215 nm), 100.00% (254 nm). MS (ESI): mass calcd. For C$_{17}$H$_{19}$C$_{12}$N$_5$O$_3$ 411.09, m/z found 412.1 [M+H]$^+$.

Compound 137

5-((3,4-Dichlorobenzyl)amino)-2-(2-(2-methoxyethoxy)ethyl)-2H-pyrazolo[4,3-d]pyrimidin-7(6H)-one was prepared according to the procedures described herein for Steps 1-3 in Scheme C-3.

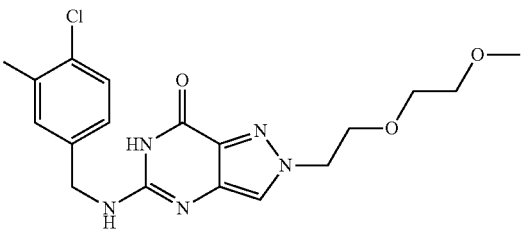

The procedure yielded the desired compound (117.3 mg, 284.52 µmol, 54.26% yield) as a white solid. $^1$H NMR (DMSO-d$_6$, 400 MHz) δ 7.84 (s, 1H), 7.62~7.58 (m, 2H), 7.34 (dd, J=2.0 Hz, 6.4 Hz, 1H), 4.49 (d, J=5.2 Hz, 2H), 4.37 (t, J=5.2 Hz, 2H), 3.81 (t, J=5.2 Hz, 2H), 3.52~3.48 (m, 2H), 3.38 (dd, J=3.8, 5.8 Hz, 2H), 3.19 (s, 3H). HPLC: 99.87% (220 nm), 99.84% (215 nm), 100.00% (254 nm). MS (ESI): mass calcd. For C$_7$H$_{19}$C2N$_5$O$_3$ 411.09, m/z found 412.1 [M+H]$^+$.

Compound 138

5-((3,4-dichlorobenzyl)amino)-1-((2-methoxyethoxy)methyl)-1H-pyrazolo[4,3-d]pyrimidin-7(6H)-one was prepared according to the procedures described herein for Steps 1-3 in Scheme C-3.

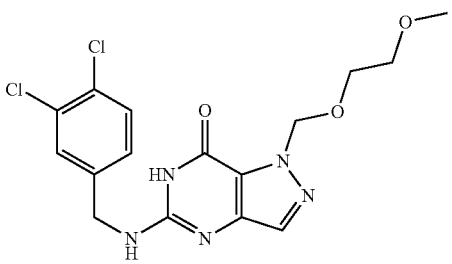 [SMILES: COCCOCn1ncc2nc(NCc3ccc(Cl)c(Cl)c3)[nH]c(=O)c21]

The procedure yielded the desired compound (83.7 mg, 209.23 μmol, 41.63% yield) as a white solid. $^1$H NMR (DMSO-d$_6$, 400 MHz) δ 7.70 (s, 1H), 7.60~7.57 (m, 2H), 7.34~7.32 (m, 1H), 6.73 (s, 1H), 5.70 (s, 2H), 4.49 (d, J=5.6 Hz, 2H), 3.58 (t, J=4.4 Hz, 2H), 3.36 (t, J=5.2 Hz, 2H), 3.18 (s, 3H). HPLC: 99.55% (220 nm), 99.51% (215 nm), 100% (254 nm). MS (ESI): mass calcd. For $C_{16}H_{17}Cl_2N_5O_3$ 397.07, m/z found 398.1 [M+H]$^+$.

Compound 139

5-((3,4-Dichlorobenzyl)amino)-1-(pyrimidin-2-yl)-1H-pyrazolo[4,3-d]pyrimidin-7(6H)-one was prepared according to the procedures described herein for Steps 1-3 in Scheme C-3.

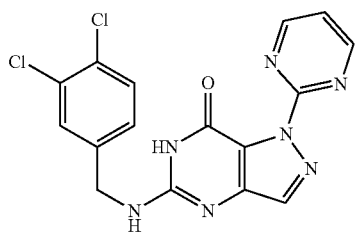 [SMILES: O=c1[nH]c(NCc2ccc(Cl)c(Cl)c2)nc2cnn(-c3ncccn3)c12]

The procedure yielded the desired compound (10.9 mg, 28.08 μmol, 3.88% yield) as a white solid. $^1$H NMR (DMSO-d$_6$, 400 MHz) δ 10.99 (s, 1H), 8.94 (d, J=4.8 Hz, 2H), 8.59 (s, 1H), 7.63~7.56 (m, 3H), 7.36 (dd, J=2.0 Hz, 8.0 Hz, 1H), 6.74 (s, 1H), 4.52 (d, J=5.6 Hz, 2H). HPLC: 96.85% (220 nm), 96.29% (215 nm), 99.83% (254 nm). MS (ESI): mass calcd. For $C_{16}H_{11}Cl_2N_7O$ 387.04, m/z found 388.1 [M+H]$^+$.

Compound 140

5-((3,4-Dichlorobenzyl)amino)-2-(pyrimidin-2-yl)-2H-pyrazolo[4,3-d]pyrimidin-7(6H)-one was prepared according to the procedures described herein for Steps 1-3 in Scheme C-3.

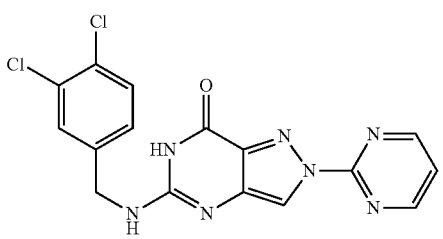 [SMILES: O=c1[nH]c(NCc2ccc(Cl)c(Cl)c2)nc2cn(-c3ncccn3)nc12]

The procedure yielded the desired compound (8 mg, 19.56 μmol, 12.16% yield) as a light yellow solid. $^1$H NMR (DMSO-d$_6$, 400 MHz) δ 11.21 (s, 1H), 8.93 (d, J=4.8 Hz, 2H), 7.98 (s, 1H), 7.62~7.57 (m, 3H), 7.35 (dd, J=2.0 Hz, 8.4 Hz, 1H), 6.82~6.72 (m, 1H), 4.53 (d, J=6.0 Hz, 2H). HPLC: 94.91% (220 nm), 94.48% (215 nm), 99.09% (254 nm). MS (ESI): mass calcd. For $C_{16}H_{11}Cl_2N_7O$ 387.04, m/z found 388.0 [M+H]$^+$.

Compound 141

2-(2-(5-((3,4-Dichlorobenzyl)amino)-7-oxo-6,7-dihydro-2H-pyrazolo[4,3-d]pyrimidin-2-yl)ethoxy)acetic acid was prepared according to the procedures described herein for Steps 1-3 in Scheme C-3.

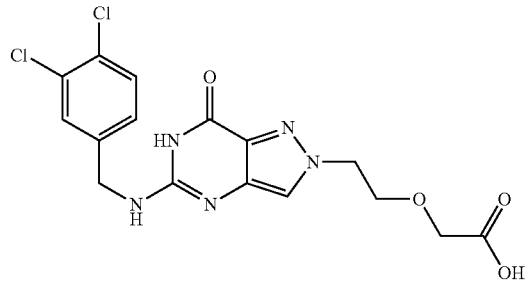 [SMILES: O=C(O)COCCn1cc2nc(NCc3ccc(Cl)c(Cl)c3)[nH]c(=O)c2n1]

The procedure yielded the desired compound (6.1 mg, 14.08 μmol, 5.48% yield) as a white solid. $^1$H NMR (DMSO-d$_6$, 400 MHz) δ 11.14 (s, 1H), 10.99 (s, 1H), 8.24 (t, J=6.0 Hz, 1H), 7.55 (d, J=8.6 Hz, 1H), 7.45 (d, J=1.6 Hz, 1H), 7.37 (s, 1H), 7.24~7.14 (m, 1H), 4.61 (t, J=5.6 Hz, 2H), 4.25 (d, J=6.0 Hz, 2H), 3.89 (s, 2H), 3.85 (t, J=5.6 Hz, 2H). HPLC: 95.12% (220 nm), 94.13% (215 nm), 87.14% (254 nm). MS (ESI): mass calcd. For $C_{16}H_{15}Cl_2N_5O_4$ 411.05, m/z found 412.0 [M+H]$^+$.

Compound 142

5-((3,4-Dichlorobenzyl)amino)-1-(oxetan-3-yl)-1H-pyrazolo[4,3-d]pyrimidin-7(6H)-one was prepared according to the procedures described herein for Steps 1-3 in Scheme C-3.

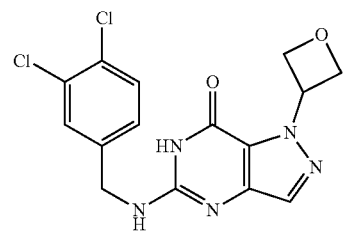 [SMILES: O=c1[nH]c(NCc2ccc(Cl)c(Cl)c2)nc2cnn(C3COC3)c12]

The procedure yielded the desired compound (19.6 mg, 50.10 μmol, 45.42% yield) as a white solid. $^1$H NMR (DMSO-d$_6$, 400 MHz) δ 7.73 (s, 1H), 7.59~7.57 (m, 2H), 7.32 (dd, J=8.0 Hz, 2.0 Hz, 1H), 6.64 (s, 1H), 6.11~6.04 (m, 1H), 4.95~4.89 (m, 4H), 4.47 (d, J=6.0 Hz, 2H). HPLC: 93.61% (220 nm), 91.82% (215 nm), 97.14% (254 nm). MS (ESI): mass calcd. For $C_{15}H_{13}Cl_2N_5O_2$ 365.04, m/z found 366.0 [M+H]$^+$.

Compound 143

5-((3,4-Dichlorobenzyl)amino)-2-(oxetan-3-yl)-2H-pyrazolo[4,3-d]pyrimidin-7(6H)-one was prepared according to the procedures described herein for Steps 1-3 in Scheme C-3.

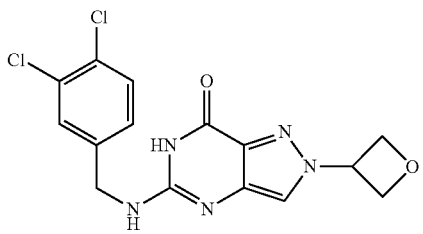 [SMILES: O=c1[nH]c(NCc2ccc(Cl)c(Cl)c2)nc2cn(C3COC3)nc12]

The procedure yielded the desired compound (16 mg, 41.96 μmol, 36.57% yield) as a white solid. $^1$H NMR (DMSO-d$_6$, 400 MHz) δ 8.00 (s, 1H), 7.60~7.58 (m, 2H), 7.33 (dd, J=8.4 Hz, 2.0 Hz, 1H), 6.88 (s, 1H), 5.70~5.63 (m, 1H), 4.97~4.93 (m, 2H), 4.91~4.88 (m, 2H), 4.48 (d, J=5.6 Hz, 2H). HPLC: 96.04% (220 nm), 94.85% (215 nm), 95.47% (254 nm). MS (ESI): mass calcd. For $C_{15}H_{13}C_2N_5O_2$ 365.04, m/z found 366.0 [M+H]$^+$.

Compound 144

5-((3,4-Dichlorobenzyl)amino)-1-(oxazol-2-ylmethyl)-1H-pyrazolo[4,3-d]pyrimidin-7(6H)-one was prepared according to the procedures described herein for Steps 1-3 in Scheme C-3.

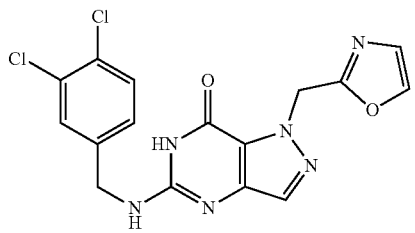 [SMILES: O=c1[nH]c(NCc2ccc(Cl)c(Cl)c2)nc2cnn(Cc3ncco3)c12]

The procedure yielded the desired compound (34.8 mg, 88.81 μmol, 37.24% yield) as a white solid. $^1$H NMR (DMSO-d$_6$, 400 MHz) δ 8.06 (s, 1H), 7.65 (s, 1H), 7.63~7.56 (m, 2H), 7.33 (d, J=8.0 Hz, 1H), 7.16 (s, 1H), 6.83 (s, 1H), 5.79 (s, 2H), 4.49 (d, J=4.6 Hz, 2H). HPLC: 99.83% (220 nm), 99.77% (215 nm), 99.88% (254 nm). MS (ESI): mass calcd. For $C_{16}H_{12}C_{12}N_6O_2$ 390.04, m/z found 391.0 [M+H]$^+$.

Compound 145

4-(5-((3,4-Dichlorobenzyl)amino)-7-oxo-6,7-dihydro-1H-pyrazolo[4,3-d]pyrimidin-1-yl)butanoic acid was prepared according to the procedures described herein for Steps 1-3 in Scheme C-3.

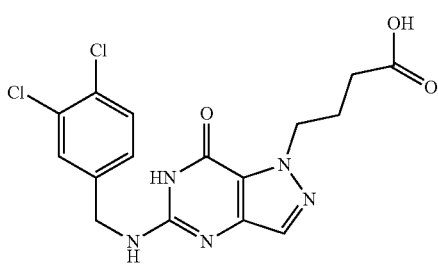 [SMILES: O=C(O)CCCn1ncc2nc(NCc3ccc(Cl)c(Cl)c3)[nH]c(=O)c21]

The procedure yielded the desired compound (97.9 mg, 223.38 μmol, 38.22% yield, 90.407% purity) as a white solid. 7.9 mg product for delivery. H NMR (DMSO-d$_6$, 400 MHz) δ 11.10 (s, 1H), 7.62~7.51 (m, 3H), 7.33 (dd, J=2.0 Hz, 8.4 Hz, 1H), 6.62 (s, 1H), 4.52~4.39 (m, 4H), 2.15 (t, J=7.2 Hz, 2H), 2.02~1.95 (m, 2H). HPLC: 90.41% (220 nm), 89.23% (215 nm), 96.19% (254 nm). MS (ESI): mass calcd. For $C_{16}H_{15}C_{12}N_5O_3$ 396.06, m/z found 396.2 [M+H]$^+$.

Compound 146

5-((3,4-Dichlorobenzyl)amino)-1-(4-(dimethylphosphoryl)butyl)-1H-pyrazolo[4,3-d]pyrimidin-7(6H)-one was prepared according to the procedures described herein for Steps 1-3 in Scheme C-3.

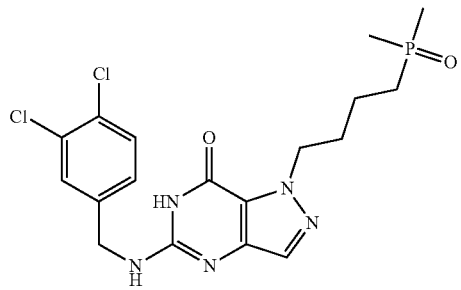 [SMILES: CP(C)(=O)CCCCn1ncc2nc(NCc3ccc(Cl)c(Cl)c3)[nH]c(=O)c21]

The procedure yielded the desired compound ((4.4 mg, 9.55 μmol, 9.64% yield, 96.037% purity) as a white solid. $^1$H NMR (DMSO-d$_6$, 400 MHz) δ 7.66~7.49 (m, 3H), 7.33 (dd, J=1.6 Hz, 8.4 Hz, 1H), 6.68 (s, 1H), 4.50~4.38 (m, 4H), 1.89~1.82 (m, 2H), 1.71~1.59 (m, 2H), 1.44~1.34 (m, 2H), 1.30 (d, J=12.8 Hz, 6H).

Compound 147

Preparation of 5-((3,4-dichlorobenzyl)amino)-1-((4-methylmorpholin-2-yl)methyl)-1H-pyrazolo[4,3-d]pyrimidin-7(6H)-one hydrochloride Compound 148

Preparation of tert-butyl 2-((5-((3,4-dichlorobenzyl)amino)-7-oxo-6,7-dihydro-1H-pyrazolo[4,3-d]pyrimidin-1-yl)methyl)morpholine-4-carboxylate (Step 1-3 in Scheme C-3)

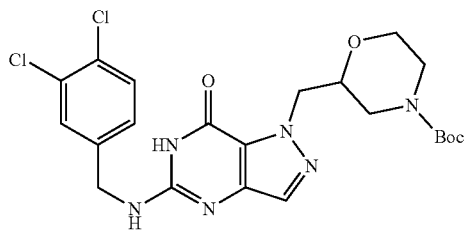 [SMILES: CC(C)(C)OC(=O)N1CCOC(Cn2ncc3nc(NCc4ccc(Cl)c(Cl)c4)[nH]c(=O)c32)C1]

A mixture of tert-butyl 2-[(5-chloro-7-oxo-6H-pyrazolo[4,3-d]pyrimidin-1-yl)methyl]morpholine-4-carboxylate (1 g, 1.08 mmol, 1 eq) and (3,4-dichlorophenyl)methanamine (380.84 mg, 2.16 mmol, 288.51 μL, 2 eq) in t-BuOH (10 mL) was stirred at 100° C. for 12 hours. LC-MS showed the reaction was completed. The reaction mixture was concentrated under reduced pressure to remove t-BuOH. The residue was diluted with EtOAc (10 mL) and washed with aq. HCl (2N, 10 mL×6). The combined organic layers were dried over Na$_2$SO$_4$, filtered and concentrated under reduced pressure. Compound tert-butyl 2-[[5-[(3,4-dichlorophenyl)methylamino]-7-oxo-6H-pyrazolo[4,3-d]pyrimidin-1-yl]methyl]morpholine-4-carboxylate (1 g, crude) was obtained as white solid. And the residue (200 mg) was purified by prep-HPLC (neutral condition column: Welch Xtimate C18 150 mm×25 mm 5 μm; mobile phase: [water (10 mM NH$_4$HCO$_3$)-MeCN]; B %: 50%-70%, 10.5 mins). The solvent was removed under freeze drying. Compound tert-butyl 2-[[5-[(3,4-dichlorophenyl)methylamino]-7-oxo-6H-pyrazolo[4,3-d]pyrimidin-1-yl]methyl]morpholine-4-carboxylate (23.4 mg, 45.88 μmol, 4.24% yield, 99.87% purity) was obtained as white solid for delivery. $^1$H NMR (DMSO-d$_6$, 400 MHz) δ 11.03 (s, 1H), 7.60~7.57 (m, 3H), 7.33 (d, J=8.0 Hz, 1H), 6.60 (s, 1H), 4.58~4.55 (m, 1H), 4.48~4.41 (m, 3H), 3.78~3.75 (m, 2H), 3.67~3.62 (m, 2H), 3.31~3.28 (m, 1H), 2.88 (s, 1H), 2.67 (s, 1H), 1.36 (s, 9H). HPLC: 99.87% (220 nm), 99.88% (215 nm), 100.00% (254 nm). MS (ESI): mass calcd. For C$_{22}$H$_{26}$Cl$_2$N$_6$O$_4$ 508.14, m/z found 509.2 [M+H]$^+$.

Compound 149

Preparation of 5-((3,4-dichlorobenzyl)amino)-1-(morpholin-2-ylmethyl)-1H-pyrazolo[4,3-d]pyrimidin-7(6H)-one hydrochloride

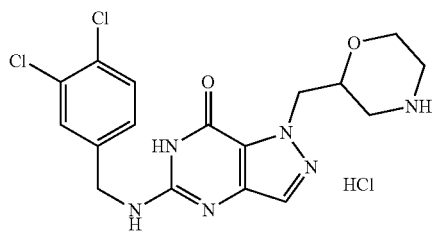 [SMILES: O=c1[nH]c(NCc2ccc(Cl)c(Cl)c2)nc2cnn(CC3CNCCO3)c12 ; Cl]

The solution of tert-butyl 2-[[5-[(3,4-dichlorophenyl)methylamino]-7-oxo-6H-pyrazolo[4,3-d]pyrimidin-1-yl]methyl]morpholine-4-carboxylate (200 mg, 392.63 μmol, 1 eq) in HCl/EtOAc (2 mL) and EtOAc (1 mL) was stirred at 25° C. for 2 hours. LC-MS showed the reaction was complete. The reaction mixture was concentrated under reduced pressure to remove EtOAc. The residue was purified by prep-HPLC (HCl condition column: Phenomenex Luna C18 100 mm×30 mm 5 μm; mobile phase: [water (0.05% HCl)-MeCN]; B %: 15%-50%, 8 mins). The solvent was removed under freeze drying. Compound 5-[(3,4-dichlorophenyl)methylamino]-1-(morpholin-2-ylmethyl)-6H-pyrazolo[4,3-d]pyrimidin-7-one (35.4 mg, 79.42 μmol, 20.23% yield, 100% purity, HCl) was obtained as white solid. $^1$H NMR (DMSO-d$_6$, 400 MHz) δ 9.33 (s, 2H), 7.67 (s, 1H), 7.63~7.59 (m, 2H), 7.36 (d, J=8.0 Hz, 1H), 4.67~4.62 (m, 1H), 4.55~4.48 (m, 3H), 4.18~4.17 (m, 1H), 3.92~3.89 (m, 1H), 3.65 (t, J=12.0 Hz, 1H), 3.21~3.12 (m, 2H), 2.90~2.87 (m, 2H). HPLC: 100.00% (220 nm), 100.00% (215 nm), 100.00% (254 nm). MS (ESI): mass calcd. For C$_{17}$H$_{19}$Cl$_3$N$_6$O$_2$ 408.09, m/z found 409.1 [M+H]$^+$.

Preparation of 5-((3,4-dichlorobenzyl)amino)-1-((4-methylmorpholin-2-yl)methyl)-1H-pyrazolo[4,3-d]pyrimidin-7(6H)-one hydrochloride

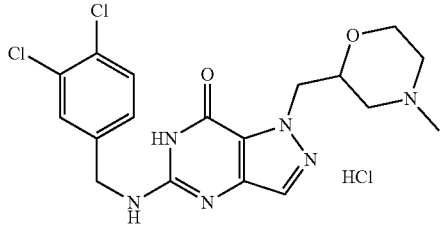 [SMILES: CN1CCOC(Cn2ncc3nc(NCc4ccc(Cl)c(Cl)c4)[nH]c(=O)c32)C1 ; Cl]

To a solution of 5-[(3,4-dichlorophenyl)methylamino]-1-(morpholin-2-ylmethyl)-6H-pyrazolo[4,3-d]pyrimidin-7-one (400 mg, 897.40 μmol, 1 eq, HCl) in MeOH (5 mL) was added HCHO (218.48 mg, 2.69 mmol, 200.44 μL, 37% purity, 3 eq) at 0° C. The mixture was stirred at 0° C. for 10 mins. Then AcOH (5.39 mg, 89.74 μmol, 5.13 μL, 0.1 eq) and NaBH$_3$CN (451.16 mg, 7.18 mmol, 8 eq) were added at 0° C. The mixture was stirred at 25° C. for 12 hours. LC-MS showed the reaction was complete. The reaction mixture was concentrated under reduced pressure. The residue was purified by prep-HPLC (HCl condition column: Phenomenex Luna C18 150 mm×30 mm 5 μm; mobile phase: [water (0.05% HCl)-MeCN]; B %: 15%-45%, 10 mins). The solvent was removed under freeze drying. Compound 5-[(3,4-dichlorophenyl)methylamino]-1-[(4-methylmorpholin-2-yl)methyl]-6H-pyrazolo[4,3-d]pyrimidin-7-one (49.1 mg, 106.69 μmol, 11.89% yield, 99.9% purity, HCl) was obtained as white solid. $^1$H NMR (DMSO-d$_6$, 400 MHz) δ 11.33 (s, 1H), 8.37 (s, 1H), 7.74 (s, 1H), 7.68 (d, J=1.2 Hz, 1H), 7.62 (d, J=8.4 Hz, 1H), 7.40 (dd, J=8.4 Hz, 1.2 Hz, 1H), 4.67~4.62 (m, 3H), 4.57~4.53 (m, 1H), 4.27~4.26 (m, 1H), 3.98~3.94 (m, 1H), 3.74 (t, J=12.0 Hz, 1H), 3.39 (d, J=12.0 Hz, 1H), 3.30 (d, J=12.0 Hz, 1H), 2.98~2.90 (m, 2H), 2.74 (m, 3H). HPLC: 99.90% (220 nm), 99.85% (215 nm), 99.57% (254 nm). MS (ESI): mass calcd. For C$_{18}$H$_{21}$Cl$_3$N$_6$O$_2$ 422.10, m/z found 423.0 [M+H]$^+$.

Compound 150

Preparation of 4-(5-((3,4-dichlorobenzyl)amino)-7-oxo-6,7-dihydro-1H-pyrazolo[4,3-d]pyrimidin-1-yl)-1-isonicotinoylpyrrolidine-2-carboxylic acid hydrochloride Preparation of 1-(tert-butoxycarbonyl)-4-(5-((3,4-dichlorobenzyl)amino)-7-oxo-6,7-dihydro-1H-pyrazolo[4,3-d]pyrimidin-1-yl)pyrrolidine-2-carboxylic Acid (Step 1-3 in Scheme C-3)

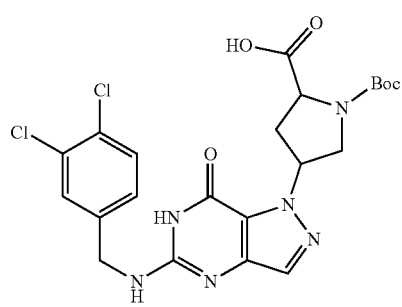 [SMILES: CC(C)(C)OC(=O)N1CC(n2ncc3nc(NCc4ccc(Cl)c(Cl)c4)[nH]c(=O)c32)CC1C(=O)O]

A solution of 1-tert-butoxycarbonyl-4-(5-chloro-7-oxo-6H-pyrazolo[4,3-d]pyrimidin-1-yl)pyrrolidine-2-carboxylic acid (520 mg, 1.35 mmol, 1 eq) and (3,4-dichlorophenyl)methanamine (477.05 mg, 2.71 mmol, 361.40 µL, 2 eq) in 2-methylbutan-2-ol (3 mL) was stirred at 130° C. for 10 hours. LCMS and HPLC showed the reaction was complete. The mixture was concentrated under reduced pressure. The residue was purified by prep-HPLC (column: Phenomenex Luna C18 150 mm×30 mm 5 µm; mobile phase: [water (0.05% HCl)-MeCN]; B %: 30%-50%, 12 mins). The mixture was dried under freeze-drying to give 1-(tert-butoxycarbonyl)-4-(5-((3,4-dichlorobenzyl)amino)-7-oxo-6,7-dihydro-1H-pyrazolo[4,3-d]pyrimidin-1-yl)pyrrolidine-2-carboxylic acid (140 mg, 267.50 µmol, 19.74% yield) as white solid. $^1$H NMR (DMSO-d$_6$, 400 MHz) δ 7.62 (s, 1H), 7.59~7.53 (m, 2H), 7.30 (d, J=8.8 Hz, 1H), 5.67~5.52 (m, 1H), 4.48 (d, J=5.6 Hz, 2H), 4.37~4.30 (m, 1H), 3.78~3.74 (m, 1H), 3.63~3.55 (m, 1H), 2.82~2.69 (m, 1H), 2.38~2.31 (m, 1H), 1.39~1.25 (m, 9H).

Compound 151

Preparation of 4-(5-((3,4-dichlorobenzyl)amino)-7-oxo-6,7-dihydro-1H-pyrazolo[4,3-d]pyrimidin-1-yl)pyrrolidine-2-carboxylic Acid Hydrochloride (Step 1 in Scheme C-3)

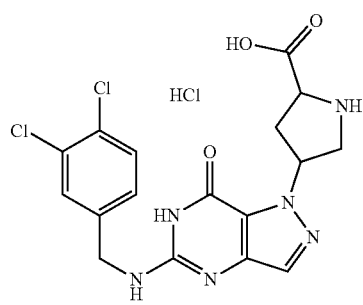 [SMILES: O=C(O)C1CC(n2ncc3nc(NCc4ccc(Cl)c(Cl)c4)[nH]c(=O)c32)CN1 ; Cl]

To a solution of 1-tert-butoxycarbonyl-4-[5-[(3,4-dichlorophenyl)methylamino]-7-oxo-6H-pyrazolo[4,3-d]pyrimidin-1-yl]pyrrolidine-2-carboxylic acid (140 mg, 267.50 µmol, 1 eq) in EtOAc (3 mL) was added HCl/EtOAc (4 M, 3 mL) at 0° C. The mixture was stirred at 25° C. for 4 hours. LCMS and HPLC showed the reaction was complete. The mixture was concentrate under reduced pressure. The residue was purified by prep-HPLC (column: Phenomenex Luna C18 150 mm×30 mm 5 µm; mobile phase: [water (0.05% HCl)-MeCN]; B %: 15%-50%, 12 mins). The mixture was dried under freeze-drying to give 4-(5-((3,4-dichlorobenzyl)amino)-7-oxo-6,7-dihydro-1H-pyrazolo[4,3-d]pyrimidin-1-yl)pyrrolidine-2-carboxylic acid hydrochloride (120 mg, 249.49 µmol, 93.27% yield, 95.577% purity, HCl) as white solid. $^1$H NMR (DMSO-d$_6$, 400 MHz) δ 10.02 (s, 1H), 9.13 (s, 1H), 7.72 (s, 1H), 7.64~7.53 (m, 2H), 7.33 (dd, J=2.0 Hz, J=8.0 Hz, 1H), 6.95 (s, 1H), 5.79 (s, 1H), 4.60 (s, 1H), 4.50 (d, J=5.6 Hz, 2H), 3.83 (s, 1H), 3.63 (d, J=11.6 Hz, 1H), 2.65~2.63 (m, 1H), 2.62~2.58 (m, 1H). HPLC: 95.58% (220 nm), 94.08% (215 nm), 94.72% (254 nm). MS (ESI): mass calcd. For C$_{17}$H$_7$C$_3$N$_6$O$_3$ 422.07, m/z found 423.1 [M+H]$^+$.

Preparation of 4-(5-((3,4-dichlorobenzyl)amino)-7-oxo-6,7-dihydro-1H-pyrazolo[4,3-d]pyrimidin-1-yl)-1-isonicotinoylpyrrolidine-2-carboxylic Acid Hydrochloride (Step 2 in Scheme C-3)

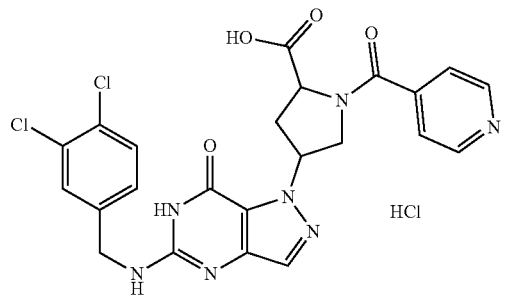 [SMILES: O=C(O)C1CC(n2ncc3nc(NCc4ccc(Cl)c(Cl)c4)[nH]c(=O)c32)CN1C(=O)c1ccncc1 ; Cl]

To a solution of 4-[5-[(3,4-dichlorophenyl)methylamino]-7-oxo-6H-pyrazolo[4,3-d]pyrimidin-1-yl]pyrrolidine-2-carboxylic acid (70 mg, 152.27 µmol, 1 eq, HCl) in DCM (3 mL) was added TEA (61.63 mg, 609.07 µmol, 84.78 µL, 4 eq). Then pyridine-4-carbonyl chloride (70.48 mg, 395.90 µmol, 2.6 eq, HCl) was added into the mixture in portions at 0° C. The mixture was stirred at 25° C. for 3 hours. LCMS showed the reaction was complete. The mixture was concentrated under reduced pressure. The residue was purified by prep-HPLC (column: Phenomenex Luna C18 150 mm×30 mm 5 µm; mobile phase: [water (0.05% HCl)-MeCN]; B %: 15%-40%, 12 mins). The mixture was dried under freeze-dry to give 4-(5-((3,4-dichlorobenzyl)amino)-7-oxo-6,7-dihydro-1H-pyrazolo[4,3-d]pyrimidin-1-yl)-1-isonicotinoylpyrrolidine-2-carboxylic acid hydrochloride (25.0 mg, 43.68 µmol, 28.69% yield, 98.683% purity, HCl) as white solid. $^1$H NMR (DMSO-d$_6$, 400 MHz) δ 8.89 (d, J=6.4 Hz, 2H), 7.92 (s, 1H), 7.88~7.73 (m, 2H), 7.72~7.66 (m, 1H), 7.65~7.59 (m, 2H), 7.42~7.33 (m, 1H), 5.75~5.64 (m, 1H), 4.72 (t, J=8.0 Hz, 1H), 4.64~4.57 (m, 2H), 4.08 (s, 1H), 3.79~3.78 (m, 1H), 2.86~2.80 (m, 1H), 2.60 (d, J=6.4 Hz, 1H). HPLC: 98.68% (220 nm), 98.30% (215 nm), 99.34% (254 nm). MS (ESI): mass calcd. For C$_{23}$H$_{20}$C3N$_7$O$_4$ 527.09, m/z found 528.1 [M+H]$^+$.

Compound 152

Preparation of 5-((3,4-dichlorobenzyl)amino)-1-(piperidin-4-yl)-1H-pyrazolo[4,3-d]pyrimidin-7(6H)-one Compound 153

Tert-butyl 4-(5-((3,4-dichlorobenzyl)amino)-7-oxo-6,7-dihydro-1H-pyrazolo[4,3-d]pyrimidin-1-yl)piperidine-1-carboxylate was prepared according to the procedures described herein for Step 1-3 in Scheme C-3

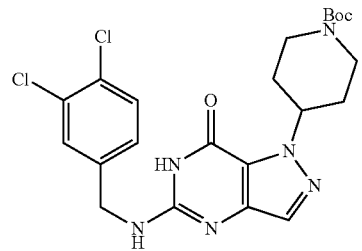 [SMILES: CC(C)(C)OC(=O)N1CCC(n2ncc3nc(NCc4ccc(Cl)c(Cl)c4)[nH]c(=O)c32)CC1]

The procedure yielded the desired compound tert-butyl4-(5-((3,4-dichlorobenzyl)amino)-7-oxo-6,7-dihydro-1H-pyrazolo[4,3-d]pyrimidin-1-yl)piperidine-1-carboxylate (33.7 mg, 65.68 µmol, 46.48% yield, 96.163% purity) as white solid. $^1$H NMR (DMSO-$d_6$, 400 MHz) δ 7.59~7.57 (m, 3H), 7.32 (dd, J=2.0 Hz, 8.0 Hz, 1H), 6.76 (s, 1H), 5.02~4.98 (m, 1H), 4.48 (d, J=5.6 Hz, 2H), 4.05 (br d, J=13.2 Hz, 2H), 2.92~2.89 (m, 2H), 1.92~1.85 (m, 4H), 1.42 (s, 9H). HPLC: 96.16% (220 nm), 96.40% (215 nm), 100.00% (254 nm). MS (ESI): mass calcd. For $C_{22}H_{26}C2N_6O_3$ 492.14, m/z found 493.2 [M+H]$^+$.

Preparation of 5-((3,4-dichlorobenzyl)amino)-1-(piperidin-4-yl)-1H-pyrazolo[4,3-d]pyrimidin-7(6H)-one

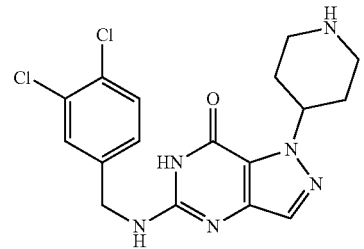 [SMILES: O=c1[nH]c(NCc2ccc(Cl)c(Cl)c2)nc2cnn(C3CCNCC3)c12]

Compound 5-((3,4-dichlorobenzyl)amino)-1-(piperidin-4-yl)-1H-pyrazolo[4,3-d]pyrimidin-7(6H)-one (1 g, 2.33 mmol, 39.64% yield, HCl) was obtained as white solid. $^1$H NMR (DMSO-$d_6$, 400 MHz) δ 8.96 (s, 1H), 8.74 (s, 1H), 7.65 (s, 1H), 7.59 (d, J=8.4 Hz, 2H), 7.34 (d, J=8.8 Hz, 1H), 7.33~7.29 (m, 1H), 5.14 (s, 1H), 4.52 (d, J=5.2 Hz, 2H), 3.41~3.37 (m, 2H), 3.14~3.10 (m, 2H), 2.24~2.10 (m, 4H). HPLC: 96.39% (220 nm), 96.35% (215 nm), 96.48% (254 nm). MS (ESI): mass calcd. For $C_{17}H_{18}C_{12}N_6O$ 392.09, m/z found 393.1 [M+H]$^+$.

Compound 154

Preparation of 5-((3,4-dichlorobenzyl)amino)-1-(piperidin-3-ylmethyl)-1H-pyrazolo[4,3-d]pyrimidin-7(6H)-one hydrochloride Tert-butyl 3-((5-((3,4-dichlorobenzyl)amino)-7-oxo-6,7-dihydro-1H-pyrazolo[4,3-d]pyrimidin-1-yl)methyl)piperidine-1-carboxylate was prepared according to the procedures described herein for Steps 1-3 in Scheme C-3.

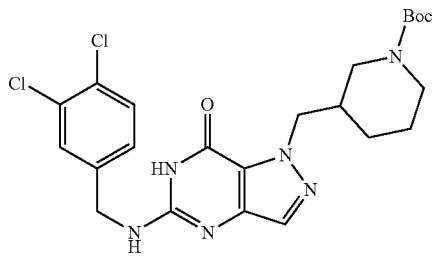 [SMILES: CC(C)(C)OC(=O)N1CCCC(Cn2ncc3nc(NCc4ccc(Cl)c(Cl)c4)[nH]c(=O)c32)C1]

The procedure yielded the desired compound tert-butyl 3-((5-((3,4-dichlorobenzyl)amino)-7-oxo-6,7-dihydro-1H-pyrazolo[4,3-d]pyrimidin-1-yl)methyl)piperidine-1-carboxylate (430 mg, crude) as a white solid. $^1$H NMR (DMSO-$d_6$, 400 MHz) δ 7.60 (d, J=2.4 Hz, 2H), 7.58 (s, 1H), 7.34 (d, J=8.4 Hz, 1H), 4.50 (d, J=5.2 Hz, 2H), 4.32 (d, J=7.2 Hz, 2H), 3.69 (s, 2H), 2.89~2.68 (m, 1H), 2.60~2.53 (m, 1H), 1.98 (s, 2H), 1.60 (d, J=10.0 Hz, 3H), 1.30 (br s, 9H).

5-((3,4-dichlorobenzyl)amino)-1-(piperidin-3-ylmethyl)-1H-pyrazolo[4,3-d]pyrimidin-7(6H)-one hydrochloride was prepared according to the procedure described herein for Step 1 in Scheme C-3.

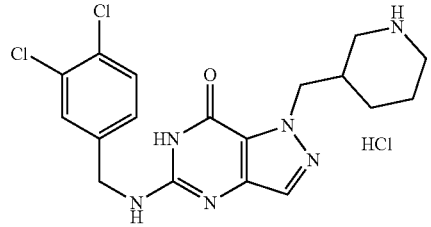 [SMILES: O=c1[nH]c(NCc2ccc(Cl)c(Cl)c2)nc2cnn(CC3CCCNC3)c12 ; Cl]

The procedure yielded the desired compound 5-((3,4-dichlorobenzyl)amino)-1-(piperidin-3-ylmethyl)-1H-pyrazolo[4,3-d]pyrimidin-7(6H)-one (500 mg, crude) as a white solid. 80 mg (crude) was purified by prep-HPLC (column: Phenomenex Luna C18 100 mm×30 mm 5 µm; mobile phase: [water (0.05% HCl)-MeCN]; B %: 15%-45%, 10 mins) to give 20.9 mg pure product for delivery. H NMR (DMSO-$d_6$, 400 MHz) δ 8.86 (d, J=6.8 Hz, 1H), 8.55 (br s, 1H), 7.62 (t, J=13.2 Hz, 3H), 7.37 (d, J=8.4 Hz, 1H), 4.54 (d, J=5.2 Hz, 2H), 4.43~4.39 (m, 2H), 3.19~3.02 (m, 2H), 2.81~2.67 (m, 2H), 2.31~2.26 (m, 1H), 1.77 (d, J=12.8 Hz, 1H), 1.66~1.58 (m, 2H), 1.27~1.18 (m, 1H). HPLC: 99.10% (220 nm), 98.78% (215 nm), 98.43% (254 nm). MS (ESI): mass calcd. For $C_{18}H_{21}C3N_6O$ 406.11, m/z found 407.11 [M+H]$^+$.

Compound 155

Preparation of 5-((3,4-dichlorobenzyl)amino)-1-(pyrrolidin-3-ylmethyl)-1H-pyrazolo[4,3-d]pyrimidin-7(6H)-one hydrochloride Tert-butyl 3-((5-((3,4-dichlorobenzyl)amino)-7-oxo-6,7-dihydro-1H-pyrazolo[4,3-d]pyrimidin-1-yl)methyl)pyrrolidine-1-carboxylate was prepared according to the procedures described herein for Steps 1-3 in Scheme C-3.

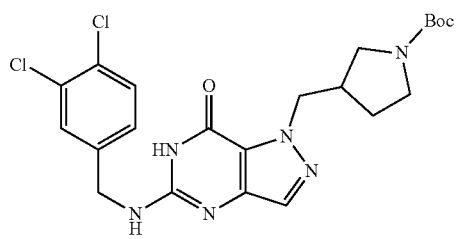

The procedure yielded the desired compound tert-butyl 3-[[5-[(3,4-dichlorophenyl)methylamino]-7-oxo-6H-pyrazolo[4,3-d]pyrimidin-1-yl]methyl]pyrrolidine-1-carboxylate (220 mg, 445.90 µmol, 43.82% yield) as a white solid. $^1$H NMR (DMSO-$d_6$, 400 MHz) δ 11.10 (s, 1H), 7.63~7.50 (m, 3H), 7.33 (d, J=8.4 Hz, 1H), 6.56 (t, J=6.0 Hz, 1H), 4.51~4.38 (m, 4H), 3.31~3.28 (m, 2H), 3.28~3.23 (m, 1H), 3.19 (s, 1H), 3.04 (br s, 1H), 1.80 (br s, 1H), 1.58 (d, J=4.0 Hz, 1H), 1.37 (s, 9H).

Preparation of 5-((3,4-dichlorobenzyl)amino)-1-(pyrrolidin-3-ylmethyl)-1H-pyrazolo[4,3-d]pyrimidin-7(6H)-one hydrochloride

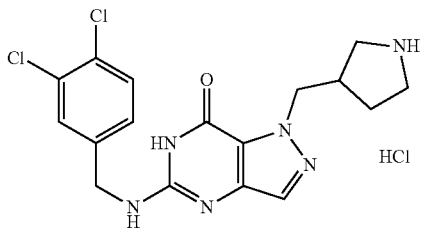 [SMILES: O=c1[nH]c(NCc2ccc(Cl)c(Cl)c2)nc2cnn(CC3CCNC3)c12 ; Cl]

To a solution of tert-butyl 3-[[5-[(3,4-dichlorophenyl)methylamino]-7-oxo-6H-pyrazolo[4,3-d]pyrimidin-1-yl]methyl]pyrrolidine-1-carboxylate (Compound 165) (220 mg, 445.90 µmol, 1 eq) in EtOAc (2 mL) was added HC/EtOAc (4 M, 2 mL, 17.94 eq) at 0° C. The mixture was stirred at 25° C. for 4 hours. LCMS showed the reaction was complete. The mixture was concentrated under reduced pressure. The residue was purified by prep-HPLC (column: Phenomenex Luna C18 100 mm×30 mm 5 µm; mobile phase: [water (0.05% HCl)-MeCN]; B %: 15%-35%, 12 mins). The mixture was freeze-dry to give 5-[(3,4-dichlorophenyl)methylamino]-1-(pyrrolidin-3-ylmethyl)-6H-pyrazolo[4,3-d]pyrimidin-7-one (180 mg, 418.87 µmol, 93.94% yield, HCl) as white solid. $^1$H NMR (DMSO-$d_6$, 400 MHz) δ 9.06 (br s, 2H), 7.67~7.57 (m, 3H), 7.34 (dd, J=2.4 Hz, 8.8 Hz, 1H), 4.60~4.41 (m, 4H), 3.18 (br s, 2H), 3.09~3.07 (m, 1H), 2.95~2.90 (m, 1H), 2.79~2.71 (m, 1H), 1.94~1.88 (m, 1H), 1.65~1.57 (m, 1H). HPLC: 99.50% (220 nm), 99.24% (215 nm), 99.65% (254 nm). MS (ESI): mass calcd. For $C_{17}H_{19}C3N_6O$ 392.09, m/z found 393.1 [M+H]$^+$.

Compound 156

Preparation of 5-((3,4-dichlorobenzyl)amino)-1-(1-(pyridin-3-ylsulfonyl)piperidin-4-yl)-1H-pyrazolo[4,3-d]pyrimidin-7(6H)-one hydrochloride

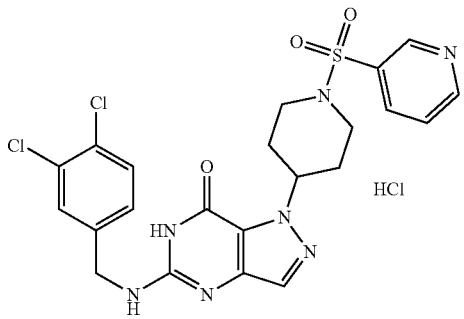 [SMILES: O=c1[nH]c(NCc2ccc(Cl)c(Cl)c2)nc2cnn(C3CCN(S(=O)(=O)c4cccnc4)CC3)c12 ; Cl]

To a mixture of 5-[(3,4-dichlorophenyl)methylamino]-1-(4-piperidyl)-6H-pyrazolo[4,3-d]pyrimidin-7-one (80 mg, 186.16 µmolmol, 1 eq, HCl) and TEA (75.35 mg, 744.65 µmol, 103.65 µL, 4 eq) in DCM (3 mL) was added pyridine-3-sulfonyl chloride (33.06 mg, 186.16 µmol, 8.53 µL, 1 eq) dropwise at 0° C. Then the mixture was stirred at 20° C. for 1 hour. LC-MS showed the reaction was complete. The mixture was quenched with ice water (5 mL) and the organic layer was separated. The aqueous was extracted with DCM (5 mL×4). The combined organic layer was washed with brine (2 mL×1), dried over $Na_2SO_4$, filtered and concentrated under reduced pressure. The residue was purified by prep-HPLC (column: Phenomenex Luna C18 100 mm×30 mm 5 µm; mobile phase: [water (0.05% HCl)-MeCN]; B %: 45%-70%, 10 mins). The eluent was removed under freeze drying. Compound 5-[(3,4-dichlorophenyl)methylamino]-1-[1-(3-pyridylsulfonyl)-4-piperidyl]-6H-pyrazolo[4,3-d]pyrimidin-7-one (26.7 mg, 46.07 µmol, 24.75% yield, 98.51% purity, HCl) was obtained as white solid. $^1$H NMR (DMSO-$d_6$, 400 MHz) δ 8.96 (s, 1H), 8.92 (d, J=4.0 Hz, 1H), 8.23~8.20 (m, 1H), 7.74~7.71 (m, 1H), 7.61~7.58 (m, 3H), 7.33 (dd, J=2.0 Hz, 8.4 Hz, 1H), 4.90~4.82 (m, 1H), 4.52 (d, J=5.2 Hz, 2H), 3.81~3.78 (m, 2H), 2.67~2.64 (m, 2H), 2.03~2.01 (m, 4H). HPLC: 98.51% (220 nm), 98.36% (215 nm), 95.74% (254 nm). MS (ESI): mass calcd. For $C_{22}H_{22}C_{13}N_7O_3S$ 533.08 m/z found 354.2 [M+H]$^+$.

Compound 157

Preparation of 5-((3,4-dichlorobenzyl)amino)-1-(1-(2-methoxyethyl) piperidin-4-yl)-1H-pyrazolo[4,3-d]pyrimidin-7(6H)-one hydrochloride

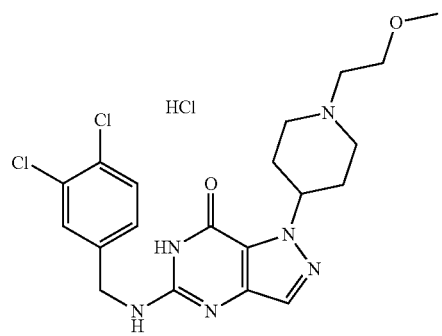 [SMILES: COCCN1CCC(n2ncc3nc(NCc4ccc(Cl)c(Cl)c4)[nH]c(=O)c32)CC1 ; Cl]

To a solution of 5-[(3,4-dichlorophenyl)methylamino]-1-(4-piperidyl)-6H-pyrazolo[4,3-d]pyrimidin-7-one hydrochloride (60 mg, 139.62 µmol, 1 eq, HCl) and 1-bromo-2-methoxy-ethane (58.22 mg, 418.87 µmol, 39.34 µL, 3 eq) in $CH_3CN$ (1 mL) was added $K_2CO_3$ (57.89 mg, 418.87 µmol, 3 eq). The mixture was stirred at 80° C. for 16 hours. LCMS and HPLC showed the reaction was complete. The mixture was filtered. The filtrate was purified by prep-HPLC (column: Phenomenex Luna C18 100 mm×30 mm 5 µm; mobile phase: [water (0.05% HCl)-MeCN]; B %: 20%-40%, 10 mins). The mixture was freeze-dry to give 5-[(3,4-dichlorophenyl)methylamino]-1-[1-(2-methoxyethyl)-4-piperidyl]-6H-pyrazolo[4,3-d]pyrimidin-7-one (18.6 mg, 40.51 µmol, 29.01% yield, 98.295% purity) as white solid. H NMR (DMSO-$d_6$, 400 MHz) δ 10.19 (s, 1H), 7.65 (s, 1H), 7.61~7.56 (m, 2H), 7.48 (s, 1H), 7.33 (dd, J=2.0 Hz, 8.4 Hz, 1H), 5.13~5.06 (m, 1H), 4.53 (d, J=5.2 Hz, 2H), 3.73~3.67 (m, 2H), 3.59 (d, J=12.0 Hz, 2H), 3.40 (s, 1H), 3.30 (s, 3H), 3.28 (d, J=5.6 Hz, 2H), 3.20 (s, 1H), 2.41~2.31 (m, 2H), 2.16~2.13 (m, 2H). HPLC: 98.30% (220 nm), 98.30% (215 nm), 98.14% (254 nm). MS (ESI): mass calcd. For $C_{20}H_{25}C_{13}N_6O_2$ 486.11, m/z found 451.2 [M+H]$^+$.

Compound 158

5-((3,4-dichlorobenzyl)amino)-1-(2-morpholino-2-oxoethyl)-1H-pyrazolo[4,3-d]pyrimidin-7(6H)-one was prepared according to the procedures described herein for Steps 1-3 in Scheme C-3.

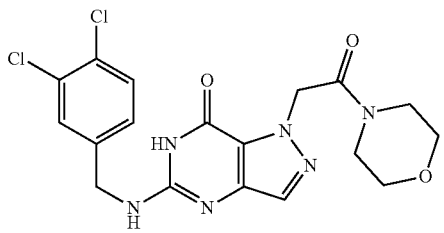 [SMILES: O=C(Cn1ncc2nc(NCc3ccc(Cl)c(Cl)c3)[nH]c(=O)c21)N1CCOCC1]

The procedure yielded the desired compound 5-((3,4-dichlorobenzyl)amino)-1-(2-morpholino-2-oxoethyl)-1H-pyrazolo[4,3-d]pyrimidin-7(6H)-one (16.8 mg, 37.65 μmol, 17.24% yield, 98.005% purity) as a white solid. $^1$H NMR (DMSO-$d_6$, 400 MHz) δ 7.64~7.59 (m, 4H), 7.36 (d, J=6.8, 1H), 5.38 (s, 2H), 5.57 (s, 2H), 3.65~3.56 (m, 4H), 3.42 (s, 4H). HPLC: 98.01% (220 nm), 97.95% (215 nm), 98.09% (254 nm). MS (ESI): mass calcd. For $C_{18}H_{18}Cl_2N_6O_3$ 436.08, m/z found 437.1 [M+H]$^+$.

Compound 159

5-((3,4-dichlorobenzyl)amino)-1-((1-methyl-5-oxopyrrolidin-3-yl)methyl)-1H-pyrazolo[4,3-d]pyrimidin-7(6H)-one was prepared according to the procedures described herein for Steps 1-3 in Scheme C-3.

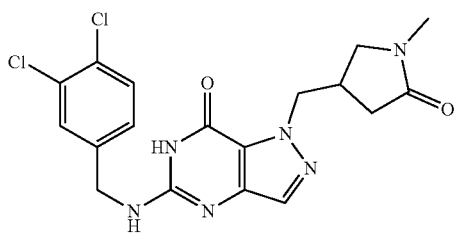 [SMILES: CN1CC(Cn2ncc3nc(NCc4ccc(Cl)c(Cl)c4)[nH]c(=O)c32)CC1=O]

The procedure yielded the desired compound 5-((3,4-dichlorobenzyl)amino)-1-((1-methyl-5-oxopyrrolidin-3-yl)methyl)-1H-pyrazolo[4,3-d]pyrimidin-7(6H)-one (56.2 mg, 132.45 μmol, 30.33% yield, 99.285% purity) as a white solid. $^1$H NMR (DMSO-$d_6$, 400 MHz) δ 8.13 (s, 1H), 7.72~7.66 (m, 2H), 7.63 (d, J=8.4 Hz, 1H), 7.40 (dd, J=1.6 Hz, 8.0 Hz, 1H), 4.64 (d, J=3.6 Hz, 2H), 4.50 (d, J=7.2 Hz, 2H), 3.37~3.33 (m, 1H), 3.18~3.14 (m, 1H), 2.92~2.80 (m, 1H), 2.67 (s, 3H), 2.35~2.29 (m, 1H), 2.12~2.09 (m, 1H). HPLC: 99.29% (220 nm), 99.21% (215 nm), 98.28% (254 nm). MS (ESI): mass calcd. For $C_{18}H_{18}Cl_2N_6O_2$ 420.09, m/z found 421.1 [M+H]$^+$.

Compound 160

5-((3,4-dichlorobenzyl)amino)-1-(2-(2-morpholinoethoxy)ethyl)-1H-pyrazolo[4,3-d]pyrimidin-7(6H)-one hydrochloride was prepared according to the procedures described herein for Steps 1-3 in Scheme C-3.

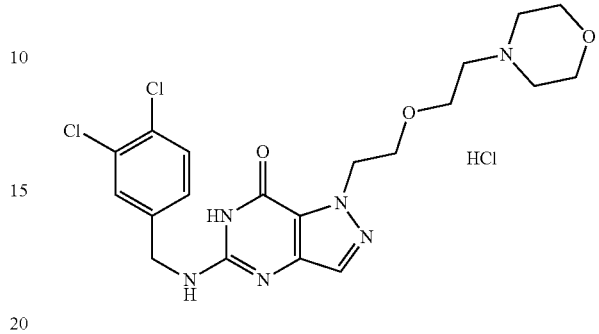

The procedure yielded the desired compound 5-[(3,4-dichlorophenyl)methylamino]-1-[2-(2-morpholinoethoxy)ethyl]-6H-pyrazolo[4,3-d]pyrimidin-7-one (54.9 mg, 105.69 μmol, 17.32% yield, 96.991% purity, HCl) as a white solid. $^1$H NMR (DMSO-$d_6$, 400 MHz) δ 10.50 (s, 1H), 7.65~7.58 (m, 3H), 7.36 (dd, J=1.6 Hz, 8.0 Hz, 1H), 4.63 (t, J=5.2 Hz, 2H), 4.56 (d, J=4.8 Hz, 2H), 3.87~3.81 (m, 4H), 3.75 (t, J=4.4 Hz, 2H), 3.66 (t, J=12.0 Hz, 2H), 3.27~3.20 (m, 4H), 3.01~2.92 (m, 2H). HPLC: 96.99% (220 nm), 94.02% (215 nm), 99.79% (254 nm). MS (ESI): mass calcd. For $C_2H_{25}C_3N_6O_3$ 466.13, m/z found 467.1 [M+H]$^+$.

Compound 161

5-((3,4-dichlorobenzyl)amino)-1-(1-(pyridin-2-yl)piperidin-4-yl)-1H-pyrazolo[4,3-d]pyrimidin-7(6H)-one dihydrochloride was prepared according to the procedures described herein for Steps 1-3 in Scheme C-3.

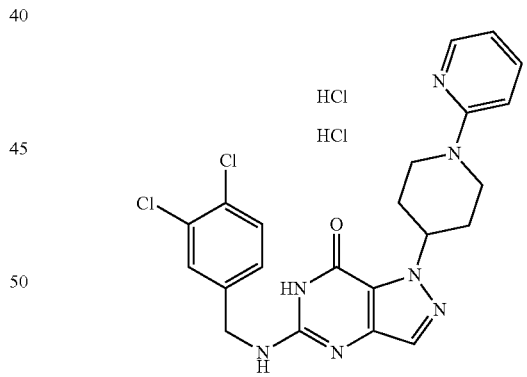

The procedure yielded the desired compound 5-((3,4-dichlorobenzyl)amino)-1-(1-(pyridin-2-yl)piperidin-4-yl)-1H-pyrazolo[4,3-d]pyrimidin-7(6H)-one dihydrochloride (40.9 mg, 85.66 μmol, 14.17% yield, 98.510% purity) as a white solid. $^1$H NMR (DMSO-$d_6$, 400 MHz) δ 8.02 (s, 1H), 8.00~7.97 (m, 1H), 7.61 (s, 1H), 7.60 (d, J=2.4 Hz, 1H), 7.58 (d, J=8.0 Hz, 1H), 7.45 (d, J=8.8 Hz, 1H), 7.34 (dd, J=1.6 Hz, 8.0 Hz, 1H), 6.94 (t, J=6.8 Hz, 1H), 5.28~5.16 (m, 1H), 4.53 (d, J=5.2 Hz, 2H), 4.38 (d, J=13.6 Hz, 2H), 3.50~3.37 (m, 2H), 2.15~2.04 (m, 4H). HPLC: 98.51% (220 nm), 98.10% (215 nm), 99.43% (254 nm). MS (ESI): mass calcd. For $C_{22}H_{23}Cl_4N_7O$ 469.12, m/z found 470.1 [M+H]$^+$.

Compound 162

5-((3,4-dichlorobenzyl)amino)-1-(1-(pyridin-4-yl) piperidin-4-yl)-1H-pyrazolo[4,3-d]pyrimidin-7(6H)-one dihydrochloride was prepared according to the procedures described herein for Steps 1-3 in Scheme C-3.

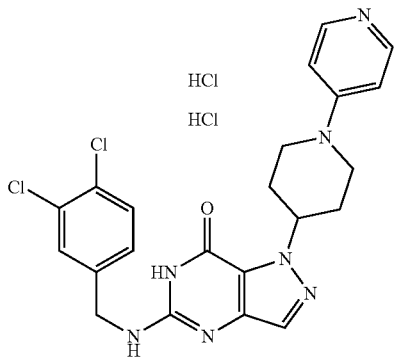 [SMILES: O=c1[nH]c(NCc2ccc(Cl)c(Cl)c2)nc2cnn(C3CCN(c4ccncc4)CC3)c12 ; Cl ; Cl]

The procedure yielded the desired compound compound 5-[(3,4-dichlorophenyl)methylamino]-1-[1-(4-pyridyl)-4-piperidyl]-6H-pyrazolo[4,3-d]pyrimidin-7-one (17.6 mg, 37.42 µmol, 10.31% yield, 95.01% purity, HCl) as a light yellow solid. $^1$H NMR (DMSO-$d_6$, 400 MHz) δ 13.55 (s 1H), 8.26~8.25 (m, 2H), 7.63~7.59 (m, 3H), 7.50 (s 1H), 7.35 (d, J=6.8 Hz, 1H), 7.27 (d, J=7.2 Hz, 2H), 5.29~5.23 (m, 1H), 4.55 (d, J=5.2 Hz, 2H), 4.35 (d, J=14.0 Hz, 2H), 3.48~3.39 (m, 2H), 2.14~2.02 (m, 4H). HPLC: 95.01% (220 nm), 90.40% (215 nm), 92.03% (254 nm). MS (ESI): mass calcd. For $C_{22}H_{23}Cl_4N_7O$ 469.12, m/z found 470.1 [M+H]$^+$.

Compound 163

5-((3,4-dichlorobenzyl)amino)-1-(1-(pyridin-3-yl)piperidin-4-yl)-1H-pyrazolo[4,3-d]pyrimidin-7(6H)-one dihydrochloride was prepared according to the procedures described herein for Steps 1-3 in Scheme C-3.

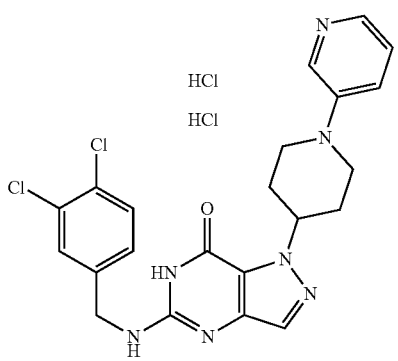 [SMILES: O=c1[nH]c(NCc2ccc(Cl)c(Cl)c2)nc2cnn(C3CCN(c4cccnc4)CC3)c12 ; Cl ; Cl]

The procedure yielded the desired compound 5-((3,4-dichlorobenzyl)amino)-1-(1-(pyridin-3-yl)piperidin-4-yl)-1H-pyrazolo[4,3-d]pyrimidin-7(6H)-one dihydrochloride (70.0 mg, 144.42 µmol, 25.01% yield, 97.038% purity) as a white solid. $^1$H NMR (DMSO-$d_6$, 400 MHz) δ 8.53 (d, J=2.8 Hz, 1H), 8.20~8.13 (m, 2H), 8.11~7.88 (m, 1H), 7.87~7.83 (m, 1H), 7.67 (s, 2H), 7.62 (d, J=8.4 Hz, 1H), 7.39 (dd, J=1.8 Hz, 8.4 Hz, 1H), 5.20~5.12 (m, 1H), 4.62 (d, J=4.4 Hz, 2H), 4.14 (d, J=12.8 Hz, 2H), 3.26~3.16 (m, 2H), 2.13~2.01 (m, 4H). HPLC: 97.04% (220 nm), 96.74% (215 nm), 98.80% (254 nm). MS (ESI): mass calcd. For $C_{22}H_{23}Cl4N_7O$ 469.12, m/z found 470.1 [M+H]$^+$.

Compound 164

Preparation of 5-((3,4-dichlorobenzyl)amino)-1-(2-((2-hydroxyethyl)sulfonyl)ethyl)-1H-pyrazolo[4,3-d]pyrimidin-7(6H)-one

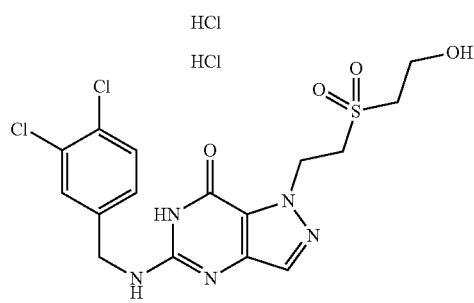 [SMILES: Cl ; O=c1[nH]c(NCc2ccc(Cl)c(Cl)c2)nc2cnn(CCS(=O)(=O)CCO)c12 ; Cl]

A mixture of 5-[(3,4-dichlorophenyl)methylamino]-1-[2-(2-hydroxyethylsulfanyl)ethyl]-6H-pyrazolo[4,3-d]pyrimidin-7-one (0.1 g, 241.37 µmol, 1 eq) (Steps 1-3 in Scheme C-3), sodium periodate (206.50 mg, 965.46 µmol, 53.50 µL, 4 eq) and trichlororuthenium (5.01 mg, 24.14 µmol, 1.61 µL, 0.1 eq) in THF (2.5 mL) and $H_2O$ (2.5 mL) was stirred at 50° C. for 3 hours. LC-MS showed the reaction was completed. The reaction mixture was concentrated under reduced pressure. The aqueous was extracted with EtOAc (10 mL×3). The combined organic layers were washed with brine (10 mL), dried over $Na_2SO_4$, filtered and concentrated under reduced pressure. The residue was purified by prep-HPLC (column: Welch Xtimate C18 100 mm×25 mm 3 µm; mobile phase: [water (0.1% TFA)-MeCN]; B %: 20%-55%, 12 mins). The aqueous solution was lyophilized to give 5-[(3,4-dichlorophenyl)methylamino]-1-[2-(2-hydroxyethylsulfonyl)ethyl]-6H-pyrazolo[4,3-d]pyrimidin-7-one (41 mg, 91.03 µmol, 37.72% yield, 99.093% purity) as white solid. $^1$H NMR (DMSO-$d_6$, 400 MHz) δ 7.62 (s, 1H), 7.59~7.58 (m, 2H), 7.32 (dd, J=1.6 Hz, 6.8 Hz, 1H), 6.75 (s, 1H), 4.86 (t, J=6.8 Hz, 2H), 4.48 (d, J=5.6 Hz, 2H), 3.76 (t, J=5.2 Hz, 2H), 3.69 (t, J=7.2 Hz, 2H), 3.24 (t, J=5.6 Hz, 2H). HPLC: 99.09% (220 nm), 98.89% (215 nm), 100.00% (254 nm). MS (ESI): mass calcd. For $C_{16}H_{17}C_{12}N_5O_4S$ 445.04, m/z found 446.0 [M+H]$^+$.

Compound 165

Preparation of 2-(5-((3,4-dichlorobenzyl)amino)-7-oxo-6,7-dihydro-1H-pyrazolo[4,3-d]pyrimidin-1-yl)-N-(methylsulfonyl)acetamide Preparation of 2-(5-((3,4-dichlorobenzyl)amino)-7-oxo-6,7-dihydro-1H-pyrazolo[4,3-d]pyrimidin-1-yl) acetic Acid

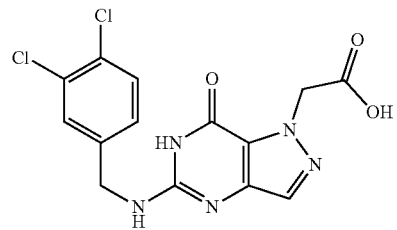 [SMILES: O=C(O)Cn1ncc2nc(NCc3ccc(Cl)c(Cl)c3)[nH]c(=O)c21]

To a solution of 2-(5-chloro-7-oxo-6H-pyrazolo[4,3-d]pyrimidin-1-yl)acetic acid (0.32 g 1.40 mmol, 1 eq) in t-BuOH (3 mL) was added (3,4-dichlorophenyl)methanamine (369.66 mg, 2.10 mmol, 280.04 μL, 1.5 eq). The mixture was stirred at 100° C. for 24 hours. LCMS showed the reaction was completed. The residue was purified by prep-HPLC (column: Phenomenex Luna C18 150 mm×30 mm 5 μm; mobile phase: [water (0.05% HCl)-MeCN]; B %: 20%-45%, 12 mins). MeCN was removed under reduced pressure at 30° C. The residue was dried over lyophilization. Compound 2-[5-[(3,4-dichlorophenyl)methylamino]-7-oxo-6H-pyrazolo[4,3-d]pyrimidin-1-yl]acetic acid (50 mg, 135.81 μmol, 9.70% yield) was obtained as white solid. $^1$H NMR (DMSO-$d_6$, 400 MHz) δ 7.62~7.58 (m, 3H), 7.35~7.33 (m, 1H), 6.94 (s, 1H), 5.16 (s, 2H), 4.51 (d, J=5.2 Hz, 2H).

Preparation of 2-(5-((3,4-dichlorobenzyl)amino)-7-oxo-6,7-dihydro-1H-pyrazolo[4,3-d]pyrimidin-1-yl)-N-(methylsulfonyl)acetamide

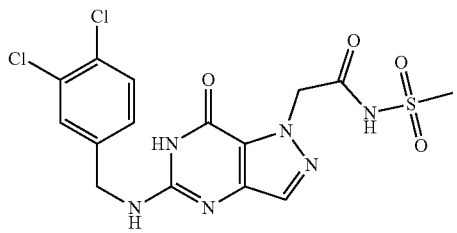 [SMILES: CS(=O)(=O)NC(=O)Cn1ncc2nc(NCc3ccc(Cl)c(Cl)c3)[nH]c(=O)c21]

To a solution of 2-[5-[(3,4-dichlorophenyl)methylamino]-7-oxo-6H-pyrazolo[4,3-d]pyrimidin-1-yl]acetic acid (40 mg, 108.64 mol, 1 eq) (Steps 1-3 in Scheme C-3) in DCM (1 mL) was added methane sulfonamide (20.67 mg, 217.29 μmol, 2 eq), DMAP (6.64 mg 54.32 μmol, 0.5 eq) and DCC (22.42 mg, 108.64 μmol, 21.98 μL, 1 eq). The mixture was stirred at 40° C. for 10 hours under $N_2$. LCMS showed the reaction was completed. The reaction mixture was concentrated under reduced pressure. The residue was purified by prep-HPLC (column: Phenomenex Luna C18 150 30 mm 5 μm; mobile phase: [water (0.05% HCl)-MeCN]; B %: 20%-45%, 12 mins). MeCN was removed under reduced pressure at 30° C. The residue was dried over lyophilization. Compound 2-(5-((3,4-dichlorobenzyl)amino)-7-oxo-6,7-dihydro-1H-pyrazolo[4,3-d]pyrimidin-1-yl)-N-(methylsulfonyl)acetamide (21.1 mg, 46.89 μmol, 43.16% yield, 98.960% purity) was obtained as white solid. H NMR (DMSO-$d_6$, 400 MHz) δ 12.25 (s, 1H), 7.66~7.58 (m, 3H), 7.35 (d, J=8.0 Hz, 1H), 7.21 (s, 1H), 5.24 (s, 2H), 4.53 (s, 2H), 3.24 (s, 3H). HPLC: 98.96% (220 nm), 98.99% (215 nm), 98.78% (254 nm). MS (ESI): mass calcd. For $C_{15}H_{14}C_{12}N_6O_4S$ 444.02, m/z found 445.0 [M+H]$^+$.

Compound 166 tert-butyl 4-[2-[2-[5-[(3,4-dichlorophenyl)methylamino]-7-oxo-6H-pyrazolo[4,3-d]pyrimidin-1-yl]ethoxy]ethyl]piperazine-1-carboxylate was prepared according to the procedures described herein for Steps 1-3 in Scheme C-3.

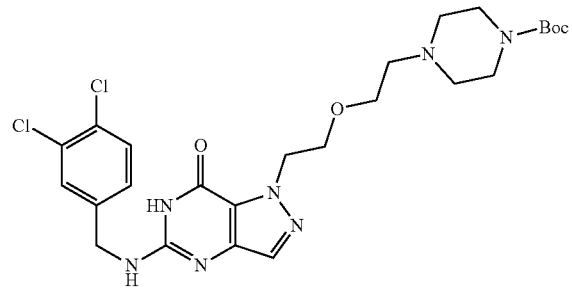 [SMILES: CC(C)(C)OC(=O)N1CCN(CCOCCn2ncc3nc(NCc4ccc(Cl)c(Cl)c4)[nH]c(=O)c32)CC1]

The procedure yielded the desired compound tert-butyl 4-[2-[2-[5-[(3,4-dichlorophenyl)methylamino]-7-oxo-6H-pyrazolo[4,3-d]pyrimidin-1-yl]ethoxy]ethyl]piperazine-1-carboxylate (20 mg, 34.80 μmol, 9.29% yield, 98.58% purity) as a white solid for delivery. $^1$H NMR (DMSO-$d_6$, 400 MHz) δ 11.00 (s, 1H), 7.58~7.56 (m, 3H), 7.33~7.31 (m, 1H), 6.56 (s, 1H), 4.56 (t, J=5.2 Hz, 2H), 4.47 (d, J=6.0 Hz, 2H), 3.75 (t, J=5.2 Hz, 2H), 3.44 (t, J=5.2 Hz, 2H), 3.20 (s, 4H), 2.35 (t, J=5.2 Hz, 2H), 2.22 (t, J=4.8 Hz, 4H), 1.38 (s, 9H). HPLC: 98.58% (220 nm), 98.17% (215 nm), 98.39% (254 nm). MS (ESI): mass calcd. For $C_{25}H_{33}C_2N_7O_4$ 565.20, m/z found 566.2 [M+H]$^+$.

Compound 167

Preparation of tert-butyl 5-((3,4-dichlorobenzyl)amino)-1-(2-(2-(piperazin-1-yl) ethoxy)ethyl)-1H-pyrazolo[4,3-d]pyrimidin-7(6H)-one dihydrochloride

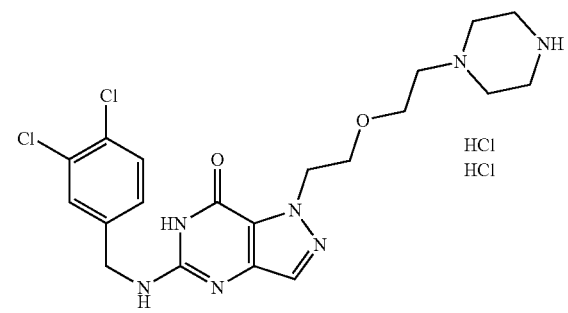 [SMILES: O=c1[nH]c(NCc2ccc(Cl)c(Cl)c2)nc2cnn(CCOCCN3CCNCC3)c12 ; Cl ; Cl]

The procedure yielded the desired compound 5-[(3,4-dichlorophenyl)methylamino]-1-[2-(2-piperazin-1-ylethoxy)ethyl]-6H-pyrazolo[4,3-d]pyrimidin-7-one (43.3 mg, 86.11 μmol, 24.39% yield, HCl) as a white solid. $^1$H NMR (DMSO-$d_6$, 400 MHz) δ 9.52 (s, 1H), 7.62~7.59 (m, 3H), 7.36~7.34 (m, 1H), 7.20 (s, 1H), 4.63 (t, J=5.2 Hz, 2H), 4.47 (d, J=5.2 Hz, 2H), 3.86 (t, J=5.2 Hz, 2H), 3.78 (t, J=3.2 Hz, 2H), 3.64~3.53 (m, 8H), 3.24~3.17 (m, 2H). HPLC: 99.61% (220 nm), 99.52% (215 nm), 100.00% (254 nm). MS (ESI): mass caled. For $C_{20}H_{27}ClN_7O_2$ 465.14, m/z found 466.1 [M+H]$^+$.

Compound 168

Preparation of 5-[(3,4-dichlorophenyl)methylamino]-1-[2-(3-hydroxypropoxy)ethyl]-6H-pyrazolo[4,3-d]pyrimidin-7-one 5-[(3,4-dichlorophenyl)methylamino]-1-[2-(3-tetrahydropyran-2-yloxy propoxy)ethyl]-6H-pyrazolo[4,3-d]pyrimidin-7-one was prepared according to the procedures described herein for Steps 1-3 in Scheme C-3.

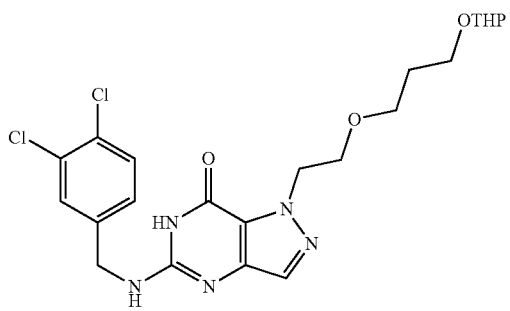

The procedure yielded the desired compound 5-[(3,4-dichlorophenyl)methylamino]-1-[2-(3-tetrahydropyran-2-yloxypropoxy)ethyl]-6H-pyrazolo[4,3-d]pyrimidin-7-one (180 mg, crude) as a white solid. $^1$H NMR (DMSO-d$_6$, 400 MHz) δ 11.02 (s, 1H), 7.59~7.56 (m, 3H), 7.32 (dd, J=8.4 Hz, 2.0 Hz, 1H), 6.74 (s, 1H), 4.55 (t, J=5.6 Hz, 2H), 4.47 (d, J=6.0 Hz, 2H), 4.41~4.40 (m, 1H), 3.75 (t, J=5.6 Hz, 2H), 3.66~3.60 (m, 2H), 3.54~3.49 (m, 2H), 3.24~3.18 (m, 2H), 1.65~1.60 (m, 2H), 1.59~1.50 (m, 2H), 1.45~1.34 (m, 4H).

Preparation of 5-[(3,4-dichlorophenyl)methylamino]-1-[2-(3-hydroxypropoxy)ethyl]-6H-pyrazolo[4,3-d]pyrimidin-7-one

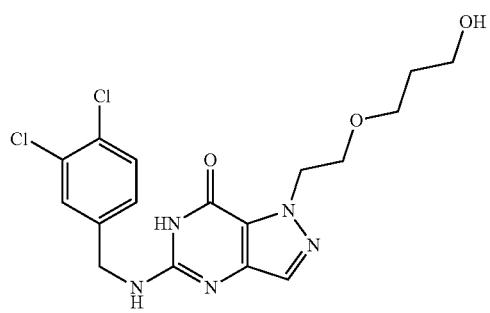 [SMILES: O=c1[nH]c(NCc2ccc(Cl)c(Cl)c2)nc2cnn(CCOCCCO)c12]

A mixture of 5-[(3,4-dichlorophenyl)methylamino]-1-[2-(3-tetrahydropyran-2-yloxypropoxy)ethyl]-6H-pyrazolo[4,3-d]pyrimidin-7-one (180 mg, 362.62 μmol, 1 eq) in MeOH (1 mL) and HCl/MeOH (5 mL, 4M) was stirred at 25° C. for 1 hours. HPLC showed the reaction was complete. The reaction mixture was concentrated under reduced pressure to remove solvent. The residue was purified by prep-HPLC (column: Phenomenex Gemini-NX C18 75 mm×30 mm 3 μm; mobile phase: [water (10 mM NH$_4$HCO$_3$)-ACN]; B %: 20%-50%, 10.5 mins). The solvent was removed under freeze drying. Compound 5-[(3,4-dichlorophenyl)methylamino]-1-[2-(3-hydroxypropoxy)ethyl]-6H-pyrazolo[4,3-d]pyrimidin-7-one (48.5 mg, 116.16 μmol, 32.03% yield, 98.74% purity) was obtained as white solid. $^1$H NMR (DMSO-d$_6$, 400 MHz) δ 11.02 (s, 1H), 7.59~7.56 (m, 3H), 7.32 (dd, J=8.4 Hz, 2.0 Hz, 1H), 6.58 (s, 1H), 4.55 (t, J=5.6 Hz, 2H), 4.47 (d, J=5.6 Hz, 2H), 4.31 (t, J=5.2 Hz, 1H), 3.73 (t, J=5.6 Hz, 2H), 3.39 (t, J=6.4 Hz, 2H), 3.36~3.34 (m, 2H), 1.57~1.51 (m, 2H). HPLC: 98.74% (220 nm), 98.25% (215 nm), 100.00% (254 nm). MS (ESI): mass calcd. For C$_{17}$H$_{19}$C$_{12}$N$_5$O$_3$ 411.09, m/z found 412.0 [M+H]$^+$.

Compound 169

Preparation of 5-[(3,4-dichlorophenyl)methylamino]-1-[3-(2-hydroxyethoxy)propyl]-6H-pyrazolo[4,3-d]pyrimidin-7-one 1-[3-(2-benzyloxyethoxy)propyl]-5-[(3,4-dichlorophenyl)methylamino]-6H-pyrazolo[4,3-d]pyrimidin-7-one was prepared according to the procedures described herein for Steps 1-3 in Scheme C-3.

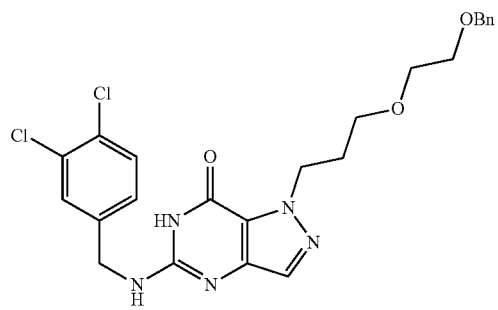 [SMILES: O=c1[nH]c(NCc2ccc(Cl)c(Cl)c2)nc2cnn(CCCOCCOCc3ccccc3)c12]

The procedure yielded the desired compound 1-[3-(2-benzyloxyethoxy)propyl]-5-[(3,4-dichlorophenyl)methylamino]-6H-pyrazolo[4,3-d]pyrimidin-7-one (180 mg, 358.29 μmol, 44.82% yield) as a white solid. $^1$H NMR (DMSO-d$_6$, 400 MHz) δ 7.62~7.54 (m, 4H), 7.33~7.29 (m, 5H), 6.63 (s, 1H), 4.49~4.46 (m, 4H), 3.53~3.49 (m, 2H), 3.39~3.36 (m, 6H), 2.01~1.98 (m, 2H).

Preparation of 5-[(3,4-dichlorophenyl)methylamino]-1-[3-(2-hydroxyethoxy)propyl]-6H-pyrazolo[4,3-d]pyrimidin-7-one

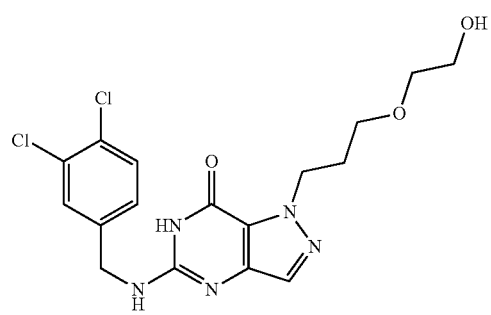 [SMILES: O=c1[nH]c(NCc2ccc(Cl)c(Cl)c2)nc2cnn(CCCOCCO)c12]

To a solution of 1-[3-(2-benzyloxyethoxy)propyl]-5-[(3,4-dichlorophenyl)methylamino]-6H-pyrazolo[4,3-d]pyrimidin-7-one (150 mg, 298.57 μmol, 1 eq) in EtOAc (10 mL) was added Pd/C (10%, 5 mg) under N$_2$ atmosphere. The suspension was degassed and purged with H$_2$ for 3 times. The mixture was stirred under H$_2$ (15 Psi.) at 25° C. for 12 hours. LC-MS showed the reaction was complete. The reaction mixture was filtered to removed the insoluble and concentrated under reduced pressure. The residue was purified by prep-HPLC (column: Phenomenex Gemini-NX C18 75 mm×30 mm 3 μm; mobile phase: [water (10 mM NH$_4$HCO$_3$)-ACN]; B %: 20%-50%, 10.5 mins). The solvent was removed under freeze drying. Compound 5-[(3,4-dichlorophenyl)methylamino]-1-[3-(2-hydroxyethoxy)propyl]-6H-pyrazolo[4,3-d]pyrimidin-7-one (6.5 mg, 15.46 μmol, 5.18% yield, 98.03% purity) was obtained as white solid. $^1$H NMR (DMSO-d$_6$, 400 MHz) δ 11.06 (s, 1H), 7.59~7.55 (m, 3H), 7.32 (dd, J=8.4 Hz, 1.6 Hz, 1H), 6.56 (s, 1H), 4.54 (t, J=5.6 Hz, 1H), 4.49~4.45 (m, 4H), 3.48~3.44 (m, 2H), 3.34~3.30 (m, 4H), 2.01~1.97 (m, 2H). HPLC: 98.03% (220 nm), 97.71% (215 nm), 96.81% (254 nm). MS (ESI): mass calcd. For C$_{17}$H$_{19}$C$_{12}$N$_5$O$_3$ 411.09, m/z found 412.2 [M+H]$^+$.

Compound 170

5-((3,4-dichlorobenzyl)amino)-1-(2-(pyridin-3-yloxy)ethyl)-1H-pyrazolo[4,3-d]pyrimidin-7(6H)-one hydrochloride was prepared according to the procedures described herein for Steps 1-3 in Scheme C-3.

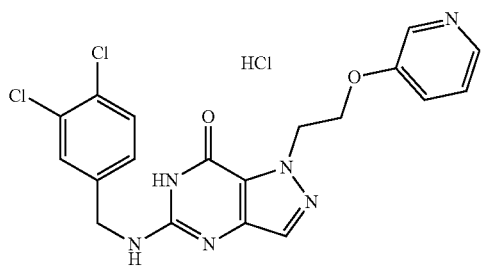 [SMILES: O=c1[nH]c(NCc2ccc(Cl)c(Cl)c2)nc2cnn(CCOc3cccnc3)c12 ; Cl]

The procedure yielded the desired compound 5-[(3,4-dichlorophenyl)methylamino]-1-[2-(3-pyridyloxy)ethyl]-6H-pyrazolo[4,3-d]pyrimidin-7-one (202 mg, 431.32 μmol, 69.90% yield, 99.873% purity, HCl) as a white solid. 59.0 mg was delivered. $^1$H NMR (DMSO-d$_6$, 400 MHz) δ 8.65 (d, J=2.4 Hz, 1H), 8.49 (d, J=5.4 Hz, 1H), 8.12 (dd, J=2.0 Hz, 8.4 Hz, 1H), 7.92 (dd, J=5.6 Hz, 8.8 Hz, 1H), 7.72 (s, 1H), 7.68 (d, J=1.6 Hz, 1H), 7.62 (d, J=8.4 Hz, 1H), 7.40 (dd, J=1.6 Hz, 8.4 Hz, 1H), 4.88 (t, J=4.8 Hz, 2H), 4.74~4.58 (m, 4H). HPLC: 99.87% (220 nm), 99.85% (215 nm), 100.00% (254 nm). MS (ESI): mass calcd. For C$_{19}$H$_{17}$C$_{13}$N$_6$O$_2$ 430.07, m/z found 431.1 [M+H]$^+$.

Compound 171

Preparation of 5-((3,4-dichlorobenzyl)amino)-1-((2-(hydroxymethyl) oxazol-4-yl)methyl)-1H-pyrazolo[4,3-d]pyrimidin-7(6H)-one Preparation of methyl 4-((5-chloro-7-methoxy-1H-pyrazolo[4,3-d]pyrimidin-1-yl)methyl) oxazole-2-carboxylate and methyl 4-((5-chloro-7-methoxy-2H-pyrazolo[4,3-d]pyrimidin-2-yl)methyl)oxazole-2-carboxylate (Step 1 in Scheme C-3)

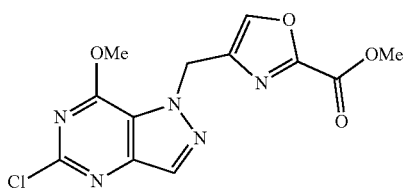

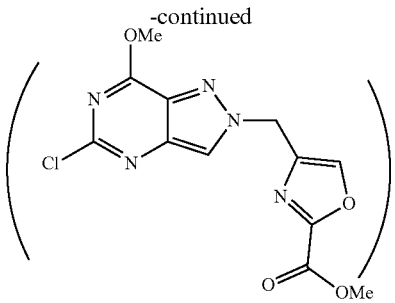

To a solution of 5-chloro-7-methoxy-1H-pyrazolo[4,3-d]pyrimidine (0.4 g 2.17 mmol, 1 eq) in THF (5 mL) was added PPh$_3$ (852.59 mg, 3.25 mmol, 1.5 eq) and methyl 4-(hydroxymethyl)oxazole-2-carboxylate (408.59 mg, 2.60 mmol, 1.2 eq). Then DIAD (657.30 mg 3.25 mmol, 632.02 μL, 1.5 eq) was added dropwise at 0° C. The mixture was stirred at 25° C. for 12 hours. TLC (PE:EtOAc=1:1) indicated the reaction was complete. The reaction mixture was quenched with H$_2$O (5 mL) and there was some white solid formed. The solid was collected after filtered. The solid was washed with EtOAc (2 mL) and concentrated under reduced pressure. A mixture of compound methyl 4-((5-chloro-7-methoxy-1H-pyrazolo[4,3-d]pyrimidin-1-yl)methyl)oxazole-2-carboxylate (0.45 g 1.39 mmol, 64.15% yield) and methyl 4-((5-chloro-7-methoxy-2H-pyrazolo[4,3-d]pyrimidin-2-yl)methyl)oxazole-2-carboxylate was obtained as white solid. H NMR (DMSO-d$_6$, 400 MHz) δ 8.40 (s, 1H), 8.29 (s, 1H), 5.71 (s, 2H), 4.16 (s, 3H), 3.84 (s, 3H). H NMR (DMSO-d$_6$, 400 MHz) δ 8.73 (s, 1H), 8.50 (s, 1H), 5.72 (s, 2H), 4.11 (s, 3H), 3.86 (s, 3H).

Preparation of 4-((5-chloro-7-methoxy-1H-pyrazolo[4,3-d]pyrimidin-1-yl)methyl)oxazol-2-yl)methanol and (4-((5-chloro-7-methoxy-2H-pyrazolo[4,3-d]pyrimidin-2-yl)methyl) oxazol-2-yl)methanol

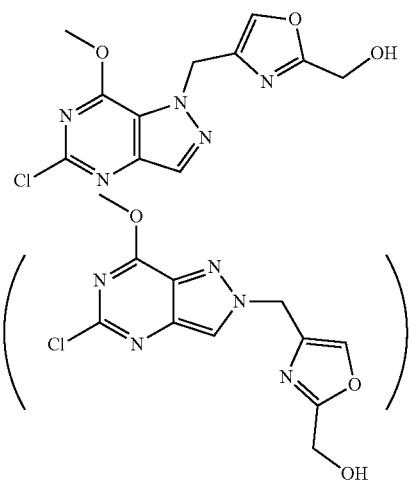

To a mixture of methyl 4-[(5-chloro-7-methoxy-pyrazolo[4,3-d]pyrimidin-1-yl)methyl]oxazole-2-carboxylate (0.36 g, 1.11 mmol, 1 eq) and methyl 4-[(5-chloro-7-methoxy-pyrazolo[4,3-d]pyrimidin-2-yl)methyl]oxazole-2-carboxylate (1.11 mmol, 1 eq) in MeOH (2 mL) was added NaBH$_4$ (167.97 mg, 4.44 mmol, 4 eq) in portions at 0° C. The mixture was stirred at 25° C. for 13 hours. Then NaBH₄ (167.97 mg, 4.44 mmol, 4 eq) was added in portions at 0° C. again. The mixture was stirred at 25° C. for 12 hours. TLC showed the reaction was complete. The reaction mixture was quenched with H₂O (10 mL) and then extracted with EtOAc (15 mL×3). The combined organic layers were washed with brine (10 mL×1), dried over Na₂SO₄, filtered and concentrated under reduced pressure. A mixture of compound (4-((5-chloro-7-methoxy-1H-pyrazolo[4,3-d]pyrimidin-1-yl)methyl)oxazol-2-yl)methanol (0.27 g, 913.15 μmol, 82.27% yield) and (4-((5-chloro-7-methoxy-2H-pyrazolo[4,3-d]pyrimidin-2-yl)methyl)oxazol-2-yl) methanol was obtained as light yellow oil. ¹H NMR (DMSO-d₆, 400 MHz) δ 8.26 (s, 1H), 8.06 (s, 1H), 5.60 (s, 2H), 5.40 (d, J=6.0 Hz, 2H), 4.17 (s, 3H). ¹H NMR (DMSO-d₆, 400 MHz) δ 8.18 (s, 1H), 8.01 (s, 1H), 5.64 (s, 2H), 5.44 (d, J=6.4 Hz, 2H), 4.11 (s, 3H).

Preparation of 5-chloro-1-((2-(hydroxymethyl)oxazol-4-yl)methyl)-1H-pyrazolo[4,3-d]pyrimidin-7(6H)-one and 5-chloro-2-((2-(hydroxymethyl)oxazol-4-yl)methyl)-2H-pyrazolo[4,3-d]pyrimidin-7(6H)-one (Step 2 in Scheme C-3)

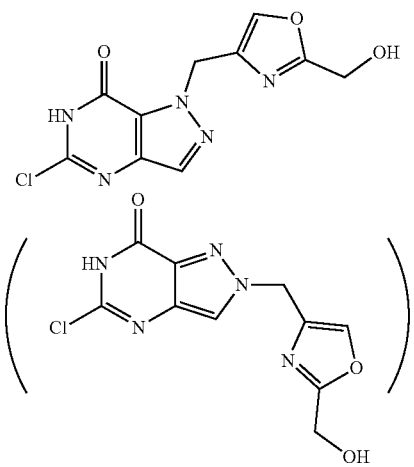

To a mixture of [4-[(5-chloro-7-methoxy-pyrazolo[4,3-d]pyrimidin-1-yl)methyl]oxazol-2-yl]methanol (0.27 g, 913.15 μmol, 1 eq) and [4-[(5-chloro-7-methoxy-pyrazolo[4,3-d]pyrimidin-2-yl)methyl]oxazol-2-yl]methanol (913.15 μmol, 1 eq) in H₂O (2 mL) and MeOH (4 mL) was added LiOH—H₂O (114.95 mg, 2.74 mmol, 3 eq). The mixture was stirred at 25° C. for 10 hours. TLC showed the reaction was complete. The reaction mixture was concentrated under reduced pressure. The aqueous was adjusted to pH=6 with HCl (3 N). Then the mixture was extracted with EtOAc (10 mL×3). The combined organic layers were washed with brine (6 mL×1), dried over Na₂SO₄, filtered and concentrated under reduced pressure. A mixture of compound 5-chloro-1-((2-(hydroxymethyl)oxazol-4-yl)methyl)-1H-pyrazolo[4,3-d]pyrimidin-7(6H)-one (0.25 g, crude) and 5-chloro-2-((2-(hydroxymethyl)oxazol-4-yl)methyl)-2H-pyrazolo[4,3-d]pyrimidin-7(6H)-one was obtained as light yellow oil. ¹H NMR (DMSO-d₆, 400 MHz) δ 7.96 (s, 1H), 7.95 (s, 1H), 5.62 (s, 2H), 4.41 (d, J=6.4 Hz, 2H). ¹H NMR (DMSO-d₆, 400 MHz) δ 8.38 (s, 1H), 8.15 (s, 1H), 5.45 (s, 2H), 4.44 (d, J=6.4 Hz, 2H).

Preparation of (5-((3,4-dichlorobenzyl)amino)-1-((2-(hydroxymethyl) oxazol-4-yl)methyl)-1H-pyrazolo[4,3-d]pyrimidin-7(6H)-one) (Step 3 in Scheme C-3)

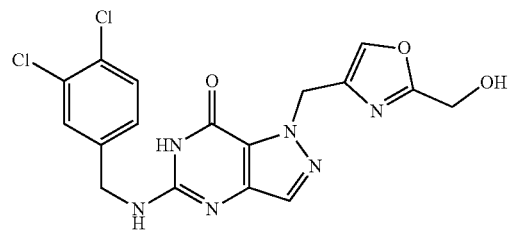 [SMILES: O=c1[nH]c(NCc2ccc(Cl)c(Cl)c2)nc2cnn(Cc3coc(CO)n3)c12]

To a mixture of 5-chloro-2-[[2-(hydroxymethyl)oxazol-4-yl]methyl]-6H-pyrazolo[4,3-d]pyrimidin-7-one (781.10 μmol, 1 eq) and 5-chloro-1-[[2-(hydroxymethyl) oxazol-4-yl]methyl]-6H-pyrazolo[4,3-d]pyrimidin-7-one (0.22 g 781.10 μmol, 1 eq) in 2-methylbutan-2-ol (5 mL) was added (3,4-dichlorophenyl)methanamine (275.01 mg, 1.56 mmol, 208.34 μL, 2 eq). The mixture was stirred at 130° C. for 10 hours. LCMS and HPLC showed the reaction was complete. The reaction mixture was concentrated under reduced pressure. The residue was purified by prep-HPLC (TFA condition column: Phenomenex Luna C18 150×30 mm 5 μm; mobile phase: [water (0.1% TFA)-ACN]; B %: 20%-35%, 12 mins). MeCN was removed under reduced pressure at 30° C. The residue was dried over lyophilization. Compound 5-[(3,4-dichlorophenyl)methylamino]-2-[[2-(hydroxymethyl)oxazol-4-yl]methyl]-6H-pyrazolo[4,3-d]pyrimidin-7-one (33.1 mg, 78.58 μmol, 10.06% yield) was obtained as white solid. Compound 5-[(3,4-dichlorophenyl)methylamino]-1-[[2-(hydroxymethyl) oxazol-4-yl]methyl]-6H-pyrazolo[4,3-d]pyrimidin-7-one (30.5 mg, 68.96 μmol, 8.83% yield, 95.236% purity) was obtained as light yellow solid and 20.1 mg was delivered. ¹H NMR (DMSO-d₆, 400 MHz) δ 7.90 (s, 1H), 7.59~7.57 (m, 3H), 7.32 (d, J=6.4 Hz, 1H), 6.70 (s, 2H), 5.51 (s, 2H), 4.47 (d, J=6.0 Hz, 2H), 4.41 (s, 2H). HPLC: 95.24% (220 nm), 94.04% (215 nm), 97.02% (254 nm). MS (ESI): mass calcd. For C₁₇H₁₄Cl₂N₆O₃ 420.05, m/z found 421.0 [M+H]⁺.

Compound 172

Preparation of 5-((3,4-dichlorobenzyl)amino)-1-((2-(1-methylpiperidin-3-yl)oxazol-4-yl)methyl)-1H-pyrazolo[4,3-d]pyrimidin-7(6H)-one hydrochloride Tert-butyl 3-[4-[[5-[(3,4-dichlorophenyl)methylamino]-7-oxo-6H-pyrazolo[4,3-d]pyrimidin-1-yl]methyl]oxazol-2-yl]piperidine-1-carboxylate was prepared according to the procedure described herein for Steps 1-3 in Scheme C-3.

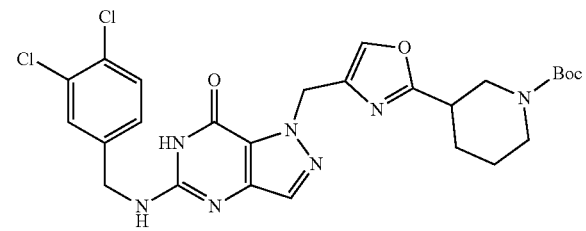 [SMILES: CC(C)(C)OC(=O)N1CCCC(c2nc(Cn3ncc4nc(NCc5ccc(Cl)c(Cl)c5)[nH]c(=O)c43)co2)C1]

The procedure yielded the desired compound tert-butyl 3-[4-[[5-[(3,4-dichlorophenyl)methylamino]-7-oxo-6H-pyrazolo[4,3-d]pyrimidin-1-yl]methyl]oxazol-2-yl]piperidine-1-carboxylate (220 mg, 382.97 μmol, 97.97% yield) as a white solid. $^1$H NMR (DMSO-$d_6$, 400 MHz) δ 7.82 (s, 1H), 7.61~7.54 (m, 4H), 7.34~7.30 (m, 1H), 6.66 (s, 1H), 5.50 (s, 2H), 4.47 (d, J=6.0 Hz, 2H), 3.90~3.72 (m, 2H), 2.91~2.85 (m, 3H), 2.03~1.99 (m, 1H), 1.70~1.66 (m, 2H), 1.46~1.40 (m, 1H), 1.35 (s, 9H).

Compound 173

Preparation of 5-((3,4-dichlorobenzyl)amino)-1-((2-(piperidin-3-yl)oxazol-4-yl)methyl)-1H-pyrazolo[4,3-d]pyrimidin-7(6H)-one hydrochloride

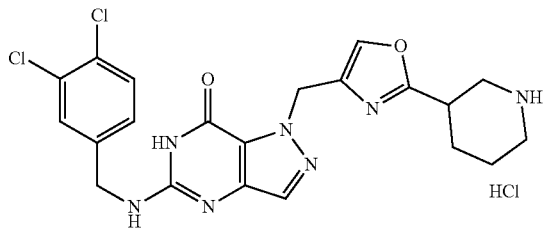 [SMILES: O=c1[nH]c(NCc2ccc(Cl)c(Cl)c2)nc2cnn(Cc3coc(C4CCCNC4)n3)c12 ; Cl]

A mixture of tert-butyl 3-[4-[[5-[(3,4-dichlorophenyl)methylamino]-7-oxo-6H-pyrazolo[4,3-d]pyrimidin-1-yl]methyl]oxazol-2-yl]piperidine-1-carboxylate (40 mg, 69.63 μmol, 1 eq) in EtOAc (1 mL) and HCl/EtOAc (4M, 3 mL) was stirred at 25° C. for 2 hours. HPLC showed the reaction was complete. The reaction mixture was concentrated under reduced pressure. The filtrate was purified by prep-HPLC (HCl condition column: Phenomenex Luna C18 150 mm×30 mm 5 μm; mobile phase: [water (0.05% HCl)-MeCN]; B %: 10%-40%, 12 mins). The solvent was removed under freeze drying. Compound 5-[(3,4-dichlorophenyl)methylamino]-1-[[2-(3-piperidyl)oxazol-4-yl]methyl]-6H-pyrazolo[4,3-d]pyrimidin-7-one (17 mg, 30.86 μmol, 44.33% yield, 92.74% purity, HCl) was obtained as white solid. $^1$H NMR (DMSO-$d_6$, 400 MHz) δ 8.93 (s, 2H), 7.92 (s, 1H), 7.62~7.59 (m, 3H), 7.35 (dd, J=8.4 Hz, 2.0 Hz, 1H), 5.52 (s, 2H), 4.53 (d, J=5.2 Hz, 2H), 3.37~3.20 (m, 3H), 3.09~3.00 (m, 1H), 2.91~2.83 (m, 1H), 2.09~2.05 (m, 1H), 1.83~1.62 (m, 3H). HPLC: 92.74% (220 nm), 88.05% (215 nm), 90.43% (254 nm). MS (ESI): mass calcd. For $C_2H_{22}Cl_3N_7O_2$ 473.11, m/z found 474.1 [M+H]$^+$.

Preparation of 5-((3,4-dichlorobenzyl)amino)-1-((2-(1-methylpiperidin-3-yl)oxazol-4-yl)methyl)-1H-pyrazolo[4,3-d]pyrimidin-7(6H)-one hydrochloride

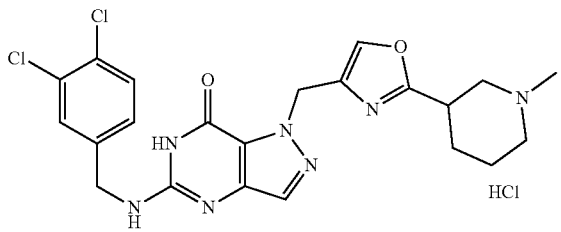 [SMILES: CN1CCCC(c2nc(Cn3ncc4nc(NCc5ccc(Cl)c(Cl)c5)[nH]c(=O)c43)co2)C1 ; Cl]

To a solution of 5-[(3,4-dichlorophenyl)methylamino]-1-[[2-(3-piperidyl)oxazol-4-yl]methyl]-6H-pyrazolo[4,3-d]pyrimidin-7-one (130 mg, 254.50 μmol, 1 eq, HCl) in MeOH (2 mL) was added formaldehyde (61.97 mg, 763.50 μmol, 56.85 μL, 37% purity, 3 eq) at 0° C. The mixture was stirred at 0° C. for 10 mins. Then AcOH (1.53 mg, 25.45 μmol, 1.46 μL, 0.1 eq) and NaBH$_3$CN (79.96 mg, 1.27 mmol, 5 eq) were added at 0° C. The mixture was stirred at 25° C. for 10 hours. LC-MS showed the reaction was complete. The reaction mixture was quenched with H$_2$O (2 mL) at 0° C., and then concentrated under reduced pressure. The aqueous was extracted with EtOAc (2 mL×3). The combined organic layers were washed with brine (2 mL), dried over Na$_2$SO$_4$, filtered and concentrated under reduced pressure. The residue was purified by prep-HPLC (HCl condition column: Phenomenex Luna C18 150 mm×30 mm 5 μm; mobile phase: [water (0.05% HCl)-MeCN]; B %: 10%-40%, 12 mins). The solvent was removed under freeze drying. Compound 5-[(3,4-dichlorophenyl)methylamino]-1-[[2-(1-methyl-3-piperidyl) oxazol-4-yl]methyl]-6H-pyrazolo[4,3-d]pyrimidin-7-one (50.6 mg, 93.65 μmol, 36.80% yield, 97.14% purity, HCl) was obtained as white solid. $^1$H NMR (DMSO-$d_6$, 400 MHz) δ 10.54 (s, 1H), 7.97 (s, 1H), 7.71 (s, 1H), 7.66~7.64 (m, 2H), 7.63 (d, J=8.0 Hz, 1H), 7.36 (dd, J=8.4 Hz, 2.0 Hz, 1H), 5.53 (s, 2H), 4.57 (d, J=5.2 Hz, 2H), 3.40~3.33 (m, 3H), 3.13~3.04 (m, 1H), 2.91~2.87 (m, 1H), 2.75 (d, J=4.8 Hz, 3H), 2.11~2.08 (m, 1H), 1.89~1.83 (m, 2H), 1.54~1.49 (m, 1H). HPLC: 97.14% (220 nm), 95.64% (215 nm), 96.18% (254 nm). MS (ESI): mass calcd. For $C_{22}H_{24}C3N_7O_2$ 487.13, m/z found 488.1 [M+H]$^+$.

Compound 174

Preparation of 5-((3,4-dichlorobenzyl)amino)-1-(2-((6-(hydroxymethyl)pyridin-3-yl)oxy)ethyl)-1H-pyrazolo[4,3-d]pyrimidin-7(6H)-one hydrochloride Preparation of methyl 5-[2-(5-chloro-7-methoxy-pyrazolo[4,3-d]pyrimidin-1-yl)ethoxy]pyridine-2-carboxylate (Step 1 in Scheme C-3)

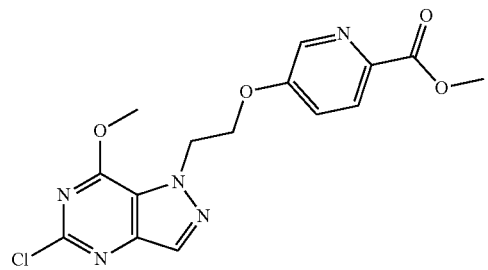 [SMILES: COC(=O)c1ccc(OCCn2ncc3nc(Cl)nc(OC)c32)cn1]

To a solution of 5-chloro-7-methoxy-1H-pyrazolo[4,3-d]pyrimidine (400 mg, 2.17 mmol, 1 eq), methyl 5-(2-hydroxyethoxy)pyridine-2-carboxylate (555.51 mg, 2.82 mmol, 1.3 eq) and PPh$_3$ (852.59 mg, 3.25 mmol, 1.5 eq) in THF (5 mL) was added DIAD (657.30 mg, 3.25 mmol, 632.02 μL, 1.5 eq) dropwise at 0° C. The mixture was stirred at 25° C. for 5 hours. TLC showed the reaction was complete. The reaction mixture was quenched with H$_2$O (2 mL) and extracted with EtOAc (2 mL×3). The combined organic layers were washed with brine (2 mL), dried over Na$_2$SO$_4$, filtered and concentrated under reduced pressure. The residue was purified by flash silica gel chromatography (Biotage®; 12 g SepaFlash® Silica Flash Column, Eluent of 0~100% Ethyl acetate/Methanol at 45 mL/min). The eluent was removed under reduced pressure. Compound methyl 5-[2-(5-chloro-7-methoxy-pyrazolo[4,3-d]pyrimidin-1-yl)ethoxy]pyridine-2-carboxylate (580 mg, 1.59 mmol, 73.58% yield) was obtained as white solid. Compound methyl 5-[2-(5-chloro-7-methoxy-pyrazolo[4,3-d]pyrimidin-2-yl)ethoxy]pyridine-2-carboxylate (280 mg, 769.75 µmol, 35.52% yield) was obtained as white solid. H NMR (DMSO-$d_6$, 400 MHz) δ 8.30 (s, 1H), 8.25 (d, J=2.8 Hz, 1H), 7.98 (d, J=8.8 Hz, 1H), 7.46 (dd, J=8.8 Hz, 2.8 Hz, 1H), 4.93 (t, J=5.2 Hz, 2H), 4.63 (t, J=5.2 Hz, 2H), 4.07 (s, 3H), 3.83 (s, 3H).

Preparation of 5-[2-(5-chloro-7-oxo-6H-pyrazolo[4,3-d]pyrimidin-1-yl)ethoxy]pyridine-2-carboxylic Acid (Step 2 in Scheme C-3)

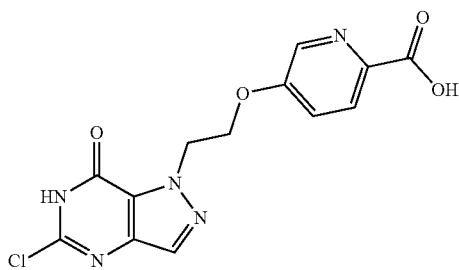 [SMILES: O=C(O)c1ccc(OCCn2ncc3nc(Cl)[nH]c(=O)c32)cn1]

To a solution of methyl 5-[2-(5-chloro-7-methoxy-pyrazolo[4,3-d]pyrimidin-1-yl)ethoxy]pyridine-2-carboxylate (100 mg, 274.91 mol, 1 eq) in MeOH (1 mL) and $H_2O$ (2 mL) was added LiOH—$H_2O$ (34.61 mg, 824.73 µmol, 3 eq). The mixture was stirred at 25° C. for 2 hours. TLC showed the reaction was complete. The reaction mixture was concentrated under reduced pressure. The aqueous was made pH=6 with 3N HCl and there was some white solid formed. The solid was collected after filtered and concentrated under reduced pressure. Compound 5-[2-(5-chloro-7-oxo-6H-pyrazolo[4,3-d]pyrimidin-1-yl)ethoxy]pyridine-2-carboxylic acid (95 mg, crude) was obtained as white solid. $^1$H NMR (DMSO-$d_6$, 400 MHz) δ 8.25 (d, J=2.8 Hz, 1H), 8.00~7.96 (m, 2H), 7.47 (dd, J=8.8 Hz, 2.8 Hz, 1H), 4.94 (t, J=5.2 Hz, 2H), 4.61 (t, J=5.2 Hz, 2H).

Compound 175

Preparation of 5-(2-(5-((3,4-dichlorobenzyl)amino)-7-oxo-6,7-dihydro-1H-pyrazolo[4,3-d]pyrimidin-1-yl)ethoxy)picolinic Acid Hydrochloride (Step 3 in Scheme C-3)

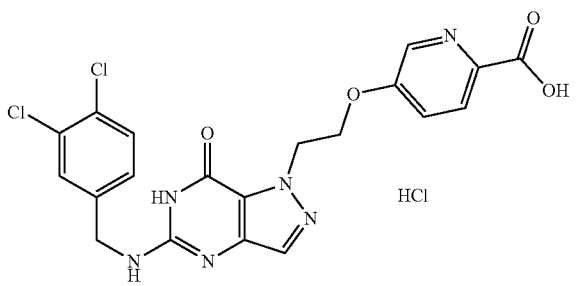 [SMILES: O=C(O)c1ccc(OCCn2ncc3nc(NCc4ccc(Cl)c(Cl)c4)[nH]c(=O)c32)cn1 ; Cl]

A mixture of 5-[2-(5-chloro-7-oxo-6H-pyrazolo[4,3-d]pyrimidin-1-yl)ethoxy]pyridine-2-carboxylic acid (90 mg, 268.09 µmol, 1 eq) and (3,4-dichlorophenyl)methanamine (94.39 mg, 536.19 µmol, 71.51 µL, 2 eq) in 2-methyl-2-butanol (2 mL) was stirred at 140° C. for 4 hours. LC-MS showed the reaction was complete. The reaction mixture was concentrated under reduced pressure. The residue was purified by prep-HPLC (column: Phenomenex Luna C18 150 mm×30 mm 5 µm; mobile phase: [water (0.05% HCl)-MeCN]; B %: 15%-45%, 12 mins). The solvent was removed under freeze drying. Compound 5-[2-[5-[(3,4-dichlorophenyl)methylamino]-7-oxo-6H-pyrazolo[4,3-d]pyrimidin-1-yl]ethoxy]pyridine-2-carboxylic acid (45.1 mg, 86.74 µmol, 32.35% yield, 98.42% purity, HCl) was obtained as white solid. $^1$H NMR (DMSO-$d_6$, 400 MHz) δ 8.26 (d, J=2.4 Hz, 1H), 7.98 (d, J=8.8 Hz, 1H), 7.65 (s, 1H), 7.62~7.59 (m, 2H), 7.48 (dd, J=8.4 Hz, 2.8 Hz, 1H), 7.36 (s, 1H), 7.35 (d, J=8.0 Hz, 1H), 4.85 (t, J=5.2 Hz, 2H), 4.58 (t, J=5.2 Hz, 2H), 4.54 (d, J=4.4 Hz, 2H). HPLC: 98.42% (220 nm), 97.74% (215 nm), 99.67% (254 nm). MS (ESI): mass calcd. For $C_{20}H_{17}C3N_6O_4$ 474.06, m/z found 475.0 $[M+H]^+$.

Preparation of [5-[2-(5-chloro-7-methoxy-pyrazolo[4,3-d]pyrimidin-1-yl)ethoxy]-2-pyridyl]methanol

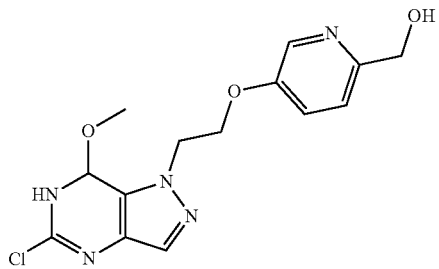 [SMILES: COC1NC(Cl)=Nc2cnn(CCOc3ccc(CO)nc3)c21]

To a solution of methyl 5-[2-(5-chloro-7-methoxy-pyrazolo[4,3-d]pyrimidin-1-yl)ethoxy]pyridine-2-carboxylate (150 mg, 412.37 µmol, 1 eq) in THF (1 mL) was added DIBAL-H (1 M, 2.06 mL, 5 eq) dropwise at 0° C. Then the mixture was stirred at 25° C. for 6 hours. TLC showed the reaction was complete. The reaction mixture was quenched with $H_2O$ (2 mL) and extracted with EtOAc (2 mL×3). The combined organic layers were washed with brine (2 mL), dried over $Na_2SO_4$, filtered and concentrated under reduced pressure. Compound [5-[2-(5-chloro-7-methoxy-pyrazolo[4,3-d]pyrimidin-1-yl)ethoxy]-2-pyridyl]methanol (130 mg, 387.20 µmol, 93.90% yield) was obtained as white solid. $^1$H NMR (DMSO-$d_6$, 400 MHz) δ 8.30 (s, 1H), 8.05~8.04 (m, 1H), 7.32~7.31 (m, 2H), 5.27 (t, J=5.6 Hz, 1H), 4.89 (t, J=5.2 Hz, 2H), 4.51 (t, J=5.2 Hz, 2H), 4.45 (d, J=6.0 Hz, 2H), 4.07 (s, 3H).

Preparation of 5-chloro-1-[2-[[6-(hydroxymethyl)-3-pyridyl]oxy]ethyl]-6H-pyrazolo[4,3-d]pyrimidin-7-one (Step 2 in Scheme C-3)

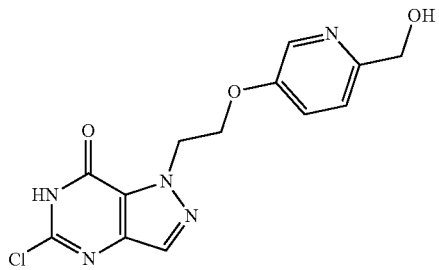 [SMILES: O=c1[nH]c(Cl)nc2cnn(CCOc3ccc(CO)nc3)c12]

To a solution of [5-[2-(5-chloro-7-methoxy-pyrazolo[4,3-d]pyrimidin-1-yl)ethoxy]-2-pyridyl]methanol (130 mg, 387.20 µmol, 1 eq) in MeOH (1 mL) and H$_2$O (1 mL) was added LiOH—H$_2$O (48.74 mg, 1.16 mmol, 3 eq). The mixture was stirred at 25° C. for 2 hours. LC-MS showed the reaction was complete. The reaction mixture was concentrated under reduced pressure. The aqueous was made pH=6 with 3N HCl and extracted with EtOAc (3 mL×3). The combined organic layers were washed with brine (3 mL), dried over Na$_2$SO$_4$, filtered and concentrated under reduced pressure. Compound 5-chloro-1-[2-[[6-(hydroxymethyl)-3-pyridyl]oxy]ethyl]-6H-pyrazolo[4,3-d]pyrimidin-7-one (100 mg, 310.83 µmol, 80.28% yield) was obtained as white solid. $^1$H NMR (DMSO-d$_6$, 400 MHz) δ 8.08~8.07 (m, 1H), 8.00 (s, 1H), 7.32 (d, J=2.0 Hz, 2H), 5.27 (s, 1H), 4.90 (t, J=5.2 Hz, 2H), 4.49 (t, J=5.2 Hz, 2H), 4.46 (d, J=4.0 Hz, 2H).

5-((3,4-dichlorobenzyl)amino)-1-(2-((6-(hydroxymethyl)pyridin-3-yl)oxy)ethyl)-1H-pyrazolo[4,3-d]pyrimidin-7(6H)-one hydrochloride was prepared according to the procedure described herein for Step 3 in Scheme C-3.

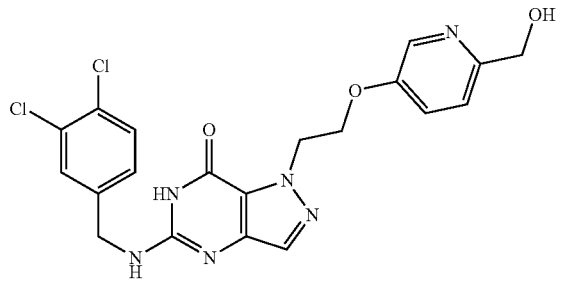 [SMILES: O=c1[nH]c(NCc2ccc(Cl)c(Cl)c2)nc2cnn(CCOc3ccc(CO)nc3)c12]

The procedure yielded the desired compound 5-[(3,4-dichlorophenyl)methylamino]-1-[2-[[6-(hydroxymethyl)-3-pyridyl]oxy]ethyl]-6H-pyrazolo[4,3-d]pyrimidin-7-one (82.6 mg, 162.01 µmol, 52.12% yield, 97.63% purity, HCl) as a white solid. $^1$H NMR (DMSO-d$_6$, 400 MHz) δ 8.40 (d, J=2.8 Hz, 1H), 8.02 (dd, J=8.0 Hz, 4.0 Hz, 1H), 7.80 (d, J=8.0 Hz, 1H), 7.66~7.59 (m, 4H), 7.35 (dd, J=8.0 Hz, 4.0 Hz, 1H), 4.86 (t, J=4.8 Hz, 2H), 4.73 (s, 2H), 4.63 (t, J=4.8 Hz, 2H), 4.55 (d, J=5.2 Hz, 2H). HPLC: 97.63% (220 nm), 96.85% (215 nm), 97.96% (254 nm). MS (ESI): mass calcd. For C$_{20}$H$_{19}$Cl$_3$N$_6$O$_3$ 460.08, m/z found 461.1 [M+H]$^+$.

Compound 176

5-((3,4-dichlorobenzyl)amino)-1-((1-(2-methoxyethyl)-5-oxopyrrolidin-3-yl)methyl)-1H-pyrazolo[4,3-d]pyrimidin-7(6H)-one was prepared according to the procedure described herein for Steps 1-3 in Scheme C-3.

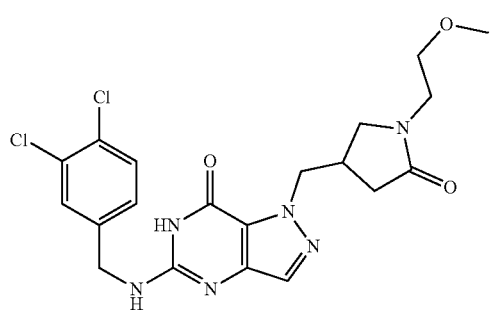 [SMILES: COCCN1CC(Cn2ncc3nc(NCc4ccc(Cl)c(Cl)c4)[nH]c(=O)c32)CC1=O]

The procedure yielded the desired compound 5-((3,4-dichlorobenzyl)amino)-1-((1-(2-methoxyethyl)-5-oxopyrrolidin-3-yl)methyl)-1H-pyrazolo[4,3-d]pyrimidin-7(6H)-one (306 mg, 642.75 µmol, 52.34% yield, 97.743% purity) as a white solid. $^1$H NMR (DMSO-d$_6$, 400 MHz) δ 7.62~7.59 (m, 3H), 7.34 (d, J=8.4 Hz, 1H), 6.70 (s, 1H), 4.50~4.46 (m, 4H), 3.39~3.36 (m, 3H), 3.30~3.29 (m, 2H), 3.28~3.19 (m, 4H), 2.75 (s, 1H), 2.34 (t, J=7.6 Hz, 1H), 2.11 (dd, J=6.0 Hz, 16.8 Hz, 1H). HPLC: 97.74% (220 nm), 97.24% (215 nm), 99.81% (254 nm). MS (ESI): mass calcd. For C$_{20}$H$_{22}$Cl$_2$N$_6$O$_3$ 464.11, m/z found 465.1 [M+H]$^+$.

Compound 177

Preparation of 5-((3,4-dichlorobenzyl)amino)-1-((1-(2-hydroxyethyl)-5-oxopyrrolidin-3-yl)methyl)-1H-pyrazolo[4,3-d]pyrimidin-7(6H)-one

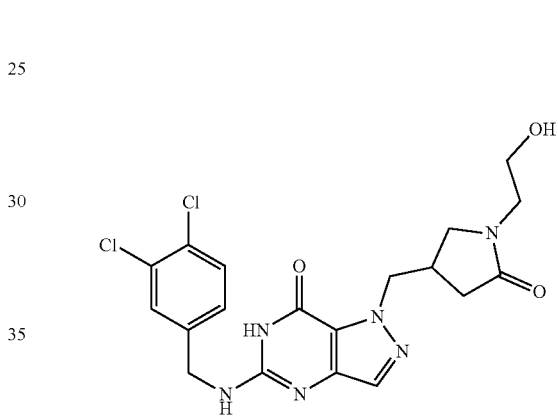

To a solution of 5-[(3,4-dichlorophenyl)methylamino]-1-[[1-(2-methoxyethyl)-5-oxo-pyrrolidin-3-yl]methyl]-6H-pyrazolo[4,3-d]pyrimidin-7-one (50 mg, 107.45 µmol, 1 eq) in DCM (2 mL) was added BBr$_3$ (80.76 mg, 322.35 µmol, 31.06 µL, 3 eq) dropwise at 0° C. The mixture was stirred at 0° C. for an hour. LCMS and HPLC showed the reaction was completed. Ice water (2 mL) was added into the mixture. The mixture was extracted with EtOAc (5 mL×3). The combined organic layers were dried over Na$_2$SO$_4$, filtered and concentrated under reduced pressure. The residue was purified by prep-HPLC (column: Phenomenex Luna C18 150 mm×30 mm 5 µm; mobile phase: [water (0.05% HCl)-MeCN]; B %: 20%-50%, 12 mins). The mixture was dryed under freeze-drying to give 5-((3,4-dichlorobenzyl)amino)-1-((1-(2-hydroxyethyl)-5-oxopyrrolidin-3-yl)methyl)-1H-pyrazolo[4,3-d]pyrimidin-7(6H)-one (13.2 mg, 29.25 µmol, 27.22% yield) as white solid. $^1$H NMR (DMSO-d$_6$, 400 MHz) δ 7.63~7.53 (m, 3H), 7.32 (d, J=10.0 Hz, 1H), 7.07~6.90 (m, 1H), 4.52~4.40 (m, 4H), 3.23~3.21 (m, 1H), 3.21~3.17 (m, 2H), 3.17~3.07 (m, 2H), 3.03~2.90 (m, 1H), 2.82 (d, J=6.4 Hz, 1H), 2.30~2.24 (m, 1H), 2.08 (dd, J=6.0 Hz, 16.8 Hz, 1H). HPLC: 97.85% (220 nm), 97.63% (215 nm), 100.00% (254 nm). MS (ESI): mass calcd. For C$_{19}$H$_{20}$Cl$_2$N$_6$O$_3$, 450.10 m/z found 451.1 [M+H]$^+$.

Compound 178

5-((3,4-Dichlorobenzyl)amino)-1-(2-(oxetan-3-yloxy)ethyl)-1H-pyrazolo[4,3-d]pyrimidin-7(6H)-one was prepared according to the procedure described herein for Steps 1-3 in Scheme C-3.

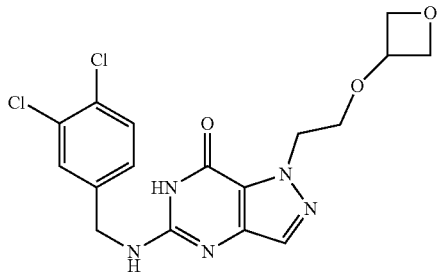 [SMILES: O=c1[nH]c(NCc2ccc(Cl)c(Cl)c2)nc2cnn(CCOC3COC3)c12]

The procedure yielded the desired compound 5-((3,4-dichlorobenzyl)amino)-1-(2-(oxetan-3-yloxy)ethyl)-1H-pyrazolo[4,3-d]pyrimidin-7(6H)-one (83.6 mg, 192.47 µmol, 52.10% yield, 94.451% purity) as a white solid. H NMR (DMSO-d$_6$, 400 MHz) δ 7.67~7.60 (m, 3H), 7.37 (dd, J=2.0 Hz, J=8.4 Hz, 1H), 4.60~4.54 (m, 6H), 4.54~4.49 (m, 1H), 4.28~4.25 (m, 2H), 3.76 (t, J=5.6 Hz, 2H). HPLC: 94.45% (220 nm), 94.06% (215 nm), 95.57% (254 nm). MS (ESI): mass calcd. For $C_{17}H_7Cl_2N_5O_3$ 409.07, m/z found 410.0 [M+H]$^+$.

Compound 179

5-((3,4-dichlorobenzyl)amino)-1-(3-(3-hydroxycyclobutoxy)propyl)-1H-pyrazolo[4,3-d]pyrimidin-7(6H)-one was prepared according to the procedure described herein for Steps 1-3 in Scheme C-3.

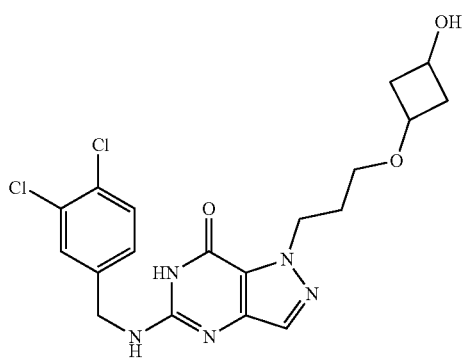 [SMILES: O=c1[nH]c(NCc2ccc(Cl)c(Cl)c2)nc2cnn(CCCOC3CC(O)C3)c12]

The procedure yielded the desired compound 5-[(3,4-dichlorophenyl)methylamino]-1-[3-(3-hydroxycyclobutoxy)propyl]-6H-pyrazolo[4,3-d]pyrimidin-7-one (88.5 mg, 200.74 µmol, 37.48% yield, 99.42% purity) as a white solid. $^1$H NMR (DMSO-d$_6$, 400 MHz) δ 11.05 (s, 1H), 7.59~7.57 (m, 2H), 7.54 (s, 1H), 7.32 (dd, J=8.0 Hz, 2.0 Hz, 1H), 6.61 (s, 1H), 4.97 (d, J=6.8 Hz, 1H), 4.48~4.43 (m, 4H), 3.69~3.60 (m, 1H), 3.42~3.37 (m, 1H), 3.21 (t, J=6.0 Hz, 2H), 2.48~2.43 (m, 2H), 1.99~1.93 (m, 2H), 1.70~1.62 (m, 2H). HPLC: 99.42% (220 nm), 99.21% (215 nm), 100.00% (254 nm). MS (ESI): mass calcd. For $C_{19}H_{21}Cl_2N_5O_3$ 437.10, m/z found 438.1 [M+H]$^+$.

Compound 180

5-((3,4-Dichlorobenzyl)amino)-1-(1-(pyridin-4-yl)pyrrolidin-3-yl)-1H-pyrazolo[4,3-d]pyrimidin-7(6H)-one dihydrochloride was prepared according to the procedures described herein for Steps 1-3 in Scheme C-3.

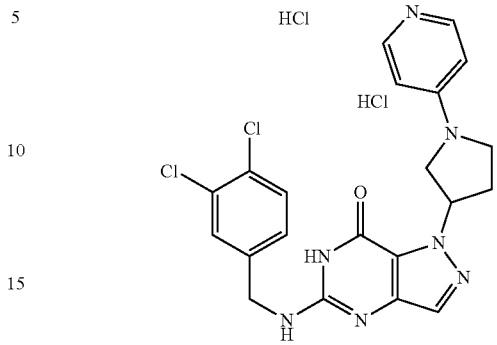

The procedure yielded the desired compound 5-((3,4-dichlorobenzyl)amino)-1-(1-(pyridin-4-yl)pyrrolidin-3-yl)-1H-pyrazolo[4,3-d]pyrimidin-7(6H)-one dihydrochloride (12.5 mg, 27.30 µmol, 18.91% yield, 99.647% purity) as a white solid. H NMR (DMSO-d$_6$, 400 MHz) δ 8.30~8.19 (m, 2H), 7.68~7.55 (m, 3H), 7.33 (d, J=8.4 Hz, 1H), 7.20 (s, 1H), 6.90 (dd, J=6.4 Hz, J=14.8 Hz, 2H), 5.85 (s, 1H), 4.51 (d, J=5.6 Hz, 2H), 4.07~3.97 (m, 1H), 3.96~3.89 (m, 1H), 3.72 (d, J=6.8 Hz, 2H), 2.62~2.55 (m, 2H). HPLC: 99.65% (220 nm), 99.59% (215 nm), 99.68% (254 nm). MS (ESI): mass calcd. For $C_{21}H_{21}Cl_4N_7O$, 455.10 m/z found 456.1 [M+H]$^+$.

Compound 181

5-((3,4-Dichlorobenzyl)amino)-1-(2-(pyridin-3-ylmethoxy)ethyl)-1H-pyrazolo[4,3-d]pyrimidin-7(6H)-one hydrochloride was prepared according to the procedures described herein for Steps 1-3 in Scheme C-3.

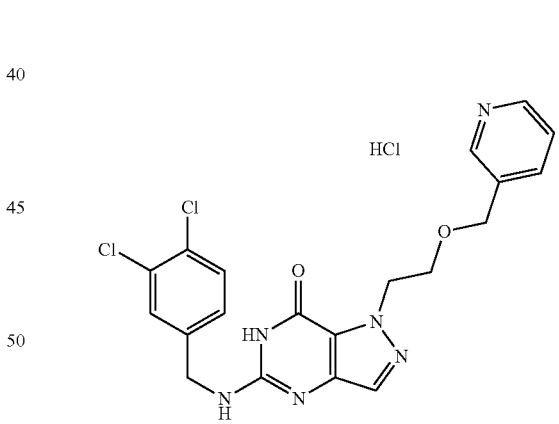

The procedure yielded the desired compound 5-[(3,4-dichlorophenyl)methylamino]-1-[2-(3-pyridylmethoxy)ethyl]-6H-pyrazolo[4,3-d]pyrimidin-7-one (183.7 mg, 378.49 µmol, 55.10% yield, 99.26% purity, HCl) as a white solid. $^1$H NMR (DMSO-d$_6$, 400 MHz) δ 8.83 (d, J=5.6 Hz, 1H), 8.73 (s, 1H), 8.37 (d, J=8.0 Hz, 1H), 8.31 (s, 1H), 8.01~7.98 (m, 1H), 7.69 (s, 1H), 7.68 (d, J=1.6 Hz, 1H), 7.62 (d, J=8.0 Hz, 1H), 7.39 (dd, J=8.0 Hz, 2.0 Hz, 1H), 4.70~4.64 (m, 6H), 3.94 (t, J=5.2 Hz, 2H). HPLC: 99.26% (220 nm), 99.19% (215 nm), 99.61% (254 nm). MS (ESI): mass calcd. For $C_{20}H_{19}Cl_3N_6O_2$ 444.09, m/z found 445.1 [M+H]$^+$.

Compound 182

Preparation of 5-((3,4-dichlorobenzyl)amino)-1-((1-(pyridin-2-yl)pyrrolidin-2-yl)methyl)-1H-pyrazolo[4,3-d]pyrimidin-7(6H)-one dihydrochloride tert-butyl 2-((5-((3,4-dichlorobenzyl)amino)-7-oxo-6,7-dihydro-1H-pyrazolo[4,3-d]pyrimidin-1-yl)methyl)pyrrolidine-1-carboxylate was prepared according to the procedure described herein for Steps 1-3 in Scheme C-3.

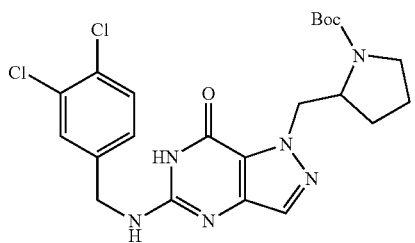 [SMILES: CC(C)(C)OC(=O)N1CCCC1Cn1ncc2nc(NCc3ccc(Cl)c(Cl)c3)[nH]c(=O)c21]

The procedure yielded the desired compound tert-butyl 2-[[5-[(3,4-dichlorophenyl)methylamino]-7-oxo-6H-pyrazolo[4,3-d]pyrimidin-1-yl]methyl]pyrrolidine-1-carboxylate (0.13 g, 263.49 μmol, 23.31% yield) as a white solid. $^1$H NMR (DMSO-d$_6$, 400 MHz) δ 7.66~7.61 (m, 3H), 7.37 (s, 1H), 4.58 (s, 2H), 4.45~4.43 (m, 2H), 4.17~4.15 (m, 1H), 3.35~3.20 (m, 2H), 1.76~1.73 (m, 4H), 1.23 (m, 9H).

Preparation of 5-((3,4-dichlorobenzyl)amino)-1-(pyrrolidin-2-ylmethyl)-1H-pyrazolo[4,3-d]pyrimidin-7(6H)-one hydrochloride

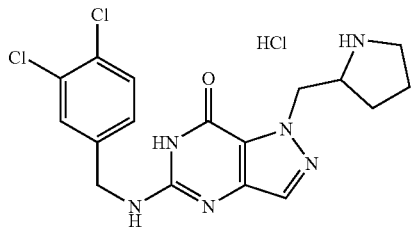 [SMILES: O=c1[nH]c(NCc2ccc(Cl)c(Cl)c2)nc2cnn(CC3CCCN3)c12 ; Cl]

To a solution of tert-butyl 2-[[5-[(3,4-dichlorophenyl)methylamino]-7-oxo-6H-pyrazolo[4,3-d]pyrimidin-1-yl]methyl]pyrrolidine-1-carboxylate (0.13 g, 263.49 mol, 1 eq) in EtOAc (1 mL) was added HCl/EtOAc (2 mL, 4 N). The mixture was stirred at 25° C. for 12 hours. LCMS showed the reaction was completed. The reaction mixture was concentrated under reduced pressure. Compound 5-[(3,4-dichlorophenyl)methylamino]-1-(pyrrolidin-2-ylmethyl)-6H-pyrazolo[4,3-d]pyrimidin-7-one (0.1 g, crude) was obtained as white solid. $^1$H NMR (DMSO-d$_6$, 400 MHz) δ 9.35 (s, 1H), 8.89 (s, 1H), 7.72 (s, 1H), 7.62~7.60 (m, 3H), 7.37~7.34 (m, 1H), 4.83~4.78 (m, 1H), 4.73~4.59 (m, 1H), 4.55 (s, 2H), 3.94~3.90 (m, 1H), 3.31~3.14 (m, 2H), 1.99~1.86 (m, 4H).

Preparation of 5-((3,4-dichlorobenzyl)amino)-1-((1-(pyridin-2-yl)pyrrolidin-2-yl)methyl)-1H-pyrazolo[4,3-d]pyrimidin-7(6H)-one dihydrochloride

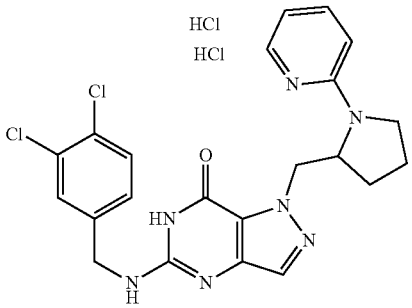 [SMILES: O=c1[nH]c(NCc2ccc(Cl)c(Cl)c2)nc2cnn(CC3CCCN3c3ccccn3)c12 ; Cl ; Cl]

To a solution of 5-[(3,4-dichlorophenyl)methylamino]-1-(pyrrolidin-2-ylmethyl)-6H-pyrazolo[4,3-d]pyrimidin-7-one (0.1 g 232.70 mol, 1 eq, HCl) in DMF (1 mL) was added 2-fluoropyridine (45.19 mg, 465.41 μmol, 39.99 μL, 2 eq) and K$_2$CO$_3$ (96.49 mg, 698.11 μmol, 3 eq). The mixture was stirred at 100° C. for 12 hours. LCMS and HPLC showed the reaction was completed. The reaction mixture was concentrated under reduced pressure. The residue was purified by prep-HPLC (HCl condition column: Phenomenex Luna C18 150×30 mm 5 μm; mobile phase: [water (0.05% HCl)-ACN]; B %: 15%-40%, 12 min). MeCN was removed under reduced pressure at 30° C. The residue was dried over lyophilization. Compound 5-[(3,4-dichlorophenyl)methylamino]-1-[[1-(2-pyridyl)pyrrolidin-2-yl]methyl]-6H-pyrazolo[4,3-d]pyrimidin-7-one (37.0 mg, 72.55 μmol, 31.18% yield, 99.374% purity, HCl) was obtained as white solid. $^1$H NMR (DMSO-d$_6$, 400 MHz) δ 8.07 (s, 3H), 7.69~7.63 (m, 3H), 7.37 (s, 1H), 7.23 (s, 1H), 6.93 (s, 1H), 4.59 (s, 5H), 3.64 (s, 1H), 3.43 (s, 1H), 1.97 (s, 3H), 1.76 (s, 1H). HPLC: 99.37% (220 nm), 99.41% (215 nm), 99.66% (254 nm). MS (ESI): mass calcd. For $C_{22}H_{23}C_{14}N_7O$ 469.12, m/z found 470.1 [M+H]$^+$.

Compound 183

Preparation of 5-((3,4-dichlorobenzyl)amino)-1-(2-((1-(dimethylamino)-3-methoxypropan-2-yl)oxy)ethyl)-1H-pyrazolo[4,3-d]pyrimidin-7(6H)-one hydrochloride tert-Butyl(2-(2-(5-((3,4-dichlorobenzyl)amino)-7-oxo-6,7-dihydro-1H-pyrazolo[4,3-d]pyrimidin-1-yl)ethoxy)-3-methoxypropyl)(methyl)carbamate was prepared according to the procedure described herein for Steps 1-3 in Scheme C-3.

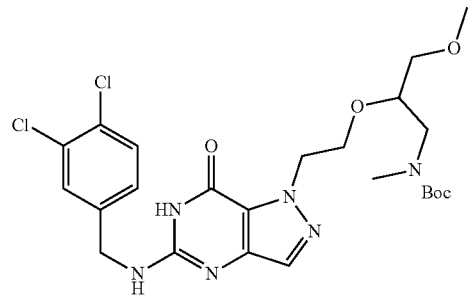 [SMILES: CNCC(COC)OCCn1ncc2nc(NCc3ccc(Cl)c(Cl)c3)[nH]c(=O)c21 ; "Boc"]

The procedure yielded the desired compound tert-butyl (2-(2-(5-((3,4-dichlorobenzyl)amino)-7-oxo-6,7-dihydro-1H-pyrazolo[4,3-d]pyrimidin-1-yl)ethoxy)-3-methoxypropyl)(methyl)carbamate (0.13 g, 234.04 μmol, 54.07% yield) as a white solid. $^1$H NMR (DMSO-$d_6$, 400 MHz) δ 7.60~7.58 (m, 3H), 7.34 (d, J 8.0 Hz, 1H), 4.55~4.52 (m, 4H), 3.90~3.77 (m, 1H), 3.56~3.51 (m, 1H), 3.25~3.22 (m, 3H), 3.21 (s, 3H), 3.18~3.00 (m, 2H), 2.64 (s, 3H), 1.34 (s, 9H).

Compound 184

Preparation of 5-((3,4-dichlorobenzyl)amino)-1-(pyrrolidin-2-ylmethyl)-1H-pyrazolo[4,3-d]pyrimidin-7(6H)-one hydrochloride

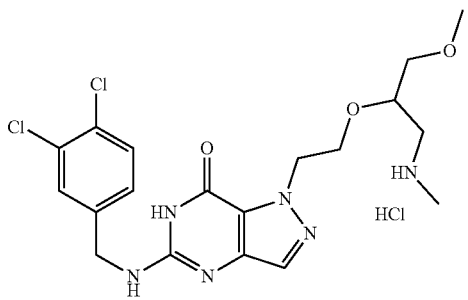 [SMILES: CNCC(COC)OCCn1ncc2nc(NCc3ccc(Cl)c(Cl)c3)[nH]c(=O)c21 ; Cl]

A solution of tert-butyl N-[2-[2-[5-[(3,4-dichlorophenyl)methylamino]-7-oxo-6H-pyrazolo[4,3-d]pyrimidin-1-yl]ethoxy]-3-methoxy-propyl]-N-methyl-carbamate (0.13 g, 234.04 μmol, 1 eq) in HCl/EtOAc (2 mL) was stirred at 25° C. for 10 hours. LCMS showed the reaction was complete. The reaction mixture was filtered under reduced pressure. There was some light yellow solid formed. The solid was collected after filtered. Compound 5-((3,4-dichlorobenzyl)amino)-1-(2-((1-methoxy-3-(methylamino)propan-2-yl)oxy)ethyl)-1H-pyrazolo[4,3-d]pyrimidin-7(6H)-one (28.5 mg, 55.75 μmol, 23.82% yield, 96.203% purity, HCl) was obtained as light yellow solid for delivery. Compound 5-((3,4-dichlorobenzyl)amino)-1-(2-((1-methoxy-3-(methylamino) propan-2-yl)oxy)ethyl)-1H-pyrazolo[4,3-d]pyrimidin-7(6H)-one (80 mg HCl) was obtained as light yellow solid. $^1$H NMR (DMSO-$d_6$, 400 MHz) δ 8.68 (s, 1H), 8.45 (s, 1H), 7.63~7.59 (m, 3H), 7.40 (s, 1H), 7.34 (d, J=8.0 Hz, 1H), 4.67~4.59 (m, 2H), 4.53 (d, J=5.6 Hz, 2H), 3.96~3.92 (m, 2H), 3.80 (s, 1H), 3.32 (d, J=4.4 Hz, 2H), 3.19 (s, 3H), 3.04~3.02 (m, 1H), 3.93~3.90 (m, 1H), 2.55 (s, 3H). HPLC: 96.20% (220 nm), 96.13% (215 nm), 95.56% (254 nm). MS (ESI): mass calcd. For $C_{19}H_{25}Cl_3N_6O_3$ 454.13, m/z found 455.1 [M+H]$^+$.

Preparation of 5-((3,4-dichlorobenzyl)amino)-1-(2-((1-(dimethylamino)-3-methoxypropan-2-yl)oxy)ethyl)-1H-pyrazolo[4,3-d]pyrimidin-7(6H)-one hydrochloride

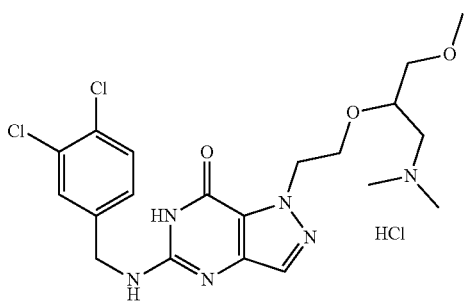 [SMILES: COCC(CN(C)C)OCCn1ncc2nc(NCc3ccc(Cl)c(Cl)c3)[nH]c(=O)c21 ; Cl]

To a solution of 5-[(3,4-dichlorophenyl)methylamino]-1-[2-[1-(methoxymethyl)-2-(methyl amino)ethoxy]ethyl]-6H-pyrazolo[4,3-d]pyrimidin-7-one (80 mg, 175.69 μmol, 1 eq) in MeOH (1 mL) was added formaldehyde (42.77 mg, 527.08 μmol, 39.24 μL, 3 eq) and AcOH (1.06 mg, 17.57 μmol, 1.00 μL, 0.1 eq) at 0° C. Then NaBH$_3$CN (33.12 mg, 527.08 μmol, 3 eq) was added at 0° C. in portions. The mixture was stirred at 25° C. for 3 hours. LCMS and HPLC showed the reaction was completed. H$_2$O (1 mL) was added to the reaction mixture. The mixture was filtered under reduced pressure. The filtrate was purified by prep-HPLC (HCl condition column: Phenomenex×Luna C18 150×30 mm×5 μm; mobile phase: [water (0.05% HCl)-ACN]; B %: 15%-45%, 12 mins). MeCN was removed under reduced pressure at 30° C. The residue was dried over lyophilization. Compound 5-((3,4-dichlorobenzyl)amino)-1-(2-((1-(dimethylamino)-3-methoxypropan-2-yl)oxy)ethyl)-1H-pyrazolo[4,3-d]pyrimidin-7(6H)-one (40.1 mg, 79.28 μmol, 45.12% yield, HCl) was obtained as white solid. $^1$H NMR (DMSO-$d_6$, 400 MHz) δ 9.54 (s, 1H), 7.61~7.59 (m, 3H), 7.33 (d, J=7.6 Hz, 1H), 7.18 (s, 1H), 4.62~4.60 (m, 2H), 4.50 (d, J=4.8 Hz, 2H), 4.00~3.93 (m, 1H), 3.92 (s, 2H), 3.34~3.29 (m, 2H), 3.20 (s, 3H), 3.14~3.13 (m, 2H), 3.71 (s, 6H). HPLC: 99.40% (220 nm), 99.24% (215 nm), 99.04% (254 nm). MS (ESI): mass calcd. For $C_{20}H_{27}Cl_3N_6O_3$ 468.14, m/z found 469.1 [M+H]$^+$.

Compound 185

5-((3,4-Dichlorobenzyl)amino)-1-(2-(2-methoxy-1-(pyridin-3-yl)ethoxy)ethyl)-1H-pyrazolo[4,3-d]pyrimidin-7(6H)-one hydrochloride was prepared according to the procedures described herein for Steps 1-3 in Scheme C-3.

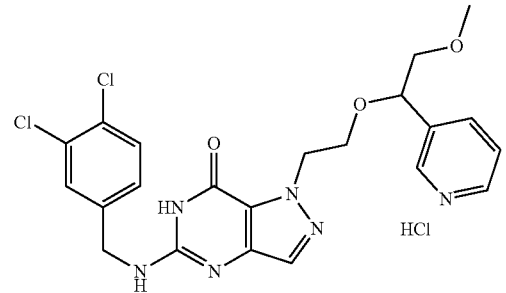 [SMILES: COCC(OCCn1ncc2nc(NCc3ccc(Cl)c(Cl)c3)[nH]c(=O)c21)c1cccnc1 ; Cl]

The procedure yielded the desired compound 5-((3,4-dichlorobenzyl)amino)-1-(2-(2-methoxy-1-(pyridin-3-yl)ethoxy)ethyl)-1H-pyrazolo[4,3-d]pyrimidin-7(6H)-one (98.1 mg, 185.02 μmol, 38.07% yield, 99.172% purity, HCl) as a white solid. $^1$H NMR (DMSO-$d_6$, 400 MHz) δ 8.80 (d, J=5.2 Hz, 1H), 8.69 (s, 1H), 8.29 (d, J=8.0 Hz, 1H), 7.96~7.94 (m, 1H), 7.78 (s, 1H), 7.65~7.63 (m, 3H), 7.39~7.37 (m, 1H), 4.78 (t, J=4.0 Hz, 1H), 4.68~4.63 (m, 1H), 4.59~4.58 (m, 2H), 4.56~4.54 (m, 1H), 3.94~3.93 (m, 1H), 3.84~3.82 (m, 1H), 4.54~4.44 (m, 2H), 3.17 (s, 3H). HPLC: 99.17% (220 nm), 99.03% (215 m), 100.00% (254 nm). MS (ESI): mass caled. For $C_{22}H_{23}Cl_3N_6O_3$ 488.11, m/z found 489.1 [M+H]$^+$.

Compound 186

Preparation of methyl 2-(2-(2-(5-((3,4-dichlorobenzyl)amino)-7-oxo-6,7-dihydro-1H-pyrazolo[4,3-d]pyrimidin-1-yl)ethoxy)ethoxy)acetate Preparation of 2-(2-(2-(5-((3,4-dichlorobenzyl)amino)-7-oxo-6,7-dihydro-1H-pyrazolo[4,3-d]pyrimidin-1-yl)ethoxy)ethoxy)acetaldehyde

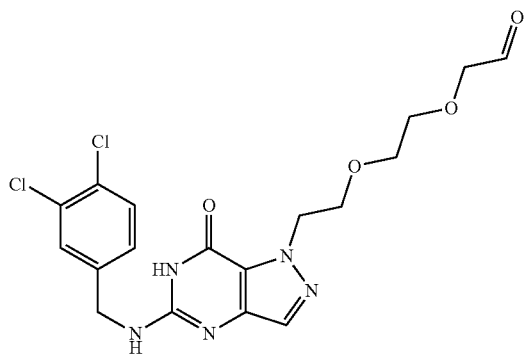 [SMILES: O=CCOCCOCCn1ncc2nc(NCc3ccc(Cl)c(Cl)c3)[nH]c(=O)c21]

To a solution of 5-[(3,4-dichlorophenyl)methylamino]-1-[2-[2-(2-hydroxyethoxy) ethoxy]ethyl]-6H-pyrazolo[4,3-d]pyrimidin-7-one (0.6 g, 1.36 mmol, 1 eq) (Steps 1-3 in Scheme C-3) in DCM (30 mL) was added DMP (2.30 g, 5.43 mmol, 1.68 mL, 4 eq) in portions at 0° C. The mixture was stirred at 25° C. for 32 hours. TLC (Ethyl acetate:Methanol=10:1, Rf-0.58) showed the reaction was complete. The reaction mixture was quenched with H$_2$O (10 mL) at 0° C. The organic layer was separated and the aqueous was then extracted with DCM (10 mL×3). The combined organic layers were washed with brine (10 mL), dried over Na$_2$SO$_4$, filtered and concentrated under reduced pressure. Compound 2-[2-[2-[5-[(3,4-dichlorophenyl)methylamino]-7-oxo-6H-pyrazolo[4,3-d]pyrimidin-1-yl]ethoxy]ethoxy]acetaldehyde (230 mg, crude) was obtained as yellow oil.

Compound 187

Preparation of 2-(2-(2-(5-((3,4-dichlorobenzyl)amino)-7-oxo-6,7-dihydro-1H-pyrazolo[4,3-d]pyrimidin-1-yl)ethoxy)ethoxy)acetic acid)

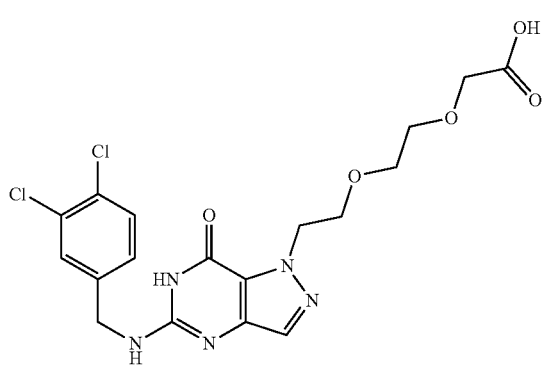 [SMILES: O=C(O)COCCOCCn1ncc2nc(NCc3ccc(Cl)c(Cl)c3)[nH]c(=O)c21]

To a solution of 2-[2-[2-[5-[(3,4-dichlorophenyl)methylamino]-7-oxo-6H-pyrazolo[4,3-d]pyrimidin-1-yl]ethoxy]ethoxy]acetaldehyde (230 mg, 522.40 μmol, 1 eq) and 2-methylbut-2-ene (732.74 mg, 10.45 mmol, 1.11 mL, 20 eq) in H$_2$O (1 mL), THF (1 mL) and t-BuOH (1 mL) was added sodium chlorite (51.97 mg, 574.63 μmol, 1.1 eq) in portions at 0° C. The mixture was stirred at 20° C. for 3 hours. LC-MS showed the reaction was nearly complete. The reaction mixture was quenched with H$_2$O (5 mL) at 20° C. and then extracted with EtOAc (10 mL×3). The combined organic layers were washed with brine (5 mL), dried over Na$_2$SO$_4$, filtered and concentrated under reduced pressure. The residue was purified by prep-HPLC (column: Nano-micro Kromasil C18 100 mm×30 mm 8 μm; mobile phase: [water (0.1% TFA)-ACN]; B %: 25%-40%, 10 mins). The aqueous solution was lyophilized. Compound 2-[2-[2-[5-[(3,4-dichlorophenyl)methylamino]-7-oxo-6H-pyrazolo[4,3-d]pyrimidin-1-yl]ethoxy]ethoxy]acetic acid (31 mg, 65.58 μmol, 12.55% yield, 96.527% purity) was obtained as brown solid. 10.8 mg was delivered. The desired compound was obtained (31 mg, 65.58 μmol, 12.55% yield) as white solid. $^1$H NMR (DMSO-d$_6$, 400 MHz) δ 7.66~7.61 (m, 3H), 7.46 (s, 1H), 7.37 (dd, J=1.6 Hz, 8.4 Hz, 1H), 6.75 (s, 1H), 5.55 (s, 1H), 4.86 (s, 1H), 4.73 (d, J=16.4 Hz, 1H), 4.62 (t, J=5.6 Hz, 2H), 4.45 (d, J=16.4 Hz, 1H), 3.83 (t, J=5.6 Hz, 2H), 3.40 (t, J=4.4 Hz, 4H). HPLC: 96.53% (220 nm), 95.61% (215 nm), 94.88% (254 nm). MS (ESI): mass calcd. For C$_{18}$H$_{19}$C$_{12}$N$_5$O$_5$ 455.08, m/z found 456.1 [M+H]$^+$.

Preparation of methyl 2-(2-(2-(5-((3,4-dichlorobenzyl)amino)-7-oxo-6,7-dihydro-1H-pyrazolo[4,3-d]pyrimidin-1-yl)ethoxy)ethoxy)acetate

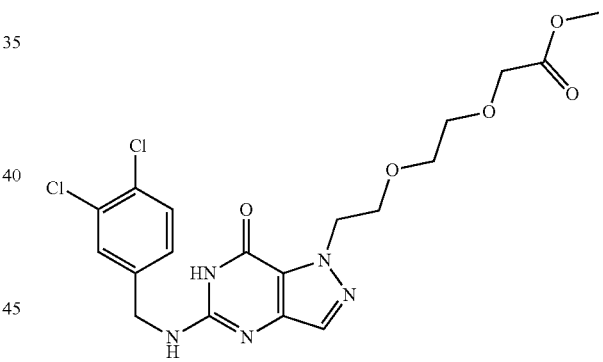

To a solution of 2-[2-[2-[5-[(3,4-dichlorophenyl)methylamino]-7-oxo-6H-pyrazolo[4,3-d]pyrimidin-1-yl]ethoxy]ethoxy]acetic acid (20 mg, 43.83 μmol, 1 eq) in MeOH (10 mL) was added SOCl$_2$ (26.07 mg, 219.16 μmol, 15.90 μL, 5 eq) dropwise at 0° C. The mixture was stirred at 25° C. for 5 hours. LC-MS showed the reaction was complete. The reaction mixture was concentrated under reduced pressure. The residue was purified by prep-HPLC (column: Xtimate C18 100 mm×30 mm 3 μm; mobile phase: [water (0.1% TFA)-MeCN]; B %: 25%-50%, 10 mins). The aqueous solution was lyophilized to give methyl 2-[2-[2-[5-[(3,4-dichlorophenyl)methylamino]-7-oxo-6H-pyrazolo[4,3-d]pyrimidin-1-yl]ethoxy]ethoxy]acetate (3.6 mg, 7.37 μmol, 16.81% yield, 96.244% purity) as white solid. H NMR (DMSO-d$_6$, 400 MHz) δ 7.61~7.56 (m, 3H), 7.33 (dd, J=1.6 Hz, 8.4 Hz, 1H), 6.70 (s, 1H), 4.62~4.53 (m, 2H), 4.48 (d, J=5.6 Hz, 2H), 4.07 (s, 1H), 4.04 (s, 1H), 3.86 (t, J=5.6 Hz, 1H), 3.79 (t, J=5.6 Hz, 1H), 3.62 (s, 2H), 3.60 (s, 2H), 3.50 (s, 3H). HPLC: 96.24% (220 nm), 96.15% (215 nm), 96.33% (254 nm). MS (ESI): mass calcd. For $C_{19}H_{21}C2N_5O_5$ 469.09, m/z found 470.1 $[M+H]^+$.

Compound 188

Preparation of 5-((3,4-dichlorobenzyl)amino)-1-(2-((1,1-dioxidotetrahydro-2H-thiopyran-4-yl)oxy)ethyl)-1H-pyrazolo[4,3-d]pyrimidin-7(6H)-one 5-((3,4-Dichlorobenzyl)amino)-1-(2-((tetrahydro-2H-thiopyran-4-yl)oxy)ethyl)-1H-pyrazolo[4,3-d]pyrimidin-7(6H)-one was prepared according to the procedure described herein for Steps 1-3 in Scheme C-3.

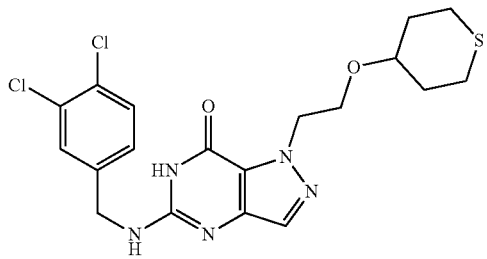 [SMILES: O=c1[nH]c(NCc2ccc(Cl)c(Cl)c2)nc2cnn(CCOC3CCSCC3)c12]

The procedure yielded the desired compound 5-((3,4-dichlorobenzyl)amino)-1-(2-((tetrahydro-2H-thiopyran-4-yl)oxy)ethyl)-1H-pyrazolo[4,3-d]pyrimidin-7(6H)-one (72 mg, 156.23 μmol, 27.32% yield, 98.591% purity) as a white solid. H NMR (DMSO-$d_6$, 400 MHz) δ 7.60~7.56 (m, 3H), 7.33 (d, J=8.4 Hz, 1H), 6.68 (s, 1H), 4.55 (t, J=5.6 Hz, 2H), 4.48 (d, J=5.6 Hz, 2H), 3.78 (t, J=5.6 Hz, 2H), 3.27 (t, J=8.0 Hz, 1H), 2.61~2.55 (m, 2H), 2.40~2.37 (m, 2H), 1.93~1.86 (m, 2H), 1.54~1.46 (m, 2H). HPLC: 98.59% (220 nm), 98.28% (215 nm), 94.36% (254 nm). MS (ESI): mass calcd. For $C_{19}H_{21}C2N_5O_2S$, 453.08 m/z found 454.1 $[M+H]^+$.

Preparation of 5-((3,4-dichlorobenzyl)amino)-1-(2-((1,1-dioxidotetrahydro-2H-thiopyran-4-yl)oxy)ethyl)-1H-pyrazolo[4,3-d]pyrimidin-7(6H)-one

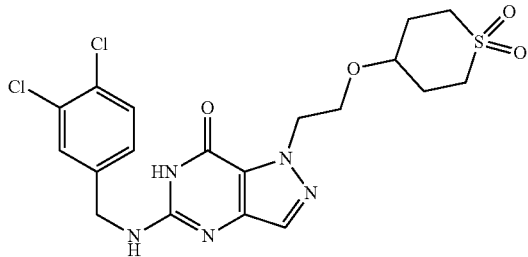 [SMILES: O=c1[nH]c(NCc2ccc(Cl)c(Cl)c2)nc2cnn(CCOC3CCS(=O)(=O)CC3)c12]

To a mixture of 5-[(3,4-dichlorophenyl)methylamino]-1-(2-tetrahydrothiopyran-4-yloxyethyl)-6H-pyrazolo[4,3-d]pyrimidin-7-one (30 mg, 66.03 μmol, 1 eq) in THF (3 mL) and H$_2$O (3 mL) was added RuCl$_3$ (1.37 mg, 6.60 μmol, 0.44 μL, 0.1 eq), then NaIO$_4$ (56.49 mg, 264.10 μmol, 14.63 μL, 4 eq) was added into the mixture at 0° C. The mixture was stirred at 50° C. for 16 hours. LC-MS and HPLC showed the reaction was complete. The mixture was poured into H$_2$O (5 mL) and then extracted with EtOAc (5 mL×3). The combined organic layers were dried over Na$_2$SO$_4$, filtered and concentrated under reduced pressure. The residue was purified by prep-HPLC (column: Nano-micro Kromasil C18 100×30 mm 8 μm; mobile phase: [water (0.1% TFA)-ACN]; B %: 20%-50%, 10 mins). The mixture was concentrated under reduced pressure to give 5-((3,4-dichlorobenzyl)amino)-1-(2-((1,1-dioxidotetrahydro-2H-thiopyran-4-yl)oxy)ethyl)-1H-pyrazolo[4,3-d]pyrimidin-7(6H)-one (8.6 mg, 16.87 μmol, 25.55% yield, 95.423% purity) as white solid. $^1$H NMR (DMSO-$d_6$, 400 MHz) δ7.61~7.56 (m, 3H), 7.33 (d, J=8.4 Hz, 1H), 6.73 (s, 1H), 4.59 (t, J=5.2 Hz, 2H), 4.48 (d, J=5.6 Hz, 2H), 3.79 (t, J=5.2 Hz, 2H), 3.61~3.60 (m, 1H), 2.94~2.84 (m, 4H), 1.95 (d, J=4.4 Hz, 4H). HPLC: 95.42% (220 nm), 93.82% (215 nm), 94.82% (254 nm). MS (ESI): mass calcd. For $C_{19}H_{21}C_{12}N_5O_4S$, 485.07 m/z found 486.0 $[M+H]^+$.

Compound 189

Preparation of 5-((3,4-dichlorobenzyl)amino)-1-(3,4-dihydroxybenzyl)-1H-pyrazolo[4,3-d]pyrimidin-7(6H)-one Compound 190

5-((3,4-Dichlorobenzyl)amino)-1-(3,4-dimethoxybenzyl)-1H-pyrazolo[4,3-d]pyrimidin-7(6H)-one was prepared according to the procedure described herein for Steps 1-3 in Scheme C-3.

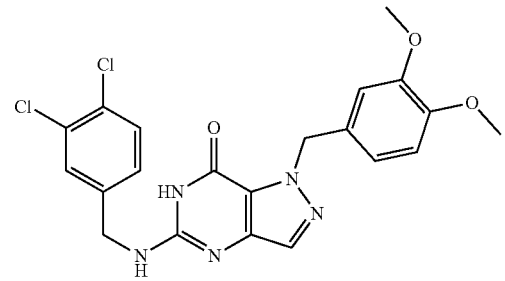 [SMILES: COc1ccc(Cn2ncc3nc(NCc4ccc(Cl)c(Cl)c4)[nH]c(=O)c32)cc1OC]

The procedure yielded the desired compound 5-[(3,4-dichlorophenyl)methylamino]-1-[(3,4-dimethoxyphenyl)methyl]-6H-pyrazolo[4,3-d]pyrimidin-7-one (40 mg, 86.90 μmol, 36.44% yield, 100.00% purity) as a white solid. 5.8 mg was delivered. $^1$H NMR (DMSO-$d_6$, 400 MHz) δ 7.60~7.54 (m, 3H), 7.32 (dd, J=2.0, 8.4 Hz, 1H), 6.95 (d, J=1.6 Hz, 1H), 6.86 (d, J=8.4 Hz, 1H), 6.74 (dd, J=2.0 Hz, 8.4 Hz, 2H), 5.52 (s, 2H), 4.47 (d, J=5.6 Hz, 2H), 3.69 (d, J=1.2 Hz, 6H). HPLC: 100.00% (220 nm), 100.00% (215 nm), 100.00% (254 nm). MS (ESI): mass calcd. For $C_{21}H_{19}C_{12}N_5O_3$ 459.09, m/z found 460.0 $[M+H]^+$.

Preparation of 5-((3,4-dichlorobenzyl)amino)-1-(3,4-dihydroxybenzyl)-1H-pyrazolo[4,3-d]pyrimidin-7(6H)-one

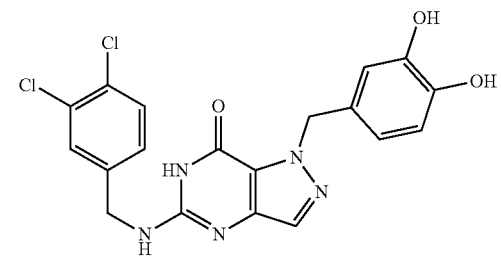 [SMILES: O=c1[nH]c(NCc2ccc(Cl)c(Cl)c2)nc2cnn(Cc3ccc(O)c(O)c3)c12]

To a solution of 5-[(3,4-dichlorophenyl)methylamino]-1-[(3,4-dimethoxyphenyl)methyl]-6H-pyrazolo[4,3-d]pyrimidin-7-one (30 mg, 65.17 µmol, 1 eq) in DCM (1 mL) was added BBr$_3$ (65.31 mg, 260.69 µmol, 25.12 µL, 4 eq) dropwise at 0° C. The mixture was stirred at 25° C. for an hour. LC-MS showed the reaction was complete. The reaction mixture was quenched with H$_2$O (0.1 mL) at 0° C. and then concentrated under reduced pressure. The residue was purified by prep-HPLC (column: Nano-micro Kromasil C18 100 mm×30 mm 8 µm; mobile phase: [water (0.1% TFA)-ACN]; B %: 20%-45%, 10 mins). The solution was lyophilized to give 5-[(3,4-dichlorophenyl)methylamino]-1-[(3,4-dihydroxyphenyl)methyl]-6H-pyrazolo[4,3-d]pyrimidin-7-one (7.2 mg, 15.48 µmol, 23.75% yield, 92.908% purity) as gray solid, the described compound was obtained (7.2 mg, 15.48 µmol, 23.75% yield) as gray solid. $^1$H NMR (DMSO-d$_6$, 400 MHz) δ 8.88 (s, 1H), 7.58 (d, J=7.6 Hz, 3H), 7.58 (d, J=7.2 Hz, 1H), 6.72~6.60 (m, 3H), 6.58~6.52 (m, 1H), 5.41 (s, 2H), 4.47 (d, J=6.0 Hz, 2H). HPLC: 92.91% (220 nm), 91.72% (215 nm), 91.74% (254 nm). MS (ESI): mass calcd. For $C_{19}H_{15}C_{12}N_5O_3$ 431.06, m/z found 432.0 [M+H]$^+$.

Compound 191

Preparation of (E)-2-(2-(5-((3,4-dichlorobenzyl)amino)-7-oxo-6,7-dihydro-1H-pyrazolo[4,3-d]pyrimidin-1-yl)ethoxy)acetaldehyde oxime Preparation of 2-[2-[5-[(3,4-dichlorophenyl)methylamino]-7-oxo-6H-pyrazolo[4,3-d]pyrimidin-1-yl]ethoxy]acetaldehyde

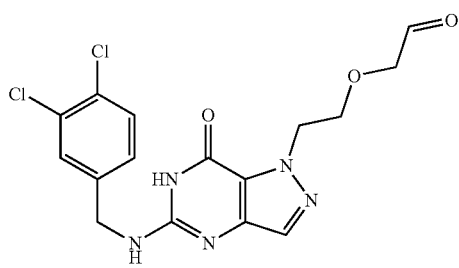 [SMILES: O=CCOCCn1ncc2nc(NCc3ccc(Cl)c(Cl)c3)[nH]c(=O)c21]

To a solution of 5-[(3,4-dichlorophenyl)methylamino]-1-[2-(2-hydroxy) ox)ethyl]-6H-pyrazolo[4,3-d]pyrimidin-7-one (70 mg, 175.77 µmol, 1 eq) in DCM (10 mL) was added DMP (134.19 mg, 316.39 µmol, 97.95 µL, 1.8 eq) in portions at 0° C. The mixture was stirred at 25° C. for 15 hours. LCMS showed the reaction was complete. The mixture was quenched with H$_2$O (5 mL) and the organic solvent was removed under reduced pressure. The aqueous was extracted with EtOAc (5 mL×5). The combined organic layers were washed with sat. NaHCO$_3$ (4 mL×1) and brine (4 mL×1), dried over Na$_2$SO$_4$, filtered and concentrated under reduced pressure. Compound 2-[2-[5-[(3,4-dichlorophenyl)methylamino]-7-oxo-6H-pyrazolo[4,3-d]pyrimidin-1-yl]ethoxy]acetaldehyde (60 mg, 151.43 µmol, 86.15% yield) was obtained as white solid.

Preparation of (E)-2-(2-(5-((3,4-dichlorobenzyl)amino)-7-oxo-6,7-dihydro-1H-pyrazolo[4,3-d]pyrimidin-1-yl)ethoxy)acetaldehyde oxime

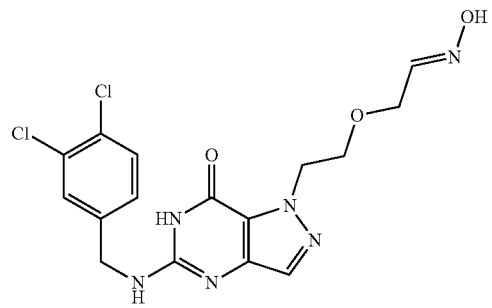 [SMILES: O=c1[nH]c(NCc2ccc(Cl)c(Cl)c2)nc2cnn(CCOC/C=N/O)c12]

To a solution of 2-[2-[5-[(3,4-dichlorophenyl)methylamino]-7-oxo-6H-pyrazolo[4,3-d]pyrimidin-1-yl]ethoxy]acetaldehyde (50 mg, 126.19 µmol, 1 eq) in EtOH (2 mL) was added NH$_2$OH—HCl (17.54 mg, 252.38 µmol, 2 eq) and TEA (31.92 mg, 315.48 µmol, 43.91 µL, 2.5 eq) at 0° C. The mixture was stirred at 25° C. for 10 hours. LCMS showed the reaction was complete. The reaction mixture was concentrated under reduced pressure. The residue was purified by prep-HPLC (neutral condition column: Phenomenex Gemini-NX C18 75 mm×30 mm 3 µm; mobile phase: [water (10 mM NH$_4$HCO$_3$)-ACN]; B %: 25%-50%, 10.5 mins). MeCN was removed under reduced pressure at 30° C. The residue was dried over lyophilization. Compound (1E)-2-[2-[5-[(3,4-dichlorophenyl)methylamino]-7-oxo-6H-pyrazolo[4,3-d]pyrimidin-1-yl]ethoxy]acetaldehyde oxime (15.0 mg, 35.10 µmol, 27.81% yield, 96.223% purity) was obtained as white solid. H NMR (DMSO-d$_6$, 400 MHz) δ 11.09 (s, 0.5H), 11.01 (s, 1H), 10.91 (s, 0.5H), 7.59~7.57 (m, 3H), 7.32 (dd, J 8.8 Hz, J 2.4 Hz, 1H), 7.25 (t, J 8.0 Hz, 1H), 6.65 (t, J 8.0 Hz, 1H), 6.58 (s, 1H), 4.58 (t, J 6.4 Hz, 2H), 4.47 (d, J 6.0 Hz, 2H), 4.18 (d, J 4.0 Hz, 1H), 3.94 (d, J 6.4 Hz, 1H), 3.83~3.77 (m, 1H), 3.34 (s, 1H). HPLC: 96.22% (220 nm), 94.69% (215 nm), 93.56% (254 nm). MS (ESI): mass calcd. For $C_{16}H_{16}C_{12}N_6O_3$ 410.07, m/z found 411.0 [M+H]$^+$.

Compound 192

Preparation of (E)-5-((3,4-dichlorobenzyl)amino)-1-(4-methoxybut-2-en-1-yl)-1H-pyrazolo[4,3-d]pyrimidin-7(6H)-one Preparation of (E)-1-(4-bromobut-2-en-1-yl)-5-chloro-7-methoxy-1H-pyrazolo[4,3-d]pyrimidine
(Step 1 in Scheme C-3)

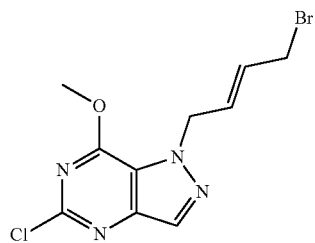 [SMILES: COc1nc(Cl)nc2cnn(C/C=C/CBr)c12]

To a solution of (E)-1,4-dibromobut-2-ene (2.90 g, 13.54 mmol, 5 eq) in DMF (5 mL) was added Cs$_2$CO$_3$ (1.77 g, 5.42 mmol, 2 eq). Then 5-chloro-7-methoxy-1H-pyrazolo[4,3-d]pyrimidine (0.5 g, 2.71 mmol, 1 eq) in DMF was added dropwise at 0° C. The mixture was stirred at 25° C. for an hour. LCMS showed the reaction was completed. H$_2$O (10 mL) was added. The reaction mixture was extracted with EtOAc (15 mL×3). The combined organic layers were washed with brine (10 mL×2), dried over Na$_2$SO$_4$, filtered and concentrated under reduced pressure. The residue was purified by flash silica gel chromatography (Biotage®; 12 g SepaFlash® Silica Flash Column, Eluent of 050% Ethyl acetate/Petroleum ether gradient at 50 mL/min). Compound (E)-1-(4-bromobut-2-en-1-yl)-5-chloro-7-methoxy-1H-pyrazolo[4,3-d]pyrimidine (0.4 g, 1.26 mmol, 46.50% yield) was obtained as light yellow solid. $^1$H NMR (DMSO-d$_6$, 400 MHz) δ 8.27 (s, 1H), 6.09~6.01 (m, 1H), 5.82~5.73 (m, 1H), 5.16 (d, J=5.6 Hz, 2H), 4.16 (s, 3H), 4.11 (d, J=7.6 Hz, 2H). Compound 2-[(E)-4-bromobut-2-enyl]-5-chloro-7-methoxy-pyrazolo[4,3-d]pyrimidine (0.28 g, 881.70 μmol, 32.55% yield) was obtained as white solid.

Preparation of (E)-5-chloro-7-methoxy-1-(4-methoxybut-2-en-1-yl)-1H-pyrazolo[4,3-d]pyrimidine

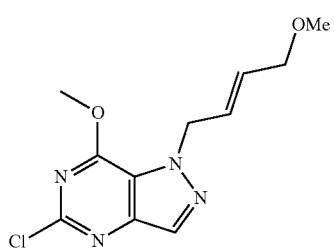 [SMILES: COC/C=C/Cn1ncc2nc(Cl)nc(OC)c21]

To a solution of 1-[(E)-4-bromobut-2-enyl]-5-chloro-7-methoxy-pyrazolo[4,3-d]pyrimidine (0.12 g, 377.87 μmol, 1 eq) in MeOH (1.5 mL) was added NaOMe (30.62 mg, 566.81 μmol, 1.5 eq). The mixture was stirred at 25° C. for 12 hours. LC-MS showed the reaction was completed. The reaction mixture was concentrated under reduced pressure. Compound (E)-5-chloro-7-methoxy-1-(4-methoxybut-2-en-1-yl)-1H-pyrazolo[4,3-d]pyrimidine (0.12 g, crude) was obtained as white solid $^1$H NMR (DMSO-d$_6$, 400 MHz) δ 8.26 (s, 1H), 5.90~5.84 (m, 1H), 5.63~5.56 (m, 1H), 5.14 (d, J=5.6 Hz, 2H), 4.15 (s, 3H), 3.83 (d, J=4.0 Hz, 2H), 3.17 (s, 3H).

Preparation of (E)-5-chloro-1-(4-methoxybut-2-en-1-yl)-1H-pyrazolo[4,3-d]pyrimidin-7(6H)-one (Step 2 in Scheme C-3)

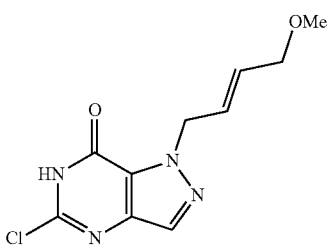 [SMILES: COC/C=C/Cn1ncc2nc(Cl)[nH]c(=O)c21]

To a solution of 5-chloro-7-methoxy-1-[(E)-4-methoxybut-2-enyl]pyrazolo[4,3-d]pyrimidine (0.12 g, 446.60 μmol, 1 eq) in H$_2$O (1 mL) and THF (1 mL) was added LiOH·H$_2$O (56.22 mg, 1.34 mmol, 3 eq). The mixture was stirred at 25° C. for 10 hours. LC-MS showed reaction was complete. The reaction mixture was concentrated under reduced pressure to remove THF. Then the mixture was adjusted pH=5 with HCl (2N), and extracted with EtOAc (10 mL×5). The combined organic layers were washed with brine (5 mL×1), dried over Na$_2$SO$_4$, filtered and concentrated under reduced pressure. Compound (E)-5-chloro-1-(4-methoxybut-2-en-1-yl)-1H-pyrazolo[4,3-d]pyrimidin-7(6H)-one (70 mg crude) was obtained as white solid $^1$H NMR (DMSO-d$_6$, 400 MHz) δ 13.30 (s, 1H), 7.98 (s, 1H), 5.88~5.82 (m, 1H), 5.61~5.55 (m, 1H), 5.13 (d, J=4.8 Hz, 2H), 3.82 (d, J=4.4 Hz, 2H), 3.18 (s, 3H).

Preparation of (E)-5-((3,4-dichlorobenzyl)amino)-1-(4-methoxybut-2-en-1-yl)-1H-pyrazolo[4,3-d]pyrimidin-7(6H)-one (Step 3 in Scheme C-3)

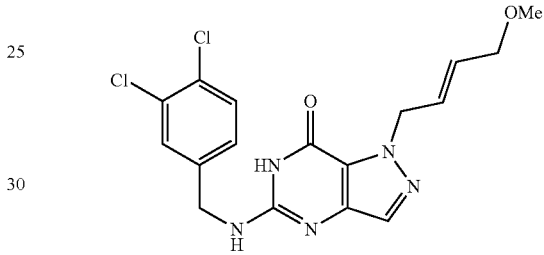

To a solution of 5-chloro-1-[(E)-4-methoxybut-2-enyl]-6H-pyrazolo[4,3-d]pyrimidin-7-one (70 mg, 274.86 μmol, 1 eq) in t-BuOH (2 mL) was added (3,4-dichlorophenyl)methanamine (96.78 mg, 549.73 μmol, 73.31 μL, 2 eq). The mixture was stirred at 100° C. for 12 hours. LC-MS and HPLC showed reaction was complete. The reaction mixture was concentrated under reduced pressure. The residue was purified by prep-HPLC (TFA condition column: Nano-micro Kromasil C18 100 mm×30 mm 5 μm; mobile phase: [water (0.1% TFA)-MeCN]; B %: 30%-45%, 10 mins). Compound (E)-5-((3,4-dichlorobenzyl)amino)-1-(4-methoxybut-2-en-1-yl)-1H-pyrazolo[4,3-d]pyrimidin-7(6H)-one (54.8 mg, 133.12 μmol, 48.43% yield, 95.77% purity) was obtained as white solid. $^1$H NMR (DMSO-d$_6$, 400 MHz) δ 11.07 (s, 1H), 7.59~7.57 (m, 3H), 7.32 (d, J=10.0 Hz, 1H), 6.60 (s, 1H), 5.85~5.80 (m, 1H), 5.55~5.51 (m, 1H), 5.03 (d, J=5.2 Hz, 2H), 4.47 (d, J=5.6 Hz, 2H), 3.81 (d, J=5.6 Hz, 2H), 3.17 (s, 3H). HPLC: 95.77% (220 nm), 95.00% (215 nm), 96.86% (254 nm). MS (ESI): mass calcd. For C$_{17}$H$_{17}$C$_{12}$N$_5$O$_2$ 393.08, m/z found 394.1 [M+H]$^+$.

Compound 193

Preparation of (E)-5-((3,4-dichlorobenzyl)amino)-1-(4-(2-methoxyethoxy)but-2-en-1-yl)-1H-pyrazolo[4,3-d]pyrimidin-7(6H)-one Preparation of sodium 2-methoxyethanolate

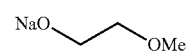

To a solution of NaH (683.36 mg, 17.08 mmol, 2.05 μL, 60% purity, 1.3 eq) in CH₃-THF (10 mL) was added 2-methoxyethanol (1 g, 13.14 mmol, 1.04 mL, 1 eq) at 0° C. dropwise. The mixture was stirred at 0° C. for 2 hours. TLC showed the reaction was completed. The reaction mixture was concentrated under reduced pressure. Compound sodium 2-methoxyethanolate (0.4 g, 4.08 mmol, 31.03% yield) was obtained as white solid.

Preparation of (E)-5-chloro-7-(2-methoxyethoxy)-1-(4-(2-methoxyethoxy)but-2-en-1-yl)-1H-pyrazolo[4,3-d]pyrimidine

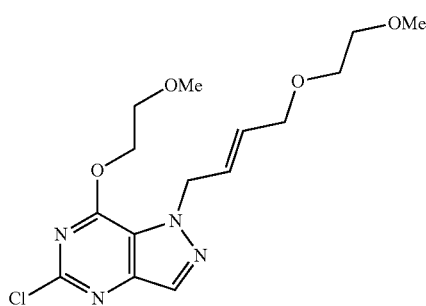 [SMILES: COCCOC/C=C/Cn1ncc2nc(Cl)nc(OCCOC)c21]

To a solution of 2-methoxyethoxy sodium (74.12 mg, 755.74 μmol, 1.5 eq) in 2-methoxy ethanol (2 mL) was added 1-[(E)-4-bromobut-2-enyl]-5-chloro-7-methoxy-pyrazolo[4,3-d]pyrimidine (0.16 g, 503.83 μmol, 1 eq). The mixture was stirred at 25° C. for 1 hour. LC-MS showed reaction was complete. H₂O (5 mL) was added. The reaction mixture was extracted with EtOAc (10 mL×3). The combined organic layers were washed with brine (5 mL×2), dried over Na₂SO₄, filtered and concentrated under reduced pressure. The residue was purified by flash silica gel chromatography (Biotage®; 4 g SepaFlash® Silica Flash Column, Eluent of 0₆₀% Ethyl acetate/Petroleum ether gradient at 36 mL/min). Then the eluent was concentrated under reduced pressure. Compound (E)-5-chloro-7-(2-methoxy-ethoxy)-1-(4-(2-methoxyethoxy)but-2-en-1-yl)-1H-pyrazolo[4,3-d]pyrimidine (70 mg, 196.19 μmol, 38.94% yield) was obtained as yellow oil. ¹H NMR (DMSO-d₆, 400 MHz) δ 8.26 (s, 1H), 5.90~5.85 (m, 1H), 5.72~5.67 (m, 1H), 5.13 (d, J=5.6 Hz, 2H), 4.68 (dd, J=6.4 Hz, 4.4 Hz, 2H), 3.91 (d, J=4.8 Hz, 2H), 3.78 (d, J=2.0 Hz, 2H), 3.44~3.40 (m, 4H), 3.39 (s, 3H), 3.20 (s, 3H).

Preparation of (E)-5-chloro-1-(4-(2-methoxyethoxy)but-2-en-1-yl)-1H-pyrazolo[4,3-d]pyrimidin-7(6H)-one (Step 2 in Scheme C-3)

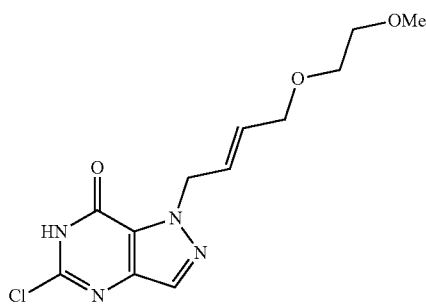 [SMILES: COCCOC/C=C/Cn1ncc2nc(Cl)[nH]c(=O)c21]

To a solution of 5-chloro-7-(2-methoxyethoxy)-1-[(E)-4-(2-methoxyethoxy)but-2-enyl]pyrazolo[4,3-d]pyrimidine (70 mg, 196.19 mol, 1 eq) in H₂O (1 mL) and THF (1 mL) was added LiOHH₂O (24.70 mg, 588.56 μmol, 3 eq). The mixture was stirred at 25° C. for 10 hours. LC-MS showed reaction was complete. The reaction mixture was concentrated under reduced pressure to remove THF. The mixture was adjusted pH=5 with HCl (2N), and then extracted with EtOAc (10 mL×5). The combined organic layers were washed with brine (5 mL×1), dried over Na₂SO₄, filtered and concentrated under reduced pressure. Compound (E)-5-chloro-1-(4-(2-methoxy ethoxy)but-2-en-1-yl)-1H-pyrazolo[4,3-d]pyrimidin-7(6H)-one (60 mg, crude) was obtained as light yellow oil. ¹H NMR (DMSO-d₆, 400 MHz) δ 13.30 (s, 1H), 7.98 (s, 1H), 5.89~5.83 (m, 1H), 5.61~5.54 (m, 1H), 4.13 (d, J=5.6 Hz, 2H), 3.90 (d, J=5.2 Hz, 2H), 3.46~3.41 (m, 4H), 3.21 (s, 3H).

Preparation of (E)-5-((3,4-dichlorobenzyl)amino)-1-(4-(2-methoxyethoxy)but-2-en-1-yl)-1H-pyrazolo[4,3-d]pyrimidin-7(6H)-one (Step 3 in Scheme C-3)

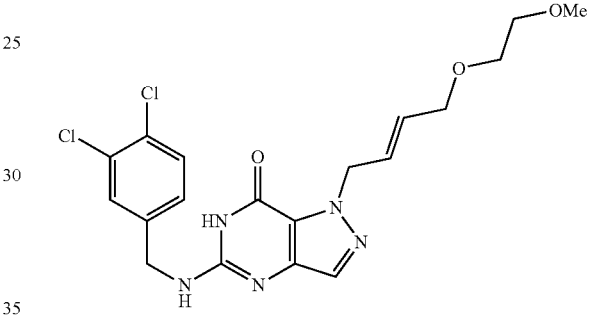

To a solution of 5-chloro-1-[(E)-4-(2-methoxyethoxy)but-2-enyl]-6H-pyrazolo[4,3-d]pyrimidin-7-one (60 mg, 200.85 μmol, 1 eq) in t-BuOH (2 mL) was added (3,4-dichlorophenyl)methanamine (70.72 mg, 401.71 μmol, 53.57 μL, 2 eq). The mixture was stirred at 100° C. for 12 hours. LC-MS and HPLC showed the reaction was completed. The reaction mixture was concentrated under reduced pressure. The residue was purified by prep-HPLC (TFA condition column: Boston Prime C18 150 mm×30 mm 5 μm; mobile phase: [water (0.1% TFA)-MeCN]; B %: 30%-55%, 10 mins). MeCN was removed under reduced pressure at 30° C. The residue was dried over lyophilization. Compound (E)-5-((3,4-dichlorobenzyl)amino)-1-(4-(2-methoxy ethoxy) but-2-en-1-yl)-1H-pyrazolo[4,3-d]pyrimidin-7(6H)-one (59.8 mg, 136.43 μmol, 67.93% yield) was obtained as white solid. H NMR (DMSO-d₆, 400 MHz) δ 7.60~7.57 (m, 3H), 7.33 (dd, J=8.4 Hz, 2.0 Hz, 1H), 6.74 (s, 1H), 5.87~5.79 (m, 1H), 5.56~5.50 (m, 1H), 4.03 (d, J=5.2 Hz, 2H), 4.48 (d, J=5.6 Hz, 2H), 3.88 (t, J=4.0 Hz, 2H), 3.45~3.39 (m, 4H), 3.21 (s, 3H). HPLC: 99.52% (220 nm), 99.29% (215 nm), 100.00% (254 nm). MS (ESI): mass calcd. For $C_{19}H_{21}C2N_5O_3$ 437.10, m/z found 438.1 [M+H]⁺.

Compound 194

Preparation of Preparation of ethyl 4-((5-((3,4-dichlorobenzyl)amino)-7-oxo-6,7-dihydro-1H-pyrazolo[4,3-d]pyrimidin-1-yl)methyl)piperidine-4-carboxylate hydrochloride 1-tert-butyl 4-ethyl 4-((5-((3,4-dichlorobenzyl)amino)-7-oxo-6,7-dihydro-1H-pyrazolo[4,3-d]pyrimidin-1-yl)methyl)

piperidine-1,4-dicarboxylate was prepared according to the procedures described herein for Steps 1-3 in Scheme C-3.

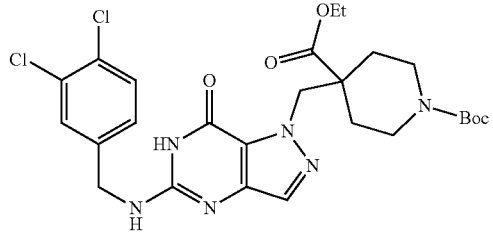 [SMILES: CCOC(=O)C1(Cn2ncc3nc(NCc4ccc(Cl)c(Cl)c4)[nH]c(=O)c32)CCN(C(=O)OC(C)(C)C)CC1]

The procedure yielded the desired compound 1-tert-butyl 4-ethyl 4-[[5-[(3,4-dichlorophenyl)methylamino]-7-oxo-6H-pyrazolo[4,3-d]pyrimidin-1-yl]methyl]piperidine-1,4-dicarboxylate (0.22 g, 379.65 μmol, 66.80% yield) as a white solid. H NMR (DMSO-d$_6$, 400 MHz) δ 7.59~7.57 (m, 3H), 7.32 (d, J=8.4 Hz, 1H), 8.82 (s, 1H), 4.61 (s, 2H), 4.46 (d, J=6.0 Hz, 2H), 4.04 (q, J=6.8 Hz, 2H), 3.76-3.73 (m, 2H), 2.78~2.74 (m, 2H). 1.85~1.81 (m, 2H), 1.45~1.37 (m, 11H), 1.12 (t, J=6.8 Hz, 3H).

Preparation of tert-butyl 4-((5-((3,4-dichlorobenzyl)amino)-7-oxo-6,7-dihydro-1H-pyrazolo[4,3-d]pyrimidin-1-yl)methyl)-4-(hydroxymethyl)piperidine-1-carboxylate

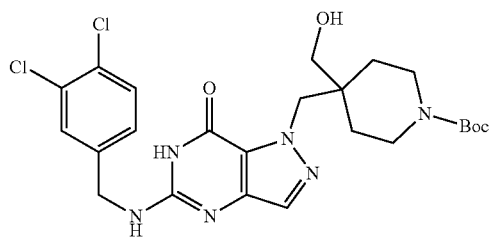 [SMILES: CC(C)(C)OC(=O)N1CCC(CO)(Cn2ncc3nc(NCc4ccc(Cl)c(Cl)c4)[nH]c(=O)c32)CC1]

To a solution of 01-tert-butyl 04-ethyl 4-[[5-[(3,4-dichlorophenyl)methylamino]-7-oxo-6H-pyrazolo[4,3-d]pyrimidin-1-yl]methyl]piperidine-1,4-dicarboxylate (0.1 g, 172.57 μmol, 1 eq) in THF (3 mL) was added LiBH$_4$ (15.04 mg, 690.28 μmol, 4 eq) at 0° C. Then the mixture was stirred at 55° C. for 6 hours. LCMS and TLC showed the reaction was complete. The mixture was quenched with ice water (2 mL) and the organic solvent was removed under reduced pressure. The aqueous was extracted with EtOAc (5 mL×4). The combined organic layer was washed with brine (2 mL), dried over Na$_2$SO$_4$, filtered and concentrated under reduced pressure to give tert-butyl 4-[[5-[(3,4-dichlorophenyl)methylamino]-7-oxo-6H-pyrazolo[4,3-d]pyrimidin-1-yl]methyl]-4-(hydroxymethyl)piperidine-1-carboxylate (90 mg, 167.46 μmol, 97.04% yield) as white solid. H NMR (DMSO-d$_6$, 400 MHz) δ 7.61~7.30 (m, 3H), 7.30 (dd, J=8.0 Hz, 2.0 Hz, 1H), 4.57 (d, J=5.6 Hz, 2H), 4.47 (s, 2H), 3.40~3.30 (m, 4H). 3.09 (s, 2H), 1.88~1.94 (m, 2H), 1.38~1.26 (m, 11H).

Compound 195

Preparation of 5-((3,4-dichlorobenzyl)amino)-1-((4-(hydroxymethyl)piperidin-4-yl)methyl)-1H-pyrazolo[4,3-d]pyrimidin-7(6H)-one hydrochloride

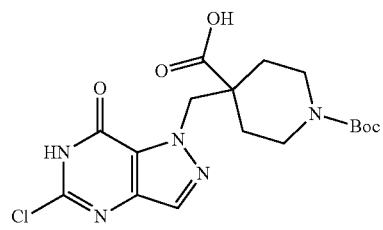 [SMILES: CC(C)(C)OC(=O)N1CCC(Cn2ncc3nc(Cl)[nH]c(=O)c32)(C(=O)O)CC1]

To a mixture of tert-butyl 4-[[5-[(3,4-dichlorophenyl)methylamino]-7-oxo-6H-pyrazolo[4,3-d]pyrimidin-1-yl]methyl]-4-(hydroxymethyl)piperidine-1-carboxylate (0.13 g, 241.89 μmol, 1 eq) in EtOAc (4 mL) was added HCl/EtOAc (4 M, 6.05 mL, 100 eq) and the mixture was stirred at 20° C. for 2 hours. LCMS showed the reaction was complete. There was some white solid formed. After filtered, the solid was collected. The solid was purified by prep-HPLC (column: Phenomenex Luna C18 100 mm×30 mm 5 μm; mobile phase: [water (0.05% HCl)-MeCN]; B %: 10%-35%, 12 mins). The eluent was removed under reduced pressure. Compound 5-[(3,4-dichlorophenyl)methylamino]-1-[[4-(hydroxymethyl)-4-piperidyl]methyl]-6H-pyrazolo[4,3-d]pyrimidin-7-one (102 mg, 210.83 μmol, 87.16% yield, 97.93% purity, HCl) was obtained as white solid. $^1$H NMR (DMSO-d$_6$, 400 MHz) δ 8.70 (s, 1H), 8.51 (s, 1H), 7.95 (s, 1H), 7.71 (s, 1H), 7.66~7.61 (m, 2H), 7.38 (dd, J=8.0 Hz, 2.0 Hz, 1H), 4.59 (d, J=4.4 Hz, 2H), 4.50 (s, 2H), 3.37 (s, 2H). 3.08~3.03 (m, 4H), 1.68~1.64 (m, 2H), 1.51~1.45 (m, 2H). HPLC: 97.93% (220 nm), 97.47% (215 nm), 100.00% (254 nm). MS (ESI): mass calcd. For $C_{19}H_{23}C3N_6O_2$ 436.12 m/z found 437.1 [M+H]$^+$.

Preparation of 1-(tert-butoxycarbonyl)-4-((5-chloro-7-oxo-6,7-dihydro-1H-pyrazolo[4,3-d]pyrimidin-1-yl)methyl)piperidine-4-carboxylic acid (Step 2 in Scheme C-3)

A solution of 01-tert-butyl 04-ethyl 4-[(5-chloro-7-methoxy-pyrazolo[4,3-d]pyrimidin-1-yl)methyl]piperidine-1,4-dicarboxylate (0.1 g, 220.30 uμmol, 1 eq) and LiOHH$_2$O (46.22 mg, 1.10 mmol, 5 eq) in MeOH (1 mL), THF (1 mL) and H$_2$O (1 mL) was stirred at 20° C. for 3 hours. Then NaOH (17.62 mg, 440.61 μmol, 2 eq) was added and the mixture was stirred at 70° C. for 5 hours. TLC showed the reaction was complete. The organic solvent was removed under reduced pressure. The aqueous was made pH=6~7 with 2N HCl slowly and some solid formed. The solid was collected after filtered. The aqueous was then extracted with EtOAc (10 mL×3). The combined organic layer was washed with brine (5 mL), dried over Na$_2$SO$_4$, filtered and concentrated under reduced pressure to give 1-tert-butoxycarbonyl-4-[(5-chloro-7-oxo-6H-pyrazolo[4,3-d]pyrimidin-1-yl)methyl]piperidine-4-carboxylic acid (80 mg, 194.25 μmol, 88.17% yield) as white solid. H NMR (DMSO-d$_6$, 400 MHz) δ 7.94 (s, 1H), 4.71 (s, 2H), 3.76~3.72 (m, 2H), 2.80~2.79 (m, 2H), 1.91~1.84 (m, 2H), 1.40~1.35 (m, 11H).

Preparation of 1-(tert-butoxycarbonyl)-4-((5-((3,4-dichlorobenzyl)amino)-7-oxo-6,7-dihydro-1H-pyrazolo[4,3-d]pyrimidin-1-yl)methyl)piperidine-4-carboxylic acid (Step 3 in Scheme C-3)

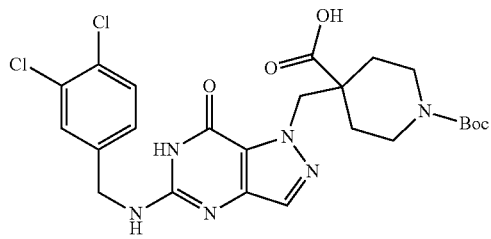 [SMILES: CC(C)(C)OC(=O)N1CCC(Cn2ncc3nc(NCc4ccc(Cl)c(Cl)c4)[nH]c(=O)c32)(C(=O)O)CC1]

A solution of (3,4-dichlorophenyl)methanamine (68.39 mg, 388.50 mol, 51.81 μL, 2 eq) and 1-tert-butoxycarbonyl-4-[(5-chloro-7-oxo-6H-pyrazolo[4,3-d]pyrimidin-1-yl)methyl]piperidine-4-carboxylic acid (80 mg, 194.25 μmol, 1 eq) in t-BuOH (2 mL) was heated at 100° C. for 30 hours. LCMS showed the reaction was nearly complete. The solvent was removed under reduced pressure. Compound 1-tert-butoxycarbonyl-4-[[5-[(3,4-dichlorophenyl)methylamino]-7-oxo-6H-pyrazolo[4,3-d]pyrimidin-1-yl]methyl]piperidine-4-carboxylic acid (0.13 g, crude) was obtained as off-white solid. MS (ESI): mass calcd. For C$_{24}$H$_{28}$C$_{12}$N$_6$O$_5$ 550.15 m/z found 495.0 [M+H-Boc]$^+$.

Compound 196

Preparation of 4-((5-((3,4-dichlorobenzyl)amino)-7-oxo-6,7-dihydro-1H-pyrazolo[4,3-d]pyrimidin-1-yl)methyl)piperidine-4-carboxylic Acid Hydrochloride

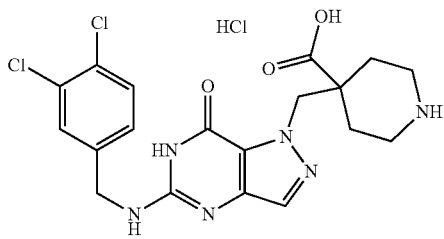 [SMILES: O=C(O)C1(Cn2ncc3nc(NCc4ccc(Cl)c(Cl)c4)[nH]c(=O)c32)CCNCC1 ; Cl]

To a mixture of 1-tert-butoxycarbonyl-4-[[5-[(3,4-dichlorophenyl)methylamino]-7-oxo-6H-pyrazolo[4,3-d]pyrimidin-1-yl]methyl]piperidine-4-carboxylic acid (0.11 g, 199.48 μmol, 1 eq) in EtOAc (5 mL) was added HCl/EtOAc (4 M, 4.99 mL, 100 eq) and the mixture was stirred at 20° C. for 2 hours. LCMS showed the reaction was complete. There was some solid formed. After filtered, the solid was collected. The solid was purified by prep-HPLC (column: Phenomenex Luna C18 150 mm×30 mm 5 μm; mobile phase: [water (0.05% HCl)-MeCN]; B %: 10%-40%, 12 mins). The eluent was dried under freeze drying. Compound 4-[[5-[(3,4-dichlorophenyl)methylamino]-7-oxo-6H-pyrazolo[4,3-d]pyrimidin-1-yl]methyl]piperidine-4-carboxylic acid (40.2 mg, 81.00 μmol, 40.60% yield, 98.28% purity, HCl) was obtained as white solid. $^1$H NMR (DMSO-d$_6$, 400 MHz) δ 8.77~8.75 (m, 1H), 8.44~8.42 (m, 1H), 7.65 (s, 1H), 7.61~7.59 (m, 2H), 7.25 (dd, J=8.0 Hz, 2.0 Hz, 1H), 7.33~7.32 (m, 1H), 4.65 (s, 2H), 4.51 (d, J=5.6 Hz, 2H), 3.24~3.21 (m, 2H), 2.77~2.66 (m, 2H), 2.00~1.97 (m, 2H), 1.73~1.67 (m, 2H). HPLC: 98.28% (220 nm), 98.41% (215 nm), 95.91% (254 nm). MS (ESI): mass calcd. For C$_{19}$H$_{21}$C$_{13}$N$_6$O$_3$ 450.10 m/z found 451.0 [M+H]$^+$.

Preparation of ethyl 4-((5-((3,4-dichlorobenzyl)amino)-7-oxo-6,7-dihydro-1H-pyrazolo[4,3-d]pyrimidin-1-yl)methyl)piperidine-4-carboxylate hydrochloride

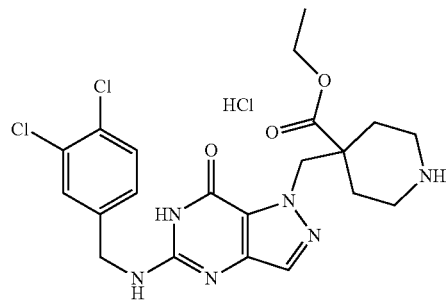 [SMILES: CCOC(=O)C1(Cn2ncc3nc(NCc4ccc(Cl)c(Cl)c4)[nH]c(=O)c32)CCNCC1 ; Cl]

To a mixture of 01-tert-butyl 04-ethyl 4-[[5-[(3,4-dichlorophenyl)methylamino]-7-oxo-6H-pyrazolo[4,3-d]pyrimidin-1-yl]methyl]piperidine-1,4-dicarboxylate (30 mg, 51.77 μmol, 1 eq) in EtOAc (1 mL) was added HCl/EtOAc (4 M, 1.29 mL, 100 eq) and the mixture was stirred at 20° C. for 2 hours. TLC showed the reaction was complete. There was some white solid formed. After filtered, the solid was collected. The solid was concentrated under reduced pressure to give ethyl 4-[[5-[(3,4-dichlorophenyl)methylamino]-7-oxo-6H-pyrazolo[4,3-d]pyrimidin-1-yl]methyl]piperidine-4-carboxylate (15.6 mg, 29.46 μmol, 56.90% yield, 97.41% purity, HCl) as white solid. $^1$H NMR (DMSO-d$_6$, 400 MHz) δ 8.77~8.74 (m, 1H), 8.52~8.48 (m, 1H), 7.63 (s, 1H), 7.60~7.58 (m, 2H), 7.33 (dd, J=8.4 Hz, 1.6 Hz, 1H), 7.09~7.07 (m, 1H), 4.65 (s, 2H), 4.49 (d, J=5.6 Hz, 2H), 4.07 (q, J=7.2 Hz, 2H), 3.27~3.23 (m, 2H), 2.77~2.67 (m, 2H), 2.02~1.99 (m, 2H), 1.79~1.76 (m, 2H), 1.15 (t, J=7.2 Hz, 3H). HPLC: 97.41% (220 nm), 96.42% (215 nm), 100.00% (254 nm). MS (ESI): mass calcd. For C$_2$H$_{25}$C$_{13}$N$_6$O$_3$ 478.13 m/z found 479.1 [M+H]$^+$.

Compound 197

Preparation of 2-(5-((3,4-dichlorobenzyl)amino)-7-oxo-6,7-dihydro-1H-pyrazolo[4,3-d]pyrimidin-1-yl)-N-((2-(trimethylsilyl)ethoxy)methyl)acetamide Preparation of 2-(5-chloro-7-methoxy-1H-pyrazolo[4,3-d]pyrimidin-1-yl)acetamide (Step 1 in Scheme C-3)

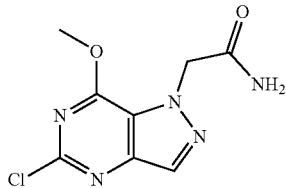 [SMILES: COc1nc(Cl)nc2cnn(CC(N)=O)c12]

To a solution of 5-chloro-7-methoxy-1H-pyrazolo[4,3-d]pyrimidine (700 mg, 3.79 mmol, 1 eq) and 2-chloroacetamide (709.26 mg, 7.58 mmol, 2 eq) in DMF (5 mL) was added K$_2$CO$_3$ (1.05 g, 7.58 mmol, 2 eq). The mixture was stirred at 70° C. for 10 hours. TLC showed the reaction was completed. The mixture was poured into H$_2$O (7 mL) and the mixture was adjusted to pH=7 with HCl (2M). The mixture was extracted with DCM and i-PrOH (3:1, 10 mL×3). The combined organic layers were dried over Na$_2$SO$_4$, filtered and concentrated under reduced pressure to give a mixture of 2-(5-chloro-7-methoxy-pyrazolo[4,3-d]pyrimidin-1-yl)acetamide (900 mg, 3.72 mmol, 98.21% yield) and 2-(5-chloro-7-methoxy-pyrazolo[4,3-d]pyrimidin-2-yl)acetamide as white solid. $^1$H NMR (DMSO-d$_6$, 400 MHz) δ 8.26 (s, 1H), 5.12 (s, 2H), 4.11 (s, 3H).

Preparation of 2-(5-chloro-7-methoxy-1H-pyrazolo[4,3-d]pyrimidin-1-yl)-N-((2-(trimethylsilyl)ethoxy)methyl)acetamide

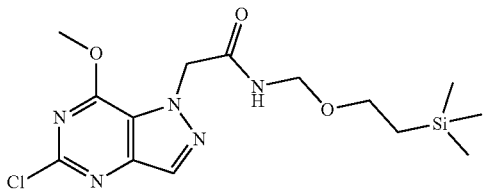 [SMILES: COc1nc(Cl)nc2cnn(CC(=O)NCOCC[Si](C)(C)C)c12]

To a mixture of 2-(5-chloro-7-methoxy-pyrazolo[4,3-d]pyrimidin-1-yl)acetamide (392 mg, 1.62 mmol, 1 eq) and 2-(5-chloro-7-methoxy-pyrazolo[4,3-d]pyrimidin-2-yl)acetamide (1.00 eq) in DMF (5 mL) was added DIEA (1.05 g, 8.11 mmol, 1.41 mL, 5 eq) and SEM-Cl (1.03 g, 6.16 mmol, 1.09 mL, 3.8 eq) at 0° C. dropwise. Then the mixture was stirred at 40° C. for 10 hours. TLC showed the reaction was completed. The mixture was poured into H$_2$O (5 mL) and adjusted to pH=7 with HCl (3 M) at 0° C. The mixture was extracted with EtOAc (8 mL×3). The combined organic layers were dried over Na$_2$SO$_4$, filtered and concentrated under reduced pressure. The residue was purified by flash silica gel chromatography (Biotage®; 4 g SepaFlash® Silica Flash Column, Eluent of 055% Ethyl acetate/Petroleum ether gradient at 40 mL/min). The eluent was concentrated under reduced pressure to give 2-(5-chloro-7-methoxy-pyrazolo[4,3-d]pyrimidin-1-yl)-N-(2-trimethylsilylethoxymethyl)acetamide (30 mg, 80.67 μmol, 4.97% yield) and 2-(5-chloro-7-methoxy-pyrazolo[4,3-d]pyrimidin-2-yl)-N-(2-trimethylsilylethoxymethyl)acetamide (60 mg, 161.34 μmol, 9.94% yield) as white solid. $^1$H NMR (DMSO-d$_6$, 400 MHz) δ 8.29 (s, 1H), 5.21 (s, 2H), 4.53 (d, J=6.8 Hz, 2H), 4.11 (s, 3H), 3.44 (t, J=8.4 Hz, 2H), 1.24 (s, 2H), −0.02 (s, 9H).

Preparation of 2-(5-chloro-7-oxo-6,7-dihydro-1H-pyrazolo[4,3-d]pyrimidin-1-yl)-N-((2-(trimethylsilyl)ethoxy)methyl)acetamide (Step 2 in Scheme C-3)

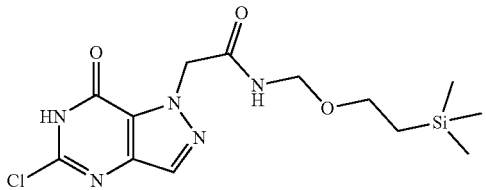 [SMILES: C[Si](C)(C)CCOCNC(=O)Cn1ncc2nc(Cl)[nH]c(=O)c21]

To a solution of 2-(5-chloro-7-methoxy-pyrazolo[4,3-d]pyrimidin-1-yl)-N-(2-trimethylsilyl ethoxymethyl)acetamide (75 mg, 201.67 mol, 1 eq) in MeOH (1 mL) and H$_2$O (1 mL) was added LiOHH$_2$O (25.39 mg, 605.01 μmol, 3 eq). The mixture was stirred at 25° C. for 10 hours. LCMS showed the reaction was complete. The mixture was concentrated under reduced pressure and then the aqueous was adjusted to pH=7 with HCl (2 M). The aqueous was extracted with EtOAc (3 mL×3). The combined organic layers were dried over Na$_2$SO$_4$, filtered and concentrated under reduced pressure to give 2-(5-chloro-7-oxo-6H-pyrazolo[4,3-d]pyrimidin-1-yl)-N-(2-trimethylsilylethoxymethyl)acetamide (72 mg, 201.19 μmol, 99.76% yield) as white solid. $^1$H NMR (DMSO-d$_6$, 400 MHz) δ 7.99 (s, 1H), 5.19 (s, 2H), 4.52 (d, J=6.4 Hz, 2H), 3.49~3.41 (m, 2H), 0.84~0.82 (m, 2H), −0.02 (s, 9H).

Preparation of 2-(5-((3,4-dichlorobenzyl)amino)-7-oxo-6,7-dihydro-1H-pyrazolo[4,3-d]pyrimidin-1-yl)-N-((2-(trimethylsilyl)ethoxy)methyl)acetamide (Step 3 in Scheme C-3)

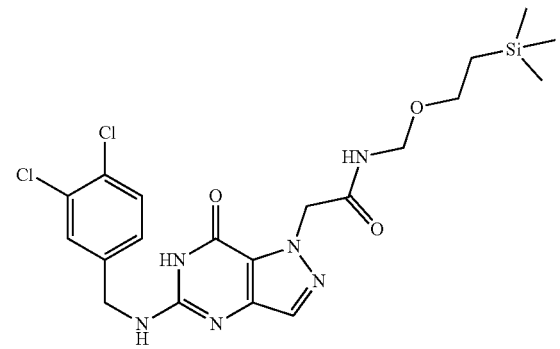 [SMILES: C[Si](C)(C)CCOCNC(=O)Cn1ncc2nc(NCc3ccc(Cl)c(Cl)c3)[nH]c(=O)c21]

A solution of 2-(5-chloro-7-oxo-6H-pyrazolo[4,3-d]pyrimidin-1-yl)-N-(2-trimethylsilylethoxy methyl)acetamide (50 mg, 139.72 μmol, 1 eq) and (3,4-dichlorophenyl)methananmine (49.19 mg, 279.43 mol, 37.27 μL, 2 eq) in t-BuOH (2 mL) was stirred at 110° C. for 10 hours. LCMS showed the reaction was completed. The mixture was concentrated under reduced pressure. The residue was purified by prep-HPLC (column: Welch Xtimate C18 100 mm×25 mm 3 μm; mobile phase: [water (0.1% TFA)-MeCN]; B %: 40%-60%, 12 mins). The mixture was dried under freeze-dry. The residue was purified by prep-HPLC (column: Phenomenex Luna C18 150 mm×30 mm 5 μm; mobile phase: [water (0.1% TFA)-MeCN]; B %: 45%-65%, 12 mins) for the second time. The mixture was dried under freeze-dry to give 2-[5-[(3,4-dichlorophenyl)methylamino]-7-oxo-6H-pyrazolo[4,3-d]pyrimidin-1-yl]-N-(2-trimethylsilylethoxymethyl)acetamide (5.4 mg, 10.20 μmol, 7.30% yield, 94.00% purity) as white solid $^1$H NMR (DMSO-d$_6$, 400 MHz) δ 11.08 (s, 1H), 8.71 (t, J=6.0 Hz, 1H), 7.58~7.55 (m, 3H), 7.31 (dd, J=2.0 Hz, 8.4 Hz, 1H), 6.64 (s, 1H), 5.06 (s, 2H), 4.47 (t, J=6.4 Hz, 4H), 3.40 (s, 2H), 0.82~0.77 (m, 2H), −0.04 (s, 9H). HPLC: 94.00% (220 nm), 92.65% (215 nm), 76.77% (254 nm). MS (ESI): mass calcd. For C$_{20}$H$_{26}$C$_{12}$N$_6$O$_3$Si 496.12, m/z found 497.1 [M+H]$^+$.

Compound 198

Preparation of 5-(5-((3,4-dichlorobenzyl)amino)-7-oxo-6,7-dihydro-1H-pyrazolo[4,3-d]pyrimidin-1-yl)-N,2,2-trimethylpentanamide Compound 199
5-(5-((3,4-Dichlorobenzyl)amino)-7-oxo-6,7-dihydro-1H-pyrazolo[4,3-d]pyrimidin-1-yl)-2,2-dimethylpentanoic acid was prepared according to the procedures described herein for Steps 1-3 in Scheme C-3.

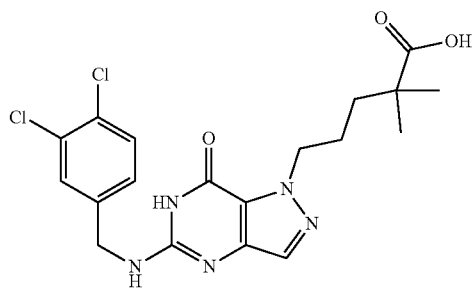 [SMILES: CC(C)(CCCn1ncc2nc(NCc3ccc(Cl)c(Cl)c3)[nH]c(=O)c21)C(=O)O]

The procedure yielded the desired compound 5-[5-[(3,4-dichlorophenyl)methylamino]-7-oxo-6H-pyrazolo[4,3-d]pyrimidin-1-yl]-2,2-dimethyl-pentanoic acid (93.4 mg, 212.99 µmol, 42.42% yield, 99.953% purity) as a white solid. 26.3 mg was delivered. $^1$H NMR (DMSO-d$_6$, 400 MHz) δ 7.65~7.51 (m, 3H), 7.33 (d, J=8.0 Hz, 1H), 6.80 (s, 1H), 4.48 (d, J=4.4 Hz, 2H), 4.39 (s, 2H), 1.72 (s, 2H), 1.44~1.33 (m, 2H), 1.03 (s, 6H). HPLC: 99.95% (220 nm), 99.94% (215 nm), 100.00% (254 nm). MS (ESI): mass calcd. For $C_{19}H_{21}C2N_5O_3$ 437.10, m/z found 438.1 [M+H]$^+$.

Preparation of 5-(5-((3,4-dichlorobenzyl)amino)-7-oxo-6,7-dihydro-1H-pyrazolo[4,3-d]pyrimidin-1-yl)-N,2,2-trimethylpentanamide

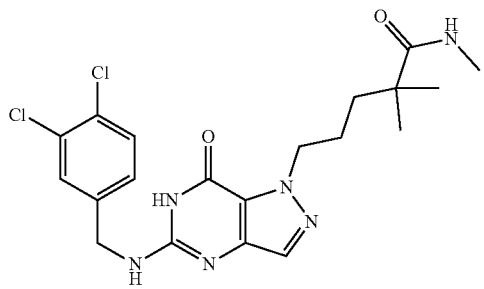 [SMILES: CNC(=O)C(C)(C)CCCn1ncc2nc(NCc3ccc(Cl)c(Cl)c3)[nH]c(=O)c21]

A mixture of 5-[5-[(3,4-dichlorophenyl)methylamino]-7-oxo-6H-pyrazolo[4,3-d]pyrimidin-1-yl]-2,2-dimethyl-pentanoic acid (30 mg, 68.45 µmol, 1 eq), methanamine hydrochloride (9.24 mg, 136.89 µmol, 2 eq), EDCl (15.75 mg, 82.13 µmol, 1.2 eq), HOBt (1.85 mg, 13.69 µmol, 0.2 eq) and DIEA (26.54 mg, 205.34 µmol, 35.77 µL, 3 eq) in DMF (1 mL) was stirred at 20° C. for 16 hours. LC-MS showed the reaction was complete. After filtered, the filtrate was purified by prep-HPLC (column: Phenomenex Luna C18 150 mm×30 mm 5 µm; mobile phase: [water (0.05% HCl)-MeCN]; B %: 15%-35%, 12 mins). The aqueous solution was lyophilized to give compound 5-[5-[(3,4-dichlorophenyl)methylamino]-7-oxo-6H-pyrazolo[4,3-d]pyrimidin-1-yl]-N,2,2-trimethyl-pentanamide (12.7 mg, 27.80 µmol, 40.62% yield, 98.800% purity) as off white solid. $^1$H NMR (DMSO-d$_6$, 400 MHz) δ 7.64 (d, J=1.2 Hz, 1H), 7.61 (t, J=3.6 Hz, 2H), 7.36 (d, J=6.8 Hz, 2H), 4.56 (d, J=4.4 Hz, 2H), 4.37 (t, J=6.8 Hz, 2H), 2.52 (s, 3H), 1.72~1.55 (m, 2H), 1.42~1.29 (m, 2H), 1.00 (s, 6H). HPLC: 98.80% (220 nm), 98.35% (215 nm), 98.34% (254 nm). MS (ESI): mass calcd. For $C_{20}H_{24}C_{12}N_6O_2$ 450.13, m/z found 451.1 [M+H]$^+$.

Compound 200

Preparation of 5-(5-((3,4-dichlorobenzyl)amino)-7-oxo-6,7-dihydro-1H-pyrazolo[4,3-d]pyrimidin-1-yl)-N-methyl-2-phenylpentanamide Preparation of diethyl 2-(3-(5-chloro-7-methoxy-1H-pyrazolo[4,3-d]pyrimidin-1-yl)propyl)-2-phenyl-malonate (Step 1 in Scheme C-3)

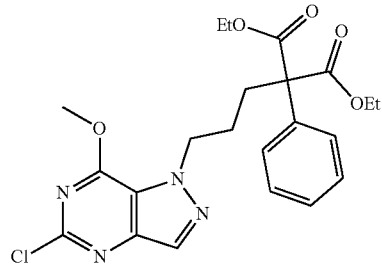 [SMILES: CCOC(=O)C(CCCn1ncc2nc(Cl)nc(OC)c21)(C(=O)OCC)c1ccccc1]

A mixture of 5-chloro-7-methoxy-1H-pyrazolo[4,3-d]pyrimidine (300 mg, 1.63 mmol, 1 eq), diethyl 2-(3-bromopropyl)-2-phenyl-propanedioate (870.92 mg, 2.44 mmol, 470.47 µL, 1.5 eq) and Cs$_2$CO$_3$ (1.06 g, 3.25 mmol, 2 eq) in DMF (3 mL) was stirred at 25° C. for 5 hours. TLC showed the reaction was complete. The reaction mixture was quenched with H$_2$O (5 mL), and extracted with EtOAc (5 mL×3). The combined organic layers were washed with brine (5 mL×3), dried over Na$_2$SO$_4$, filtered and concentrated under reduced pressure. The residue was purified by flash silica gel chromatography (Biotage®; 4 g SepaFlash® Silica Flash Column, Eluent of 040% Ethyl acetate/Petroleum ether gradient at 65 mL/min). The eluent was removed under reduced pressure. Compound diethyl 2-[3-(5-chloro-7-methoxy-pyrazolo[4,3-d]pyrimidin-1-yl)propyl]-2-phenyl-propanedioate (450 mg, 976.33 µmol, 60.07% yield) was obtained as colorless oil. $^1$H NMR (CDCl$_3$, 400 MHz) δ 7.99 (s, 1H), 7.27 (s, 5H), 4.51 (t, J=6.8 Hz, 2H), 4.22~4.16 (m, 7H), 2.29~2.25 (m, 2H), 1.88~1.84 (m, 2H), 1.25~1.18 (m, 6H). Compound diethyl 2-[3-(5-chloro-7-methoxy-pyrazolo[4,3-d]pyrimidin-2-yl)propyl]-2-phenyl-propanedioate (270 mg, 585.80 µmol, 36.04% yield) was obtained as colorless oil. H NMR (CDCl$_3$, 400 MHz) δ 7.94 (s, 1H), 7.32~7.27 (m, 5H), 4.40 (t, J=7.2 Hz, 2H), 4.24~4.20 (m, 7H), 2.29~2.24 (m, 2H), 2.00~1.96 (m, 2H), 1.23~1.20 (m, 6H).

Preparation of 5-(5-chloro-7-oxo-6,7-dihydro-1H-pyrazolo[4,3-d]pyrimidin-1-yl)-2-phenylpentanoic Acid

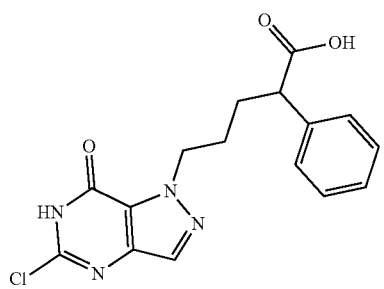 [SMILES: O=C(O)C(CCCn1ncc2nc(Cl)[nH]c(=O)c21)c1ccccc1]

A mixture of diethyl 2-[3-(5-chloro-7-methoxy-pyrazolo[4,3-d]pyrimidin-1-yl)propyl]-2-phenyl-propanedioate (200 mg, 433.92 mol, 1 eq) and NaOH (104.13 mg, 2.60 mmol, 6 eq) in MeOH (1 mL) and $H_2O$ (1 mL) was stirred at 80° C. for 3 hours. LC-MS showed the reaction was complete. The reaction mixture was concentrated under reduced pressure. The aqueous was made pH=6 with 3N HCl and extracted with EtOAc (6 mL×3). The combined organic layers were washed with brine (6 mL), dried over $Na_2SO_4$, filtered and concentrated under reduced pressure. Compound 5-(5-chloro-7-oxo-6H-pyrazolo[4,3-d]pyrimidin-1-yl)-2-phenyl-pentanoic acid (175 mg, crude) was obtained as white solid. $^1$H NMR (DMSO-$d_6$, 400 MHz) δ 13.27 (s, 1H), 12.25 (s, 1H), 7.94 (s, 1H), 7.29~7.20 (m, 5H), 4.51 (t, J=6.4 Hz, 2H), 3.49 (t, J=7.6 Hz, 1H), 1.90~1.58 (m, 4H).

Compound 201

Preparation of 5-(5-((3,4-dichlorobenzyl)amino)-7-oxo-6,7-dihydro-1H-pyrazolo[4,3-d]pyrimidin-1-yl)-2-phenylpentanoic acid (Step 3 in Scheme C-3)

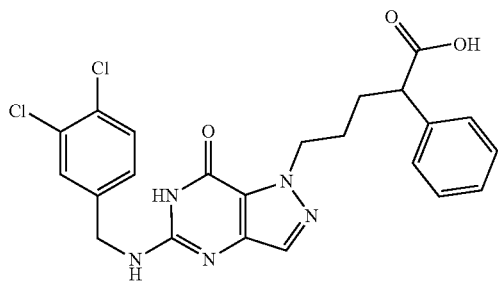 [SMILES: O=C(O)C(CCCn1ncc2nc(NCc3ccc(Cl)c(Cl)c3)[nH]c(=O)c21)c1ccccc1]

A mixture of 5-(5-chloro-7-oxo-6H-pyrazolo[4,3-d]pyrimidin-1-yl)-2-phenyl-pentanoic acid (175 mg, 504.66 μmol, 1 eq) and (3,4-dichlorophenyl)methanamine (177.68 mg, 1.01 mmol, 134.61 μL, 2 eq) in 2-methyl-2-butanol (3 mL) was stirred at 140° C. for 4 hours. LC-MS showed the reaction was complete. The reaction mixture was concentrated under reduced pressure. The residue was purified by prep-HPLC (column: Nano-micro Kromasil C18 100 mm×30 mm 8 μm; mobile phase: [water (0.1% TFA)-MeCN]; B %: 45%-60%, 10 mins). The solvent was removed under freeze drying. Compound 5-[5-[(3,4-dichlorophenyl)methylamino]-7-oxo-6H-pyrazolo[4,3-d]pyrimidin-1-yl]-2-phenyl-pentanoic acid (131.2 mg, 264.99 μmol, 52.51% yield, 98.23% purity) was obtained as white solid. 31.2 mg was delivered. $^1$H NMR (DMSO-$d_6$, 400 MHz) δ 7.60~7.56 (m, 3H), 7.34~7.20 (m, 6H), 6.82 (s, 1H), 4.48 (d, J=5.2 Hz, 2H), 4.42 (t, J=6.0 Hz, 2H), 3.49 (t, J=8.0 Hz, 1H), 1.87~1.82 (m, 1H), 1.76~1.70 (m, 1H), 1.68~1.62 (m, 1H), 1.60~1.51 (m, 1H). HPLC: 98.23% (220 nm), 97.82% (215 nm), 100.00% (254 nm). MS (ESI): mass calcd. For $C_{23}H_{21}C_{12}N_5O_3$ 485.10, m/z found 486.1 [M+H]$^+$.

Preparation of 5-(5-((3,4-dichlorobenzyl)amino)-7-oxo-6,7-dihydro-1H-pyrazolo[4,3-d]pyrimidin-1-yl)-N-methyl-2-phenylpentanamide

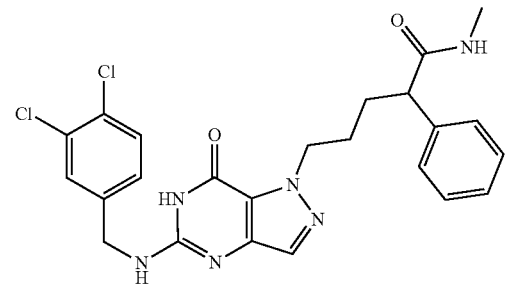 [SMILES: CNC(=O)C(CCCn1ncc2nc(NCc3ccc(Cl)c(Cl)c3)[nH]c(=O)c21)c1ccccc1]

A mixture of 5-[5-[(3,4-dichlorophenyl)methylamino]-7-oxo-6H-pyrazolo[4,3-d]pyrimidin-1-yl]-2-phenyl-pentanoic acid (30 mg, 61.68 μmol, 1 eq), methanamine hydrochloride (8.33 mg, 123.37 μmol, 2 eq), DIEA (23.92 mg, 185.05 μmol, 32.23 μL, 3 eq), HOBt (1.67 mg, 12.34 μmol, 0.2 eq) and EDCl (14.19 mg, 74.02 μmol, 1.2 eq) in DMF (0.5 mL) was stirred at 25° C. for 12 hours. LC-MS showed the reaction was complete. The reaction mixture was filtered to removed the insoluble. The filtrate was purified by prep-HPLC (HCl condition column: Phenomenex Luna C18 150 mm×30 mm 5 μm; mobile phase: [water (0.04% HCl)-MeCN]; B %: 25%-50%, 12 mins). The solvent was removed under freeze drying. Compound 5-[5-[(3,4-dichlorophenyl)methylamino]-7-oxo-6H-pyrazolo[4,3-d]pyrimidin-1-yl]-N-methyl-2-phenyl-pentanamide (13.8 mg, 27.59 μmol, 44.73% yield, 99.85% purity) was obtained as white solid. $^1$H NMR (DMSO-$d_6$, 400 MHz) δ 7.94 (s, 1H), 7.78 (s, 1H), 7.65~7.60 (m, 3H), 7.37 (d, J=7.2 Hz, 1H), 7.24~7.19 (m, 5H), 4.57 (s, 2H), 4.42 (s, 2H), 3.38 (s, 1H), 2.50 (s, 3H), 1.85~1.84 (m, 1H), 1.71~1.57 (m, 2H), 1.53~1.51 (m, 1H). HPLC: 99.85% (220 nm), 99.93% (215 nm), 99.21% (254 nm). MS (ESI): mass calcd. For $C_{24}H_{24}C2N_6O_2$ 498.13, m/z found 499.1 [M+H]$^+$.

Compound 202

Preparation of 5-(5-((3,4-dichlorobenzyl)amino)-7-oxo-6,7-dihydro-1H-pyrazolo[4,3-d]pyrimidin-1-yl)-2-methylpentanoic acid diethyl 2-(3-(5-chloro-7-methoxy-1H-pyrazolo[4,3-d]pyrimidin-1-yl)propyl)-2-methylmalonate was prepared according to the procedure described herein for Step 1 in Scheme C-3.

157

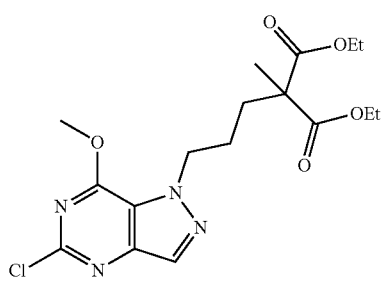 [SMILES: CCOC(=O)C(C)(CCCn1ncc2nc(Cl)nc(OC)c21)C(=O)OCC]

A mixture of 5-chloro-7-methoxy-H-pyrazolo[4,3-d]pyrimidine (0.3 g, 1.63 mmol, 1 eq), diethyl 2-(3-bromopropyl)-2-methyl-propanedioate (623.65 mg, 2.11 mmol, 201.22 µL, 1.3 eq) and Cs$_2$CO$_3$ (1.06 g, 3.25 mmol, 2 eq) in DMF (2 mL) was stirred at 25° C. for 4 hours. TLC indicated the reaction was complete. The reaction mixture was quenched with H$_2$O (15 mL) at 20° C., and then extracted with EtOAc (15 mL×3). The combined organic layers were washed with brine (10 mL), dried over Na$_2$SO$_4$, filtered and concentrated under reduced pressure. The residue was purified by flash silica gel chromatography (Biotage®; 12 g SepaFlash® Silica Flash Column, Eluent of 0~30% Ethyl acetate/Petroleum ether gradient @35 mL/min). The eluent was removed under reduced pressure. Compound diethyl 2-[3-(5-chloro-7-methoxy-pyrazolo[4,3-d]pyrimidin-1-yl) propyl]-2-methyl-propanedioate (440 mg, 1.10 mmol, 67.88% yield) was obtained as white solid. $^1$H NMR (DMSO-d$_6$, 400 MHz) δ 8.25 (s, 1H), 4.51 (t, J=5.6 Hz, 2H), 4.16 (s, 3H), 4.05 (q, J=7.2 Hz, 4H), 1.73 (s, 4H), 1.27 (s, 3H), 1.09 (t, J=6.8 Hz, 6H).

Preparation of 5-(5-((3,4-dichlorobenzyl)amino)-7-oxo-6,7-dihydro-1H-pyrazolo[4,3-d]pyrimidin-1-yl)-2-methylpentanoic acid (Step 2 in Scheme C-3)

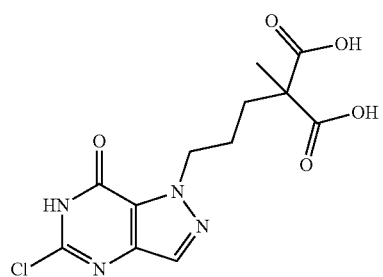 [SMILES: CC(CCCn1ncc2nc(Cl)[nH]c(=O)c21)(C(=O)O)C(=O)O]

A mixture of diethyl 2-[3-(5-chloro-7-methoxy-pyrazolo[4,3-d]pyrimidin-1-yl) propyl]-2-methyl-propanedioate (380 mg, 952.76 mol, 1 eq) and NaOH (266.77 mg, 6.67 mmol, 7 eq) in H$_2$O (2 mL) and MeOH (2 mL) was stirred at 100° C. for 3 hours. LC-MS showed the reaction was complete. The reaction mixture was concentrated under reduced pressure. The aqueous was adjusted to pH=5 with HCl (3M), and extracted with EtOAc (10 mL×3). The combined organic layers were washed with brine (5 mL), dried over Na$_2$SO$_4$, filtered and concentrated under reduced pressure. Compound 2-[3-(5-chloro-7-hydroxy-pyrazolo[4,3-d]pyrimidin-2-yl)propyl]-2-methyl-propanedioic acid (230 mg, 699.71 µmol, 73.44% yield) was obtained as white solid. $^1$H NMR (DMSO-d$_6$, 400 MHz) δ 13.27 (s, 1H), 12.66 (s, 1H), 7.96 (s, 1H), 4.50 (t, J=6.4 Hz, 2H), 1.80~1.69 (m, 2H), 1.68~1.60 (m, 2H), 1.20 (s, 3H).

158

Preparation of 5-(5-((3,4-dichlorobenzyl)amino)-7-oxo-6,7-dihydro-1H-pyrazolo[4,3-d]pyrimidin-1-yl)-2-methylpentanoic Acid

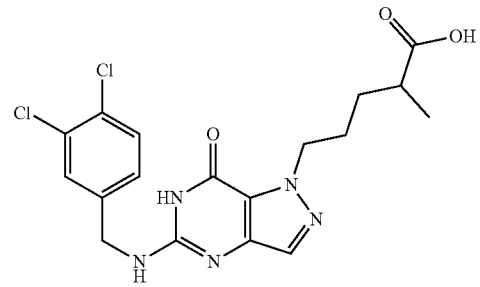 [SMILES: CC(CCCn1ncc2nc(NCc3ccc(Cl)c(Cl)c3)[nH]c(=O)c21)C(=O)O]

A mixture of 2-[3-(5-chloro-7-hydroxy-pyrazolo[4,3-d]pyrimidin-2-yl)propyl]-2-methyl-propanedioic acid (170 mg, 517.18 µmol, 1 eq) and (3,4-dichlorophenyl)methanamine (182.09 mg, 1.03 mmol, 137.95 µL, 2 eq) in 2-methylbutan-2-ol (3 mL) was stirred at 140° C. for 16 hours. LC-MS showed the reaction was complete. The reaction mixture was concentrated under reduced pressure. The residue was purified by prep-HPLC (column: Nano-micro Kromasil C18 100 mm×30 mm 8 µm; mobile phase: [water (0.1% TFA)-MeCN]; B %: 30%-50%, 10 mins). The aqueous solution was removed under lyophilization to give compound 5-[5-[(3,4-dichlorophenyl)methylamino]-7-oxo-6H-pyrazolo[4,3-d]pyrimidin-1-yl]-2-methyl-pentanoic acid (80 mg, 187.63 µmol, 36.28% yield, 99.510% purity) as white solid. 30.0 mg was delivered. H NMR (DMSO-d$_6$, 400 MHz) δ 7.65~7.55 (m, 3H), 7.33 (dd, J=2.0 Hz, 8.4 Hz, 1H), 6.84 (s, 1H), 4.49 (d, J=5.6 Hz, 2H), 4.41 (t, J=7.2 Hz, 2H), 2.35~2.26 (m, 1H), 1.76 (m, 2H), 1.53~1.41 (m, 1H), 1.31~1.19 (m, 1H), 1.00 (d, J=6.8 Hz, 3H). HPLC: 99.51% (220 nm), 99.27% (215 nm), 100.00% (254 nm). MS (ESI): mass calcd. For C$_{18}$H$_{19}$C$_{12}$N$_5$O$_3$ 423.09, m/z found 424.1 [M+H]$^+$.

Compound 203

Preparation of ethyl 5-(5-((3,4-dichlorobenzyl)amino)-7-oxo-6,7-dihydro-1H-pyrazolo[4,3-d]pyrimidin-1-yl)pentanoate

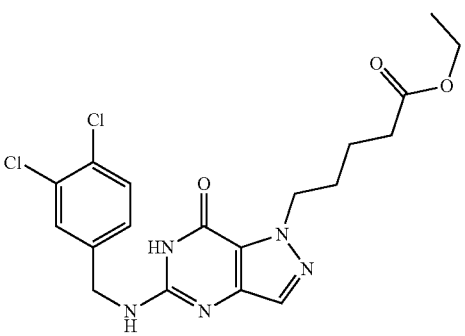 [SMILES: CCOC(=O)CCCCn1ncc2nc(NCc3ccc(Cl)c(Cl)c3)[nH]c(=O)c21]

To a solution of 5-[5-[(3,4-dichlorophenyl)methylamino]-7-oxo-6H-pyrazolo[4,3-d]pyrimidin-1-yl]pentanoic acid (60 mg, 146.25 µmol, 1 eq) (steps 1-3 in Scheme C-3) in EtOH (2 mL) was added SOCl$_2$ (87.00 mg, 731.25 µmol, 53.05 µL, 5 eq) dropwise at 0° C. Then the mixture was stirred at 80°

C. for 10 hours. LCMS showed the reaction was complete. There was some white solid formed. The solid was collected after filtered and then concentrated under reduced pressure. Compound ethyl 5-[5-[(3,4-dichlorophenyl)methylamino]-7-oxo-6H-pyrazolo[4,3-d]pyrimidin-1-yl]pentanoate (57.1 mg, 127.37 µmol, 87.09% yield, 97.77% purity) was obtained as white solid. $^1$H NMR (DMSO-$d_6$, 400 MHz) δ 7.62~7.59 (m, 3H), 7.35 (dd, J=2.0 Hz, 8.4 Hz, 1H), 7.26 (s, 1H), 4.52 (d, J=5.2 Hz, 2H), 4.43 (t, J=6.8 Hz, 2H), 4.02 (t, J=7.2 Hz, 2H), 2.28 (t, J=7.2 Hz, 2H), 1.80~1.76 (m, 2H), 1.44~1.41 (m, 2H), 1.14 (t, J=7.2 Hz, 3H). HPLC: 97.77% (220 nm), 97.72% (215 nm), 98.01% (254 nm). MS (ESI): mass calcd. For $C_{19}H_{21}C_{12}N_5O_3$ 437.10 m/z found 438.0 [M+H]$^+$.

Compound 204

Preparation of isopropyl 5-(5-((3,4-dichlorobenzyl)amino)-7-oxo-6,7-dihydro-1H-pyrazolo[4,3-d]pyrimidin-1-yl)pentanoate

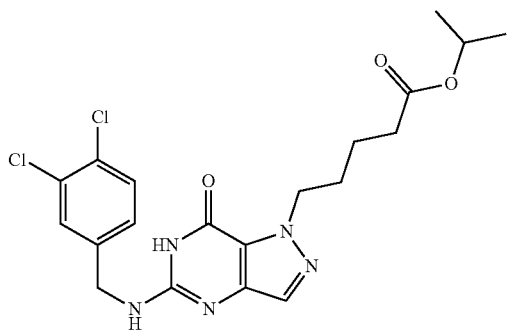 [SMILES: CC(C)OC(=O)CCCCn1ncc2nc(NCc3ccc(Cl)c(Cl)c3)[nH]c(=O)c21]

To a solution of 5-[5-[(3,4-dichlorophenyl)methylamino]-7-oxo-6H-pyrazolo[4,3-d]pyrimidin-1-yl]pentanoic acid (40 mg, 97.50 µmol, 1 eq) (steps 1-3 in Scheme C-3) in i-PrOH (1 mL) was added $SOCl_2$ (58.00 mg, 487.50 µmol, 35.36 µL, 5 eq) dropwise at 0° C. Then the mixture was stirred at 80° C. for 20 hours. LCMS showed the reaction was complete. There was some white solid formed. The solid was collected after filtered and then concentrated under reduced pressure. Compound isopropyl 5-[5-[(3,4-dichlorophenyl)methylamino]-7-oxo-6H-pyrazolo[4,3-d]pyrimidin-1-yl]pentanoate (23.9 mg, 51.15 µmol, 52.46% yield, 96.81% purity) was obtained as white solid. $^1$H NMR (DMSO-$d_6$, 400 MHz) δ 7.61~7.59 (m, 3H), 7.33 (d, J=2.0 Hz, 8.0 Hz, 1H), 4.85~4.82 (m, 1H), 4.51 (d, J=5.6 Hz, 2H), 4.42 (t, J=6.4 Hz, 2H), 2.24 (t, J=7.6 Hz, 2H), 1.79~1.75 (m, 2H), 1.43~1.40 (m, 2H), 1.13 (d, J=6.0 Hz, 6H). HPLC: 96.81% (220 nm), 96.76% (215 nm), 94.56% (254 nm). MS (ESI): mass calcd. For $C_{20}H_{23}C_{12}N_5O_3$ 451.12 m/z found 452.1 [M+H]$^+$.

Compound 205

Preparation of ethyl 4-(5-((3,4-dichlorobenzyl)amino)-7-oxo-6,7-dihydro-1H-pyrazolo[4,3-d]pyrimidin-1-yl)butanoate

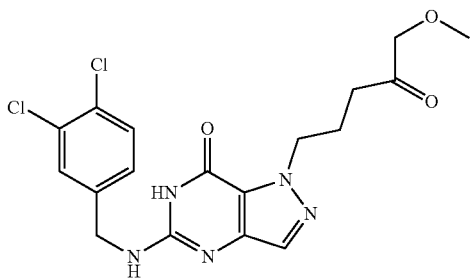 [SMILES: COCC(=O)CCCn1ncc2nc(NCc3ccc(Cl)c(Cl)c3)[nH]c(=O)c21]

To a solution of 4-[5-[(3,4-dichlorophenyl)methylamino]-7-oxo-6H-pyrazolo[4,3-d]pyrimidin-1-yl]butanoic acid (45 mg, 113.57 µmol, 1 eq) (steps 1-3 in Scheme C-3) in EtOH (5 mL) was added $SOCl_2$ (67.56 mg, 567.86 µmol, 41.19 µL, 5 eq) at 0° C. The mixture was stirred at 80° C. for 16 hours. LC-MS showed the reaction was complete. The reaction mixture was filtered to removed the insoluble and concentrated under reduced pressure to remove solvent. The residue was purified by prep-HPLC (column: Nano-micro Kromasil C18 100 mm×30 mm 8 µm; mobile phase: [water (0.1% TFA)-MeCN]; B %: 30%-60%, 10 mins). The aqueous solution was lyophilized to give compound. Compound ethyl 4-[5-[(3,4-dichlorophenyl)methylamino]-7-oxo-6H-pyrazolo[4,3-d]pyrimidin-1-yl]butanoate (15.6 mg 36.65 µmol, 32.27% yield, 99.67% purity) was obtained as light yellow solid. $^1$H NMR (DMSO-$d_6$, 400 MHz) δ 7.66~7.59 (m, 3H), 7.37 (dd, J=2.0 Hz, 8.4 Hz, 1H), 4.57 (d, J=4.8 Hz, 2H), 4.46 (t, J=6.8 Hz, 2H), 3.99 (d, J=7.2 Hz, 2H), 2.25 (t, J=7.2 Hz, 2H), 2.07~2.00 (m, 2H), 1.14 (t, J=6.8 Hz, 3H). HPLC: 99.67% (220 nm), 99.65% (215 nm), 100.00% (254 nm). MS (ESI): mass calcd. For $C_{18}H_{19}C2N_5O_3$ 423.09, m/z found 424.1 [M+H]$^+$.

Compound 206

Preparation of isopropyl 4-(5-((3,4-dichlorobenzyl)amino)-7-oxo-6,7-dihydro-1H-pyrazolo[4,3-d]pyrimidin-1-yl)butanoate

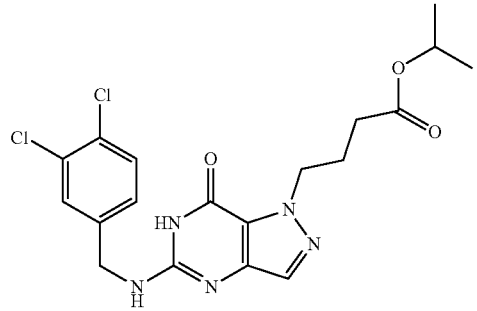 [SMILES: CC(C)OC(=O)CCCn1ncc2nc(NCc3ccc(Cl)c(Cl)c3)[nH]c(=O)c21]

To a solution of 4-[5-[(3,4-dichlorophenyl)methylamino]-7-oxo-6H-pyrazolo[4,3-d]pyrimidin-1-yl]butanoic acid (steps 1-3 in Scheme C-3) (45 mg, 113.57 µmol, 1 eq) in i-PrOH (5 mL) was added $SOCl_2$ (67.56 mg, 567.86 µmol, 41.19 µL, 5 eq) at 0° C. The mixture was stirred at 80° C. for 16 hours. LC-MS showed the reaction was complete. The reaction mixture was filtered to removed the insoluble and concentrated under reduced pressure to remove solvent. The residue was purified by prep-HPLC (column: Nano-micro Kromasil C18 100 mm×30 mm 8 µm mobile phase: [water (0.1% TFA)-MeCN]; B %: 35%-55%, 10 mins). The aqueous solution was lyophilized to give compound. Compound isopropyl 4-[5-[(3,4-dichlorophenyl)methylamino]-7-oxo-6H-pyrazolo[4,3-d]pyrimidin-1-yl]butanoate (17.0 mg, 38.79 µmol, 34.15% yield, 100.00% purity) was obtained as white solid. $^1$H NMR (DMSO-$d_6$, 400 MHz) δ 7.67~7.58 (m, 3H), 7.36 (dd, J=2.0 Hz, 8.4 Hz, 1H), 4.86~4.80 (m, 1H), 4.55 (d, J=5.6 Hz, 2H), 4.46 (t, J=6.4 Hz, 2H), 2.20 (t, J=7.6 Hz, 2H), 2.05~1.98 (m, 2H), 1.14 (d, J=6.4 Hz, 6H). HPLC: 100.00% (220 nm), 100.00% (215 nm), 100.00% (254 nm). MS (ESI): mass calcd. For $C_{19}H_{21}C_{12}N_5O_3$ 437.10, m/z found 438.1 [M+H]$^+$.

Compound 207

Preparation of 5-((3,4-dichlorobenzyl)amino)-1-(((2R,5R)-5-(hydroxymethyl)-1,4-dioxan-2-yl)methyl)-1H-pyrazolo[4,3-d]pyrimidin-7(6H)-one Preparation of ((2R,5R)-5-((5-chloro-7-methoxy-1H-pyrazolo[4,3-d]pyrimidin-1-yl)methyl)-1,4-dioxan-2-yl)methanol and ((2S,5R)-5-((5-chloro-7-methoxy-1H-pyrazolo[4,3-d]pyrimidin-1-yl)methyl)-1,4-dioxan-2-yl)methanol (Step 1 in Scheme C-3)

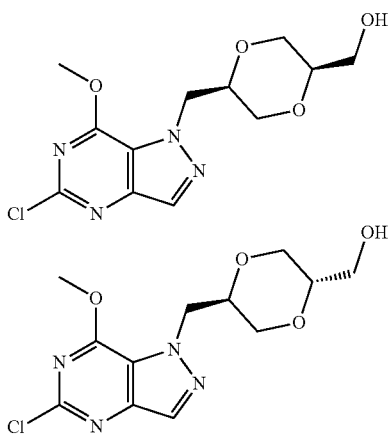

To a solution of ((2S,5R)-5-(iodomethyl)-1,4-dioxan-2-yl)methanol (838.82 mg, 3.25 mmol, 2 eq) and ((2R,5R)-5-(iodomethyl)-1,4-dioxan-2-yl)methanol and 5-chloro-7-methoxy-1H-pyrazolo[4,3-d]pyrimidine (0.3 g 1.63 mmol, 1 eq) in ACETONE (1 mL) was added Cs$_2$CO$_3$ (1.59 g 4.88 mmol, 3 eq). The mixture was stirred at 70° C. for 16 hours. LCMS showed the reaction was complete. The reaction mixture was filtered to removed the insoluble, filtered and concentrated under reduced pressure. The residue was purified by prep-HPLC (column: Nano-micro Kromasil C18 100 mm×30 mm 8 μm; mobile phase: [water (0.1% TFA)-MeCN]; B %: 10%-30%, 10 mins). The aqueous solution was lyophilized to give compound [(2S,5R)-5-[(5-chloro-7-methoxy-pyrazolo[4,3-d]pyrimidin-1-yl)methyl]-1,4-dioxan-2-yl]methanol (40 mg, 127.10 μmol, 7.82% yield) as off white solid. $^1$H NMR (CDC$_3$, 400 MHz) δ 8.08 (s, 1H), 5.05 (dd, J=8.4 Hz, 14.0 Hz, 1H), 4.62 (dd, J=5.6 Hz, 14.4 Hz, 1H), 4.26~4.24 (m, 3H), 4.21~4.10 (m, 1H), 3.97~3.56 (m, 8H). Compound [(2R,5R)-5-[(5-chloro-7-methoxy-pyrazolo[4,3-d]pyrimidin-1-yl)methyl]-1,4-dioxan-2-yl]methanol (40 mg 127.10 μmol, 7.82% yield) was obtained as off white solid. $^1$H NMR (CDCl$_3$, 400 MHz) δ 8.03~8.01 (m, 1H), 4.60~4.55 (m, 1H), 4.49~4.44 (m, 1H), 4.23~4.18 (m, 3H), 3.95~3.93 (m, 1H), 3.81~3.72 (m, 2H), 3.56~3.35 (m, 6H).

Preparation of 5-chloro-1-(((2R,5R)-5-(hydroxymethyl)-1,4-dioxan-2-yl)methyl)-1H-pyrazolo[4,3-d]pyrimidin-7(6H)-one (Step 2 in Scheme C-3)

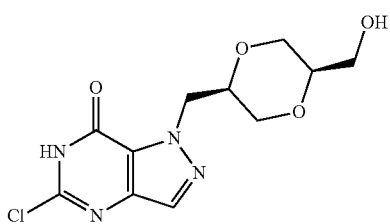 [SMILES: O=c1[nH]c(Cl)nc2cnn(C[C@@H]3CO[C@H](CO)CO3)c12]

To a solution of [(2R,5R)-5-[(5-chloro-7-methoxy-pyrazolo[4,3-d]pyrimidin-1-yl)methyl]-1,4-dioxan-2-yl]methanol (40 mg, 127.10 mol, 1 eq) in MeOH (2 mL) and H$_2$O (2 mL) was added LiOH—H$_2$O (16.00 mg, 381.29 μmol, 3 eq). The mixture was stirred at 25° C. for 3 hours. TLC showed the reaction was complete. The reaction mixture was concentrated under reduced pressure to remove MeOH. And then the mixture was adjusted to pH=4 with HCl (3M) at 0° C., and extracted with EtOAc (10 mL×4). The combined organic layers were dried over Na$_2$SO$_4$, filtered and concentrated under reduced pressure. Compound 5-chloro-1-(((2R,5R)-5-(hydroxymethyl)-1,4-dioxan-2-yl)methyl)-1H-pyrazolo[4,3-d]pyrimidin-7(6H)-one (50 mg, crude) was obtained as white solid. $^1$H NMR (DMSO-d$_6$, 400 MHz) δ 7.99 (s, 1H), 4.81~4.64 (m, 1H), 4.64~4.54 (m, 1H), 4.52~4.44 (m, 1H), 4.09~3.98 (m, 1H), 3.96~3.85 (m, 2H), 3.79~3.72 (m, 2H), 3.29~3.25 (m, 3H), 3.24~3.17 (m, 1H).

Compound 208

Preparation of 5-((3,4-dichlorobenzyl)amino)-1-(((2R,5R)-5-(hydroxymethyl)-1,4-dioxan-2-yl)methyl)-1H-pyrazolo[4,3-d]pyrimidin-7(6H)-one (Step 3 in Scheme C-3)

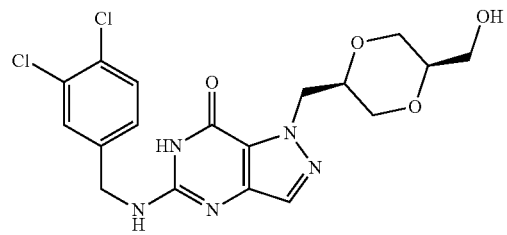 [SMILES: O=c1[nH]c(NCc2ccc(Cl)c(Cl)c2)nc2cnn(C[C@@H]3CO[C@H](CO)CO3)c12]

A mixture of 5-chloro-1-[[(2R,5R)-5-(hydroxymethyl)-1,4-dioxan-2-yl]methyl]-6H-pyrazolo[4,3-d]pyrimidin-7-one (50 mg, 166.28 μmol, 1 eq) and (3,4-dichlorophenyl)methanamine (58.54 mg, 332.56 μmol, 44.35 μL, 2 eq) in t-BuOH (1 mL) and 2-methylbutan-2-ol (1 mL) was stirred at 105° C. for 32 hours. LCMS showed the reaction was complete. The reaction mixture was concentrated under reduced pressure to remove solvent. The residue was purified by prep-HPLC (column: Nano-micro Kromasil C18 100 mm×30 mm 8 μm; mobile phase: [water (0.1% TFA)-MeCN]; B %: 20%-40%, 10 mins). The aqueous solution was lyophilized to give compound 5-((3,4-dichlorobenzyl)amino)-1-(((2R,5R)-5-(hydroxymethyl)-1,4-dioxan-2-yl)methyl)-1H-pyrazolo[4,3-d]pyrimidin-7(6H)-one (16.9 mg, 37.60 μmol, 22.61% yield, 97.965% purity) as white solid. $^1$H NMR (DMSO-d$_6$, 400 MHz) δ 7.66~7.55 (m, 3H), 7.33 (dd, J=8.4 Hz, 2.0 Hz, 1H), 6.76 (s, 1H), 4.55~4.45 (m, 3H), 4.37 (dd, J=14.0 Hz, 5.2 Hz, 1H), 3.89~3.83 (m, 1H), 3.76~3.69 (m, 2H), 3.36 (dd, J=11.2 Hz, 3.6 Hz, 2H), 3.32~3.24 (m, 2H), 3.24~3.18 (m, 1H). HPLC: 97.97% (220 nm), 97.83% (215 nm), 98.59% (254 nm). MS (ESI): mass calcd. For C$_{18}$H$_{19}$C$_{12}$N$_5$O$_4$ 439.08, m/z found 440.1 [M+H]$^+$.

Preparation of 5-chloro-1-(((2R,5S)-5-(hydroxymethyl)-1,4-dioxan-2-yl)methyl)-1H-pyrazolo[4,3-d]pyrimidin-7(6H)-one (Step 2 in Scheme C-3)

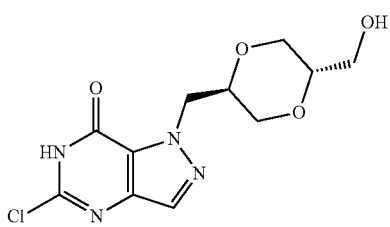 [SMILES: O=c1[nH]c(Cl)nc2cnn(C[C@@H]3CO[C@@H](CO)CO3)c12]

To a solution of [(2S,5R)-5-[(5-chloro-7-methoxy-pyrazolo[4,3-d]pyrimidin-1-yl)methyl]-1,4-dioxan-2-yl]methanol (40 mg, 127.10 mol, 1 eq) in MeOH (2 mL) and H$_2$O (2 mL) was added LiOHH$_2$O (16.00 mg, 381.29 µmol, 3 eq). The mixture was stirred at 25° C. for 4 hours. TLC showed reaction was complete. The reaction mixture was concentrated under reduced pressure to remove THF. And then the mixture was adjusted to pH=3 by HCl (3M) at 0° C., and extracted with EtOAc (5 mL×5). The combined organic layers were washed with brine (5 mL), dried over Na$_2$SO$_4$, filtered and concentrated under reduced pressure. Compound 5-chloro-1-(((2R,5S)-5-(hydroxymethyl)-1,4-dioxan-2-yl)methyl)-1H-pyrazolo[4,3-d]pyrimidin-7(6H)-one (30 mg, 99.77 µmol, 78.50% yield) was obtained as off white oil. $^1$H NMR (DMSO-d$_6$, 400 MHz) δ 13.31 (s, 1H), 8.00 (s, 1H), 5.08 (dd, J=14.0 Hz, 9.2 Hz, 1H), 4.51 (dd, J=14.0 Hz, 4.4 Hz, 1H), 4.07~4.02 (m, 2H), 3.77~3.63 (m, 4H), 3.48 (s, 1H), 3.46 (d, J=4.8 Hz, 1H).

Preparation of 5-((3,4-dichlorobenzyl)amino)-1-(((2R,5S)-5-(hydroxymethyl)-1,4-dioxan-2-yl)methyl)-1H-pyrazolo[4,3-d]pyrimidin-7(6H)-one (Step 3 in Scheme C-3)

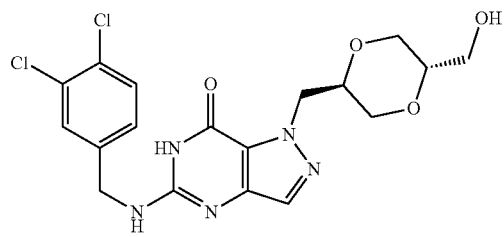 [SMILES: O=c1[nH]c(NCc2ccc(Cl)c(Cl)c2)nc2cnn(C[C@@H]3CO[C@@H](CO)CO3)c12]

A mixture of 5-chloro-1-[[(2R,5S)-5-(hydroxymethyl)-1,4-dioxan-2-yl]methyl]-6H-pyrazolo[4,3-d]pyrimidin-7-one (30.00 mg, 99.77 µmol, 1 eq) and (3,4-dichlorophenyl)methanamine (35.13 mg, 199.54 µmol, 26.61 µL, 2 eq) in 2-methylbutan-2-ol (1 mL) and t-BuOH (1 mL) was stirred at 105° C. for 32 hours. LCMS showed the reaction was complete. The reaction mixture was concentrated under reduced pressure to remove solvent. The residue was purified by prep-HPLC (column: Nano-micro Kromasil C18 100 mm×30 mm 8 µm; mobile phase: [water (0.1% TFA)-MeCN]; B %: 20%-40%, 10 mins). The aqueous solution was lyophilized to give compound 5-((3,4-dichlorobenzyl)amino)-1-(((2R,5S)-5-(hydroxymethyl)-1,4-dioxan-2-yl)methyl)-1H-pyrazolo[4,3-d]pyrimidin-7(6H)-one (21.0 mg 47.06 µmol, 47.17% yield, 98.675% purity) as white solid. $^1$H NMR (DMSO-d$_6$, 400 MHz) δ 7.60-.57 (m, 3H), 7.33 (dd, J=8.4 Hz, 2.0 Hz, 1H), 6.72 (s, 1H), 4.98 (dd, J=13.6 Hz, 8.8 Hz, 1H), 4.48 (d, J=6.0 Hz, 2H), 4.41 (dd, J=14.0 Hz, 4.8 Hz, 1H), 4.05~3.98 (m, 1H), 3.80~3.67 (m, 3H), 3.67~3.57 (m, 4H). HPLC: 98.68% (220 nm), 98.32% (215 nm), 100.00% (254 nm). MS (ESI): mass calcd. For C$_{18}$H$_{19}$C$_{12}$N$_5$O$_4$ 439.08, m/z found 440.0 [M+H]$^+$.

Compound 209

Preparation of 5-(5-((3,4-dichlorobenzyl)amino)-3-fluoro-7-oxo-6,7-dihydro-1H-pyrazolo[4,3-d]pyrimidin-1-yl)pentanoic acid Preparation of ethyl 5-(5-chloro-3-fluoro-7-methoxy-1H-pyrazolo[4,3-d]pyrimidin-1-yl)pentanoate (Step 1 in Scheme C-3)

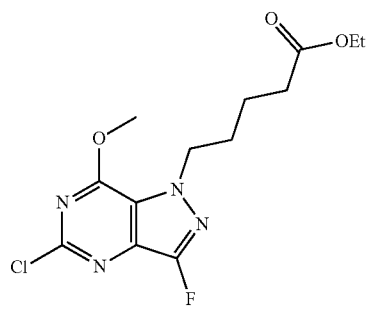 [SMILES: CCOC(=O)CCCCn1nc(F)c2nc(Cl)nc(OC)c21]

To a solution of ethyl 5-bromopentanoate (536.71 mg, 2.57 mmol, 409.70 µL, 1.3 eq), 5-chloro-3-fluoro-7-methoxy-1H-pyrazolo[4,3-d]pyrimidine (0.4 g, 1.97 mmol, 1 eq) and 3,5-dichloro-7-methoxy-1H-pyrazolo[4,3-d]pyrimidine (1.97 mmol, 1 eq) in DMF (3 mL) was added Cs$_2$CO$_3$ (1.29 g, 3.95 mmol, 2 eq). The mixture was stirred at 25° C. for 3 hours. LCMS and HPLC showed reaction was complete. After filtered, the filtrate was purified by prep-HPLC (column: Phenomenex Luna C18 100 mm×30 mm 5 µm; mobile phase: [water (0.1% TFA)-MeCN]; B %: 35%-65%, 10 mins). The aqueous solution was adjusted to pH=8 with sat. NaHCO$_3$ and extracted with EtOAc (15 mL×3). The combined organic layers were dried over Na$_2$SO$_4$, filtered and concentrated under reduced pressure. Compound ethyl 5-(5-chloro-3-fluoro-7-methoxy-pyrazolo[4,3-d]pyrimidin-1-yl) pentanoate (130 mg, 393.06 µmol, 19.91% yield) was obtained as off white solid. $^1$H NMR (CDC$_3$, 400 MHz) δ 4.42 (t, J=6.8 Hz, 2H), 4.24 (s, 3H), 4.12 (q, J=7.2 Hz, 2H), 2.34 (t, J=7.2 Hz, 2H), 1.97~1.87 (m, 2H), 1.65~1.59 (m, 2H), 1.25 (t, J=7.2 Hz, 3H).

Preparation of 5-(5-chloro-3-fluoro-7-oxo-6,7-dihydro-1H-pyrazolo[4,3-d]pyrimidin-1-yl)pentanoic Acid (Step 2 in Scheme C-3)

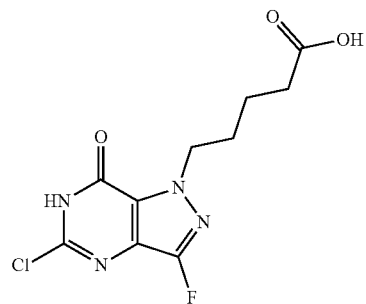 [SMILES: O=C(O)CCCCn1nc(F)c2nc(Cl)[nH]c(=O)c21]

To a solution of ethyl 5-(5-chloro-3-fluoro-7-methoxy-pyrazolo[4,3-d]pyrimidin-1-yl) pentanoate (130 mg, 393.06 µmol, 1 eq) in MeOH (1 mL) and H₂O (1 mL) was added LiOH—H₂O (49.48 mg, 1.18 mmol, 3 eq). The mixture was stirred at 25° C. for 2 hours. TLC indicated the reaction was complete. The reaction mixture was concentrated under reduced pressure. The aqueous was made pH=6 with 3N HCl and extracted with EtOAc (3 mL×3). The combined organic layers were washed with brine (3 mL), dried over Na₂SO₄, filtered and concentrated under reduced pressure. Compound 5-(5-chloro-3-fluoro-7-oxo-6H-pyrazolo[4,3-d]pyrimidin-1-yl)pentanoic acid (114 mg, crude) was obtained as white solid. H NMR (DMSO-d₆, 400 MHz) δ 13.49 (s, 1H), 12.02 (s, 1H), 4.41 (t, J=6.8 Hz, 2H), 2.22 (t, J=7.2 Hz, 2H), 1.82~1.75 (m, 2H), 1.46~1.40 (m, 2H).

Preparation of 5-(5-((3,4-dichlorobenzyl)amino)-3-fluoro-7-oxo-6,7-dihydro-1H-pyrazolo[4,3-d]pyrimidin-1-yl)pentanoic acid (Step 2 in Scheme C-3)

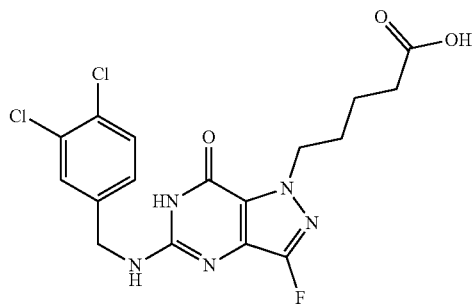 [SMILES: O=C(O)CCCCn1nc(F)c2nc(NCc3ccc(Cl)c(Cl)c3)[nH]c(=O)c21]

A solution of 5-(5-chloro-3-fluoro-7-oxo-6H-pyrazolo[4,3-d]pyrimidin-1-yl)pentanoic acid (20 mg, 69.29 µmol, 1 eq) and (3,4-dichlorophenyl)methanamine (24.39 mg, 138.57 µmol, 2 eq) in t-BuOH (2 mL) was stirred at 100° C. for 20 hours. TLC showed the reaction was nearly complete. The organic solvent was removed under reduced pressure. The residue was purified by prep-HPLC (column: Nano-micro Kromasil C18 100 mm×30 mm 8 µm; mobile phase: [water (0.1% TFA)-MeCN]; B %: 30%-60%, 10 mins). The eluent was removed under reduced pressure. Compound 5-[5-[(3,4-dichlorophenyl)methylamino]-3-fluoro-7-oxo-6H-pyrazolo[4,3-d]pyrimidin-1-yl]pentanoic acid (13.5 mg, 31.42 µmol, 45.35% yield, 99.67% purity) was obtained as white solid. ¹H NMR (DMSO-d₆, 400 MHz) δ 11.29 (s, 1H), 7.60~7.58 (m, 2H), 7.34 (dd, J=2.0 Hz, 8.0 Hz, 1H), 6.69 (t, J=5.6 Hz, 1H), 4.46 (d, J=5.6 Hz, 2H), 4.31 (t, J=6.8 Hz, 2H), 2.21 (t, J=7.2 Hz, 2H), 1.75~1.72 (m, 2H), 1.41~1.38 (m, 2H). HPLC: 99.67% (220 nm), 99.67% (215 nm), 99.02% (254 nm). MS (ESI): mass calcd. For C₁₇H₁₆Cl₂FN₅O₃ 427.06 m/z found 428.0 [M+H]⁺.

Compound 210

5-(5-((3,4-Difluorobenzyl)amino)-3-fluoro-7-oxo-6,7-dihydro-1H-pyrazolo[4,3-d]pyrimidin-1-yl)pentanoic acid was prepared according to the procedures described herein for Steps 1-3 in Scheme C-3.

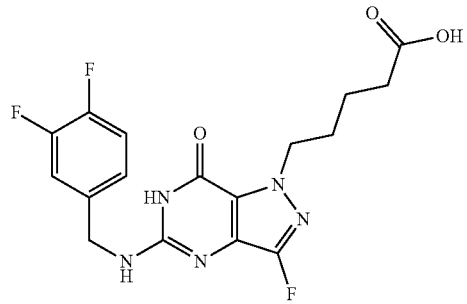 [SMILES: O=C(O)CCCCn1nc(F)c2nc(NCc3ccc(F)c(F)c3)[nH]c(=O)c21]

The procedure yielded the desired compound (13.3 mg, 33.52 µmol, 48.37% yield) as an off white solid. ¹H NMR (DMSO-d₆, 400 MHz) δ 11.23 (s, 1H), 7.45~7.33 (m, 2H), 7.20~7.19 (m, 1H), 6.65 (t, J=5.6 Hz, 1H), 4.45 (d, J=5.6 Hz, 2H), 4.31 (t, J=6.4 Hz, 2H), 2.21 (t, J=7.2 Hz, 2H), 1.77~1.70 (m, 2H), 1.43~1.36 (m, 2H). HPLC: 99.62% (220 nm), 99.31% (215 nm), 99.65% (254 nm). MS (ESI): mass calcd. For C₁₇H₁₆F₃N₅O₃ 395.12, m/z found 396.0 [M+H]⁺.

Compound 211

Preparation of 5-((3,4-dichlorobenzyl)amino)-1-(2-(2-(dimethylamino)ethoxy)ethyl)-1H-pyrazolo[4,3-d]pyrimidin-7(6H)-one hydrochloride

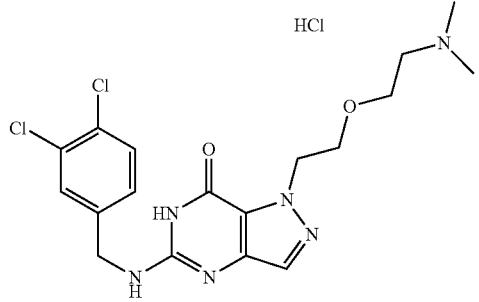 [SMILES: CN(C)CCOCCn1ncc2nc(NCc3ccc(Cl)c(Cl)c3)[nH]c(=O)c21 ; Cl]

To a solution of 1-[2-(2-aminoethoxy)ethyl]-5-[(3,4-dichlorophenyl)methylamino]-6H-pyrazolo[4,3-d]pyrimidin-7-one (0.1 g, 251.73 µmol, 1 eq, HCl) (Steps 1-3 in Scheme C-3) in MeOH (3 mL) was added formaldehyde (163.42 mg, 2.01 mmol, 149.93 µL, 37% purity, 8 eq) and AcOH (1.51 mg, 25.17 µmol, 1.44 µL, 0.1 eq). The mixture was stirred at 20° C. for 10 mins. Then NaBH₃CN (126.55 mg, 2.01 mmol, 8 eq) was added in portions at 0° C. The resulting mixture was stirred at 20° C. for 16 hours. LC-MS and HPLC showed the reaction was complete. The reaction mixture was quenched with H₂O (5 mL) and then concentrated under reduced pressure. The aqueous was extracted with EtOAc (10 mL×3). The combined organic layers were washed with brine (5 mL), dried over Na₂SO₄, filtered and concentrated under reduced pressure. The residue was purified by prep-HPLC (column: Phenomenex Luna C18 150 mm×30 mm 5 µm; mobile phase: [water (0.05% HCl)-MeCN]; B %: 15%-45%, mins). The aqueous solution was lyophilized to give 5-[(3,4-dichlorophenyl)methylamino]-1-[2-[2-(dimethylamino)ethoxy]ethyl]-6H-pyrazolo[4,3-d]pyrimidin-7-one hydrochloride (29.3 mg, 68.89 µmol, 27.37% yield, 100.00% purity) as white solid. $^1$H NMR (DMSO-d$_6$, 400 MHz) δ 9.99 (s, 1H), 7.95 (s, 1H), 7.78~7.50 (m, 3H), 7.38 (s, 1H), 4.62 (d, J=11.6 Hz, 4H), 3.86 (s, 2H), 3.71 (s, 2H), 3.21 (s, 2H), 2.67 (s, 6H). HPLC: 100.00% (220 nm), 100.00% (215 nm), 100.00% (254 nm). MS (ESI): mass calcd. For $C_{18}H_{23}C_{13}N_6O_2$ 424.12, m/z found 425.1 [M+H]$^+$.

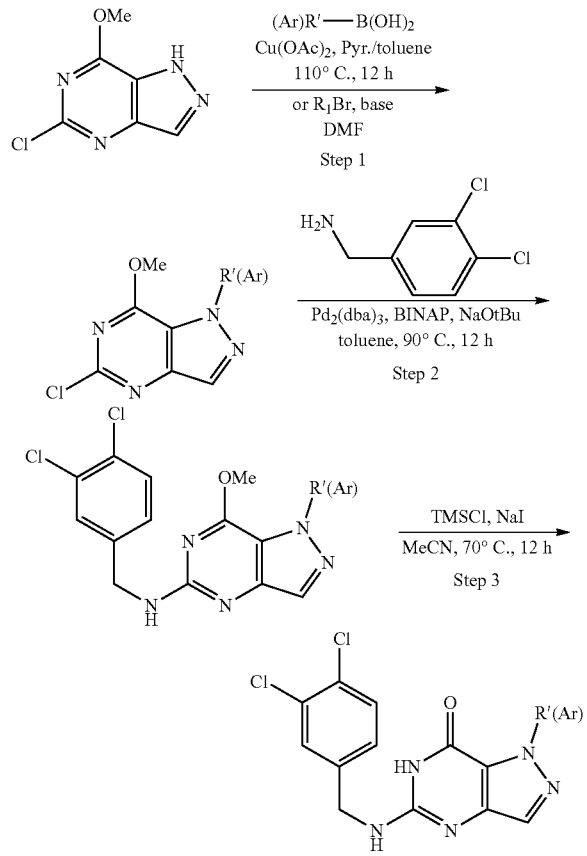

General Procedures for Preparing Compounds in Scheme C-4

Preparation of Compounds in Scheme C-4 (Step 1 in Scheme C-4)

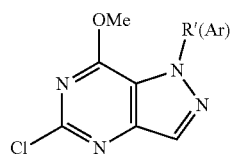

A mixture of 5-chloro-7-methoxy-1H-pyrazolo[4,3-d]pyrimidine (3.79 mmol, 1.0 eq), R'(Ar)CHB(OH)$_2$ (4.55 mmol, 1.2 eq), pyridine (7.58 mmol, 2.0 eq) and Cu(OAc)$_2$ (7.58 mmol, 2.0 eq) in toluene (2.5 mL/mmol) was degassed and purged with O2 for 3 times and then the mixture was stirred at 110° C. for 12 hours under O2 atmosphere. LCMS and TLC indicated the reaction was complete. After filtered, the filtrate was concentrated under reduced pressure. The residue was purified by column chromatography (SiO$_2$, Petroleum ether: Ethyl acetate=15:1 to 1:1) to give the desired product.

Preparation of Compounds in Scheme C-4 (Step 2 in Scheme C-4)

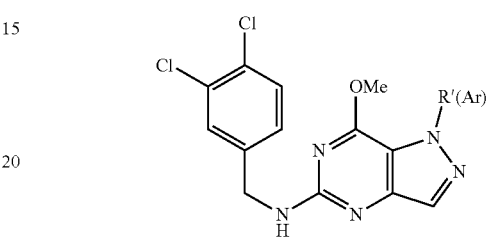

A mixture of 1-(R'(Ar)methyl)-5-chloro-7-methoxy-1H-pyrazolo[4,3-d]pyrimidine (806 µmol, 1.0 eq), (3,4-dichlorophenyl)methanamine (1.21 mmol, 1.5 eq), BINAP (75.2 mg 121 µmol, 0.15 eq), Pd$_2$(dba)$_3$ (40.3 µmol, 0.05 eq) and t-BuONa (1.61 mmol, 2.0 eq) in toluene (4 mL/mmol 6 mL/mmol) was degassed and purged with N$_2$ for 3 times and then the mixture was stirred at 90° C. for 12 hours under N$_2$ atmosphere. LCMS and TLC showed the reaction was complete. The reaction mixture was concentrated under reduced pressure. The residue was purified by column chromatography (SiO$_2$, Petroleum ether: Ethyl acetate=15:1 to 1:1) to give the desired product.

Preparation of Compounds in Scheme C-4 (Step 3 in Scheme C-4)

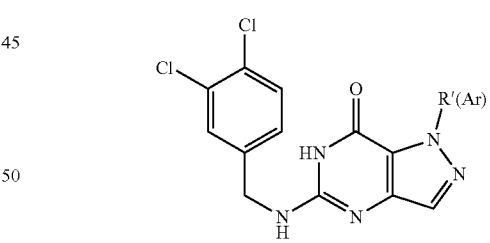

A mixture of 1-('(Ar)methyl)-N-(3,4-dichlorobenzyl)-7-methoxy-1H-pyrazolo[4,3-d]pyrimidin-5-amine (450 µmol, 1.0 eq), TMSCl (899 µmol, 2.0 eq) and NaI (899 µmol, 2.0 eq) in MeCN (3 mL/mmol 7 mL/mmol) was degassed and purged with N$_2$ for 3 times and then the mixture was stirred at 70° C. for 12 hours under N$_2$ atmosphere. TLC showed the reaction was complete. The reaction mixture was quenched with water and then extracted with EtOAc. The combined organic layers were washed with brine, dried over Na$_2$SO$_4$, filtered and concentrated under reduced pressure. The residue was purified by column chromatography (SiO$_2$, Petroleum ether: Ethyl acetate=4:1 to 1:1) to give the desired product.

Compound 212

Preparation of 5-[(3,4-dichlorophenyl)methyl-amino]-1-phenyl-6H-pyrazolo[4,3-d]pyrimidin-7-one Preparation of 5-chloro-7-methoxy-1-phenyl-pyrazolo[4,3-d]pyrimidine (Step 1 in Scheme C-4)

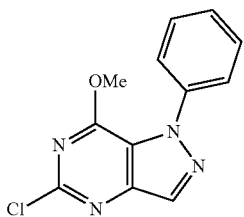 [SMILES: COc1nc(Cl)nc2cnn(-c3ccccc3)c12]

A mixture of 5-chloro-7-methoxy-1H-pyrazolo[4,3-d]pyrimidine (700 mg, 3.79 mmol, 1.0 eq), phenylboronic acid (555 mg, 4.55 mmol, 1.2 eq), pyridine (600 mg, 7.58 mmol, 612 μL, 2.0 eq) and Cu(OAc)$_2$ (1.38 g, 7.58 mmol, 2.0 eq) in toluene (1.0 mL) was degassed and purged with 02 for 3 times and then the mixture was stirred at 110° C. for 12 hours under 02 atmosphere. LCMS and TLC indicated the reaction was complete. After filtered, the filtrate was concentrated under reduced pressure. The residue was purified by column chromatography (SiO$_2$, Petroleum ether: Ethyl acetate=15:1 to 1:1). Compound 5-chloro-7-methoxy-1-phenyl-pyrazolo[4,3-d]pyrimidine (210 mg, 806 μmol, 21.2% yield) was obtained as a white solid.

Preparation of N-[(3,4-dichlorophenyl)methyl]-7-methoxy-1-phenyl-pyrazolo[4,3-d]pyrimidin-5-amine (Step 2 in Scheme C-4)

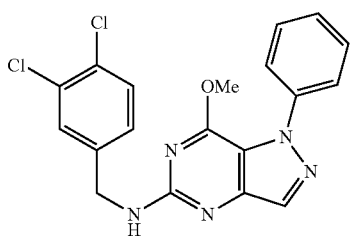 [SMILES: COc1nc(NCc2ccc(Cl)c(Cl)c2)nc2cnn(-c3ccccc3)c12]

A mixture of 5-chloro-7-methoxy-1-phenyl-pyrazolo[4,3-d]pyrimidine (210 mg, 806 μmol, 1.0 eq), (3,4-dichlorophenyl)methanamine (213 mg, 1.21 mmol, 161 μL, 1.5 eq), [1-(2-diphenylphosphanyl-1-naphthyl)-2-naphthyl]-diphenyl-phosphane (75.2 mg, 121 μmol, 0.15 eq), (1E,4E)-1,5-diphenylpenta-1,4-dien-3-one palladium (36.9 mg, 40.3 mol, 0.05 eq) and sodium 2-methylpropan-2-olate (155 mg, 1.61 mmol, 2.0 eq) in toluene (5.0 mL) was degassed and purged with N$_2$ for 3 times and then the mixture was stirred at 90° C. for 12 hours under N$_2$ atmosphere. LCMS and TLC showed the reaction was complete. The reaction mixture was concentrated under reduced pressure. The residue was purified by column chromatography (SiO$_2$, Petroleum ether: Ethyl acetate=15:1 to 1:1) to give compound N-[(3,4-dichlorophenyl)methyl]-7-methoxy-1-phenyl-pyrazolo[4,3-d]pyrimidin-5-amine (180 mg, crude) as white solid. $^1$H NMR (CDC$_3$, 400 MHz) δ 7.90 (s, 1H), 7.50 (d, J=8.0 Hz, 2H), 7.40~7.42 (m, 3H), 7.30~7.38 (m, 2H), 7.16 (s, 1H), 5.24 (s, 1H), 4.59 (d, J=8 Hz, 2H), 3.89 (s, 3H).

Preparation of 5-[(3,4-dichlorophenyl)methyl-amino]-1-phenyl-6H-pyrazolo[4,3-d]pyrimidin-7-one (Step 3 in Scheme C-4)

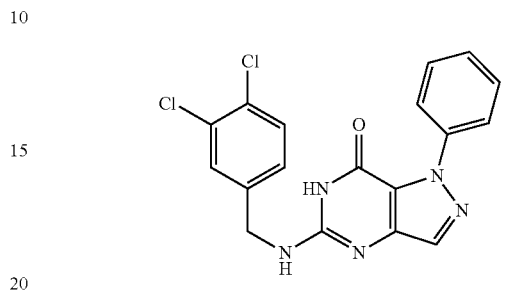

A mixture of N-[(3,4-dichlorophenyl)methyl]-7-methoxy-1-phenyl-pyrazolo[4,3-d]pyrimidin-5-amine (180 mg, 450 mol, 1.0 eq), TMSCl (97.7 mg, 899 μmol, 114 μL, 2.0 eq) and NaI (135 mg, 899 μmol, 2.0 eq) in MeCN (1.0 mL) was degassed and purged with N$_2$ for 3 times and then the mixture was stirred at 70° C. for 12 hours under N$_2$ atmosphere. TLC showed the reaction was complete. The reaction mixture was quenched with water (2.0 mL) and then extracted with EtOAc (5.0 mL, 3.0). The combined organic layers were washed with brine (3.0 mL), dried over Na$_2$SO$_4$, filtered and concentrated under reduced pressure. The residue was purified by column chromatography (SiO$_2$, Petroleum ether: Ethyl acetate=6:1 to 1:1). Compound 5-[(3,4-dichlorophenyl)methylamino]-1-phenyl-6H-pyrazolo[4,3-d]pyrimidin-7-one (50.0 mg, 129 μmol, 28.8% yield) was obtained as white solid. $^1$H NMR (DMSO-d$_6$, 400 MHz) δ 11.22 (s, 1H), 7.86 (s, 1H), 7.67 (d, J=7.8 Hz, 2H), 7.55~7.62 (m, 2H), 7.47 (t, J=7.8 Hz, 2H), 7.30~7.40 (m, 2H), 6.67 (s, 1H), 4.51 (d, J=6.0 Hz, 2H). HPLC: 97.5% (220 nm), 97.3% (215 nm), 97.1% (254 nm). LCMS: For C$_{18}$H$_{13}$C$_{12}$N$_5$O 385.05, m/z found 386.0 [M+H]$^+$.

Compound 213

1-Cyclopropyl-5-((3,4-dichlorobenzyl)amino)-1H-pyrazolo[4,3-d]pyrimidin-7(6H)-one was prepared according to the procedure described herein for Steps 1-3 in Scheme C-4.

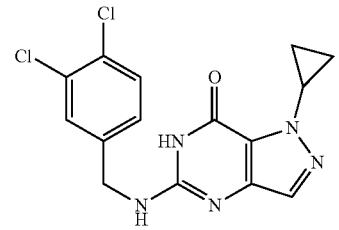 [SMILES: O=c1[nH]c(NCc2ccc(Cl)c(Cl)c2)nc2cnn(C3CC3)c12]

The procedure yielded the desired compound (80.0 mg, 228 μmol, 48.9% yield) as a white solid. $^1$H NMR (DMSO-d$_6$, 400 MHz) δ 11.0 (s, 1H), 7.56 (d, J=8.0 Hz 2H), 7.47 (s, 1H), 7.31 (d, J=8.4 Hz, 1H), 6.54 (s, 1H), 4.45 (d, J=4.0 Hz, 2H), 4.19 (br s, 1H), 1.08~1.13 (m, 2H), 0.96~0.99 (m, 2H). HPLC: 95.4% (220 nm), 92.0% (215 nm), 93.7% (254 nm). LCMS: For C$_{15}$H$_{13}$C$_{12}$N$_5$O 349.05, m/z found 350.0 [M+H]$^+$.

Compound 214

Preparation of 1-cyclopentyl-5-((3,4-dichlorobenzyl)amino)-1H-pyrazolo[4,3-d]pyrimidin-7(6H)-one Preparation of 5-chloro-1-cyclopentyl-7-methoxy-1H-pyrazolo[4,3-d]pyrimidine (Step 1 in Scheme C-4)

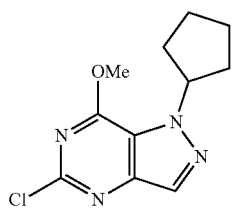 [SMILES: COc1nc(Cl)nc2cnn(C3CCCC3)c12]

A mixture of compound 5-chloro-7-methoxy-1H-pyrazolo[4,3-d]pyrimidine (1 g, 5.42 mmol, 1 eq), bromocyclopentane (968.86 mg, 6.50 mmol, 697.02 μL, 1.2 eq), Cs$_2$CO$_3$ (3.53 g, 10.84 mmol, 2 eq) in DMF (10 mL) was degassed and purged with N$_2$ for 3 times and then the mixture was stirred at 50° C. for 12 hours under N$_2$ atmosphere. TLC indicated the reaction was complete. The mixture was diluted with H$_2$O (10 mL) and extracted with EtOAc (10 mL). The combined organic layers were washed with brine (20 mL×3), dried over Na$_2$SO$_4$, filtered and concentrated under reduced pressure. The residue was purified by silica gel chromatography (column height: 250 mm, diameter: 100 mm, 100-200 mesh silica gel, Petroleum ether/Ethyl acetate=1/1) to afford compound 5-chloro-1-cyclopentyl-7-methoxy-1H-pyrazolo[4,3-d]pyrimidine (500 mg, 1.98 m mol, 36.55% yield) as white solid. Compound 5-chloro-2-cyclopentyl-7-methoxy-pyrazolo[4,3-d]pyrimidine (500 mg, 1.98 mmol, 36.52% yield) was obtained as a white solid. $^1$H NMR (CDC$_3$, 400 MHz) δ 7.94 (s, 1H), 5.23~5.30 (m, 1H), 4.15 (s, 3H), 2.04~2.09 (m, 4H), 1.88~1.89 (m, 2H), 1.65~1.68 (m, 2H).

Preparation of 1-cyclopentyl-N-(3,4-dichlorobenzyl)-7-methoxy-1H-pyrazolo[4,3-d]pyrimidin-5-amine (Step 2 in Scheme C-4)

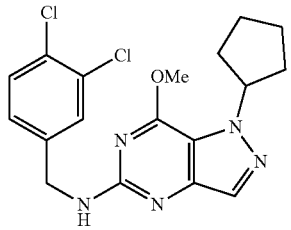 [SMILES: COc1nc(NCc2ccc(Cl)c(Cl)c2)nc2cnn(C3CCCC3)c12]

A mixture of compound 5-chloro-1-cyclopentyl-7-methoxy-1H-pyrazolo[4,3-d]pyrimidine (0.5 g, 1.98 mmol, 1 eq), (3,4-dichlorophenyl)methanamine (452.82 mg, 2.57 mmol, 343.05 μL, 1.3 eq), t-BuONa (285.23 mg, 2.97 mmol, 1.5 eq), BINAP (123.20 mg, 197.8pμmol, 0.1 eq) and Pd$_2$(dba)$_3$ (113.77 mg, 197.86 μmol, 0.1 eq) in toluene (5 mL) was degassed and purged with N$_2$ for 3 times, and then the mixture was stirred at 80° C. for 15 hours under N$_2$ atmosphere. TLC indicated the reaction was complete. The reaction mixture was concentrated under reduced pressure. The residue was purified by silica gel chromatography (column height: 250 mm, diameter: 100 mm, 300-400 mesh silica gel, Petroleum ether/Ethyl acetate=30/1, 15/1) to afford compound 1-cyclopentyl-N-(3,4-dichlorobenzyl)-7-methoxy-1H-pyrazolo[4,3-d]pyrimidin-5-amine (300 mg, 764.76 μmol, 38.65% yield) as a yellow solid. $^1$H NMR (CDCl$_3$, 400 MHz) δ 7.66 (s, 1H), 7.30 (d, J=5.6 Hz, 1H), 7.28~7.30 (m, 1H), 7.12~7.14 (m, 1H), 5.23~5.28 (m, 1H), 5.15~5.18 (t, J=5.6 Hz, 1H), 4.52~4.54 (d, J=6.0 Hz, 3H), 1.99~2.04 (m, 4H), 1.84~1.85 (m, 2H), 1.60~1.62 (m, 2H).

Preparation of 1-cyclopentyl-5-((3,4-dichlorobenzyl)amino)-1H-pyrazolo[4,3-d]pyrimidin-7(6H)-one (Step 3 in Scheme C-4)

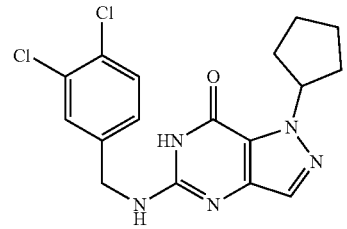 [SMILES: O=c1[nH]c(NCc2ccc(Cl)c(Cl)c2)nc2cnn(C3CCCC3)c12]

To a solution of 1-cyclopentyl-N-(3,4-dichlorobenzyl)-7-methoxy-1H-pyrazolo[4,3-d]pyrimidin-5-amine (200 mg, 509.84 μmol, 1.00 eq) in MeCN (2 mL) was added TMSCl (110.78 mg, 1.02 mmol, 129.42 μL, 2.00 eq) and NaI (152.84 mg, 1.02 mmol, 2.00 eq). The mixture was stirred at 70° C. for 15 hours. TLC indicated the reaction was complete. The reaction mixture was concentrated under reduced pressure. The mixture was further purification by pre-HPLC (column: Phenomenex Luna C18 200 mm×40 mm 10 μm; mobile phase: [water (0.1% TFA)-MeCN]; B %: 40%-60%, 10 mins) to give compound 1-cyclopentyl-5-((3,4-dichlorobenzyl)amino)-1H-pyrazolo[4,3-d]pyrimidin-7(6H)-one (24 mg 63.45 μmol, 12.44% yield) as white solid. $^1$H NMR (MeOD, 400 MHz) δ 7.52~7.56 (m, 2H), 7.50-7.52 (m, 1H), 7.30~7.32 (m, 1H), 5.47~5.55 (m, 1H), 4.56~4.57 (d, J=6.8 Hz, 2H), 2.07-2.12 (m, 4H), 2.03~2.07 (m, 2H), 1.65~1.92 (m, 2H). HPLC: 98.7% (215 nm), 98.8% (220 nm), 98.5% (254 nm). MS (ESI): mass calcd. For C$_{17}$H$_7$C$_{12}$N$_5$O 377.10, m/z found 378.1 [M+H]$^+$.

Compound 215

Preparation of 5-((3,4-dichlorobenzyl)amino)-1-(pyrrolidin-3-yl)-1H-pyrazolo[4,3-d]pyrimidin-7(6H)-one TFA Salt Preparation of tert-butyl 3-(5-chloro-7-methoxy-1H-pyrazolo[4,3-d]pyrimidin-1-yl)pyrrolidine-1-carboxylate and tert-butyl 3-(5-chloro-7-methoxy-pyrazolo[4,3-d]pyrimidin-2-yl)pyrrolidine-1-carboxylate (Step 1 in Scheme C-4)

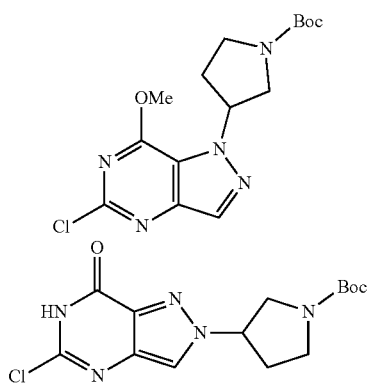

To a solution of 5-chloro-7-methoxy-1H-pyrazolo[4,3-d]pyrimidine (2.00 g, 10.8 mmol, 1 eq) in DMF (20.0 mL) was added K$_2$CO$_3$ (3.00 g, 21.7 mmol, 2.00 eq) and tert-butyl 3-bromopyrrolidine-1-carboxylate (3.52 g, 14.0 mmol, 1.30 eq). The mixture was stirred at 50° C. for 12 hours. TLC (Petroleum ether: Ethyl acetate=1:1, R$_{f\,1}$=0.65, R$_{f\,2}$=0.47) indicated compound Int-B was consumed completely and many new spots formed. The reaction mixture was quenched by addition H$_2$O (100 mL) at 25° C., and then extracted with EtOAc (50.0 mL, 30.0 mL, 20.0 mL). The combined organic layers were dried over anhydrous Na$_2$SO$_4$, filtered and concentrated under reduced pressure to give a residue. The residue was purified by column chromatography on silica gel (Petroleum ether: Ethyl acetate=10:1 to 1:1). Compound tert-butyl 3-(5-chloro-7-methoxy-pyrazolo[4,3-d]pyrimidin-1-yl)pyrrolidine-carboxylate (1.20 g, 3.39 mmol, 31.3% yield) was obtained as a white solid. $^1$H NMR (CDCl$_3$, 400 MHz) δ 8.03 (d, J 16.40, 1H), 5.51~5.54 (m, 1H), 4.24 (br s, 3H), 3.68-3.91 (m, 3H), 3.55~3.57 (m, 1H), 2.34~2.63 (m, 2H), 1.48 (s, 9H). Compound tert-butyl 3-(5-chloro-7-methoxy-pyrazolo[4,3-d]pyrimidin-2-yl)pyrrolidine-1-carboxylate (500 mg, 1.41 mmol, 13.0% yield) was obtained as white solid. $^1$H NMR (CDCl$_3$, 400 MHz) δ 8.04 (s, 1H), 5.18~5.21 (m, 1H), 4.25 (s, 3H), 3.97~4.02 (m, 2H), 3.59~3.61 (m, 2H), 2.52~2.59 (m, 2H), 1.49 (s, 9H).

Preparation of tert-butyl 3-(5-((3,4-dichlorobenzyl)amino)-7-methoxy-1H-pyrazolo[4,3-d]pyrimidin-1-yl)pyrrolidine-1-carboxylate (Step 2 in Scheme C-4)

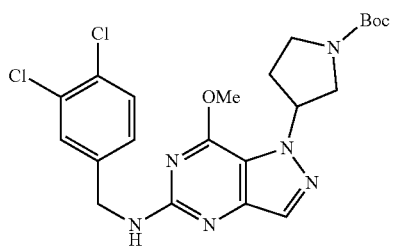 [SMILES: COc1nc(NCc2ccc(Cl)c(Cl)c2)nc2cnn(C3CCN(C(=O)OC(C)(C)C)C3)c12]

Tert-butyl 3-(5-chloro-7-methoxy-pyrazolo[4,3-d]pyrimidin-1-yl)pyrrolidine-1-carboxylate (400 mg, 1.13 mmol, 1.00 eq), (3,4-dichlorophenyl)methanamine (239 mg, 1.36 mmol, 180 µL, 1.20 eq), t-BuONa (162 mg, 1.70 mmol, 1.50 eq), BINAP (70.4 mg, 113 µmol, 0.10 eq) and Pd$_2$(dba)$_3$ (103 mg, 113 µmol, 0.10 eq) were taken up into a microwave tube in 1,4-dioxane (8.00 mL). The sealed tube was heated at 120° C. for 20 mins under microwave. TLC (Petroleum ether: Ethyl acetate=1:2, R$_f$=0.54) indicated tert-butyl 3-(5-chloro-7-methoxy-1H-pyrazolo[4,3-d]pyrimidin-1-yl)pyrrolidine-1-carboxylate was consumed completely and many new spots formed. 2 reactions were combined for work-up. The crude product on notebook page ET23828-10 (100 mg) was combined to ET23828-11 for further work-up. The combined reaction mixture was concentrated under reduced pressure to remove solvent. The residue was purified by column chromatography on silica gel (Petroleum ether: Ethyl acetate=10:1 to 1:1). Compound tert-butyl 3-[5-[(3,4-dichlorophenyl)methylamino]-7-methoxy-pyrazolo[4,3-d]pyrimidin-1-yl]pyrrolidine-1-carboxylate (450 mg, 912 mol, 35.9 yield) was obtained as yellow solid. $^1$H NMR (CDC$_3$, 400 MHz) δ 7.77 (d, J=5.60 Hz, 1H), 7.49 (d, J=1.60 Hz, 1H), 7.39 (d, J=8.40 Hz, 1H), 7.23 (dd, J=8.40, 2.00 Hz, 1H), 5.38~5.45 (m, 1H), 4.63 (d, J=6.40 Hz, 2H), 4.07 (d, J=4.80 Hz, 3H), 3.68~3.83 (m, 3H), 3.51~3.54 (m, 1H), 2.49~2.62 (m, 1H), 2.30~2.37 (m, 1H), 1.47 (s, 9H).

Compound 216

Preparation of 5-((3,4-dichlorobenzyl)amino)-1-(pyrrolidin-3-yl)-1H-pyrazolo[4,3-d]pyrimidin-7(6H)-one TFA salt (Step 3 in Scheme C-4)

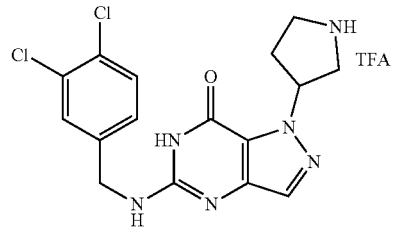 [SMILES: O=c1[nH]c(NCc2ccc(Cl)c(Cl)c2)nc2cnn(C3CCNC3)c12]

To a solution of tert-butyl 3-[5-[(3,4-dichlorophenyl)methylamino]-7-methoxy-pyrazolo[4,3-d]pyrimidin-1-yl]pyrrolidine-1-carboxylate (260 mg, 527 mol, 1.00 eq) in MeCN (2.00 mL) was added TMSCl (171 mg, 1.58 mmol, 200 µL, 3.00 eq) and NaI (237 mg, 1.58 mmol, 3.00 eq). The mixture was stirred at 70° C. for 12 hours. LCMS showed tert-butyl 3-(5-((3,4-dichlorobenzyl)amino)-7-methoxy-1H-pyrazolo[4,3-d]pyrimidin-1-yl)pyrrolidine-1-carboxylate was consumed completely and one main peak with desired mass was detected. The reaction mixture was quenched by addition H$_2$O (20.0 mL) at 25° C. and extracted with EtOAc (10.0 mL×3). The combined organic layers were dried over anhydrous Na$_2$SO$_4$, filtered and concentrated under reduced pressure to give a residue. The crude product on notebook page ET23828-13 (100 mg) was combined to ET23828-14 for further purification. The combined crude product was purified by prep-HPLC (TFA condition: column: Phenomenex Luna C18 200 mm×40 mm 10 µm; mobile phase: [water (0.1% TFA)-MeCN]; B %: 20%-40%, 10 mins) to give desired compound. Compound 5-[(3,4-dichlorophenyl)methylamino]-1-pyrrolidin-3-yl-6H-pyrazolo[4,3-d]pyrimidin-7-one (80 mg, 160.56 µmol, 22.0% yield, 99% purity, TFA) was obtained as a white solid. $^1$H NMR (DMSO-d$_6$, 400 MHz) δ 11.30 (s, 1H), 8.99~9.03 (m, 2H), 7.69 (s, 1H), 7.57~7.59 (m, 2H), 7.30-7.32 (m, 1H), 6.75~6.79 (m, 1H), 5.75~5.78 (m, 1H), 4.48 (d, J=5.60 Hz, 2H), 3.60-3.65 (m, 2H), 3.35~3.38 (m, 2H), 2.37~2.42 (m, 1H), 2.32~2.33 (m, 1H). HPLC: 99.05% (220 nm), 98.82% (215 nm), 98.60% (254 nm). MS (ESI): mass calcd. For C$_{16}$H$_{16}$C$_{12}$N$_6$O 378, m/z found 379.0 [M+H]$^+$.

5-((3,4-Dichlorobenzyl)amino)-2-(pyrrolidin-3-yl)-2H-pyrazolo[4,3-d]pyrimidin-7(6H)-one TFA salt was prepared according to the procedure described herein for Step 2-3 in Scheme C-4.

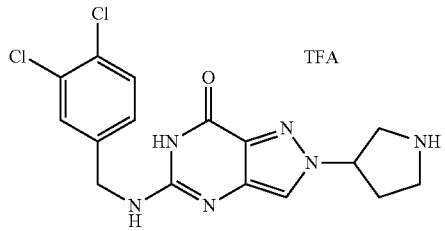 [SMILES: O=c1[nH]c(NCc2ccc(Cl)c(Cl)c2)nc2cn(C3CCNC3)nc12]

The procedure yielded the desired compound (25.4 mg, 67.0 μmol, 22.0% yield, TFA) as a white solid. ¹H NMR (DMSO-d₆, 400 MHz) δ 10.78-10.80 (m, 1H), 8.92~9.05 (m, 2H), 7.98 (s, 1H), 7.54~7.59 (m, 2H), 7.32 (dd, J=8.40 Hz, 2.00 Hz, 1H), 6.59~6.61 (m, 1H), 5.25 (m, 1H), 4.45 (d, J=6.00 Hz, 2H), 3.37~3.42 (m, 4H), 2.31~2.32 (m, 2H). HPLC: 97.01% (220 nm), 97.25% (215 nm), 95.78% (254 nm). LCMS: For C₁₆H₁₆C₁₂N₆O 378.03, m/z found 379.0 [M+H]⁺.

Compound 217

Preparation of 5-[5-[(3,4-dichlorophenyl)methyl-amino]-7-oxo-6H-pyrazolo[4,3-d]pyrimidin-1-yl]pentanehydroxamic Acid Compound 218
Methyl 5-(5-chloro-7-methoxy-pyrazolo[4,3-d]pyrimidin-1-yl) pentanoate was prepared according to the procedure described herein for Steps 1-3 in Scheme C-4.

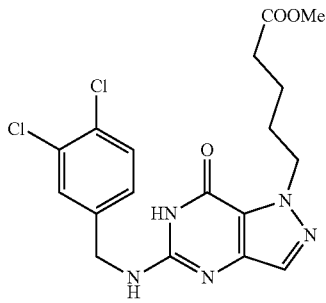 [SMILES: COC(=O)CCCCn1ncc2nc(NCc3ccc(Cl)c(Cl)c3)[nH]c(=O)c21]

The procedure yielded the desired compound methyl 5-[5-[(3,4-dichlorophenyl)methylamino]-7-oxo-6H-pyrazolo[4,3-d]pyrimidin-1-yl]pentanoate (110 mg, 259.26 μmol, 45.45% yield) as a white solid. ¹H NMR (CDCl₃, 400 MHz) δ 11.30 (d, J=1.2 Hz 1H), 7.57 (s, 1H), 7.39 (m, 1H), 7.34 (m, 1H), 7.17 (m, 1H), 5.38 (s, 1H), 4.54 (d, J=5.6 Hz, 2H), 4.43 (t, J=7.2 Hz, 2H), 3.55 (s, 3H), 2.26 (m, 2H), 1.85 (m, 2H), 1.53 (m, 2H). MS (ESI): mass calcd. For C₁₈H₁₉C2N₅O₃ 423.1, m/z found 424.1 [M+H]⁺. HPLC: 94.32% (220 nm), 92.49% (215 nm), 93.91% (254 nm).

Compound 219

Preparation of 5-[5-[(3,4-dichlorophenyl)methyl-amino]-7-oxo-6H-pyrazolo[4,3-d]pyrimidin-1-yl]pentanoic acid

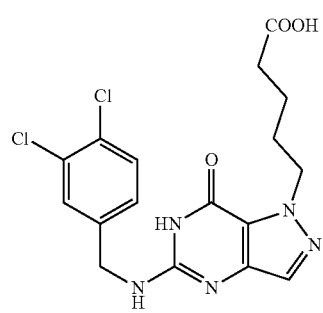 [SMILES: O=C(O)CCCCn1ncc2nc(NCc3ccc(Cl)c(Cl)c3)[nH]c(=O)c21]

To a solution of ethyl 5-[5-[(3,4-dichlorophenyl)methyl-amino]-7-oxo-6H-pyrazolo4,3-d]pyrimidin-1-yl]pentanoate (100 mg, 235.69 μmol, 1 eq) in MeOH (1 mL), THF (1 mL) and H₂O (1 mL) was added LiOH—H₂O (9.89 mg, 235.69 μmol, 1 eq). The mixture was stirred at 25° C. for 12 hours. TLC indicated the reaction was complete. The reaction mixture was diluted with water (5 mL) and adjusted pH=2 with 2N HCl. The mixture was extracted with EtOAc (10 mL×2). After filtered, the filtrate was concentrated to give 5-[5-[(3,4-dichlorophenyl)methylamino]-7-oxo-6H-pyrazolo[4,3-d]pyrimidin-1-yl]pentanoic acid (65 mg, 158.44 μmol, 67.22% yield) as white solid. ¹H NMR (DMSO-d₆, 400 MHz) δ 11.97 (s, 1H), 11.04 (s, 1H), 7.56 (m, 3H), 7.30 (m, 1H), 6.53 (s, 1H), 4.44 (m, 2H), 4.40 (m, 2H), 2.17 (m, 2H), 1.73 (m, 2H), 1.37 (m, 2H). MS (ESI): mass calcd. For C₁₇H₇Cl₂N₅O₃ 409.1, m/z found 410.1 [M+H]⁺. HPLC: 97.79% (220 nm), 99.35% (215 nm), 98.41% (254 nm).

Preparation of 5-[5-[(3,4-dichlorophenyl)methyl-amino]-7-oxo-6H-pyrazolo[4,3-d]pyrimidin-1-yl]pentanehydroxamic Acid

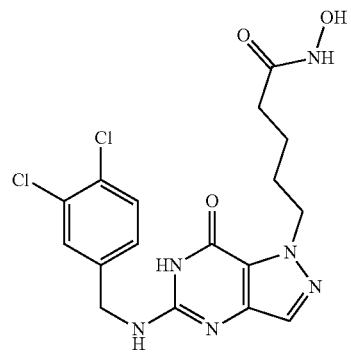 [SMILES: O=C(CCCCn1ncc2nc(NCc3ccc(Cl)c(Cl)c3)[nH]c(=O)c21)NO]

To a solution of 5-[5-[(3,4-dichlorophenyl)methylamino]-7-oxo-6H-pyrazolo[4,3-d]pyrimidin-1-yl]pentanoic acid (40 mg, 97.50 μmol, 1 eq) in DMF (0.4 mL) was added DIPEA (50.41 mg, 390.00 μmol, 67.93 μL, 4 eq) and HATU (40.78 mg, 107.25 μmol, 1.1 eq) at 25° C. After addition, the mixture was stirred at this temperature for 10 mins, and then NH₂OH.HCl (13.55 mg, 195.00 μmol, 2 eq) was added at 25° C. The resulting mixture was stirred at 25° C. for 12 hours. LC-MS showed 20% of 5-[5-[(3,4-dichlorophenyl)methylamino]-7-oxo-6H-pyrazolo[4,3-d]pyrimidin-1-yl]pentanoic acid was remained. Several new peaks were shown on LC-MS and ~70% of desired compound was detected. The mixture was purified by preparative HPLC (column: Nano-micro Kromasil C18 100 mm×40 mm 10 μm; mobile phase: [water (0.1% TFA)-MeCN]; B %: 20%-50%, 10 mins). Compound 5-[5-[(3,4-dichlorophenyl)methylamino]-7-oxo-6H-pyrazolo[4,3-d]pyrimidin-1-yl]pentanehydroxamic acid (27 mg, 63.49 μmol, 65.12% yield) was obtained as yellow solid. ¹H NMR (DMSO-d₆, 400 MHz) δ 10.31 (d, J=5.6 Hz 1H), 7.57 (m, 2H), 7.32 (m, 1H), 6.63 (m, 1H), 4.45 (m, 2H), 4.38 (m, 2H), 1.91 (m, 2H), 1.74 (m, 2H), 1.35 (m, 2H). MS (ESI): mass calcd. For C₁₇H₁₈C₁₂N₆O₃ 424.1, m/z found 425.1 [M+H]⁺. HPLC: 99.36% (220 nm), 98.61% (215 nm), 99.45% (254 nm).

Compound 220

Preparation of 5-((3,4-dichlorobenzyl)amino)-1-(2-(2-(methylsulfonyl)ethoxy)ethyl)-1H-pyrazolo[4,3-d]pyrimidin-7(6H)-one 1-(2-(2-bromoethoxy)ethyl)-5-chloro-7-methoxy-1H-pyrazolo[4,3-d]pyrimidine was prepared according to the procedure described herein for Step 1 in Scheme C-4.

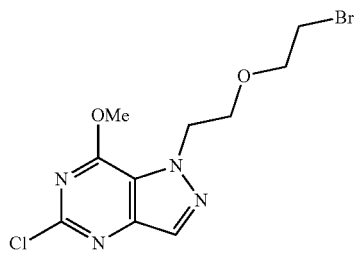 [SMILES: COc1nc(Cl)nc2cnn(CCOCCBr)c12]

The procedure yielded the desired compound 1-[2-(2-bromoethoxy)ethyl]-5-chloro-7-methoxy-pyrazolo[4,3-d]pyrimidine (370 mg, 1.10 mmol, 40.70% yield) as a white solid. $^1$H NMR (CDCl$_3$, 400 MHz) δ 8.06 (s, 1H), 4.75 (t, J=5.6 Hz, 2H), 4.24 (s, 3H), 3.95 (t, J=6.0 Hz, 2H), 3.68 (t, J=6.0 Hz, 2H), 3.31 (t, J=6.0 Hz, 2H). Compound 2-[2-(2-bromoethoxy)ethyl]-5-chloro-7-methoxy-pyrazolo[4,3-d]pyrimidine (400 mg, 1.19 mmol, 44.00% yield) was obtained as white solid. $^1$H NMR (CDCl$_3$, 400 MHz) δ8.17 (s, 1H), 4.63 (t, J=4.8 Hz, 2H), 4.25 (s, 3H), 3.95 (t, J=5.2 Hz, 2H), 3.74 (t, J=5.6 Hz, 2H), 3.39 (t, J=6.4 Hz, 2H).

Preparation of 5-chloro-7-methoxy-1-(2-(2-(methylsulfonyl)ethoxy)ethyl)-1H-pyrazolo[4,3-d]pyrimidine

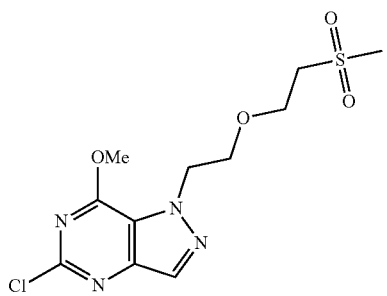 [SMILES: COc1nc(Cl)nc2cnn(CCOCCS(C)(=O)=O)c12]

A mixture of 1-[2-(2-bromoethoxy)ethyl]-5-chloro-7-methoxy-pyrazolo[4,3-d]pyrimidine (370 mg, 1.10 mmol, 1 eq) and sodium methanesulfinate (225.12 mg, 2.21 mmol, 2 eq) in DMSO (4 mL) was stirred at 25° C. for 12 hours. LCMS showed the reaction was complete. The residue was diluted with H$_2$O (4 mL) and extracted with EtOAc (4 mL×2). The combined organic layers were washed with brine (2 mL×2), dried over Na$_2$SO$_4$, filtered and concentrated under reduced pressure. Compound 5-chloro-7-methoxy-1-[2-(2-methylsulfonylethoxy)ethyl]pyrazolo[4,3-d]pyrimidine (280 mg, 836.37 μmol, 75.8600 yield) was obtained as white solid. $^1$H NMR(CDC$_3$, 400 MHz) δ 8.04 (s, 1H), 4.75 (t, J=5.6 Hz, 2H), 4.24 (s, 3H), 3.97 (t, J=5.6 Hz, 2H), 3.86 (t, J=5.2 Hz, 2H), 3.12 (t, J=5.2 Hz, 2H), 2.75 (s, 3H).

Preparation of 5-chloro-1-(2-(2-(methylsulfonyl)ethoxy)ethyl)-1H-pyrazolo[4,3-d]pyrimidin-7(6H)-one

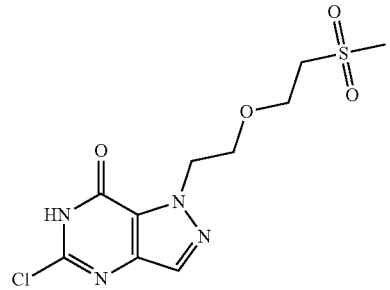 [SMILES: CS(=O)(=O)CCOCCn1ncc2nc(Cl)[nH]c(=O)c21]

To a mixture of 5-chloro-7-methoxy-1-[2-(2-methylsulfonylethoxy)ethyl]pyrazolo[4,3-d]pyrimidine (130 mg, 388.32μmol, 1 eq) and NaI (174.61 mg, 1.16 mmol, 3 eq) in MeCN (3 mL) was added TMSCl (126.56 mg, 1.16 mmol, 147.85 μL, 3 eq) dropwise at 0° C. Then the mixture was stirred at 25° C. for 12 hours. TLC indicated the reaction was complete. The reaction mixture was quenched with H$_2$O (3 mL) and extracted with EtOAc (3 mL×3). The combined organic layers were washed with brine (3 mL), dried over Na$_2$SO$_4$, filtered and concentrated under reduced pressure. Compound 5-iodo-1-[2-(2-methylsulfonylethoxy)ethyl]-6H-pyrazolo[4,3-d]pyrimidin-7-one (220 mg, crude) was obtained as brown solid. $^1$H NMR (DMSO-d$_6$, 400 MHz) δ 8.02 (s, 1H), 4.73~4.68 (m, 2H), 3.88-3.84 (m, 2H), 3.77~3.68 (m, 2H), 3.27~3.24 (m, 2H), 2.78~2.77 (m, 3H).

Preparation of 5-((3,4-dichlorobenzyl)amino)-1-(2-(2-(methylsulfonyl)ethoxy)ethyl)-1H-pyrazolo[4,3-d]pyrimidin-7(6H)-one

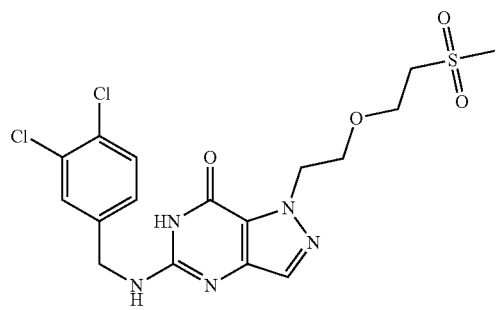 [SMILES: CS(=O)(=O)CCOCCn1ncc2nc(NCc3ccc(Cl)c(Cl)c3)[nH]c(=O)c21]

A mixture of 5-iodo-1-[2-(2-methylsulfonylethoxy)ethyl]-6H-pyrazolo[4,3-d]pyrimidin-7-one (160 mg, 388.16 μmol, 1 eq) and (3,4-dichlorophenyl)methanamine (136.66 mg, 776.32 μmol, 103.53 μL, 2 eq) in NMP (2 mL) was stirred at 160° C. for 2 hours. LC-MS showed the reaction was complete. After filtered, the filtrate was purified by prep-HPLC (column: Nano-micro Kromasil C18 100 mm×30 mm 5 μm; mobile phase: [water (0.1% TFA)-MeCN]; B %: 30%-50%, 10 mins). Compound 5-[(3,4-dichlorophenyl)methylamino]-1-[2-(2-methylsulfonylethoxy)ethyl]-6H-pyrazolo[4,3-d]pyrimidin-7-one (39.5 mg, 85.46 μmol, 22.02% yield, 99.6% purity) was obtained as white solid. $^1$H NMR (DMSO-d$_6$, 400 MHz) δ 11.07 (s, 1H), 7.59~7.57 (m, 3H), 7.33~7.31 (m, 1H), 6.56 (t, J=5.6

Hz, 1H), 4.60 (t, J=5.2 Hz, 2H), 4.47 (d, J=6.0 Hz, 2H), 3.83 (t, J=5.6 Hz, 2H), 3.71 (t, J=5.6 Hz, 2H), 3.27 (t, J=5.6 Hz, 2H), 2.80 (s, 3H). HPLC: 99.57% (220 nm), 99.37% (215 nm), 100.00% (254 nm). MS (ESI): mass calcd. For $C_{17}H_{19}C_{12}N_5O_4S$ 459.05, m/z found 460.1 $[M+H]^+$.

Compound 221

Preparation of (1-(3-(1H-tetrazol-5-yl)propyl)-5-((3, 4-dichlorobenzyl)amino)-1H-pyrazolo[4,3-d]pyrimidin-7(6H)-one)

Preparation of 1-(3-(1H-tetrazol-5-yl)propyl)-N-(3, 4-dichlorobenzyl)-7-methoxy-1H-pyrazolo[4,3-d]pyrimidin-5-amine

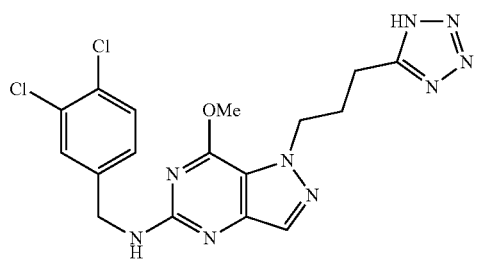 [SMILES: COc1nc(NCc2ccc(Cl)c(Cl)c2)nc2cnn(CCCc3nnn[nH]3)c12]

To a solution of 4-[5-[(3,4-dichlorophenyl)methylamino]-7-methoxy-pyrazolo[4,3-d]pyrimidin-1-yl]butanenitrile (0.600 g, 1.53 mmol, 1.00 eq) in toluene (10.0 mL) was added $TMSN_3$ (1.10 g, 9.51 mmol, 1.25 mL, 6.20 eq) and dibutyl(oxo)tin (458 mg, 1.84 mmol, 1.20 eq). The mixture was stirred at 110° C. for 15 hours. LC-MS showed the reaction was complete. The reaction mixture was diluted with water (10.0 mL) and extracted with EtOAc (5.00 mL×2). The combined organic layers were washed with brine (10.0 mL), dried over $Na_2SO_4$, filtered and concentrated under reduced pressure. The crude product was used into the next step without further purification. Compound N-[(3,4-dichlorophenyl)methyl]-7-methoxy-1-[3-(1H-tetrazol-5-yl)propyl]pyrazolo[4,3-d]pyrimidin-5-amine (0.300 g, 691 μmol, 45.1% yield) was obtained as yellow solid. $^1H$ NMR (CDCl3, 400 MHz) δ 7.67 (s, 1H), 7.40 (s, 1H), 7.31 (d, J=8.0 Hz, 1H), 7.13 (d, J=8.0 Hz, 1H), 4.55~4.17 (m, 4H), 4.00 (s, 3H), 2.79~2.76 (m, 2H), 2.25 (s, 2H).

Preparation of (1-(3-(1H-tetrazol-5-yl)propyl)-5-((3, 4-dichlorobenzyl)amino)-1H-pyrazolo[4,3-d]pyrimidin-7(6H)-one) (Step 3 in Scheme C-4)

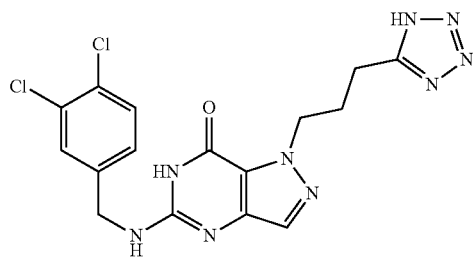 [SMILES: O=c1[nH]c(NCc2ccc(Cl)c(Cl)c2)nc2cnn(CCCc3nnn[nH]3)c12]

To a solution of N-[(3,4-dichlorophenyl)methyl]-7-methoxy-1-[3-(1H-tetrazol-5-yl)propyl]pyrazolo[4,3-d]pyrimidin-5-amine (0.300 g, 691 μmol, 1.00 eq) in MeCN (10.0 mL) was added TMSCl (150 mg, 1.38 mmol, 175 μL, 2.00 eq) and NaI (207 mg, 1.38 mmol, 2.00 eq). The mixture was stirred at 70° C. for 12 hours. LC-MS showed the reaction was complete. The reaction mixture was diluted with water (10.0 mL) and extracted with EtOAc (10.0 mL×2). The combined organic layers were washed with brine (5.00 mL), dried over $Na_2SO_4$, filtered and concentrated under reduced pressure. The residue was purified by prep-HPLC (column: Nano-micro Kromasil C18 100 mm×40 mm 10 μm; mobile phase: [water (0.1% TFA)-MeCN]; B %: 33%-53%, 10 mins). Compound 5-[(3,4-dichlorophenyl)methylamino]-1-[3-(1H-tetrazol-5-yl)propyl]-6H-pyrazolo[4,3-d]pyrimidin-7-one (0.100 g, 238 μmol, 34.5% yield) was obtained as white solid. $^1H$ NMR (DMSO-$d_6$, 400 MHz) δ 11.25 (s, 1H), 7.58 (d, J=5.2 Hz, 3H), 7.31 (d, J=8.4 Hz, 1H), 6.79 (s, 1H), 4.52~4.46 (m, 4H), 2.82~2.78 (m, 2H), 2.25~2.18 (m, 2H). HPLC: 98.61% (220 nm), 98.07% (254 nm), 98.98% (215 nm). LCMS (ESI): mass calcd. For $C_8H_{15}C_{12}N_9O$ 419.08, m/z found 420.0 $[M+H]^+$.

Compound 222

Preparation of 5-[(3,4-dichlorophenyl)methylamino]-1-(4-pyridyl)-6H-pyrazolo[4,3-d]pyrimidin-7-one Preparation of N-[(3,4-dichlorophenyl)methyl]-7-methoxy-1-(4-pyridyl)pyrazolo[4,3-d]pyrimidin-5-amine (Step 2 in Scheme C-4)

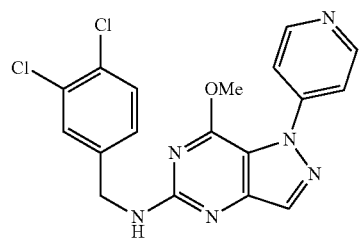 [SMILES: COc1nc(NCc2ccc(Cl)c(Cl)c2)nc2cnn(-c3ccncc3)c12]

A mixture of N-[(3,4-dichlorophenyl)methyl]-7-methoxy-1H-pyrazolo[4,3-d]pyrimidin-5-amine (210 mg, 444 μmol, 1.00 eq), 4-pyridylboronic acid (65.5 mg, 533 μmol, 1.20 eq), $Cu(OAc)_2$ (161 mg, 888 μmol, 2.00 eq) and pyridine (70.2 mg, 888 μmol, 71.6 μL, 2.00 eq) in toluene (10.0 mL) was degassed and purged with O2 for 3 times, and then the mixture was stirred at 110° C. for 12 hours under $O_2$ atmosphere. LC-MS showed the reaction was complete. The reaction mixture was filtered and the filtrate was concentrated under reduced pressure. The residue was purified by prep-TLC ($SiO_2$, DCM:MeOH=20:1, $R_f$=0.55). Compound N-[(3,4-dichlorophenyl)methyl]-7-methoxy-1-(4-pyridyl)pyrazolo[4,3-d]pyrimidin-5-amine (40.0 mg, 99.7 mol, 22.5% yield) was obtained as yellow solid. $^1H$ NMR (DMSO-$d_6$, 400 MHz) δ 8.66 (d, J=6.00 Hz, 2H), 8.20 (s, 1H), 7.71~7.78 (m, 3H), 7.56~.60 (m, 2H), 7.34~7.36 (m, 1H), 4.53 (d, J=6.00 Hz, 2H), 4.00~4.03 (m, 3H).

Preparation of 5-[(3,4-dichlorophenyl)methyl-amino]-1-(4-pyridyl)-6H-pyrazolo[4,3-d]pyrimidin-7-one (Step 3 in Scheme C-4)

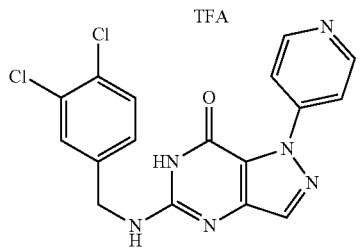 [SMILES: O=c1[nH]c(NCc2ccc(Cl)c(Cl)c2)nc2cnn(-c3ccncc3)c12]

To a solution of N-[(3,4-dichlorophenyl)methyl]-7-methoxy-1-(4-pyridyl)pyrazolo[4,3-d]pyrimidin-5-amine (40.0 mg, 99.7 mol, 1.00 eq) in MeCN (2.00 mL) was added TMSCl (32.5 mg, 299 μmol, 38.0 μL, 3.00 eq) and NaI (44.8 mg, 299 mol, 3.00 eq). The mixture was stirred at 70° C. for 3 hours. LC-MS showed the reaction was complete. The reaction mixture was quenched with $H_2O$ (20.0 mL) at 25° C. and extracted with EtOAc (10.0 mL×3). The combined organic layers were dried over anhydrous $Na_2SO_4$, filtered and concentrated under reduced pressure. The residue was purified by prep-HPLC (TFA condition: column: Welch Ultimate AQ-C18 150 mm×30 mm 5 μm; mobile phase: [water (0.1% TFA)-MeCN]; B %: 25%-55%, 12 mins). Compound 5-[(3,4-dichlorophenyl)methylamino]-1-(4-pyridyl)-6H-pyrazolo[4,3-d]pyrimidin-7-one (10.0 mg, 20.0 μmol, 20.0% yield, TFA) was obtained as white solid. $^1$H NMR (DMSO-$d_6$, 400 MHz) δ 11.60-11.63 (m, 1H), 8.77 (d, J=4.80 Hz, 2H), 8.27~8.32 (m, 2H), 8.21 (s, 1H), 7.60~7.61 (m, 2H), 7.36 (dd, J=8.40 Hz, 2.00 Hz, 1H), 6.94~6.95 (m, 1H), 4.53~4.54 (d, J=6.00 Hz, 2H). LCMS: For $C_{17}H_{12}C_{12}N_6O$ 386, m/z found 387.0 [M+H]$^+$. HPLC: 99.18% (220 nm), 99.13% (215 nm), 98.62% (254 nm).

Compound 223

Preparation of 2-(5-((3,4-dichlorobenzyl)amino)-7-oxo-6,7-dihydro-2H-pyrazolo[4,3-d]pyrimidin-2-yl)propanoic acid Compound 224

Methyl 2-(5-((3,4-dichlorobenzyl)amino)-7-oxo-6,7-dihydro-2H-pyrazolo[4,3-d]pyrimidin-2-yl)propanoate was prepared according to the procedure described herein for Steps 1-3 in Scheme C-4.

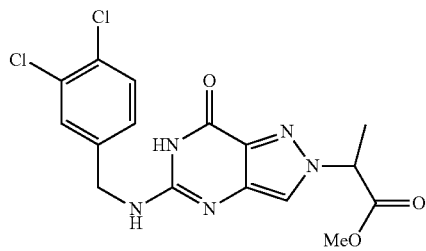 [SMILES: COC(=O)C(C)n1cc2nc(NCc3ccc(Cl)c(Cl)c3)[nH]c(=O)c2n1]

The procedure yielded the desired compound methyl 2-(5-((3,4-dichlorobenzyl)amino)-7-oxo-6,7-dihydro-2H-pyrazolo[4,3-d]pyrimidin-2-yl)propanoate (20.0 mg, 50.22 μmol, 19.42% yield) as a white solid. $^1$H NMR (DMSO-$d_6$, 400 MHz) δ 7.98 (s, 1H), 7.61~7.59 (m, 2H), 7.35~7.33 (m, 1H), 7.14 (s, 1H), 5.45 (q, J=7.2 Hz, 1H), 4.50 (d, J=5.2 Hz, 2H), 3.66 (s, 3H), 1.70 (d, J=7.2 Hz, 3H). HPLC: 96.94% (220 nm), 96.74% (215 nm), 100.00% (254 nm). MS (ESI): mass calcd. For $C_{16}H_{15}C_{12}N_5O_3$ 395.06, m/z found 396.1 [M+H]$^+$.

Compound 225

Preparation of 5-((3,4-dichlorobenzyl)amino)-2-(1-hydroxypropan-2-yl)-2H-pyrazolo[4,3-d]pyrimidin-7 (6H)-one

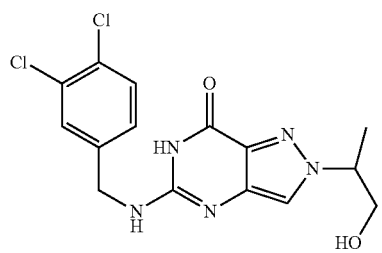 [SMILES: CC(CO)n1cc2nc(NCc3ccc(Cl)c(Cl)c3)[nH]c(=O)c2n1]

To a solution of methyl 2-[5-[(3,4-dichlorophenyl)methylamino]-7-oxo-6H-pyrazolo[4,3-d]pyrimidin-2-yl]propanoate (100 mg, 252.38 μmol, 1 eq) in THF (2 mL) was added DIBAL-H (1 M, 1.26 mL, 5 eq) at 0° C. Then the mixture was stirred at 25° C. for 6 hours. LCMS showed reaction was complete. The reaction mixture was quenched with $H_2O$ (2 mL) at 0° C., and extracted with EtOAc (2 mL×3). The combined organic layers were washed with brine (2 mL), dried over $Na_2SO_4$, filtered and concentrated under reduced pressure. The residue was purified by prep-HPLC (TFA condition column: Nano-micro Kromasil C18 100 mm×30 mm 5 μm; mobile phase: [water (0.1% TFA)-MeCN]; B %: 20%-35%, 10 mins) to give 5-[(3,4-dichlorophenyl)methylamino]-2-(2-hydroxy-1-methyl-ethyl)-6H-pyrazolo[4,3-d]pyrimidin-7-one (29.5 mg, 79.80 μmol, 31.62% yield, 99.6% purity) as white solid. $^1$H NMR (DMSO-$d_6$, 400 MHz) δ 7.87 (s, 1H), 7.61~7.59 (m, 2H), 7.35~7.33 (m, 1H), 7.21 (s, 1H), 4.51~4.45 (m, 3H), 3.69~3.65 (m, 2H), 1.39 (d, J=6.8 Hz, 3H). HPLC: 99.60% (220 nm), 99.44% (215 nm), 100.00% (254 nm). MS (ESI): mass calcd. For $C_{15}H_{15}C_{12}N_5O_2$ 367.06, m/z found 368.1 [M+H]$^+$.

Preparation of 2-(5-((3,4-dichlorobenzyl)amino)-7-oxo-6,7-dihydro-2H-pyrazolo[4,3-d]pyrimidin-2-yl) propanoic Acid

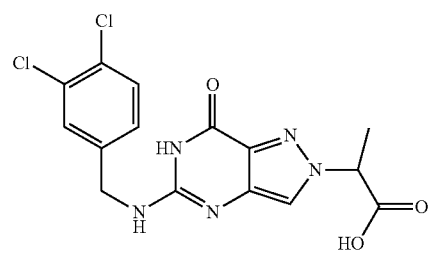 [SMILES: CC(C(=O)O)n1cc2nc(NCc3ccc(Cl)c(Cl)c3)[nH]c(=O)c2n1]

To a solution of methyl 2-[5-[(3,4-dichlorophenyl)methylamino]-7-oxo-6H-pyrazolo[4,3-d]pyrimidin-2-yl]propanoate (100 mg, 252.38 mol, 1 eq) in MeOH (1 mL) and H₂O (1 mL) was added LiOH·H₂O (31.77 mg, 757.14 μmol, 3 eq). The mixture was stirred at 25° C. for 3 hours. LC-MS showed reaction was complete. The reaction mixture was concentrated under reduced pressure to remove MeOH. The aqueous was made pH=4 with 2N HCl. There was solid formed which was collected by filtration. The residue was purified by prep-HPLC (TFA condition column: Luna C18 100 mm×30 mm 5 u; mobile phase: [water (0.1% TFA)-MeCN]; B %: 20%-50%, 10 mins). Compound 2-[5-[(3,4-dichlorophenyl)methylamino]-7-oxo-6H-pyrazolo[4,3-d]pyrimidin-2-yl]propanoic acid (19.1 mg, 49.97 μmol, 19.80% yield) was obtained as white solid. H NMR (DMSO-d₆, 400 MHz) δ 11.04 (s, 1H), 7.95 (s, 1H), 7.61~7.59 (m, 2H), 7.35~7.33 (m, 1H), 7.03 (s, 1H), 5.29 (d, J=6.8 Hz, 1H), 4.50 (d, J=3.6 Hz, 2H), 1.69 (d, J=6.8 Hz, 3H). HPLC: 100.00% (220 nm), 100.00% (215 nm), 100.00% (254 nm). MS (ESI): mass calcd. For C₁₅H₁₃C₁₂N₅O₃ 381.04, m/z found 382.0 [M+H]⁺.

Compound 226

Preparation of 2-(5-((3,4-dichlorobenzyl)amino)-7-oxo-6,7-dihydro-1H-pyrazolo[4,3-d]pyrimidin-1-yl)propanoic Acid Compound 227
Methyl 2-(5-((3,4-dichlorobenzyl)amino)-7-oxo-6,7-dihydro-1H-pyrazolo[4,3-d]pyrimidin-1-yl)propanoate was prepared according to the procedure described herein for Steps 1-3 in Scheme C-4.

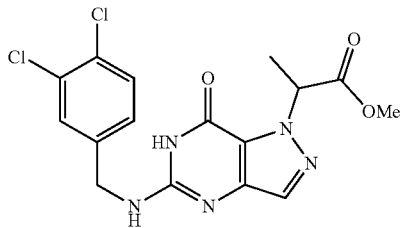 [SMILES: COC(=O)C(C)n1ncc2nc(NCc3ccc(Cl)c(Cl)c3)[nH]c(=O)c21]

The procedure yielded the desired compound methyl 2-(5-((3,4-dichlorobenzyl)amino)-7-oxo-6,7-dihydro-1H-pyrazolo[4,3-d]pyrimidin-1-yl)propanoate (22.1 mg, 55.78 μmol, 19.42% yield) as a white solid. ¹H NMR (DMSO-d₆, 400 MHz) δ 7.63 (s, 1H), 7.60~7.58 (m, 2H), 7.34~7.32 (m, 1H), 6.73 (s, 1H), 5.73 (q, J=7.2 Hz, 1H), 4.49 (d, J=5.6 Hz, 2H), 3.62 (s, 3H), 1.69 (d, J=7.6 Hz, 3H). HPLC: 99.27% (220 nm), 99.09% (215 nm), 99.58% (254 nm). MS (ESI): mass calcd. For C₁₆H₁₅C₁₂N₅O₃ 395.06, m/z found 396.1 [M+H]⁺.

Compound 228

Preparation of 5-((3,4-dichlorobenzyl)amino)-1-(1-hydroxypropan-2-yl)-1H-pyrazolo[4,3-d]pyrimidin-7(6H)-one

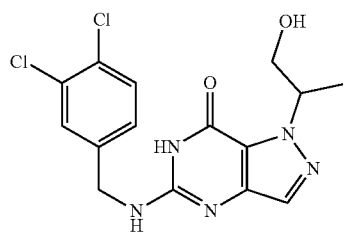 [SMILES: CC(CO)n1ncc2nc(NCc3ccc(Cl)c(Cl)c3)[nH]c(=O)c21]

To a solution of methyl 2-[5-[(3,4-dichlorophenyl)methylamino]-7-oxo-6H-pyrazolo[4,3-d]pyrimidin-1-yl]propanoate (90 mg, 227.14 μmol, 1 eq) in THF (1 mL) was added DIBAL-H (1 M, 1.36 mL, 6 eq) at 0° C. Then the mixture was stirred at 25° C. for 6 hours. LC-MS showed reaction was complete. The reaction mixture was quenched with H₂O (2 mL) at 0° C., and extracted with EtOAc (2 mL×3). The combined organic layers were washed with brine (2 mL), dried over Na₂SO₄, filtered and concentrated under reduced pressure. The residue was purified by prep-HPLC (TFA condition column: Nano-micro Kromasil C18 100 mm×30 mm 5 μm; mobile phase: [water (0.1% TFA)-MeCN]; B %: 25%-45%, 10 mins). Compound 5-[(3,4-dichlorophenyl)methylamino]-1-(2-hydroxy-1-methyl-ethyl)-6H-pyrazolo[4,3-d]pyrimidin-7-one (14.3 mg, 38.84 μmol, 17.10% yield) was obtained as white solid. ¹H NMR (DMSO-d₆, 400 MHz) δ 7.60-7.58 (m, 3H), 7.34~7.32 (m, 1H), 6.85 (s, 1H), 5.10 (q, J=6.8 Hz, 1H), 4.49 (d, J=5.6 Hz, 2H), 3.62~3.58 (m, 2H), 1.36 (d, J=6.8 Hz, 3H). HPLC: 99.23% (220 nm), 98.64% (215 nm), 100.00% (254 nm). MS (ESI): mass calcd. For C₁₅H₁₅C₁₂N₅O₂ 367.06, m/z found 368.1 [M+H]⁺.

Preparation of 2-(5-chloro-7-oxo-6,7-dihydro-1H-pyrazolo[4,3-d]pyrimidin-1-yl)propanoic Acid

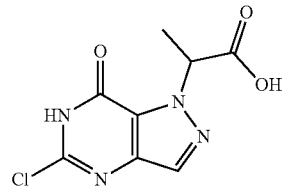 [SMILES: CC(C(=O)O)n1ncc2nc(Cl)[nH]c(=O)c21]

To a solution of methyl 2-(5-chloro-7-methoxy-pyrazolo[4,3-d]pyrimidin-1-yl)propanoate (160 mg, 591.12 μmol, 1 eq) in MeOH (1 mL) and H₂O (1 mL) was added LiOH—H₂O (74.42 mg, 1.77 mmol, 3 eq). The mixture was stirred at 25° C. for 2 hours. LC-MS showed reaction was complete. The reaction mixture was concentrated under reduced pressure to remove MeOH. The aqueous was made pH=4 with 3N HCl, and extracted with EtOAc (2 mL×3). The combined organic layers were washed with brine (2 mL), dried over Na₂SO₄, filtered and concentrated under reduced pressure. Compound 2-(5-chloro-7-oxo-6H-pyrazolo[4,3-d]pyrimidin-1-yl)propanoic acid (200 mg crude) was obtained as white solid. ¹H NMR (CDC₃, 400 MHz) δ 7.62~7.61 (m, 1H), 5.67~5.65 (m, 1H), 1.03~1.04 (m, 3H).

Preparation of 2-(5-((3,4-dichlorobenzyl)amino)-7-oxo-6,7-dihydro-1H-pyrazolo[4,3-d]pyrimidin-1-yl)propanoic Acid

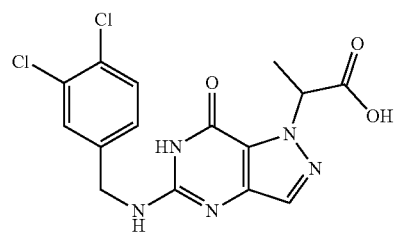 [SMILES: CC(C(=O)O)n1ncc2nc(NCc3ccc(Cl)c(Cl)c3)[nH]c(=O)c21]

A mixture of 2-(5-chloro-7-oxo-6H-pyrazolo[4,3-d]pyrimidin-1-yl)propanoic acid (100 mg, 412.17 μmol, 1 eq) and (3,4-dichlorophenyl)methanamine (145.12 mg, 824.34 μmol, 109.94 μL, 2 eq) in t-BuOH (3 mL) was stirred at 100° C. for 12 hours. LC-MS showed reaction was complete. The reaction mixture was concentrated under reduced pressure to remove t-BuOH. The residue was purified by prep-HPLC (TFA condition column: Waters Xbridge 150 mm×25 mm 5 u; mobile phase: [water (0.1% TFA)-MeCN]; B %: 20%-40%, 20 mins). Compound 2-[5-[(3,4-dichlorophenyl)methylamino]-7-oxo-6H-pyrazolo[4,3-d]pyrimidin-1-yl]propanoic acid (26 mg, 68.03 μmol, 16.50% yield) was obtained as white solid. $^1$H NMR (DMSO-$d_6$, 400 MHz) δ 7.60-7.57 (m, 3H), 7.34~7.32 (m, 1H), 6.67 (s, 1H), 5.62 (q, J=7.6 Hz, 1H), 4.48 (d, J=5.6 Hz, 2H), 1.69 (d, J=7.6 Hz, 3H). HPLC: 99.16% (220 nm), 99.07% (215 nm), 100.00% (254 nm). MS (ESI): mass calcd. For $C_{15}H_{13}C_{12}N_5O_3$ 381.04, m/z found 382.0 [M+H]$^+$.

General Procedures for Preparing Compounds in Scheme C-5

Preparation of Compounds in Scheme C-5 (Step 1 in Scheme C-5)

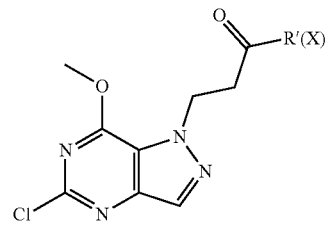

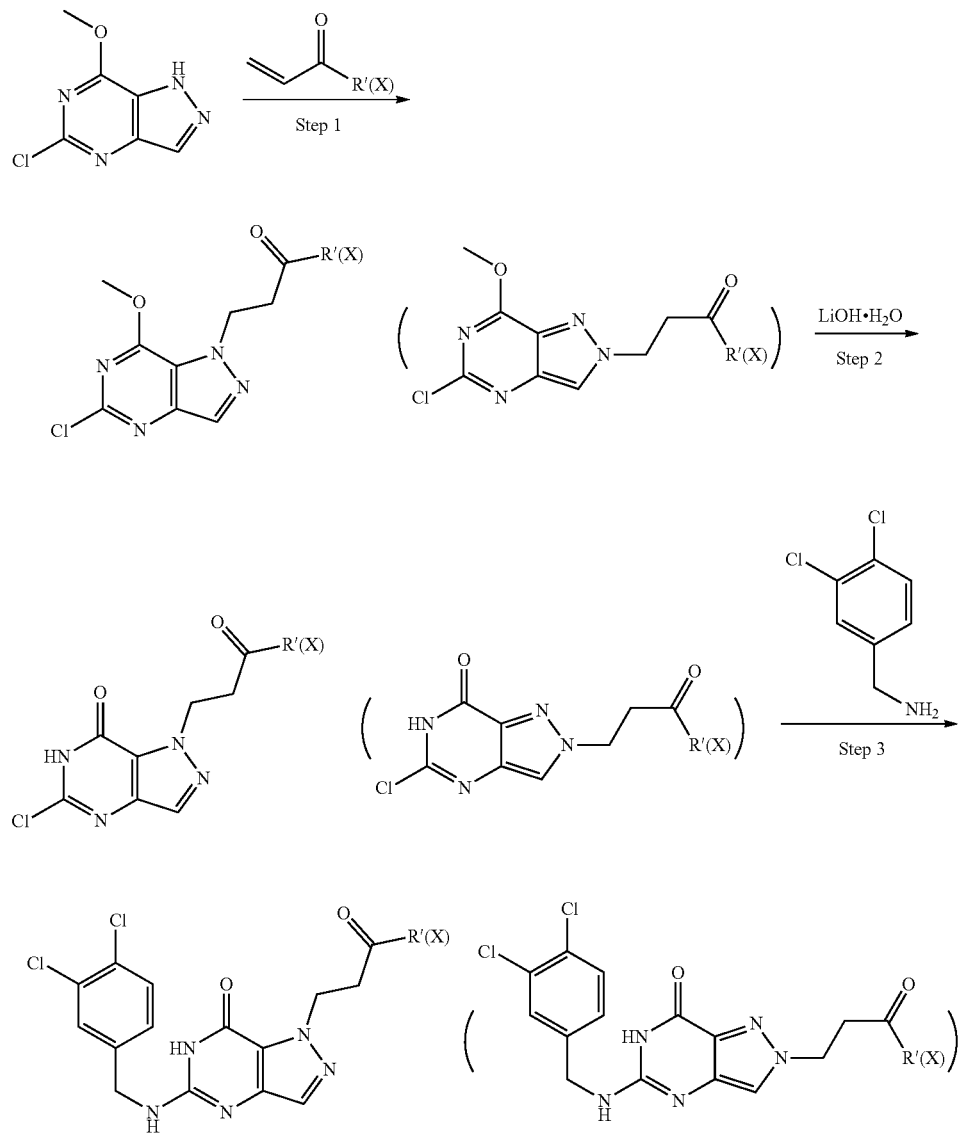

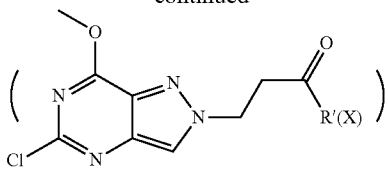

To a mixture of 5-chloro-7-methoxy-1H-pyrazolo[4,3-d]pyrimidine (3.79 mmol, 1 eq) and alkene (4.93 mmol, 1.3 eq) in dioxane (4 mL/mmol) was added Cs$_2$CO$_3$ (189.62 µmol, 0.05 eq) at 25° C. Then the mixture was stirred at 100° C. for 10 hours. TLC and LCMS showed the reaction was complete. The solvent was removed under reduced pressure. The residue dissolved in EtOAc and washed with brine, dried over Na$_2$SO$_4$, filtered and concentrated under reduced pressure. The residue was purified by flash silica gel chromatography (Biotage®; 12 g SepaFlash® Silica Flash Column, Eluent of 025% Ethyl acetate/Petroleum ether gradient at 30 mL/min). The eluent was removed under reduced pressure to give the desired compound.

Preparation of Compounds in Scheme C-5 (Step 2 in Scheme C-5)

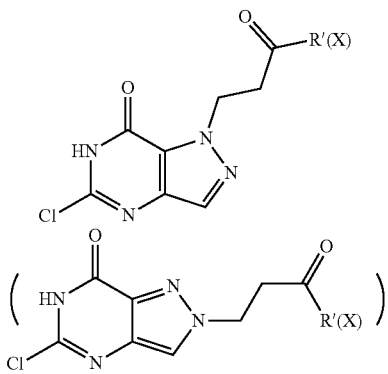

A solution of 3-(5-chloro-7-methoxy-1H-pyrazolo[4,3-d]pyrimidin-1-yl)propanoyl-R'(X) (554.18 µmol, 1 eq) and LiOH—H$_2$O (1.66 mmol, 3 eq) in MeOH (3 mL/mmol 5 mL/mmol) or THF (3 mL/mmol 5 mL/mmol) and H$_2$O (3 mL/mmol 5 mL/mmol) was stirred at 25° C. for 3 hours. LCMS showed the reaction was complete. The organic solvent was removed under reduced pressure. The aqueous was made pH=5 with 2N HCl slowly and there was some solid formed. After filtered, the solid was collected and concentrated under reduced pressure.

Preparation of Compounds in Scheme C-5 (Step 3 in Scheme C-5)

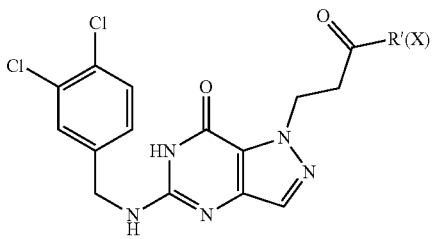

A mixture of 3-(5-chloro-7-oxo-6,7-dihydro-1H-pyrazolo[4,3-d]pyrimidin-1-yl)propanoyl-R'(X) (412.17 µmol, 1 eq) and (3,4-dichlorophenyl)methanamine (618.26 µmol 1.24 mmol, 1.5 eq 3 eq) in t-BuOH (3 mL/mmol 10 mL/mmol) was stirred at 100° C. 140° C. for 10 hours 20 hours. LC-MS showed the reaction was complete. The reaction mixture was concentrated under reduced pressure. The residue was purified by prep-HPLC. Column: a) Luna C18 100 mm×30 mm 5 µm; b) Nano-micro Kromasil C18 100 mm×30 mm 5 µm; c) Xtimate C18 150 mm×25 mm 5 µm. Mobile phase: a) [water (0.1% TFA)-MeCN]; B %: 20%-50%, 10 mins; b) [water (10 mM NH$_4$HCO$_3$)-ACN]; B %: 32%-52%, 10.5 mins. The solvent was removed under freeze drying to give desired product.

Compound 229

Preparation of 3-(5-((3,4-dichlorobenzyl)amino)-7-oxo-6,7-dihydro-1H-pyrazolo[4,3-d]pyrimidin-1-yl)propanoic Acid Preparation of methyl 3-(5-chloro-7-methoxy-1H-pyrazolo[4,3-d]pyrimidin-1-yl)propanoate (Step 1 in Scheme C-5)

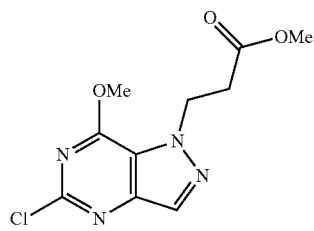 [SMILES: COC(=O)CCn1ncc2nc(Cl)nc(OC)c21]

To a mixture of 5-chloro-7-methoxy-1H-pyrazolo[4,3-d]pyrimidine (0.7 g, 3.79 mmol, 1 eq) and methyl prop-2-enoate (424.42 mg, 4.93 mmol, 443.96 µL, 1.3 eq) in dioxane (15 mL) was added Cs$_2$CO$_3$ (61.78 mg, 189.62 µmol, 0.05 eq) at 25° C. Then the mixture was stirred at 100° C. for 10 hours. TLC and LCMS showed the reaction was complete. The solvent was removed under reduced pressure. The residue dissolved in EtOAc (50 mL) and washed with brine (10 mL×2), dried over Na$_2$SO$_4$, filtered and concentrated under reduced pressure. The residue was purified by flash silica gel chromatography (Biotage®; 12 g SepaFlash® Silica Flash Column, Eluent of 025% Ethyl acetate/Petroleum ether gradient at 30 mL/min). The eluent was removed under reduced pressure. Compound methyl 3-(5-chloro-7-methoxy-pyrazolo[4,3-d]pyrimidin-2-yl)propanoate (0.4 g, 1.48 mmol, 38.97% yield) was obtained as white solid. $^1$H NMR (CDCl$_3$, 400 MHz) δ 8.02 (s, 1H), 4.84 (t, J=6.8 Hz, 2H), 4.24 (s, 3H), 3.67 (s, 3H), 2.98 (t, J=6.8 Hz, 2H). Compound methyl 3-(5-chloro-7-methoxy-pyrazolo[4,3-d]pyrimidin-1-yl) propanoate (0.3 g, 1.11 mmol, 29.23% yield) was obtained as white solid. $^1$H NMR (CDCl$_3$, 400 MHz) δ 8.09 (s, 1H), 4.72 (t, J=6.0 Hz, 2H), 4.23 (s, 3H), 3.68 (s, 3H), 3.07 (t, J=6.8 Hz, 2H).

Preparation of 3-(5-chloro-7-oxo-6,7-dihydro-1H-pyrazolo[4,3-d]pyrimidin-1-yl)propanoic acid (Step 2 in Scheme C-5)

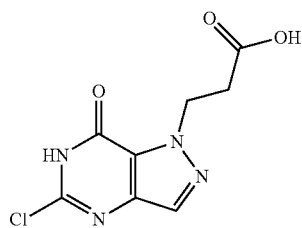 [SMILES: O=C(O)CCn1ncc2nc(Cl)[nH]c(=O)c21]

A solution of methyl 3-(5-chloro-7-methoxy-pyrazolo[4,3-d]pyrimidin-1-yl)propanoate (0.15 g, 554.18 μmol, 1 eq) and LiOH—H$_2$O (69.76 mg, 1.66 mmol, 3 eq) in MeOH (1 mL), H$_2$O (1 mL) and THF (1 mL) was stirred at 25° C. for 3 hours. LCMS showed the reaction was complete. The organic solvent was removed under reduced pressure. The aqueous was made pH=5 with 2N HCl slowly and there was some solid formed. After filtered, the solid was collected and concentrated under reduced pressure. The residue was used to the next step without further purification. Compound 3-(5-chloro-7-oxo-6H-pyrazolo[4,3-d]pyrimidin-1-yl)propanoic acid (0.11 g, 453.39 μmol, 81.81% yield) was obtained as white solid. 1H NMR (DMSO-d$_6$, 400 MHz) δ 13.28 (s, 1H), 12.37 (s, 1H), 7.95 (s, 1H), 4.72 (t, J=6.8 Hz, 2H), 2.85 (t, J=6.8 Hz, 2H).

Preparation of 3-(5-((3,4-dichlorobenzyl)amino)-7-oxo-6,7-dihydro-1H-pyrazolo[4,3-d]pyrimidin-1-yl)propanoic Acid (Step 3 in Scheme C-5)

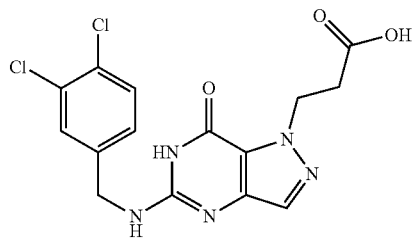 [SMILES: O=C(O)CCn1ncc2nc(NCc3ccc(Cl)c(Cl)c3)[nH]c(=O)c21]

A solution of (3,4-dichlorophenyl)methanamine (217.68 mg, 1.24 mmol, 164.91 μL, 3 eq) and 3-(5-chloro-7-oxo-6H-pyrazolo[4,3-d]pyrimidin-1-yl)propanoic acid (0.1 g, 412.17 μmol, 1 eq) in t-BuOH (3 mL) was heated at 100° C. for 10 hours. LC-MS and HPLC showed the reaction was complete. The solvent was removed under reduced pressure. The residue was purified by prep-HPLC (column: Luna C18 100 mm×30 mm 5 μm; mobile phase: [water (0.1% TFA)-MeCN]; B %: 25%-50%, 10 mins). Compound 3-[5-[(3,4-dichlorophenyl)methylamino]-7-oxo-6H-pyrazolo[4,3-d]pyrimidin-1-yl]propanoic acid (88.8 mg, 232.34 μmol, 56.37% yield) was obtained as white solid. $^1$H NMR (DMSO-d$_6$, 400 MHz) δ 12.34 (s, 1H), 11.11 (s, 1H), 7.59~7.57 (m, 2H), 7.55 (s, 1H), 7.33 (dd, J=2.8 Hz, 8.0 Hz, 1H), 6.59 (s, 1H), 4.62 (t, J=6.8 Hz, 2H), 4.47 (d, J=6.0 Hz, 2H), 2.79 (t, J=6.8 Hz, 2H). HPLC: 98.91% (220 nm), 98.72% (215 nm), 100.00% (254 nm). MS (ESI): mass calcd. For C$_{15}$H$_{13}$C$_{12}$N$_5$O$_3$ 381.04, m/z found 382.0 [M+H]$^+$.

Compound 230

3-(5-((3,4-Dichlorobenzyl)amino)-7-oxo-6,7-dihydro-2H-pyrazolo[4,3-d]pyrimidin-2-yl)propanoic acid was prepared according to the procedure described herein for Steps 2-3 in Scheme C-5.

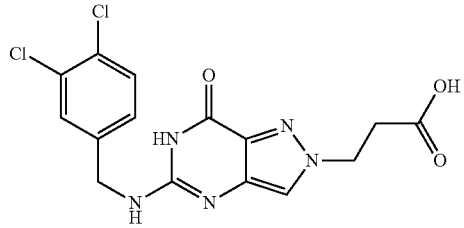 [SMILES: O=C(O)CCn1cc2nc(NCc3ccc(Cl)c(Cl)c3)[nH]c(=O)c2n1]

The procedure yielded the desired compound (22.4 mg, 58.61 μmol, 20.31% yield) as a white solid. $^1$H NMR (DMSO-d$_6$, 400 MHz) δ 12.47 (s, 1H), 10.80 (s, 1H), 7.82 (s, 1H), 7.60~7.58 (m, 2H), 7.32 (dd, J=2.0 Hz, 8.0 Hz, 1H), 6.67~6.63 (m, 1H), 4.45 (d, J=6.0 Hz, 2H), 4.40 (t, J=6.8 Hz, 2H), 2.86 (t, J=6.8 Hz, 2H). HPLC: 99.06% (220 nm), 98.84% (215 nm), 95.66% (254 nm). MS (ESI): mass caled. For C$_{15}$H$_{13}$C$_{12}$N$_5$O$_3$ 381.04, m/z found 382.0 [M+H]$^+$.

Compound 231

Methyl 3-(5-((3,4-dichlorobenzyl)amino)-7-oxo-6,7-dihydro-1H-pyrazolo[4,3-d]pyrimidin-1-yl)propanoate was prepared according to the procedure described herein for Steps 1-3 in Scheme C-5.

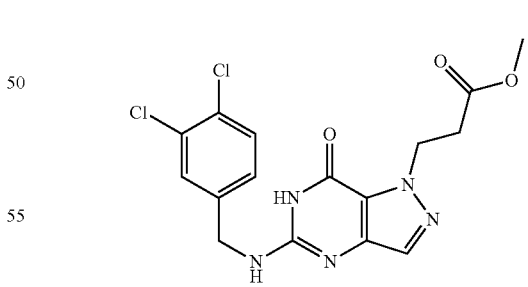

The procedure yielded the desired compound (53.3 mg, 134.52 μmol, 28.77% yield) as a white solid. $^1$H NMR (DMSO-d$_6$, 400 MHz) δ 7.59-7.57 (m, 2H), 7.56 (s, 1H), 7.32 (dd, J=2.0 Hz, 8.4 Hz, 1H), 6.72 (s, 1H), 4.65 (t, J=7.2 Hz, 2H), 4.47 (d, J=6.0 Hz, 2H), 3.56 (s, 3H), 2.88 (t, J=6.8 Hz, 2H). HPLC: 97.26% (220 nm), 97.07% (215 nm), 100.00% (254 nm). MS (ESI): mass calcd. For C$_{16}$H$_{15}$C$_{12}$N$_5$O$_3$ 395.06, m/z found 396.1 [M+H]$^+$.

Compound 232

Methyl 3-(5-((3,4-dichlorobenzyl)amino)-7-oxo-6,7-dihydro-2H-pyrazolo[4,3-d]pyrimidin-2-yl)propanoate was prepared according to the procedure described herein for Steps 1-3 in Scheme C-5.

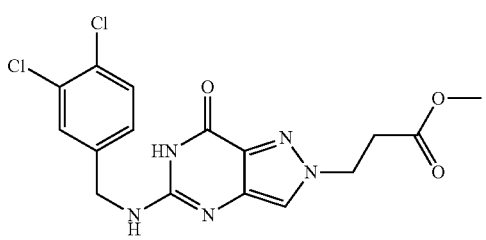 [SMILES: COC(=O)CCn1cc2nc(NCc3ccc(Cl)c(Cl)c3)[nH]c(=O)c2n1]

The procedure yielded the desired compound (114.1 mg, 287.97 μmol, 49.27% yield) as a white solid. $^1$H NMR (DMSO-$d_6$, 400 MHz) δ 7.88 (s, 1H), 7.61~7.59 (m, 2H), 7.33 (dd, J=2.0 Hz, 8.0 Hz, 1H), 7.15 (s, 1H), 4.50~4.45 (m, 4H), 3.59 (s, 3H), 2.97 (t, J=6.8 Hz, 2H). HPLC: 100.00% (220 nm), 100.00% (215 nm), 100.00% (254 nm). MS (ESI): mass calcd. For $C_{16}H_{15}Cl_2N_5O_3$ 395.06, m/z found 396.1 $[M+H]^+$.

Compound 233

Preparation of 5-((3,4-dichlorobenzyl)amino)-1-(2-(5-methyl-1,3,4-oxadiazol-2-yl)ethyl)-1H-pyrazolo[4,3-d]pyrimidin-7(6H)-one Preparation of tert-butyl 3-(5-chloro-7-methoxy-1H-pyrazolo[4,3-d]pyrimidin-1-yl)propanoate (Step 1 in Scheme C-5)

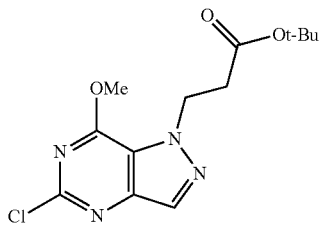 [SMILES: COc1nc(Cl)nc2cnn(CCC(=O)OC(C)(C)C)c12]

To a mixture of 5-chloro-7-methoxy-1H-pyrazolo[4,3-d]pyrimidine (0.5 g, 2.71 mmol, 1 eq) and tert-butyl prop-2-enoate (451.34 mg, 3.52 mmol, 511.14 μL, 1.3 eq) in dioxane (10 mL) was added $Cs_2CO_3$ (44.13 mg, 135.44 μmol, 0.05 eq) at 25° C. Then the mixture was stirred at 100° C. for 10 hours. TLC and LCMS showed the reaction was complete. The solvent was removed under reduced pressure. The residue dissolved in EtOAc (50 mL) and washed with brine (10 mL×2). The combined organic layer was dried over $Na_2SO_4$, filtered and concentrated under reduced pressure. The residue was purified by flash silica gel chromatography (Biotage®; 12 g SepaFlash® Silica Flash Column, Eluent of 025% Ethyl acetate/Petroleum ether gradient at 30 mL/min). The eluent was removed under reduced pressure. Compound tert-butyl 3-(5-chloro-7-methoxy-pyrazolo[4,3-d]pyrimidin-1-yl) propanoate (0.14 g, 447.64 μmol, 16.53% yield) was obtained as white solid. $^1$H NMR (CDCl$_3$, 400 MHz) δ 8.01 (s, 1H), 4.79 (t, J=6.8 Hz, 2H), 4.23 (s, 3H), 2.88 (t, J=6.8 Hz, 2H), 1.38 (s, 9H).

Preparation of 3-(5-chloro-7-methoxy-1H-pyrazolo[4,3-d]pyrimidin-1-yl)propanoic Acid (Step 2 in Scheme C-5)

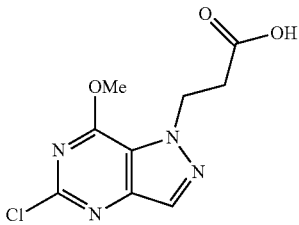 [SMILES: COc1nc(Cl)nc2cnn(CCC(=O)O)c12]

To a solution of tert-butyl 3-(5-chloro-7-methoxy-pyrazolo[4,3-d]pyrimidin-1-yl)propanoate (0.2 g, 639.49 μmol, 1 eq) in EtOAc (5 mL) was added HC/EtOAc (4 M, 4.00 mL, 25 eq) at 25° C. Then the mixture was stirred at 25° C. for 10 hours. TLC and LCMS showed the reaction was nearly complete. The solvent was removed under reduced pressure. The residue was used to the next step without further purification. Compound 3-(5-chloro-7-methoxy-pyrazolo[4,3-d]pyrimidin-1-yl)propanoic acid (0.16 g, 623.43 μmol, 97.49% yield) was obtained as white solid. $^1$H NMR (DMSO-$d_6$, 400 MHz) δ 8.24 (s, 1H), 4.72 (t, J=6.8 Hz, 2H), 4.16 (s, 3H), 2.88 (t, J=6.8 Hz, 2H).

Preparation of N'-acetyl-3-(5-chloro-7-methoxy-1H-pyrazolo[4,3-d]pyrimidin-1-yl)propanehydrazide

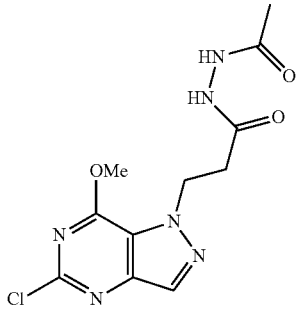 [SMILES: COc1nc(Cl)nc2cnn(CCC(=O)NNC(C)=O)c12]

To a mixture of acetohydrazide (86.60 mg, 1.17 mmol, 1 eq), 3-(5-chloro-7-methoxy-pyrazolo[4,3-d]pyrimidin-1-yl)propanoic acid (0.3 g, 1.17 mmol, 1 eq) and DIEA (453.22 mg, 3.51 mmol, 610.80 μL, 3 eq) in $CH_3CN$ (5 mL) was added HATU (488.91 mg, 1.29 mmol, 1.1 eq). Then the mixture was stirred at 20° C. for 3 hours. TLC and LCMS showed the reaction was complete. The mixture was quenched with ice water (4 mL) slowly and there was some solid formed. The solid was collected after filtered. The residue was used to the next step without further purification. Compound N'-acetyl-3-(5-chloro-7-methoxy-pyrazolo[4,3-d]pyrimidin-1-yl)propanehydrazide (0.17 g, 543.63 μmol, 46.51% yield) was obtained as off white solid. $^1$H NMR (DMSO-$d_6$, 400 MHz) δ 9.82 (s, 1H), 9.72 (s, 1H), 8.23 (s, 1H), 4.74 (t, J=6.8 Hz, 2H), 4.17 (s, 3H), 2.80 (t, J=6.8 Hz, 2H), 1.81 (s, 3H).

Preparation of 2-(2-(5-chloro-7-methoxy-1H-pyrazolo[4,3-d]pyrimidin-1-yl)ethyl)-5-methyl-1,3,4-oxadiazole

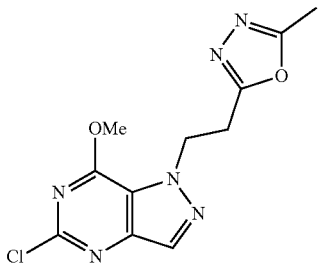 [SMILES: COc1nc(Cl)nc2cnn(CCc3nnc(C)o3)c12]

A solution of N'-acetyl-3-(5-chloro-7-methoxy-pyrazolo[4,3-d]pyrimidin-1-yl)propane hydrazide (0.17 g 543.63 μmol, 1 eq) in POCl$_3$ (4.17 g 27.18 mmol, 2.53 mL, 50 eq) was stirred at 100° C. for half an hour under N$_2$. TLC and LCMS showed the reaction was complete. The solvent was removed under reduced pressure. The residue was dissolved in DCM (30 mL) and washed with brine (5 mL×6). The organic layer was dried over Na$_2$SO$_4$, filtered and concentrated under reduced pressure to give 2-[2-(5-chloro-7-methoxy-pyrazolo[4,3-d]pyrimidin-1-yl)ethyl]-5-methyl-1,3,4-oxadiazole (0.15 g, 509.00 μmol, 93.63% yield) as yellow oil. $^1$H NMR (CDCl$_3$, 400 MHz) δ 8.05 (s, 1H), 4.99 (t, J=6.8 Hz, 2H), 4.22 (s, 3H), 3.46 (t, J=6.8 Hz, 2H), 2.47 (s, 3H).

Preparation of 5-chloro-1-(2-(5-methyl-1,3,4-oxadiazol-2-yl)ethyl)-1H-pyrazolo[4,3-d]pyrimidin-7(6H)-one (Step 2 in Scheme C-5)

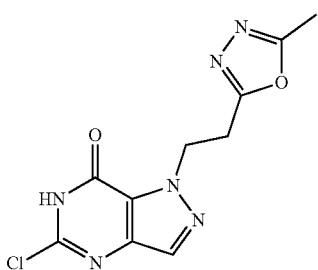 [SMILES: Cc1nnc(CCn2ncc3nc(Cl)[nH]c(=O)c32)o1]

A solution of 2-[2-(5-chloro-7-methoxy-pyrazolo[4,3-d]pyrimidin-1-yl)ethyl]-5-methyl-1,3,4-oxadiazole (0.15 g, 509.00 μmol, 1 eq) and LiOH·H$_2$O (64.07 mg, 1.53 mmol, 3 eq) in THF (2 mL) and H$_2$O (2 mL) was stirred at 25° C. for 3 hours. LCMS showed the reaction was complete. The organic solvent was removed under reduced pressure. The aqueous was made pH=5 with 2N HCl slowly and then extracted with EtOAc (10 mL×5). The combined organic layer was washed with brine (5 mL), dried over Na$_2$SO$_4$, filtered and concentrated under reduced pressure. The residue was used to the next step without further purification. Compound 5-chloro-1-[2-(5-methyl-1,3,4-oxadiazol-2-yl)ethyl]-6H-pyrazolo[4,3-d]pyrimidin-7-one (0.13 g, 463.18 μmol, 91.00% yield) was obtained as white solid. $^1$H NMR (DMSO-d$_6$, 400 MHz) δ 13.36 (s, 1H), 7.97 (s, 1H), 4.88 (t, J=6.4 Hz, 2H), 3.42 (t, J=6.8 Hz, 2H), 2.37 (s, 3H).

Preparation of 5-((3,4-dichlorobenzyl)amino)-1-(2-(5-methyl-1,3,4-oxadiazol-2-yl)ethyl)-1H-pyrazolo[4,3-d]pyrimidin-7(6H)-one (Step 3 in Scheme C-5)

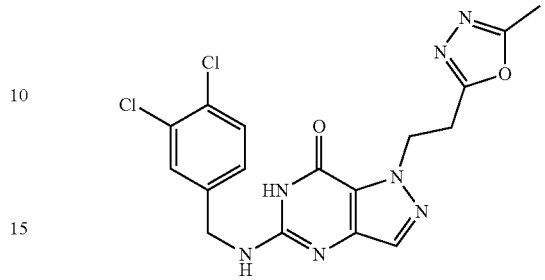

A solution of (3,4-dichlorophenyl)methanamine (163.08 mg, 926.35 μmol, 123.54 μL, 2 eq) and 5-chloro-1-[2-(5-methyl-1,3,4-oxadiazol-2-yl)ethyl]-6H-pyrazolo[4,3-d]pyrimidin-7-one (0.13 g, 463.18 μmol, 1 eq) in t-BuOH (3 mL) was heated at 100° C. for 10 hours. LC-MS and HPLC showed the reaction was complete. The solvent was removed under reduced pressure. The residue was purified by prep-HPLC (column: Luna C18 100 mm×30 mm 5 μm; mobile phase: [water (0.05% HCl)-MeCN]; B %: 25%-40%, 10 mins) and then purified by prep-HPLC (column: column: Xtimate C18 150 mm×25 mm 5 μm; mobile phase: [water (10 mM NH$_4$HCO$_3$)-MeCN]; B %: 32%-52%, 10.5 mins). The eluent was removed under freeze drying. The eluent was removed under freeze drying. Compound 5-[(3,4-dichlorophenyl)methylamino]-1-[2-(5-methyl-1,3,4-oxadiazol-2-yl)ethyl]-6H-pyrazolo[4,3-d]pyrimidin-7-one (28.6 mg, 68.05 μmol, 14.69% yield) was obtained as white solid. $^1$H NMR (DMSO-d$_6$, 400 MHz) δ 7.59-7.57 (m, 2H), 7.53 (s, 1H), 7.32 (dd, J=2.0 Hz, 8.8 Hz, 1H), 6.74 (s, 1H), 4.77 (t, J=6.8 Hz, 2H), 4.46 (d, J=5.6 Hz, 2H), 3.35 (t, J=6.8 Hz, 2H), 2.50 (s, 3H). HPLC: 100.00% (220 nm), 100.00% (215 nm), 100.00% (254 nm). MS (ESI): mass calcd. For C$_{17}$H$_{15}$Cl$_2$N$_7$O$_2$ 419.07, m/z found 420.1 [M+H]$^+$.

Compound 234

Preparation of 5-((3,4-dichlorobenzyl)amino)-1-(2-(5-(hydroxymethyl)-1,3,4-oxadiazol-2-yl)ethyl)-1H-pyrazolo[4,3-d]pyrimidin-7(6H)-one hydrochloride

Preparation of tert-butyl 3-(5-chloro-7-methoxy-1H-pyrazolo[4,3-d]pyrimidin-1-yl)propanoate (Step 1 in Scheme C-5)

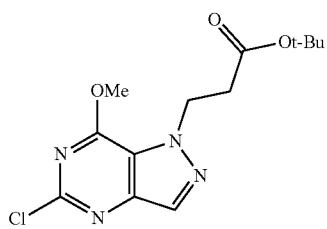 [SMILES: COc1nc(Cl)nc2cnn(CCC(=O)OC(C)(C)C)c12]

To a solution of 5-chloro-7-methoxy-1H-pyrazolo[4,3-d]pyrimidine (2 g, 10.84 mmol, 1 eq) in dioxane (20 mL) was added tert-butyl prop-2-enoate (1.81 g, 14.09 mmol, 2.04 mL, 1.3 eq) and Cs$_2$CO$_3$ (282.43 mg, 866.82 μmol, 0.08 eq).

The mixture was stirred at 100° C. for 12 hours. TLC showed 5-chloro-7-methoxy-1H-pyrazolo[4,3-d]pyrimidine was consumed completely and new spots formed. H₂O (15 mL) was added to the reaction mixture. Then the mixture was extracted with EtOAc (20 mL×3). The combined organic layers were washed with brine (20 mL×1), dried over Na₂SO₄, filtered and concentrated under reduced pressure. The residue was purified by flash silica gel chromatography (Biotage®; 40 g SepaFlash® Silica Flash Column, Eluent of 025% Ethyl acetate/Petroleum ether gradient at 45 mL/min). Then the eluent was concentrated under reduced pressure. Compound tert-butyl 3-(5-chloro-7-methoxy-1H-pyrazolo[4,3-d]pyrimidin-1-yl)propanoate (0.59 g, 1.89 mmol, 17.41% yield) was obtained as light yellow solid and compound tert-butyl 3-(5-chloro-7-methoxy-2H-pyrazolo[4,3-d]pyrimidin-2-yl) propanoate (2 g, 6.39 mmol, 59.02% yield) was obtained as white solid. ¹H NMR (CDCl₃, 400 MHz) δ 8.03 (s, 1H), 4.81 (t, J 6.8 Hz, 2H), 4.24 (s, 3H), 2.89 (t, J 7.2 Hz, 2H), 1.39 (s, 9H).

Preparation of 3-(5-chloro-7-methoxy-1H-pyrazolo[4,3-d]pyrimidin-1-yl)propanoic Acid

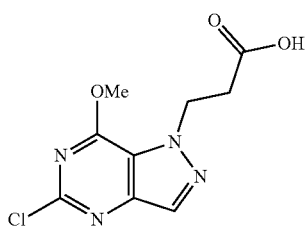 [SMILES: COc1nc(Cl)nc2cnn(CCC(=O)O)c12]

To a solution of tert-butyl 3-(5-chloro-7-methoxy-pyrazolo[4,3-d]pyrimidin-1-yl)propanoate (0.59 g, 1.89 mmol, 1 eq) in EtOAc (2 mL) was added HCl/EtOAc (5 mL, 4 N). The mixture was stirred at 25° C. for 12 hours. LCMS showed the reaction was completed. The reaction mixture was concentrated under reduced pressure. Compound 3-(5-chloro-7-methoxy-1H-pyrazolo[4,3-d]pyrimidin-1-yl)propanoic acid (0.45 g, crude) was obtained as white solid. ¹H NMR (DMSO-d₆, 400 MHz) δ 8.24 (s, 1H), 4.72 (t, J 6.8 Hz, 2H), 4.16 (s, 3H), 2.88 (t, J 7.2 Hz, 2H).

Preparation of 3-(5-chloro-7-methoxy-1H-pyrazolo[4,3-d]pyrimidin-1-yl)-N'-(2-methoxyacetyl) propanehydrazide

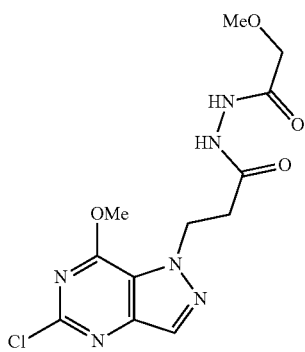 [SMILES: COCC(=O)NNC(=O)CCn1ncc2nc(Cl)nc(OC)c21]

To a solution of 3-(5-chloro-7-methoxy-pyrazolo[4,3-d]pyrimidin-1-yl)propanoic acid (0.3 g, 1.17 mmol, 1 eq), 2-methoxyacetohydrazide (121.69 mg, 1.17 mmol, 1 eq), DIEA (453.23 mg, 3.51 mmol, 610.82 μL, 3 eq) was added HATU (488.91 mg, 1.29 mmol, 1.1 eq) in MeCN (4 mL) was stirred at 25° C. for 12 hours. LC-MS and TLC showed the reaction was completed. H₂O (7 mL) was added to the reaction mixture. The reaction mixture was concentrated under reduced pressure to remove MeCN. Then the mixture was extracted with EtOAc (10 mL×3). The combined organic layers were washed with brine (6 mL×1), dried over Na₂SO₄, filtered and concentrated under reduced pressure to give a residue. The residue was purified by flash silica gel chromatography (Biotage®; 12 g SepaFlash® Silica Flash Column, Eluent of 08% EtOAc/MeOH gradient at 40 mL/min). Then the eluent was concentrated under reduced pressure. Compound 3-(5-chloro-7-methoxy-1H-pyrazolo[4,3-d]pyrimidin-1-yl)-N'-(2-methoxyacetyl)propanehydrazide (0.39 g, 1.14 mmol, 97.35% yield) was obtained as pale yellow solid. H NMR (DMSO-d₆, 400 MHz) δ 9.88 (s, 1H), 9.72 (s, 1H), 8.24 (s, 1H), 4.74 (t, J 6.8 Hz, 2H), 4.16 (s, 3H), 3.86 (s, 2H), 3.32 (s, 3H), 2.82 (d, J=7.2 Hz, 2H).

Preparation of 2-(2-(5-chloro-7-methoxy-1H-pyrazolo[4,3-d]pyrimidin-1-yl)ethyl)-5-(methoxymethyl)-1,3,4-oxadiazole

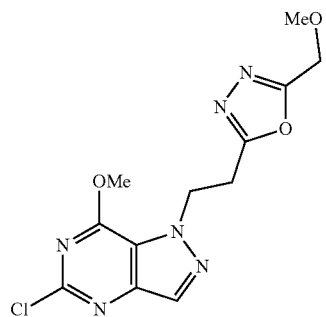 [SMILES: COCc1nnc(CCn2ncc3nc(Cl)nc(OC)c32)o1]

A solution of 3-(5-chloro-7-methoxy-pyrazolo[4,3-d]pyrimidin-1-yl)-N'-(2-methoxyacetyl) propanehydrazide (0.38 g, 1.11 mmol, 1 eq) in POCl₃ (4 mL) was stirred at 100° C. for 0.5 hr. TLC showed the reaction was complete. The reaction mixture was concentrated under reduced pressure to give 2-(2-(5-chloro-7-methoxy-1H-pyrazolo[4,3-d]pyrimidin-1-yl)ethyl)-5-(methoxy methyl)-1,3,4-oxadiazole (0.37 g, crude) as brown oil. ¹H NMR (CDC₃, 400 MHz) δ 7.79 (s, 1H), 4.79 (t, J 6.8 Hz, 2H), 4.34 (s, 2H), 3.98 (s, 3H), 3.24 (t, J 8.8 Hz, 2H), 3.21 (s, 3H).

Preparation of 5-chloro-1-(2-(5-(methoxymethyl)-1,3,4-oxadiazol-2-yl)ethyl)-1H-pyrazolo[4,3-d]pyrimidin-7(6H)-one (Step 2 in Scheme C-5)

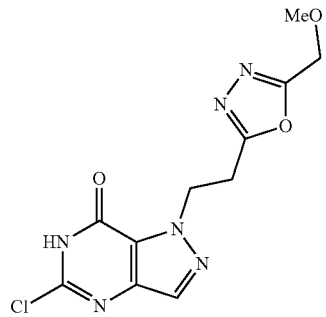 [SMILES: COCc1nnc(CCn2ncc3nc(Cl)[nH]c(=O)c32)o1]

To a solution of 2-[2-(5-chloro-7-methoxy-pyrazolo[4,3-d]pyrimidin-1-yl)ethyl]-5-(methoxymethyl)-1,3,4-oxadiazole (0.1 g, 307.96 µmol, 1 eq) in H₂O (2 mL) and MeOH (2 mL) was added LiOHH₂O (38.77 mg, 923.87 µmol, 3 eq). The mixture was stirred at 25° C. for 2 hours. TLC showed the reaction was completed. H₂O (4 mL) was added to the reaction mixture. The reaction mixture was concentrated under reduced pressure to remove MeOH. The aqueous was adjusted to pH=6 with HCl (3 N). Then the mixture was extracted with EtOAc (7 mL×3). The combined organic layers were washed with brine (6 mL×1), dried over Na₂SO₄, filtered and concentrated under reduced pressure. The residue was purified by flash silica gel chromatography (Biotage®; 12 g SepaFlash® Silica Flash Column, Eluent of 0-9% MeOH/Ethyl acetate gradient at 40 mL/min). Then the eluent was concentrated under reduced pressure. Compound 5-chloro-1-(2-(5-methoxymethyl)1,3,4-oxadiazol-2-yl)ethyl)-1H-pyrazolo[4,3-d]pyrimidin-7(6H)-one (30 mg, 96.56 µmol, 31.35% yield) was obtained as pale yellow solid. H NMR (DMSO-d₆, 400 MHz) δ 7.97 (s, 1H), 4.91 (t, J 6.4 Hz, 2H), 4.56 (s, 2H), 3.47 (d, J 6.4 Hz, 2H), 3.28 (s, 3H).

Compound 235

Preparation of 5-((3,4-dichlorobenzyl)amino)-1-(2-(5-(methoxymethyl)-1,3,4-oxadiazol-2-yl)ethyl)-1H-pyrazolo[4,3-d]pyrimidin-7(6H)-one hydrochloride (Step 3 in Scheme C-5)

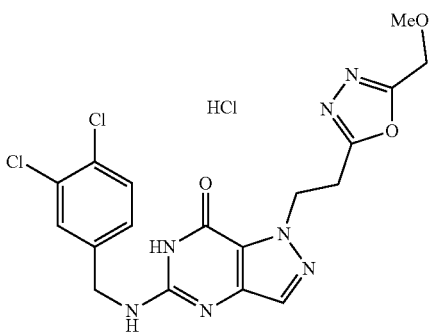 [SMILES: COCc1nnc(CCn2ncc3nc(NCc4ccc(Cl)c(Cl)c4)[nH]c(=O)c32)o1 ; Cl]

To a solution of 5-chloro-1-[2-[5-(methoxymethyl)-1,3,4-oxadiazol-2-yl]ethyl]-6H-pyrazolo 4,3-d]pyrimidin-7-one (25 mg, 80.46 µmol, 1 eq) in t-BuOH (1 mL) was added (3,4-dichlorophenyl)methanamine (21.25 mg, 120.70 µmol, 16.10 µL, 1.5 eq). The mixture was stirred at 100° C. for 10 hours. HPLC showed the reaction was completed. The reaction mixture was concentrated under reduced pressure. The residue was purified by prep-HPLC (column: Phenomenex Luna C18 100 mm×30 mm 5 µm; mobile phase: [water (0.04% HCl)-ACN]; B %: 25%-45%, 10 mins). MeCN was removed under reduced pressure at 30° C. The residue was dried over lyophilization. Compound 5-((3,4-dichlorobenzyl)amino)-1-(2-(5-(methoxymethyl)-1,3,4-oxadiazol-2-yl)ethyl)-1H-pyrazolo[4,3-d]pyrimidin-7(6H)-one hydrochloride (3.6 mg, 7.56 µmol, 9.39% yield, 94.542% purity, HCl) was obtained as white solid. ¹H NMR (DMSO-d₆, 400 MHz) δ 7.61~7.58 (m, 4H), 7.33 (dd, J 8.8 Hz, 1.2 Hz, 1H), 7.18 (s, 1H), 4.81 (t, J 6.4 Hz, 2H), 4.56 (s, 2H), 4.51 (d, J 5.2 Hz, 2H), 3.42 (t, J 6.8 Hz, 2H), 3.27 (s, 3H). HPLC: 94.54% (220 nm), 93.28% (215 nm), 94.36% (254 nm). MS (ESI): mass calcd. For C₁₈H₁₈C₁₃N₇O₃ 449.08, m/z found 450.0 [M+H]⁺.

Preparation of 5-((3,4-dichlorobenzyl)amino)-1-(2-(5-(hydroxymethyl)-1,3,4-oxadiazol-2-yl)ethyl)-1H-pyrazolo[4,3-d]pyrimidin-7(6H)-one hydrochloride

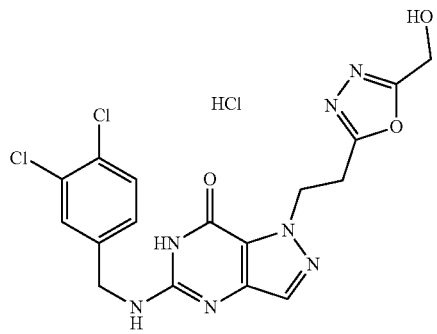 [SMILES: O=c1[nH]c(NCc2ccc(Cl)c(Cl)c2)nc2cnn(CCc3nnc(CO)o3)c12 ; Cl]

To a solution of 5-[(3,4-dichlorophenyl)methylamino]-1-[2-[5-(methoxymethyl)-1,3,4-oxadiazol-2-yl]ethyl]-6H-pyrazolo[4,3-d]pyrimidin-7-one (20 mg, 44.42 µmol, 1 eq) in DCM (0.5 mL) was added a solution of BBr₃ (55.64 mg, 222.09 µmol, 21.40 µL, 5 eq) in DCM (0.2 mL) at -78° C. Then the mixture was warmed to 25° C. The mixture was stirred at 25° C. for 3 hours. LCMS showed the reaction was complete. The reaction mixture was added to sat. NaHCO₃ (2 mL) dropwise at 0° C. The mixture was adjusted to pH=7 with sat. Na₂CO₃. Then the mixture was extracted with DCM and i-PrOH (v:v=3:1, 5 mL×6). The combined organic layers were dried over Na₂SO₄, filtered and concentrated under reduced pressure. The residue was purified by prep-HPLC (HCl condition column: Phenomenex Luna C18 100 mm×30 mm 5 µm; mobile phase: [water (0.04% HCl)-MeCN]; B %: 15%-45%, 10 mins). MeCN was removed under reduced pressure at 30° C. The residue was dried over lyophilization. Compound 5-((3,4-dichlorobenzyl)amino)-1-(2-(5-(hydroxymethyl)-1,3,4-oxadiazol-2-yl)ethyl)-1H-pyrazolo[4,3-d]pyrimidin-7(6H)-one hydrochloride (2.9 mg, 5.27 µmol, 11.86% yield, 85.862% purity, HCl) was obtained as light yellow solid. ¹H NMR (DMSO-d₆, 400 MHz) δ 7.60-7.58 (m, 3H), 7.33 (dd, J 8.4 Hz, 2.0 Hz, 1H), 6.99 (s, 1H), 4.81 (t, J 6.4 Hz, 2H), 4.56 (s, 2H), 4.50 (d, J 5.2 Hz, 2H), 3.41~3.36 (m, 2H). HPLC: 85.86% (220 nm), 84.13% (215 nm), 85.12% (254 nm). MS (ESI): mass calcd. For C₁₇H₁₆C3N₇O₃ 435.06, m/z found 436.0 [M+H]⁺.

Compound 236

5-((3,4-Dichlorobenzyl)amino)-1-((3-hydroxyquinuclidin-2-yl)methyl)-1H-pyrazolo[4,3-d]pyrimidin-7(6H)-one was prepared according to the procedure described herein for Steps 1-3 in Scheme C-5.

Preparation of 2-[(5-chloro-7-methoxy-pyrazolo[4,3-d]pyrimidin-1-yl)methyl]quinuclidin-3-one (Step 1 in Scheme C-5)

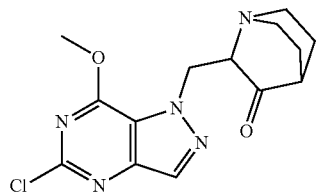 [SMILES: COc1nc(Cl)nc2cnn(CC3C(=O)C4CCN3CC4)c12]

A mixture of 5-chloro-7-methoxy-1H-pyrazolo[4,3-d]pyrimidine (0.42 g, 2.28 mmol, 1 eq), 2-methylenequinuclidin-3-one (405.78 mg, 2.96 mmol, 1.3 eq) and Cs$_2$CO$_3$ (370.68 mg, 1.14 mmol, 0.5 eq) in MeCN (5 mL) was stirred at 20° C. for 24 hours. TLC indicated the reaction was complete. The reaction mixture was quenched with H$_2$O (5 mL) and then concentrated under reduced pressure. The aqueous was extracted with DCM and i-PrOH (3:1, 12 mL×5). The combined organic layers were washed with brine (10 mL×2), dried over Na$_2$SO$_4$, filtered and concentrated under reduced pressure to give a mixture of 2-[(5-chloro-7-methoxy-pyrazolo[4,3-d]pyrimidin-1-yl)methyl]quinuclidin-3-one (0.7 g, crude) and 2-[(5-chloro-7-methoxy-pyrazolo[4,3-d]pyrimidin-2-yl)methyl]quinuclidin-3-one (crude) as light yellow solid. $^1$H NMR (DMSO-d$_6$, 400 MHz) δ 8.74-8.12 (m, 1H), 4.81~4.72 (m, 2H), 4.18-4.10 (m, 3H), 3.92~3.70 (m, 1H), 3.25~3.14 (m, 1H), 2.91~2.63 (m, 3H), 2.39~2.30 (m, 1H), 2.04~1.87 (m, 4H).

Preparation of 2-[(5-chloro-7-methoxy-pyrazolo[4,3-d]pyrimidin-1-yl)methyl]quinuclidin-3-ol

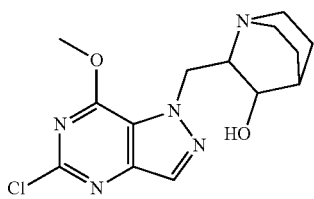 [SMILES: COc1nc(Cl)nc2cnn(CC3C(O)C4CCN3CC4)c12]

To a mixture of 2-[(5-chloro-7-methoxy-pyrazolo[4,3-d]pyrimidin-1-yl)methyl]quinuclidin-3-one (0.7 g, 2.18 mmol, 1 eq) and 2-[(5-chloro-7-methoxy-pyrazolo[4,3-d]pyrimidin-2-yl)methyl]quinuclidin-3-one in MeOH (10 mL) was added NaBH$_4$ (164.94 mg, 4.36 mmol, 2 eq) at 0° C. The mixture was stirred at 20° C. for an hour. TLC indicated the reaction was complete. The reaction mixture was quenched with H$_2$O (10 mL) at 20° C. and then extracted with DCM and i-PrOH (3:1, 24 mL×4). The combined organic layers were washed with brine (10 mL), dried over Na$_2$SO$_4$, filtered and concentrated under reduced pressure to give a mixture of 2-[(5-chloro-7-methoxy-pyrazolo[4,3-d]pyrimidin-1-yl)methyl]quinuclidin-3-ol (0.7 g crude) and 2-[(5-chloro-7-methoxy-pyrazolo[4,3-d]pyrimidin-2-yl)methyl]quinuclidin-3-ol (crude) as yellow solid. $^1$H NMR (DMSO-d$_6$, 400 MHz) δ 8.63~8.13 (m, 1H), 5.02~4.88 (m, 1H), 4.72~4.42 (m, 2H), 4.17~4.08 (m, 3H), 3.95~3.81 (m, 1H), 3.18~3.04 (m, 1H), 3.01~2.53 (m, 4H), 1.89~1.63 (m, 4H).

Preparation of 5-chloro-2-[(3-hydroxyquinuclidin-2-yl)methyl]-6H-pyrazolo[4,3-d]pyrimidin-7-one (Step 2 in Scheme C-5)

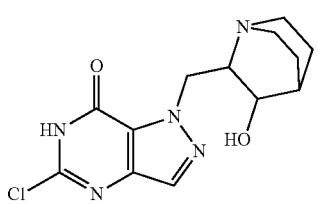 [SMILES: O=c1[nH]c(Cl)nc2cnn(CC3C(O)C4CCN3CC4)c12]

A mixture of 2-[(5-chloro-7-methoxy-pyrazolo[4,3-d]pyrimidin-1-yl)methyl]quinucidin-3-ol and 2-[(5-chloro-7-methoxy-pyrazolo[4,3-d]pyrimidin-2-yl)methyl]quinucidin-3-ol (0.7 g, 2.16 mmol, 1 eq) and LiOH·H$_2$O (272.15 mg, 6.48 mmol, 3 eq) in H$_2$O (5 mL) and THF (5 mL) was stirred at 20° C. for 3 hours. TLC indicated the reaction was complete. The reaction mixture was concentrated under reduced pressure. The aqueous was adjusted to pH=5 with 3N HCl. The aqueous was directly purified by prep-HPLC (column: Xtimate C18 100 mm×30 mm 3 µm; mobile phase: [water (0.1% TFA)-MeCN]; B %: 1%-20%, 10 mins). The eluent was lyophilized to give a mixture of 5-chloro-2-[(3-hydroxyquinuclidin-2-yl)methyl]-6H-pyrazolo[4,3-d]pyrimidin-7-one (170 mg, 548.83 µmol, 25.41% yield) and 5-chloro-1-[(3-hydroxyquinuclidin-2-yl)methyl]-6H-pyrazolo[4,3-d]pyrimidin-7-one as white solid. $^1$H NMR (DMSO-d$_6$, 400 MHz) δ 8.41 (s, 2H), 8.06 (s, 1H), 5.98~5.67 (m, 2H), 5.07~5.01 (m, 1H), 4.88~4.71 (m, 4H), 4.37~4.23 (m, 2H), 4.16 (s, 2H), 3.80 (s, 1H), 3.65~3.58 (m, 2H), 3.26-3.10 (m, 9H), 2.12~2.02 (m, 4H), 1.85 (s, 4H), 1.66 (d, J=6.8 Hz, 3H).

Preparation of 5-((3,4-dichlorobenzyl)amino)-1-((3-hydroxyquinuclidin-2-yl)methyl)-1H-pyrazolo[4,3-d]pyrimidin-7(6H)-one (Step 3 in Scheme C-5)

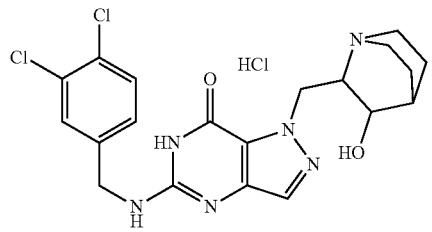 [SMILES: O=c1[nH]c(NCc2ccc(Cl)c(Cl)c2)nc2cnn(CC3C(O)C4CCN3CC4)c12 ; Cl]

The procedure yielded the desired compound 5-[(3,4-dichlorophenyl)methylamino]-1-[(3-hydroxyquinuclidin-2-yl)methyl]-6H-pyrazolo[4,3-d]pyrimidin-7-one (50 mg, 102.92 µmol, 25.66% yield, 100% purity, HCl) as a light yellow solid and 5-[(3,4-dichlorophenyl)methylamino]-2-[(3-hydroxyquinuclidin-2-yl)methyl]-6H-pyrazolo[4,3-d]pyrimidin-7-one (70.3 mg, 144.71 µmol, 36.07% yield, HCl) as white solid. $^1$H NMR (DMSO-d$_6$, 400 MHz) δ 9.39 (s, 1H), 7.73 (s, 1H), 7.63~7.58 (m, 2H), 7.36 (dd, J=1.6, 8.0 Hz, 1H), 4.97~4.91 (m, 1H), 4.71 (dd, J=5.6 Hz, 15.2 Hz, 1H), 4.56 (d, J=5.2 Hz, 2H), 3.78 (s, 1H), 3.61~3.57 (m, 1H), 3.50~3.43 (m, 1H), 3.20~3.07 (m, 3H), 2.10~2.00 (m, 2H), 1.85 (d, J=1.2 Hz, 2H), 1.66 (d, J=4.8 Hz, 1H). HPLC: 100.00% (220 nm), 100.00% (215 nm), 100.00% (254 nm). MS (ESI): mass calcd. For C$_{20}$H$_{23}$C$_{13}$N$_6$O$_2$ 448.12, m/z found 449.1 [M+H]$^+$.

Scheme C-6

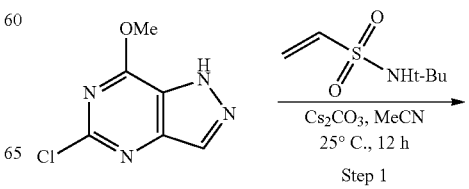

Step 1

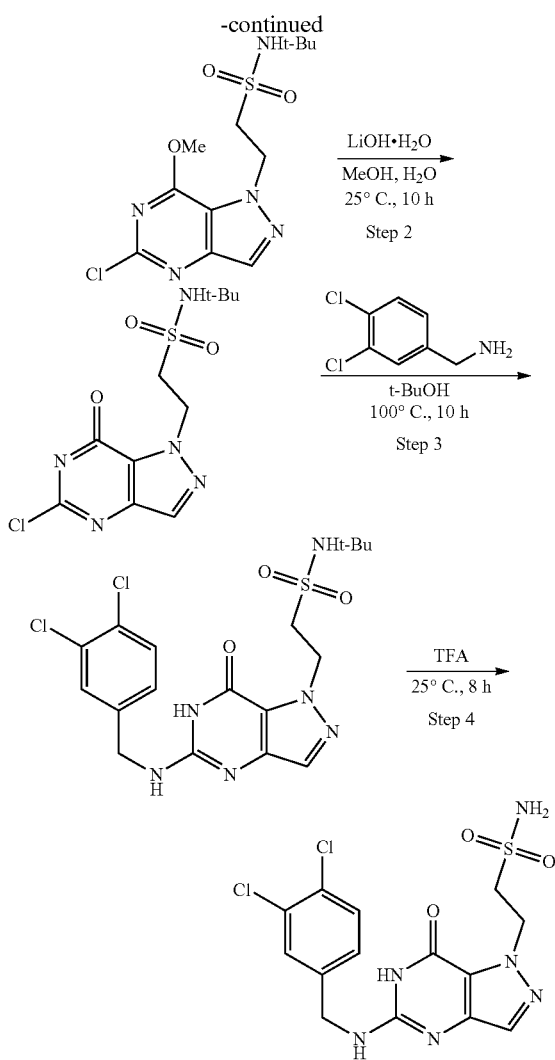

Compound 237

Preparation of 2-(5-((3,4-dichlorobenzyl)amino)-7-oxo-6,7-dihydro-1H-pyrazolo[4,3-d]pyrimidin-1-yl)ethanesulfonamide Preparation of N-(tert-butyl)-2-(5-chloro-7-methoxy-1H-pyrazolo[4,3-d]pyrimidin-1-yl)ethanesulfonamide (Step 1 in Scheme C-6)

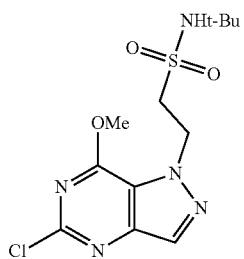

A mixture of 5-chloro-7-methoxy-1H-pyrazolo[4,3-d]pyrimidine (500 mg, 2.71 mmol, 1 eq), N-tert-butylethenesulfonamide (517.35 mg, 3.17 mmol, 1.17 eq) and Cs$_2$CO$_3$ (441.29 mg, 1.35 mmol, 0.5 eq) in MeCN (10 mL) was stirred at 25° C. for 12 hours. TLC indicated the reaction was complete. The reaction mixture was concentrated under reduced pressure. The residue was purified by flash silica gel chromatography (Biotage® 10 g SepaFlash® Silica Flash Column, Eluent of 0-50% Ethylacetate/Petroleum ether gradient at 60 mL/min). The eluent was removed under pressure. Compound N-tert-butyl-2-(5-chloro-7-methoxy-pyrazolo[4,3-d]pyrimidin-1-yl)ethane sulfonamide (70 mg, 201.25 μmol, 7.43% yield) was obtained as white solid. $^1$H NMR (DMSO-d$_6$, 400 MHz) δ 8.30 (s, 1H), 7.03 (s, 1H), 4.88 (t, J=7.2 Hz, 2H), 4.16 (s, 3H), 3.58 (t, J=7.2 Hz, 2H), 1.22 (s, 9H). Compound N-tert-butyl-2-(5-chloro-7-methoxy-pyrazolo[4,3-d]pyrimidin-2-yl)ethanesulfonamide (380 mg, 1.09 mmol, 40.33% yield) was obtained as white solid. $^1$H NMR (DMSO-d$_6$, 400 MHz) δ 8.73 (s, 1H), 7.10 (s, 1H), 4.83 (t, J=6.8 Hz, 2H), 4.13 (s, 3H), 3.70 (t, J=6.8 Hz, 2H), 1.212 (s, 9H).

Preparation of N-(tert-butyl)-2-(5-chloro-7-oxo-6,7-dihydro-1H-pyrazolo[4,3-d]pyrimidin-1-yl)ethanesulfonamide (Step 2 in Scheme C-6)

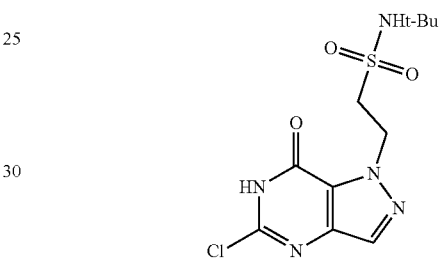

To a solution of N-tert-butyl-2-(5-chloro-7-methoxy-pyrazolo[4,3-d]pyrimidin-1-yl) ethanesulfonamide (70 mg, 201.25 μmol, 1 eq) in MeOH (0.5 mL) and H$_2$O (0.5 mL) was added LiOH—H$_2$O (50.67 mg, 1.21 mmol, 6 eq). The mixture was stirred at 25° C. for 10 hours. LC-MS showed the reaction was complete. The reaction mixture was concentrated under reduced pressure. The aqueous was made pH=6 with 3N HCl and extracted with EtOAc (2 mL×3). The combined organic layers were washed with brine (2 mL), dried over Na$_2$SO$_4$, filtered and concentrated under reduced pressure to give N-tert-butyl-2-(5-chloro-7-oxo-6H-pyrazolo[4,3-d]pyrimidin-1-yl)ethanesulfonamide (50 mg, 149.79 μmol, 74.43% yield) as white solid. $^1$H NMR (DMSO-d$_6$, 400 MHz) δ 8.01 (s, 1H), 7.02 (s, 1H), 4.88 (t, J=7.2 Hz, 2H), 3.56 (t, J=7.2 Hz, 2H), 1.25 (s, 9H).

Compound 238

Preparation of N-(tert-butyl)-2-(5-((3,4-dichlorobenzyl)amino)-7-oxo-6,7-dihydro-1H-pyrazolo[4,3-d]pyrimidin-1-yl)ethanesulfonamide (Step 3 in Scheme C-6)

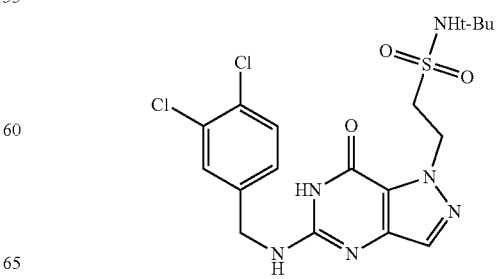

A mixture of N-tert-butyl-2-(5-chloro-7-oxo-6H-pyrazolo[4,3-d]pyrimidin-1-yl)ethane sulfonamide (50 mg, 149.79 µmol, 1 eq) and (3,4-dichlorophenyl)methanamine (52.74 mg, 299.59 µmol, 39.95 µL, 2 eq) in t-BuOH (1 mL) was stirred at 100° C. for 12 hours. LC-MS showed the reaction was complete. The reaction mixture was concentrated under reduced pressure. The residue was purified by prep-HPLC (column: Boston Prime C18 150 mm×30 mm 5 µm; mobile phase: [water (0.1% TFA)-MeCN]; B %: 35%-65%, 10 mins). Compound N-tert-butyl-2-[5-[(3,4-dichlorophenyl)methylamino]-7-oxo-6H-pyrazolo[4,3-d]pyrimidin-1-1]ethane sulfonamide (25.7 mg, 54.29 µmol, 36.24% yield, 98.63% purity) was obtained as white solid. $^1$H NMR (DMSO-$d_6$, 400 MHz) δ 7.61~7.58 (m, 3H), 7.33~7.31 (m, 1H), 7.01 (s, 1H), 6.73 (s, 1H), 4.77 (t, J=7.2 Hz, 2H), 4.47 (d, J=5.2 Hz, 2H), 3.50 (t, J=7.2 Hz, 2H), 1.24 (s, 9H). HPLC: 98.63% (220 nm), 98.11% (215 nm), 99.23% (254 nm). MS (ESI): mass calcd. For $C_{18}H_{22}Cl_2N_6O_3S$ 472.09, m/z found 473.1 $[M+H]^+$.

Preparation of 2-(5-((3,4-dichlorobenzyl)amino)-7-oxo-6,7-dihydro-1H-pyrazolo[4,3-d]pyrimidin-1-yl)ethanesulfonamide (Step 4 in Scheme C-6)

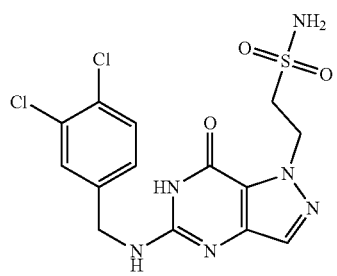 [SMILES: NS(=O)(=O)CCn1ncc2nc(NCc3ccc(Cl)c(Cl)c3)[nH]c(=O)c21]

A mixture of N-tert-butyl-2-[5-[(3,4-dichlorophenyl)methylamino]-7-oxo-6H-pyrazolo[4,3-d]pyrimidin-1-yl]ethanesulfonamide (150 mg, 316.87 µmol, 1 eq) in TFA (2 mL) was stirred at 25° C. for 8 hours. LC-MS showed the reaction was complete. The reaction mixture was concentrated under reduced pressure. The residue was purified by prep-HPLC (column: Boston Prime C18 150 mm×30 mm 5 µm; mobile phase: [water (0.1% TFA)-MeCN]; B %: 30%-45%, 10 mins). The solvent was removed under freeze drying. Compound 2-[5-[(3,4-dichlorophenyl)methylamino]-7-oxo-6H-pyrazolo[4,3-d]pyrimidin-1-yl]ethanesulfonamide (40.2 mg, 96.34 µmol, 30.40% yield, 96.77% purity) was obtained as white solid. $^1$H NMR (DMSO-$d_6$, 400 MHz) δ 11.25 (s, 1H), 7.61~7.58 (m, 3H), 7.33~7.31 (m, 1H), 7.04 (s, 2H), 6.70 (s, 1H), 4.79 (t, J=7.2 Hz, 2H), 4.47 (d, J=5.6 Hz, 2H), 3.51 (t, J=7.2 Hz, 2H). HPLC: 96.77% (220 nm), 95.58% (215 nm), 94.88% (254 nm). MS (ESI): mass calcd. For $C_{14}H_{14}C2N_6O_3S$ 416.02, m/z found 417.0 $[M+H]^+$.

Scheme C-7

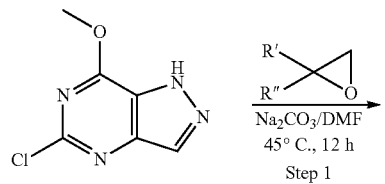

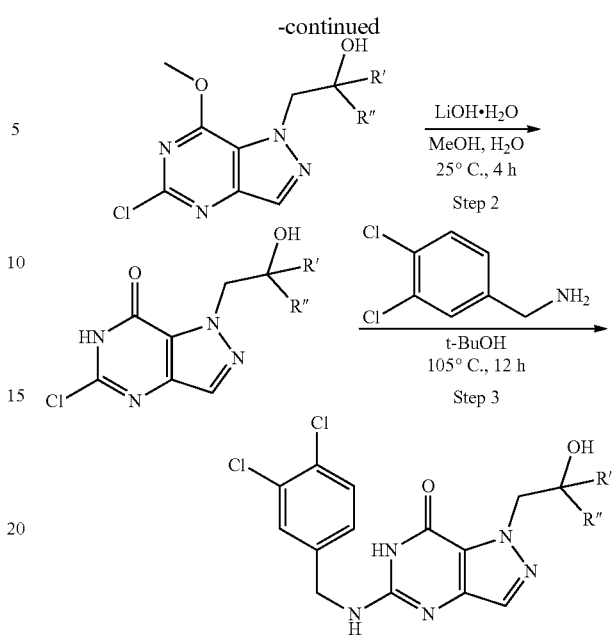

General Procedures for Preparing Compounds in Scheme C-7

Preparation of Compounds (Step 1 in Scheme C-7)

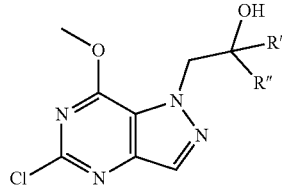

To a solution of 5-chloro-7-methoxy-1H-pyrazolo[4,3-d]pyrimidine (921.00 µmol, 1 eq) in DMF (2 mL/mmol 3 mL/mmol) was added different oxirane R'R"COCH$_2$(1.84 mmol 3.68 mmol, 2 eq 4 eq) and Na$_2$CO$_3$ (2.76 mmol, 3 eq). The mixture was stirred at 45° C. for 12 hours. TLC showed the reaction was completed. H$_2$O was added to the reaction mixture. The reaction mixture was extracted with EtOAc. The combined organic layers were washed with brine, dried over Na$_2$SO$_4$, filtered and concentrated under reduced pressure. The residue was purified by flash silica gel chromatography (Biotage®; 4 g SepaFlash® Silica Flash Column, Eluent of 0-100% Ethyl acetate/Petroleum ether gradient at 50 mL/min). Then the eluent was concentrated under reduced pressure to give desired compound.

Preparation of Compounds (Step 2 in Scheme C-7)

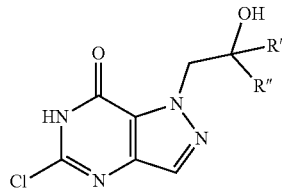

To a solution of 2-(5-chloro-7-methoxy-1H-pyrazolo[4,3-d]pyrimidin-1-yl)-1-R', 1'-R"-ethanol (4.36 mmol, 1 eq) in MeOH (3 mL/mmol 5 mL/mmol) or THF (3 mL/mmol 5 mL/mmol) and H₂O (3 mL/mmol 5 mL/mmol) was added LiOH—H₂O (13.08 mmol 21.80 mmol, 3 eq 5 eq). The mixture was stirred at 20° C. 25° C. for 2 hours 16 hours. TLC showed the reaction was complete. The reaction mixture was concentrated under reduced pressure. The aqueous was made pH=6 with 3N HCl and then extracted with EtOAc. The combined organic layers were washed with brine, dried over Na₂SO₄, filtered and concentrated under reduced pressure to give desired product.

Preparation of Compounds (Step 3 in Scheme C-7)

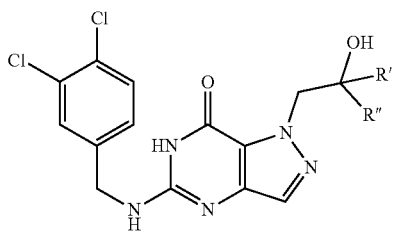

A solution of 1-(2-R'-2R"R-2-hydroxyethyl)-5-chloro-1H-pyrazolo[4,3-d]pyrimidin-7(6H)-one (393.64 µmol, 1 eq), (3,4-dichlorophenyl)methanamine (590.46 mmol 787.28 mmol, 1.5 eq 2 eq) in t-BuOH (6 mL/mmol 8 mL/mmol) was stirred at 100° C. 110° C. for 10 hours 30 hours. LC-MS showed the reaction was complete. The reaction mixture was concentrated under reduced pressure. The residue was purified by prep-HPLC. Column: a) Phenomenex Luna C18 150 mm×30 mm 5 µm; b) Welch Xtimate C18 150 mm×25 mm 5 µm. Mobile phase: a) [water (0.1% TFA)-MeCN], B %: 30%-50%, 12 mins; b) [water (0.05% HCl)-MeCN], B %: 15%-45%, 12 mins). The solvent was removed under freeze drying to give desired product.

Compound 239

Preparation of (R)-5-((3,4-dichlorobenzyl)amino)-1-(2-hydroxypropyl)-1H-pyrazolo[4,3-d]pyrimidin-7(6H)-one Preparation of (R)-1-(5-chloro-7-methoxy-1H-pyrazolo[4,3-d]pyrimidin-1-yl)propan-2-ol (Step 1 in Scheme C-7)

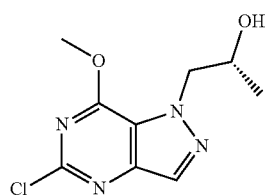 [SMILES: COc1nc(Cl)nc2cnn(C[C@@H](C)O)c12]

To a solution of 5-chloro-7-methoxy-1H-pyrazolo[4,3-d]pyrimidine (0.17 g, 921.00 µmol, 1 eq) in DMF (2 mL) was added (2R)-2-methyloxirane (213.96 mg, 3.68 mmol, 258.10 µL, 4 eq) and Na₂CO₃ (292.85 mg, 2.76 mmol, 3 eq). The mixture was stirred at 45° C. for 12 hours. TLC showed the reaction was completed. H₂O (6 mL) was added to the reaction mixture. The reaction mixture was extracted with EtOAc (8 mL×3). The combined organic layers were washed with brine (5 mL×5), dried over Na₂SO₄, filtered and concentrated under reduced pressure. The residue was purified by flash silica gel chromatography (Biotage®; 4 g SepaFlash® Silica Flash Column, Eluent of 0-100% Ethyl acetate/Petroleum ether gradient at 50 mL/min). Then the eluent was concentrated under reduced pressure. Compound (R)-1-(5-chloro-7-methoxy-1H-pyrazolo[4,3-d]pyrimidin-1-yl)propan-2-ol (90 mg, 370.89 µmol, 40.27% yield) was obtained as white solid. ¹H NMR (DMSO-d₆, 400 MHz) δ 8.25 (s, 1H), 4.87 (d, J=5.2 Hz, 1H), 4.46~4.38 (m, 2H), 4.20 (s, 3H), 4.15~4.03 (m, 1H), 1.05 (d, J=6.0 Hz, 3H). Compound (R)-1-(5-chloro-7-methoxy-2H-pyrazolo[4,3-d]pyrimidin-2-yl)propan-2-ol (40 mg, 164.84 µmol, 17.90% yield) was obtained as light yellow solid. ¹H NMR (DMSO-d₆, 400 MHz) δ 8.56 (s, 1H), 5.03 (d, J=4.8 Hz, 1H), 4.43~4.39 (m, 1H), 4.34~4.28 (m, 1H), 4.12 (s, 3H), 4.32~4.30 (m, 1H), 1.09 (d, J=6.0 Hz, 3H).

Preparation of (R)-5-chloro-1-(2-hydroxypropyl)-1H-pyrazolo[4,3-d]pyrimidin-7(6H)-one (Step 2 in Scheme C-7)

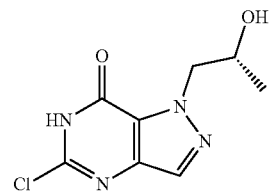

To a solution of (2R)-1-(5-chloro-7-methoxy-pyrazolo[4,3-d]pyrimidin-1-yl)propan-2-ol (90 mg, 370.89 µmol, 1 eq) in MeOH (1 mL) and H₂O (1 mL) was added LiOH·H₂O (46.69 mg, 1.11 mmol, 3 eq). The mixture was stirred at 25° C. for 4 hours. TLC showed the reaction was completed. The reaction mixture was concentrated under reduced pressure to remove MeOH. H₂O (3 mL) was added to the reaction mixture. Then the aqueous was adjusted pH=5 with HCl (2 N) and extracted with EtOAc (10 mL×5). The combined organic layers were washed with brine (5 mL×1), dried over Na₂SO₄, filtered and concentrated under reduced pressure. Compound (R)-5-chloro-1-(2-hydroxypropyl)-1H-pyrazolo[4,3-d]pyrimidin-7(6H)-one (90 mg, crude) was obtained as light yellow solid. ¹H NMR (DMSO-d₆, 400 MHz) δ 7.95 (s, 1H), 4.46-4.44 (m, 1H), 4.38~4.36 (m, 1H), 4.06~4.04 (m, 1H), 1.01 (d, J=6.4 Hz, 3H).

Preparation of (R)-5-((3,4-dichlorobenzyl)amino)-1-(2-hydroxypropyl)-1H-pyrazolo[4,3-d]pyrimidin-7(6H)-one (Step 3 in Scheme C-7)

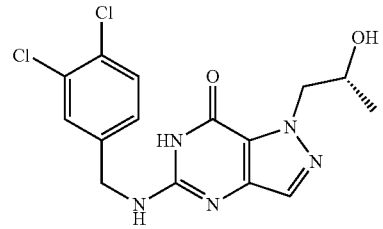 [SMILES: C[C@@H](O)Cn1ncc2nc(NCc3ccc(Cl)c(Cl)c3)[nH]c(=O)c21]

To a solution of 5-chloro-1-[(2R)-2-hydroxypropyl]-6H-pyrazolo[4,3-d]pyrimidin-7-one (0.09 g, 393.64 µmol, 1 eq)

in t-BuOH (6 mL) was added (3,4-dichlorophenyl)methanamine (138.60 mg, 787.28 µmol, 105.00 µL, 2 eq). The mixture was stirred at 105° C. for 12 hours. LCMS and HPLC showed the reaction was completed. The reaction mixture was concentrated under reduced pressure. The residue was purified by prep-HPLC (column: Phenomenex Luna C18 150 mm×30 mm 5 µm; mobile phase: [water (0.05% HCl)-MeCN]; B %: 15%-45%, 12 mins). MeCN was removed under reduced pressure at 30° C. The residue was dried over lyophilization. Compound (R)-5-((3,4-dichlorobenzyl)amino)-1-(2-hydroxypropyl)-1H-pyrazolo[4,3-d]pyrimidin-7(6H)-one (22.8 mg, 61.66 µmol, 15.66% yield, 99.586% purity) was obtained as white solid. $^1$H NMR (DMSO-$d_6$, 400 MHz) δ 7.64-7.60 (m, 3H), 7.37 (s, 1H), 7.37~7.35 (m, 1H), 4.55 (d, J=5.2 Hz, 2H), 4.40~4.37 (m, 1H), 4.31~4.26 (m, 1H), 4.04~4.02 (m, 1H), 1.00 (d, J=6.0 Hz, 3H). HPLC: 99.59% (220 nm), 99.50% (215 nm), 99.90% (254 nm). MS (ESI): mass calcd. For $C_{15}H_{15}C_{12}N_5O_2$ 367.06, m/z found 368.0 [M+H]$^+$.

Compound 240

(S)-5-((3,4-dichlorobenzyl)amino)-1-(2-hydroxypropyl)-1H-pyrazolo[4,3-d]pyrimidin-7(6H)-one was prepared according to the procedure described herein for Steps 1-3 in Scheme C-7.

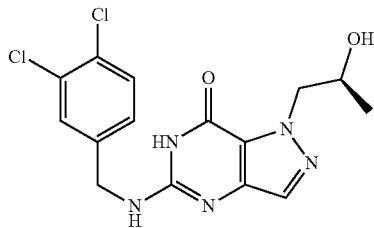 [SMILES: C[C@H](O)Cn1ncc2nc(NCc3ccc(Cl)c(Cl)c3)[nH]c(=O)c21]

The procedure yielded the desired compound (69.5 mg, 186.03 µmol, 38.67% yield) as a white solid. $^1$H NMR (DMSO-$d_6$, 400 MHz) δ 7.63~7.54 (m, 3H), 7.34 (dd, J=2.0 Hz, 8.4 Hz, 1H), 6.77 (s, 1H), 4.49 (d, J=5.6 Hz, 2H), 4.42~4.35 (m, 1H), 4.32~4.24 (m, 1H), 4.06-4.00 (m, 1H), 0.99 (d, J=6.0 Hz, 3H). HPLC: 98.56% (220 nm), 98.50% (215 nm), 97.26% (254 nm). MS (ESI): mass calcd. For $C_{15}H_{15}C_{12}N_5O_2$ 367.06, m/z found 368.0 [M+H]$^+$.

Compound 241

Preparation of 5-((3,4-dichlorobenzyl)amino)-1-((4-hydroxy-1-methylpiperidin-4-yl)methyl)-1H-pyrazolo[4,3-d]pyrimidin-7(6H)-one hydrochloride 5-((3,4-dichlorobenzyl)amino)-1-((4-hydroxypiperidin-4-yl)methyl)-1H-pyrazolo[4,3-d]pyrimidin-7(6H)-one hydrochloride was prepared according to the procedure described herein for Steps 1-3 in Scheme C-7.

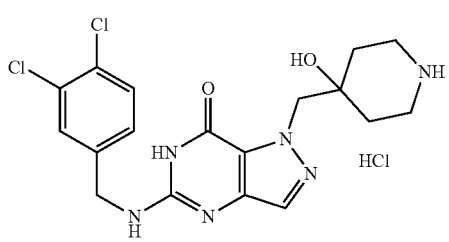 [SMILES: O=c1[nH]c(NCc2ccc(Cl)c(Cl)c2)nc2cnn(CC3(O)CCNCC3)c12 ; Cl]

The procedure yielded the desired compound 5-[(3,4-dichlorophenyl)methylamino]-1-[(4-hydroxy-4-piperidyl)methyl]-6H-pyrazolo[4,3-d]pyrimidin-7-one as a white solid for delivery. The left solid (0.15 g) was used to the next step without further purification. $^1$H NMR (DMSO-$d_6$, 400 MHz) δ 8.74 (s, 1H), 8.23 (s, 1H), 7.68 (s, 1H), 7.63~7.50 (m, 3H), 7.35 (d, J=8.4 Hz, 1H), 4.54 (d, J=4.4 Hz, 2H), 4.47 (s, 2H), 3.09~3.07 (m, 2H), 3.01~2.95 (m, 2H), 1.70~1.57 (m, 4H). HPLC: 99.31% (220 nm), 98.62% (215 nm), 98.46% (254 nm). MS (ESI): mass calcd. For $C_{18}H_{21}C_{13}N_6O_2$ 422.12 m/z found 423.1 [M+H]$^+$.

Preparation of 5-((3,4-dichlorobenzyl)amino)-1-((4-hydroxy-1-methylpiperidin-4-yl)methyl)-1H-pyrazolo[4,3-d]pyrimidin-7(6H)-one hydrochloride

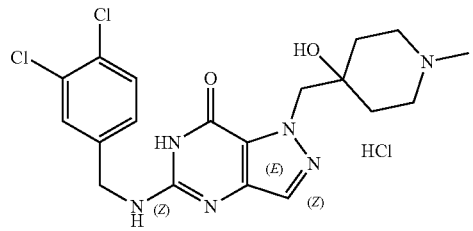 [SMILES: CN1CCC(O)(Cn2ncc3nc(NCc4ccc(Cl)c(Cl)c4)[nH]c(=O)c32)CC1 ; Cl]

To a solution of 4-[[5-[(3,4-dichlorophenyl)methylamino]-7-methoxy-pyrazolo[4,3-d]pyrimidin1-yl]methyl]piperidin-4-ol (0.15 g, 316.60 µmol, 1 eq, HCl) and HCHO (128.48 mg, 1.58 mmol, 117.87 µL, 37% purity, 5 eq) in MeOH (1 mL) was added NaBH$_3$CN (59.69 mg, 949.80 µmol, 3 eq) in portion at 0° C. Then the mixture was stirred at 25° C. for 2 hours. LCMS showed the reaction was complete. The mixture was quenched with ice water (1 mL) and extracted with EtOAc (10 mL×3). The combined organic layer was washed with brine (5 mL), dried over Na$_2$SO$_4$, filtered and concentrated under reduced pressure. The residue was purified by prep-HPLC (column: Phenomenex Luna C18 150 mm×30 mm 5 µm; mobile phase: [water (0.05% HCl)-MeCN]; B %: 10%-30%, 12 mins). The eluent was removed under reduced pressure. Compound 5-[(3,4-dichlorophenyl)methylamino]-1-[(4-hydroxy-1-methyl-4-piperidyl)methyl]-6H-pyrazolo[4,3-d]pyrimidin-7-one (55.9 mg, 117.44 µmol, 37.10% yield, 99.54% purity, HCl) was obtained as white solid. H NMR (DMSO-$d_6$, 400 MHz) δ 9.98 (s, 1H), 8.21 (s, 1H), 7.73 (s, 1H), 7.67 (s, 1H), 7.62 (d, J=8.4 Hz, 1H), 7.39 (d, J=8.0 Hz, 1H), 4.63 (d, J=4.4 Hz, 2H), 4.47 (s, 2H), 3.21~3.19 (m, 2H), 3.06-3.03 (m, 2H), 2.67 (d, J=4.8 Hz, 3H), 1.86~1.80 (m, 2H), 1.64~1.61 (m, 2H). HPLC: 99.54% (220 nm), 99.50% (215 nm), 98.86% (254 nm). MS (ESI): mass calcd. For $C_{19}H_{23}C3N_6O_2$ 436.12 m/z found 437.1 [M+H]$^+$.

Scheme C-8

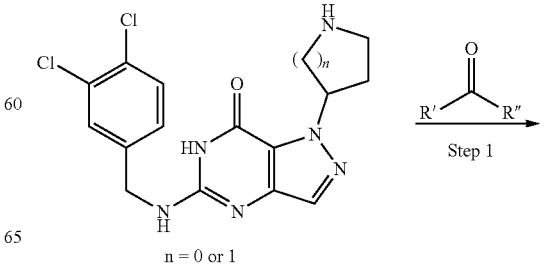

n = 0 or 1

-continued

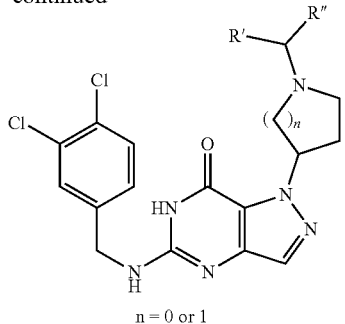

n = 0 or 1

General Procedures for Preparing Compounds in Scheme C-8

Preparation of Compounds in Scheme C-8 (Step 1 in Scheme C-8)

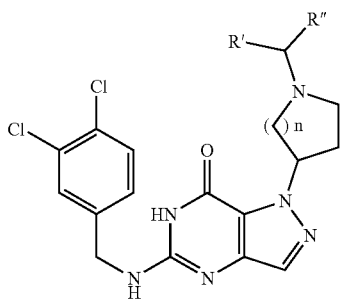

n = 0 or 1

To a solution of amine (101.71 μmol, 1 eq) and R'COR" (122.05 915.39 μmol, 1.2 9 eq) in MeOH (10 mL/mmol) was added NaBH₃CN (152.56 813.68 μmol, 3 8 eq) in portions at 0° C. The mixture was stirred at 0 25° C. for a period of time (2 16 hours). LCMS and HPLC showed the reaction was complete. After filtered, the filtrate was purified by prep-HPLC. Column: a) Nano-micro Kromasil C18 100 mm×30 mm 5 μm; b) Boston Prime C18 150×30 mm 5 μm; c) Phenomenex Luna C18 150 mm×30 mm 5 μm; d) Xbridge 150 mm×30 mm 10 μm. Mobile phase: a) [water (0.1% TFA)-MeCN], B %: 25%-55%, 10 mins; b) [water (0.05% HCl)-MeCN], B %: 5%-55%, 8 mins or 10 mins or 12 mins. Acetonitrile was removed under reduced pressure at 30° C. The aqueous was dried over lyophilization to give desired product.

Compound 242

Preparation of 5-((3,4-dichlorobenzyl)amino)-1-(1-(tetrahydro-2H-pyran-4-yl)piperidin-4-yl)-1H-pyrazolo[4,3-d]pyrimidin-7(6H)-one hydrochloride (Step 1 in Scheme C-8)

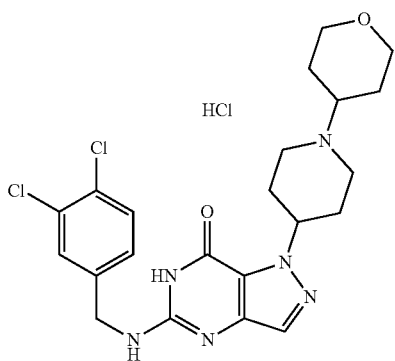 [SMILES: O=c1[nH]c(NCc2ccc(Cl)c(Cl)c2)nc2cnn(C3CCN(C4CCOCC4)CC3)c12 ; Cl]

To a solution of 5-[(3,4-dichlorophenyl)methylamino]-1-(4-piperidyl)-6H-pyrazolo[4,3-d]pyrimidin-7-one (40 mg, 101.71 μmol, 1 eq) in MeOH (1 mL) was added tetrahydropyran-4-one (91.65 mg, 915.40 μmol, 84.08 μL, 9 eq). The mixture was stirred at 25° C. for 2 hours. Then NaBH₃CN (19.18 mg, 305.13 μmol, 3 eq) was added at 0° C. in portions. The mixture was stirred at 0° C. for an hour. LCMS and HPLC showed the reaction was complete. The reaction mixture was filtered under reduced pressure. The filtrate was purified by prep-HPLC (column: Phenomenex Luna C18 150×30 mm×5 μm; mobile phase: [water (0.05% HCl)-MeCN]; B %: 20%-35%, 10 mins). MeCN was removed under reduced pressure at 30° C. The aqueous was dried over lyophilization to give compound 5-[(3,4-dichlorophenyl)methylamino]-1-(1-tetrahydropyran-4-yl-4-piperidyl)-6H-pyrazolo[4,3-d]pyrimidin-7-one (20.4 mg, 38.76 μmol, 38.10% yield, 97.620% purity, HCl) as light yellow solid. $^1$H NMR (DMSO-d$_6$, 400 MHz) δ 10.29 (s, 1H), 7.67 (s, 1H), 7.61~7.59 (m, 2H), 7.34 (dd, J=8.4 Hz, 1.2 Hz, 1H), 5.20~5.13 (m, 1H), 4.53 (d, J=4.8 Hz, 2H), 3.99~3.96 (m, 2H), 3.63~3.60 (m, 2H), 3.41 (s, 1H), 3.40~3.34 (m, 2H), 3.32~3.29 (m, 2H), 2.33~2.27 (m, 2H), 2.24-2.21 (m, 2H), 2.20~2.04 (m, 2H), 2.01~1.75 (m, 2H). HPLC: 97.62% (220 nm), 97.65% (215 nm), 98.71% (254 nm). MS (ESI): mass calcd. For $C_{22}H_{27}C3N_6O_2$ 476.15, m/z found 477.1 [M+H]$^+$.

Compound 243

5-((3,4-Dichlorobenzyl)amino)-1-(1-methylpyrrolidin-3-yl)-1H-pyrazolo[4,3-d]pyrimidin-7(6H)-one TFA salt was prepared according to the procedure described herein for Step 1 in Scheme C-8.

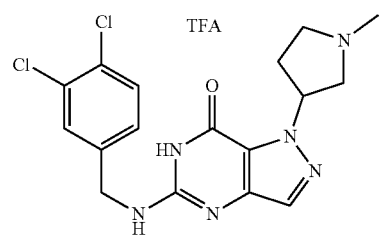 [SMILES: CN1CCC(n2ncc3nc(NCc4ccc(Cl)c(Cl)c4)[nH]c(=O)c32)C1 ; "TFA"]

The procedure yielded the desired compound (12.5 mg, 24.6 μmol, 30.4% yield, TFA) as a white solid. $^1$H NMR (DMSO-d$_6$, 400 MHz) δ 11.4211.45 (m, 1H), 10.04-10.61 (m, 1H), 7.68~7.71 (m, 1H), 7.57~7.59 (m, 2H), 7.31 (dd, J=8.00 Hz, 1.60 Hz, 1H), 6.94~7.08 (m, 1H), 5.82 (s, 1H), 4.48 (d, J=5.60 Hz, 2H), 4.08 (s, 1H), 3.74 (s, 3H), 3.27~3.31 (m, 1H), 2.91 (s, 3H). HPLC: 98.84% (220 nm), 98.98% (215 nm), 99.33% (254 nm). MS (ESI): mass calcd. For $C_{17}H_{18}C_{12}N_6O$ 392.0, m/z found 393.1 [M+H]$^+$.

Compound 244

5-((3,4-Dichlorobenzyl)amino)-1-(1-(pyridin-2-ylmethyl) piperidin-4-yl)-1H-pyrazolo[4,3-d]pyrimidin-7(6H)-one dihydrochloride was prepared according to the procedure described herein for Step 1 in Scheme C-8.

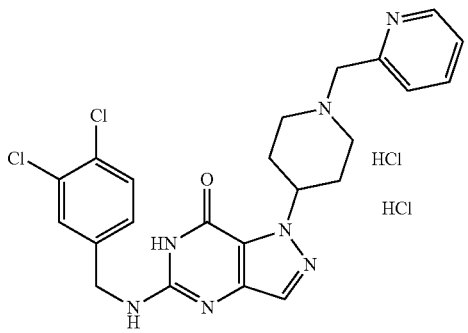 [SMILES: O=c1[nH]c(NCc2ccc(Cl)c(Cl)c2)nc2cnn(C3CCN(Cc4ccccn4)CC3)c12 ; Cl ; Cl]

The procedure yielded the desired compound (11.8 mg, 20.90 μmol, 29.93% yield) as a white solid. $^1$H NMR (DMSO-d$_6$, 400 MHz) δ 10.51 (s, 1H), 8.70 (d, J=4.8 Hz, 1H), 7.95 (t, J=7.6 Hz, 1H), 7.67~7.59 (m, 4H), 7.52~7.49 (m, 1H), 7.35~7.34 (m, 1H), 5.17~5.13 (m, 1H), 4.62~4.52 (m, 4H), 3.56~3.53 (m, 2H), 3.37~3.33 (m, 2H), 2.42~2.39 (m, 2H), 2.20~2.17 (m, 2H). HPLC: 98.69% (220 nm), 98.74% (215 nm), 100.00% (254 nm). MS (ESI): mass calcd. For C$_{23}$H$_{25}$C$_{14}$N$_7$O$_1$ 483.13 m/z found 484.2 [M+H]$^+$.

Compound 245

5-((3,4-Dichlorobenzyl)amino)-1-(1-(pyridin-3-ylmethyl)piperidin-4-yl)-1H-pyrazolo[4,3-d]pyrimidin-7(6H)-one dihydrochloride was prepared according to the procedure described herein for Step 1 in Scheme C-8.

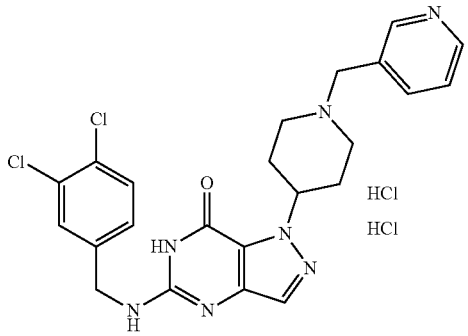 [SMILES: O=c1[nH]c(NCc2ccc(Cl)c(Cl)c2)nc2cnn(C3CCN(Cc4cccnc4)CC3)c12 ; Cl ; Cl]

The procedure yielded the desired compound (22.3 mg, 39.76 μmol, 56.96% yield) as a pale yellow solid. H NMR (DMSO-d$_6$, 400 MHz) δ 11.25 (s, 1H), 9.00 (s, 1H), 8.86 (d, J=4.8 Hz, 1H), 8.47 (d, J=8.4 Hz, 1H), 7.86 (t, J=5.6 Hz, 1H), 7.66 (s, 1H), 7.62~7.59 (m, 2H), 7.53 (s, 1H), 7.34 (dd, J=2.0 Hz, 8.4 Hz, 1H), 5.16~5.10 (m, 1H), 4.55~4.48 (m, 4H), 3.54~3.51 (m, 2H), 3.26~3.24 (m, 2H), 2.43~2.40 (m, 2H), 2.33~2.18 (m, 2H). HPLC: 99.37% (220 nm), 99.47% (215 nm), 97.96% (254 nm). MS (ESI): mass calcd. For C$_{23}$H$_{25}$C$_{14}$N$_7$O$_1$ 483.13 m/z found 484.2 [M+H]$^+$.

Compound 246

5-((3,4-Dichlorobenzyl)amino)-1-(1-(pyridin-4-ylmethyl) piperidin-4-yl)-1H-pyrazolo[4,3-d]pyrimidin-7(6H)-one dihydrochloride was prepared according to the procedure described herein for Step 1 in Scheme C-8.

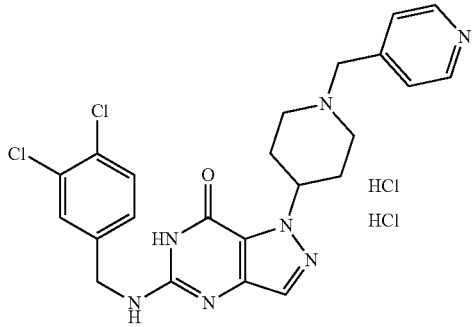 [SMILES: O=c1[nH]c(NCc2ccc(Cl)c(Cl)c2)nc2cnn(C3CCN(Cc4ccncc4)CC3)c12 ; Cl ; Cl]

The procedure yielded the desired compound (20 mg, 35.79 μmol, 51.27% yield) as a white solid. $^1$H NMR (DMSO-d$_6$, 400 MHz) δ 11.56 (s, 1H), 8.91 (d, J=5.6 Hz, 2H), 8.12~8.08 (m, 2H), 7.67 (s, 1H), 7.61~7.59 (m, 2H), 7.34 (dd, J=2.0 Hz, 8.4 Hz, 1H), 5.16~5.12 (m, 1H), 4.55-4.53 (m, 4H), 3.52~3.49 (m, 2H), 3.26~3.22 (m, 2H), 2.43~2.40 (m, 2H), 2.17~2.14 (m, 2H). HPLC: 99.73% (220 nm), 99.73% (215 nm), 100.00% (254 nm). MS (ESI): mass calcd. For C$_{23}$H$_{25}$C$_{14}$N$_7$O$_1$ 483.13 m/z found 484.2 [M+H]$^+$.

Compound 247

Preparation of (5-((3,4-dichlorobenzyl)amino)-1-(1-(piperidin-4-ylmethyl)piperidin-4-yl)-1H-pyrazolo[4,3-d]pyrimidin-7(6H)-one dihydrochloride) (Step 1 in Scheme C-8)

Compound 248 tert-Butyl 4-((4-(5-((3,4-dichlorobenzyl)amino)-7-oxo-6,7-dihydro-1H-pyrazolo[4,3-d]pyrimidin-1-yl)piperidin-1-yl)methyl)piperidine-1-carboxylate 2,2,2-trifluoroacetate was prepared according to the procedure described herein for Step 1 in Scheme C-8.

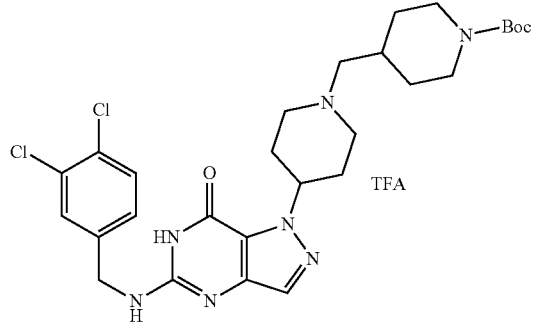 [SMILES: CC(C)(C)OC(=O)N1CCC(CN2CCC(n3ncc4nc(NCc5ccc(Cl)c(Cl)c5)[nH]c(=O)c43)CC2)CC1 ; "TFA"]

The procedure yielded the desired compound (17.1 mg, 22.70 μmol, 24.39% yield) as a white solid. $^1$H NMR (DMSO-d$_6$, 400 MHz) δ 10.17-9.92 (m, 1H), 7.66 (s, 1H), 7.60 (d, J=8.0 Hz, 2H), 7.42 (s, 1H), 7.34 (d, J=8.0 Hz, 1H), 5.16~5.11 (m, 1H), 4.53 (d, J=4.4 Hz, 2H), 3.94-3.91 (m, 2H), 3.64~3.61 (m, 1H), 3.19~3.12 (m, 2H), 2.98 (s, 2H), 2.73 (s, 2H), 2.39-2.33 (m, 3H), 2.16~2.13 (m, 2H), 2.01 (s, 1H), 1.80~1.77 (m, 2H), 1.39 (s, 9H), 1.13-1.03 (m, 2H). HPLC: 93.54% (220 nm), 93.45% (215 nm), 96.13% (254 nm). MS (ESI): mass calcd. For C$_{30}$H$_{38}$C$_{12}$F$_3$N$_7$O$_5$ 589.23, m/z found 590.3 [M+H]$^+$.

Preparation of (5-((3,4-dichlorobenzyl)amino)-1-(1-(piperidin-4-ylmethyl)piperidin-4-yl)-1H-pyrazolo[4,3-d]pyrimidin-7(6H)-one dihydrochloride) (Step 1 in Scheme C-8)

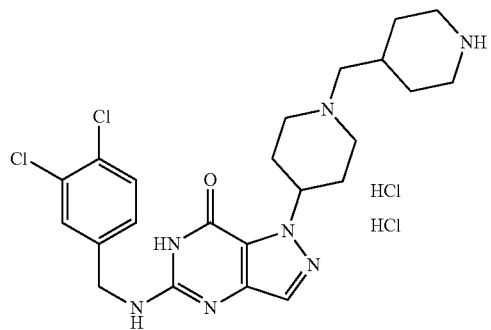 [SMILES: O=c1[nH]c(NCc2ccc(Cl)c(Cl)c2)nc2cnn(C3CCN(CC4CCNCC4)CC3)c12 ; Cl ; Cl]

The a solution of tert-butyl 4-[[4-[5-[(3,4-dichlorophenyl)methylamino]-7-oxo-6H-pyrazolo[4,3-d]pyrimidin-1-yl]-1-piperidyl]methyl]piperidine-1-carboxylate (150 mg, 254.00 μmol, 1 eq) in HCl/EtOAc (3 mL) and EtOAc (1 mL) was stirred at 25° C. for 2 hours. LC-MS showed tert-butyl 4-[[4-[5-[(3,4-dichlorophenyl)methylamino]-7-oxo-6H-pyrazolo[4,3-d]pyrimidin-1-yl]-1-piperidyl]methyl]piperidine-1-carboxylate was consumed completely and one main peak with desired mass was detected. The reaction mixture was concentrated under reduced pressure. The residue was purified by prep-HPLC (HCl condition column: Phenomenex Luna C18 150 mm×30 mm 5 μm; mobile phase: [water (0.05% HCl)-MeCN]; B %: 15%-45%, mins). The solvent was removed under freeze drying. Compound 5-[(3,4-dichlorophenyl)methylamino]-1-[1-(4-piperidylmethyl)-4-piperidyl]-6H-pyrazolo[4,3-d]pyrimidin-7-one (23.3 mg, 44.09 μmol, 17.36% yield, 99.7% purity, HCl) was obtained as white solid. $^1$H NMR (DMSO-d$_6$, 400 MHz) δ 10.74~10.60 (m, 1H), 9.08 (s, 1H), 8.95~8.93 (m, 1H), 8.23 (s, 1H), 7.71 (s, 1H), 7.66 (s, 1H), 7.61 (d, J=8.0 Hz, 1H), 7.38 (d, J=8.0 Hz, 1H), 5.16~5.10 (m, 1H), 4.62 (s 2H), 3.64 (d, J=11.2 Hz, 2H), 3.27~3.24 (m, 2H), 3.18~3.13 (m, 2H), 3.01 (s, 2H), 2.88~2.80 (m, 2H), 2.67~2.57 (m, 1H), 2.36~2.33 (m, 1H), 2.16~2.13 (m, 3H), 2.03~1.99 (m, 2H), 1.50~1.41 (m, 2H). HPLC: 99.70% (220 nm), 99.62% (215 nm), 99.81% (254 nm). MS (ESI): mass calcd. For $C_{23}H_{31}Cl_4N_7O$ 489.18, m/z found 490.2 [M+H]$^+$.

Compound 249

Preparation of (5-((3,4-dichlorobenzyl)amino)-1-(1-(piperidin-2-ylmethyl) piperidin-4-yl)-1H-pyrazolo[4,3-d]pyrimidin-7(6H)-one dihydrochloride) (Step 1 in Scheme C-8)

Compound 250 tert-Butyl 3-((4-(5-((3,4-dichlorobenzyl)amino)-7-oxo-6,7-dihydro-1H-pyrazolo4,3-d]pyrimidin-1-yl)piperidin-1-yl) methyl)piperidine-1-carboxylate hydrochloride) was prepared according to the procedure described herein for Step 1 in Scheme C-8.

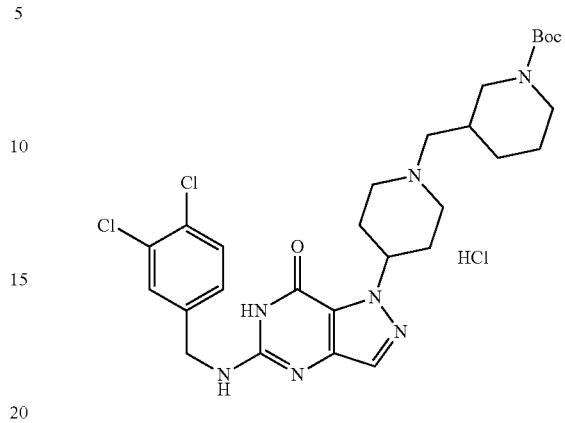

The procedure yielded the desired compound (22.2 mg, 33.60 μmol, 13.21% yield) as a white solid. $^1$H NMR (DMSO-d$_6$, 400 MHz) δ 10.1~19.86 (m, 1H), 7.67 (d, J=5.2 Hz, 1H), 7.62~7.59 (m, 2H), 7.52~7.48 (m, 1H), 7.35 (d, J=8.0 Hz, 1H), 5.14 (s, 1H), 4.55 (d, J=4.4 Hz, 2H), 4.00~3.86 (m, 2H), 3.74~3.71 (m, 2H), 3.62~3.59 (m, 1H), 3.22~3.19 (m, 2H), 3.98-3.97 (m, 2H), 2.70 (s, 1H), 2.43~2.33 (m, 2H), 2.30~2.25 (m, 2H), 2.18~1.94 (m, 2H), 1.60~1.55 (m, 1H), 1.40 (s, 9H), 1.35 (s, 1H), 1.24 (m, 1H). HPLC: 94.89% (220 nm), 95.03% (215 nm), 94.11% (254 nm). MS (ESI): mass calcd. For $C_{2-8}H_{38}Cl_{13}N_7O_3$ 589.23, m/z found 590.3 [M+H]$^+$.

Compound 251

Preparation of (5-((3,4-dichlorobenzyl)amino)-1-(1-(piperidin-3-ylmethyl) piperidin-4-yl)-1H-pyrazolo[4,3-d]pyrimidin-7(6H)-one dihydrochloride) (Step 1 in Scheme C-8)

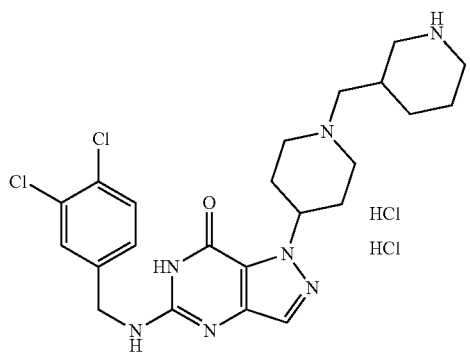 [SMILES: O=c1[nH]c(NCc2ccc(Cl)c(Cl)c2)nc2cnn(C3CCN(CC4CCCNC4)CC3)c12 ; Cl ; Cl]

To a solution of tert-butyl 3-[[4-[5-[(3,4-dichlorophenyl)methylamino]-7-oxo-6H-pyrazolo[4,3-d]pyrimidin-1-yl]-1-piperidyl]methyl]piperidine-1-carboxylate (0.1 g, 169.34 μmol, 1 eq) in EtOAc (1 mL) was added HC/EtOAc (8 mL, 4N). The mixture was stirred at 25° C. for 12 hours. LC-MS and HPLC showed the reaction was complete. The reaction mixture was concentrated under reduced pressure. The residue was purified by prep-HPLC (column: Phenomenex Luna C18 150 mm×30 mm 5 μm; mobile phase: [water (0.05% HCl)-MeCN]; B %: 10%-50%, 8 mins). MeCN was removed under reduced pressure at 30° C. The residue was dried over lyophilization. Compound 5-((3,4-dichlorobenzyl)amino)-1-(1-(piperidin-3-ylmethyl) piperidin-4-yl)-1H-pyrazolo[4,3-d]pyrimidin-7(6H)-one (41.1 mg 71.96 μmol, 42.50% yield, 98.635% purity, 2HCl) was obtained as light yellow solid. $^1$H NMR (DMSO-d$_6$, 400 MHz) δ 10.78-10.63 (m, 1H), 9.28~9.25 (m, 1H), 8.84~8.82 (m, 1H), 7.78 (s, 1H), 7.69~7.60 (m, 3H), 7.36 (d, J=8.4 Hz, 1H), 5.12~5.15 (m, 1H), 4.57 (s, 2H), 3.61~3.57 (m, 2H), 3.53 (s, 1H), 3.18~3.12 (m, 4H), 3.00~2.97 (m, 1H), 2.76~2.67 (m, 2H), 2.36 (d, J=2.8 Hz, 2H), 2.33~2.17 (m, 2H), 2.14~1.70 (m, 4H), 1.30~1.27 (m, 1H). HPLC: 98.64% (220 nm), 98.39% (215 nm), 98.48% (254 nm). MS (ESI): mass calcd. For $C_{23}H_{31}C1_4N_7O$ 489.18, m/z found 490.2 [M+H]$^+$.

Preparation of (5-((3,4-dichlorobenzyl)amino)-1-(1-(piperidin-2-ylmethyl) piperidin-4-yl)-1H-pyrazolo[4,3-d]pyrimidin-7(6H)-one dihydrochloride) (Step 1 in Scheme C-8)

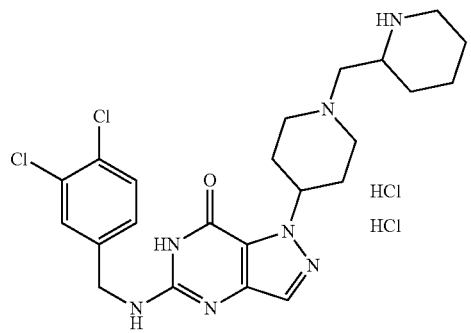 [SMILES: O=c1[nH]c(NCc2ccc(Cl)c(Cl)c2)nc2cnn(C3CCN(CC4CCCCN4)CC3)c12 ; Cl ; Cl]

A mixture of tert-butyl 2-[[4-[5-[(3,4-dichlorophenyl)methylamino]-7-oxo-6H-pyrazolo[4,3-d]pyrimidin-1-yl]-1-piperidyl]methyl]piperidine-1-carboxylate (150 mg, 254.00 μmol, 1 eq) (Step 1 in Scheme C-8) in EtOAc (1 mL) and HC/EtOAc (4M, 3 mL) was stirred at 25° C. for 2 hours. HPLC showed the reaction was complete. The reaction mixture was filtered to removed the insoluble. The filtrate was concentrated and purified by prep-HPLC (column: Phenomenex Luna C18 150 mm×30 mm 5 μm; mobile phase: [water (0.05% HCl)-MeCN]; B %: 5%-50%, 12 mins). The solvent was removed under freeze drying. Compound 5-[(3,4-dichlorophenyl)methylamino]-1-[1-(2-piperidylmethyl)-4-piperidyl]-6H-pyrazolo[4,3-d]pyrimidin-7-one (33.5 mg, 65.88 μmol, 25.94% yield, 96.45% purity, HCl) was obtained as white solid. $^1$H NMR (DMSO-d$_6$, 400 MHz) δ 10.77 (s, 1H), 9.53~9.46 (m, 2H), 7.84 (s, 1H), 7.69 (s, 1H), 7.64~7.60 (m, 2H), 7.37 (d, J=7.6 Hz, 1H), 5.20~5.14 (m, 1H), 4.58 (d, J=4.4 Hz, 2H), 3.91 (d, J=10.8 Hz, 1H), 3.81~3.79 (m, 1H), 3.65 (d, J=10.8 Hz, 1H), 3.49~3.45 (m, 1H), 3.34~3.29 (m, 4H), 2.93~2.91 (m, 1H), 2.43~2.38 (m, 2H), 2.21 (d, J=12.8 Hz, 2H), 1.92 (d, J=12.0 Hz, 1H), 1.77~1.48 (m, 5H). HPLC: 96.45% (220 nm), 95.99% (215 nm), 99.39% (254 nm). MS (ESI): mass calcd. For $C_{23}H_{31}C1_4N_7O$ 489.18, m/z found 490.2 [M+H]$^+$.

Scheme C-9

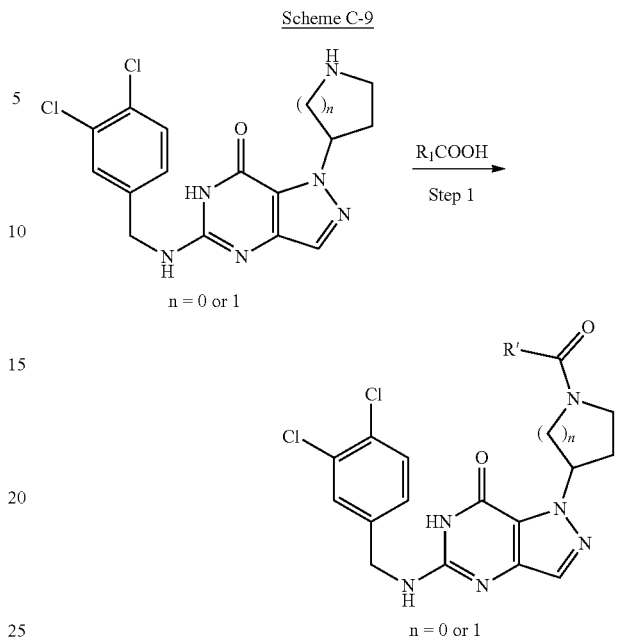

General Procedures for Preparing Compounds in Scheme C-9

Preparation of Compounds (Step 1 in Scheme C-9)

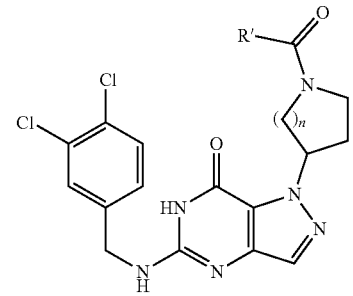

A mixture of 5-((3,4-dichlorobenzyl)amino)-1-(pyrrolidin-3-yl)-1H-pyrazolo[4,3-d]pyrimidin-7(6H)-one or 5-((3,4-dichlorobenzyl)amino)-1-(piperidin-4-yl)-1H-pyrazolo[4,3-d]pyrimidin-7(6H)-one (283.12 μmol, 1 eq), R'COOH (283.12 μmol 368.06 μmol, 1 eq 1.3 eq), EDCI (339.74 μmol, 1.2 eq), HOBt (56.62 μmol, 0.2 eq) and DIEA (849.36 μmol, 147.94 μL, 3 eq) in DMF (3 mL/mmol) was stirred at 20° C. 25° C. for a period of time (10 hours 32 hours). The reaction mixture was stirred at 0° C. 25° C. for a period of time (1 hour 3 hours). LC-MS showed the reaction was complete. The reaction mixture was quenched with H$_2$O and then extracted with EtOAc. The combined organic layers were washed with brine, dried over Na$_2$SO$_4$, filtered and concentrated under reduced pressure. The residue was purified by prep-HPLC. Column: a) Phenomenex luna C18 250 mm×50 mm 10 μm; b) Phenomenex Luna C18 100 mm×30 mm 5 μm; c) Phenomenex Luna C18 150 mm×30 mm 5 μm; d) Luna C18 100 mm×30 mm 5 μm; e) Boston Prime C18

150 mm×30 mm 5 µm; f) Nano-micro Kromasil C18 100 mm×30 mm 5 µm; g) Welch Xtimate C18 100 mm×25 mm 3 µm. Mobile phase: a) [water (0.1% TFA)-MeCN], B %: 30%-65%, 10 mins or 20 mins; b) [water (0.05% HCl)-MeCN], B %: 10%-55%, 10 mins or 9 mins; c) [water (10 mM NH$_4$HCO$_3$)-MeCN], B %: 20%-50%, 20 mins. The aqueous solution was lyophilized to give desired compound.

Compound 252

Preparation of 5-((3,4-dichlorobenzyl)amino)-1-(1-isonicotinoylpiperidin-4-yl)-1H-pyrazolo[4,3-d]pyrimidin-7(6H)-one hydrochloride (Step 1 in Scheme C-9)

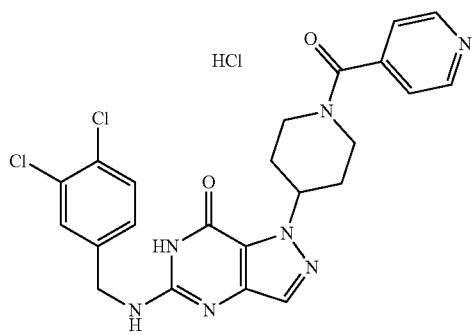 [SMILES: O=C(c1ccncc1)N1CCC(n2ncc3nc(NCc4ccc(Cl)c(Cl)c4)[nH]c(=O)c32)CC1 ; Cl]

A mixture of 5-[(3,4-dichlorophenyl)methylamino]-1-(4-piperidyl)-6H-pyrazolo[4,3-d]pyrimidin-7-one (0.7 g 1.63 mmol, 1 eq, HCl), isonicotinic acid (200.54 mg, 1.63 mmol, 1 eq), HOBt (44.02 mg, 325.79 µmol, 0.2 eq), EDCl (374.72 mg, 1.95 mmol, 1.2 eq) and DIEA (631.57 mg, 4.89 mmol, 851.17 µL, 3 eq) in DMF (5 mL) was stirred at 25° C. for 12 hours. LCMS and HPLC showed the reaction was complete. The reaction mixture was filtered under reduced pressure. The filtrate was purified by prep-HPLC (HCl condition column: Phenomenexluna C18 250 mm×50 mm 10 µm; mobile phase: [water (0.05% HCl)-MeCN]; B %: 20%-50%, 10 mins). MeCN was removed under reduced pressure at 30° C. The residue was dried over lyophilization. Compound 5-((3,4-dichlorobenzyl)amino)-1-(1-isonicotinoylpiperidin-4-yl)-1H-pyrazolo[4,3-d]pyrimidin-7(6H)-one (456.1 mg, 903.34 µmol, 55.46% yield, 98.705% purity, HCl) was obtained as light yellow solid. $^1$H NMR (DMSO-d$_6$, 400 MHz) δ 8.92 (d, J=6.0 Hz, 2H), 7.93 (d, J=6.0 Hz, 2H), 7.85 (s, 1H), 7.68 (s, 1H), 7.65~7.60 (m, 2H), 7.38 (d, J=2.0 Hz, 1H), 5.17~5.12 (m, 1H), 4.59 (d, J=4.8 Hz, 2H), 4.54 (s, 1H), 3.55~3.51 (m, 1H), 3.33~3.27 (m, 1H), 3.12~3.05 (m, 1H), 2.09~1.90 (m, 4H). HPLC: 98.71% (220 nm), 98.68% (215 nm), 98.91% (254 nm). MS (ESI): mass calcd. For C$_{23}$H$_{22}$C3N$_7$O$_2$ 497.11, m/z found 498.1 [M+H]$^+$.

Compound 253

5-[(3,4-Dichlorophenyl)methylamino]-1-[1-(oxazole-4-carbonyl)-4-piperidyl]-6H-pyrazolo[4,3-d]pyrimidin-7-one was prepared according to the procedure described herein for Step 1 in Scheme C-9.

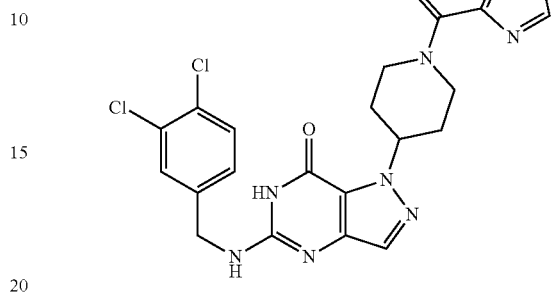

The procedure yielded the desired compound (52.6 mg, 107.71 µmol, 60.52% yield) as a white solid. $^1$H NMR (DMSO-d$_6$, 400 MHz) δ 8.60 (s, 1H), 8.51 (s, 1H), 7.60~7.58 (m, 3H), 7.34-7.32 (m, 1H), 6.82 (s, 1H), 5.20~5.13 (m, 1H), 4.65~4.55 (m, 2H), 4.50~4.48 (m, 2H), 3.33~3.32 (m, 1H), 2.97~2.96 (m, 1H), 2.02~2.01 (m, 4H). HPLC: 99.67% (220 nm), 99.67% (215 nm), 100.00% (254 nm). MS (ESI): mass calcd. For C$_2$H$_{19}$C$_{12}$N$_7$O$_3$ 487.09, m/z found 488.1 [M+H]$^+$.

Compound 254

5-[(3,4-Dichlorophenyl)methylamino]-1-[1-(thiazole-2-carbonyl)-4-piperidyl]-6H-pyrazolo[4,3-d]pyrimidin-7-one was prepared according to the procedure described herein for Step 1 in Scheme C-9.

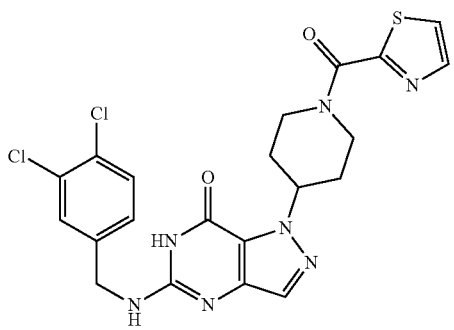 [SMILES: O=C(c1nccs1)N1CCC(n2ncc3nc(NCc4ccc(Cl)c(Cl)c4)[nH]c(=O)c32)CC1]

The procedure yielded the desired compound (33.1 mg, 65.62 µmol, 36.87% yield) as an off-white solid. $^1$H NMR (DMSO-d$_6$, 400 MHz) δ 8.05-8.02 (m, 2H), 7.60~7.58 (m, 3H), 7.34~7.32 (m, 1H), 6.75 (s, 1H), 5.39~5.36 (m, 1H), 5.21~5.19 (m, 1H), 4.58~4.55 (m, 1H), 4.49 (d, J=5.6 Hz, 2H), 3.46~3.44 (m, 1H), 3.12~3.06 (m, 1H), 2.07~2.06 (m, 4H). HPLC: 100.00% (220 nm), 100.00% (215 nm), 100.00% (254 nm). MS (ESI): mass calcd. For C$_{21}$H$_{19}$C2N$_7$O$_2$S 503.07, m/z found 504.1 [M+H]$^+$.

Compound 255

5-((3,4-Dichlorobenzyl)amino)-1-(1-picolinoylpiperidin-4-yl)-1H-pyrazolo[4,3-d]pyrimidin-7(6H)-one hydrochloride was prepared according to the procedure described herein for Step 1 in Scheme C-9.

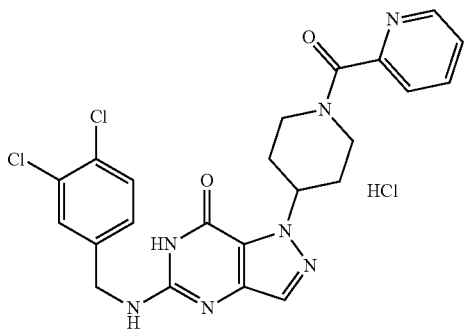 [SMILES: O=C(c1ccccn1)N1CCC(n2ncc3nc(NCc4ccc(Cl)c(Cl)c4)[nH]c(=O)c32)CC1 ; Cl]

The procedure yielded the desired compound (41.5 mg, 77.60 μmol, 41.68% yield, HCl) as a white solid. $^1$H NMR (DMSO-d$_6$, 400 MHz) δ 8.61 (d, J=4.4 Hz, 1H), 7.97 (t, J=8.0 Hz, 1H), 7.70 (s, 1H), 7.66~7.60 (m, 3H), 7.53~7.49 (m, 1H), 7.38 (dd, J=8.4 Hz, 2.0 Hz, 1H), 5.17~5.15 (m, 1H), 4.62 (s, 2H), 4.61 (s, 1H), 3.82~3.78 (m, 1H), 3.30~3.23 (m, 1H), 3.07-3.01 (m, 1H), 2.07~1.91 (m, 4H). HPLC: 100.00% (220 nm), 100.00% (215 nm), 95.43% (254 nm). MS (ESI): mass calcd. For $C_{23}H_{22}C3N_7O_2$ 497.11 m/z found 498.2 [M+H]$^+$.

Compound 256

5-((3,4-Dichlorobenzyl)amino)-1-(1-nicotinoylpiperidin-4-yl)-1H-pyrazolo[4,3-d]pyrimidin-7(6H)-one hydrochloride was prepared according to the procedure described herein for Step 1 in Scheme C-9.

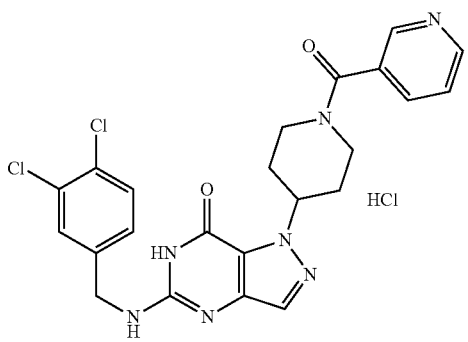 [SMILES: O=C(c1cccnc1)N1CCC(n2ncc3nc(NCc4ccc(Cl)c(Cl)c4)[nH]c(=O)c32)CC1 ; Cl]

The procedure yielded the desired compound (54.4 mg, 101.22 μmol, 54.37% yield, HCl) as a white solid. $^1$H NMR (DMSO-d$_6$, 400 MHz) δ 8.85 (s, 1H), 8.81~8.80 (m, 1H), 8.21 (d, J=6.8 Hz, 1H), 7.79~7.75 (m, 1H), 7.66 (s, 1H), 7.64~7.59 (m, 2H), 7.36 (dd, J=7.6 Hz, 2.0 Hz, 1H), 5.14 (s, 1H), 4.57~4.56 (m, 3H), 3.95 (s, 1H), 3.07~3.05 (m, 2H), 2.05~1.94 (m, 4H). HPLC: 99.51% (220 nm), 99.24% (215 nm), 99.54% (254 nm). MS (ESI): mass calcd. For $C_{23}H_{22}C3N_7O_2$ 497.11, m/z found 498.1 [M+H]$^+$.

Compound 257

5-((3,4-Dichlorobenzyl)amino)-1-(1-picolinoylpyrrolidin-3-yl)-1H-pyrazolo[4,3-d]pyrimidin-7(6H)-one was prepared according to the procedure described herein for Step 1 in Scheme C-9.

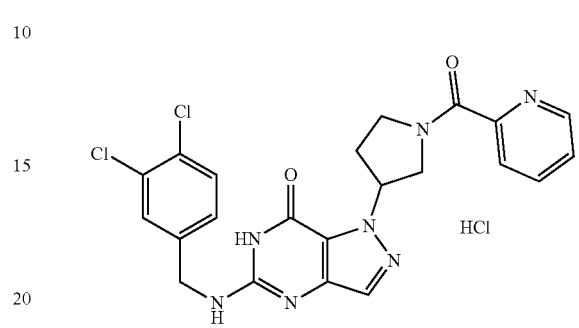

The procedure yielded the desired compound (28.2 mg, 54.15 μmol, 25.67% yield, HCl) as a light yellow solid. H NMR (DMSO-d$_6$, 400 MHz) δ 8.60 (dd, J=8.4 Hz, 2.4 Hz, 1H), 7.95 (q, J=7.6 Hz, 1H), 7.80~7.76 (m, 1H), 7.71~7.59 (m, 3H), 7.55~7.49 (m, 1H), 7.39~7.34 (m, 1H), 5.68~5.63 (m, 1H), 4.58 (d, J=4.4 Hz, 2H), 4.19~4.04 (m, 1H), 4.03~4.00 (m, 1H), 3.96-3.89 (m, 1H), 3.76~3.73 (m, 1H), 2.40~2.32 (m, 2H). HPLC: 100.00% (220 nm), 100.00% (215 nm), 100.00% (254 nm). MS (ESI): mass calcd. For $C_{22}H_{20}C_{13}N_7O_2$ 483.10, m/z found 484.2 [M+H]$^+$.

Compound 258

5-((3,4-Dichlorobenzyl)amino)-1-(1-nicotinoylpyrrolidin-3-yl)-1H-pyrazolo[4,3-d]pyrimidin-7(6H)-one was prepared according to the procedure described herein for Step 1 in Scheme C-9.

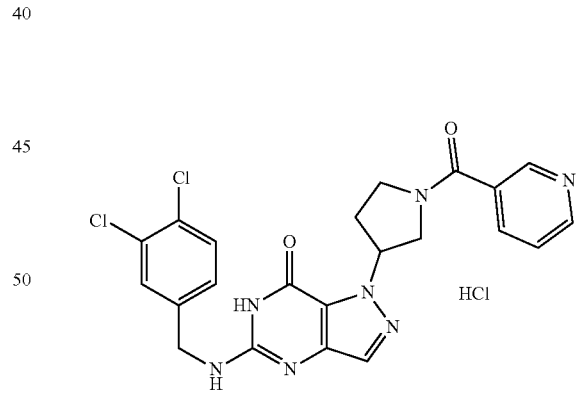

The procedure yielded the desired compound (35.2 mg, 67.59 μmol, 32.04% yield, HCl) as a yellow solid. $^1$H NMR (DMSO-d$_6$, 400 MHz) δ 8.95-8.84 (m, 2H), 8.40~8.34 (m, 1H), 8.21 (s, 1H), 7.86~7.82 (m, 1H), 7.43~7.60 (m, 3H), 7.40~7.35 (m, 1H), 5.73~5.60 (m, 1H), 4.62 (d, J=12.8 Hz, 2H), 4.03~3.99 (m, 1H), 3.92~3.85 (m, 1H), 3.78~3.76 (m, 1H), 3.70~3.67 (m, 1H), 2.32~2.38 (m, 2H). HPLC: 100.00% (220 nm), 100.00% (215 nm), 100.00% (254 nm). MS (ESI): mass calcd. For $C_{22}H_{20}C3N_7O_2$ 483.10 m/z found 484.2 [M+H]$^+$.

Compound 259

5-[(3,4-Dichlorophenyl)methylamino]-1-[1-(pyridine-4-carbonyl)pyrrolidin-3-yl]-6H-pyrazolo[4,3-d]pyrimidin-7-one was prepared according to the procedure described herein for Step 1 in Scheme C-9.

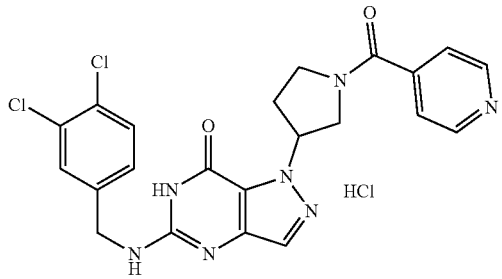 [SMILES: O=C(c1ccncc1)N1CCC(n2ncc3nc(NCc4ccc(Cl)c(Cl)c4)[nH]c(=O)c32)C1 ; Cl]

The procedure yielded the desired compound (34.1 mg, 65.48 μmol, 31.04% yield, HCl) as a white solid. $^1$H NMR (DMSO-$d_6$, 400 MHz) δ 8.91~8.88 (m, 2H), 7.88~7.87 (m, 2H), 7.71~7.59 (m, 4H), 7.36~7.35 (m, 1H), 5.73~5.60 (m, 1H), 4.56 (dd, J=13.2 Hz, 4.8 Hz, 2H), 3.92~3.55 (m, 4H), 2.44~2.38 (m, 2H). HPLC: 99.11% (220 nm), 99.33% (215 nm), 98.46% (254 nm). MS (ESI): mass calcd. For $C_{22}H_2Cl_{13}N_7O_2$ 483.10, m/z found 484.2 [M+H]$^+$.

Compound 260

5-((3,4-Dichlorobenzyl)amino)-1-(1-(5-methoxynicotinoyl) piperidin-4-yl)-1H-pyrazolo[4,3-d]pyrimidin-7(6H)-one hydrochloride was prepared according to the procedure described herein for Step 1 in Scheme C-9).

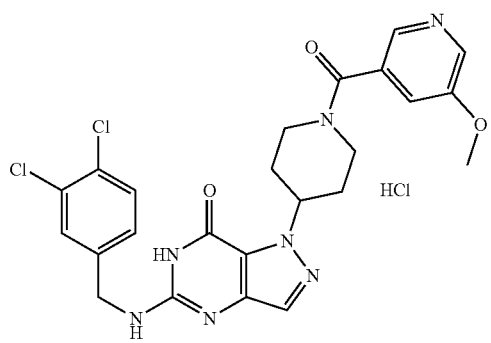 [SMILES: COc1cncc(C(=O)N2CCC(n3ncc4nc(NCc5ccc(Cl)c(Cl)c5)[nH]c(=O)c43)CC2)c1 ; Cl]

The procedure yielded the desired compound (23.4 mg, 41.36 μmol, 25.39% yield, HCl) as a white solid. $^1$H NMR (DMSO-$d_6$, 400 MHz) δ 9.03 (s, 1H), 8.47 (s, 1H), 8.33 (s, 1H), 7.66-7.59 (m, 4H), 7.36 (dd, J=9.6 Hz, 2.0 Hz, 1H), 5.13 (s, 1H), 4.61 (s, 1H), 4.56 (d, J=4.4 Hz, 2H), 3.90 (s, 3H), 3.67 (s, 1H), 3.72 (s, 1H), 3.05 (s, 1H), 2.08~1.94 (m, 4H). HPLC: 99.84% (220 nm), 99.51% (215 nm), 100.00% (254 nm). MS (ESI): mass calcd. For $C_{24}H_{23}Cl_{12}N_7O_3$ 527.12 m/z found 528.2 [M+H]$^+$.

Compound 261

5-((3,4-Dichlorobenzyl)amino)-1-(1-(5-methylnicotinoyl)piperidin-4-yl)-1H-pyrazolo[4,3-d]pyrimidin-7(6H)-one hydrochloride was prepared according to the procedure described herein for Step 1 in Scheme C-9.

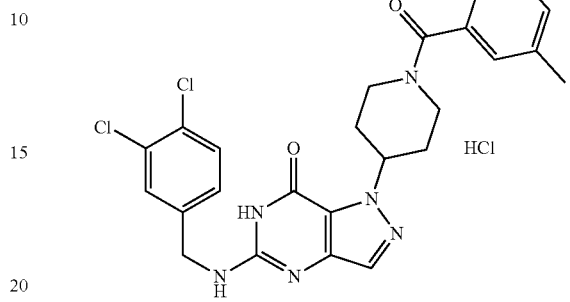

The procedure yielded the desired compound (24.2 mg, 44.09 μmol, 27.07% yield, HCl) as a yellow solid. $^1$H NMR (DMSO-$d_6$, 400 MHz) δ 8.75 (s, 2H), 8.22 (s, 1H), 7.76 (s, 1H), 7.67 (s, 1H), 7.64 (s, 1H), 7.61 (d, J=8.4 Hz, 1H), 7.36 (d, J=8.0 Hz, 1H), 5.14 (s, 1H), 4.58 (d, J=4.8 Hz, 2H), 4.54 (s, 1H), 3.67 (s, 1H), 3.33 (s, 1H), 3.12 (s, 1H), 2.33 (s, 3H), 2.08~1.94 (m, 4H). HPLC: 100.00% (220 nm), 100.00% (215 nm), 100.00% (254 nm). MS (ESI): mass calcd. For $C_{24}H_{23}Cl_{12}N_7O_2$ 511.03, m/z found 512.2 [M+H]$^+$.

Compound 262

5-((3,4-Dichlorobenzyl)amino)-1-(1-(3-methylpicolinoyl) piperidin-4-yl)-1H-pyrazolo[4,3-d]pyrimidin-7(6H)-one hydrochloride was prepared according to the procedure described herein for Step 1 in Scheme C-9.

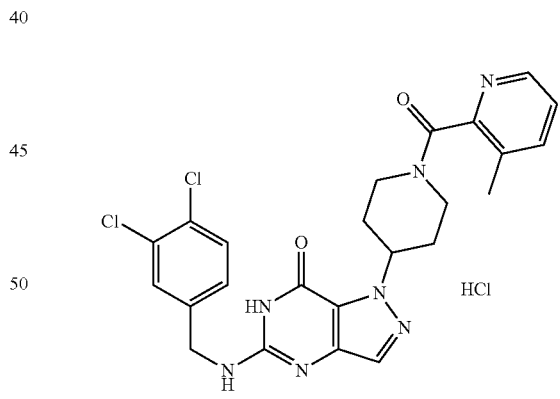

The procedure yielded the desired compound (30.8 mg, 60.11 μmol, 36.90% yield, HCl) as a white solid. $^1$H NMR (DMSO-$d_6$, 400 MHz) δ 8.45 (d, J=4.0 Hz, 1H), 7.81 (d, J=8.0 Hz, 1H), 7.68 (s, 1H), 7.64 (d, J=1.6 Hz, 1H), 7.61 (d, J=8.0 Hz, 1H), 7.43 (q, J=4.0 Hz, 1H), 7.37 (dd, J=8.0 Hz, 4.0 Hz, 1H), 5.17~5.12 (m, 1H), 4.63 (d, J=12.0 Hz, 1H), 4.58 (d, J=4.0 Hz, 2H), 3.34~3.31 (m, 1H), 3.25~3.22 (m, 1H), 3.05~3.02 (m, 1H), 2.29 (s, 3H), 2.11~1.89 (m, 4H). HPLC: 98.99% (220 nm), 98.83% (215 nm), 99.29% (254 nm). MS (ESI): mass calcd. For $C_{24}H_{24}C3N_7O_2$ 511.13, m/z found 512.2 [M+H]$^+$.

Compound 263

5-((3,4-dichlorobenzyl)amino)-1-(1-(4-methoxypicolinoyl)piperidin-4-yl)-1H-pyrazolo[4,3-d]pyrimidin-7(6H)-one hydrochloride was prepared according to the procedure described herein for Step 1 in Scheme C-9.

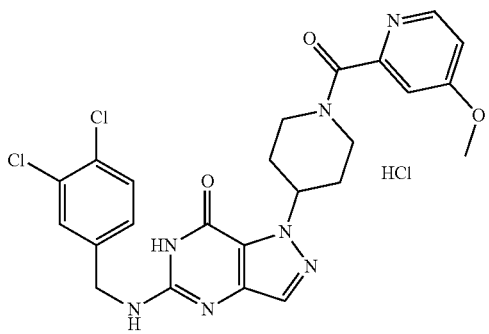 [SMILES: COc1ccnc(C(=O)N2CCC(n3ncc4nc(NCc5ccc(Cl)c(Cl)c5)[nH]c(=O)c43)CC2)c1 ; Cl]

The procedure yielded the desired compound (28.4 mg, 50.28 mol, 30.87% yield, HCl) as a white solid. $^1$H NMR (DMSO-d$_6$, 400 MHz) δ 8.57 (d, J=5.6 Hz, 1H), 7.65 (s, 1H), 7.63~7.58 (m, 2H), 7.40 (d, J=2.4 Hz, 1H), 7.35 (dd, J=2.0 Hz, 8.4 Hz, 1H), 7.27 (dd, J=2.4 Hz, 8.4 Hz, 1H), 5.16 (t, J=4.4 Hz, 1H), 4.60~4.51 (m, 3H), 3.97 (s, 3H), 3.73 (d, J=12.4 Hz, 1H), 3.28 (t, J=13.2 Hz, 1H), 3.06 (t, J=10.4 Hz, 1H), 2.12~1.99 (m, 3H), 1.95-1.89 (m, 1H). HPLC: 99.44% (220 nm), 99.43% (215 nm), 99.31% (254 nm). MS (ESI): mass calcd. For C$_{24}$H$_{24}$C3N$_7$O$_3$ 527.12, m/z found 528.2 [M+H]$^+$.

Compound 264

5-((3,4-Dichlorobenzyl)amino)-1-(1-(4-methylpicolinoyl)piperidin-4-yl)-1H-pyrazolo[4,3-d]pyrimidin-7(6H)-one hydrochloride was prepared according to the procedure described herein for Step 1 in Scheme C-9.

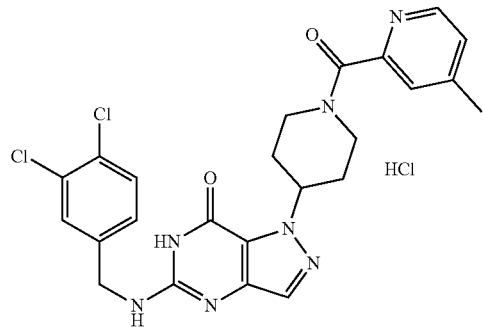 [SMILES: Cc1ccnc(C(=O)N2CCC(n3ncc4nc(NCc5ccc(Cl)c(Cl)c5)[nH]c(=O)c43)CC2)c1 ; Cl]

The procedure yielded the desired compound (22.1 mg, 40.27 μmol, 24.72% yield, HCl) as a white solid. $^1$H NMR (DMSO-d$_6$, 400 MHz) δ 8.49 (d, J=5.2 Hz, 1H), 7.65 (s, 1H), 7.64-7.58 (m, 2H), 7.50 (s, 1H), 7.40~7.33 (m, 2H), 5.20~5.12 (m, 1H), 4.60 (s, 1H), 4.55 (d, J=4.8 Hz, 2H), 3.78 (d, J=11.6 Hz, 1H), 3.25 (t, J=12.0 Hz, 1H), 3.02 (t, J=12.0 Hz, 1H), 2.40 (s, 3H), 2.11~1.96 (m, 3H), 1.94~1.88 (m, 1H). HPLC: 100.00% (220 nm), 100.00% (215 nm), 100.00% (254 nm). MS (ESI): mass calcd. For C$_{24}$H$_{24}$C3N$_7$O$_2$ 511.13, m/z found 512.2 [M+H]$^+$.

Compound 265

1-(1-(4H-1,2,4-triazole-3-carbonyl)piperidin-4-yl)-5-((3,4-dichlorobenzyl)amino)-1H-pyrazolo[4,3-d]pyrimidin-7(6H)-one hydrochloride was prepared according to the procedure described herein for Step 1 in Scheme C-9.

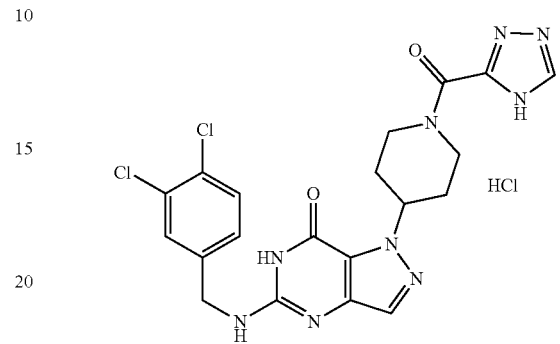

The procedure yielded the desired compound (24.0 mg, 44.27 μmol, 27.18% yield, HCl) as a white solid. $^1$H NMR (DMSO-d$_6$, 400 MHz) δ 8.48-8.47 (m, 1H), 7.62~7.58 (m, 3H), 7.33 (dd, J=8.4 Hz, 2.4 Hz, 1H), 6.84 (s, 1H), 5.21~5.15 (m, 1H), 4.62~4.56 (m, 1H), 4.48 (d, J=3.6 Hz, 3H), 3.30~3.29 (m, 1H), 3.00~2.88 (m, 1H), 2.05~1.97 (m, 4H). HPLC: 96.80% (220 nm), 96.70% (215 nm), 100.00% (254 nm). MS (ESI): mass calcd. For C$_2$H$_{20}$Cl$_3$N$_9$O$_2$ 487.10 m/z found 488.2 [M+H]$^+$.

Compound 266

5-((3,4-Dichlorobenzyl)amino)-1-(1-(4-methoxynicotinoyl)piperidin-4-yl)-1H-pyrazolo[4,3-d]pyrimidin-7(6H)-one hydrochloride was prepared according to the procedure described herein for Step 1 in Scheme C-9.

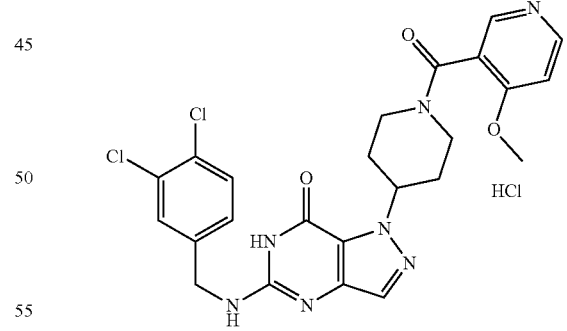

The procedure yielded the desired compound (36.2 mg, 63.92 μmol, 39.24% yield, HCl) as a yellow solid. $^1$H NMR (DMSO-d$_6$, 400 MHz) δ 8.86-8.76 (m, 2H), 7.68 (d, J=6.8 Hz, 1H), 7.62~7.58 (m, 3H), 7.33 (dd, J=9.6 Hz, 2.0 Hz, 1H), 6.95 (m, 1H), 5.11 (s, 1H), 5.59~5.56 (m, 1H), 4.50 (d, J=5.6 Hz, 2H), 4.11 (s, 3H), 3.51~3.48 (m, 1H), 3.26~3.22 (m, 1H), 3.08-3.04 (m, 1H), 2.07~1.89 (m, 4H). HPLC: 99.73% (220 nm), 99.76% (215 nm), 100.00% (254 nm). MS (ESI): mass calcd. For C$_{24}$H$_{24}$C3N$_7$O$_3$ 527.12, m/z found 528.2 [M+H]$^+$.

Compound 267

5-((3,4-Dichlorobenzyl)amino)-1-(1-(4-methylnicotinoyl) piperidin-4-yl)-1H-pyrazolo[4,3-d]pyrimidin-7(6H)-one hydrochloride was prepared according to the procedure described herein for Step 1 in Scheme C-9.

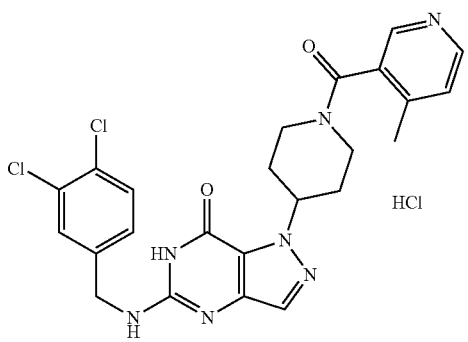 [SMILES: Cc1ccncc1C(=O)N1CCC(n2ncc3nc(NCc4ccc(Cl)c(Cl)c4)[nH]c(=O)c32)CC1 ; Cl]

The procedure yielded the desired compound (38.1 mg, 69.24 µmol, 42.50% yield, HCl) as a light yellow solid. $^1$H NMR (DMSO-d$_6$, 400 MHz) δ 8.77-8.68 (m, 2H), 7.72 (d, J=5.6 Hz, 1H), 7.62~5.58 (m, 3H), 7.33 (dd, J=8.0 Hz, 2.0 Hz, 1H), 5.15~5.09 (m, 1H), 4.65~5.60 (m, 1H), 4.50 (d, J=5.6 Hz, 2H), 3.43~3.32 (m, 1H), 3.32~3.29 (m, 1H), 3.28~3.07 (m, 1H), 2.49-2.46 (m, 3H), 2.33~1.87 (m, 4H). HPLC: 99.74% (220 nm), 99.43% (215 nm), 97.66% (254 nm). MS (ESI): mass calcd. For C$_{24}$H$_{24}$C3N$_7$O$_2$ 511.13, m/z found 512.2 [M+H]$^+$.

Compound 268

5-((3,4-Dichlorobenzyl)amino)-1-(1-(3-methoxypicolinoyl)piperidin-4-yl)-1H-pyrazolo[4,3-d]pyrimidin-7(6H)-one hydrochloride was prepared according to the procedure described herein for Step 1 in Scheme C-9.

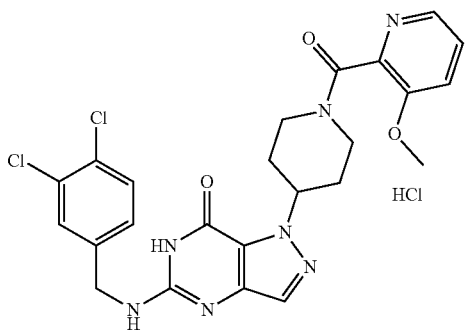 [SMILES: COc1cccnc1C(=O)N1CCC(n2ncc3nc(NCc4ccc(Cl)c(Cl)c4)[nH]c(=O)c32)CC1 ; Cl]

The procedure yielded the desired compound (29.2 mg, 55.26 µmol, 29.68% yield) as a white solid. $^1$H NMR (DMSO-d$_6$, 400 MHz) δ 8.34 (s, 1H), 8.18 (d, J=4.4 Hz, 1H), 7.73 (s, 1H), 7.68 (s, 1H), 7.62 (d, J=8.0 Hz, 2H), 7.49~7.46 (m, 1H), 7.39 (d, J=8.0 Hz, 1H), 5.18~5.12 (m, 1H), 4.65 (s, 2H), 4.59 (d, J=12.8 Hz, 1H), 3.85 (s, 3H), 3.31 (d, J=14.0 Hz, 1H), 3.20 (t, J=12.0 Hz, 1H), 3.01 (t, J=12.0 Hz, 1H), 2.06~1.87 (m, 4H). HPLC: 99.10% (220 nm), 99.06% (215 nm), 97.83% (254 nm). MS (ESI): mass calcd. For C$_{24}$H$_{24}$C3N$_7$O$_3$ 527.12, m/z found 528.2 [M+H]$^+$.

Compound 269

1-(1-(1H-imidazole-2-carbonyl)piperidin-4-yl)-5-((3,4-dichlorobenzyl)amino)-1H-pyrazolo[4,3-d]pyrimidin-7(6H)-one hydrochloride was prepared according to the procedure described herein for Step 1 in Scheme C-9.

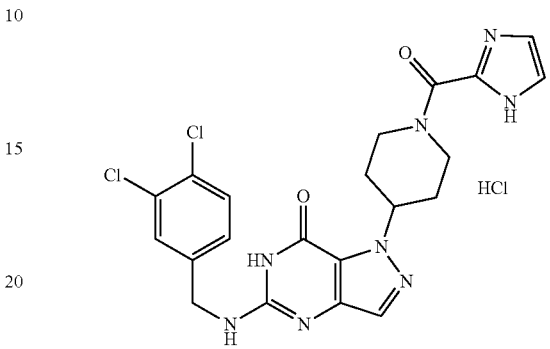

The procedure yielded the desired compound (31.9 mg, 63.81 µmol, 39.18% yield) as a white solid. $^1$H NMR (DMSO-d$_6$, 400 MHz) δ 7.68 (s, 1H), 7.64 (d, J=2.0 Hz, 1H), 7.62 (s, 1H), 7.60 (s, 1H), 7.56 (s, 2H), 5.23~5.18 (m, 1H), 4.60~4.54 (m, 4H), 3.45~3.44 (m, 1H), 3.14-3.11 (m, 1H), 2.09~2.03 (m, 4H). HPLC: 97.49% (220 nm), 95.89% (215 nm), 98.22% (254 nm). MS (ESI): mass calcd. For C$_{21}$H$_{21}$C1$_3$N$_8$O$_2$ 486.11 m/z found 487.2 [M+H]$^+$.

Compound 270

1-(1-(1H-imidazole-5-carbonyl)piperidin-4-yl)-5-((3,4-dichlorobenzyl)amino)-1H-pyrazolo[4,3-d]pyrimidin-7(6H)-one hydrochloride was prepared according to the procedure described herein for Step 1 in Scheme C-9.

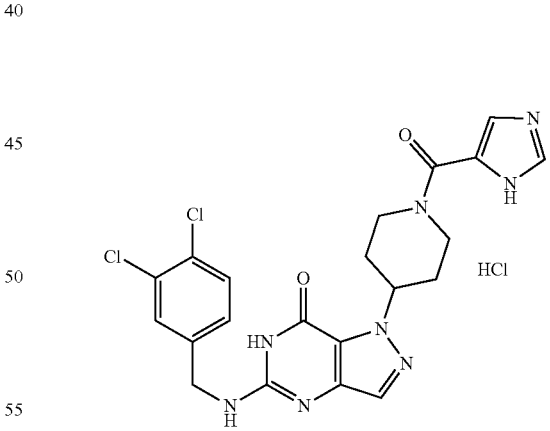

The procedure yielded the desired compound (26.9 mg, 54.80 µmol, 29.44% yield) as a white solid. $^1$H NMR (DMSO-d$_6$, 400 MHz) δ 9.22 (s, 1H), 8.19 (s, 1H), 8.12 (s, 1H), 7.69~7.60 (m, 3H), 7.38 (d, J=7.6 Hz, 1H), 5.19 (s, 1H), 4.63 (s, 2H), 4.51 (s, 1H), 4.03 (s, 1H), 3.54 (s, 1H), 3.10 (s, 1H), 2.07 (s, 4H). HPLC: 99.28% (220 nm), 98.88% (215 nm), 97.87% (254 nm). MS (ESI): mass calcd. For C$_2$H$_{21}$C3N$_8$O$_2$ 486.11, m/z found 487.2 [M+H]$^+$.

Compound 271

1-(1-(1H-pyrazole-3-carbonyl)piperidin-4-yl)-5-((3,4-dichlorobenzyl)amino)-1H-pyrazolo[4,3-d]pyrimidin-7(6H)-one hydrochloride was prepared according to the procedure described herein for Step 1 in Scheme C-9.

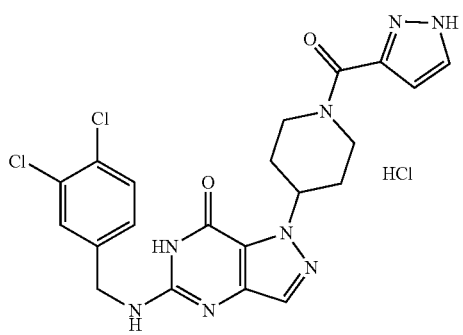 [SMILES: O=C(c1cc[nH]n1)N1CCC(n2ncc3nc(NCc4ccc(Cl)c(Cl)c4)[nH]c(=O)c32)CC1 ; Cl]

The procedure yielded the desired compound (22.8 mg, 45.01 µmol, 27.63% yield) as a white solid. $^1$H NMR (DMSO-d$_6$, 400 MHz) δ 7.78 (d, J=2.0 Hz, 1H), 7.67 (d, J=8.0 Hz, 2H), 7.61 (d, J=8.0 Hz, 1H), 7.37 (d, J=8.0 Hz, 1H), 6.58 (d, J=2.0 Hz, 1H), 5.21~5.13 (m, 1H), 4.77~4.73 (m, 1H), 4.59 (s, 3H), 3.31~3.28 (m, 1H), 2.99~2.93 (m, 1H), 2.04~2.00 (m, 4H). HPLC: 96.19% (220 nm), 92.51% (215 nm), 100.00% (254 nm). MS (ESI): mass calcd. For $C_{21}H_{21}C_{13}N_8O2$ 486.11, m/z found 487.2 [M+H]$^+$.

Compound 272

1-(1-(2H-1,2,3-triazole-4-carbonyl)piperidin-4-yl)-5-((3,4-dichlorobenzyl)amino)-1H-pyrazolo[4,3-d]pyrimidin-7(6H)-one hydrochloride was prepared according to the procedure described herein for Step 1 in Scheme C-9.

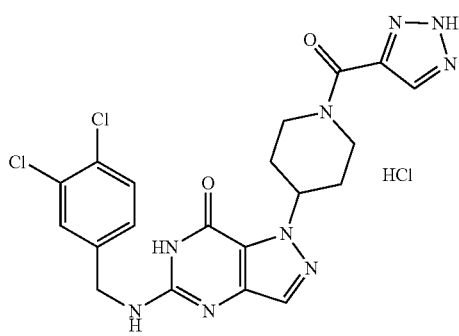 [SMILES: O=C(c1cn[nH]n1)N1CCC(n2ncc3nc(NCc4ccc(Cl)c(Cl)c4)[nH]c(=O)c32)CC1 ; Cl]

The procedure yielded the desired compound (26.8 mg, 50.39 µmol, 27.07% yield, HCl) as a light yellow solid. $^1$H NMR (DMSO-d$_6$, 400 MHz) δ 8.32 (s, 1H), 7.64~7.59 (m, 3H), 7.35 (dd, J=8.4 Hz, 2.0 Hz, 1H), 5.21~5.17 (m, 1H), 4.71~4.65 (m, 1H), 4.61~4.54 (m, 1H), 4.51 (d, J=8.8 Hz, 2H), 3.39~3.35 (m, 1H), 3.03~2.98 (m, 1H), 2.07~1.94 (m, 4H). HPLC: 98.67% (220 nm), 97.49% (215 nm), 100.00% (254 nm). MS (ESI): mass calcd. For $C_{20}H_{20}C_{13}N_9O_2$ 487.10, m/z found 488.2 [M+H]$^+$.

Compound 273

Preparation of 4-(4-(5-((3,4-dichlorobenzyl)amino)-7-oxo-6,7-dihydro-1H-pyrazolo[4,3-d]pyrimidin-1-yl)piperidin-1-yl)-4-oxobutanoic Acid

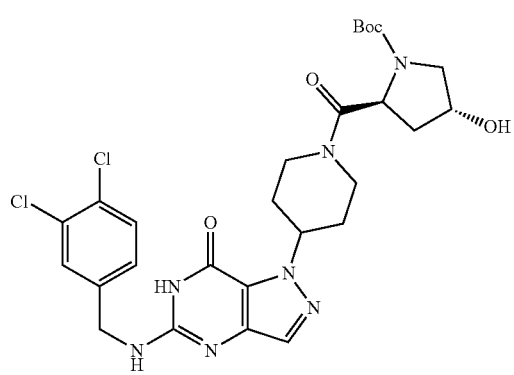 [SMILES: CC(C)(C)OC(=O)N1C[C@H](O)C[C@H]1C(=O)N1CCC(n2ncc3nc(NCc4ccc(Cl)c(Cl)c4)[nH]c(=O)c32)CC1]

To a solution of 5-[(3,4-dichlorophenyl)methylamino]-1-(4-piperidyl)-6H-pyrazolo[4,3-d]pyrimidin-7-one hydrochloride (80 mg, 203.42 µmol, 1 eq) and tetrahydrofuran-2,5-dione (20.36 mg, 203.42 µmol, 1 eq) in CH$_3$CN (3 mL) was added TEA (30.88 mg, 305.13 µmol, 42.47 µL, 1.5 eq) and DMAP (4.97 mg, 40.68 µmol, 0.2 eq). The mixture was stirred at 25° C. for 10 hours. LCMS and HPLC showed the reaction was complete. The mixture was filtered, the filtrate was purified by prep-HPLC (column: Waters Xbridge BEH C18 100 mm×25 mm 5 µm; mobile phase: [water (10 mM NH$_4$HCO$_3$)-MeCN]; B %: 20%-50%, 20 mins). The mixture was dried under freeze-drying to give 4-[4-[5-[(3,4-dichlorophenyl)methylamino]-7-oxo-6H-pyrazolo[4,3-d]pyrimidin-1-yl]-1-piperidyl]-4-oxo-butanoic acid (24.9 mg, 50.07 µmol, 24.61% yield, 99.197% purity) as white solid. $^1$H NMR (DMSO-d$_6$, 400 MHz) δ 7.59-7.56 (m, 2H), 7.55 (s, 1H), 7.32 (d, J=8.4 Hz, 1H), 7.14 (s, 1H), 5.09 (s, 1H), 4.46 (d, J=6.0 Hz, 2H), 4.02 (d, J=13.6 Hz, 1H), 3.26~3.23 (m, 1H), 2.60~2.55 (m, 2H), 2.47~2.43 (m, 2H), 2.42~2.37 (m, 2H), 2.00~1.89 (m, 3H), 1.81 (d, J=12.8 Hz, 1H). HPLC: 99.20% (220 nm), 99.18% (215 nm), 98.21% (254 nm). MS (ESI): mass calcd. For $C_{21}H_{22}C_2N_6O_4$ 492.1, m/z found 493.1 [M+H]$^+$.

Compound 274

Preparation of 5-((3,4-dichlorobenzyl)amino)-1-(1-((2S,4R)-4-hydroxypyrrolidine-2-carbonyl) piperidin-4-yl)-1H-pyrazolo[4,3-d]pyrimidin-7(6H)-one hydrochloride Compound 275

(2S,4R)-tert-Butyl 2-(4-(5-((3,4-dichlorobenzyl)amino)-7-oxo-6,7-dihydro-1H-pyrazolo[4,3-d]pyrimidin-1-yl)piperidine-1-carbonyl)-4-hydroxypyrrolidine-1-carboxylate was prepared according to the procedure described herein for Step 1 in Scheme C-9.

The procedure yielded the desired compound (14.0 mg, 22.14 μmol, 29.02% yield) as a white solid. $^1$H NMR (DMSO-d$_6$, 400 MHz) δ 7.62~7.59 (m, 3H), 7.34 (d, J=8.6 Hz, 1H), 6.94 (s, 1H), 5.10 (s, 1H), 4.72 (t, J=7.6 Hz, 1H), 4.51 (d, J=6.0 Hz, 2H), 4.21 (br s, 1H), 4.04 (d, J=17.6 Hz, 2H), 3.30 (s, 2H), 3.19~3.09 (m, 1H), 2.80~2.71 (m, 1H), 2.14~2.02 (m, 2H), 2.00 (br s, 2H), 1.84 (br d, J=7.8 Hz, 2H), 1.36 (t, J=14.4 Hz, 9H). HPLC: 95.90% (220 nm), 95.94% (215 nm), 95.95% (254 nm). MS (ESI): mass calcd. For $C_{27}H_{33}C_2N_7O_5$ 605.19, m/z found 606.2 [M+H]$^+$.

Preparation of 5-((3,4-dichlorobenzyl)amino)-1-(1-((2S,4R)-4-hydroxypyrrolidine-2-carbonyl) piperidin-4-yl)-1H-pyrazolo[4,3-d]pyrimidin-7(6H)-one hydrochloride

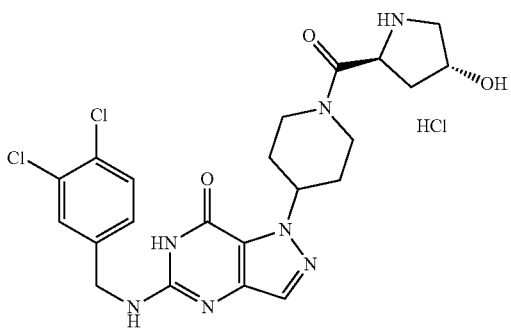 [SMILES: O=C([C@@H]1C[C@@H](O)CN1)N1CCC(n2ncc3nc(NCc4ccc(Cl)c(Cl)c4)[nH]c(=O)c32)CC1 ; Cl]

To a solution of tert-butyl(2S,4R)-2-[4-[5-[(3,4-dichlorophenyl)methylamino]-7-oxo-6H-pyrazolo[4,3-d]pyrimidin-1-yl]piperidine-1-carbonyl]-4-hydroxy-pyrrolidine-1-carboxylate (120 mg, 197.86 μmol, 1 eq) (Step 1 in Scheme C-9) in EtOAc (2 mL) was added HCl/EtOAc (4 M, 2 mL) at 0° C. The mixture was stirred at 25° C. for 10 hours. LCMS and HPLC showed the reaction was complete. The reaction mixture was concentrated under reduced pressure. The residue was purified by prep-HPLC (column: Phenomenex Luna C18 150 mm×30 mm 5 μm; mobile phase: [water (0.05% HCl)-MeCN]; B %: 15%-40%, 10 mins). The mixture was dried under freeze-drying to give 5-((3,4-dichlorobenzyl)amino)-1-(1-((2S,4R)-4-hydroxypyrrolidine-2-carbonyl)piperidin-4-yl)-1H-pyrazolo[4,3-d]pyrimidin-7(6H)-one hydrochloride (20.6 mg, 40.13 μmol, 20.28% yield, 98.651% purity) as white solid. $^1$H NMR (DMSO-d$_6$, 400 MHz) δ 7.64-7.52 (m, 3H), 7.32 (d, J=8.6 Hz, 1H), 6.82 (d, J=6.4 Hz, 1H), 5.47 (br s, 1H), 5.12 (s, 1H), 4.83~4.65 (m, 1H), 4.47 (d, J=5.8 Hz, 2H), 4.45-4.42 (m, 1H), 3.92 (d, J=14.4 Hz, 1H), 3.30~3.24 (m, 2H), 3.06 (d, J=11.6 Hz, 1H), 2.98-2.89 (m, 1H), 2.18~2.02 (m, 2H), 2.00 (br s, 2H), 1.95~1.85 (m, 2H). HPLC: 98.65% (220 nm), 97.98% (215 nm), 98.52% (254 nm). MS (ESI): mass calcd. For $C_{22}H_{26}C_3N_7O_3$ 505.14, m/z found 506.1 [M+H]$^+$.

Compound 276

Preparation of 5-((3,4-dichlorobenzyl)amino)-1-(1-((2S,3R)-2,3,4-trihydroxybutanoyl)piperidin-4-yl)-1H-pyrazolo[4,3-d]pyrimidin-7(6H)-one

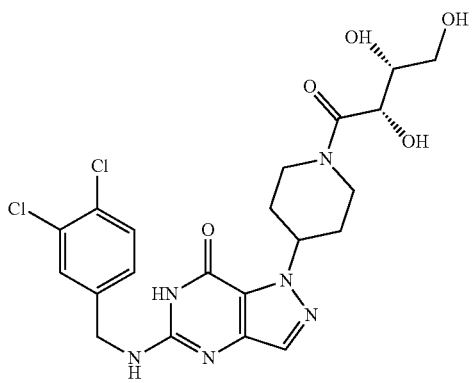 [SMILES: O=C([C@@H](O)[C@H](O)CO)N1CCC(n2ncc3nc(NCc4ccc(Cl)c(Cl)c4)[nH]c(=O)c32)CC1]

A mixture of 5-[(3,4-dichlorophenyl)methylamino]-1-(4-piperidyl)-6H-pyrazolo[4,3-d]pyrimidin-7-one (60 mg, 139.62 μmol, 1 eq, HCl), (3R,4R)-3,4-dihydroxytetrahydrofuran-2-one (49.46 mg, 418.87 μmol, 3 eq) and NaOMe (22.63 mg, 418.87 μmol, 3 eq) in MeOH (2 mL) was stirred at 50° C. for 16 hours. HPLC and LCMS showed the reaction was complete. The reaction mixture was cooled to room temperature and quenched with H$_2$O (5 mL). The mixture was extracted with EtOAc (10 mL×3). The combined organic layers were washed with brine (10 mL), dried over Na$_2$SO$_4$, filtered and concentrated under reduced pressure. The residue was purified by prep-HPLC (column: Phenomenex Luna C18 150 mm×30 mm 5 μm; mobile phase: [water (0.05% HCl)-MeCN]; B %: 15%-35%, 12 mins). The aqueous solution was lyophilized to give 5-[(3,4-dichlorophenyl)methylamino]-1-[1-[(2S,3R)-2,3,4-trihydroxybutanoyl]-4-piperidyl]-6H-pyrazolo[4,3-d]pyrimidin-7-one (25.9 mg, 50.30 μmol, 36.02% yield, 99.307% purity) as light yellow solid. H NMR (DMSO-d$_6$, 400 MHz) δ 7.67-7.58 (m, 3H), 7.36 (d, J=8.4 Hz, 1H), 5.11 (s, 1H), 4.57 (d, J=4.4 Hz, 2H), 4.59 (s, 1H), 4.30 (s, 1H), 4.20 (d, J=14.8 Hz, 1H), 3.61 (t, J=6.4 Hz, 1H), 3.57~3.50 (m, 1H), 3.46~3.42 (m, 1H), 3.30 (dd, J=10.4 Hz, 5.6 Hz, 1H), 3.18 (t, J=8.8 Hz, 1H), 2.80 (t, J=11.2 Hz, 1H), 2.07~1.74 (m, 4H). HPLC: 99.31% (220 nm), 99.16% (215 nm), 98.79% (254 nm). MS (ESI): mass calcd. For $C_2H_{24}C2N_6O_5$ 510.12, m/z found 511.1 [M+H]$^+$.

Compound 277

Preparation of 5-((3,4-dichlorobenzyl)amino)-1-(1-(4-(dimethylamino)-2,3-dihydroxybutanoyl) piperidin-4-yl)-1H-pyrazolo[4,3-d]pyrimidin-7(6H)-one hydrochloride Preparation of (E)-5-((3,4-dichlorobenzyl)amino)-1-(1-(4-(dimethylamino)but-2-enoyl)piperidin-4-yl)-1H-pyrazolo[4,3-d]pyrimidin-7(6H)-one (Step 1 in Scheme C-9)

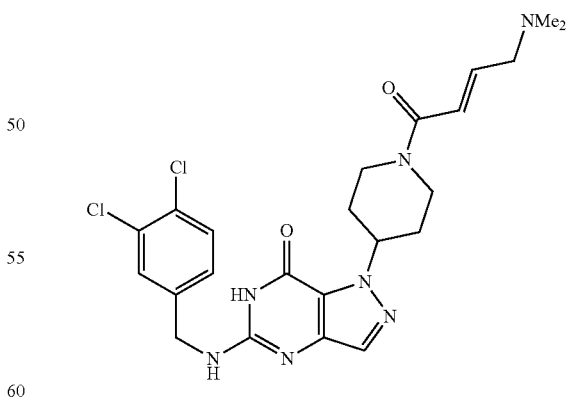

A mixture of (E)-4-(dimethylamino)but-2-enoic acid; hydrochloride (84.79 mg, 511.95 μmol, 1.1 eq), 5-[(3,4-dichlorophenyl)methylamino]-1-(4-piperidyl)-6H-pyrazolo[4,3-d]pyrimidin-7-one (0.2 g 465.41 μmol, 1 eq, HCl), DIEA (180.45 mg, 1.40 mmol, 243.19 μL, 3 eq), HOBt (12.58 mg, 93.08 μmol, 0.2 eq) and EDCl (107.06 mg, 558.49 μmol, 1.2 eq) in DMF (2 mL) was stirred at 25° C. for 6 hours. LC-MS and HPLC showed 5-((3,4-dichlorobenzyl)amino)-1-(piperidin-4-yl)-1H-pyrazolo[4,3-d]pyrimidin-7(6H)-one hydrochloride was consumed completely and one main peak with desired mass was detected. The reaction mixture was quenched with H₂O (5 mL) at 25° C., and then extracted with DCM and i-PrOH (v:v=3:1, 12 mL×6). The combined organic layers were washed with brine (5 mL), dried over Na₂SO₄, filtered and concentrated under reduced pressure to give 5-[(3,4-dichlorophenyl)methylamino]-1-[1-[(E)-4-(dimethylamino)but-2-enoyl]-4-piperidyl]-6H-pyrazolo[4,3-d]pyrimidin-7-one (0.3 g, crude) as black brown oil. ¹H NMR (DMSO-d₆, 400 MHz) δ 11.18 (s, 1H), 7.57 (t, J=5.2 Hz, 3H), 7.32 (dd, J=1.6 Hz, 8.4 Hz, 1H), 6.67~6.56 (m, 2H), 5.16~5.03 (m, 1H), 4.47 (d, J=5.6 Hz, 2H), 4.23~4.10 (m, 1H), 3.42~3.20 (m, 4H), 3.17 (d, J=6.0 Hz, 2H), 2.25 (s, 6H), 2.01~1.82 (m, 4H).

Preparation of 5-((3,4-dichlorobenzyl)amino)-1-(1-(4-(dimethylamino)-2,3-dihydroxybutanoyl) piperidin-4-yl)-1H-pyrazolo[4,3-d]pyrimidin-7(6H)-one hydrochloride

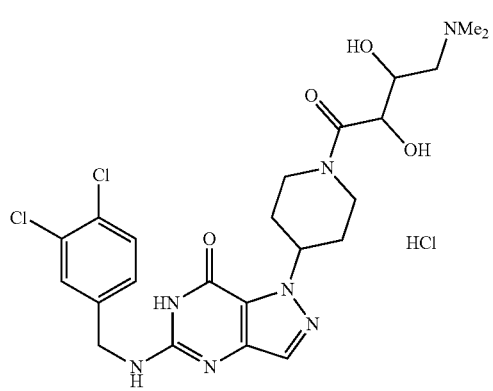 [SMILES: CN(C)CC(O)C(O)C(=O)N1CCC(n2ncc3nc(NCc4ccc(Cl)c(Cl)c4)[nH]c(=O)c32)CC1 ; Cl]

To a solution of 5-[(3,4-dichlorophenyl)methylamino]-1-[1-[(E)-4-(dimethylamino)but-2-enoyl]-4-piperidyl]-6H-pyrazolo[4,3-d]pyrimidin-7-one (0.3 g, 594.75 μmol, 1 eq) in THF (2.5 mL) and H₂O (2.5 mL) was added OsO₄ (30.24 mg, 118.95 μmol, 0.2 eq). After half an hour, NMO (209.02 mg, 1.78 mmol, 188.31 μL, 3 eq) was added. The mixture was stirred at 25° C. for 3 hours. HPLC showed (E)-5-((3,4-dichlorobenzyl)amino)-1-(1-(4-(dimethylamino)but-2-enoyl)piperidin-4-yl)-1H-pyrazolo[4,3-d]pyrimidin-7(6H)-one was consumed completely. The reaction mixture was concentrated under reduced pressure. The aqueous was extracted with EtOAc (5 mL×4). The combined organic layers were washed with brine (5 mL), dried over Na₂SO₄, filtered and concentrated under reduced pressure. The residue was purified by prep-HPLC (column: Phenomenex Luna C18 150 mm×30 mm 5 μm; mobile phase: [water (0.05% HCl)-MeCN]; B %: 15%-55%, 12 mins). The aqueous solution was lyophilized to give compound 5-[(3,4-dichlorophenyl)methylamino]-1-[1-[4-(dimethylamino)-2,3-dihydroxy-butanoyl]-4-piperidyl]-6H-pyrazolo[4,3-d]pyrimidin-7-one (10 mg, 17.09 μmol, 2.87% yield, 98.22% purity, HCl) as off white solid. ¹H NMR (DMSO-d₆, 400 MHz) δ 9.42 (s, 1H), 7.68~7.57 (m, 3H), 7.44~7.30 (m, 1H), 7.13 (s, 1H), 5.32~5.01 (m, 1H), 4.54~4.42 (m, 3H), 4.31~4.20 (m, 1H), 4.17~3.99 (m, 2H), 3.27~3.20 (m, 4H), 2.86-2.79 (m, 6H), 2.09~1.97 (m, 4H). HPLC: 98.22% (220 nm), 97.59% (215 nm), 98.12% (254 nm). MS (ESI): mass calcd. For C₂₃H₃₀Cl₃N₇O₄ 537.17, m/z found 538.2 [M+H]⁺.

Compound 278

Preparation of 5-((3,4-dichlorobenzyl)amino)-1-(1-((2S,4S)-4-hydroxypyrrolidine-2-carbonyl) piperidin-4-yl)-1H-pyrazolo[4,3-d]pyrimidin-7(6H)-one hydrochloride Preparation of (2S,4S)-tert-butyl 2-(4-(5-((3,4-dichlorobenzyl)amino)-7-oxo-6,7-dihydro-1H-pyrazolo[4,3-d]pyrimidin-1-yl)piperidine-1-carbonyl)-4-hydroxypyrrolidine-1-carboxylate (Step 1 in Scheme C-9)

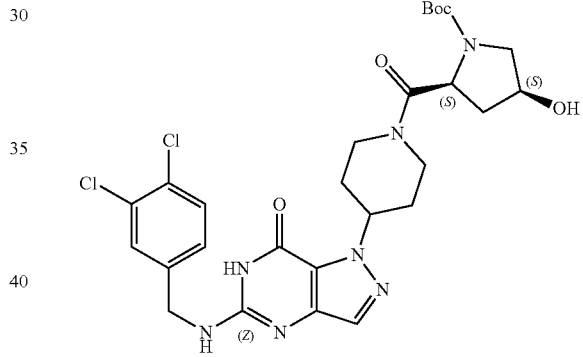

To a solution of 5-[(3,4-dichlorophenyl)methylamino]-1-(4-piperidyl)-6H-pyrazolo[4,3-d]pyrimidin-7-one (60 mg, 139.62 μmol, 1 eq, HCl), (2S,4S)-1-tert-butoxycarbonyl-4-hydroxy-pyrrolidine-2-carboxylic acid (41.97 mg, 181.51 μmol, 1.3 eq) and DIEA (108.27 mg, 837.73 μmol, 145.91 μL, 6 eq) in THF (2 mL) was added T3P (266.55 mg, 418.87 μmol, 249.11 μL, 50% purity, 3 eq) dropwise at 0° C. The mixture was stirred at 25° C. for 3 hours. LC-MS showed 20% of 5-((3,4-dichlorobenzyl)amino)-1-(piperidin-4-yl)-1H-pyrazolo[4,3-d]pyrimidin-7(6H)-one hydrochloride was remained. Several new peaks were shown on LC-MS and ~70% of desired compound was detected. The reaction mixture was quenched with H₂O (5 mL) at 20° C. and then extracted with EtOAc (10 mL×3). The combined organic layers were washed with brine (5 mL), dried over Na₂SO₄, filtered and concentrated under reduced pressure to give tert-butyl(2S,4S)-2-[4-[5-[(3,4-dichlorophenyl)methylamino]-7-oxo-6H-pyrazolo[4,3-d]pyrimidin-1-yl]piperidine-1-carbonyl]-4-hydroxy-pyrrolidine-1-carboxylate (270 mg, crude) as off white solid.

Preparation of 5-((3,4-dichlorobenzyl)amino)-1-(1-((2S,4S)-4-hydroxypyrrolidine-2-carbonyl) piperidin-4-yl)-1H-pyrazolo[4,3-d]pyrimidin-7(6H)-one hydrochloride

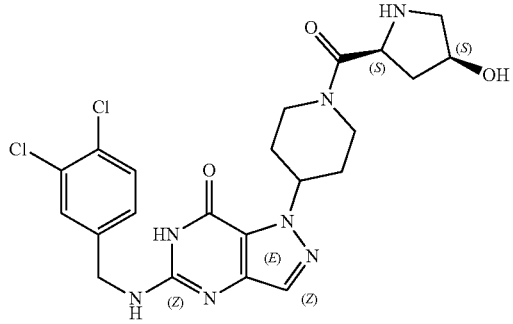

A mixture of tert-butyl(2S,4S)-2-[4-[5-[(3,4-dichlorophenyl)methylamino]-7-oxo-6H-pyrazolo[4,3-d]pyrimidin-1-yl]piperidine-1-carbonyl]-4-hydroxy-pyrrolidine-1-carboxylate (270 mg, 445.18 μmol, 1 eq) in EtOAc (2 mL) and HCl/EtOAc (8 mL 4M) was stirred at 20° C. for 2 hours. LC-MS showed the reaction was complete. The reaction mixture was concentrated under reduced pressure. The residue was purified by prep-HPLC (column: Phenomenex Luna C18 150 mm×30 mm 5 μm; mobile phase: [water (0.05% HCl)-MeCN]; B %: 10%-25%, 12 mins). The aqueous solution was lyophilized to give compound 5-[(3,4-dichlorophenyl)methylamino]-1-[1-[(2S,4S)-4-hydroxypyrrolidine-2-carbonyl]-4-piperidyl]-6H-pyrazolo[4,3-d]pyrimidin-7-one (17.5 mg, 31.50 μmol, 7.08% yield, 97.711% purity, HCl) as off white solid. H NMR (DMSO-d$_6$, 400 MHz) δ 10.20-9.79 (m, 1H), 8.57~8.43 (m, 1H), 7.66~7.53 (m, 3H), 7.39~7.18 (m, 2H), 5.19~5.07 (m, 1H), 4.69~4.54 (m, 1H), 4.53~4.37 (m, 4H), 3.96~3.79 (m, 2H), 3.18 (s, 2H), 3.02~2.89 (m, 1H), 2.64~2.57 (m, 1H), 2.05-1.73 (m, 5H). HPLC: 97.71% (220 nm), 95.90% (215 nm), 100.00% (254 nm). MS (ESI): mass calcd. For $C_{22}H_{26}Cl_3N_7O_3$ 505.14, m/z found 506.1 [M+H]$^+$.

Compound 279

Preparation of 5-((3,4-dichlorobenzyl)amino)-1-(1-(2-(dimethylamino)-3-hydroxypropanoyl) piperidin-4-yl)-1H-pyrazolo[4,3-d]pyrimidin-7(6H)-one hydrochloride

Preparation of tert-butyl(1-(4-(5-((3,4-dichlor672obenzyl)amino)-7-oxo-6,7-dihydro-1H-pyrazolo[4,3-d]pyrimidin-1-yl)piperidin-1-yl)-3-hydroxy-1-oxopropan-2-yl)carbamate (Step 1 in Scheme C-9)

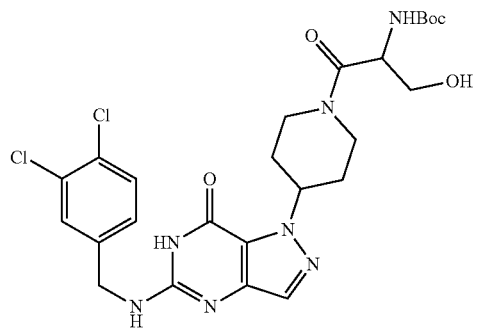 [SMILES: CC(C)(C)OC(=O)NC(CO)C(=O)N1CCC(n2ncc3nc(NCc4ccc(Cl)c(Cl)c4)[nH]c(=O)c32)CC1]

A mixture of 5-[(3,4-dichlorophenyl)methylamino]-1-(4-piperidyl)-6H-pyrazolo[4,3-d]pyrimidin-7-one (300 mg, 698.11 μmol, 1 eq, HCl), 2-(tert-butoxycarbonylamino)-3-hydroxy-propanoic acid (214.89 mg, 1.05 mmol, 1.5 eq), EDCl (160.59 mg, 837.73 μmol, 1.2 eq), HOBt (18.87 mg, 139.62 μmol, 0.2 eq) and DIEA (270.67 mg, 2.09 mmol, 364.79 μL, 3 eq) in DMF (3 mL) was stirred at 25° C. for 12 hours. LC-MS showed 5-[(3,4-dichlorophenyl)methylamino]-1-(4-piperidyl)-6H-pyrazolo[4,3-d]pyrimidin-7-one (HCl) was consumed completely and one peak with desired mass was detected. The reaction mixture was quenched with H$_2$O (2 mL). Then the mixture was extracted with EtOAc (4 mL×3). The combined organic layers were washed with brine (4 mL), dried over Na$_2$SO$_4$, filtered and concentrated under reduced pressure. Compound tert-butyl N-[2-[4-[5-[(3,4-dichloro phenyl)methylamino]-7-oxo-6H-pyrazolo[4,3-d]pyrimidin-1-yl]-1-piperidyl]-1-(hydroxymethyl)-2-oxo-ethyl]carbamate (800 mg, crude) was obtained as brown oil. $^1$H NMR (DMSO-d$_6$, 400 MHz) δ 11.17 (s, 1H), 7.58~7.56 (m, 2H), 7.32 (dd, J=8.4 Hz, 1.6 Hz, 1H), 7.61~7.59 (m, 1H), 5.10 (s, 1H), 4.47 (d, J=5.6 Hz, 3H), 3.61~3.55 (m, 1H), 3.50~3.42 (m, 1H), 3.32 (s, 2H), 3.25~3.17 (m, 1H), 3.01~2.98 (m, 1H), 2.03~1.95 (m, 3H), 1.87~1.80 (m, 1H), 1.37 (s, 9H).

Preparation of 1-(1-(2-amino-3-hydroxypropanoyl) piperidin-4-yl)-5-((3,4-dichlorobenzyl)amino)-1H-pyrazolo[4,3-d]pyrimidin-7(6H)-one

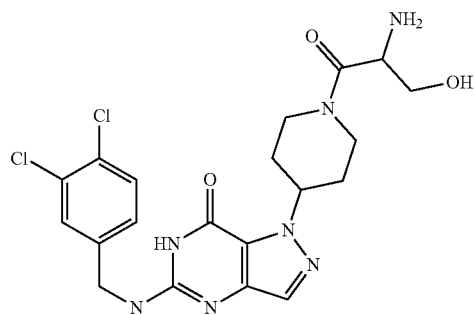

A mixture of tert-butyl N-[2-[4-[5-[(3,4-dichlorophenyl)methylamino]-7-oxo-6H-pyrazolo[4,3-d]pyrimidin-1-yl]-1-piperidyl]-1-(hydroxymethyl)-2-oxo-ethyl]carbamate (700 mg, 1.21 mmol, 1 eq) in EtOAc (3 mL) and HCl/EtOAc (4M, 7 mL) was stirred at 25° C. for an hour. LC-MS showed the reaction was complete. The reaction mixture was concentrated under reduced pressure to give 1-(1-(2-amino-3-hydroxypropanoyl) piperidin-4-yl)-5-((3,4-dichloro benzyl) amino)-1H-pyrazolo[4,3-d]pyrimidin-7(6H)-one (650 mg, crude) as white solid. $^1$H NMR (DMSO-d$_6$, 400 MHz) δ 8.95 (s, 1H), 8.19 (s, 2H), 7.74 (d, J=14.0 Hz, 2H), 7.64 (d, J=8.4 Hz, 1H), 7.74 (d, J=8.4 Hz, 1H), 5.14~5.10 (m, 1H), 4.75 (s, 1H), 4.48~4.46 (m, 2H), 3.74-3.70 (m, 1H), 3.68~3.58 (m, 1H), 3.09~3.03 (m, 1H), 3.00~2.93 (m, 1H), 2.70~2.67 (m, 2H), 2.06~1.98 (m, 4H).

Preparation of 5-((3,4-dichlorobenzyl)amino)-1-(1-(2-(dimethylamino)-3-hydroxypropanoyl) piperidin-4-yl)-1H-pyrazolo[4,3-d]pyrimidin-7(6H)-one hydrochloride

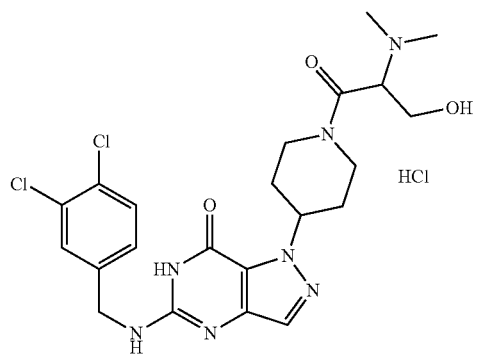 [SMILES: CN(C)C(CO)C(=O)N1CCC(n2ncc3nc(NCc4ccc(Cl)c(Cl)c4)[nH]c(=O)c32)CC1 ; Cl]

To a solution of 1-[1-(2-amino-3-hydroxy-propanoyl)-4-piperidyl]-5-[(3,4-dichlorophenyl)methylamino]-6H-pyrazolo[4,3-d]pyrimidin-7-one (640 mg, 1.33 mmol, 1 eq) in MeOH (2 mL) was added formaldehyde (324.41 mg, 4.00 mmol, 297.63 μL, 37% purity, 3 eq) at 0° C. The mixture was stirred at 0° C. for 10 mins. Then AcOH (8.00 mg, 133.24 μmol, 7.62 μL, 0.1 eq) and NaBH$_3$CN (669.81 mg, 10.66 mmol, 8 eq) were added at 0° C. The mixture was stirred at 25° C. for 2 hours. TLC indicated the reaction was complete. The reaction mixture was quenched with H$_2$O (2 mL) and then extracted with EtOAc (4 mL×3). The combined organic layers were washed with brine (4 mL), dried over Na$_2$SO$_4$, filtered and concentrated under reduced pressure. The residue was purified by prep-HPLC (HCl condition column: Phenomenex Luna C18 150 mm×30 mm 5 μm; mobile phase: [water (0.05% HCl)-MeCN]; B %: 20%-30%, 12 mins). The solvent was removed under freeze drying. Compound 5-[(3,4-dichlorophenyl)methylamino]-1-[1-[2-(dimethylamino)-3-hydroxy-propanoyl]-4-piperidyl]-6H-pyrazolo[4,3-d]pyrimidin-7-one (90 mg, 176.02 μmol, 13.21% yield, 99.43% purity, HCl) was obtained as white solid. $^1$H NMR (DMSO-d$_6$, 400 MHz) δ 9.64 (s, 1H), 7.86 (s, 1H), 7.67 (d, J=3.2 Hz, 1H), 7.65 (s, 1H), 7.61 (d, J=8.4 Hz, 1H), 7.37 (d, J=7.6 Hz, 1H), 5.16~5.11 (m, 1H), 4.71~4.70 (m, 1H), 4.64~4.59 (m, 2H), 4.52~4.45 (m, 1H), 4.04-3.98 (m, 1H), 3.89~3.79 (m, 2H), 3.36~3.30 (m, 1H), 3.00~2.91 (m, 1H), 2.86~2.75 (m, 6H), 2.09~2.03 (m, 3H), 1.96~1.88 (m, 1H). HPLC: 99.43% (220 nm), 99.28% (215 nm), 99.19% (254 nm). MS (ESI): mass calcd. For C$_{22}$H$_{28}$C$_3$N$_7$O$_3$ 507.16, m/z found 508.1 [M+H]$^+$.

Scheme C-10

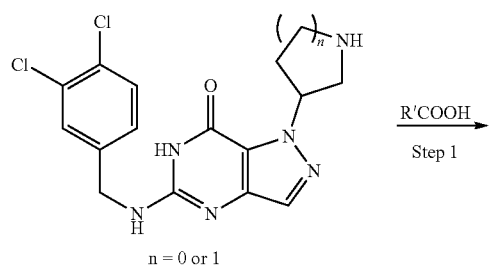

n = 0 or 1

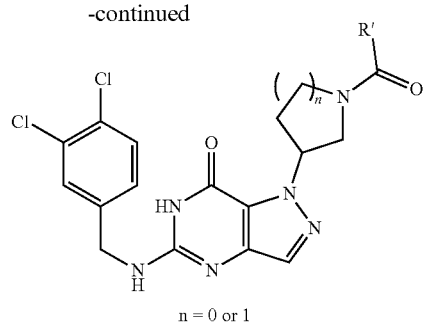

n = 0 or 1

General Procedures for Preparing Compounds in Scheme C-10

Preparation of Compounds (Step 1 in Scheme C-10)

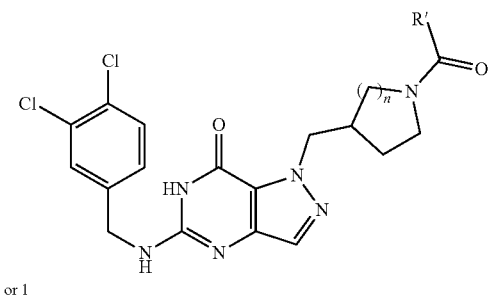

n = 0 or 1

To a solution of R'COOH (306.90 μmol, 1 eq) in DMF or DCM (10 mL/mmol) was added EDCI (613.80 μmol, 2 eq), HOBt (92.07 μmol, 0.3 eq) and DIEA (920.71 μmol, 3 eq) at 0° C. After half an hour, 5-((3,4-dichlorobenzyl)amino)-1-(pyrrolidin-3-ylmethyl)-1H-pyrazolo[4,3-d]pyrimidin-7 (6H)-one or 5-((3,4-dichlorobenzyl)amino)-1-(piperidin-3-ylmethyl)-1H-pyrazolo[4,3-d]pyrimidin-7(6H)-one (306.90 μmol, 1 eq) was added into the mixture. The mixture was stirred at 25° C. for 10 hours. LC-MS showed the reaction was complete. The reaction mixture was quenched with H$_2$O and then extracted with EtOAc. The combined organic layers were washed with brine, dried over Na$_2$SO$_4$, filtered and concentrated under reduced pressure. The residue was purified by prep-HPLC. Column: a) Phenomenex Luna C18 150 mm×30 mm 5 μm; b) Nano-micro Kromasil C18 100 mm×30 mm 5 μm. Mobile phase: [water (0.05% HCl)-MeCN]; B %: 20%-50%, 12 mins or 10 mins. The aqueous solution was lyophilized to give desired compound.

Compound 280

Preparation of 5-((3,4-dichlorobenzyl)amino)-1-((1-nicotinoylpiperidin-3-yl)methyl)-1H-pyrazolo[4,3-d]pyrimidin-7(6H)-one hydrochloride (Step 1 in Scheme C-10)

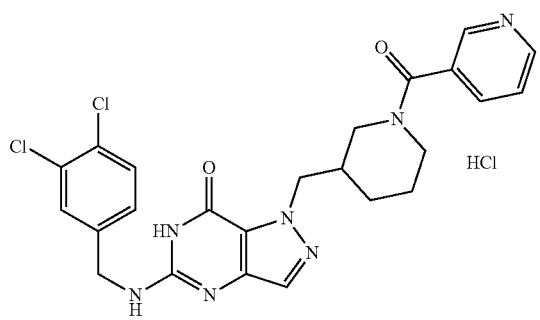 [SMILES: O=C(c1cccnc1)N1CCCC(Cn2ncc3nc(NCc4ccc(Cl)c(Cl)c4)[nH]c(=O)c32)C1 ; Cl]

To a solution of nicotinic acid (37.78 mg, 306.90 μmol, 25.70 μL, 1 eq) in DCM (3 mL) was added EDCl (117.67 mg, 613.80 μmol, 2 eq), HOBt (12.44 mg, 92.07 μmol, 0.3 eq) and DIEA (118.99 mg, 920.71 μmol, 160.37 μL, 3 eq) at 0° C. After half an hour, 5-((3,4-dichlorobenzyl)amino)-1-(piperidin-3-ylmethyl)-1H-pyrazolo[4,3-d]pyrimidin-7(6H)-one (125 mg, 306.90 μmol, 1 eq) was added into the mixture. The mixture was stirred at 25° C. for 10 hours. LCMS and HPLC showed the reaction was complete. The mixture was concentrated under reduced pressure. The residue was purified by prep-HPLC (column: Nano-micro Kromasil C18 100 mm×30 mm 5 μm; mobile phase: [water (0.05% HCl)-MeCN]; B %: 20%-50%, 10 mins). The mixture was freeze-dry to give 5-((3,4-dichlorobenzyl)amino)-1-((1-nicotinoylpiperidin-3-yl)methyl)-1H-pyrazolo[4,3-d]pyrimidin-7(6H)-one (42.7 mg, 74.97 μmol, 24.43% yield, 96.362% purity, HCl) as white solid. $^1$H NMR (DMSO-$d_6$, 400 MHz) δ 8.94-8.79 (m, 1H), 8.75 (s, 1H), 8.24 (s, 1H), 8.13~7.89 (m, 1H), 7.83 (s, 1H), 7.73 (s, 1H), 7.68 (s, 1H), 7.64 (d, J=8.4 Hz, 1H), 7.54 (s, 1H), 7.40 (d, J=8.4 Hz, 1H), 4.63 (d, J=4.8 Hz, 2H), 4.26~4.14 (m, 3H), 3.39 (d, J=11.6 Hz, 1H), 3.27 (d, J=14.0 Hz, 1H), 3.12~3.09 (m, 0.5H), 2.92~2.85 (m, 1.5H), 2.20 (br s, 1H), 1.80~1.58 (m, 2H), 1.45 (br s, 1H), 1.34~1.26 (m, 1H). HPLC: 96.36% (220 nm), 95.85% (215 nm), 95.29% (254 nm). MS (ESI): mass calcd. For $C_{24}H_{24}Cl_3N_7O_2$ 511.13, m/z found 512.1 [M+H]$^+$.

Compound 2811-((1-Acetylpyrrolidin-3-yl)methyl)-5-((3,4-dichlorobenzyl)amino)-1H-pyrazolo[4,3-d]pyrimidin-7(6H)-one was prepared according to the procedure described herein for Step 1 in Scheme C-10.

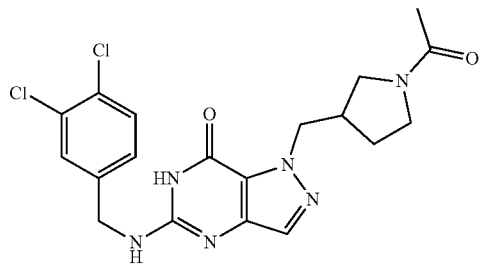 [SMILES: CC(=O)N1CCC(Cn2ncc3nc(NCc4ccc(Cl)c(Cl)c4)[nH]c(=O)c32)C1]

The procedure yielded the desired compound (37.0 mg, 84.32 μmol, 41.45% yield) as a white solid. $^1$H NMR (DMSO-$d_6$, 400 MHz) δ 7.73~7.59 (m, 3H), 7.59~7.38 (m, 1H), 7.37 (d, J=6.8 Hz, 1H), 4.56 (d, J=4.8 Hz, 2H), 4.53~4.42 (m, 2H), 3.51~3.22 (m, 4H), 3.08~3.03 (m, 1H), 2.80~2.69 (m, 1H), 1.90 (d, J=6.4 Hz, 3H), 1.89~1.76 (m, 1H), 1.71~1.53 (m, 1H). HPLC: 99.21% (220 nm), 98.93% (215 nm), 98.52% (254 nm). MS (ESI): mass calcd. For $C_{19}H_{20}Cl_2N_6O_2$ 434.10, m/z found 435.1 [M+H]$^+$.

Scheme C-11

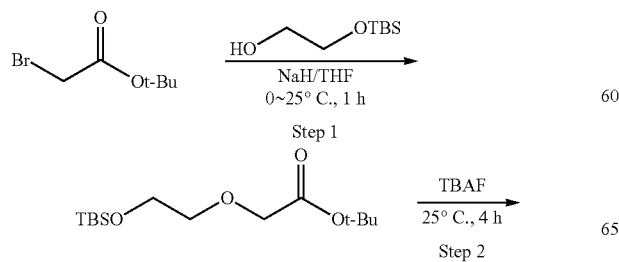

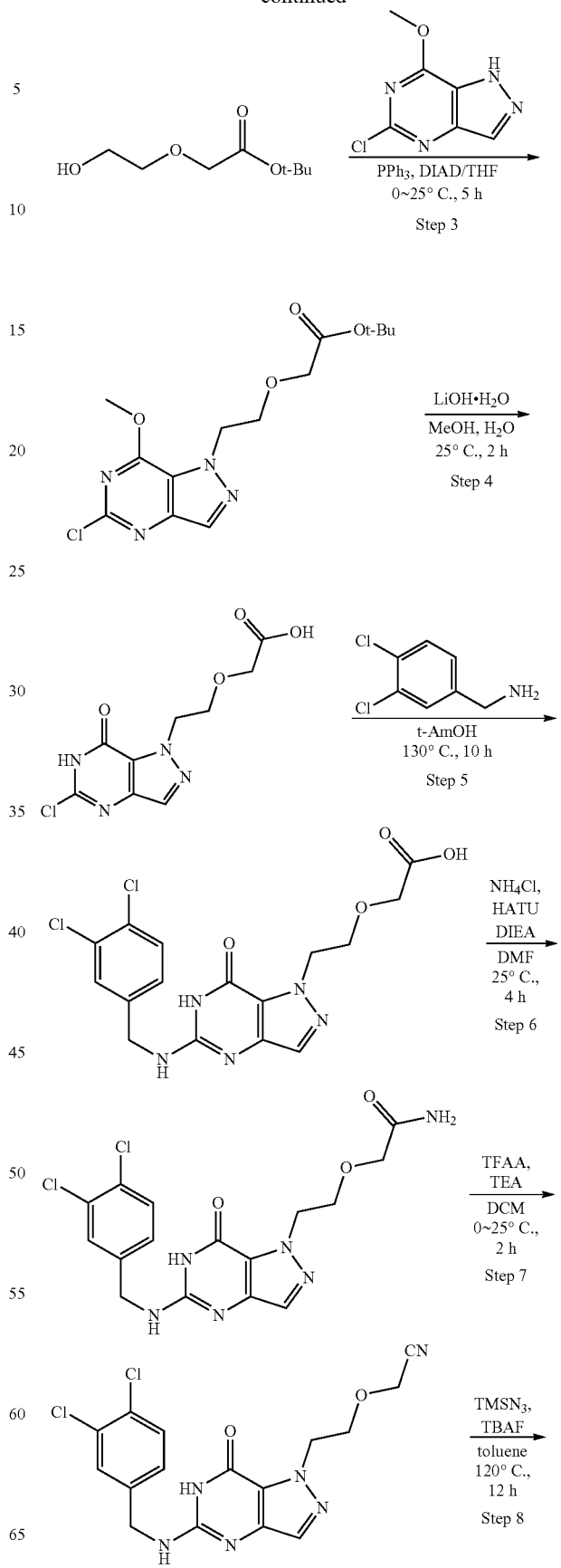

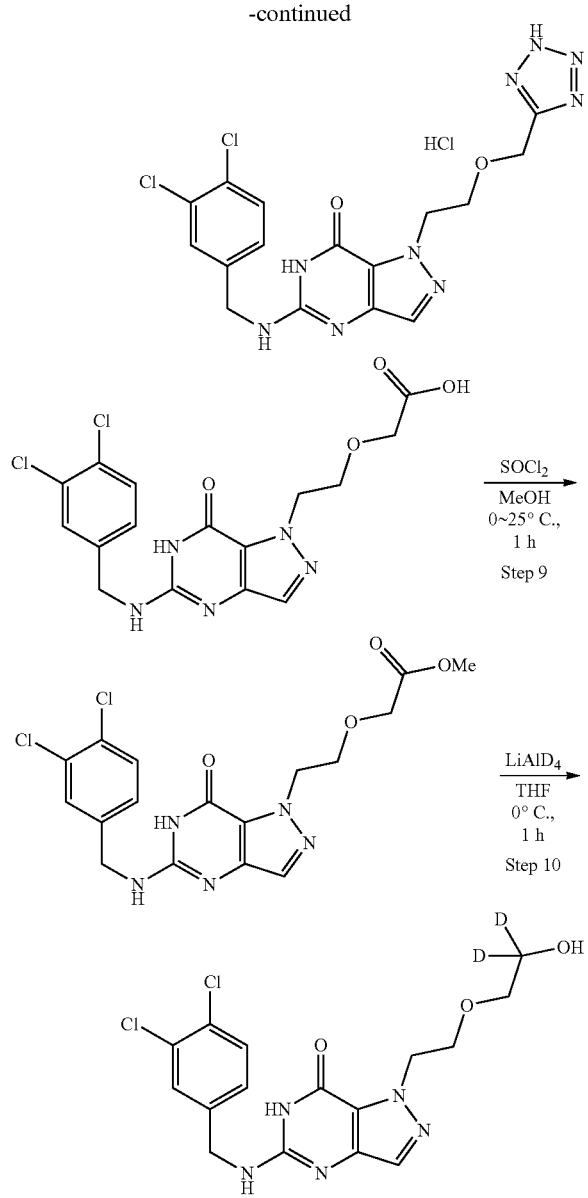

Compound 282

Preparation of 1-(2-((2H-tetrazol-5-yl)methoxy) ethyl)-5-((3,4-dichlorobenzyl)amino)-1H-pyrazolo [4,3-d]pyrimidin-7(6H)-one hydrochloride (Scheme C-11)

Preparation of tert-butyl 2-[2-[tert-butyl(dimethyl) silyl]oxyethoxy]acetate (Step 1 in Scheme C-11)

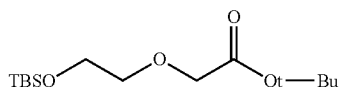

To a mixture of NaH (7.37 g, 184.32 mmol, 60% purity, 1.3 eq) in THF (500 mL) was added 2-[tertbutyl(dimethyl) silyl]oxyethanol (25 g, 141.78 mmol, 1 eq) dropwise at 0° C. After 30 min, tert-butyl 2-bromoacetate (35.95 g, 184.32 mmol, 27.24 mL, 1.3 eq) was added dropwise at 0° C. The mixture was stirred at 25° C. for 1 hour. TLC indicated the reaction was complete. The mixture was poured into ice water (500 mL) and concentrated under reduced pressure to remove THF and then extracted with EtOAc (500 mL×3). The combined organic layers were washed with brine (500 mL×3), dried over Na$_2$SO$_4$, filtered and concentrated under reduced pressure. Compound tert-butyl 2-[2-[tert-butyl(dimethyl)silyl]oxyethoxy]acetate (40 g crude) was obtained as brown oil. $^1$H NMR (CDC$_3$, 400 MHz) δ 4.04 (s, 2H), 3.81 (t, J=5.2 Hz, 2H), 3.63 (t, J=5.2 Hz, 2H), 1.48 (s, 9H), 0.90 (s, 9H), 0.08 (s, 6H).

Preparation of tert-butyl 2-(2-hydroxyethoxy)acetate (Step 2 in Scheme C-11)

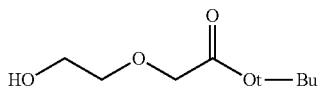

A mixture of tert-butyl 2-[2-[tert-butyl(dimethyl)silyl] oxyethoxy]acetate (40 g, 137.71 mmol, 1 eq) in tetrabutylammonium fluoride (1 M in THF, 206.56 mL, 1.5 eq) was stirred at 25° C. for 4 hours. TLC indicated the reaction was complete. The reaction mixture was quenched with H$_2$O (100 mL) at 0° C. and then extracted with EtOAc (200 mL×3). The combined organic layers were washed with brine (200 mL×3), dried over Na$_2$SO$_4$, filtered and concentrated under reduced pressure. The residue was purified by flash silica gel chromatography (Biotage®; 220 g Sepa-Flash® Silica Flash Column, Eluent of 060% Petroleum ether/Ethyl acetate at 100 mL/min). The eluent was removed under reduced pressure. Compound tert-butyl 2-(2-hydroxyethoxy)acetate (3.1 g, 17.59 mmol, 12.78% yield) was obtained as brown oil. $^1$H NMR (CDC$_3$, 400 MHz) δ 4.02 (s, 2H), 3.75~3.73 (m, 2H), 3.68~3.66 (m, 2H), 1.49 (s, 9H).

Preparation of tert-butyl 2-[2-(5-chloro-7-methoxypyrazolo[4,3-d]pyrimidin-1-yl) ethoxy]acetate (Step 3 in Scheme C-11)

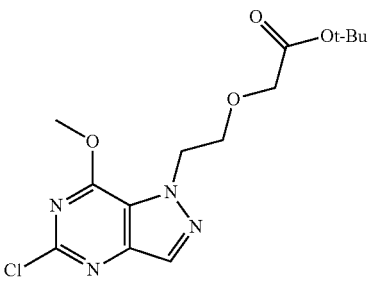 [SMILES: COc1nc(Cl)nc2cnn(CCOCC(=O)OC(C)(C)C)c12]

To a solution of 5-chloro-7-methoxy-1H-pyrazolo[4,3-d] pyrimidine (800 mg, 4.33 mmol, 1 eq), tert-butyl 2-(2-hydroxyethoxy)acetate (992.82 mg, 5.63 mmol, 1.3 eq) and PPh$_3$ (1.71 g, 6.50 mmol, 1.5 eq) in THF (10 mL) was added DIAD (1.31 g, 6.50 mmol, 1.26 mL, 1.5 eq) dropwise at 0° C. The mixture was stirred at 25° C. for 5 hours. TLC indicated the reaction was complete. The reaction mixture was quenched with H$_2$O (10 mL) and concentrated under reduced pressure. Then the aqueous was extracted with EtOAc (10 mL×3). The combined organic layers were washed with brine (10 mL), dried over Na₂SO₄, filtered and concentrated under reduced pressure. The residue was purified by flash silica gel chromatography (Biotage®; 12 g SepaFlash® Silica Flash Column, Eluent of 060% Petroleum ether/Ethyl acetate at 60 mL/min). The eluent was removed under reduced pressure. Compound tert-butyl 2-[2-(5-chloro-7-methoxy-pyrazolo[4,3-d]pyrimidin-1-yl)ethoxy]acetate (1.7 g, crude) was obtained as white solid. Compound tert-butyl 2-[2-(5-chloro-7-methoxy-pyrazolo[4,3-d]pyrimidin-2-yl)ethoxy]acetate (0.74 g crude) was obtained as white solid. ¹H NMR (CDCl₃, 400 MHz) δ 8.05 (s, 1H), 4.76 (t, J=5.6 Hz, 2H), 4.23 (s, 3H), 4.00 (t, J=5.6 Hz, 2H), 3.88 (s, 2H), 1.43 (s, 9H).

Preparation of 2-[2-(5-chloro-7-oxo-6H-pyrazolo[4,3-d]pyrimidin-1-yl)ethoxy]acetic acid (Step 4 in Scheme C-11)

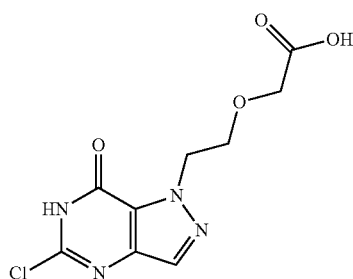 [SMILES: O=C(O)COCCn1ncc2nc(Cl)[nH]c(=O)c21]

To a solution of tert-butyl 2-[2-(5-chloro-7-methoxy-pyrazolo[4,3-d]pyrimidin-1-yl)ethoxy]acetate (1.7 g 4.96 mmol, 1 eq) in MeOH (10 mL) and H₂O (10 mL) was added LiOH—H₂O (624.30 mg, 14.88 mmol, 3 eq). The mixture was stirred at 25° C. for 2 hours. LC-MS showed the reaction was complete. The reaction mixture was concentrated under reduced pressure. The aqueous was made pH=6 with 3N HCl and there was some white solid formed. The solid was collected after filtered and concentrated under reduced pressure. Compound 2-[2-(5-chloro-7-oxo-6H-pyrazolo[4,3-d]pyrimidin-1-yl)ethoxy]acetic acid (750 mg, 2.75 mmol, 55.47% yield) was obtained as white solid. ¹H NMR (DMSO-d₆, 400 MHz) δ 7.59 (s, 1H), 4.65 (t, J=5.2 Hz, 2H), 3.73 (t, J=5.2 Hz, 2H), 3.61 (s, 2H).

Compound 283

Preparation of 2-[2-[5-[(3,4-dichlorophenyl)methylamino]-7-oxo-6H-pyrazolo[4,3-d]pyrimidin-1-yl]ethoxy]acetic Acid (Step 5 in Scheme C-11)

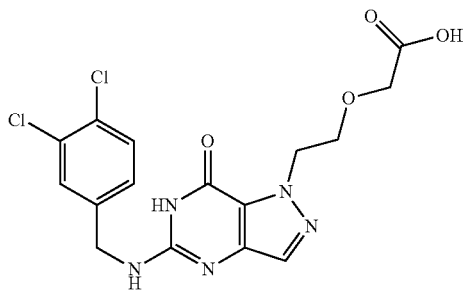 [SMILES: O=C(O)COCCn1ncc2nc(NCc3ccc(Cl)c(Cl)c3)[nH]c(=O)c21]

A mixture of 2-[2-(5-chloro-7-oxo-6H-pyrazolo[4,3-d]pyrimidin-1-yl)ethoxy]acetic acid (50 mg, 183.39 μmol, 1 eq) and (3,4-dichlorophenyl)methanamine (64.57 mg, 366.78 μmol, 48.92 μL, 2 eq) in 2-methyl-2-butanol (2 mL) was stirred at 130° C. for 10 hours. LC-MS showed the reaction was complete. The reaction mixture was concentrated under reduced pressure. The residue was purified by prep-HPLC (column: Welch Xtimate C18 100 mm×25 mm 3 m; mobile phase: [water (0.1% TFA)-MeCN]; B %: 15%-45%, 12 mins). The solvent was removed under freeze drying. Compound 2-[2-[5-[(3,4-dichlorophenyl)methylamino]-7-oxo-6H-pyrazolo[4,3-d]pyrimidin-1-yl]ethoxy]acetic acid (31.8 mg, 76.83 μmol, 41.89% yield, 99.59% purity) was obtained as white solid. H NMR (DMSO-d₆, 400 MHz) δ 7.60-7.58 (m, 3H), 7.33 (dd, J=8.4 Hz, 2.0 Hz, 1H), 6.80 (s, 1H), 4.59 (t, J=5.2 Hz, 2H), 4.48 (d, J=5.6 Hz, 2H), 3.96 (s, 2H), 3.86 (t, J=5.2 Hz, 2H). HPLC: 99.59% (220 nm), 99.30% (215 nm), 100.00% (254 nm). MS (ESI): mass calcd. For C₁₆H₁₅C₁₂N₅O₄ 411.05, m/z found 412.0 [M+H]⁺.

Compound 284

Preparation of 2-[2-[5-[(3,4-dichlorophenyl)methylamino]-7-oxo-6H-pyrazolo[4,3-d]pyrimidin-1-yl]ethoxy]acetamide (Step 6 in Scheme C-11)

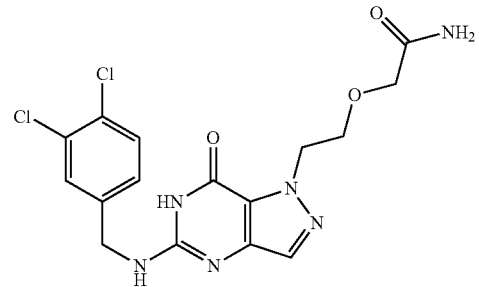 [SMILES: NC(=O)COCCn1ncc2nc(NCc3ccc(Cl)c(Cl)c3)[nH]c(=O)c21]

A mixture of 2-[2-[5-[(3,4-dichlorophenyl)methylamino]-7-oxo-6H-pyrazolo[4,3-d]pyrimidin-1-yl]ethoxy]acetic acid (50 mg, 121.29 mol, 1 eq), HATU (59.95 mg, 157.68 μmol, 1.3 eq), DIEA (47.03 mg, 363.88 μmol, 63.38 μL, 3 eq) and NH₄Cl (64.88 mg, 1.21 mmol, 10 eq) in DMF (1 mL) was stirred at 25° C. for 4 hours. LC-MS showed the reaction was complete. The reaction mixture was filtered to removed the insoluble. The filtrate was purified by prep-HPLC (column: Phenomenex Luna C18 150 mm×30 mm 5 μm; mobile phase: [water (0.1% TFA)-MeCN]; B %: 20%-40%, 12 mins). The solvent was removed under freeze drying. Compound 2-[2-[5-[(3,4-dichlorophenyl)methylamino]-7-oxo-6H-pyrazolo[4,3-d]pyrimidin-1-yl]ethoxy]acetamide (21.8 mg, 51.83 μmol, 42.73% yield, 97.77% purity) was obtained as white solid. ¹H NMR (DMSO-d₆, 400 MHz) δ 7.60-7.58 (m, 3H), 7.33 (dd, J=8.4 Hz, 1.6 Hz, 1H), 7.25 (s, 1H), 7.01 (s, 1H), 6.79 (s, 1H), 4.62 (t, J=5.2 Hz, 2H), 4.48 (d, J=5.6 Hz, 2H), 3.83 (t, J=5.2 Hz, 2H), 3.75 (s, 2H). HPLC: 97.77% (220 nm), 96.38% (215 nm), 97.03% (254 nm). MS (ESI): mass calcd. For C₁₆H₁₆C2N₆O₃ 410.07, m/z found 411.0 [M+H]⁺.

243

Compound 285

Preparation of 2-(2-(5-((3,4-dichlorobenzyl)amino)-7-oxo-6,7-dihydro-1H-pyrazolo[4,3-d]pyrimidin-1-yl)ethoxy)acetonitrile (Step 7 in Scheme C-11)

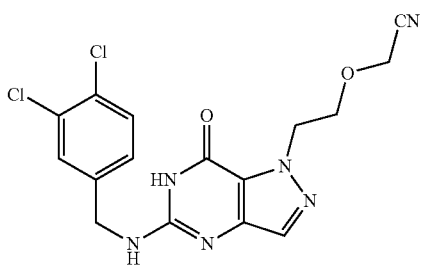 [SMILES: N#CCOCCn1ncc2nc(NCc3ccc(Cl)c(Cl)c3)[nH]c(=O)c21]

To a solution of 2-[2-[5-[(3,4-dichlorophenyl)methylamino]-7-oxo-6H-pyrazolo[4,3-d]pyrimidin-1-yl]ethoxy]acetamide (45 mg, 109.42 mol, 1 eq) and TEA (44.29 mg, 437.70 μmol, 60.92 μL, 4 eq) in DCM (1 mL) was added TEA (91.93 mg, 437.70 μmol, 60.88 μL, 4 eq) in DCM (1 mL) at 0° C. The mixture was stirred at 25° C. for 2 hours. LC-MS showed the reaction was complete. The reaction mixture was quenched with $H_2O$ (2 mL) at 0° C. and then extracted with DCM (2 mL×3). The combined organic layers were washed with brine (2 mL), dried over $Na_2SO_4$, filtered and concentrated under reduced pressure. The residue was purified by prep-HPLC (TFA condition column: Nano-micro Kromasil C18 100 mm×30 mm 8 μm; mobile phase: [water (0.1% TFA)-MeCN]; B %: 25%-50%, 10 mins). The solvent was removed under freeze drying. Compound 2-[2-[5-[(3,4-dichlorophenyl)methylamino]-7-oxo-6H-pyrazolo[4,3-d]pyrimidin-1-yl]ethoxy]acetonitrile (10.1 mg, 25.18 μmol, 23.01% yield, 98.02% purity) was obtained as white solid. H NMR (DMSO-$d_6$, 400 MHz) δ 7.60-7.58 (m, 3H), 7.33 (dd, J=8.4 Hz, 1.6 Hz, 1H), 6.75 (s, 1H), 4.63 (t, J=5.2 Hz, 2H), 4.48 (d, J=5.6 Hz, 2H), 4.43 (s, 2H), 3.91 (t, J=5.2 Hz, 2H). HPLC: 98.02% (220 nm), 96.58% (215 nm), 97.87% (254 nm). MS (ESI): mass calcd. For $C_{16}H_{14}C_{12}N_6O_2$ 392.06, m/z found 393.0 $[M+H]^+$.

Preparation of 1-(2-((2H-tetrazol-5-yl)methoxy)ethyl)-5-((3,4-dichlorobenzyl)amino)-1H-pyrazolo[4,3-d]pyrimidin-7(6H)-one hydrochloride (Step 8 in Scheme C-11)

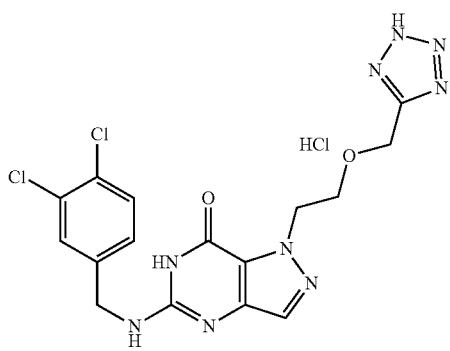 [SMILES: O=c1[nH]c(NCc2ccc(Cl)c(Cl)c2)nc2cnn(CCOCc3nn[nH]n3)c12 ; Cl]

244

To a solution of 2-[2-[5-[(3,4-dichlorophenyl)methylamino]-7-oxo-6H-pyrazolo[4,3-d]pyrimidin-1-yl]ethoxy]acetonitrile (30 mg, 76.29 μmol, 1 eq) in toluene (1 mL) was added TBAF (1 M, 91.55 μL, 1.2 eq) and $TMSN_3$ (17.58 mg, 152.58 μmol, 20.07 μL, 2 eq) dropwise. The mixture was stirred at 120° C. for 12 hours. HPLC showed the reaction was complete. The reaction mixture was quenched with $H_2O$ (1 mL) and then extracted with EtOAc (1 mL×3). The combined organic layers were washed with brine (1 mL), dried over $Na_2SO_4$, filtered and concentrated under reduced pressure. The residue was purified by prep-HPLC (column: Phenomenex Luna C18 150 mm×30 mm 5 μm; mobile phase: [water (0.05% HCl)-MeCN]; B %: 20%-50%, 12 mins). The solvent was removed under freeze drying. Compound 5-[(3,4-dichlorophenyl)methylamino]-1-[2-(2H-tetrazol-5-ylmethoxy)ethyl]-6H-pyrazolo[4,3-d]pyrimidin-7-one (19.1 mg, 39.36 μmol, 51.59% yield, 97.42% purity, HCl) was obtained as white solid. $^1H$ NMR (DMSO-$d_6$, 400 MHz) δ 7.62~7.59 (m, 3H), 7.35 (dd, J=8.0 Hz, 1.6 Hz, 1H), 7.30 (s, 1H), 4.80 (s, 2H), 4.64 (t, J=5.2 Hz, 2H), 4.53 (d, J=5.2 Hz, 2H), 3.92 (t, J=5.2 Hz, 2H). HPLC: 97.42% (220 nm), 95.83% (215 nm), 96.97% (254 nm). MS (ESI): mass calcd. For $C_{16}H_{16}C3N_9O_2$ 435.07, m/z found 436.0 $[M+H]^+$.

Compound 286

Preparation of 5-[(3,4-dichlorophenyl)methylamino]-1-[2-(2,2-dideuterio-2-hydroxyl-ethoxy)ethyl]-6H-pyrazolo[4,3-d]pyrimidin-7-one (Scheme C-11)

Compound 287

Preparation of methyl 2-(2-(5-((3,4-dichlorobenzyl)amino)-7-oxo-6,7-dihydro-1H-pyrazolo[4,3-d]pyrimidin-1-yl)ethoxy)acetate (Step 9 in Scheme C-11)

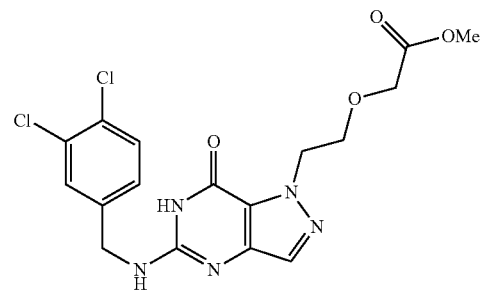 [SMILES: COC(=O)COCCn1ncc2nc(NCc3ccc(Cl)c(Cl)c3)[nH]c(=O)c21]

To a solution of 2-[2-[5-[(3,4-dichlorophenyl)methylamino]-7-oxo-6H-pyrazolo[4,3-d]pyrimidin-1-yl]ethoxy]acetic acid (40 mg, 97.03 μmol, 1 eq) in MeOH (1 mL) was added $SOCl_2$ (57.72 mg, 485.17 μmol, 35.20 μL, 5 eq) dropwise at 0° C. The mixture was stirred at 25° C. for an hour. LC-MS showed the reaction was complete. There was some solid formed. After filtered, the solid was washed with MeOH (2 mL×3) and collected. Compound methyl 2-[2-[5-[(3,4-dichlorophenyl)methylamino]-7-oxo-6H-pyrazolo[4,3-d]pyrimidin-1-yl]ethoxy]acetate (39.5 mg, 87.66 μmol, 90.34% yield, 94.6% purity) was obtained as white solid and 15.2 mg was delivered. $^1H$ NMR (DMSO-$d_6$, 400 MHz) δ 7.61~7.59 (m, 3H), 7.34 (dd, J=8.4 Hz, 2.0 Hz, 1H), 4.60 (t, J=5.6 Hz, 2H), 4.50 (d, J=5.6 Hz, 2H), 4.08 (s, 2H), 3.87 (t, J=5.26 Hz, 2H), 3.60 (s, 3H). HPLC: 94.60% (220 nm), 92.18% (215 nm), 95.05% (254 nm). MS (ESI): mass calcd. For $C_{17}H_7Cl_2N_5O_4$ 425.07, m/z found 426.1 $[M+H]^+$.

Preparation of 5-[(3,4-dichlorophenyl)methyl-amino]-1-[2-(2,2-dideuterio-2-hydroxyl-ethoxy)ethyl]-6H-pyrazolo[4,3-d]pyrimidin-7-one (Step 10 in Scheme C-11)

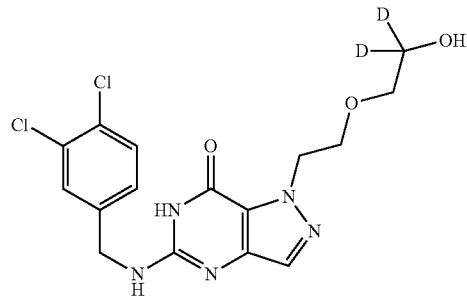 [SMILES: [2H]C([2H])(O)COCCn1ncc2nc(NCc3ccc(Cl)c(Cl)c3)[nH]c(=O)c21]

To a solution of methyl 2-[2-[5-[(3,4-dichlorophenyl)methylamino]-7-oxo-6H-pyrazolo[4,3-d]pyrimidin-1-yl]ethoxy]acetate (30 mg, 70.38 µmol, 1 eq) in THF (1 mL) was added LiAlD$_4$ (4.12 mg, 105.57 µmol, 1.5 eq) in portions at 0° C. The mixture was stirred at 0° C. for an hour. HPLC showed the reaction was complete. The reaction mixture was quenched with D$_2$O (1 mL) and then extracted with EtOAc (1 mL×3). The combined organic layers were washed with brine (1 mL), dried over Na$_2$SO$_4$, filtered and concentrated under reduced pressure. The residue was purified by prep-HPLC (column: Nano-micro Kromasil C18 100 mm×30 mm 8 µm; mobile phase: [water (0.1% TFA)-MeCN]; B %: 20%-40%, 10 mins). The solvent was removed under freeze drying. Compound 5-[(3,4-dichlorophenyl)methylamino]-1-[2-(2,2-dideuterio-2-hydroxyl-ethoxy)ethyl]-6H-pyrazolo[4,3-d]pyrimidin-7-one (10.8 mg, 25.42 µmol, 36.12% yield, 94.22% purity) was obtained as white solid. $^1$H NMR (DMSO-d$_6$, 400 MHz) δ 7.60-7.56 (m, 3H), 7.33 (dd, J=8.4 Hz, 2.0 Hz, 1H), 6.81 (s, 1H), 4.57 (t, J=5.6 Hz, 2H), 4.48 (d, J=5.6 Hz, 2H), 3.79 (t, J=5.6 Hz, 2H), 3.37 (s, 2H). HPLC: 94.22% (220 nm), 94.05% (215 nm), 94.77% (254 nm). MS (ESI): mass calcd. For $C_{16}H_{15}D_2Cl_2N_5O_3$ 399.08, m/z found 400.2 $[M+H]^+$.

Scheme C-12

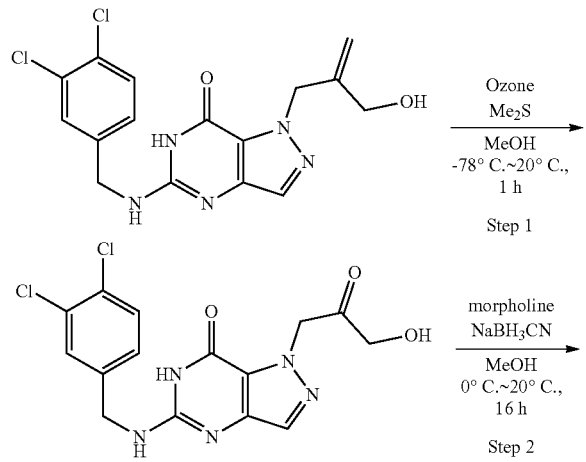

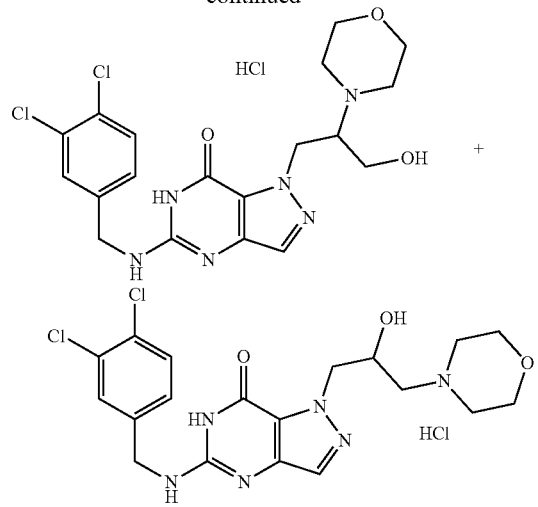

Compound 288 and Compound 289

Preparation of 5-((3,4-dichlorobenzyl)amino)-1-(3-hydroxy-2-morpholinopropyl)-1H-pyrazolo[4,3-d]pyrimidin-7(6H)-one hydrochloride and 5-((3,4-dichlorobenzyl)amino)-1-(2-hydroxy-3-morpholinopropyl)-1H-pyrazolo[4,3-d]pyrimidin-7(6H)-one hydrochloride Compound 290

Preparation of 5-((3,4-dichlorobenzyl)amino)-1-(3-hydroxy-2-oxopropyl)-1H-pyrazolo[4,3-d]pyrimidin-7(6H)-one (Step 1 in Scheme C-12)

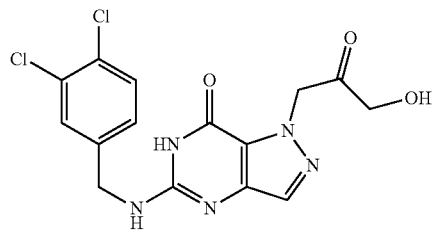 [SMILES: O=C(CO)Cn1ncc2nc(NCc3ccc(Cl)c(Cl)c3)[nH]c(=O)c21]

Ozone was bubbled into a solution of 5-[(3,4-dichlorophenyl)methylamino]-1-[2-(hydroxymethyl)allyl]-6H-pyrazolo[4,3-d]pyrimidin-7-one (80 mg, 210.40 µmol, 1 eq) in MeOH (5 mL) at −78° C. for 15 minutes. After excess O$_3$ was purged by O$_2$, Me$_2$S (26.14 mg, 420.80 µmol, 30.90 µL, 2 eq) was added at 20° C. The mixture was stirred at 20° C. for an hour. HPLC showed the reaction was complete. The reaction mixture was concentrated under reduced pressure. The residue was purified by prep-HPLC (column: Phenomenex Luna C18 150 mm×30 mm 5 µm; mobile phase: [water (0.05% HCl)-MeCN]; B %: 20%-40%, 12 mins). The aqueous solution was lyophilized to give compound 5-[(3,4-dichlorophenyl)methylamino]-1-(3-hydroxy-2-oxo-propyl)-6H-pyrazolo[4,3-d]pyrimidin-7-one (6.8 mg, 17.01 µmol, 8.08% yield, 95.598% purity) as off white solid. H NMR (DMSO-d$_6$, 400 MHz) δ 7.71~7.53 (m, 3H), 7.36 (d, J=7.6 Hz, 2H), 5.43 (s, 2H), 4.54 (s, 2H), 4.21 (s, 2H). HPLC:

95.60% (220 nm), 94.95% (215 nm), 97.53% (254 nm). MS (ESI): mass calcd. For $C_{15}H_{13}C_{12}N_5O_3$ 381.04, m/z found 382.1 $[M+H]^+$.

Preparation of 5-((3,4-dichlorobenzyl)amino)-1-(3-hydroxy-2-morpholinopropyl)-1H-pyrazolo[4,3-d]pyrimidin-7(6H)-one hydrochloride and 5-((3,4-dichlorobenzyl)amino)-1-(2-hydroxy-3-morpholinopropyl)-1H-pyrazolo[4,3-d]pyrimidin-7(6H)-one hydrochloride (Step 2 in Scheme C-12)

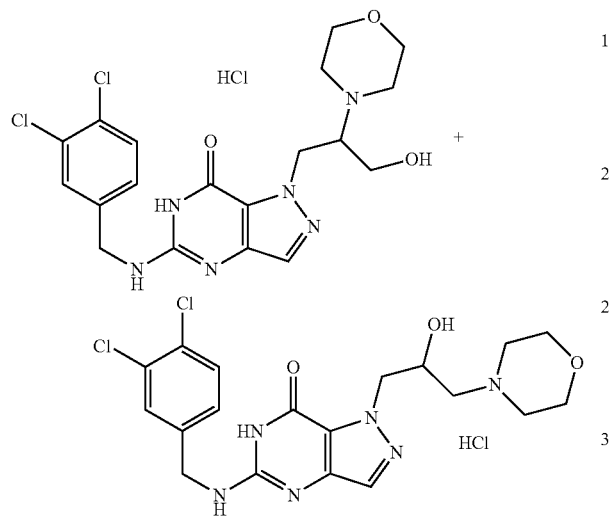

To a solution of 5-[(3,4-dichlorophenyl)methylamino]-1-(3-hydroxy-2-oxo-propyl)-6H-pyrazolo[4,3-d]pyrimidin-7-one (50 mg, 130.82 mol, 1 eq) in MeOH (20 mL) was added morpholine (56.99 mg, 654.11 µmol, 57.56 µL, 5 eq) and NaBH₃CN (24.66 mg, 392.46 µmol, 3 eq) at 0° C. The mixture was stirred at 20° C. for 16 hours. LC-MS showed the reaction was complete. The reaction mixture was quenched with H₂O (5 mL) at 0° C., and then concentrated under reduced pressure. The aqueous was extracted with EtOAc (10 mL×3). The combined organic layers were washed with brine (10 mL), dried over Na₂SO₄, filtered and concentrated under reduced pressure. The residue was purified by prep-HPLC (column: Phenomenex Luna C18 150 mm×30 mm 5 µm; mobile phase: [water (0.05% HCl)-MeCN]; B %: 15%-30%, 12 mins). The aqueous solution was lyophilized to give 5-[(3,4-dichlorophenyl)methylamino]-1-(3-hydroxy-2-morpholino-propyl)-6H-pyrazolo[4,3-d]pyrimidin-7-one (Compound 288) (9.5 mg, 19.02 µmol, 14.54% yield, 98.060% purity, HCl) as off white solid. ¹H NMR (DMSO-d₆, 400 MHz) δ 10.22 (s, 1H), 7.86~7.69 (m, 1H), 7.68-7.59 (m, 3H), 7.36 (d, J=7.2 Hz, 1H), 4.57 (d, J=5.2 Hz, 2H), 4.53~4.45 (m, 2H), 3.90 (t, J=11.6 Hz, 2H), 3.80~3.75 (m, 2H), 3.70 (d, J=12.0 Hz, 1H), 3.36 (d, J=12.0 Hz, 2H), 3.16~3.06 (m, 4H). HPLC: 98.06% (220 nm), 97.40% (215 nm), 98.35% (254 nm). MS (ESI): mass caled. For $C_{19}H_{23}C_{13}N_6O_3$ 452.11, m/z found 453.1 $[M+H]^+$.
5-[(3,4-dichlorophenyl)methylamino]-1-(2-hydroxy-3-morpholino-propyl)-6H-pyrazolo[4,3-d]pyrimidin-7-one (Compound 289) (13.1 mg, 25.28 µmol, 19.32% yield, 94.507% purity, HCl) as red brown solid. ¹H NMR (DMSO-d₆, 400 MHz) δ 10.77-10.38 (m, 1H), 7.72 (s, 1H), 7.64~7.56 (m, 3H), 7.35 (dd, J=1.6, 8.4 Hz, 1H), 4.99 (dd, J=5.2, 14.8 Hz, 1H), 4.82 (dd, J=6.8, 14.4 Hz, 1H), 4.55 (d, J=5.2 Hz, 2H), 3.95~3.79 (m, 6H), 3.34~3.06 (m, 5H). HPLC: 94.51% (220 nm), 93.99% (215 nm), 94.51% (254 nm). MS (ESI): mass caled. For $C_{19}H_{23}C3N_6O_3$ 452.11, m/z found 453.1 $[M+H]^+$.

Scheme C-13

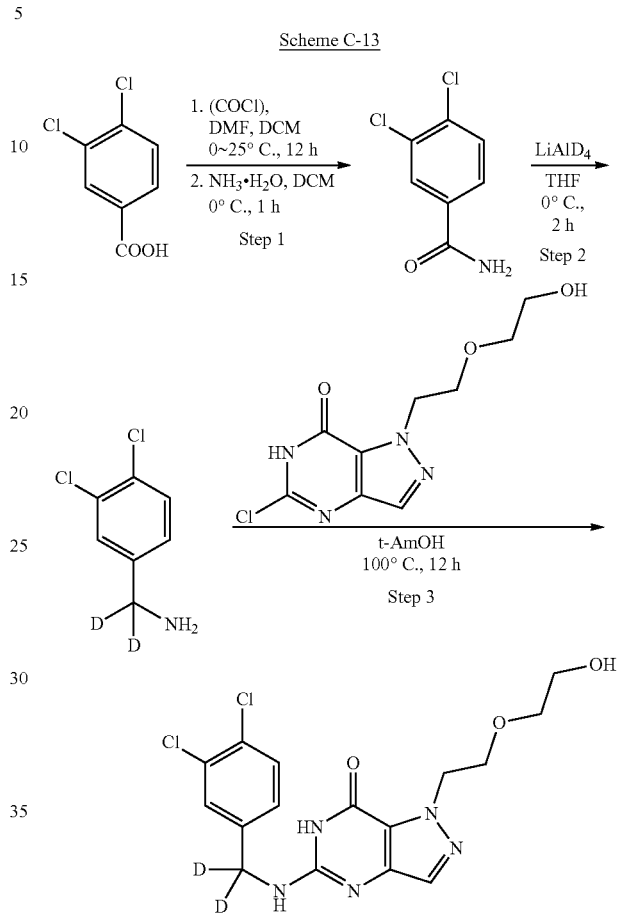

Compound 291

Preparation of 5-[[dideuterio-(3,4-dichlorophenyl)methyl]amino]-1-[2-(2-hydroxyethoxy)ethyl]-6H-pyrazolo[4,3-d]pyrimidin-7-one Preparation of 3,4-dichlorobenzamide (Step 1 in Scheme C-13)

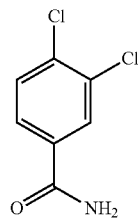

To a solution of 3,4-dichlorobenzoic acid (2 g 10.47 mmol, 1 eq) in oxalyl dichloride (6.65 g, 52.35 mmol, 4.58 mL, 5 eq) was added DMF (38.26 mg, 523.53 µmol, 40.28 µL, 0.05 eq) dropwise at 0° C. The mixture was stirred at 25° C. for 12 hours. The solvent was removed under reduced pressure. The residue was diluted with DCM (2 mL) and added to NH$_3$—H$_2$O (7.34 g, 52.35 mmol, 8.07 mL, 25% purity, 5 eq) dropwise at 0° C. Then the mixture was stirred at 0° C. for 1 hour. TLC showed the reaction was complete. There was some white solid formed. After filtered, the solid was washed with H$_2$O (10 mL×3) and collected. Compound 3,4-dichlorobenzamide (1.7 g, 8.95 mmol, 85.44% yield) was obtained as white solid. $^1$H NMR (DMSO-d$_6$, 400 MHz) δ 8.15 (s, 1H), 8.09 (d, J=2.4 Hz, 1H), 7.84 (dd, J=8.4 Hz, 2.0 Hz, 1H), 7.74 (d, J=8.4 Hz, 1H), 7.61 (s, 1H).

Preparation of dideuterio-(3,4-dichlorophenyl) methanamine) (Step 2 in Scheme C-13)

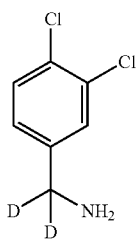

To a mixture of LiAlD$_4$ (205.23 mg, 5.26 mmol, 2 eq) in THF (5 mL) was added 3,4-dichlorobenzamide (500 mg, 2.63 mmol, 1 eq) in portions at 0° C. The mixture was stirred at 0° C. for 2 hours. TLC showed the reaction was complete. The reaction mixture was quenched with D$_2$O (2 mL) at 0° C. and diluted with H$_2$O (5 mL). The organic solvent was removed under reduced pressure. The aqueous was extracted with EtOAc (10 mL×3). The combined organic layers were washed with brine (10 mL), dried over Na$_2$SO$_4$, filtered and concentrated under reduced pressure. The residue was purified by flash silica gel chromatography (Biotage®; 12 g SepaFlash® Silica Flash Column, Eluent of 010% Ethyl acetate/MeOH at 60 mL/min). The eluent was removed under reduced pressure. Compound dideuterio-(3,4-dichlorophenyl) methanamine (280 mg, 1.57 mmol, 59.77% yield) was obtained as yellow oil. $^1$H NMR (CDC$_3$, 400 MHz) δ 7.44 (d, J=2.0 Hz, 1H), 7.40 (d, J=8.0 Hz, 1H), 7.16 (dd, J=8.0 Hz, 2.0 Hz, 1H).

Preparation of 5-[[dideuterio-(3,4-dichlorophenyl) methyl]amino]-1-[2-(2-hydroxyethoxy)ethyl]-6H-pyrazolo[4,3-d]pyrimidin-7-one (Step 3 in Scheme C-13)

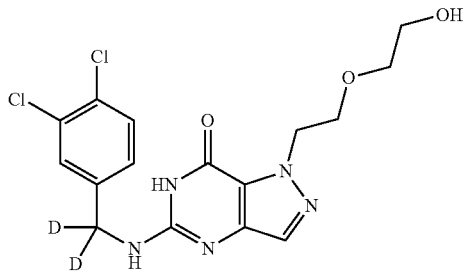 [SMILES: [2H]C([2H])(Nc1nc2cnn(CCOCCO)c2c(=O)[nH]1)c1ccc(Cl)c(Cl)c1]

A mixture of 5-chloro-1-[2-(2-hydroxyethoxy)ethyl]-6H-pyrazolo[4,3-d]pyrimidin-7-one (80 mg, 309.28 μmol, 1 eq) and dideuterio-(3,4-dichlorophenyl)methanamine (82.60 mg, 463.93 μmol, 1.5 eq) in 2-methyl-2-butanol (1 mL) was stirred at 100° C. for 12 hours. LC-MS showed the reaction was complete. The reaction mixture was concentrated under reduced pressure. The residue was purified by prep-HPLC (column: Nano-micro Kromasil C18 100 mm×30 mm 8 μm; mobile phase: [water (0.1% TFA)-ACN]; B %: 20%-40%, 10 mins). The solvent was removed under freeze drying. Compound 5-[[dideuterio-(3,4-dichlorophenyl)methyl]amino]-1-[2-(2-hydroxyethoxy)ethyl]-6H-pyrazolo[4,3-d]pyrimidin-7-one (10.8 mg, 25.54 μmol, 8.26% yield, 94.67% purity) was obtained as white solid. $^1$H NMR (DMSO-d$_6$, 400 MHz) δ 7.60-7.58 (m, 3H), 7.33 (dd, J=8.4 Hz, 2.0 Hz, 1H), 6.72 (s, 1H), 4.57 (t, J=5.6 Hz, 2H), 3.79 (t, J=5.6 Hz, 2H), 3.42~3.38 (m, 4H). HPLC: 94.67% (220 nm), 91.25% (215 nm), 97.10% (254 nm). MS (ESI): mass calcd. For C$_{16}$H$_{15}$D$_2$C$_2$N$_5$O$_3$ 399.08, m/z found 400.1 [M+H]$^+$.

Scheme C-14

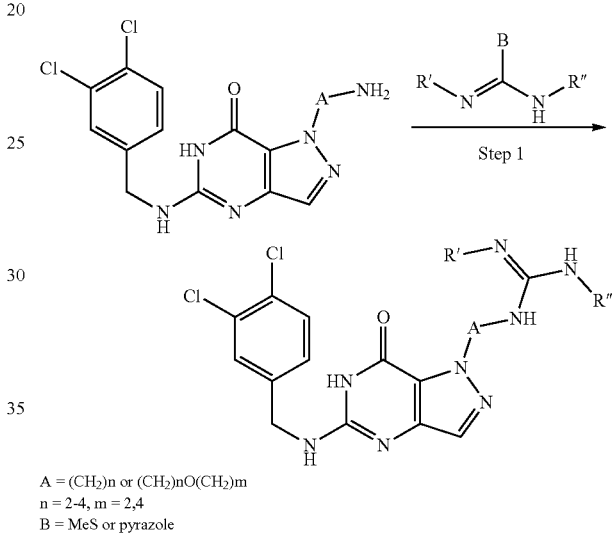

A = (CH$_2$)n or (CH$_2$)nO(CH$_2$)m
n = 2-4, m = 2,4
B = MeS or pyrazole

General Procedures for Preparing Compounds in Scheme C-14

Preparation of Compounds (Step 1 in Scheme C-14)

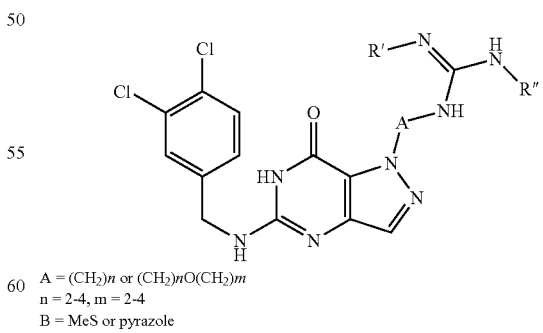

A = (CH$_2$)n or (CH$_2$)nO(CH$_2$)m
n = 2-4, m = 2-4
B = MeS or pyrazole

A mixture of 1-(2-amino-A)-5-[(3,4-dichlorophenyl) methylamino]-6H-pyrazolo[4,3-d]pyrimidin-7-one (169.87 μmol, HCl salt, 1 eq), pyrazole-1-carboxamidine or (Z)-methyl N—R$_1$—N'—R$_1$'carbamimidothioate (169.87 μmol 339.74 µmol, 1 eq 1.5 eq) and DIEA (339.75 µmol, 2 eq) in MeCN (3 mL/mmol) and DMF (3 mL/mmol) or pyridine (5 mL/mmol) was stirred at 20° C. 120° C. for a period of time (10 hours~16 hours). LC-MS showed the reaction was complete. The reaction mixture was concentrated under reduced pressure. The residue was purified by prep-HPLC. Column: Phenomenex Luna C18 150 mm×30 mm 5 µm. Mobile phase: [water (0.05% HCl)-MeCN]; B %: 5%-45%, 12 mins. The aqueous solution was lyophilized to give desired product.

Compound 292

Preparation of 1-(2-(5-((3,4-dichlorobenzyl)amino)-7-oxo-6,7-dihydro-1H-pyrazolo[4,3-d]pyrimidin-1-yl)ethyl)guanidine hydrochloride (Step 1 in Scheme C-14)

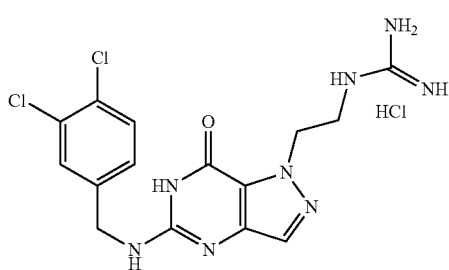 [SMILES: N=C(N)NCCn1ncc2nc(NCc3ccc(Cl)c(Cl)c3)[nH]c(=O)c21 ; Cl]

A mixture of 1-(2-aminoethyl)-5-[(3,4-dichlorophenyl)methylamino]-6H-pyrazolo[4,3-d]pyrimidin-7-one (60 mg, 169.87 µmol, HCl salt, 1 eq), pyrazole-1-carboxamidine (24.90 mg, 169.87 µmol, 1 eq, HCl) and DIEA (43.91 mg, 339.75 µmol, 59.18 µL, 2 eq) in MeCN (0.5 mL) and DMF (0.5 mL) was stirred at 20° C. for 16 hours. LC-MS showed the reaction was complete. The reaction mixture was concentrated under reduced pressure to remove MeCN. After filtered, the filtrate was purified by prep-HPLC (column: Phenomenex Luna C18 150 mm×30 mm 5 µm; mobile phase: [water (0.05% HCl)-MeCN]; B %: 20%-45%, 12 mins). The aqueous solution was lyophilized to give 1-[2-[5-[(3,4-dichlorophenyl)methylamino]-7-oxo-6H-pyrazolo[4,3-d]pyrimidin-1-yl]ethyl]guanidine (40.6 mg, 88.10 µmol, 51.86% yield, 93.679% purity, HCl) as light yellow solid. $^1$H NMR (DMSO-d$_6$, 400 MHz) δ 8.03 (d, J=6.8 Hz, 1H), 7.71~7.60 (m, 3H), 7.46 (t, J=6.0 Hz, 1H), 7.38 (dd, J=2.0 Hz, 8.4 Hz, 1H), 7.34~6.84 (m, 2H), 4.61 (d, J=4.8 Hz, 2H), 4.54 (t, J=5.2 Hz, 2H), 3.59 (q, J=6.0 Hz, 2H). HPLC: 93.68% (220 nm), 93.40% (215 nm), 96.08% (254 nm). MS (ESI): mass calcd. For $C_{15}H_{17}C_{13}N8O$ 394.08, m/z found 395.1 [M+H]$^+$.

Compound 293

1-(2-(2-(5-((3,4-Dichlorobenzyl)amino)-7-oxo-6,7-dihydro-1H-pyrazolo[4,3-d]pyrimidin-1-yl)ethoxy)ethyl) guanidine hydrochloride was prepared according to the procedure described herein for Step 1 in Scheme C-14.

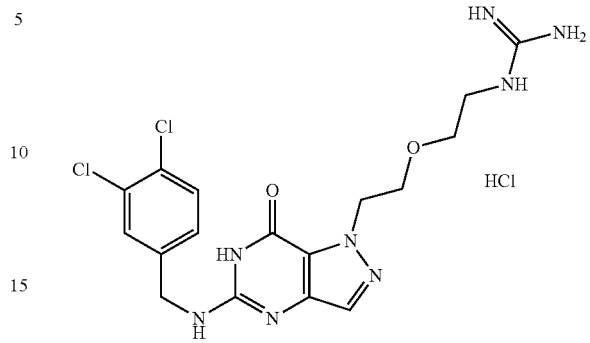

The procedure yielded the desired compound (36.2 mg, 81.96 µmol, 81.40% yield) as a white solid. $^1$H NMR (DMSO-d$_6$, 400 MHz) δ 7.67-7.58 (m, 3H), 7.49 (s, 1H), 7.37 (d, J=8.0 Hz, 1H), 7.11 (s, 3H), 4.67-.51 (m, 4H), 3.83 (t, J=4.8 Hz, 2H), 3.47 (t, J=4.8 Hz, 2H), 3.21 (d, J=4.8 Hz, 2H). HPLC: 99.46% (220 nm), 99.37% (215 nm), 99.54% (254 nm). MS (ESI): mass calcd. For $C_{17}H_{21}C_{13}N_8O_2$ 438.11, m/z found 439.1 [M+H]$^+$.

Compound 294

1-(2-(5-((3,4-Dichlorobenzyl)amino)-7-oxo-6,7-dihydro-1H-pyrazolo[4,3-d]pyrimidin-1-yl)ethyl)-3-methylguanidine hydrochloride was prepared according to the procedure described herein for Step 1 in Scheme C-14.

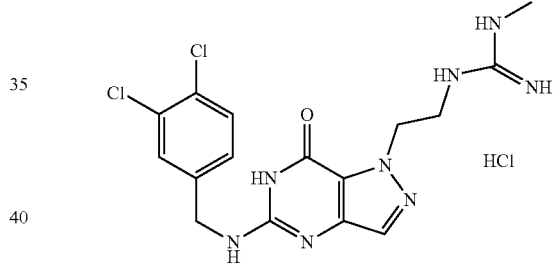

The procedure yielded the desired compound (30.2 mg, 67.75 µmol, 34.19% yield) as a white solid. $^1$H NMR (DMSO-d$_6$, 400 MHz) δ 8.25 (s, 1H), 7.77~7.52 (m, 4H), 7.42 (d, J=12.0 Hz, 4H), 4.68~4.50 (m, 4H), 3.60 (s, 2H), 2.67 (s, 3H). HPLC: 98.66% (220 nm), 98.75% (215 nm), 98.55% (254 nm). MS (ESI): mass calcd. For $C_{16}H_{19}C3N_8O$ 408.10, m/z found 409.1 [M+H]$^+$.

Compound 295

5-((3,4-Dichlorobenzyl)amino)-1-(2-((4,5-dihydro-1H-imidazol-2-yl)amino)ethyl)-1H-pyrazolo[4,3-d]pyrimidin-7 (6H)-one hydrochloride was prepared according to the procedure described herein for Step 1 in Scheme C-14.

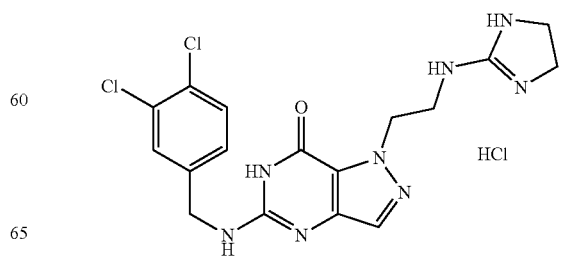

The procedure yielded the desired compound (30.2 mg, 65.65 μmol, 51.16% yield) as a white solid. $^1$H NMR (DMSO-$d_6$, 400 MHz) δ 8.54-8.43 (m, 1H), 8.16 (t, J=6.0 Hz, 1H), 7.89 (s, 1H), 7.67~7.60 (m, 3H), 7.37 (d, J=8.0 Hz, 1H), 4.58~4.56 (m, 4H), 3.85~3.55 (m, 6H). HPLC: 99.50% (220 nm), 99.55% (215 nm), 99.61% (254 nm). MS (ESI): mass calcd. For $C_{17}H_{19}Cl_3N_8O$ 420.10 m/z found 421.0 $[M+H]^+$.

Scheme C-15

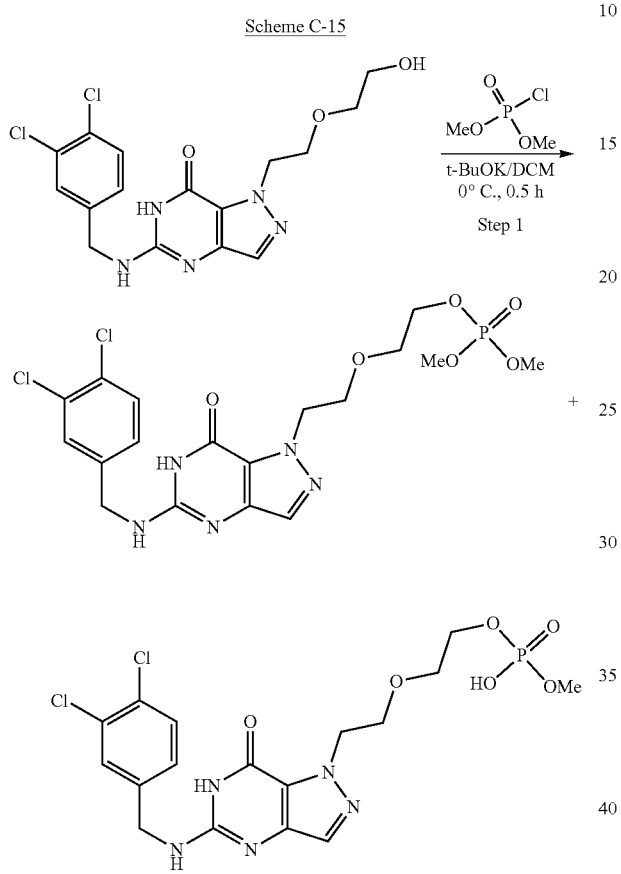

Compound 296

Preparation of 2-(2-(5-((3,4-dichlorobenzyl)amino)-7-oxo-6,7-dihydro-1H-pyrazolo[4,3-d]pyrimidin-1-yl)ethoxy)ethyl dihydrogen phosphate Compound 297 and Compound 298

Preparation of 2-(2-(5-((3,4-dichlorobenzyl)amino)-7-oxo-6,7-dihydro-1H-pyrazolo[4,3-d]pyrimidin-1-yl)ethoxy)ethyl dimethyl phosphate and 2-(2-(5-((3,4-dichlorobenzyl)amino)-7-oxo-6,7-dihydro-1H-pyrazolo[4,3-d]pyrimidin-1-yl)ethoxy)ethyl methyl hydrogen phosphate (Step 1 in Scheme C-15)

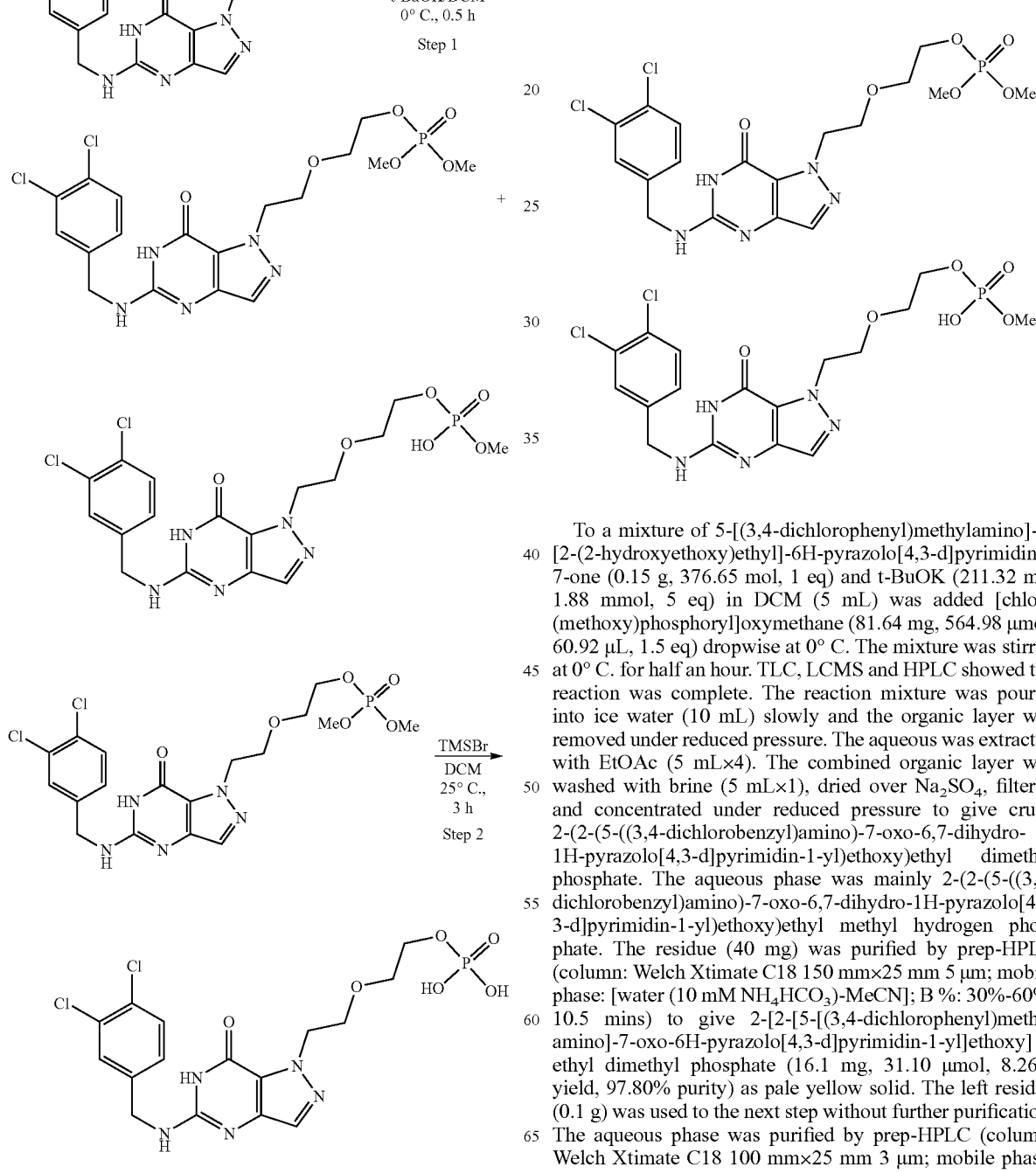

To a mixture of 5-[(3,4-dichlorophenyl)methylamino]-1-[2-(2-hydroxyethoxy)ethyl]-6H-pyrazolo[4,3-d]pyrimidin-7-one (0.15 g, 376.65 mol, 1 eq) and t-BuOK (211.32 mg, 1.88 mmol, 5 eq) in DCM (5 mL) was added [chloro(methoxy)phosphoryl]oxymethane (81.64 mg, 564.98 μmol, 60.92 μL, 1.5 eq) dropwise at 0° C. The mixture was stirred at 0° C. for half an hour. TLC, LCMS and HPLC showed the reaction was complete. The reaction mixture was poured into ice water (10 mL) slowly and the organic layer was removed under reduced pressure. The aqueous was extracted with EtOAc (5 mL×4). The combined organic layer was washed with brine (5 mL×1), dried over $Na_2SO_4$, filtered and concentrated under reduced pressure to give crude 2-(2-(5-((3,4-dichlorobenzyl)amino)-7-oxo-6,7-dihydro-1H-pyrazolo[4,3-d]pyrimidin-1-yl)ethoxy)ethyl dimethyl phosphate. The aqueous phase was mainly 2-(2-(5-((3,4-dichlorobenzyl)amino)-7-oxo-6,7-dihydro-1H-pyrazolo[4,3-d]pyrimidin-1-yl)ethoxy)ethyl methyl hydrogen phosphate. The residue (40 mg) was purified by prep-HPLC (column: Welch Xtimate C18 150 mm×25 mm 5 μm; mobile phase: [water (10 mM $NH_4HCO_3$)-MeCN]; B %: 30%-60%, 10.5 mins) to give 2-[2-[5-[(3,4-dichlorophenyl)methyl amino]-7-oxo-6H-pyrazolo[4,3-d]pyrimidin-1-yl]ethoxy] ethyl dimethyl phosphate (16.1 mg, 31.10 μmol, 8.26% yield, 97.80% purity) as pale yellow solid. The left residue (0.1 g) was used to the next step without further purification. The aqueous phase was purified by prep-HPLC (column: Welch Xtimate C18 100 mm×25 mm 3 μm; mobile phase: [water (0.1% TFA)-MeCN]; B %: 20%-40%, 12 mins) to give 2-[2-[5-[(3,4-dichlorophenyl)methylamino]-7-oxo-6H-pyrazolo[4,3-d]pyrimidin-1-yl]ethoxy]ethyl methyl hydrogen phosphate (Compound 297) (24.5 mg, 47.23 μmol, 12.54% yield, 94.89% purity) as white solid. $^1$H NMR (DMSO-$d_6$, 400 MHz) δ 11.09 (s, 1H), 7.59~7.57 (m, 3H), 7.32 (dd, J=8.0 Hz, 2.0 Hz, 1H), 6.58 (t, J=5.6 Hz, 1H), 4.57 (t, J=5.6 Hz, 2H), 4.46 (d, J=6.0 Hz, 2H), 3.97 (d, J=2.0 Hz, 2H), 3.83 (t, J=5.6 Hz, 2H), 3.60 (s, 3H), 3.56 (s, 3H), 3.35 (t, J=4.8 Hz, 2H). HPLC: 97.80% (220 nm), 97.61% (215 nm), 97.57% (254 nm). MS (ESI): mass calcd. For $C_{18}H_{22}C_2N_5O_6P$ 505.07 m/z found 506.0 [M+H]$^+$. 2-(2-(5-((3,4-Dichlorobenzyl)amino)-7-oxo-6,7-dihydro-1H-pyrazolo[4,3-d]pyrimidin-1-yl)ethoxy)ethyl methyl hydrogen phosphate (Compound 298) was also isolated: $^1$H NMR (DMSO-$d_6$, 400 MHz) δ 7.59-7.57 (m, 3H), 7.32 (dd, J=8.0 Hz, 2.0 Hz, 1H), 6.66 (t, J=5.6 Hz, 1H), 4.58 (t, J=5.6 Hz, 2H), 4.47 (d, J=6.0 Hz, 2H), 3.87 (d, J=2.0 Hz, 2H), 3.81 (t, J=5.6 Hz, 2H), 3.55~3.47 (m, 5H). HPLC: 94.86% (220 nm), 92.75% (215 nm), 96.17% (254 nm). MS (ESI): mass calcd. For $C_{17}H_{20}C2N_5O_6P$ 491.05 m/z found 492.0 [M+H]$^+$.

Preparation of 2-(2-(5-((3,4-dichlorobenzyl)amino)-7-oxo-6,7-dihydro-1H-pyrazolo[4,3-d]pyrimidin-1-yl)ethoxy)ethyl dihydrogen phosphate (Step 2 in Scheme C-15)

To a solution of 2-[2-[5-[(3,4-dichlorophenyl)methylamino]-7-oxo-6H-pyrazolo[4,3-d]pyrimidin-1-yl]ethoxy]ethyl dimethyl phosphate (0.1 g, 197.52 μmol, 1 eq) in DCM (5 mL) was added TMSBr (302.39 mg, 1.98 mmol, 256.26 μL, 10 eq) dropwise at 0° C. Then the mixture was stirred at 25° C. for 3 hours. LCMS and HPLC showed the reaction was complete. The mixture was poured into ice water (5 mL) and the organic layer was separated. The aqueous phase was extracted with DCM (5 mL×5). The combined organic layer was washed with sat. NaHCO$_3$ to pH=7, dried over Na$_2$SO$_4$, filtered and concentrated under reduced pressure. The residue was purified by prep-HPLC (column: Phenomenex Luna C18 150 mm×30 mm 5 μm; mobile phase: [water (0.05% HCl)-MeCN]; B %: 15%-35%, 12 mins). The eluent was removed under reduced pressure to give 2-[2-[5-[(3,4-dichlorophenyl)methylamino]-7-oxo-6H-pyrazolo[4,3-d]pyrimidin-1-yl]ethoxy]ethyl dihydrogen phosphate (14.2 mg, 27.67 μmol, 14.01% yield, 93.17% purity) as white solid. $^1$H NMR (DMSO-$d_6$, 400 MHz) δ 7.60-7.58 (m, 3H), 7.33 (dd, J=8.0 Hz, 2.0 Hz, 1H), 4.58 (t, J=5.2 Hz, 2H), 4.50 (d, J=5.6 Hz, 2H), 3.89~3.80 (m, 4H), 3.53 (t, J=4.8 Hz, 2H). HPLC: 93.17% (220 nm), 88.83% (215 nm), 87.24% (254 nm). MS (ESI): mass calcd. For $C_{16}H_{18}C_{12}N_5O_6P$ 477.04 m/z found 478.0 [M+H]$^+$.

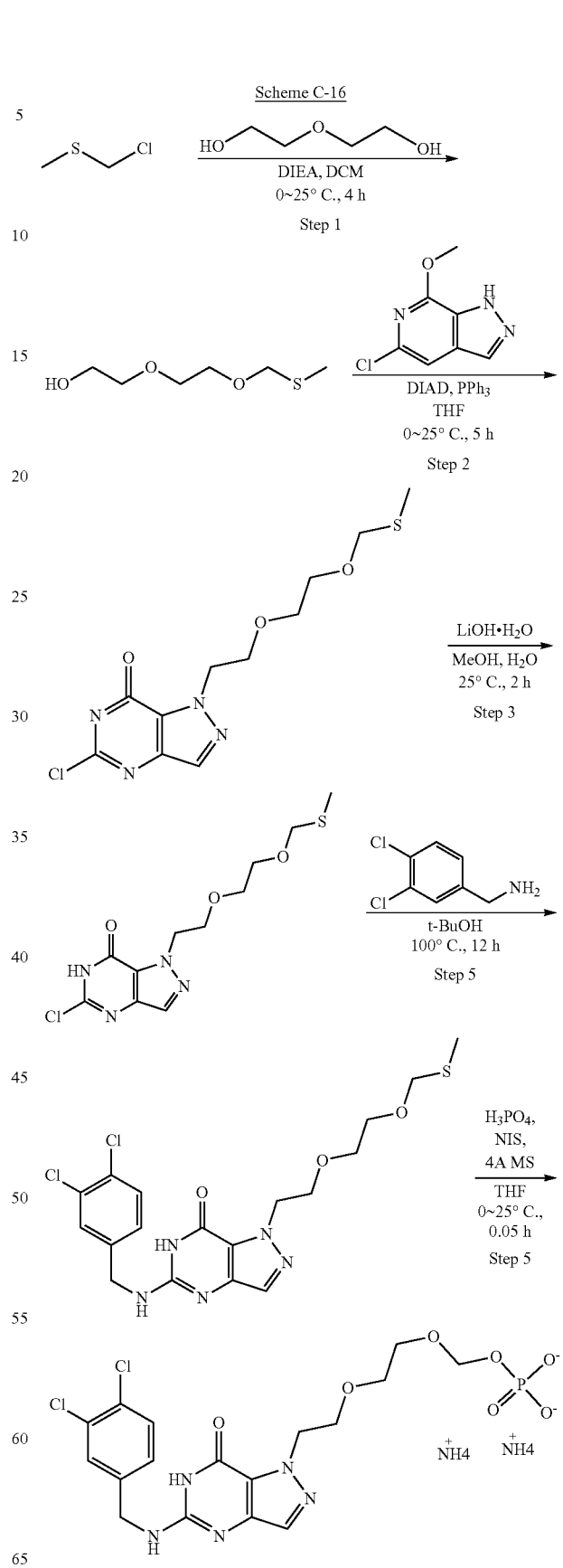

Scheme C-16

Compound 299

Preparation of ammonium (2-(2-(5-((3,4-dichlorobenzyl)amino)-7-oxo-6,7-dihydro-1H-pyrazolo[4,3-d]pyrimidin-1-yl)ethoxy)ethoxy)methyl Phosphate Preparation of 2-[2-(methylsulfanylmethoxy)ethoxy]ethanol (Step 1 in Scheme C-16)

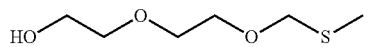

To a solution of 2-(2-hydroxyethoxy)ethanol (3.30 g, 31.06 mmol, 2.94 mL, 3 eq) and DIEA (4.01 g, 31.06 mmol, 5.41 mL, 3 eq) in DCM (20 mL) was added chloro(methylsulfanyl) methane (1 g, 10.35 mmol, 869.57 μL, 1 eq) dropwise at 0° C. The mixture was stirred at 25° C. for 4 hours. TLC indicated the reaction was complete. The reaction mixture was quenched with $H_2O$ (20 mL) and then extracted with DCM and i-PrOH (3:1, 20 mL×2). The combined organic layers were washed with brine (20 mL), dried over $Na_2SO_4$, filtered and concentrated under reduced pressure. The residue was purified by flash silica gel chromatography (Biotage®; 40 g SepaFlash® Silica Flash Column, Eluent of 0-100% Petroleum ether/Ethyl acetate at 100 mL/min). The eluent was removed under reduced pressure. Compound 2-[2-(methylsulfanyl methoxy)ethoxy]ethanol (1.25 g, 7.52 mmol, 72.62% yield) was obtained as colorless oil. $^1$H NMR ($CDC_3$, 400 MHz) δ 4.69 (s, 2H), 3.75~3.70 (m, 6H), 3.62~3.60 (m, 2H), 2.15 (s, 3H).

Preparation of 5-chloro-7-methoxy-1-[2-[2-(methylsulfanylmethoxy)ethoxy]ethyl]pyrazolo[4,3-d]pyrimidine (Step 2 in Scheme C-16)

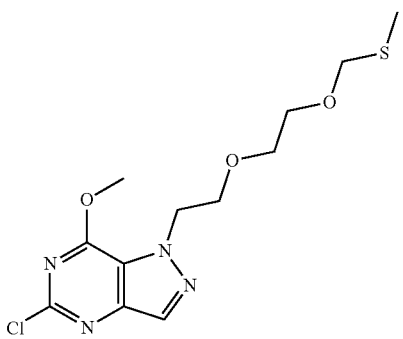 [SMILES: COc1nc(Cl)nc2cnn(CCOCCOCSC)c12]

To a solution of 5-chloro-7-methoxy-1H-pyrazolo[4,3-d]pyrimidine (300 mg, 1.63 mmol, 1 eq), 2-[2-(methylsulfanylmethoxy)ethoxy]ethanol (324.22 mg, 1.95 mmol, 1.2 eq) and $PPh_3$ (639.44 mg, 2.44 mmol, 1.5 eq) in THF (5 mL) was added DIAD (492.97 mg, 2.44 mmol, 474.01 μL, 1.5 eq) dropwise at 0° C. The mixture was stirred at 25° C. for 5 hours. TLC indicated the reaction was complete. The reaction mixture was quenched with $H_2O$ (5 mL) and concentrated under reduced pressure. The aqueous was extracted with EtOAc (5 mL×3). The combined organic layers were washed with brine (5 mL), dried over $Na_2SO_4$, filtered and concentrated under reduced pressure. The residue was purified by flash silica gel chromatography (Biotage®; 12 g SepaFlash® Silica Flash Column, Eluent of 0-100% Petroleum ether/Ethyl acetate at 60 mL/min). The eluent was removed under reduced pressure. Compound 5-chloro-7-methoxy-1-[2-[2-(methylsulfanylmethoxy)ethoxy]ethyl]pyrazolo[4,3-d]pyrimidine (790 mg, crude) was obtained as white solid. $^1$H NMR ($CDCl_3$, 400 MHz) δ 8.05 (s, 1H), 4.74 (t, J=5.6 Hz, 2H), 4.57 (s, 2H), 4.23 (s, 3H), 3.93 (t, J=5.6 Hz, 2H), 3.57 (s, 4H), 2.08 (s, 3H).

Preparation of 5-chloro-1-[2-[2-(methylsulfanylmethoxy)ethoxy]ethyl]-6H-pyrazolo[4,3-d]pyrimidin-7-one (Step 3 in Scheme C-16)

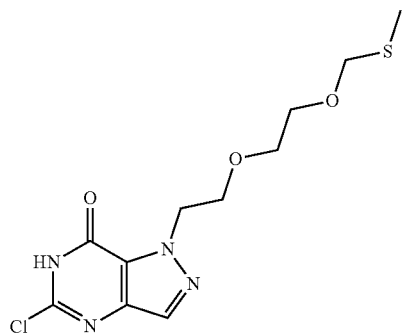 [SMILES: CSCOCCOCCn1ncc2nc(Cl)[nH]c(=O)c21]

To a solution of 5-chloro-7-methoxy-1-[2-[2-(methylsulfanylmethoxy)ethoxy]ethyl]pyrazolo[4,3-d]pyrimidine (300 mg, 901.43 μmol, 1 eq) in MeOH (1 mL) and $H_2O$ (1 mL) was added LiOH·$H_2O$ (113.47 mg, 2.70 mmol, 3 eq). The mixture was stirred at 25° C. for 2 hours. TLC indicated the reaction was complete. The reaction mixture was concentrated under reduced pressure. The aqueous was made pH=6 with 3N HCl and extracted with EtOAc (3 mL×3). The combined organic layers were washed with brine (3 mL), dried over $Na_2SO_4$, filtered and concentrated under reduced pressure. Compound 5-chloro-1-[2-[2-(methylsulfanylmethoxy) ethoxy]ethyl]-6H-pyrazolo[4,3-d]pyrimidin-7-one (215 mg, 674.45 μmol, 74.82% yield) was obtained as white solid. $^1$H NMR ($CDC_3$, 400 MHz) δ 7.88 (s, 1H), 6.44 (s, 1H), 4.81 (t, J=5.6 Hz, 2H), 4.59 (s, 2H), 3.97 (t, J=5.6 Hz, 2H), 3.62 (s, 4H), 2.09 (s, 3H).

Compound 300

Preparation of 5-[(3,4-dichlorophenyl)methylamino]-1-[2-[2-(methylsulfanylmethoxy)ethoxy]ethyl]-6H-pyrazolo[4,3-d]pyrimidin-7-one (Step 4 in Scheme C-16)

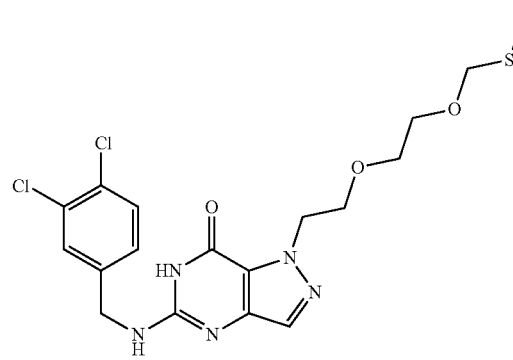

A mixture of 5-chloro-1-[2-[2-(methylsulfanylmethoxy)ethoxy]ethyl]-6H-pyrazolo[4,3-d]pyrimidin-7-one (30 mg, 94.11 μmol, 1 eq) and (3,4-dichlorophenyl)methanamine (33.13 mg, 188.22 μmol, 25.10 μL, 2 eq) in t-BuOH (2 mL) was stirred at 100° C. for 12 hours. TLC indicated the reaction was complete. The reaction mixture was concentrated under reduced pressure. The residue was purified by prep-HPLC (column: Welch Xtimate C18 100 mm×25 mm 3 μm; mobile phase: [water (10 mM NH$_4$HCO$_3$)-MeCN]; B %: 35%-65%, 10.5 mins). The solvent was removed under freeze drying. Compound 5-[(3,4-dichlorophenyl)methylamino]-1-[2-[2-(methylsulfanylmethoxy)ethoxy]ethyl]-6H-pyrazolo[4,3-d]pyrimidin-7-one (13.8 mg, 30.11 μmol, 31.99% yield, 100% purity) was obtained as white solid. $^1$H NMR (DMSO-d$_6$, 400 MHz) δ 11.06 (s, 1H), 7.59~7.56 (m, 3H), 7.32 (dd, J=8.4 Hz, 1.6 Hz, 1H), 6.55 (t, J=6.0 Hz, 1H), 4.58~4.56 (m, 4H), 4.47 (d, J=5.6 Hz, 2H), 3.79 (t, J=5.6 Hz, 2H), 3.49 (s, 4H), 2.00 (s, 3H). HPLC: 100.00% (220 nm), 99.80% (215 nm), 99.12% (254 nm). MS (ESI): mass calcd. For C$_{18}$H$_{21}$C$_{12}$N$_5$O$_3$S 457.07, m/z found 458.0 [M+H]$^+$.

Preparation of ammonium (2-(2-(5-((3,4-dichlorobenzyl)amino)-7-oxo-6,7-dihydro-1H-pyrazolo[4,3-d]pyrimidin-1-yl)ethoxy)ethoxy)methyl phosphate (Step 5 in Scheme C-16)

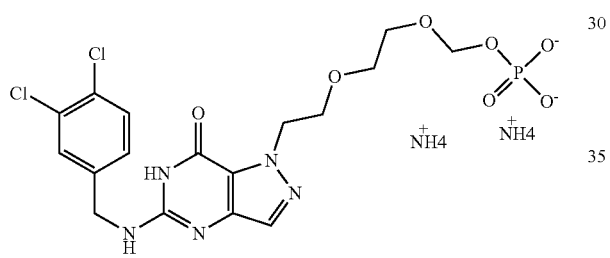

To a mixture of 5-[(3,4-dichlorophenyl)methylamino]-1-[2-[2-(methylsulfanylmethoxy)ethoxy]ethyl]-6H-pyrazolo[4,3-d]pyrimidin-7-one (0.1 g, 218.17 μmol, 1 eq), H$_3$PO$_4$ (213.79 mg, 2.18 mmol, 127.26 μL 10 eq) and 4A MS (0.2 g, 2.18 mmol) in THF (2 mL) was added NIS (73.63 mg, 327.25 μmol, 1.5 eq) in portions at 0° C. under N$_2$. Then the mixture was stirred at 25° C. for 15 minutes. TLC showed the reaction was complete. The mixture was quenched with sat. NaHCO$_3$ (3 mL) and made to pH=7 with sat. Na$_2$CO$_3$ slowly at 0° C. The aqueous phase was separated and purified directly by prep-HPLC (column: Welch Xtimate C18 100 mm×25 mm 3 μm; mobile phase: [water (10 mM NH$_4$HCO$_3$)-MeCN]; B %: 12%-42%, 10.5 mins). The solvent was removed under freeze drying. The obtained (80 mg) was further purified by prep-HPLC (column: Welch Xtimate C18 100 mm×25 mm 3 μm; mobile phase: [water (10 mM NH$_4$HCO$_3$)-MeCN]; B %: 12%-42%, 10.5 mins) for the second time. The solvent was removed under freeze drying. Compound [azaniumyloxy-[2-[2-[5-[(3,4-dichlorophenyl)methylamino]-7-oxo-6H-pyrazolo[4,3-d]pyrimidin-1-yl]ethoxy]ethoxymethoxy]phosphoryl]oxyammonium (30 mg 54.54 μmol, 25.00% yield, 98.23% purity) was obtained as white solid. $^1$H NMR (DMSO-d$_6$, 400 MHz) δ 7.58 (d, J=2.4 Hz, 1H), 7.57 (d, J=8.4 Hz, 1H), 7.53 (s, 1H), 7.35 (dd, J=8.0 Hz, 2.0 Hz, 2H), 4.77 (d, J=8.4 Hz, 2H), 4.57 (t, J=4.8 Hz, 2H), 4.45 (d, J=5.6 Hz, 2H), 3.71 (t, J=5.6 Hz, 2H), 3.52~3.50 (m, 2H), 3.46~3.44 (m, 2H). HPLC: 98.23% (220 nm), 97.71% (215 nm), 99.09% (254 nm). MS (ESI): mass calcd. For C$_{17}$H$_{26}$C$_{12}$N$_7$O$_7$P 507.05, m/z found 508.1 [M+H]$^+$.

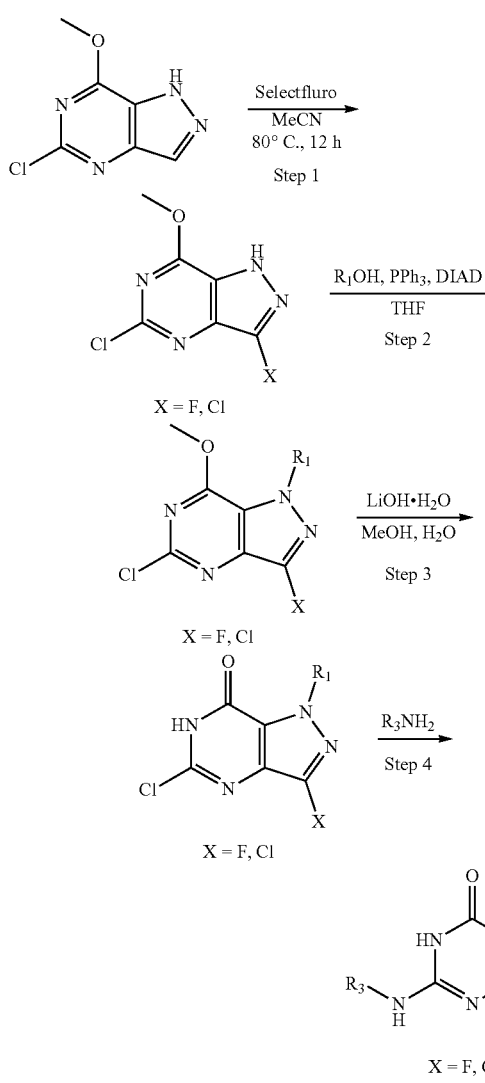

General Procedures for Preparing Compounds in Scheme D

Preparation of Compounds (Step 1 in Scheme D)

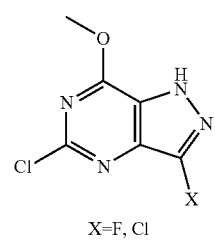

A mixture of 5-chloro-7-methoxy-H-pyrazolo[4,3-d]pyrimidine (2.71 mmol, 1 eq) and Select F (4.06 mmol, 1.5 eq) in MeCN (2.5 mL/mmol) was stirred at 80° C. for 12 hours. TLC showed the reaction was complete. The reaction mixture was quenched with H$_2$O and extracted with EtOAc. The combined organic layer was dried over Na$_2$SO$_4$, filtered and concentrated under reduced pressure. The residue was purified by flash silica gel chromatography (Biotage®; 10 g SepaFlash® Silica Flash Column, Eluent of 050% Ethylacetate/Petroleum ether gradient at 65 mL/min) to give a mixture of 5-chloro-3-fluoro-7-methoxy-1H-pyrazolo[4,3-d]pyrimidine and 3,5-dichloro-7-methoxy-1H-pyrazolo[4,3-d]pyrimidine.

Preparation of Compounds (Step 2 in Scheme D)

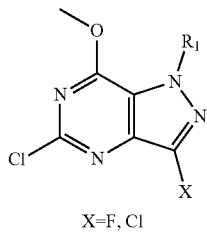

X=F, Cl

To a mixture of 5-chloro-3-X-7-methoxy-H-pyrazolo[4,3-d]pyrimidine (1.48 mmol, 1 eq), R$_1$OH (1.48 mmol 4.44 mmol, 1 eq 3 eq) and PPh$_3$ (1.63 mmol 2.96 mmol, 1.1 eq 2 eq) in THF (5 mL/mmol) was added DIAD (1.63 mmol 2.96 mmol, 1.1 eq 2 eq) dropwise at 0° C. Then the mixture was stirred at 0° C. 25° C. for a period of time (2 hours 16 hours). TLC showed the reaction was complete. The mixture was quenched with ice water and the organic layer was separated. The aqueous was extracted with EtOAc. The combined organic layer was washed with brine, dried over Na$_2$SO$_4$, filtered and concentrated under reduced pressure. The residue was purified by prep-HPLC. Column: a) Phenomenex Luna C18 150 mm×30 mm 5 μm; b) Phenomenex luna C18 250 mm×50 mm 10 μm; c) Nano-micro Kromasil C18 100 mm×30 mm 5 μm; d) Welch Xtimate C18 100 mm×25 mm 3 μm; e) Xbridge 150 mm×30 mm 10 μm. Mobile phase: a) [water (0.1% TFA)-MeCN], B %: 15%-45%, 10 mins or 12 mins; b) [water (10 mM NH$_4$HCO$_3$)-MeCN]; B %: 1%-25%, 10 mins. The eluent was dried over lyophilization to give desired product.

Preparation of Compounds (Step 3 in Scheme D)

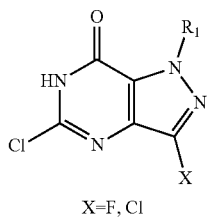

X=F, Cl

To a solution of 5-chloro-3-X-7-methoxy-1-R—H-pyrazolo[4,3-d]pyrimidine (137.61 μmol, 1 eq) in MeOH (3 mL/mmol 5 mL/mmol) or THF (3 mL/mmol 5 mL/mmol) and H$_2$O (3 mL/mmol 5 mL/mmol) was added LiOHH$_2$O (412.83 μmol-688.05 μmol, 3 eq 5 eq). The mixture was stirred at 20° C. 25° C. for a period of time (2 hours 16 hours). TLC showed the reaction was complete. The reaction mixture was concentrated under reduced pressure. The aqueous was made pH=6 with 3N HCl and then extracted with EtOAc. The combined organic layers were washed with brine, dried over Na$_2$SO$_4$, filtered and concentrated under reduced pressure to give desired product.

Preparation of Compounds (Step 4 in Scheme D)

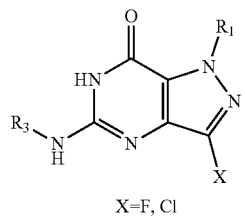

X=F, Cl

A mixture of 5-chloro-3-X-1-R-1H-pyrazolo[4,3-d]pyrimidin-7(6H)-one (108.44 μmol, 1 eq), R$_3$NH$_2$ (162.66 μmol 216.88 μmol, 1.5 eq 2 eq) and DIEA (433.76 μmol, 4 eq, DIEA was added only when R$_3$NH$_2$ was HCl salt) in t-BuOH or t-AmOH or NMP (3 mL/mmol 10 mL/mmol) was stirred at 100° C. 160° C. for a period of time (2 hours 16 hours). LC-MS showed the reaction was complete. The reaction mixture was concentrated under reduced pressure. The residue was purified by prep-HPLC. Column: a) Xtimate C18 100 mm×30 mm 3 μm; b) Nano-micro Kromasil C18 100 mm×30 mm 5 μm; c) Waters Xbridge BEH C18 100 mm×25 mm 5 μm; d) Welch Xtimate C18 150 mm×25 mm 5 μm; e) Phenomenex Gemini-NX 150 30 mm 5 μm; f) Kromasil C18 250 mm×50 mm 10 μm). Mobile phase: a) [water (0.1% TFA)-MeCN], B %: 25%-55%, 7 mins, 10 mins; b) [water (0.05% HCl)-MeCN], B %: 20%-45%, 10 mins; c) [water (10 mM NH$_4$HCO$_3$)-MeCN], B %: 20%-50%, 10 mins; d) [water (10 mM NH$_4$HCO$_3$)-MeCN], B %: 15%-70%, 8 mins or 10 mins or 10.5 mins. The solvent was removed under freeze drying to give desired product.

Compound 301

Preparation of 5-((3,4-difluorobenzyl)amino)-3-fluoro-1-(2-(2-hydroxyethoxy)ethyl)-1H-pyrazolo[4,3-d]pyrimidin-7(6H)-one Preparation of 5-chloro-3-fluoro-7-methoxy-1H-pyrazolo[4,3-d]pyrimidine and 3,5-dichloro-7-methoxy-1H-pyrazolo[4,3-d]pyrimidine (Step 1 in Scheme D)

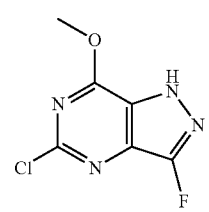

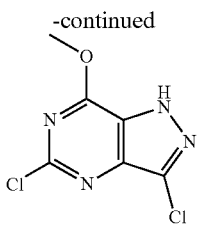

A mixture of 5-chloro-7-methoxy-1H-pyrazolo[4,3-d]pyrimidine (3 g, 16.25 mmol, 1 eq) and Select F (8.64 g, 24.38 mmol, 1.5 eq) in MeCN (40 mL) was stirred at 90° C. for 12 hours. TLC showed the reaction was complete. The reaction mixture was quenched with $H_2O$ (20 mL) and concentrated under reduced pressure. The aqueous was extracted with EtOAc (30 mL×3). The combined organic layers were washed with brine (50 mL), dried over $Na_2SO_4$, filtered and concentrated under reduced pressure. The residue was purified by flash silica gel chromatography (Biotage®; 40 g SepaFlash® Silica Flash Column, Eluent of 050% Ethylacetate/Petroleum ether gradient at 100 mL/min). The eluent was removed under reduced pressure. A mixture of compound 5-chloro-3-fluoro-7-methoxy-1H-pyrazolo[4,3-d]pyrimidine (1.54 g, 7.60 mmol, 46.77% yield) and 3,5-dichloro-7-methoxy-1H-pyrazolo[4,3-d]pyrimidine was obtained as white solid. $^1$H NMR (DMSO-$d_6$, 400 MHz) δ 14.62 (s, 1H), 13.99 (s, 1H), 4.16 (s, 6H).

Preparation of 2-(2-(5-chloro-3-fluoro-7-methoxy-1H-pyrazolo[4,3-d]pyrimidin-1-yl)ethoxy)ethanol (Step 2 in Scheme D)

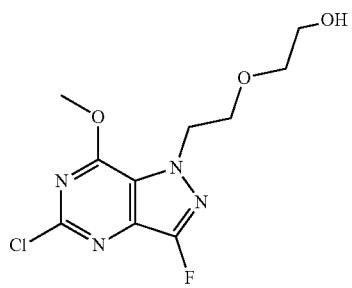 [SMILES: COc1nc(Cl)nc2c(F)nn(CCOCCO)c12]

To a mixture of 5-chloro-3-fluoro-7-methoxy-1H-pyrazolo[4,3-d]pyrimidine (300 mg, 1.48 mmol, 1 eq) and 3,5-dichloro-7-methoxy-1H-pyrazolo[4,3-d]pyrimidine (1.48 mmol, 1 eq), 2-(2-hydroxyethoxy)ethanol (314.32 mg, 2.96 mmol, 280.64 µL, 2 eq) and PPh$_3$ (582.66 mg, 2.22 mmol, 1.5 eq) in THF (4 mL) was added DIAD (449.19 mg, 2.22 mmol, 431.92 µL, 1.5 eq) dropwise at 0° C. under N$_2$. The mixture was stirred at 25° C. for 5 hours. TLC showed the reaction was complete. The reaction mixture was quenched with H$_2$O (3 mL) and extracted with EtOAc (5 mL×3). The combined organic layers were washed with brine (5 mL), dried over Na$_2$SO$_4$, filtered and concentrated under reduced pressure. The residue was purified by prep-HPLC (column: Nano-micro Kromasil C18 100 mm×30 mm 8 µm; mobile phase: [water (0.1% TFA)-MeCN]; B %: 25%-40%, 10 mins). The solvent was removed under freeze drying. Compound 2-[2-(5-chloro-3-fluoro-7-methoxy-pyrazolo[4,3-d]pyrimidin-1-yl)ethoxy]ethanol (40 mg, 137.61 µmol, 9.29% yield) was obtained as white solid. $^1$H NMR (DMSO-$d_6$, 400 MHz) δ 4.54 (t, J=5.2 Hz, 2H), 4.17 (s, 3H), 3.79 (t, J=5.2 Hz, 2H), 3.36 (s, 4H). Compound 2-[2-(3,5-dichloro-7-methoxy-pyrazolo[4,3-d]pyrimidin-1-yl)ethoxy]ethanol (70 mg, 227.91 µmol, 15.39% yield) was obtained as white solid. $^1$H NMR (DMSO-$d_6$, 400 MHz) δ 4.63 (t, J=5.6 Hz, 2H), 4.17 (s, 3H), 3.83 (t, J=5.6 Hz, 2H), 3.37 (s, 4H).

Preparation of 5-chloro-3-fluoro-1-(2-(2-hydroxyethoxy)ethyl)-1H-pyrazolo[4,3-d]pyrimidin-7(6H)-one (Step 3 in Scheme D)

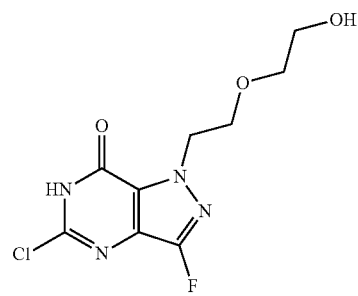 [SMILES: O=c1[nH]c(Cl)nc2c(F)nn(CCOCCO)c12]

To a solution of 2-[2-(5-chloro-3-fluoro-7-methoxy-pyrazolo[4,3-d]pyrimidin-1-yl)ethoxy]ethanol (40 mg, 137.61 µmol, 1 eq) in MeOH (1 mL) and H$_2$O (1 mL) was added LiOH—H$_2$O (17.32 mg, 412.83 µmol, 3 eq). The mixture was stirred at 25° C. for 2 hours. TLC showed the reaction was complete. The reaction mixture was concentrated under reduced pressure. The aqueous was made pH=6 with 3N HCl and then extracted with EtOAc (3 mL×3). The combined organic layers were washed with brine (3 mL), dried over Na$_2$SO$_4$, filtered and concentrated under reduced pressure. Compound 5-chloro-3-fluoro-1-[2-(2-hydroxyethoxy)ethyl]-6H-pyrazolo[4,3-d]pyrimidin-7-one (30 mg, 108.44 µmol, 78.80% yield) was obtained as white solid. $^1$H NMR (DMSO-$d_6$, 400 MHz) δ 4.56 (t, J=5.6 Hz, 2H), 3.79 (t, J=5.6 Hz, 2H), 3.38 (s, 4H).

Preparation of 5-((3,4-difluorobenzyl)amino)-3-fluoro-1-(2-(2-hydroxyethoxy)ethyl)-1H-pyrazolo[4,3-d]pyrimidin-7(6H)-one (Step 4 in Scheme D)

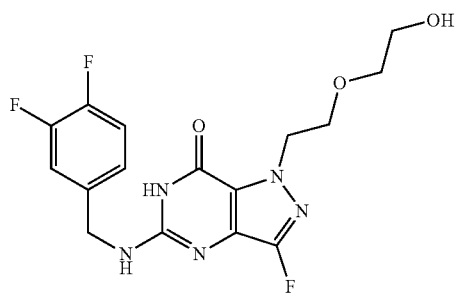 [SMILES: O=c1[nH]c(NCc2ccc(F)c(F)c2)nc2c(F)nn(CCOCCO)c12]

A mixture of 5-chloro-3-fluoro-1-[2-(2-hydroxyethoxy)ethyl]-6H-pyrazolo[4,3-d]pyrimidin-7-one (30 mg, 108.44 mol, 1 eq) and (3,4-difluorophenyl)methanamine (31.04 mg, 216.88 µmol, 25.66 µL, 2 eq) in t-BuOH (2 mL) was stirred at 100° C. for 12 hours. LC-MS showed the reaction was complete. The reaction mixture was concentrated under reduced pressure. The residue was purified by prep-HPLC (column: Waters Xbridge BEH C18 100 mm×25 mm 5 µm;

mobile phase: [water (10 mM NH₄HCO₃)-MeCN]; B %: 20%-50%, 10 mins). The solvent was removed under freeze drying. Compound 5-[(3,4-difluorophenyl)methylamino]-3-fluoro-1-[2-(2-hydroxyethoxy)ethyl]-6H-pyrazolo[4,3-d]pyrimidin-7-one (14 mg, 36.52 µmol, 33.68% yield, 100% purity) was obtained as white solid. ¹H NMR (DMSO-d₆, 400 MHz) δ 11.21 (s, 1H), 7.42~7.35 (m, 2H), 7.19 (s, 1H), 6.66 (s, 1H), 4.53 (s, 1H), 4.46~4.45 (m, 4H), 3.76~3.73 (m, 2H), 3.40~3.37 (m, 4H). HPLC: 100.00% (220 nm), 99.87% (215 nm), 100.00% (254 nm). MS (ESI): mass calcd. For $C_{16}H_{16}F3N_5O_3$ 383.12, m/z found 384.1 [M+H]⁺.

Compound 302

5-[(3,4-Dichlorophenyl)methylamino]-3-fluoro-1-[2-(2-hydroxyethoxy)ethyl]-6H-pyrazolo[4,3-d]pyrimidin-7-one was prepared according to the procedure described herein for Steps 2-4 in Scheme D.

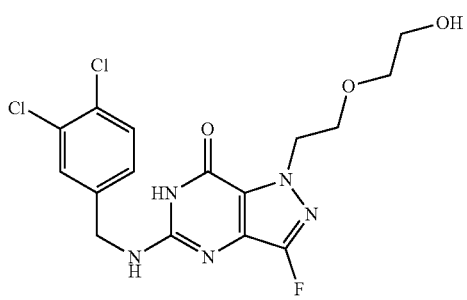 [SMILES: O=c1[nH]c(NCc2ccc(Cl)c(Cl)c2)nc2c(F)nn(CCOCCO)c12]

The procedure yielded the desired compound ((262.6 mg, 612.85 µmol, 60.55% yield) as a white solid. ¹H NMR (DMSO-d₆, 400 MHz) δ 11.29 (m, 1H), 7.60~7.58 (m, 2H), 7.33 (dd, J=8.0 Hz, 1.6 Hz, 1H), 6.70 (t, J=6.0 Hz, 1H), 4.47~4.44 (m, 4H), 3.75 (t, J=5.6 Hz, 2H), 3.42~3.37 (m, 4H). HPLC: 98.68% (220 nm), 98.69% (215 nm), 98.46% (254 nm). MS (ESI): mass calcd. For $C_{16}H_{16}C_{12}FN_5O_3$ 415.06, m/z found 416.0 [M+H]⁺.

Compound 303

3-Chloro-5-[(3,4-dichlorophenyl)methylamino]-1-[2-(2-hydroxyethoxy)ethyl]-6H-pyrazolo[4,3-d]pyrimidin-7-one) was prepared according to the procedure described herein for Steps 2-4 in Scheme D.

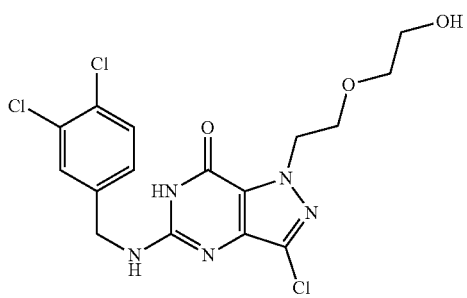 [SMILES: O=c1[nH]c(NCc2ccc(Cl)c(Cl)c2)nc2c(Cl)nn(CCOCCO)c12]

The procedure yielded the desired compound (105.6 mg, 237.42 µmol, 53.53% yield) as a white solid. ¹H NMR (DMSO-d₆, 400 MHz) δ 11.29 (m, 1H), 7.64 (s, 1H), 7.59 (d, J=8.0 Hz, 1H), 7.35 (dd, J=8.0 Hz, 1.6 Hz, 1H), 6.76 (t, J=5.6 Hz, 1H), 4.54 (t, J=5.6 Hz, 2H), 4.48 (d, J=6.0 Hz, 2H), 3.78 (t, J=5.6 Hz, 2H), 3.42~3.38 (m, 4H). HPLC: 97.28% (220 nm), 97.27% (215 nm), 97.07% (254 nm). MS (ESI): mass calcd. For $C_{16}H_{16}C3N_5O_3$ 431.03, m/z found 432.0 [M+H]⁺.

Compound 304

3-Chloro-5-((3,4-dichlorobenzyl)amino)-1-(2-methoxyethyl)-1H-pyrazolo[4,3-d]pyrimidin-7(6H)-one) was prepared according to the procedure described herein for Steps 2-4 in Scheme D.

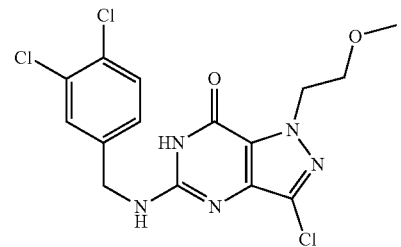 [SMILES: COCCn1nc(Cl)c2nc(NCc3ccc(Cl)c(Cl)c3)[nH]c(=O)c21]

The procedure yielded the desired compound (123.9 mg, 304.08 µmol, 31.25% yield) as an off-white solid. ¹H NMR (DMSO-d₆, 400 MHz) δ 11.28 (s, 1H), 6 7.65 (s, 1H), 7.64~7.58 (m, 1H), 7.37~7.35 (m, 1H), 6.76~6.73 (m, 1H), 4.55 (t, J 5.6 Hz, 2H), 4.48 (d, J 5.6 Hz, 2H), 3.70 (t, J 5.6 Hz, 2H), 3.19 (s, 3H). HPLC: 98.82% (220 nm), 99.12% (215 m), 99.50% (254 nm). MS (ESI): mass caled. For $C_{15}H_{14}C3N_5O_2$ 401.02, m/z found 402.0 [M+H]⁺.

Compound 305

5-((3,4-Dichlorobenzyl)amino)-3-fluoro-1-(2-methoxyethyl)-1H-pyrazolo[4,3-d]pyrimidin-7(6H)-one was prepared according to the procedure described herein for Steps 2-4 in Scheme D.

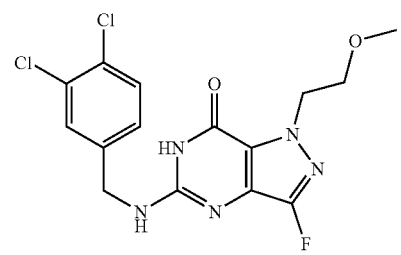 [SMILES: COCCn1nc(F)c2nc(NCc3ccc(Cl)c(Cl)c3)[nH]c(=O)c21]

The procedure yielded the desired compound (47.9 mg, 119.51 µmol, 12.28% yield) as a white solid. H NMR (DMSO-d₆, 400 MHz) δ 7.59-7.57 (m, 2H), 7.33 (s, 1H), 7.72 (m, 2H), 4.64 (s, 4H), 3.66 (s, 2H), 3.18 (s, 3H). HPLC: 96.36% (220 nm), 94.86% (215 m), 94.63% (254 nm). MS (ESI): mass calcd. For $C_{15}H_{14}C_{12}FN_5O_2$ 385.05, m/z found 386.0 [M+H]⁺.

Compound 306

5-((3,4-Dichlorobenzyl)amino)-3-fluoro-1-(oxazol-4-yl-methyl)-1H-pyrazolo[4,3-d]pyrimidin-7(6H)-one was prepared according to the procedure described herein for Steps 2-4 in Scheme D.

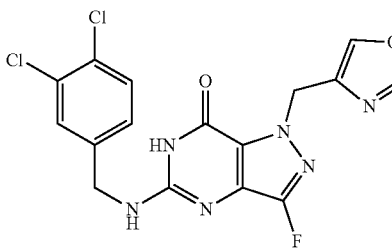

The procedure yielded the desired compound (20.0 mg, 48.49 μmol, 8.72% yield) as a white solid. ¹H NMR (DMSO-d₆, 400 MHz) δ 8.30 (s, 1H), 8.02 (s, 1H), 7.59 (d, J=8.4 Hz, 2H), 7.33 (dd, J=2.0 Hz, 8.4 Hz, 1H), 6.75 (t, J=5.6 Hz, 1H), 5.44 (s, 2H), 4.47 (d, J=6.0 Hz, 2H). HPLC: 99.22% (220 nm), 99.28% (215 nm), 100.00% (254 nm). MS (ESI): mass calcd. For $C_{16}H_{11}C_{12}FN_6O_2$ 408.03, m/z found 409.1 [M+H]⁺.

Compound 307

3-Chloro-5-((3,4-dichlorobenzyl)amino)-1-(oxazol-4-yl-methyl)-1H-pyrazolo[4,3-d]pyrimidin-7(6H)-one was prepared according to the procedure described herein for Steps 2-4 in Scheme D.

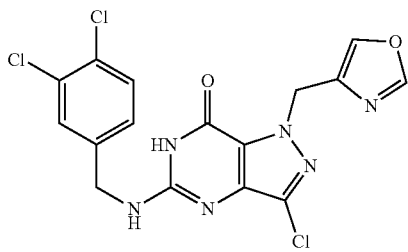 [SMILES: O=c1[nH]c(NCc2ccc(Cl)c(Cl)c2)nc2c(Cl)nn(Cc3cocn3)c12]

The procedure yielded the desired compound (16.8 mg, 36.19 μmol, 7.96% yield) as an off-white solid. ¹H NMR (DMSO-d₆, 400 MHz) δ 8.29 (s, 1H), 8.04 (s, 1H), 7.64 (s, 1H), 7.59 (d, J=8.0 Hz, 1H), 7.35 (d, J=8.8 Hz, 1H), 6.79 (t, J=5.2 Hz, 1H), 5.52 (s, 2H), 4.48 (d, J=5.6 Hz, 2H). HPLC: 91.69% (220 nm), 88.44% (215 nm), 93.54% (254 nm). S (ESI): mass calcd. For $C_{16}H_{11}C_{13}N_6O_2$ 424.00, m/z found 425.0 [M+H]⁺.

Compound 308

5-((3,4-Difluorobenzyl)amino)-3-fluoro-1-(2-methoxy-ethyl)-1H-pyrazolo[4,3-d]pyrimidin-7(6H)-one was prepared according to the procedure described herein for Steps 2-4 in Scheme D.

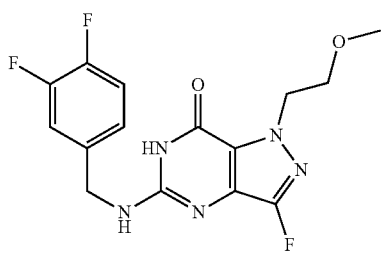 [SMILES: COCCn1nc(F)c2nc(NCc3ccc(F)c(F)c3)[nH]c(=O)c21]

The procedure yielded the desired compound (28.5 mg, 80.05 μmol, 39.48% yield) as a white solid. ¹H NMR (DMSO-d₆, 400 MHz) δ 11.26 (s, 1H), 7.39 (t, J=8.0 Hz, 2H), 7.19 (s, 1H), 6.66 (s, 1H), 4.46 (s, 4H), 3.58 (s, 2H), 3.19 (s, 3H). HPLC: 99.23% (220 nm), 92.78% (215 nm), 100.00% (254 nm). MS (ESI): mass calcd. For $C_{15}H_{14}F3N_5O_2$ 353.11, m/z found 354.1 [M+H]⁺.

Compound 309

3-Chloro-5-[(3,4-difluorophenyl)methylamino]-1-[2-(2-hydroxyethoxy)ethyl]-6H-pyrazolo[4,3-d]pyrimidin-7-one was prepared according to the procedure described herein for Steps 2-4 in Scheme D.

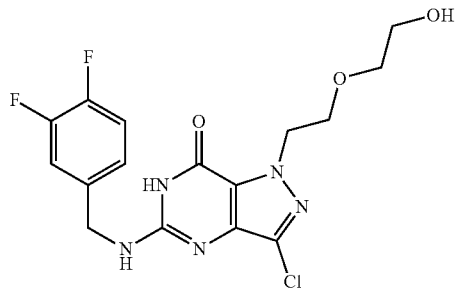 [SMILES: O=c1[nH]c(NCc2ccc(F)c(F)c2)nc2c(Cl)nn(CCOCCO)c12]

The procedure yielded the desired compound (48.8 mg, 121.69 μmol, 54.87% yield) as a white solid. ¹H NMR (DMSO-d₆, 400 MHz) δ 11.21 (s, 1H), 7.45~7.35 (m, 2H), 7.22 (s, 1H), 6.70 (s, 1H), 4.54~4.46 (m, 5H), 3.78 (s, 2H), 3.397 (s, 4H). HPLC: 99.69% (220 nm), 99.72% (215 nm), 99.75% (254 nm). MS (ESI): mass calcd. For $C_{16}H_{16}ClF_2N_5O_3$ 399.09, m/z found 400.0 [M+H]⁺.

Compound 310

5-[(4-Chloro-3-methyl-phenyl)methylamino]-3-fluoro-1-[2-(2-hydroxyethoxy)ethyl]-6H-pyrazolo[4,3-d]pyrimidin-7-one was prepared according to the procedure described herein for Steps 2-4 in Scheme D.

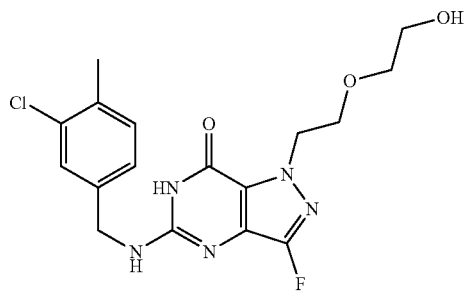 [SMILES: Cc1ccc(CNc2nc3c(F)nn(CCOCCO)c3c(=O)[nH]2)cc1Cl]

The procedure yielded the desired compound (7.2 mg, 17.67 μmol, 24.44% yield) as an off-white solid. ¹H NMR (DMSO-d₆, 400 MHz) δ 10.92 (s, 1H), 7.36 (d, J=8.0 Hz, 1H), 7.31 (s, 1H), 7.18 (d, J=8.4 Hz, 1H), 6.64 (t, J=6.0 Hz, 1H), 4.53 (s, 1H), 4.47~4.42 (m, 4H), 3.75 (d, J=5.6 Hz, 2H), 3.39~3.36 (m, 4H), 2.31 (m, 3H). HPLC: 97.15% (220 nm), 96.73% (215 nm), 96.78% (254 nm). MS (ESI): mass calcd. For $C_{17}H_{19}ClFN_5O_3$ 395.12, m/z found 396.1 [M+H]⁺.

Compound 311

3-Fluoro-5-((4-fluoro-3-methylbenzyl)amino)-1-(2-(2-hydroxyethoxy)ethyl)-1H-pyrazolo[4,3-d]pyrimidin-7(6H)-one was prepared according to the procedure described herein for Steps 2-4 in Scheme D.

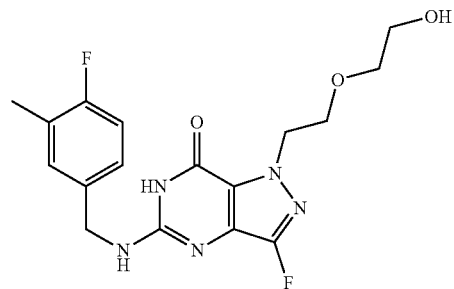 [SMILES: Cc1cc(CNc2nc3c(F)nn(CCOCCO)c3c(=O)[nH]2)ccc1F]

The procedure yielded the desired compound (8.5 mg, 21.82 μmol, 35.51% yield) as a white solid. $^1$H NMR (DMSO-d$_6$, 400 MHz) δ11.12 (s, 1H), 7.25 (d, J=7.2 Hz, 1H), 7.21~7.15 (m, 1H), 7.14~7.05 (m, 1H), 6.55 (t, J=5.6 Hz, 1H), 4.46 (t, J=5.2 Hz, 2H), 4.40 (d, J=5.6 Hz, 2H), 3.75 (t, J=5.6 Hz, 2H), 3.41~3.37 (m, 4H), 2.21 (d, J=1.2 Hz, 3H). HPLC: 97.38% (220 nm), 97.37% (215 nm), 97.86% (254 nm). MS (ESI): mass calcd. For C$_{17}$H$_{19}$F2N$_5$O$_3$ 379.15, m/z found 380.1 [M+H]$^+$.

Compound 312

5-[(3-Chloro-4-methyl-phenyl)methylamino]-3-fluoro-1-[2-(2-hydroxy ethoxy)ethyl]-6H-pyrazolo[4,3-d]pyrimidin-7-one was prepared according to the procedure described herein for Steps 2-4 in Scheme D.

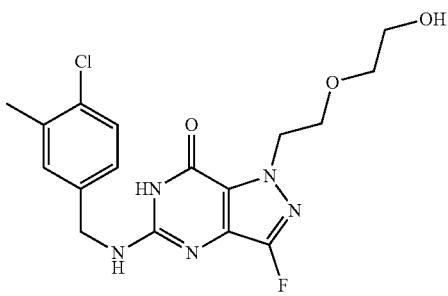 [SMILES: Cc1cc(CNc2nc3c(F)nn(CCOCCO)c3c(=O)[nH]2)ccc1Cl]

The procedure yielded the desired compound (10.3 mg, 25.97 μmol, 35.92% yield) as a white solid. $^1$H NMR (DMSO-d$_6$, 400 MHz) δ 11.12 (s, 1H), 7.38 (s, 1H), 7.30 (d, J=8.0 Hz, 1H), 7.20 (d, J=7.6 Hz, 1H), 6.62 (t, J=6.0 Hz, 1H), 4.53 (t, J=5.2 Hz, 1H), 4.47~4.42 (m, 4H), 3.75 (t, J=5.6 Hz, 2H), 3.41~3.37 (m, 4H), 2.29 (m, 3H). HPLC: 99.78% (220 nm), 99.73% (215 nm), 99.71% (254 nm). MS (ESI): mass calcd. For C$_{17}$H$_{19}$CFN$_5$O$_3$ 395.12, m/z found 396.1 [M+H]$^+$.

Compound 313

3-Fluoro-5-((3-fluoro-4-methylbenzyl)amino)-1-(2-(2-hydroxyethoxy)ethyl)-1H-pyrazolo[4,3-d]pyrimidin-7(6H)-one was prepared according to the procedure described herein for Steps 2-4 in Scheme D.

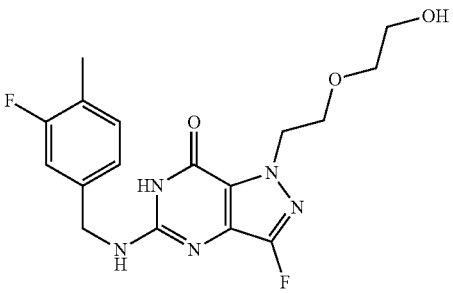 [SMILES: Cc1ccc(CNc2nc3c(F)nn(CCOCCO)c3c(=O)[nH]2)cc1F]

The procedure yielded the desired compound (6.1 mg, 15.08 μmol, 20.86% yield) as a light yellow solid. $^1$H NMR (DMSO-d$_6$, 400 MHz) δ 11.18 (s, 1H), 7.23 (t, J 8.0 Hz, 1H), 7.11~7.06 (m, 2H), 6.61~6.58 (m, 1H), 4.47~4.43 (m, 4H), 3.75 (t, J 5.6 Hz, 2H), 3.29-3.25 (m, 4H), 2.20 (s, 3H). HPLC: 93.77% (220 nm), 93.53% (215 nm), 94.33% (254 nm). MS (ESI): mass calcd. For C$_{17}$H$_{19}$F$_2$N$_5$O$_3$ 379.15, m/z found 380.1 [M+H]$^+$.

Compound 314

5-[(3,4-Difluorophenyl)methylamino]-1-(4-dimethylphosphorylbutyl)-3-fluoro-6H-pyrazolo[4,3-d]pyrimidin-7-one) was prepared according to the procedure described herein for Steps 3-4 in Scheme D.

Preparation of (4-(5-chloro-3-fluoro-7-methoxy-1H-pyrazolo[4,3-d]pyrimidin-1-yl)butyl)dimethylphosphine oxide

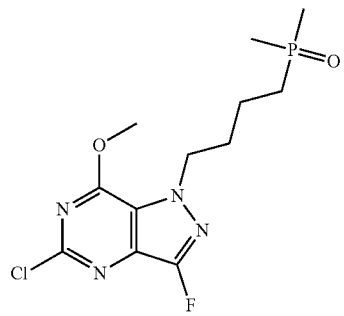 [SMILES: COc1nc(Cl)nc2c(F)nn(CCCCP(C)(C)=O)c12]

A mixture of 5-chloro-3-fluoro-7-methoxy-1H-pyrazolo[4,3-d]pyrimidine (400 mg, 1.97 mmol, 1 eq), 1-chloro-4-dimethylphosphoryl-butane (498.22 mg, 2.96 mmol, 1.5 eq) and Cs$_2$CO$_3$ (1.28 g, 3.94 mmol, 2 eq) in acetone (2 mL) was stirred at 60° C. for 12 hours. LC-MS showed the reaction was complete. The reaction mixture was concentrated under reduced pressure. The residue was purified by prep-HPLC (column: Phenomenex Luna C18 100 mm×30 mm 5 μm; mobile phase: [water (0.1% TFA)-MeCN]; B %: 15%-45%, 10 mins). The solvent was removed under freeze drying. Compound 5-chloro-1-(4-dimethylphosphorylbutyl)-3-fluoro-7-methoxy-pyrazolo[4,3-d]pyrimidine (30 mg, 89.63 μmol, 4.55% yield) was obtained as white solid. $^1$H NMR (CDCl$_3$, 400 MHz) δ 4.54 (t, J=6.8 Hz, 2H), 4.25 (d, J=3.2 Hz, 3H), 2.06~2.03 (m, 2H), 1.81~1.77 (m, 2H), 1.67~1.63 (m, 2H), 1.52 (d, J=12.4 Hz, 6H).

(5-[(3,4-difluorophenyl)methylamino]-1-(4-dimethylphosphorylbutyl)-3-fluoro-6H-pyrazolo[4,3-d]pyrimidin-7-one)

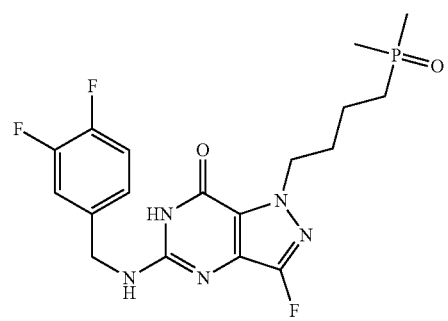 [SMILES: CP(C)(=O)CCCCn1nc(F)c2nc(NCc3ccc(F)c(F)c3)[nH]c(=O)c21]

The procedure yielded the desired compound (13 mg, 29.60 μmol, 63.28% yield) as an off-white solid. $^1$H NMR (DMSO-d$_6$, 400 MHz) δ 7.42~7.37 (m, 2H), 7.20~7.17 (m, 1H), 6.66 (t, J=5.6 Hz, 1H), 7.20 (t, J=4.4 Hz, 2H), 4.34 (t, J=6.8 Hz, 2H), 1.84~1.81 (m, 2H), 1.68~1.63 (m, 2H), 1.41~1.39 (m, 2H), 1.34 (s, 3H), 1.31 (s, 3H). HPLC:

97.30% (220 nm), 96.48% (215 nm), 98.01% (254 nm). MS (ESI): mass calcd. For $C_{18}H_{21}F_3N_5O_2P$ 427.14, m/z found 428.1 $[M+H]^+$.

Compound 315

5-[(3,4-difluorophenyl)methylamino]-3-fluoro-1-(oxetan-2-ylmethyl)-6H-pyrazolo[4,3-d]pyrimidin-7-one was prepared according to the procedure described herein for Steps 2-4 in Scheme D.

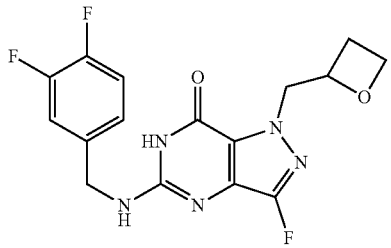 [SMILES: O=c1[nH]c(NCc2ccc(F)c(F)c2)nc2c(F)nn(CC3CCO3)c12]

The procedure yielded the desired compound (12.4 mg, 33.34 μmol, 28.75% yield) as a white solid. $^1$H NMR (DMSO-d$_6$, 400 MHz) δ 11.24 (s, 1H), 7.42~7.35 (m, 2H), 7.17 (dd, J 10.8 Hz, J 5.6 Hz, 1H), 6.64 (t, J 5.6 Hz, 1H), 4.95~4.92 (m, 1H), 4.66~4.61 (m, 1H), 4.50-4.44 (m, 4H), 4.34~4.31 (m, 1H), 2.63~2.52 (m, 1H), 2.43~2.42 (s, 1H). HPLC: 98.23% (220 nm), 98.16% (215 nm), 93.65% (254 nm). MS (ESI): mass calcd. For $C_{16}H_{14}F_3N_5O_2$ 365.11, m/z found 366.2 $[M+H]^+$.

Compound 316

5-((3,4-Difluorobenzyl)amino)-3-fluoro-1-(oxazol-4-ylmethyl)-1H-pyrazolo[4,3-d]pyrimidin-7(6H)-one) was prepared according to the procedure described herein for Steps 2-4 in Scheme D.

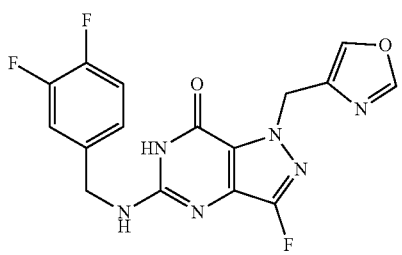 [SMILES: O=c1[nH]c(NCc2ccc(F)c(F)c2)nc2c(F)nn(Cc3cocn3)c12]

The procedure yielded the desired compound (9.9 mg, 26.27 μmol, 11.80% yield) as a white solid. $^1$H NMR (DMSO-d$_6$, 400 MHz) δ 11.23 (s, 1H), 8.29 (s, 1H), 8.02 (s, 1H), 7.43~7.33 (m, 2H), 7.19 (s, 1H), 6.69 (t, J=5.6 Hz, 1H), 5.44 (s, 2H), 4.46 (d, J=6.0 Hz, 2H). HPLC: 99.84% (220 nm), 100.00% (215 nm), 100.00% (254 nm). MS (ESI): mass calcd. For $C_{16}H_{11}F_3N_6O_2$ 376.09, m/z found 377.2 $[M+H]^+$.

Compound 317 and Compound 318

Preparation of (5-((3,4-dichlorobenzyl)amino)-3-fluoro-1-(1-nicotinoylpiperidin-4-yl)-1H-pyrazolo[4,3-d]pyrimidin-7(6H)-one hydrochloride) and 3-Chloro-5-[(3,4-dichlorophenyl)methylamino]-1-[1-(pyridine-3-carbonyl)-4-piperidyl]-6H-pyrazolo[4,3-d]pyrimidin-7-one Preparation of 4-(5-chloro-3-fluoro-7-methoxy-1H-pyrazolo[4,3-d]pyrimidin-1-yl)piperidin-1-yl)(pyridin-3-yl) methanone and (4-(3,5-dichloro-7-methoxy-1H-pyrazolo[4,3-d]pyrimidin-1-yl)piperidin-1-yl)(pyridin-3-yl)methanone (Step 2 in Scheme D)

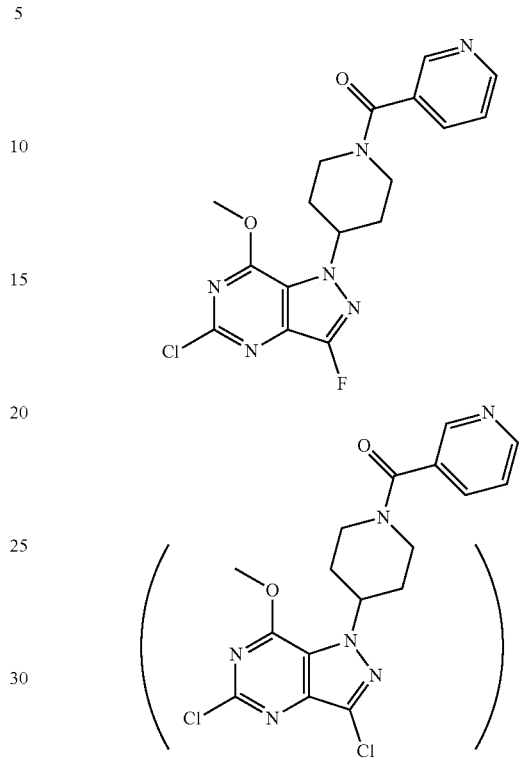

To a mixture of 5-chloro-3-fluoro-7-methoxy-H-pyrazolo[4,3-d]pyrimidine and 5-chloro-3-chloro-7-methoxy-1H-pyrazolo[4,3-d]pyrimidine (0.4 g, 1.97 mmol, 1 eq), (4-hydroxy-1-piperidyl)-(3-pyridyl)methanone (366.52 mg, 1.78 mmol, 0.9 eq) and PPh$_3$ (776.86 mg, 2.96 mmol, 1.5 eq) in THF (10 mL) was added DIAD (598.92 mg, 2.96 mmol, 575.88 μL, 1.5 eq) dropwise at 0° C. Then the mixture was stirred at 20° C. for 3 hours. TLC showed the reaction was complete. The mixture was quenched with ice water (10 mL) and the organic layer was separated. The aqueous was extracted with EtOAc (15 mL×5). The combined organic layer was washed with brine (5 mL×1), dried over Na$_2$SO$_4$, filtered and concentrated under reduced pressure. The residue was purified by prep-HPLC (column: Nano-micro Kromasil C18 100 mm×30 mm 5 μm; mobile phase: [water (0.1% TFA)-MeCN]; B %: 25%-40%, 10 mins). The eluent was made pH=6 with sat. NaHCO$_3$ and then extracted with EtOAc (20 mL×4). The combined organic layer was washed with brine (5 mL×1), dried over Na$_2$SO$_4$, filtered and concentrated under reduced pressure. Compound [4-(5-chloro-3-fluoro-7-methoxy-pyrazolo[4,3-d]pyrimidin-1-yl)-1-piperidyl]-(3-pyridyl)methanone (45 mg, 115.15 μmol, 5.83% yield) was obtained as white solid. Compound [4-(3,5-dichloro-7-methoxy-pyrazolo[4,3-d]pyrimidin-1-yl)-1-piperidyl]-(3-pyridyl)methanone (70 mg, 171.88 μmol, 8.70% yield) was obtained as white solid. $^1$H NMR (DMSO-d$_6$, 400 MHz) δ 8.76-8.73 (m, 2H), 8.08~8.06 (m, 1H), 7.65~7.62 (m, 1H), 5.01~5.00 (m, 1H), 4.61~4.58 (m, 1H), 4.19 (s, 3H), 3.69~3.66 (m, 1H), 3.35~3.28 (m, 1H), 3.09~3.07 (m, 1H), 2.14~1.95 (m, 4H). $^1$H NMR (DMSO-d$_6$, 400 MHz) δ 8.73~8.70 (m, 2H), 8.02~8.00 (m, 1H), 7.60~7.57 (m, 1H), 5.10-5.06 (m, 1H), 4.60~4.59 (m, 1H), 4.19 (s, 3H), 3.69~3.67 (m, 1H), 3.35~3.28 (m, 1H), 3.09-3.07 (m, 1H), 2.18~2.00 (m, 4H).

Preparation of 5-chloro-3-fluoro-1-(1-nicotinoylpiperidin-4-yl)-1H-pyrazolo[4,3-d]pyrimidin-7(6H)-one (Step 3 in Scheme D)

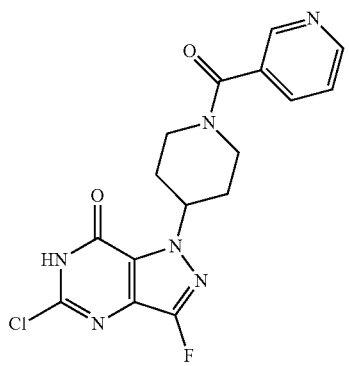 [SMILES: O=C(c1cccnc1)N1CCC(n2nc(F)c3nc(Cl)[nH]c(=O)c32)CC1]

A solution of [4-(5-chloro-3-fluoro-7-methoxy-pyrazolo[4,3-d]pyrimidin-1-yl)-1-piperidyl]-(3-pyridyl)methanone (45 mg, 115.15 µmol, 1 eq) and LiOH—H$_2$O (14.49 mg, 345.45 µmol, 3 eq) in MeOH (1 mL) and H$_2$O (1 mL) was stirred at 25° C. for 3 hours. LCMS showed the reaction was complete. The organic solvent was removed under reduced pressure. The aqueous was made pH=6-7 with 2N HCl slowly and then extracted with EtOAc (10 mL×5). The combined organic layer was washed with brine (5 mL), dried over Na$_2$SO$_4$, filtered and concentrated under reduced pressure. The residue was used to the next step without further purification. Compound 5-chloro-3-fluoro-1-[1-(pyridine-3-carbonyl)-4-piperidyl]-6H-pyrazolo[4,3-d]pyrimidin-7-one (42 mg, 111.47 µmol, 96.81% yield) was obtained as white solid. $^1$H NMR (DMSO-d$_6$, 400 MHz) δ 9.07 (s, 1H), 8.79~8.78 (m, 1H), 7.89 (d, J=8.0 Hz, 1H), 7.56~7.50 (m, 1H), 5.19~5.16 (m, 1H), 4.58~4.56 (m, 1H), 3.47~3.36 (m, 1H), 3.26-2.93 (m, 2H), 2.32~1.90 (m, 4H).

Preparation of (5-((3,4-dichlorobenzyl)amino)-3-fluoro-1-(1-nicotinoylpiperidin-4-yl)-1H-pyrazolo[4,3-d]pyrimidin-7(6H)-one hydrochloride) (Step 4 in Scheme D)

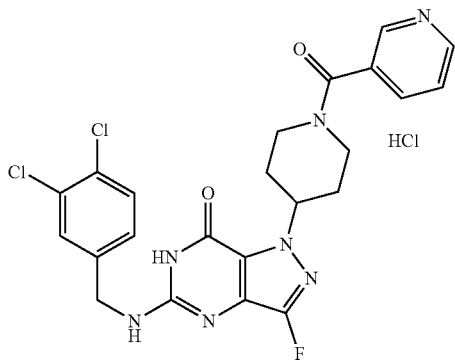 [SMILES: O=C(c1cccnc1)N1CCC(n2nc(F)c3nc(NCc4ccc(Cl)c(Cl)c4)[nH]c(=O)c32)CC1 ; Cl]

A mixture of 5-chloro-3-fluoro-1-[1-(pyridine-3-carbonyl)-4-piperidyl]-6H-pyrazolo[4,3-d]pyrimidin-7-one (38 mg, 100.86 µmol, 1 eq) and (3,4-dichlorophenyl)methanamine (35.51 mg, 201.71 µmol, 26.90 µL, 2 eq) in t-BuOH (2 mL) was stirred at 100° C. for 10 hours under N$_2$. TLC showed the reaction was complete. The solvent was removed under reduced pressure. The residue was purified by prep-HPLC (column: Phenomenex Luna C18 100 mm×30 mm 5 µm; mobile phase: [water (0.05% HCl)-MeCN]; B %: 30%-45%, 10 mins). The eluent was removed under lyophilization. 5-[(3,4-Dichlorophenyl)methylamino]-3-fluoro-1-[1-(pyridine-3-carbonyl)-4-piperidyl]-6H-pyrazolo[4,3-d]pyrimidin-7-one (Compound 317) (20.6 mg, 37.05 µmol, 36.73% yield, 99.42% purity, HCl) was obtained as pale yellow solid. $^1$H NMR (DMSO-d$_6$, 400 MHz) δ 8.95-8.88 (m, 2H), 8.35 (d, J=8.0 Hz, 1H), 7.90~7.89 (m, 1H), 7.60~7.58 (m, 2H), 7.34~7.32 (m, 1H), 7.12 (t, J=6.8 Hz, 1H), 5.12~5.06 (m, 1H), 4.58-4.54 (m, 1H), 4.47 (d, J=5.2 Hz, 2H), 3.67~3.62 (m, 1H), 3.30~3.27 (m, 1H), 3.02~2.99 (m, 1H), 2.07~1.90 (m, 4H). HPLC: 99.42% (220 nm), 99.53% (215 nm), 100.00% (254 nm). MS (ESI): mass calcd. For C$_{23}$H$_{21}$Cl$_3$FN$_7$O$_2$ 515.10 m/z found 516.2 [M+H]$^+$.

Preparation of 3,5-dichloro-1-(1-nicotinoylpiperidin-4-yl)-1H-pyrazolo[4,3-d]pyrimidin-7(6H)-one (Step 2 in Scheme D)

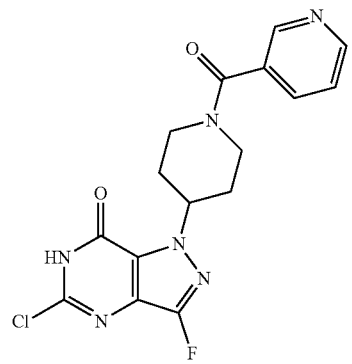

A solution of [4-(3,5-dichloro-7-methoxy-pyrazolo[4,3-d]pyrimidin-1-yl)-1-piperidyl]-(3-pyridyl)methanone (60 mg, 147.33 µmol, 1 eq) and LiOH—H$_2$O (18.55 mg, 441.99 µmol, 3 eq) in MeOH (1 mL) and H$_2$O (1 mL) was stirred at 20° C. for 3 hours. LCMS showed the reaction was complete. The organic solvent was removed under reduced pressure. The aqueous was made pH=6-7 with N HCl slowly and then extracted with EtOAc (10 mL×5). The combined organic layer was washed with brine (5 mL), dried over Na$_2$SO$_4$, filtered and concentrated under reduced pressure. The residue was used to the next step without further purification. Compound 3,5-dichloro-1-[1-(pyridine-3-carbonyl)-4-piperidyl]-6H-pyrazolo[4,3-d]pyrimidin-7-one (50 mg, 127.15 µmol, 86.31% yield) was obtained as white solid. $^1$H NMR (DMSO-d$_6$, 400 MHz) δ 9.07 (s, 1H), 8.79 (d, J=4.0 Hz, 1H), 7.90~7.88 (m, 1H), 7.50~7.49 (m, 1H), 5.25~5.23 (m, 1H), 4.61~4.58 (m, 1H), 3.68~3.66 (m, 1H), 3.20~2.94 (m, 2H), 2.33~2.03 (m, 4H).

Preparation of (3-chloro-5-((3,4-dichlorobenzyl)amino)-1-(1-nicotinoylpiperidin-4-yl)-1H-pyrazolo[4,3-d]pyrimidin-7(6H)-one hydrochloride) (Step 3 in Scheme D)

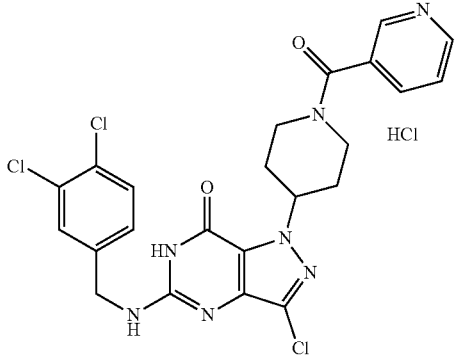 [SMILES: O=C(c1cccnc1)N1CCC(n2nc(Cl)c3nc(NCc4ccc(Cl)c(Cl)c4)[nH]c(=O)c32)CC1 ; Cl]

A mixture of 3,5-dichloro-1-[1-(pyridine-3-carbonyl)-4-piperidyl]-6H-pyrazolo[4,3-d]pyrimidin-7-one (50 mg, 127.15 µmol, 1 eq) and (3,4-dichlorophenyl)methanamine (44.77 mg, 254.31 µmol, 33.92 µL, 2 eq) in t-BuOH (2 mL) was stirred at 100° C. for 10 hours under $N_2$. LCMS and HPLC showed the reaction was complete. The solvent was removed under reduced pressure. The residue was purified by prep-HPLC (column: Phenomenex Luna C18 100 mm 30 mmmm 5 µm; mobile phase: [water (0.05% HCl)-MeCN]; B %: 30%-60%, 10 mins). The eluent was removed under lyophilization. 3-Chloro-5-[(3,4-dichlorophenyl)methylamino]-1-[1-(pyridine-3-carbonyl)-4-piperidyl]-6H-pyrazolo[4,3-d]pyrimidin-7-one (Compound 318) (7.5 mg, 12.86 µmol, 10.12% yield, 97.64% purity, HCl) was obtained as white solid. $^1$H NMR (DMSO-$d_6$, 400 MHz) δ 8.93-8.85 (m, 2H), 8.36~8.35 (m, 1H), 7.89-7.85 (m, 1H), 7.68~7.62 (m, 2H), 7.7.38-7.34 (m, 1H), 7.11 (t, J=6.8 Hz, 1H), 5.15-5.10 (m, 1H), 4.48~4.44 (m, 1H), 4.43 (d, J=5.2 Hz, 2H), 3.67~3.64 (m, 1H), 3.32~3.27 (m, 1H), 3.05~2.99 (m, 1H), 2.07~2.00 (m, 4H). HPLC: 97.64% (220 nm), 97.97% (215 nm), 99.39% (254 nm). MS (ESI): mass calcd. For $C_{23}H_{21}C_{14}N_7O_2$ 531.07 m/z found 532.1 [M+H]$^+$.

Compound 319

Preparation of (5-((3,4-difluorobenzyl)amino)-3-fluoro-1-(1-isonicotinoylpiperidin-4-yl)-1H-pyrazolo[4,3-d]pyrimidin-7(6H)-one hydrochloride

Preparation of (4-hydroxypiperidin-1-yl)(pyridin-4-yl)methanone (Step 1 in Scheme D)

Preparation of (4-(5-chloro-3-fluoro-7-methoxy-1H-pyrazolo[4,3-d]pyrimidin-1-yl)piperidin-1-yl)(pyridin-4-yl)methanone and (4-(3,5-dichloro-7-methoxy-1H-pyrazolo[4,3-d]pyrimidin-1-yl)piperidin-1-yl) (pyridin-4-yl)methanone (Step 1 in Scheme D)

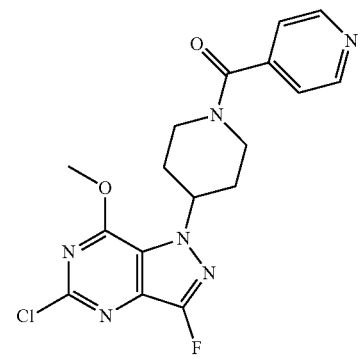

-continued

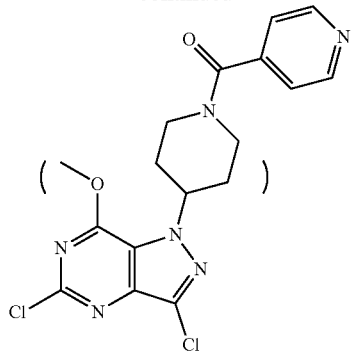

To a solution of 5-chloro-3-fluoro-7-methoxy-1H-pyrazolo[4,3-d]pyrimidine (0.3 g, 1.48 mmol, 1 eq) and 3,5-dichloro-7-methoxy-1H-pyrazolo[4,3-d]pyrimidine (1.48 mmol, 1 eq) in THF (3 mL) was added (4-hydroxy-1-piperidyl)-(4-pyridyl)methanone (458.15 mg, 2.22 mmol, 1.5 eq), PPh$_3$ (582.66 mg, 2.22 mmol, 1.5 eq). Then DIAD (449.19 mg, 2.22 mmol, 431.92 µL, 1.5 eq) was added dropwise at 0° C. The mixture was stirred at 25° C. for 10 hours. LCMS and HPLC showed the reaction was completed. $H_2O$ (6 mL) was added. The reaction mixture was extracted with EtOAc (8 mL×3). The combined organic layers were washed with brine (5 mL×1), dried over $Na_2SO_4$, filtered and concentrated under reduced pressure to give a residue. The residue was purified by prep-HPLC (TFA condition column: Phenomenex Luna C18 100×30 mm×5 µm; mobile phase: [water (0.1% TFA)-MeCN]; B %: 25%-40%, 10 mins). MeCN was removed under reduced pressure at 30° C. Then the aqueous phase was extracted with EtOAc (15 mL×3). The combined organic layers were washed with brine (15 mL×2), dried over $Na_2SO_4$, filtered and concentrated under reduced pressure to give a residue. Compound (4-(5-chloro-3-fluoro-7-methoxy-1H-pyrazolo[4,3-d]pyrimidin-1-yl)piperidin-1-yl)(pyridin-4-yl)methanone (0.19 g, 218.78 µmol, 14.77% yield, 45% purity) was obtained as brown oil. Compound (4-(3,5-dichloro-7-methoxy-1H-pyrazolo[4,3-d]pyrimidin-1-yl)piperidin-1-yl) (pyridin-4-yl) methanone (0.35 g, 300.80 µmol, 20.31% yield, 35% purity) was obtained as light yellow solid. $^1$H NMR (DMSO-$d_6$, 400 MHz) δ 8.69-8.67 (m, 2H), 7.45~7.43 (m, 2H), 5.00 (s, 1H), 4.60~4.56 (m, 2H), 4.18 (s, 3H), 3.59-3.55 (m, 2H), 3.09~3.01 (m, 2H), 1.99~1.97 (m, 2H). $^1$H NMR (CDCl$_3$, 400 MHz) δ 8.78-8.77 (m, 2H), 7.41~7.39 (m, 2H), 4.96~4.95 (m, 1H), 4.27 (s, 3H), 3.76~3.78 (m, 1H), 3.25-3.27 (m, 1H), 3.02~3.04 (m, 1H), 2.27~2.24 (m, 4H), 2.05~2.02 (m, 1H).

Preparation of 5-chloro-3-fluoro-1-(1-isonicotinoylpiperidin-4-yl)-1H-pyrazolo[4,3-d]pyrimidin-7(6H)-one (Step 2 in Scheme D)

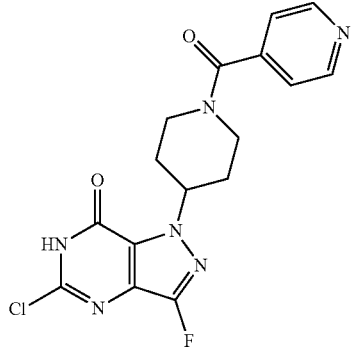 [SMILES: O=C(c1ccncc1)N1CCC(n2nc(F)c3nc(Cl)[nH]c(=O)c32)CC1]

To a solution of [4-(5-chloro-3-fluoro-7-methoxy-pyrazolo[4,3-d]pyrimidin-1-yl)-1-piperidyl]-(4-pyridyl)methanone (0.19 g, 291.71 mol, 1 eq) in $H_2O$ (2 mL) and MeOH (2 mL) was added LiOH·$H_2O$ (36.72 mg, 875.13 μmol, 3 eq). The mixture was stirred at 25° C. for 10 hours. TLC showed the reaction was completed. $H_2O$ (5 mL) was added to the reaction mixture. The reaction mixture was concentrated under reduced pressure to remove MeOH. The mixture was adjusted to pH=6 with HCl (3 N). Then the mixture was extracted with EtOAc (8 mL×3). The combined organic layers were washed with brine (6 mL×1), dried over $Na_2SO_4$, filtered and concentrated under reduced pressure. Compound 5-chloro-3-fluoro-1-(1-isonicotinoylpiperidin-4-yl)-1H-pyrazolo[4,3-d]pyrimidin-7(6H)-one (0.17 g 157.92 μmol, 54.14% yield, 35% purity) was obtained as yellow oil. $^1$H NMR (DMSO-$d_6$, 400 MHz) δ 8.68 (d, J 6.0 Hz, 2H), 7.44~7.43 (m, 3H), 5.18 (m, 1H), 4.59~4.55 (m, 2H), 4.04-4.02 (m, 2H), 3.02 (d, J 11.6 Hz, 2H), 1.98~1.94 (m, 2H).

Preparation of (5-((3,4-difluorobenzyl)amino)-3-fluoro-1-(1-isonicotinoylpiperidin-4-yl)-1H-pyrazolo[4,3-d]pyrimidin-7(6H)-one hydrochloride) (Step 3 in Scheme D)

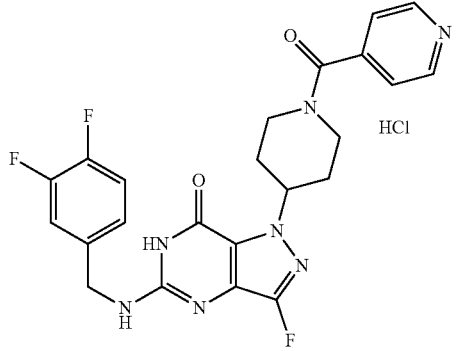 [SMILES: O=C(c1ccncc1)N1CCC(n2nc(F)c3nc(NCc4ccc(F)c(F)c4)[nH]c(=O)c32)CC1 ; Cl]

To a solution of 5-chloro-3-fluoro-1-[1-(pyridine-4-carbonyl)-4-piperidyl]-6H-pyrazolo[4,3-d]pyrimidin-7-one (0.12 g 111.47 μmol, 1 eq) in t-BuOH (2 mL) was added (3,4-difluorophenyl) methanamine (31.91 mg, 222.95 μmol, 26.37 μL, 2 eq). The mixture was stirred at 100° C. for 12 hours. LCMS and HPLC showed the reaction was completed. The reaction mixture was concentrated under reduced pressure to give a residue. The residue was purified by prep-HPLC (HCl condition column: Phenomenex Luna C18 100×30 mm×5 μm; mobile phase: [water (0.04% HCl)-MeCN]; B %: 20%-45%, 10 mins). MeCN was removed under reduced pressure at 30° C. The residue was dried over lyophilization. Compound 5-((3,4-difluorobenzyl)amino)-3-fluoro-1-(1-isonicotinoylpiperidin-4-yl)-1H-pyrazolo[4,3-d]pyrimidin-7(6H)-one hydrochloride (26.7 mg, 54.15 μmol, 48.58% yield, 98.049% purity) was obtained as white solid. $^1$H NMR (DMSO-$d_6$, 400 MHz) δ 8.95-8.93 (m, 2H), 7.99~7.97 (m, 2H), 7.42~7.34 (m, 2H), 7.20~7.10 (m, 2H), 5.10~5.07 (m, 1H), 4.56-4.53 (m, 1H), 4.46 (d, J 4.0 Hz, 2H), 3.54~3.52 (m, 1H), 3.28~3.26 (m, 1H), 3.05-3.03 (m, 1H), 2.06~1.89 (m, 4H). HPLC: 98.05% (220 nm), 97.14% (215 nm), 98.68% (254 nm). MS (ESI): mass calcd. For $C_{23}H_{21}ClF_3N_7O_2$ 483.16, m/z found 484.1 [M+H]$^+$.

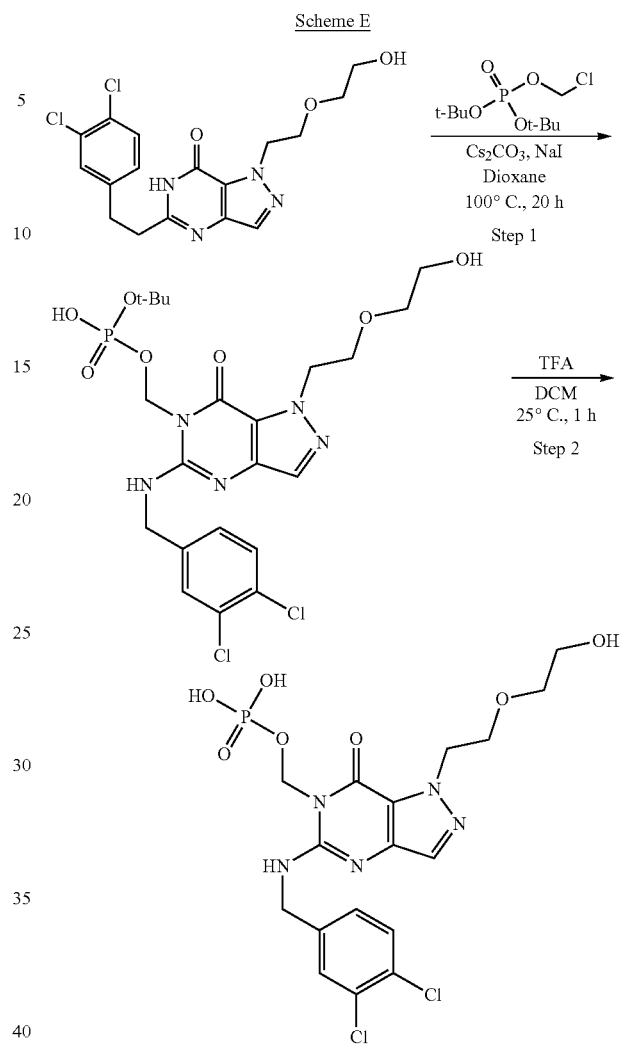

Compound 320

Preparation of (5-((3,4-dichlorobenzyl)amino)-1-(2-(2-hydroxyethoxy)ethyl)-7-oxo-1H-pyrazolo[4,3-d]pyrimidin-6(7H)-yl)methyl dihydrogen phosphate Preparation of ((5-((3,4-dichlorobenzyl)amino)-1-(2-(2-hydroxyethoxy)ethyl)-7-oxo-1H-pyrazolo[4,3-d]pyrimidin-6(7H)-yl)methyl) hydrogen phosphate (Step 1 in Scheme E)

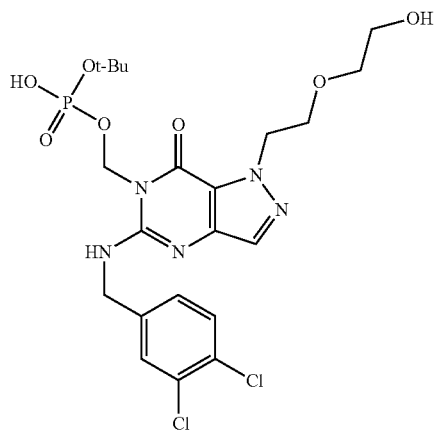 [SMILES: CC(C)(C)OP(=O)(O)OCn1c(NCc2ccc(Cl)c(Cl)c2)nc2cnn(CCOCCO)c2c1=O]

To a solution of 5-[(3,4-dichlorophenyl)methylamino]-1-[2-(2-hydroxyethoxy)ethyl]-6H-pyrazolo[4,3-d]pyrimidin-7-one (500 mg, 1.26 mmol, 1 eq) and ditert-butyl chloromethyl phosphate (974.32 mg, 3.77 mmol, 3 eq) in dioxane (20 mL) was added $Cs_2CO_3$ (1.64 g, 5.02 mmol, 4.56 μL, 4 eq) and NaI (28.23 mg, 188.33 μmol, 1.5 eq). The mixture was stirred at 100° C. for 20 hours. LCMS showed 5-[(3,4-dichlorophenyl)methylamino]-1-[2-(2-hydroxy ethoxy) ethyl]-6H-pyrazolo[4,3-d]pyrimidin-7-one was nearly consumed and one desired peak was detected. After filtered, the filtrate was concentrated under reduced pressure. Compound tert-butyl[5-[(3,4-dichlorophenyl)methylamino]-1-[2-(2-hydroxyethoxy)ethyl]-7-oxo-pyrazolo[4,3-d]pyrimidin-6-yl]methyl hydrogen phosphate (1.3 g, crude) was obtained as white solid. MS (ESI): mass calcd. For $C_2H_{28}C2N_5O_7P$ 563.11 m/z found 564.1 $[M+H]^+$.

Preparation of (5-((3,4-dichlorobenzyl)amino)-1-(2-(2-hydroxyethoxy)ethyl)-7-oxo-1H-pyrazolo[4,3-d]pyrimidin-6(7H)-yl)methyl dihydrogen phosphate (Step 2 in Scheme E)

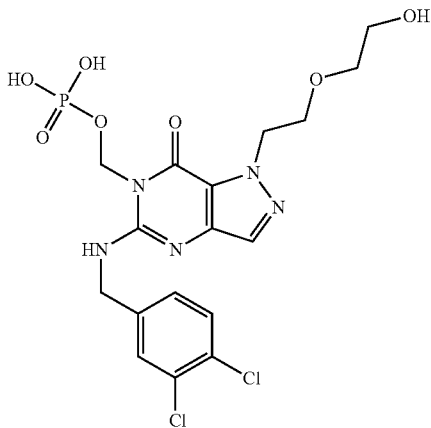 [SMILES: O=c1c2c(cnn2CCOCCO)nc(NCc2ccc(Cl)c(Cl)c2)n1COP(=O)(O)O]

To a solution of tert-butyl[5-[(3,4-dichlorophenyl)methylamino]-1-[2-(2-hydroxyethoxy)ethyl]-7-oxo-pyrazolo[4,3-d]pyrimidin-6-yl]methyl hydrogen phosphate (1.3 g, 921.41 μmol, 1 eq) in DCM (10 mL) was added TFA (1 mL) dropwise at 0° C. Then the mixture was stirred at 25° C. for an hour. LCMS showed the reaction was complete. The mixture was concentrated under reduced pressure. The residue was purified by prep-HPLC (column: Welch Xtimate C18 100 mm×25 mm 3 μm; mobile phase: [water (0.1% TFA)-MeCN]; B %: 20%-50%, 10 mins). The eluent was removed under reduced pressure. Compound [5-[(3,4-dichlorophenyl)methylamino]-1-[2-(2-hydroxyethoxy)ethyl]-7-oxo-pyrazolo[4,3-d]pyrimidin-6-yl]methyl dihydrogen phosphate (97.1 mg, 187.51 μmol, 20.35% yield, 98.15% purity) was obtained as yellow solid. $^1H$ NMR (DMSO-$d_6$, 400 MHz) δ 7.95 (s, 1H), 7.64 (d, J=6.0 Hz, 1H), 7.61 (s, 1H), 7.55 (d, J=8.4 Hz, 1H), 7.37 (dd, J=8.4 Hz, 2.0 Hz, 1H), 5.84 (d, J=10.0 Hz, 2H), 4.59 (t, J=6.0 Hz, 2H), 4.53 (s, 2H), 3.80 (t, J=6.0 Hz, 2H), 3.42~3.37 (m, 4H). HPLC: 98.15% (220 nm), 97.83% (215 nm), 96.75% (254 nm). MS (ESI): mass calcd. For $C_{17}H_{20}C_{12}N_5O_7P$ 507.05 m/z found 508.1 $[M+H]^+$.

Compound Efficacy

The ability of a compound to inhibit the activity of DNA pol IIIC enzyme can be tested by using a DNA polymerase assay as described, for example, in Barnes and Brown, Nucl. Acids Res. 1979, 6, 1203-1219; Trantolo et al., J. Med. Chem. 1986, 29, 676-681; Mills et al., J. Bacterial. 1977, 132, 641-649; Low et al., J. Biol. Chem. 1976, 251, 1311-1325. This rapid screening method can use natural or recombinant DNA pol III enzymes in a standard DNA polymerase activity assay. By including a test compound in a side-by-side assay with a control, the effect of the test compound on polymerase activity can be assessed. Compounds with an appropriate level (Ki<5 μM) of inhibition of the natural or recombinant bacterial DNA polymerase III are preferred.

Antimicrobial efficacy may be determined by standard methods of microbial culture in growth medium or on plates of agar supplemented with appropriate growth media. For example, microbes are grown in the presence of serial dilutions of compounds in an appropriate vehicle, and, after a suitable period of growth, the microbial density is measured by visual or instrumental means. The concentration of compound at which no growth occurs is the minimum inhibitory concentration (MIC) of the compound. Compounds with an appropriate level (MIC <4 μg/ml) of growth inhibition are preferred.

Toxicity

The compounds of the invention demonstrate low toxicity to animals. Because the compounds target essential enzymes in DNA replication that have not previously been a target for any marketed antibiotic, development of drug resistance will be minimized. The compounds can be used to circumvent the natural and acquired resistance of pathogenic Gram-positive bacteria to conventional antimicrobials without harmful effects to the infected animal.

The toxicity of the compounds toward mammalian cells can be evaluated according to standard methods known to those skilled in the art (see, e.g., Gootz, Clin. Microbial. Rev. 1990, 3, 13-31). The toxic concentration (or "$IC_{50}$") can be determined by using protocols well known in the field of pharmacology. A suitable range of $IC_{50}$ values for a compound to be considered for further therapeutic evaluation will be greater than the MIC in bacterial cultures, i.e., the therapeutic index should be greater than 10.

Therapeutic Administration of Compounds

The compounds described herein are useful for the treatment of microbial infections in humans caused by Gram-positive bacteria, including strains resistant to common antibiotic drugs. They are also useful for the treatment of related Gram-positive bacterial infections in animals such as pigs, cows, horses, goats, chickens, turkeys, sheep, rats, mice, and rabbits, and for eliminating or avoiding bacterial or mycoplasmal infections of eukaryotic cell cultures or other media, e.g., foods, cosmetics, medical devices, and hospital supplies.

The compounds of the invention can be formulated for pharmaceutical, veterinary, and tissue culture use, optionally together with an acceptable diluent, carrier, or excipient and/or in unit dosage form. In using the compounds of the invention, conventional pharmaceutical, veterinary, or culture practice can be employed to provide suitable formulations or compositions, all of which are encompassed by the pharmaceutical compositions of this invention.

For human or animal use, the formulations of this invention can be administered by parenteral administration, for example, intravenous, subcutaneous, intramuscular, intraorbital, ophthalmic, intraventricular, intracranial, intracapsular, intraspinal, intracisternal, or intraperitoneal administration, or by intranasal, aerosol, scarification, oral, buccal, rectal, vaginal, or topical administration. The formulations of this invention may also be administered by the use of surgical implants which release the compounds of the invention, either as a bolus or slowly over a pre-selected period of time.

Without limitation, parenteral formulations can be, for example, in the form of liquid solutions or suspensions for oral administration, formulations can be, for example, in the form of tablets, capsules, liquid solutions and suspensions (wherein such solutions and suspensions are particularly for formulations intended for pediatric use); and for intranasal administration, the formulations can be, for example, in the form of powders, nasal drops, or aerosols. Other suitable formulations for parenteral, oral or intranasal delivery of the compounds of this invention will be well known to those of ordinary skill in the art. Methods well known in the art for making formulations can be found in, for example, "Remington's Pharmaceutical Sciences." formulations for parenteral administration may contain as excipients sterile water or saline, ethanol, propylene glycol, polyalkylene glycols such as polyethylene glycol, oils of vegetable origin, hydrogenated naphthalenes, or biocompatible, biodegradable lactide polymers. Polyoxyethylene-polyoxypropylene copolymers can be used to control the release of the present compounds. Other potentially useful parenteral delivery systems for the pounds of the invention include ethylene-vinyl acetate copolymer particles, osmotic pumps, implantable infusion systems, and liposomes. Formulations for inhalation may contain lactose as an excipient, or can be aqueous solutions containing, for example, polyoxyethylene-9-lauryl ether, glycocholate and deoxycholate, or can be oily solutions for administration in the form of nasal drops, or can be gels to be applied intranasally. Formulations for parenteral administration may also include glycocholate for buccal administration, methoxysalicylate for rectal administration, or citric acid for vaginal administration.

The concentration of the compound in the formulations of the invention will vary depending on a number of factors, including the dosage to be administered, and the route of administration. In general, the compounds of the invention can be provided in an aqueous physiological buffer solution containing about 0.1 to 10% w/v compound for parenteral administration. General dose ranges are from about 0.01 mg/kg to about 1 g/kg of body weight per day, e.g., from about 0.01 mg/kg to 100 mg/kg of body weight per day. The dosage to be administered depends upon the type and extent of progression of the infection being addressed, the overall health of the patient, and the route of administration. For topical and oral administration, formulations and dosages can be similar to those used for other antibiotic drugs.

In one embodiment, a compound or composition of the invention is administered to an animal, such as a human, patient, that has been diagnosed with a Gram-positive bacterial infection. The compounds can also be administered to the animal or human to inhibit or reduce the likelihood of a Gram-positive bacterial infection, particularly in an animal or human susceptible to such infections (including, without limitation, a human patient who is immunodeficient or immunocompromised or one who has recently undergone a medical procedure). In other embodiments, cultured eukaryotic cells are treated with the new compositions, or the compositions are added to inhibit or reduce the likelihood of such infections (e.g., prophylactic treatment). The compounds of the invention may also be used the prevent bacterial growth in food products, cosmetics, and medical supplies, and on surfaces.

The compounds can be administered both prophylactically and after infection has occurred. Prophylaxis can be most appropriate for immunocompromised human patients and animals and for patients and animals following surgery or dental procedures. This list of relevant conditions for application of the methods of the invention is not intended to be limiting, and any appropriate infection responsive to the compounds can be treated using the 25 methods and/or compounds described herein.

The compounds may also be used to treat or coat media or surfaces to prevent or reduce the extent of microbial growth. For example, the compounds of the invention can be mixed with eukaryotic culture media (e.g., solid or liquid media) in order to prevent Gram-positive bacterial growth. In addition, the compounds of the invention may be used in disinfectant formulations for treating surfaces, e.g., a liquid formulation for cleaning and disinfecting surfaces, such as those in kitchens, bathrooms, hospitals, or other areas of medical treatment or potential microbial growth. Medical devices and other surfaces can also be treated or coated with compounds of the invention in order to control microbial growth. Medical devices include those that are wholly or partially implanted in an animal and those external to an animal. Examples of medical devices include, without limitation, catheters, dialysis pumps, blood collection equipment, stents, and drug delivery devices. Standard formulations for the use of the compounds of the invention for surface treatments or in coatings are known to those skilled in the art.

DNA Polymerase IIIC Production

The DNA polymerase IIIC coding genes were amplified from genomic DNA. The primers were designed so the 5'-terminal and 3'-terminal contain BamHI and XhoI cutting site respectively. The fragment was directly inserted into expression plasmid pET-28a(+) between BamHI and XhoI sites. The recombinant protein had full length of original protein and a His tag, a thrombin site and a T7 tag at N-terminus. The coding sequence of recombinant protein was confirmed by Sanger sequencing using 8 primers to cover the entire coding regions.

The plasmid was transferred into BL21 (DE3) competent $E.$ $coli$ cells. The positive colonies were inoculated into 1 L LB medium and incubated at 37° C. with 200 rpm rotation to reach OD600=0.6. The inducer IPTG 1 mM was then added to induce the expression for 18 hours at 16° C. The cells were harvested and suspended in lysis buffer (25 mM Tris-HCl pH=7.5, 0.15 M NaCl, 20 mM imidazole, 2 mM β-mercaptoethanol and 1×Roche proteinase inhibitor cocktail). The cells were lyzed by sonication, and the debris was spun down at 50000 g for 1 hour.

The protein was isolated first by passing through the lysate through Ni column. The column was washed with 50 column volume (CV) binding buffer (lysis buffer without proteinase inhibitor) and then 10 CVs of washing buffer (binding buffer with total 40 mM imidazole). The protein was eluted out with elusion buffer (binding buffer with total 300 mM imidazole).

The crude extract was then further purified by size exclusion chromatography using a Superdex 200 increase 10/300 column with 25 mM Tris-HCl pH 7.5, 0.15 M NaCl, 5% Glycerol and 1 mM DTT. The final product was stored as 50-100 μL aliquots at −80° C.

Ki Assay for DNA Polymerase IIIC

The compounds were dissolved in DMSO to 1 mg/ml (or 10 mg/ml) as compound working solution. On the day of the test, 180 μL of DMSO was added into well A, and 100 μL of DMSO was added into wells B through well H in a round bottom 96 well plate (Corning-3788). An aliquot of 20 μL compound working solution was added into well A and mixed by pipetting. From well A, 50 µL solution was transferred to well B and mixed by pipetting to make a 3× dilution. The procedure was repeated for well B to well C, and so forth until well G. Well H contained DMSO only. This generated a serial of compound working solutions with concentrations at 100, 33.3, 11.1, 3.7, 1.2, 0.4, 0.14, and 0 µg/ml in pure DMSO. This was deemed the 'mother plate'.

Using a 96-head pipette station (CyBio), 1 µL compound working solutions were transferred from the mother plate into an identical 96-well plate. This was the 'testing plate'. The testing plate was kept at room temperature.

The enzyme (DNA polymerase IIIC) samples were taken out from −80° C. freezer. It was thawed and kept on ice. The enzyme was diluted to 0.025-0.06 U/L with dilution buffer (25 mM Tris-HCl, pH=7.5, 0.15M NaCl, 5% Glycerol, 1 mM DTT). One unit of enzyme is defined as the amount of enzyme could incorporate 250 µmole of dTTP in 30 minutes in a standard assay (with the presence of all nucleotide as substrate, in contrast to "truncated assay" from which dGTP was omitted) in the same system. The diluted enzymes were added into a new 96-well plate (Corning-3788) 20 µL per well. This plate was kept on ice. This was the 'enzyme plate'.

To make a master reaction mix, the following reagents were added and mixed in an appropriate tube in order (keep the master mix on ice at all time):

a) 500 µL/ml 40% glycerol
b) 30 µL/ml 1 M Tris-HCl (pH=7.5) (Aldrich-154563)
c) 20 µL/ml 0.5 M MgAc (Hushi 30110518)
d) 4 µL/ml 1M DTT (Aladdin D104859)
e) 25 µL/ml 1 mM dATP (Sangon Biotech)
f) 25 µL/ml 1 mM dCTP (Sangon Biotech)
g) 10 µl/ml 1 mM dTTP (Sangon Biotech)
h) 400/ml 1 mg/ml activated calf thymus DNA (Sigma D4522)

The master mix was mixed briefly and spiked with 5 µL/ml 2'-dTTP tetra Na Salt[methy-$^3$H] 2.5 mCi/ml (PerkinElmer). This was the final master mix. The final master mix was poured into a reservoir and 25 µL was added into each well of the testing plate containing 1 µL compounds already. Then an aliquot of 1 µL diluted enzyme from enzyme plate was added into the corresponding wells of the testing plate.

The testing plate contained 0.025 U of enzyme, a serial of concentrations of compounds for each well and with total volume of 27 µL. The plate was immediately placed in a 31° C. incubator and incubated for 30 minutes with agitation.

The plate was taken out of the incubator and immediately 100 µL of 4° C. 10% TCA (Sa En Chemical 10000253) was added into each well to stop the reaction. The plate was incubated at 4° C. for 30 minutes to allow the macromolecular to precipitate. A Unifilter GF/B filter plate (PerkinElmer) was pre-wet with 50l/well 1 M HCl+100 mM sodium pyrophosphate (Alfa Aesar A17546). The samples were harvested onto the filter plate, using a PerkinElmer cell harvester. The filter plate was washed with ~200 µL of cold 1 M HCl+100 mM sodium pyrophosphate four times and then with ~200 µL of cold 90% ethanol twice on the cell harvester. The filter plate was dried in a 50° C. oven for 20 min.

The bottom of the filter plate was sealed with a compatible sticker (PerkinElmer), 50 µL of scintillation cocktail (MicroScint-O) was added into each well, and the top of the plate was sealed with a transparent film. The plate was analyzed using a MicroBeta counter. A conventional 3H protocol was used to measure the scintillation for 30 s each well. The data were read as count per minute (CPM).

The raw data were analyzed in GraphPad Prism using a built-in nonlinear regression equation, log (inhibitor) vs. normalized response-variable slope. The assay used provides a Ki value directly for the multi-substrate enzyme (the Ki of a given inhibitor is defined as the concentration which yielded 50% inhibition of the control activity) (Wright, et al.; Cer, et al.; Torti, et al.)

Determination of Minimum Inhibitory Concentration

Materials and Methods

Test Articles:

Levofloxacin (Sigma-28266-1G-F) and Vancomycin (Sigma-94747-1G) were purchased from SIGMA.

Bacterial Isolates:

Bacteria tested are *Staphylococcus aureus* NRS384 (a methicillin-resistant *Staphylococcus aureus*, MRSA), *Staphylococcus aureus* ATCC 29213 (a methicillin-sensitive *Staphylococcus aureus*, MSSA), *Streptococcus pneumoniae* ATCC 49619, *Enterococcus faecalis* ATCC 29212, *Enterococcus faecium* ATCC 700221 (a vancomycin-resistant enterococcus, VRE), *Bacillus subtilis* ATCC 6633, and *Escherichia coli* ATCC 25922. The details are listed in Table 1.

*Staphylococcus aureus* NRS384 was obtained from NARSA (Network on Antimicrobial Resistance in *Staphylococcus aureus*, now the strain collection is in BEI resources). Other bacterial isolates were from ATCC (The American Type Culture Collection). Upon receiving the bacteria samples from aforementioned institutes, the bacteria were cultured according to the manuals provided by the suppliers. The bacteria were stored in 25% glycerol (final concentration) at −80° C.

TABLE 1

MIC Screening Panel

| Species | Strain | Traits | Source | Growth Plate | Test Media |
|---|---|---|---|---|---|
| Staphylococcus aureus | NRS384 | MRSA | NARSA | MHA | MHIIB |
| Staphylococcus aureus | ATCC 29213 | MSSA | ATCC | MHA | MHIIB |
| Enterococcus faecalis | ATCC 29212 | Sensitive | ATCC | Blood agar | MHIIB |
| Enterococcus faecium | ATCC 700221 | VRE | ATCC | Blood agar | MHIIB |
| Streptococcus pneumoniae | ATCC 49619 | Sensitive | ATCC | Blood agar | MHIIB + 5% LHB |
| Bacillus subtilis | ATCC 6633 | Model bacterium | ATCC | MHA | MHIIB |
| Escherichia coli | ATCC 25922 | Sensitive | ATCC | MHA | MHIIB w & w/o 4 mM EDTA |

NHA: Mueller-Hinton IIAgar (BD-211438)

MHIIT: Mueller-Hinton II Broth (BD-212322)

LHB: Lysed Horse Blood (Shanghai YuanMu Biological Technology Co. Ltd. YMV-U161)

EDTA: Ethylenediaminetetraacetic acid (Invitrogen AM9260G)

Broth Microdilution Based Minimum Inhibition Concentration (MIC) determination

On the day of testing, the compounds were dissolved in pure DMSO (Sigma 276855-1L) to 20 mg as stock. In a v-bottom 96-well plate (Axygen-wipp02280), 20 µl DMSO was added into well 2 to well 12 by manual pipetting. Into well 1, 12.8 µL of compound DMSO stock (20 mg/ml) was added and mixed with 27.2 l DMSO by pipetting. Two fold serial dilutions were performed by transferring and mixing 20 l of solution from well 1 to well 2, then well 2 to well 3 and so forth until well 11. The well 12 was loaded with 20 l DMSO without compounds. This was drug 'mother plate'. From well 1 to well 12, the drug concentrations in the mother plate were 6.4, 3.2, 1.6, 0.8, 0.4, 0.2, 0.1, 0.05, 0.025, 0.0125 and 0.00625 μg/ml in DMSO. A multi-pipette was used to perform the serial dilutions. The concentration may be adjusted according to the potency of the compounds. An Echo® Acoustic liquid handling system may be used to replace manual pipetting to make the daughter plates.

One day prior to the day of MIC testing, bacterial strains were streaked out from −80° C. glycerol stocks onto MHA plates and incubated at 37° C. for 20 hours. *Streptococcus pneumoniae* was streaked on blood agar and incubated at 37° C. in 5% $CO_2$. The single colonies were picked by using an inoculation loop (Greiner-731175) and suspended into 5 ml sterile saline. The turbidity of the suspension was adjusted to 0.10 (Siemens MicroScan turbidity meter), equal to ~$1.0 \times 10^8$ cfu/ml. The bacterial suspension was diluted 200× in corresponding test medium (Table 1). This was used to inoculate daughter plates.

For preparing u-bottom 96-well 'daughter plates' (Costar 3788), an aliquot of 1 μl solution from mother plate was then replicating transferred into the daughter plate using a multi-pipette.

An aliquot of 99 l of the bacterial suspension was inoculated into each well of the daughter plates using a multi-pipette. Each well contained ~$5.0 \times 10^5$ cfu/ml bacteria, 1% DMSO and serially diluted compounds at 64, 32, 16, 8, 4, 2, 1, 0.5, 0.25, 0.125, 0.0625 and 0 μg/ml from well 1 to well 12 respectively, in 100 l corresponding test medium.

The plates were incubated in ambient atmosphere and in a 37° C. incubator for 20 hours.

The MIC values were determined by visual inspection as the lowest compound concentration that completely or significantly inhibits the growth of bacteria in the test medium. Compounds of the present invention were tested for antibacterial activity against a variety of bacterial organism including *Bacillus subtilis, Staphylococcus aureus, Enterococcus faecalis, Enterococcus faecium, Streptococcus pneumoniae* and *Escherichia coli*. Compounds described in Examples 2, 44, 56, 77, 126, 149, 167, 211, 212, 213, 214, 218, 242, 273 and 276 had Ki of 0.053-1.00 M against *Staphylococcus aureus* DNA pol IIIC enzyme. Compounds described in Examples 2, 44, 53, 56, 90, 134, 212, 213, 214, 218, 222, 304, 305, and 307 had MIC of ≤1 μg/ml against *S. aureus* NRS 384 (MRSA) (g/ml) and *E. faecium* ATCC 700221 (VRE) (μg/m).

The compounds showed weak Gram-negative activity with MICs of 16→64 g/ml against *Escherichia coli*. The MIC data of 320 compounds are shown in Table 2.

TABLE 2

MIC Data

| Compd # | Molecular weight | Purity | MIC *B. subtilis* ATCC 6633 (μg/ml) | MIC NRS 384 (MRSA) (μg/ml) | MIC *S. aureus* ATCC 29213 (MSSA) (μg/ml) | MIC *S. pneumoniae* ATCC 49619 (μg/ml) | MIC *E. faecalis* ATCC 29212 (μg/ml) | MIC *E. faecium* ATCC 700221 (VRE) (μg/ml) | MIC *E. coli* ATCC 25922 + 4 mM EDTA (μg/ml) | MIC *E. coli* ATCC 25922 (μg/ml) |
|---|---|---|---|---|---|---|---|---|---|---|
| 1 | 307.71 | 99.0% | 4 | 8 | 8 | 4 | 16 | 8 | 32 | >64 |
| 2 | 324.17 | 99.2% | 1 | 1 | 2 | 4 | 2 | 1 | >64 | >64 |
| 3 | 255.28 | 100.0% | 32 | 64 | 32 | 32 | 64 | 32 | >64 | >64 |
| 4 | 256.26 | 100.0% | >64 | >64 | >64 | >64 | >64 | >64 | >64 | >64 |
| 5 | 256.26 | 97.3% | >64 | >64 | >64 | >64 | >64 | >64 | >64 | >64 |
| 6 | 256.26 | 96.8% | >64 | >64 | >64 | >64 | >64 | >64 | >64 | >64 |
| 7 | 291.26 | 100.0% | 8 | 16 | 16 | 8 | 16 | 8 | >64 | >64 |
| 8 | 338.19 | 98.2% | >64 | >64 | >64 | >64 | >64 | >64 | >64 | >64 |
| 9 | 310.14 | 100.0% | >64 | >64 | >64 | >64 | >64 | >64 | >64 | >64 |
| 10 | 241.25 | 100.0% | >64 | >64 | >64 | >64 | >64 | >64 | >64 | >64 |
| 11 | 257.25 | 100.0% | >64 | >64 | >64 | >64 | >64 | >64 | >64 | >64 |
| 12 | 257.25 | 100.0% | >64 | >64 | >64 | >64 | >64 | >64 | >64 | >64 |
| 13 | 295.30 | 99.7% | >64 | >64 | >64 | >64 | >64 | >64 | >64 | >64 |
| 14 | 294.31 | 96.9% | >64 | >64 | >64 | >64 | >64 | >64 | >64 | >64 |
| 15 | 262.29 | 100.0% | >64 | >64 | >64 | >64 | >64 | >64 | >64 | >64 |
| 16 | 245.24 | 98.4% | >64 | >64 | >64 | >64 | >64 | >64 | >64 | >64 |
| 17 | 246.23 | 98.4% | >64 | >64 | >64 | >64 | >64 | >64 | >64 | >64 |
| 18 | 312.35 | 96.4% | >64 | >64 | >64 | >64 | >64 | >64 | >64 | >64 |
| 19 | 295.30 | 99.3% | >64 | >64 | >64 | >64 | >64 | >64 | >64 | >64 |
| 20 | 262.29 | 96.8% | >64 | >64 | >64 | >64 | >64 | >64 | >64 | >64 |
| 21 | 246.23 | 96.0% | >64 | >64 | >64 | >64 | >64 | >64 | >64 | >64 |
| 22 | 245.24 | 99.7% | >64 | >64 | >64 | >64 | >64 | >64 | >64 | >64 |
| 23 | 257.25 | 99.2% | >64 | >64 | >64 | >64 | >64 | >64 | >64 | >64 |
| 24 | 307.71 | 98.6% | 8 | 8 | 8 | 4 | >64 | 8 | >64 | >64 |
| 25 | 289.72 | 99.5% | 8 | 8 | 8 | 4 | 16 | 16 | 64 | >64 |
| 26 | 289.72 | 97.5% | 16 | 32 | 32 | 16 | 64 | 32 | 64 | >64 |
| 27 | 289.72 | 97.6% | >64 | >64 | >64 | >64 | >64 | >64 | 64 | >64 |
| 28 | 324.17 | 96.7% | 64 | >64 | >64 | 64 | >64 | 16 | 64 | >64 |
| 29 | 324.17 | 100.0% | >64 | >64 | >64 | >64 | >64 | >64 | >64 | >64 |
| 30 | 324.17 | 100.0% | >64 | >64 | >64 | >64 | >64 | >64 | >64 | >64 |
| 31 | 303.75 | 97.1% | 2 | 4 | 4 | 8 | 8 | 4 | 16 | >64 |
| 32 | 315.33 | 99.4% | >64 | >64 | >64 | >64 | >64 | >64 | >64 | >64 |
| 33 | 283.33 | 100.0% | 8 | 16 | 16 | 16 | 32 | 16 | >64 | >64 |
| 34 | 319.75 | 100.0% | >64 | >64 | >64 | 64 | >64 | >64 | >64 | >64 |
| 35 | 303.75 | 99.9% | 2 | 2 | 4 | 4 | 8 | 4 | >64 | >64 |
| 36 | 439.18 | 100.0% | >64 | >64 | >64 | >64 | >64 | >64 | >64 | >64 |
| 37 | 314.13 | 100.0% | >64 | >64 | >64 | >64 | >64 | >64 | >64 | >64 |

TABLE 2-continued

MIC Data

| Compd # | Molecular weight | Purity | MIC B. subtilis ATCC 6633 (µg/ml) | MIC NRS 384 (MRSA) (µg/ml) | MIC S. aureus ATCC 29213 (MSSA) (µg/ml) | MIC S. pneumoniae ATCC 49619 (µg/ml) | MIC E. faecalis ATCC 29212 (µg/ml) | MIC E. faecium ATCC 700221 (VRE) (µg/ml) | MIC E. coli ATCC 25922 + 4 mM EDTA (µg/ml) | MIC E. coli ATCC 25922 (µg/ml) |
|---|---|---|---|---|---|---|---|---|---|---|
| 38 | 344.20 | 99.0% | >64 | >64 | >64 | >64 | >64 | >64 | >64 | >64 |
| 39 | 283.29 | 97.6% | >64 | >64 | >64 | >64 | >64 | >64 | >64 | >64 |
| 40 | 382.20 | 99.6% | >64 | >64 | >64 | >64 | >64 | >64 | >64 | >64 |
| 41 | 368.17 | 97.4% | >64 | >64 | >64 | >64 | >64 | >64 | >64. | >64. |
| 42 | 381.22 | 98.7% | >64 | >64 | >64 | >64 | >64 | >64 | >64 | >64 |
| 43 | 395.24 | 93.4% | 64 | >64 | >64 | 64 | >64 | >64 | >64 | >64 |
| 44 | 338.19 | 97.1% | 2 | 2 | 2 | 4 | 4 | 4 | >64 | >64 |
| 45 | 349.17 | 97.2% | 2 | 4/4 | 4 | 16 | 4 | 2/2 | 64 | >64 |
| 46 | 392.24 | 97.7% | 4 | 8 | 4 | 16 | 16 | 8 | >64 | >64 |
| 47 | 394.26 | 94.9% | 8 | 16 | 16 | 32 | >64 | 16 | >64 | >64 |
| 48 | 368.22 | 100.0% | 4 | 4 | 8 | 4 | 16 | 8 | >64 | >64 |
| 49 | 396.27 | 99.6% | 8 | 8 | 16 | 16 | >64 | 16 | >64 | >64 |
| 50 | 465.29 | 95.8% | >64 | >64 | >64 | >64 | >64 | >64 | >64 | >64 |
| 51 | 423.25 | 98.8% | 1 | 2 | 2 | 2 | 2 | 0.5 | >64 | >64 |
| 52 | 477.14 | 99.4% | 1 | 4 | 2 | 16 | 4 | 2 | >64 | >64 |
| 53 | 342.16 | 95.4% | 0.5 | 0.5 | 0.5 | 2 | 2 | 0.5 | 64 | >64 |
| 54 | 328.13 | 94.2% | 4 | 8 | 8 | 32 | 16 | 4 | >64 | >64 |
| 55 | 344.58 | 98.1% | 2 | 4 | 4 | 8 | 8 | 4 | 64 | >64 |
| 56 | 350.20 | 99.1% | 0.25 | 0.5 | 1 | 2 | 2 | 0.5 | >64 | >64 |
| 57 | 423.30 | 100.0% | 1 | 2 | 2 | 2 | 4 | 1 | >64 | >64 |
| 58 | 436.34 | 99.6% | 2 | 8 | 16 | 4 | 8 | 4 | >64 | >64 |
| 59 | 471.36 | 99.9% | 4 | 8 | 8 | 4 | 8 | 2 | >64 | >64 |
| 60 | 450.32 | 100.0% | 4 | 8 | 8 | 4 | 8 | 2 | >64 | >64 |
| 61 | 367.23 | 98.9% | 8 | 64 | 64 | 16 | 32 | 16 | >64 | >64 |
| 62 | 409.31 | 98.1% | 4 | 16 | 16 | 4 | 8 | 8 | 32 | >64 |
| 63 | 353.21 | 99.2% | 8 | 64 | 64 | 8 | 32 | 32 | >64 | >64 |
| 64 | 464.35 | 98.1% | 2 | 8 | 8 | 4 | 4 | 2 | >64 | >64 |
| 65 | 473.78 | 95.9% | 4 | 16 | 16 | 4 | 8 | 8 | 64 | >64 |
| 66 | 500.81 | 95.9% | 8 | 32 | 64 | 8 | 32 | 16 | 64 | >64 |
| 67 | 537.31 | 98.0% | 8 | 32 | 32 | 8 | 16 | 16 | >64 | >64 |
| 68 | 471.77 | 99.1% | 1 | 4 | 4 | 4 | 4 | 4/2 | 64 | >64 |
| 69 | 521.27 | 95.4% | 4 | 64 | 32 | 8 | 32 | >64 | >64 | >64 |
| 70 | 445.73 | 94.8% | 16 | 64 | >64 | 8 | 64 | >64 | 64 | >64 |
| 71 | 539.29 | 99.8% | 4 | 64 | 32 | 4 | 32 | 16 | >64 | >64 |
| 72 | 530.84 | 98.7% | 4 | 16 | 16 | 8 | 8 | 8 | >64 | >64 |
| 73 | 553.31 | 95.0% | 4 | 16 | 16 | 8 | 16 | 8 | >64 | >64 |
| 74 | 422.31 | 100.0% | 8 | 64 | 32 | 16 | 64 | 16 | >64 | >64 |
| 75 | 384.22 | 100.0% | 8 | 16 | 16 | 4 | 16 | 8 | >64 | >64 |
| 76 | 354.19 | 99.5% | 2 | 4 | 4 | 4 | 4 | 2 | >64 | >64 |
| 77 | 310.14 | 98.3% | 4 | 8 | 8 | 4 | 8 | 4 | >64 | >64 |
| 78 | 689.38 | 100.0% | 4 | 32 | 64 | 32 | 8 | 2 | >64 | >64 |
| 79 | 476.32 | 96.1% | 16 | 32 | 16 | 8 | 16 | 8 | >64 | >64 |
| 80 | 490.34 | 98.0% | 16 | 32 | 32 | 8 | 32 | 16 | 64 | >64 |
| 81 | 523.76 | 97.5% | 64 | 64 | 64 | 8 | 32 | 32 | 64 | >64 |
| 82 | 462.29 | 99.7% | 8 | 16 | 16 | 8 | 8 | 4 | >64 | >64 |
| 83 | 509.73 | 100.0% | 64 | >64 | >64 | 8 | >64 | >64 | >64 | >64 |
| 84 | 509.73 | 97.3% | 64 | 64 | 64 | 16 | 64 | 32 | >64 | >64 |
| 85 | 542.21 | 100.0% | 4 | 8 | 8 | 8 | 8 | 4 | 16 | >64 |
| 86 | 448.26 | 99.4% | >64 | >64 | >64 | >64 | >64 | >64 | >64 | >64 |
| 87 | 523.76 | 99.8% | 64 | >64 | 64 | 8 | 32 | 32 | >64 | >64 |
| 88 | 398.24 | 98.5% | 2 | 4 | 4 | 2 | 4 | 2 | >64 | >64 |
| 89 | 382.20 | 99.0% | 1 | 2 | 4 | 2 | 4 | 1 | 64 | >64 |
| 90 | 424.30 | 99.0% | 0.5 | 1 | 2 | 2 | 2 | 1 | >64 | >64 |
| 91 | 407.28 | 100.0% | 1 | 2 | 4 | 4 | 4 | 2 | 32 | >64 |
| 92 | 391.21 | 100.0% | 2 | 4 | 4 | 4 | 4 | 2 | 8 | >64 |
| 93 | 407.25 | 100.0% | 4 | 16 | 8 | 2 | 8 | 4 | 64 | >64 |
| 94 | 421.28 | 98.2% | 8 | 16 | 16 | 4 | 16 | 4 | >64 | >64 |
| 95 | 498.40 | 99.0% | 2 | 4 | 4 | 8 | 16 | 4 | >64 | >64 |
| 96 | 455.30 | 95.0% | >64 | >64 | >64 | 64 | >64 | 64 | 32 | >64 |
| 97 | 404.25 | 95.3% | 8 | 8 | 8 | 4 | >64 | 8 | >64 | >64 |
| 98 | 479.36 | 98.3% | 2 | 8 | 8 | 16 | >64 | 4 | >64 | >64 |
| 99 | 433.72 | 100.0% | 2 | 64 | 64 | 4 | 32 | 32 | 64 | >64 |
| 100 | 497.37 | 99.2% | 2 | >64 | >64 | 8 | >64 | 4 | >64 | >64 |
| 101 | 427.68 | 95.1% | 2 | 8/8 | 4 | 4 | 4 | 2/4 | 64 | >64 |
| 102 | 394.26 | 99.7% | 1 | 4/4 | 4 | 4 | 4 | 2/4 | >64 | >64 |
| 103 | 427.68 | 92.5% | 32 | 64 | 64 | 16 | >64 | 64 | 64 | >64 |
| 104 | 414.31 | 99.3% | 1 | 4/4 | 4 | 4 | 4 | 2/2 | >64 | >64 |
| 105 | 410.25 | 96.6% | 1 | 4/2 | 4 | 4 | 8 | 4/2 | >64 | >64 |
| 106 | 412.27 | 95.1% | 32 | 32 | 64 | 32 | >64 | 32 | >64 | >64 |
| 107 | 384.22 | 95.6% | 32 | >64 | >64 | 16 | >64 | >64 | >64 | >64 |

TABLE 2-continued

MIC Data

| Compd # | Molecular weight | Purity | MIC B. subtilis ATCC 6633 (µg/ml) | MIC NRS 384 (MRSA) (µg/ml) | MIC S. aureus ATCC 29213 (MSSA) (µg/ml) | MIC S. pneumoniae ATCC 49619 (µg/ml) | MIC E. faecalis ATCC 29212 (µg/ml) | MIC E. faecium ATCC 700221 (VRE) (µg/ml) | MIC E. coli ATCC 25922 + 4 mM EDTA (µg/ml) | MIC E. coli ATCC 25922 (µg/ml) |
|---|---|---|---|---|---|---|---|---|---|---|
| 108 | 438.31 | 99.6% | 2 | 8/4 | 4 | 4 | 8 | 4/2 | >64 | >64 |
| 109 | 437.71 | 92.6% | 2 | 64 | >64 | 4 | >64 | 4 | >64 | >64 |
| 110 | 451.74 | 98.7% | 1 | 2/2 | 4 | 4 | 4 | 2/2 | >64 | >64 |
| 111 | 451.74 | 98.6% | 1 | 2/2 | 4 | 4 | 8 | 2/2 | >64 | >64 |
| 112 | 438.70 | 93.8% | 1 | 4/4 | 4 | 4 | 8 | 2/2 | >64 | >64 |
| 113 | 437.71 | 98.5% | 1 | 4/4 | 4 | 8 | 8 | 2/2 | >64 | >64 |
| 114 | 402.24 | 94.7% | 2 | 4/4 | 8 | 4 | 16 | 4/4 | 32 | >64 |
| 115 | 442.30 | 99.8% | 8 | 32 | 32 | 16 | 32 | 8 | >64 | >64 |
| 116 | 486.35 | 98.4% | 8 | 32 | 64 | 8 | 16 | 8 | >64 | >64 |
| 117 | 416.26 | 92.7% | 2 | 8 | 8 | 4 | 8 | 4 | >64 | >64 |
| 118 | 380.23 | 93.8% | 0.5 | 2 | 2 | 2 | 2 | 1 | >64 | >64 |
| 119 | 380.23 | 94.3% | 1 | 4 | 2 | 4 | 4 | 2 | >64 | >64 |
| 120 | 394.26 | 98.7% | 1 | 2 | 2 | 4 | 4 | 2 | >64 | >64 |
| 121 | 394.26 | 98.8% | 0.5 | 2 | 4 | 4 | 4 | 2 | >64 | >64 |
| 122 | 380.23 | 94.5% | 1 | 2 | 2 | 4 | 4 | 2 | >64 | >64 |
| 123 | 368.22 | 100.0% | 0.5 | 2 | 2 | 2 | 4 | 1 | >64 | >64 |
| 124 | 452.72 | 93.8% | 1 | 2 | 4 | 8 | 4 | 2 | >64 | >64 |
| 125 | 347.32 | 99.8% | 32 | 32 | 32 | 8 | 32 | 32 | >64 | >64 |
| 126 | 368.22 | 99.3% | 1 | 2 | 2 | 2 | 4 | 2 | >64 | >64 |
| 127 | 400.26 | 98.8% | 1 | >64 | >64 | >64 | >64 | 32 | >64 | >64 |
| 128 | 368.22 | 98.1% | 16 | 32 | 32 | 16 | 32 | 32 | >64 | >64 |
| 129 | 400.26 | 98.1% | >64 | >64 | >64 | >64 | >64 | >64 | >64 | >64 |
| 130 | 352.22 | 100.0% | 1 | 2 | 2 | 4 | 4 | 2 | 16 | >64 |
| 131 | 410.30 | 97.7% | 1 | 2 | 2 | 4 | 4 | 2 | >64 | >64 |
| 132 | 352.22 | 100.0% | 8 | >64 | >64 | 16 | >64 | 16 | >64 | >64 |
| 133 | 410.30 | 100.0% | 8 | >64 | >64 | 16 | >64 | 64 | >64 | >64 |
| 134 | 378.26 | 96.5% | 0.5 | 1 | 1 | 8 | >64 | 1 | >64 | >64 |
| 135 | 378.26 | 100.0% | 4 | 8 | 32 | 16 | >64 | 8 | 8 | >64 |
| 136 | 412.27 | 98.1% | 1 | 4 | 4 | 2 | 4 | 2 | >64 | >64 |
| 137 | 412.27 | 99.9% | 16 | 32 | 32 | 16 | 32 | 16 | >64 | >64 |
| 138 | 398.24 | 90.5% | 1 | 2 | 2 | 2 | 4 | 2 | >64 | >64 |
| 139 | 388.21 | 96.8% | >64 | >64 | >64 | >64 | >64 | >64 | >64 | >64 |
| 140 | 388.21 | 94.9% | 4 | >64 | >64 | 4 | >64 | 32 | >64 | >64 |
| 141 | 412.23 | 95.1% | >64 | >64 | >64 | >64 | >64 | >64 | >64 | >64 |
| 142 | 366.20 | 93.6% | 1 | 2 | 4 | 4 | 4 | 2 | >64 | >64 |
| 143 | 366.20 | 96.0% | 16 | 32 | 64 | 16 | 32 | 32 | >64 | >64 |
| 144 | 391.21 | 99.8% | 2 | 4 | 4 | 8 | 16 | 2 | >64 | >64 |
| 145 | 396.23 | 90.4% | 32 | 64 | 64 | 16 | 64 | 16 | >64 | >64 |
| 146 | 442.28 | 96.0% | 32 | >64 | >64 | 32 | 64 | 32 | >64 | >64 |
| 147 | 459.76 | 99.9% | 2 | 4 | 8 | 4 | 8 | 2 | 64 | >64 |
| 148 | 509.39 | 99.9% | 2 | 4 | 8 | 16 | 16 | 4 | >64 | >64 |
| 149 | 445.73 | 100.0% | 2 | 32 | 16 | 4 | 16 | 8 | 64 | >64 |
| 150 | 564.81 | 98.7% | >64 | >64 | >64 | >64 | >64 | >64 | >64 | >64 |
| 151 | 459.71 | 95.6% | >64 | >64 | >64 | 64 | >64 | >64 | >64 | >64 |
| 152 | 393.27 | 96.4% | 4 | 16 | 16 | 2 | 16 | 8 | 32 | >64 |
| 153 | 493.39 | 96.2% | 2 | 4 | 8 | 16 | 4 | 2 | n/a | >64 |
| 154 | 443.76 | 99.1% | 8 | 32 | 32 | 4 | 32 | 32 | 32 | >64 |
| 155 | 429.73 | 99.5% | 4 | 64 | 32 | 8 | 64 | 32 | >64 | >64 |
| 156 | 570.88 | 98.5% | 1 | 2 | 2 | 4 | >64 | 1 | >64 | >64 |
| 157 | 487.81 | 98.3% | 2 | 4 | 8 | 4 | 8 | 2 | 64 | >64 |
| 158 | 437.28 | 98.0% | 8 | 32 | 16 | 4 | 16 | 8 | >64 | >64 |
| 159 | 421.28 | 99.3% | 2 | 8 | 8 | 2 | 8 | 2 | >64 | >64 |
| 160 | 503.81 | 97.0% | 4 | 16 | 16 | 4 | 16 | 8 | 64 | >64 |
| 161 | 543.28 | 98.5% | 2 | 4 | 8 | 16 | >64 | 2 | >64 | >64 |
| 162 | 543.28 | 95.0% | 1 | 2/4 | 4 | 2 | 4 | 2/2 | 8 | >64 |
| 163 | 543.28 | 97.0% | 0.5 | 2/2 | 2 | 8 | >64 | 2/2 | >64 | >64 |
| 164 | 446.31 | 99.1% | 16 | 64 | 32 | 4 | 32 | 16 | >64 | >64 |
| 165 | 445.28 | 99.0% | >64 | >64 | >64 | >64 | >64 | >64 | >64 | >64 |
| 166 | 566.48 | 98.6% | 4 | >64 | >64 | 16 | >64 | 8 | >64 | >64 |
| 167 | 539.29 | 99.6% | 16 | >64 |  | 16 | 64 | 64 | >64 | >64 |
| 168 | 412.27 | 98.7% | 4 | 8 | 8 | 8 | 8 | 4 | >64 | >64 |
| 169 | 412.27 | 98.0% | 2 | 8 | 8 | 8 | 8 | 4 | >64 | >64 |
| 170 | 467.74 | 99.9% | 1 | 2/2 | 4 | 8 | 4 | 4/1 | >64. | >64. |
| 171 | 421.24 | 95.2% | 4 | 16 | 32 | 8 | 16 | 8 | >64 | >64 |
| 172 | 524.83 | 97.1% | 4 | 16 | 16 | 8 | 16 | 8 | 64 | >64 |
| 173 | 510.80 | 92.7% | 8 | 32 | 32 | 8 | 32 | 32 | 64 | >64 |
| 174 | 497.76 | 97.6% | 2 | 8/8 | 8 | 8 | 8 | 2/2 | >64 | >64 |
| 175 | 511.75 | 98.4% | >64 | >64 | >64 | >64 | >64 | >64 | >64 | >64 |
| 176 | 465.33 | 97.7% | 4 | 16 | 16 | 4 | 8 | 4 | >64 | >64 |
| 177 | 451.31 | 97.9% | 16 | 64 | 64 | 4 | 32 | 16 | >64 | >64 |

TABLE 2-continued

MIC Data

| Compd # | Molecular weight | Purity | MIC B. subtilis ATCC 6633 (μg/ml) | MIC NRS 384 (MRSA) (μg/ml) | MIC S. aureus ATCC 29213 (MSSA) (μg/ml) | MIC S. pneumoniae ATCC 49619 (μg/ml) | MIC E. faecalis ATCC 29212 (μg/ml) | MIC E. faecium ATCC 700221 (VRE) (μg/ml) | MIC E. coli ATCC 25922 + 4 mM EDTA (μg/ml) | MIC E. coli ATCC 25922 (μg/ml) |
|---|---|---|---|---|---|---|---|---|---|---|
| 178 | 410.25 | 94.5% | 2 | 4/4 | 4 | 4 | 8 | 4/4 | >64 | >64 |
| 179 | 438.31 | 99.4% | 1 | 4 | 8 | 4 | 4 | 2 | >64 | >64 |
| 180 | 529.25 | 99.7% | 2 | 4/4 | 8 | 4 | 8 | 4/4 | 16 | 64 |
| 181 | 481.76 | 99.3% | 1 | 4/2 | 4 | 4 | 8 | 4/1 | >64. | >64. |
| 182 | 506.82 | 99.4% | 2 | 4/8 | 4 | 8 | 8 | 4/2 | >64. | >64. |
| 183 | 505.83 | 99.4% | 8 | 64 | 64 | 8 | 32 | 32 | >64 | >64 |
| 184 | 491.80 | 96.2% | 8 | 64 | 64 | 8 | 64 | 64 | 64 | >64. |
| 185 | 525.82 | 99.2% | 4 | 16 | 16 | 8 | 16 | 16 | >64. | >64. |
| 186 | 470.31 | 96.2% | 4 | 8 | 16 | >64 | 16 | 4 | >64 | >64 |
| 187 | 456.28 | 96.5% | 64 | >64 | >64 | >64 | 64 | 64 | >64 | >64 |
| 188 | 486.37 | 95.4% | 4 | 16 | 16 | 8 | 8 | 4 | >64 | >64 |
| 189 | 432.26 | 92.9% | 16 | 16 | 16 | 64 | 16 | 8 | 64 | >64 |
| 190 | 460.31 | 100.0% | >64 | >64 | >64 | >64 | >64 | >64 | >64 | >64 |
| 191 | 411.24 | 96.2% | 2 | 8 | 4 | 4 | 8 | 2 | >64 | >64 |
| 192 | 394.26 | 95.8% | 1 | 2 | 2 | 4 | 4 | 2 | >64 | >64 |
| 193 | 438.31 | 99.5% | 1 | 4 | 4 | 4 | 8 | 4 | >64 | >64 |
| 194 | 515.82 | 97.4% | 8 | >64 | 64 | 16 | 32 | 32 | 64 | >64 |
| 195 | 473.78 | 97.9% | 8 | >64 | >64 | 16 | 64 | 64 | >64 | >64 |
| 196 | 487.77 | 98.3% | >64 | >64 | >64 | >64 | >64 | >64 | >64 | >64 |
| 197 | 497.45 | 94.0% | >64 | >64 | >64 | >64 | >64 | >64. | >64 | >64 |
| 198 | 451.35 | 98.8% | 4 | 16 | 16 | 16 | 16 | 16 | >64 | >64 |
| 199 | 438.31 | 100.0% | 32 | 16 | 16 | 8 | 16 | 8 | >64. | >64. |
| 200 | 499.39 | 99.9% | 2 | 8 | 8 | 16 | 16 | 8 | >64 | >64 |
| 201 | 486.35 | 98.2% | 64 | 32 | 32 | 16 | 32 | 16 | >64. | >64. |
| 202 | 424.28 | 99.5% | 32 | 32 | 32 | 8 | 32 | 16 | >64 | >64 |
| 203 | 438.31 | 97.8% | 0.5 | 2 | 2 | 8 | >64 | 2 | >64 | >64 |
| 204 | 452.33 | 96.8% | 1 | 2 | 4 | 16 | >64 | 2 | >64 | >64 |
| 205 | 424.28 | 99.7% | 1 | 2 | 4 | 8 | 4 | 2 | >64 | >64 |
| 206 | 438.31 | 100.0% | 1 | >64 | >64 | 16 | >64 | 4 | >64 | >64 |
| 207 | 440.28 | 98.7% | 2 | 16 | 16 | 8 | 8 | 4 | >64 | >64 |
| 208 | 440.28 | 98.0% | 2 | 16 | 16 | 8 | 8 | 4 | >64 | >64 |
| 209 | 428.25 | 99.7% | 4 | 16 | 8 | 4 | 4 | 1 | >64 | >64 |
| 210 | 395.34 | 99.6% | 64 | 64 | 32 | 16 | 32 | 16 | >64 | >64 |
| 211 | 461.77 | 100.0% | 2 | 32 | 32 | 4 | 16 | 8 | >64 | >64 |
| 212 | 385.05 | 99.0% | 1 | 1 | 1 | 8 | >64 | 1 | >64 | >64 |
| 213 | 349.05 | 99.0% | 0.5 | 1 | 1 | 4 | 2 | 1 | >64 | >64 |
| 214 | 377.10 | 98.0% | 0.5 | 1 | 2 | 8 | 2 | 1 | >64 | >64 |
| 215 | 493.27 | 98.5% | 64 | >64 | >64 | 16 | >64 | >64 | 64 | >64 |
| 216 | 379.24 | 99.0% | 4 | 16 | 16 | 4 | 16 | 16 | >64 | >64 |
| 217 | 425.30 | 99.0% | 8 | 32 | 32 | 4 | 16 | 16 | >64 | >64 |
| 218 | 424.30 | 99.0% | 0.5 | 1 | 1 | 2 | 2 | 1 | >64 | >64 |
| 219 | 410.30 | 98.0% | 32 | 16 | 32 | 4 | 16 | 4 | >64 | >64 |
| 220 | 460.33 | 99.6% | 4 | 16 | 8 | 2 | 8 | 2 | >64 | >64 |
| 221 | 419.08 | 98.5% | >64 | >64 | >64 | 64 | >64 | 32 | >64 | >64 |
| 222 | 501.25 | 98.5% | 1 | 1 | 2 | 2 | 4 | 2 | 64 | >64 |
| 223 | 382.20 | 100.0% | >64 | >64 | >64 | >64 | >64 | >64 | >64 | >64 |
| 224 | 396.23 | 96.9% | >64 | >64 | >64 | 32 | >64 | >64 | >64 | >64 |
| 225 | 368.22 | 99.6% | 32 | 64 | 64 | 16 | 64 | 32 | >64 | >64 |
| 226 | 382.20 | 99.2% | 64 | 64 | >64 | >64 | >64 | 64 | >64 | >64 |
| 227 | 396.23 | 99.3% | 4 | 8 | 8 | 16 | 16 | 4 | 32 | >64 |
| 228 | 368.22 | 99.2% | 4 | 8 | 16 | 8 | 16 | 8 | 64 | >64 |
| 229 | 382.20 | 98.9% | >64 | >64 | >64 | 16 | 64 | 64 | >64 | >64 |
| 230 | 382.20 | 99.1% | 64 | 64 | >64 | 32 | 64 | 64 | 64 | >64 |
| 231 | 396.23 | 97.3% | 1 | 2 | 4 | 4 | 4 | 2 | >64 | >64 |
| 232 | 396.23 | 100.0% | 16 | 32 | >64 | 16 | >64 | 16 | >64 | >64 |
| 233 | 420.25 | 100.0% | 2 | 4 | 4 | 2 | 4 | 2 | 64 | >64 |
| 234 | 472.71 | 85.9% | 16 | 64 | 64 | 16 | 32 | 8 | >64 | >64 |
| 235 | 486.74 | 94.5% | 4 | 16 | 8 | 8 | 8 | 4 | >64 | >64 |
| 236 | 485.79 | 100.0% | 32 | >64 | >64 | 8 | 64 | 64 | 64 | >64 |
| 237 | 417.27 | 96.8% | 16 | 32 | 32 | 4 | 32 | 16 | 64 | >64 |
| 238 | 473.38 | 98.6% | 4 | 4 | 8 | 8 | 8 | 2 | >64 | >64 |
| 239 | 368.22 | 99.6% | 2 | 4 | 4 | 8 | 8 | 2 | >64 | >64 |
| 240 | 368.22 | 98.6% | 2 | 4 | 4 | 4 | 8 | 4 | >64 | >64 |
| 241 | 473.78 | 99.5% | 4 | 64 | 32 | 8 | 32 | 64 | >64 | >64 |
| 242 | 513.85 | 97.6% | 2 | 4 | 8 | 2 | 4 | 2 | 32 | >64 |
| 243 | 507.29 | 98.5% | 4 | 8 | 8 | 4 | 8 | 4 | 32 | >64 |
| 244 | 557.30 | 98.7% | 1 | 2 | 2 | 4 | 4 | 2 | 16 | >64 |
| 245 | 557.30 | 99.4% | 1 | 2 | 2 | 2 | 4 | 1 | 32 | >64 |
| 246 | 557.30 | 99.7% | 1 | 2 | 2 | 4 | 4 | 2 | >64 | >64 |
| 247 | 563.35 | 99.7% | 8 | 64 | 32 | 8 | 32 | 32 | 64 | >64 |

TABLE 2-continued

MIC Data

| Compd # | Molecular weight | Purity | MIC B. subtilis ATCC 6633 (μg/ml) | MIC NRS 384 (MRSA) (μg/ml) | MIC S. aureus ATCC 29213 (MSSA) (μg/ml) | MIC S. pneumoniae ATCC 49619 (μg/ml) | MIC E. faecalis ATCC 29212 (μg/ml) | MIC E. faecium ATCC 700221 (VRE) (μg/ml) | MIC E. coli ATCC 25922 + 4 mM EDTA (μg/ml) | MIC E. coli ATCC 25922 (μg/ml) |
|---|---|---|---|---|---|---|---|---|---|---|
| 248 | 704.57 | 93.5% | 4 | 16 | 16 | 8 | 4 | 4 | 8 | >64 |
| 249 | 563.35 | 96.5% | 4 | 16 | 16 | 4 | 16 | 8 | 64 | >64 |
| 250 | 637.01 | 94.9% | 4 | >64 | >64 | 8 | >64 | 4 | >64 | >64 |
| 251 | 563.35 | 98.6% | 4 | 16 | 16 | 8 | 16 | 16 | 64 | >64 |
| 252 | 534.83 | 99.7% | 1 | 4 | 4 | 2 | 4 | 2 | >64 | >64 |
| 253 | 488.33 | 99.7% | 1 | 2 | 2 | 2 | 4 | 2 | >64 | >64 |
| 254 | 504.39 | 100.0% | 1 | 2 | 2 | 4 | 4 | 2 | >64 | >64 |
| 255 | 498.36 | 100.0% | 2 | 4 | 4 | 2 | 4 | 2 | >64 | >64 |
| 256 | 498.36 | 100.0% | 2 | 4 | 8 | 4 | 4 | 2 | >64 | >64 |
| 257 | 520.80 | 100.0% | 2 | 4 | 4 | 4 | 8 | 4 | >64 | >64 |
| 258 | 520.80 | 100.0% | 2 | 8 | 8 | 4 | 8 | 4 | >64 | >64 |
| 259 | 520.80 | 99.1% | 2 | 8 | 8 | 4 | 4 | 4 | >64 | >64 |
| 260 | 564.85 | 99.8% | 1 | 4 | 4 | 4 | 4 | 2 | >64 | >64 |
| 261 | 548.85 | 100.0% | 1 | 4 | 4 | 4 | 4 | 2 | >64 | >64 |
| 262 | 548.85 | 99.0% | 1 | 4 | 4 | 4 | 4 | 2 | >64 | >64 |
| 263 | 564.85 | 99.4% | 1 | 2 | 4 | 2 | 4 | 1 | >64 | >64 |
| 264 | 548.85 | 100.0% | 1 | 2 | 4 | 4 | 4 | 1 | >64 | >64 |
| 265 | 524.79 | 96.8% | 4 | 8 | 8 | 4 | 4 | 4 | >64 | >64 |
| 266 | 564.85 | 99.7% | 2 | 8 | 8 | 4 | 4 | 2 | >64 | >64 |
| 267 | 548.85 | 99.8% | 1 | 4 | 4 | 4 | 4 | 2 | >64 | >64 |
| 268 | 564.85 | 99.1% | 2 | 8 | 8 | 4 | 8 | 4 | >64 | >64 |
| 269 | 523.80 | 97.5% | 1 | 4 | 4 | 4 | 4 | 2 | >64 | >64 |
| 270 | 523.80 | 99.3% | 4 | 16 | 16 | 8 | 8 | 4 | >64 | >64 |
| 271 | 523.80 | 96.2% | 2 | 8 | 8 | 4 | 4 | 4 | >64 | >64 |
| 272 | 524.79 | 98.7% | 4 | 8 | 16 | 8 | 4 | 2 | >64 | >64 |
| 273 | 493.34 | 99.2% | >64 | >64 | >64 | 32 | 64 | 32 | >64 | >64 |
| 274 | 542.85 | 98.7% | 16 | 64 | 32 | 16 | 64 | 16 | >64 | >64 |
| 275 | 606.50 | 95.9% | 8 | 32 | 32 | 8 | 16 | 8 | >64 | >64 |
| 276 | 511.36 | 99.3% | 16 | 64 | >64 | 8 | 64 | 32 | >64 | >64 |
| 277 | 574.89 | 98.2% | 16 | 64 | >64 | 16 | 64 | 32 | >64 | >64 |
| 278 | 542.85 | 97.7% | 32 | >64 | >64 | 32 | >64 | 64 | >64 | >64 |
| 279 | 544.86 | 99.4% | 4 | 32 | 32 | 4 | 16 | 16 | >64 | >64 |
| 280 | 548.85 | 95.7% | 16 | 16 | 16 | 8 | 16 | 8 | >64 | >64 |
| 281 | 435.31 | 99.2% | 2 | 4/8 | 8 | 2 | 4 | 2 | >64 | >64 |
| 282 | 472.72 | 97.4% | >64 | >64 | >64 | >64 | >64 | >64 | >64 | >64 |
| 283 | 412.23 | 99.6% | >64 | >64 | >64 | >64 | >64 | >64 | >64 | >64 |
| 284 | 411.24 | 97.8% | 8 | 64 | 16 | 8 | 16 | 8 | >64 | >64 |
| 285 | 393.23 | 98.0% | 1 | 4/4 | 4 | 4 | 4 | 2/2 | >64 | >64 |
| 286 | 400.26 | 94.2% | 4 | 8 | 8 | 4 | 4 | 2 | >64 | >64 |
| 287 | 426.25 | 94.6% | 2 | 4/4 | 4 | 16 | 8 | 4/4 | >64 | >64 |
| 288 | 489.78 | 98.1% | 8 | 32 | 32 | 16 | 32 | 16 | >64 | >64 |
| 289 | 489.78 | 94.5% | 8 | 32 | 32 | 8 | 16 | 8 | >64 | >64 |
| 290 | 382.20 | 95.6% | 8 | 16 | 32 | 16 | 16 | 8 | >64 | >64 |
| 291 | 400.26 | 94.7% | 4 | 16 | 16 | 8 | 16 | 4 | >64 | >64 |
| 292 | 431.71 | 93.7% | 16 | 16 | 16 | 64 | 64 | 64 | >64 | >64 |
| 293 | 475.76 | 99.5% | 8 | 16 | 16 | 16 | 64 | >64 | 32 | >64 |
| 294 | 445.73 | 98.7% | 16 | 32 | 32 | 32 | 64 | 64 | 64 | >64 |
| 295 | 457.74 | 99.5% | 32 | 64 | >64 | 32 | 64 | 64 | 64 | >64 |
| 296 | 478.22 | 93.2% | 32 | >64 | >64 | 8 | >64 | 64 | >64 | >64 |
| 297 | 506.28 | 97.8% | 8 | 32 | 16 | 8 | 16 | 8 | >64 | >64 |
| 298 | 492.25 | 94.9% | >64 | >64 | >64 | >64 | >64 | >64 | >64 | >64 |
| 299 | 542.31 | 97.5% | 64 | >64 | >64 | 16 | >64 | 16 | >64 | >64 |
| 300 | 458.36 | 100.0% | 1 | 4/4 | 4 | 4 | 8 | 2/4 | >64 | >64 |
| 301 | 383.33 | 100.0% | 8 | 4 | 8 | 4 | 8 | 4 | >64 | >64 |
| 302 | 416.23 | 98.7% | 0.5 | 2 | 2 | 2 | 2 | 1 | >64 | >64 |
| 303 | 432.69 | 97.3% | 0.5 | 2 | 2 | 2 | 2 | 1 | >64 | >64 |
| 304 | 402.66 | 98.8% | 0.5 | 1 | 1 | 2 | 2 | 0.5 | >64 | >64 |
| 305 | 386.21 | 96.4% | 0.5 | 1 | 1 | 4 | 2 | 1 | >64 | >64 |
| 306 | 409.20 | 93.3% | 0.5 | 2 | 2 | 4 | 2 | 1 | >64 | >64 |
| 307 | 425.66 | 91.7% | 0.5 | 1 | 1 | 4 | 2 | 1 | >64 | >64 |
| 308 | 353.30 | 99.2% | 2 | 4 | 4 | 4 | 8 | 4 | >64 | >64 |
| 309 | 399.78 | 99.7% | 8 | 16 | 16 | 8 | 32 | 16 | >64 | >64 |
| 310 | 395.82 | 97.2% | 2 | 8 | 4 | 32 | 8 | 4 | >64 | >64 |
| 311 | 379.36 | 97.4% | 8 | 16 | 16 | 32 | 16 | 16 | >64 | >64 |
| 312 | 395.82 | 99.8% | 1 | 8 | 4 | 8 | 8 | 2 | >64 | >64 |
| 313 | 379.36 | 93.8% | 2 | 16 | 8 | 8 | 16 | 8 | >64 | >64 |
| 314 | 427.36 | 97.3% | 16 | 32 | 64 | 16 | >64 | 32 | >64 | >64 |
| 315 | 365.31 | 98.2% | 1 | 4 | 4 | 2 | 8 | 2 | >64 | >64 |
| 316 | 376.29 | 99.8% | 2 | 2 | 4 | 2 | 8 | 4 | >64 | >64 |
| 317 | 552.82 | 99.4% | 1 | 4 | 4 | 4 | 4 | 2 | >64 | >64 |

TABLE 2-continued

MIC Data

| Compd # | Molecular weight | Purity | MIC B. subtilis ATCC 6633 (μg/ml) | MIC NRS 384 (MRSA) (μg/ml) | MIC S. aureus ATCC 29213 (MSSA) (μg/ml) | MIC S. pneumoniae ATCC 49619 (μg/ml) | MIC E. faecalis ATCC 29212 (μg/ml) | MIC E. faecium ATCC 700221 (VRE) (μg/ml) | MIC E. coli ATCC 25922 + 4 mM EDTA (μg/ml) | MIC E. coli ATCC 25922 (μg/ml) |
|---|---|---|---|---|---|---|---|---|---|---|
| 318 | 569.27 | 97.6% | 1 | 2 | 2 | 4 | 2 | 1 | >64 | >64 |
| 319 | 519.91 | 98.0% | 2 | 8 | 8 | 4 | 8 | 4 | >64 | >64 |
| 320 | 508.25 | 96.6% | >64 | >64 | >64 | >64 | >64 | >64 | >64 | >64 |

REFERENCES

Wright, et al., "Inhibition of Bacillus subtilis DNA Polymerase III by Arylhydrazinopyrimidine" Biochimica et Biophysica Acta 1976, 432, 37-48 Kornberg, et al., "DNA replication" 1992, W. H. Freeman & Co., New York, N.Y.

Wright, et al., "DNA polymerase III: A new target for antibiotic development", Current Op. Anti-Infective Investigat. Drugs 1999, 1, 45-48.

Tarantino, et al., "6-Anilinouracil-Based Inhibitors of Bacillus subtilis DNA Polymerase III: Antipolymerase and Antimicrobial Structure-Activity Relationships Based on Substitution at Uracil N3" J. Med. Chem. 1999, 42, 2035-2040.

Tarantino, et al., "Inhibitors of DNA polymerase III as novel antimicrobial agents against Gram-positive eubacteria" Antimicr. Agents Chemother. 1999, 43, 1982-1987.

Daly, et al., "In vitro antimicrobial activity of novel anilinouracils which selectively inhibit DNA polymerase III of Gram-positive bacteria" Antimicr. Agents Chemother. 2000, 44, 2217-2221.

Ali, et al., "Design and Synthesis of Novel Antibacterial Agents with Inhibitory Activity against DNA Polymerase III" Bioorg. Med. Chem. Lett. 2001, 11, 2185-2188.

Muto, et al., "SHEA Guideline for Preventing Nosocomial Transmission of Multidrug-Resistant Strains of Staphylococcus aureus and Enterococcus" Infection Control and Hospital Epidemiology 2003, 362-386.

Ali, et al., "Novel Pyrazolo[3,4-d]pyrimidine-Based Inhibitors of Staphylococcus aureus DNA Polymerase III: Design, Synthesis, and Biological Evaluation" J. Med. Chem. 2003, 46, 1824-1830.

Zhi, et al., "Synthesis and Antibacterial Activity of 3-Substituted-6-(3-ethyl-4-methylanilino) uracils" J. Med. Chem. 2005, 48, 7063-7074.

Wright, et al., "Active site directed inhibitors of replication-specific bacterial DNA polymerases" Bioorg Med Chem Lett. 2005, 15, 729-732.

Kuhl, et al., "Biological Characterization of Novel Inhibitors of the Gram-Positive DNA Polymerase IIIC Enzyme" Antimicr. Agents Chemother. 2005, 49, 987-995.

Wright, et al., "Purine and Isosteric Antibacterial Compounds" U.S. Pat. No. 6,926,763 (2005)

Zhi, et al., "Hybrid Antibacterials. DNA polymerase topoisomerase inhibitors." J. Med. Chem. 2006, 49, 1455-1465.

Evans, et al., "Structure of Po/C reveals unique DNA binding and fidelity determinants" Proc Natl Acad Sci USA 2008, 105, 20695-700.

Cer, et al., "$IC_{50}$-to-Ki: a web-based tool for converting $IC_{50}$ to Ki values for inhibitors of enzyme activity and ligand binding" Nucleic Acids Research, 2009, Vol. 37, Web Server issue W441-W445 doi:10.1093/nar/gkp253

Hookman, et al., "Clostridium difficile associated infection, diarrhea and colitis," World J. Gastroenterol 2009, 15, 1554-1580.

Torti, et al., "Clostridium difficile DNA polymerase IIIC: Basis for activity of Anti-Bacterial Compounds" Current Enzyme Inhibition 2011, 7, 147-153.

Xu, et al., "7-Alkyl-N2-substituted-3-deazaguanines. Synthesis, DNA polymerase III inhibition and antibacterial activity" Bioorg Med Chem Lett. 2011, 21, 4197-202.

Dvoskin, et al., "A novel agent effective against infection with Clostridium difficile" Antimicr. Agents Chemother. 2012, 56, 1624-1626.

Guile, et al., "Antibacterial sulfone and sulfoxide substituted heterocyclic urea compounds" U.S. Pat. No. 8,293,919 (2012), Guile, et al., "Antibacterial heterocyclic ureas" U.S. Pat. No. 8,716,320 (2014).

Wright, et al., "Selective Antibacterials for Clostridium difficile Infections" U.S. Pat. No. 8,796,292 (2014).

Magill, et al., "Changes in Prevalence of Health Care-Associated Infections in U.S. Hospitals" The New England Journal of Medicine 2018, 379, 1732-1744.

Xu, W-C.; Silverman, M. H.; Yu, X. Y. Wright, G. E.; Brown, N. C.; Long, "Discovery and development of DNA polymerase IIIC inhibitors to treat Gram-positive infections" Bioorg. Med. Chem. Vol. 27, Issue 15, 3209-3217 (2019).

Those skilled in the art will recognize, or be able to ascertain, using no more than routine experimentation, numerous equivalents to the specific procedures described herein. Such equivalents are considered to be within the scope of the inventions. Various substitutions, alterations and modifications may be made to the invention without departing from the spirit and scope of the invention. Other aspects, advantages, and modifications are within the scope of the invention. The contents of all references, issued patents, and published patent applications cited through this application are hereby incorporated by reference. The appropriate component, process and methods of those patents, applications and other documents may be selected for the invention and embodiments thereof

What is claimed is:

1. A method of inhibiting the growth of Gram-positive bacteria, said method comprising contacting a medium with an effective amount of a compound corresponding to formula I

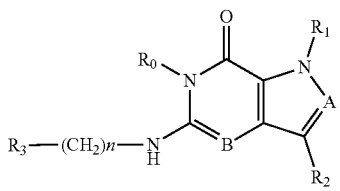

Formula I wherein A and B are N;
wherein n is 1;
wherein $R_1$ is $(CH_2)_m$—{$(V)_o$—$(CH_2)_p$}$_q$—W;
wherein V is $CH_2$, CH=CH, C≡C, CO, O, S, SO, $SO_2$, $NR_4$, $CHR_5$, OC(O), (O)CO, $CONR_6$, $NR_7CO$, $SO_2NH$, $NHSO_2$; $C_{3-8}$ cycloalkyl,
wherein each of $R_4$, $R_6$, and $R_7$ is, independently, H or $C_{1-6}$ alkyl;
wherein $R_5$ is OH or $C_{1-6}$ alkyl, $CH(R_8R_9)$,
wherein each of $R_8$ and $R_9$ is, independently, H, halo, or $C_{1-6}$ alkyl;
wherein W is H, halo, substituted or unsubstituted $C_{1-6}$ alkyl, substituted or unsubstituted $C_{3-8}$ cycloalkyl, substituted or unsubstituted $C_{2-8}$ heterocyclyl, substituted or unsubstituted $C_{6-14}$ aryl, substituted or unsubstituted $C_{1-10}$ heteroaryl, $NH_2$, CN, $OR_{10}$, $SR_{11}$, $COR_{12}$, $OCOR_{13}$, $NR_{14}COR_{15}$, $NR_{16}R_{17}$, $NR_{18}(CO)NHR_{19}$, $CH(CO_2R_{20})_2$, $CO_2R_{21}$, $NHSO_2R_{22}$, $CONR_{23}R_{24}$, $CH_2CO_2R_{25}$, $S(O)R_{26}$ or $S(O_2)R_{27}$
wherein each of $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ is, independently, H, substituted or unsubstituted $C_{1-6}$ alkyl, substituted or unsubstituted $C_{3-8}$ cycloalkyl, substituted or unsubstituted $C_{2-8}$ heterocyclyl, substituted or unsubstituted $C_{6-14}$ aryl, substituted or unsubstituted $C_{1-10}$ heteroaryl,
in which m is 1-5, o is 0-4, p is 0-4, and q is 0-4;
wherein $R_2$ is H, CN, F, or Cl;
wherein $R_3$ is a 3- or 4-F, Cl, Me, or ethyl substituted phenyl group, a 3,4-dichloro, 3,4-difluoro, 3-Me-4-Cl, 3-Me-4-F, 3-Cl-4-Me, 3-F-4-Me, 3-ethyl-4-Cl, 3-ethyl-4-F, 3-Cl-4-ethyl, or 3-F-4-ethyl substituted phenyl group; a benzo[d][1,3]dioxole group; a 2,2-dimethyl-benzo[d]-[1,3]dioxole group; or a 2,2-difluorobenzo[d][1,3]dioxole group;
wherein $R_0$ is H, $CH_2OPO(OH)_2$, $CH_2OCONHCH_2(CH_2)_tOPO(OH)_2$, $CH_2OCOCH_2(CH_2)_tOPO(OH)_2$, $COO(CH_2)_tOPO(OH)_2$, $CH_2OPO(OH)OPO(OH)_2$, or $(CR_{30}R_{31}O)_s$—X—Y—$(CR_{30}R_{31})_t$—$OPO(OR_{28})(OR_{29})$;
wherein X is a direct bond or (C=O), Y is a direct bond or oxygen
s is 0 or 1
t is 1, 2, or 3
$R_{28}$ and $R_{29}$ each are independently hydrogen or a hydrolysable ester group, wherein when $R_{28}$ is hydrogen, $R_{29}$ is —$P(O)OR_{32}OR_{33}$;
$R_{30}$ and $R_{31}$ each are independently hydrogen or $C_{1-4}$ alkyl; and
$R_{32}$ and $R_{33}$ each are independently hydrogen or a hydrolysable ester group,
or an optical isomer thereof, an isotopic isomer thereof, or a pharmaceutically acceptable salt thereof.

2. The method of claim 1, wherein said medium is a surface of a medical device.

3. A method of treating a Gram-positive bacterial infection in a subject in need thereof, said method comprising administering to the subject a therapeutically effective amount of a compound corresponding to formula I

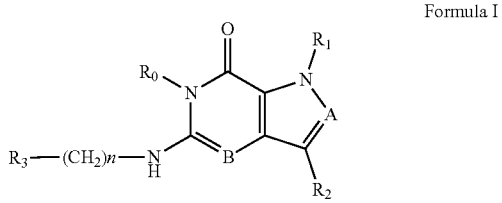

Formula I wherein A and B are N;
wherein n is 1;
wherein $R_1$ is $(CH_2)_m$—{$(V)_o$—$(CH_2)_p$}$_q$—W;
wherein V is $CH_2$, CH=CH, C≡C, CO, O, S, SO, $SO_2$, $NR_4$, $CHR_5$, OC(O), (O)CO, $CONR_6$, $NR_7C$, $SO_2NH$, $NHSO_2$; $C_{3-8}$ cycloalkyl,
wherein each of $R_{46}$, and $R_7$ is, independently, H or $C_{16}$ alkyl;
wherein $R_5$ is OH or $C_6$ alkyl, $CH(R_8R_9)$,
wherein each of $R_8$ and $R_9$ is, independently, H, halo, or $C_{16}$ alkyl;
wherein W is H, halo, substituted or unsubstituted $C_{1-6}$ alkyl substituted or unsubstituted $C_{3-8}$ cycloalkyl, substituted or unsubstituted $C_{2-8}$ heterocyclyl, substituted or unsubstituted $C_{6-14}$ aryl, substituted or unsubstituted $C_{1-10}$ heteroaryl, $NH_2$, CN, $OR_{10}$, $SR_{11}$, $COR_{12}$, $OCOR_{13}$, $NR_{14}COR_{15}$, $NR_{16}R_{17}$, $NR_{18}(CO)NHR_{19}$, $CH(CO_2R_{20})_2$, $CO_2R_{21}$, $NHSO_2R_{22}$, $CONR_{23}R_{24}$, $CH_2CO_2R_{25}$, $S(O)R_{26}$ or $S(O_2)R_{27}$
wherein each of $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ is, independently, H, substituted or unsubstituted $C_{1-6}$ alkyl, substituted or unsubstituted $C_{3-8}$ cycloalkyl, substituted or unsubstituted $C_{2-8}$ heterocyclyl, substituted or unsubstituted $C_{6-14}$ aryl, substituted or unsubstituted $C_{1-10}$ heteroaryl,
in which m is 1-5, o is 0-4, p is 0-4, and q is 0-4;
wherein $R_2$ is H, CN, F, or Cl;
wherein $R_3$ is a 3- or 4-F, Cl, Me, or ethyl substituted phenyl group; a 3,4-dichloro, 3,4-difluoro, 3-Me-4-Cl, 3-Me-4-F, 3-Cl-4-Me, 3-F-4-Me, 3-ethyl-4-Cl, 3-ethyl-4-F, 3-Cl-4-ethyl, or 3-F-4-ethyl substituted phenyl group; a benzo[d][1,3]dioxole group; a 2,2-dimethyl-benzo[d]-[1,3]dioxole group; or a 2,2-difluorobenzo[d][1,3]dioxole group;
wherein $R_0$ is H, $CH_2OPO(OH)_2$, $CH_2OCONHCH_2(CH_2)_tOPO(OH)_2$, $CH_2OCOCH_2(CH_2)_tOPO(OH)_2$, $COO(CH_2)_tOPO(OH)_2$, $CH_2OPO(OH)OPO(OH)_2$, or $(CR_{30}R_{31}O)_s$—X—Y—$(CR_{30}R_{31})_t$—$OPO(OR_{28})(OR_{29})$;
wherein X is a direct bond or (C=O), Y is a direct bond or oxygen
s is 0 or 1
t is 1, 2, or 3
$R_{28}$ and $R_{29}$ each are independently hydrogen or a hydrolysable ester group, wherein when $R_{28}$ is hydrogen, $R_{29}$ is —$P(O)OR_{32}OR_{33}$;
$R_{30}$ and $R_{31}$ each are independently hydrogen or $C_{1-4}$ alkyl; and
$R_{32}$ and $R_{33}$ each are independently hydrogen or a hydrolysable ester group, or an optical isomer thereof, an isotopic isomer thereof, or a pharmaceutically acceptable salt thereof.

4. A method of inhibiting the growth of Gram-positive bacteria, said method comprising contacting a medium with an effective amount of a compound selected from the group consisting of:

5-((3,4-Dichlorobenzyl)amino)-1-methyl-1H-pyrazolo[4,3-d]pyrimidin-7(6H)-one,
5-((3,4-Dichlorobenzyl)amino)-3-fluoro-1-methyl-1H-pyrazolo[4,3-d]pyrimidin-7(6H)-one,
1-Allyl-5-((3,4-dichlorobenzyl)amino)-1H-pyrazolo[4,3-d]pyrimidin-7(6H)-one,
4-(5-((3,4-Dichlorobenzyl)amino)-7-oxo-6,7-dihydro-1H-pyrazolo[4,3-d]pyrimidin-1-yl)butyl acetate,
1-(Cyclobutylmethyl)-5-((3,4-dichlorobenzyl)amino)-1H-pyrazolo[4,3-d]pyrimidin-7(6H)-one,
5-[(3,4-Cichlorophenyl)methylamino]-1-phenyl-6H-pyrazolo[4,3-d]pyrimidin-7-one, 1-Cyclopropyl-5-((3,4-dichlorobenzyl)amino)-1H-pyrazolo[4,3-d]pyrimidin-7(6H)-one,
Cyclopentyl-5-((3,4-dichlorobenzyl)amino)-1H-pyrazolo[4,3-d]pyrimidin-7(6H)-one,
Cethyl 5-(5-chloro-7-methoxy-pyrazolo[4,3-d]pyrimidin-1-yl) pentanoate,
5-[(3,4-Cichlorophenyl)methylamino]-1-(4-pyridyl)-6H-pyrazolo[4,3-d]pyrimidin-7-one,
3-Chloro-5-((3,4-dichlorobenzyl)amino)-1-(2-methoxyethyl)-1H-pyrazolo[4,3-d]pyrimidin-7(6H)-one,
5-((3,4-Cichlorobenzyl)amino)-3-fluoro-1-(2-methoxyethyl)-1H-pyrazolo[4,3-d]pyrimidin-7(6H)-one,
3-Chloro-5-((3,4-dichlorobenzyl)amino)-1-(oxazol-4-ylmethyl)-1H-pyrazolo[4,3-d]pyrimidin-7(6H)-one,
1-(2-(4-Acetylpiperazin-1-yl)ethyl)-5-((3,4-dichlorobenzyl)amino)-1H-pyrazolo[4,3-d]pyrimidin-7(6H)-one hydrochloride,
5-((3,4-Dichlorobenzyl)amino)-1-(2-(2-hydroxyethoxy)ethyl)-1H-pyrazolo[4,3-d]pyrimidin-7(6H)-one,
5-((3,4-Dichlorobenzyl)amino)-1-(2-methoxyethyl)-1H-pyrazolo[4,3-d]pyrimidin-7(6H)-one,
5-((3,4-Dichlorobenzyl)amino)-1-((4-methylmorpholin-2-yl)methyl)-1H-pyrazolo[4,3-d]pyrimidin-7(6H)-one hydrochloride,
5-((3,4-Dichlorobenzyl)amino)-1-(1-(3-methylpicolinoyl) piperidin-4-yl)-1H-pyrazolo[4,3-d]pyrimidin-7(6H)-one hydrochloride,
5-((3,4-Difluorobenzyl)amino)-3-fluoro-1-(2-(2-hydroxyethoxy)ethyl)-1H-pyrazolo[4,3-d]pyrimidin-7(6H)-one,
5-((4-Chloro-3-methylbenzyl)amino)-1-methyl-1H-pyrazolo[4,3-d]pyrimidin-7(6H)-one,
5-((3,4-Dichlorobenzyl)amino)-1,3-dimethyl-1H-pyrazolo[4,3-d]pyrimidin-7(6H)-one,
5-((3,4-Dichlorobenzyl)amino)-1-(2-morpholinoethyl)-1H-pyrazolo[4,3-d]pyrimidin-7(6H)-one hydrochloride,
5-((3,4-Dichlorobenzyl)amino)-1-(4-hydroxybutyl)-1H-pyrazolo[4,3-d]pyrimidin-7(6H)-one),
5-((3,4-Dichlorobenzyl)amino)-1-(thiazol-2-ylmethyl)-1H-pyrazolo[4,3-d]pyrimidin-7(6H)-one,
5-((3,4-Dichlorobenzyl)amino)-1-(oxetan-3-ylmethyl)-1H-pyrazolo[4,3-d]pyrimidin-7(6H)-one,
5-((3,4-Dichlorobenzyl)amino)-1-((tetrahydrofuran-3-yl)methyl)-1H-pyrazolo[4,3-d]pyrimidin-7(6H)-one,
5-((3,4-Dichlorobenzyl)amino)-1-(tetrahydro-2H-pyran-4-yl)-1H-pyrazolo[4,3-d]pyrimidin-7(6H)-one,
5-((3,4-Dichlorobenzyl)amino)-1-(oxetan-2-ylmethyl)-1H-pyrazolo[4,3-d]pyrimidin-7(6H)-one,
5-((3,4-Dichlorobenzyl)amino)-1-(3-hydroxypropyl)-1H-pyrazolo[4,3-d]pyrimidin-7(6H)-one,
5-((3,4-Dichlorobenzyl)amino)-1-(2-(pyrazin-2-yl)ethyl)-1H-pyrazolo[4,3-d]pyrimidin-7(6H)-one hydrochloride,
5-((3,4-Dichlorobenzyl)amino)-1-isopropyl-1H-pyrazolo[4,3-d]pyrimidin-7(6H)-one, 5-((3,4-Dichlorobenzyl)amino)-1-(5-methoxypentyl)-1H-pyrazolo[4,3-d]pyrimidin-7(6H)-one,
5-((3,4-Dichlorobenzyl)amino)-1-((2-methoxyethoxy)methyl)-1H-pyrazolo[4,3-d]pyrimidin-7(6H)-one,
5-((3,4-Dichlorobenzyl)amino)-1-(oxetan-3-yl)-1H-pyrazolo[4,3-d]pyrimidin-7(6H)-one,
5-((3,4-Dichlorobenzyl)amino)-1-(1-(pyridin-3-ylsulfonyl)piperidin-4-yl)-1H-pyrazolo[4,3-d]pyrimidin-7(6H)-one hydrochloride,
(E)-5-((3,4-dichlorobenzyl)amino)-1-(4-methoxybut-2-en-1-yl)-1H-pyrazolo[4,3-d]pyrimidin-7(6H)-one,
Ethyl 5-(5-((3,4-dichlorobenzyl)amino)-7-oxo-6,7-dihydro-1H-pyrazolo[4,3-d]pyrimidin-1-yl)pentanoate,
Isopropyl 5-(5-((3,4-dichlorobenzyl)amino)-7-oxo-6,7-dihydro-1H-pyrazolo[4,3-d]pyrimidin-1-yl)pentanoate,
Ethyl 4-(5-((3,4-dichlorobenzyl)amino)-7-oxo-6,7-dihydro-1H-pyrazolo[4,3-d]pyrimidin-1-yl)butanoate,
Methyl 3-(5-((3,4-dichlorobenzyl)amino)-7-oxo-6,7-dihydro-1H-pyrazolo[4,3-d]pyrimidin-1-yl)propanoate,
5-((3,4-Dichlorobenzyl)amino)-1-(1-(pyridin-2-ylmethyl) piperidin-4-yl)-1H-pyrazolo[4,3-d]pyrimidin-7(6H)-one dihydrochloride,
5-((3,4-Dichlorobenzyl)amino)-1-(1-(pyridin-3-ylmethyl)piperidin-4-yl)-1H-pyrazolo[4,3-d]pyrimidin-7(6H)-one dihydrochloride,
5-((3,4-Dichlorobenzyl)amino)-1-(1-(pyridin-4-ylmethyl) piperidin-4-yl)-1H-pyrazolo[4,3-d]pyrimidin-7(6H)-one dihydrochloride,
5-[(3,4-Dichlorophenyl)methylamino]-1-[1-(oxazole-4-carbonyl)-4-piperidyl]-6H-pyrazolo[4,3-d]pyrimidin-7-one,
5-[(3,4-Dichlorophenyl)methylamino]-1-[1-(thiazole-2-carbonyl)-4-piperidyl]-6H-pyrazolo[4,3-d]pyrimidin-7-one,
5-((3,4-Dichlorobenzyl)amino)-1-(1-(4-methoxypicolinoyl)piperidin-4-yl)-1H-pyrazolo[4,3-d]pyrimidin-7(6H)-one hydrochloride,
5-((3,4-Dichlorobenzyl)amino)-1-(1-(4-methylpicolinoyl)piperidin-4-yl)-1H-pyrazolo[4,3-d]pyrimidin-7(6H)-one hydrochloride,
5-[(3,4-Dichlorophenyl)methylamino]-3-fluoro-1-[2-(2-hydroxyethoxy)ethyl]-6H-pyrazolo[4,3-d]pyrimidin-7-one,
3-Chloro-5-[(3,4-dichlorophenyl)methylamino]-1-[2-(2-hydroxyethoxy)ethyl]-6H-pyrazolo[4,3-d]pyrimidin-7-one,
5-((3,4-Difluorobenzyl)amino)-3-fluoro-1-(oxazol-4-ylmethyl)-1H-pyrazolo[4,3-d]pyrimidin-7(6H)-one,
3-Chloro-5-((3,4-dichlorobenzyl)amino)-1-(1-nicotinoylpiperidin-4-yl)-1H-pyrazolo[4,3-d]pyrimidin-7(6H)-one hydrochloride,
Ammonium (2-(2-(5-((3,4-dichlorobenzyl)amino)-7-oxo-6,7-dihydro-1H-pyrazolo[4,3-d]pyrimidin-1-yl)ethoxy)ethoxy)methyl phosphate,
(5-((3,4-Dichlorobenzyl)amino)-1-(2-(2-hydroxyethoxy)ethyl)-7-oxo-1H-pyrazolo[4,3-d]pyrimidin-6(7H)-yl) methyl dihydrogen phosphate,
and pharmaceutically acceptable salts thereof.

5. The method of claim 4, wherein said medium is a surface of a medical device.

6. A method of treating a Gram-positive bacterial infection in a subject in need thereof, said method comprising administering to the subject a therapeutically effective amount of a compound selected from the group consisting of:

5-((3,4-Dichlorobenzyl)amino)-1-methyl-1H-pyrazolo[4,3-d]pyrimidin-7(6H)-one,
5-((3,4-Dichlorobenzyl)amino)-3-fluoro-1-methyl-1H-pyrazolo[4,3-d]pyrimidin-7(6H)-one,
1-Allyl-5-((3,4-dichlorobenzyl)amino)-1H-pyrazolo[4,3-d]pyrimidin-7(6H)-one,
4-(5-((3,4-Dichlorobenzyl)amino)-7-oxo-6,7-dihydro-1H-pyrazolo[4,3-d]pyrimidin-1-yl)butyl acetate,
1-(Cyclobutylmethyl)-5-((3,4-dichlorobenzyl)amino)-1H-pyrazolo[4,3-d]pyrimidin-7(6H)-one,
5-[(3,4-Cichlorophenyl)methylamino]-1-phenyl-6H-pyrazolo[4,3-d]pyrimidin-7-one,
1-Cyclopropyl-5-((3,4-dichlorobenzyl)amino)-1H-pyrazolo[4,3-d]pyrimidin-7(6H)-one,
Cyclopentyl-5-((3,4-dichlorobenzyl)amino)-1H-pyrazolo[4,3-d]pyrimidin-7(6H)-one,
Cethyl 5-(5-chloro-7-methoxy-pyrazolo[4,3-d]pyrimidin-1-yl) pentanoate,
5-[(3,4-Cichlorophenyl)methylamino]-1-(4-pyridyl)-6H-pyrazolo[4,3-d]pyrimidin-7-one,
3-Chloro-5-((3,4-dichlorobenzyl)amino)-1-(2-methoxyethyl)-1H-pyrazolo[4,3-d]pyrimidin-7(6H)-one,
5-((3,4-Cichlorobenzyl)amino)-3-fluoro-1-(2-methoxyethyl)-1H-pyrazolo[4,3-d]pyrimidin-7(6H)-one,
3-Chloro-5-((3,4-dichlorobenzyl)amino)-1-(oxazol-4-ylmethyl)-1H-pyrazolo[4,3-d]pyrimidin-7(6H)-one,
1-(2-(4-Acetylpiperazin-1-yl)ethyl)-5-((3,4-dichlorobenzyl)amino)-1H-pyrazolo[4,3-d]pyrimidin-7(6H)-one hydrochloride,
5-((3,4-Dichlorobenzyl)amino)-1-(2-(2-hydroxyethoxy)ethyl)-1H-pyrazolo[4,3-d]pyrimidin-7(6H)-one,
5-((3,4-Dichlorobenzyl)amino)-1-(2-methoxyethyl)-1H-pyrazolo[4,3-d]pyrimidin-7(6H)-one,
5-((3,4-Dichlorobenzyl)amino)-1-((4-methylmorpholin-2-yl)methyl)-1H-pyrazolo[4,3-d]pyrimidin-7(6H)-one hydrochloride,
5-((3,4-Dichlorobenzyl)amino)-1-(1-(3-methylpicolinoyl) piperidin-4-yl)-1H-pyrazolo[4,3-d]pyrimidin-7(6H)-one hydrochloride,
5-((3,4-Difluorobenzyl)amino)-3-fluoro-1-(2-(2-hydroxyethoxy)ethyl)-1H-pyrazolo[4,3-d]pyrimidin-7(6H)-one,
5-((4-Chloro-3-methylbenzyl)amino)-1-methyl-1H-pyrazolo[4,3-d]pyrimidin-7(6H)-one,
5-((3,4-Dichlorobenzyl)amino)-1,3-dimethyl-1H-pyrazolo[4,3-d]pyrimidin-7(6H)-one,
5-((3,4-Dichlorobenzyl)amino)-1-(2-morpholinoethyl)-1H-pyrazolo[4,3-d]pyrimidin-7(6H)-one hydrochloride,
5-((3,4-Dichlorobenzyl)amino)-1-(4-hydroxybutyl)-1H-pyrazolo[4,3-d]pyrimidin-7(6H)-one),
5-((3,4-Dichlorobenzyl)amino)-1-(thiazol-2-ylmethyl)-1H-pyrazolo[4,3-d]pyrimidin-7(6H)-one,
5-((3,4-Dichlorobenzyl)amino)-1-(oxetan-3-ylmethyl)-1H-pyrazolo[4,3-d]pyrimidin-7(6H)-one,
5-((3,4-Dichlorobenzyl)amino)-1-((tetrahydrofuran-3-yl)methyl)-1H-pyrazolo[4,3-d]pyrimidin-7(6H)-one,
5-((3,4-Dichlorobenzyl)amino)-1-(tetrahydro-2H-pyran-4-yl)-1H-pyrazolo[4,3-d]pyrimidin-7(6H)-one,
5-((3,4-Dichlorobenzyl)amino)-1-(oxetan-2-ylmethyl)-1H-pyrazolo[4,3-d]pyrimidin-7(6H)-one,
5-((3,4-Dichlorobenzyl)amino)-1-(3-hydroxypropyl)-1H-pyrazolo[4,3-d]pyrimidin-7(6H)-one,
5-((3,4-Dichlorobenzyl)amino)-1-(2-(pyrazin-2-yl)ethyl)-1H-pyrazolo[4,3-d]pyrimidin-7(6H)-one hydrochloride,
5-((3,4-Dichlorobenzyl)amino)-1-isopropyl-1H-pyrazolo[4,3-d]pyrimidin-7(6H)-one, 5-((3,4-Dichlorobenzyl)amino)-1-(5-methoxypentyl)-1H-pyrazolo[4,3-d]pyrimidin-7(6H)-one,
5-((3,4-Dichlorobenzyl)amino)-1-((2-methoxyethoxy)methyl)-1H-pyrazolo[4,3-d]pyrimidin-7(6H)-one,
5-((3,4-Dichlorobenzyl)amino)-1-(oxetan-3-yl)-1H-pyrazolo[4,3-d]pyrimidin-7(6H)-one,
5-((3,4-Dichlorobenzyl)amino)-1-(1-(pyridin-3-ylsulfonyl)piperidin-4-yl)-1H-pyrazolo[4,3-d]pyrimidin-7(6H)-one hydrochloride,
(E)-5-((3,4-dichlorobenzyl)amino)-1-(4-methoxybut-2-en-1-yl)-1H-pyrazolo[4,3-d]pyrimidin-7(6H)-one,
Ethyl 5-(5-((3,4-dichlorobenzyl)amino)-7-oxo-6,7-dihydro-1H-pyrazolo[4,3-d]pyrimidin-1-yl)pentanoate,
Isopropyl 5-(5-((3,4-dichlorobenzyl)amino)-7-oxo-6,7-dihydro-1H-pyrazolo[4,3-d]pyrimidin-1-yl)pentanoate,
Ethyl 4-(5-((3,4-dichlorobenzyl)amino)-7-oxo-6,7-dihydro-1H-pyrazolo[4,3-d]pyrimidin-1-yl)butanoate,
Methyl 3-(5-((3,4-dichlorobenzyl)amino)-7-oxo-6,7-dihydro-1H-pyrazolo[4,3-d]pyrimidin-1-yl)propanoate,
5-((3,4-Dichlorobenzyl)amino)-1-(1-(pyridin-2-ylmethyl) piperidin-4-yl)-1H-pyrazolo[4,3-d]pyrimidin-7(6H)-one dihydrochloride,
5-((3,4-Dichlorobenzyl)amino)-1-(1-(pyridin-3-ylmethyl)piperidin-4-yl)-1H-pyrazolo[4,3-d]pyrimidin-7(6H)-one dihydrochloride,
5-((3,4-Dichlorobenzyl)amino)-1-(1-(pyridin-4-ylmethyl) piperidin-4-yl)-1H-pyrazolo[4,3-d]pyrimidin-7(6H)-one dihydrochloride,
5-[(3,4-Dichlorophenyl)methylamino]-1-[1-(oxazole-4-carbonyl)-4-piperidyl]-6H-pyrazolo[4,3-d]pyrimidin-7-one,
5-[(3,4-Dichlorophenyl)methylamino]-1-[1-(thiazole-2-carbonyl)-4-piperidyl]-6H-pyrazolo[4,3-d]pyrimidin-7-one,
5-((3,4-Dichlorobenzyl)amino)-1-(1-(4-methoxypicolinoyl)piperidin-4-yl)-1H-pyrazolo[4,3-d]pyrimidin-7(6H)-one hydrochloride,
5-((3,4-Dichlorobenzyl)amino)-1-(1-(4-methylpicolinoyl)piperidin-4-yl)-1H-pyrazolo[4,3-d]pyrimidin-7(6H)-one hydrochloride,
5-[(3,4-Dichlorophenyl)methylamino]-3-fluoro-1-[2-(2-hydroxyethoxy)ethyl]-6H-pyrazolo[4,3-d]pyrimidin-7-one,
3-Chloro-5-[(3,4-dichlorophenyl)methylamino]-1-[2-(2-hydroxyethoxy)ethyl]-6H-pyrazolo[4,3-d]pyrimidin-7-one,
5-((3,4-Difluorobenzyl)amino)-3-fluoro-1-(oxazol-4-ylmethyl)-1H-pyrazolo[4,3-d]pyrimidin-7(6H)-one,
3-Chloro-5-((3,4-dichlorobenzyl)amino)-1-(1-nicotinoylpiperidin-4-yl)-1H-pyrazolo[4,3-d]pyrimidin-7(6H)-one hydrochloride,
Ammonium (2-(2-(5-((3,4-dichlorobenzyl)amino)-7-oxo-6,7-dihydro-1H-pyrazolo[4,3-d]pyrimidin-1-yl)ethoxy)ethoxy)methyl phosphate,
(5-((3,4-Dichlorobenzyl)amino)-1-(2-(2-hydroxyethoxy)ethyl)-7-oxo-1H-pyrazolo[4,3-d]pyrimidin-6(7H)-yl) methyl dihydrogen phosphate,
and pharmaceutically acceptable salts thereof.

* * * * *